US009585374B2

(12) United States Patent
Wells et al.

(10) Patent No.: US 9,585,374 B2
(45) Date of Patent: Mar. 7, 2017

(54) UNGULATES WITH GENETICALLY MODIFIED IMMUNE SYSTEMS

(75) Inventors: Kevin Wells, Christianburg, VA (US); David Ayares, Blacksburg, VA (US)

(73) Assignee: Revivicor, Inc., Blacksburg, VA (US)

( * ) Notice: Subject to any disclaimer, the term of this patent is extended or adjusted under 35 U.S.C. 154(b) by 0 days.

(21) Appl. No.: 12/433,477

(22) Filed: Apr. 30, 2009

(65) Prior Publication Data

US 2010/0077494 A1 Mar. 25, 2010

Related U.S. Application Data

(63) Continuation of application No. 11/789,961, filed on Apr. 26, 2007, now abandoned, which is a continuation-in-part of application No. 11/257,817, filed on Oct. 24, 2005.

(60) Provisional application No. 60/621,433, filed on Oct. 22, 2004, provisional application No. 60/794,963, filed on Apr. 26, 2006.

(51) Int. Cl.

| | |
|---|---|
| ***C12N 15/63*** | (2006.01) |
| ***C12P 1/00*** | (2006.01) |
| ***C07H 21/00*** | (2006.01) |
| ***A01K 67/027*** | (2006.01) |
| ***C12N 15/85*** | (2006.01) |

(52) U.S. Cl.

CPC ...... *A01K 67/0275* (2013.01); *A01K 67/0276* (2013.01); *C12N 15/8509* (2013.01); *A01K 2217/075* (2013.01); *A01K 2227/108* (2013.01); *A01K 2267/02* (2013.01); *A01K 2267/025* (2013.01)

(58) Field of Classification Search

CPC .......... A01K 2267/025; A01K 67/0275; A01K 2227/108; A01K 67/0276; C12N 15/8509

See application file for complete search history.

(56) References Cited

U.S. PATENT DOCUMENTS

| | | | |
|---|---|---|---|
| 5,545,806 | A | 8/1996 | Lonberg et al. |
| 5,545,807 | A | 8/1996 | Surani et al. |
| 5,569,825 | A | 10/1996 | Lonberg et al. |
| 5,591,669 | A | 1/1997 | Krimpenfort et al. |
| 5,612,205 | A | 3/1997 | Kay et al. |
| 5,625,126 | A | 4/1997 | Lonberg et al. |
| 5,625,825 | A | 4/1997 | Rostoker et al. |
| 5,633,425 | A | 5/1997 | Lonberg et al. |
| 5,643,763 | A | 7/1997 | Dunn et al. |
| 5,661,016 | A | 8/1997 | Lonberg et al. |
| 5,721,367 | A | 2/1998 | Kay et al. |
| 5,770,429 | A | 6/1998 | Lonberg et al. |
| 5,789,215 | A | 8/1998 | Berns et al. |
| 5,789,650 | A | 8/1998 | Lonberg et al. |
| 5,814,318 | A | 9/1998 | Lonberg et al. |
| 7,074,983 | B2 | 7/2006 | Robl et al. |
| 7,414,170 | B2 | 8/2008 | Robl et al. |
| 2003/0037347 | A1 | 2/2003 | Robl et al. |
| 2003/0056237 | A1 | 3/2003 | Goldsby et al. |
| 2004/0068760 | A1 | 4/2004 | Robl et al. |
| 2005/0155095 | A1 | 7/2005 | Koike |
| 2005/0223418 | A1 | 10/2005 | Koike |
| 2006/0068479 | A1 | 3/2006 | Koike |
| 2006/0117394 | A1 | 6/2006 | Robl et al. |
| 2006/0130157 | A1 | 6/2006 | Wells et al. |

FOREIGN PATENT DOCUMENTS

| | | | |
|---|---|---|---|
| EP | 0 843 961 | A1 | 5/1998 |
| WO | WO 91/10741 | A1 | 7/1991 |
| WO | WO 92/03918 | A1 | 3/1992 |
| WO | WO 92/22645 | A1 | 12/1992 |
| WO | WO 92/22647 | A1 | 12/1992 |
| WO | WO 92/22670 | A1 | 12/1992 |
| WO | WO 93/12227 | A1 | 6/1993 |
| WO | WO 94/00569 | A1 | 1/1994 |
| WO | WO 94/02602 | A1 | 2/1994 |
| WO | WO 94/25585 | A1 | 11/1994 |
| WO | WO 96/14436 | A1 | 5/1996 |
| WO | WO 96/34096 | A1 | 10/1996 |
| WO | WO 97/13852 | A1 | 4/1997 |
| WO | WO 98/24884 | A1 | 6/1998 |
| WO | WO 98/24893 | A2 | 6/1998 |
| WO | WO 00/51424 | A2 | 9/2000 |
| WO | WO 01/35735 | | 5/2001 |
| WO | WO 02/07648 | A1 | 1/2002 |

(Continued)

OTHER PUBLICATIONS

Schwartz et al., Immunogenetics, (64): 399-407, 2012.*
Parng et al., Immunology, 157: 5478-5486, 1996.*
Kaushik et al., Veterinary Immunology and Immunopathology, 87: 347-350, 2000.*
Robl et al., Theriogenology, 59: 107-113, 2003.*
Butler et al., Frontiers in Immunology, 3: 1-14, Jun. 2012.*
Baguisi, A., et al., "Production of goats by somatic cell nuclear transfer," *Nat. Biotechnology,* 17(5): 456-461 (May 1999).
Betthauser, J., et al., "Production of cloned pigs from in vitro systems," *Nat. Biotechnology,* 18(10):1055-1059 (Oct. 2000).
Binns, R.M., and Licence, S.T., "Patterns of migration of labelled blood lymphocyte subpopulations: evidence for two types of Peyer's patch in the young pig," *Adv. Exp. Med. Biol.,* 186: 661-668 (1985).

(Continued)

*Primary Examiner* — Thaian N Ton
(74) *Attorney, Agent, or Firm* — King & Spalding

(57) ABSTRACT

The present invention provides ungulate animals, tissue and organs as well as cells and cell lines derived from such animals, tissue and organs, which lack expression of functional endogenous immunoglobulin loci. The present invention also provides ungulate animals, tissue and organs as well as cells and cell lines derived from such animals, tissue and organs, which express xenogenous, such as human, immunoglobulin loci. The present invention further provides ungulate, such as porcine genomic DNA sequence of porcine heavy and light chain immunogobulins. Such animals, tissues, organs and cells can be used in research and medical therapy. In addition, methods are provided to prepare such animals, organs, tissues, and cells.

20 Claims, 7 Drawing Sheets

(56) References Cited

FOREIGN PATENT DOCUMENTS

| | | | |
|---|---|---|---|
| WO | WO 02/070648 | | 9/2002 |
| WO | WO 02/070648 | A2 | 9/2002 |
| WO | WO 03/047336 | | 6/2003 |
| WO | WO 2004/028243 | A2 | 4/2004 |
| WO | WO 2006/047603 | A2 | 5/2006 |

OTHER PUBLICATIONS

Bodey, B., "Human cancer detection and immunotherapy with conjugated and non-conjugated monoclonal antibodies," *Anticancer Res.*, 16(2):661-674 (Mar.-Apr. 1996).

Bonnefoy-Berard, N., and Revillard, J.P., "Mechanisms of immunosuppression induced by antithymocyte globulins and OKT3," *J. Heart Lung Transplant,* 15(5):435-442 (May 1996).

Brown, W.R., and Butler, J.E. "Characterization of a C alpha gene of swine," *Mol. Immunol.,* 31(8):633-642 (Jun. 1994).

Brüggemann, M., et al. "A repertoire of monoclonal antibodies with human heavy chains from transgenic mice," *Proc. Nat'l. Acad. Sci. USA,* 86(17):6709-6713 (Sep. 1989).

Brüggemann, M., et al., "The immunogenicity of chimeric antibodies," *J. Exp. Med.,* 170(6):2153-2157 (Dec. 1, 1989).

Burnett, R. C, et al., "The IgA heavy-chain gene family in rabbit: cloning and sequence analysis of 13 C alpha genes," *EMBO J.,* 8(13):4041-4047 (Dec. 20, 1989).

Butler, J.E., and Brown, W.R., et al , "The immunoglobulins and immunoglobulin genes of swine," *Vet. Immunol. Immunopathol.,* 43(1-3):5-12 (Oct. 1994).

Butler, J.E., et al, "Swine have a single $J_H$, <20 $V_H$ genes and no IgD," Chapter 27 in *Advances in Swine in Biomedical Research,* Tumbleson and Schook, eds. (Plenum Press, New York, 1996), pp. 291-305.

Butler, J.E., et al., "The swine Ig heavy chain locus has a single JH and no identifiable IgD," *Intl. Immunol.,* 8(12):1897-1904 (Dec. 1996).

Casadevall, A., and Scharff, M.D., "Return to the past: the case for antibody-based therapies in infectious diseases," *Clinical Infectious Diseases,* 21(1):150-161 (Jul. 1995).

Casadevall, Arturo, "Passive Antibody Administration (Immediate Immunity) as a Specific Defense Against Biological Weapons" *Emerging Infectious Diseases* (Centers for Disease Control and Prevention (CDC)), 8(8):833-841 (Aug. 2002).

Cendrowski, W., "Antilymphocyte globulin and adrenal steroids in the treatment of multiple sclerosis: short report based on seven cases," *Boll. Ist. Sieroter. Milan,* 58(4):339-343 (Sep. 30, 1979).

Chen, J., et al., "Immunoglobulin gene rearrangement in B cell deficient mice generated by targeted deletion of the JH locus," *International Immunology,* 5(6):647-656 (Jun. 1993).

Choi, T.K., et al., "Transgenic mice containing a human heavy chain immunoglobulin gene fragment cloned in a yeast artificial chromosome," *Nature Genetics,* 4(2):117-123 (Jun. 1993).

Cibelli, J.B., et al., "Cloned transgenic calves produced from nonquiescent fetal fibroblasts," *Science,* 280(5367):1256-1258 (May 22, 1998).

Colby, C., et al., "Antithymocyte immunoglobulin in severe aplastic anemia and bone marrow transplantation," *Ann. Pharmacother.,* 30(10):1164-1174 (Oct. 1996).

Dai, Y., et al., "Targeted disruption of the $\alpha$1,3-galactosyltransferase gene in cloned pigs," *Nature Biotechnology,* 20:251-255 (Mar. 2002).

Dufour, V, et al., "The sheep Ig variable region repertoire consists of a single VH family," *J. Immunol,.* 156(6):2163-2170 (Mar. 15, 1996).

Dugan, M.J., et al, "ATG plus corticosteroid therapy for acute graft-versus-host disease: predictors of response and survival," *Ann. Hematol.,* 75(1-2):41-46 (Jul.-Aug. 1997).

Fishwild, D.M., et al., "High-avidity human IgG kappa monoclonal antibodies from a novel strain of minilocus transgenic mice," *Nature Biotech.,* 14(7):845-851 (Jul. 1996).

Green, L.L., et al., "Antigen-specific human monoclonal antibodies from mice engineered with human Ig heavy and light chain YACs," *Nature Genetics,* 7(1):13-21 (May 1994).

Green, L.L., and Jakobovits, A., "Regulation of B cell development by variable gene complexity in mice reconstituted with human immunoglobulin yeast artificial chromosomes," *J. Exp. Med.,* 188(3):483-495 (Aug. 3, 1998).

Honjo, T., et al., "Constant-region genes of the immunoglobulin heavy chain and the molecular mechanism of class switching," Chapter 7 in Honjo, T, Alt. F. W. T. H. eds, *Immunoglobulin Genes* (Academic Press, New York, 1989) pp. 123-149.

Jones, P.T.,, et al., "Replacing the complementarity-determining regions in a human antibody with those from a mouse," *Nature,* 321(6069):522-525 (May 29-Jun. 4, 1986).

Kacskovics, I, et al., "Five putative subclasses of swine IgG identified from the cDNA sequences of a single animal," *J. Immunol.,* 153(8):3565-3573 (Oct. 15, 1994).

Kastrukoff, L. K.,, et al., "Multiple sclerosis treated with antithymocyte globulin—a five year follow-up," *Can. J. Neurol. Sci.,* 5(2):175-178 (May 1978).

Kolber-Simonds, D., et al., "Production of alpha-1,3-galactosyltransferase null pigs by means of nuclear transfer with fibroblasts bearing loss of heterozygosity mutations," *Proc. Natl. Acad. Sci. USA,* 101(19):7335-7340 (May 11, 2004) (Electronic publication May 3, 2004).

Kubota, C., et al., "Six cloned calves produced from adult fibroblast cells after long-term culture," *Proc. Nat'l. Acad. Sci. USA,* 97(3):990-995 (Feb. 1, 2000).

Kuroiwa, Y., et al., "Cloned transchromosomic calves producing human immunoglobulin," *Nature Biotechnology,* 20(9):889-894 (Sep. 2002) (Electronic publication Aug. 12, 2002).

Kuroiwa, Y., et al., "Sequential targeting of the genes encoding immunoglobulin-mu and prion protein in cattle," *Nat. Genet.,* 36(7):775-780 (Jul. 2004) (Electronic publication Jun. 6, 2004).

Lai, L., et al., "Production of $\alpha$-1,3-galactosyltransferase knockout pigs by nuclear transfer cloning," *Science* 295:1089-1092 (Feb. 8, 2002) and supplementary data, *Science Express,* Jan. 3, 2002.

Lonberg, N., et al., "Antigen-specific human antibodies from mice comprising four distinct genetic modifications," *Nature,* 368(6474):856-859 (Apr. 28, 1994).

Mendez, M.J., et al., "Functional transplant of megabase human immunoglobulin loci recapitulates human antibody response in mice," *Nature Genetics,* 15(2):146-156 (Feb. 1997).

Morrison, S.L.,, et al., "Chimeric human antibody molecules: mouse antigen-binding domains with human constant region domains," *Proc. Natl. Acad. Sci. USA,* 81(21):6851-6855 (Nov. 1984).

Phelps, C.J., et al., "Production of $\alpha$1,3-galactosyltransferase-deficient pigs," *Science,* 299:411-414 (Jan. 17, 2003).

Polejaeva, I.A., et al., "Cloned pigs produced by nuclear transfer from adult somatic cells," *Nature,* 407:86-90 (Sep. 7, 2000).

Ramsoondar, J.J., et al., "Production of $\alpha$1,3-galactosyltransferase-knockout cloned pigs expressing human $\alpha$1,2-fucosyltransferase," *Biol. of Reproduction,* 69:437-445 (online before print Apr. 2, 2003).

Rathbun, G., "Organization and expression of the mammalian heavy-chain variable-region locus," Chapter 4 in *Immunoglobulin Genes,* Honjo, T. Alt. F. W. and Rabbits, T. H., eds, (Academic Press, New York, 1989), pp. 63-90.

Renner, C.,, et al, "Monoclonal antibodies in the treatment of non-Hodgkin's lymphoma: recent results and future prospects," *Leukemia,* 11( Suppl 2):S55-S59 (1997), miscite as Botti, C., et al., & w/o title.

Reynaud, C.A., et al., "Formation of the chicken B-cell repertoire: ontogenesis, regulation of Ig gene rearrangement, and diversification by gene conversion," *Adv. Immunol.,* 57:353-378 (1994).

Sendai, Y., et al., "Heterozygous disruption of the alpha1,3-galactosyltransferase gene in cattle," *Transplantation,* (2003) 76(6):900-902 (Sep. 27, 2003).

Sinclair, M.C., et al, "Bovine IgG repertoire is dominated by a single diversified VH gene family," *J. Immunol.,* 159(8): 3883-3889, (Oct. 15, 1997).

(56) References Cited

OTHER PUBLICATIONS

Sun, J., et al., "Expressed swine VH genes belong to a small VH gene family homologous to human VHIII," *J. Immunol.,* 153(12): 5618-5627, (Dec. 15, 1994).
Taylor, L.D., et al., "Human immunoglobulin transgenes undergo rearrangement, somatic mutation and class switching in mice that lack endogenous IgM," *Intl. Immunol.,* 6(4):579-591 (Apr. 1994).
Taylor, L.D., et al., "A transgenic mouse that expresses a diversity of human sequence heavy and light chain immunoglobulins," *Nucleic Acids Research,* 20(23):6287-6295 (Dec. 11, 1992).
Tsai, H.F., et al., "Gene conversion-like sequence transfers in a mouse antibody transgene: antigen selection allows sensitive detection of V region interactions based on homology," *International Immunology,* vol. 14(1):55-64 (Jan. 2002).
Tuaillon, N., et al., "Analysis of direct and inverted DJH rearrangements in a human Ig heavy chain transgenic minilocus," *J. Immunol.,* 154(12):6453-6465 (Jun. 15, 1995).
Walker, J. E.,, et al., "A trial of antilymphocyte globulin in the treatment of chronic progressive multiple sclerosis," *J. Neurol. Sci.,* 29(2-4):303-309 (Oct. 1976).
Wilmut, I.,, et al., "Viable offspring derived from fetal and adult mammalian cells," *Nature,* 385(6619):810-813 (Feb. 27, 1997).
Zhao, Y., et al., "Physical mapping of the bovine immunoglobulin heavy chain constant region gene locus," *J. Biol. Chem.,* 278(37):35024-35032 (Sep. 12, 2003) (Electronic publication Jun. 26, 2003).
Zhao, Y., et al., "The porcine Ig delta gene: unique chimeric splicing of the first constant region domain in its heavy chain transcripts.," *J. Immunol.,* 171(3):1312-8 (Aug. 1, 2003).
Zou et al., *J. Immunol.,* 170(3):1354-1361 (Feb. 2003).
Kitamura et al., (1991) Nature 350, 423-426.
Extended European Search Report for EP 09824080.7 issued on Feb. 27, 2012.
International Search Report, for PCT/US09/62265 issued on Dec. 9, 2009.
Couronne et al.; Strategies and Tools for Whole-Genome Alignments; *Genome Research;* vol. 13:73-80; Sep. 4, 2002.
Jeon et al.; *Mol. Cells;* vol. 16, No. 1, pp. 113-116; Apr. 10, 2003.
Uenishi et al.; *Nucleic Acids Research,* Aug. 16, 2003; vol. 32; pp. 2-6.
Sutherland et al.; *Transplantation,* 2000, vol. 69, pp. 1806-1812.
Yates et al.; *Blood,* 2002, vol. 100, pp. 3942-3949.
Hao-Chih, Tai et al., Progress in xenotransplantation following the introduction of gene-knockout technology, *Transplant International,* vol. 20, No. 2, Feb. 1, 2007, pp. 107-117.
Mendicino, M. et al., "Generation of antibody- and B cell-deficient pigs by targeted disruption of the J-region gene segment of the heavy chain locus," Transgenic Research, Kluwer Academic Publishers, vol. 20, No. 3, Sep. 26, 2010, pp. 625-641.
Ramsoondar J. et al., "Targeted disruption of the porcine immunoglobin kappa light chain locus," *Transgenic Research,* Kluwer Academic Publishers, vol. 20, No. 3, Sep. 26, 2010 pp. 643-653.
Patel et al., Animal Pharming for the Production of Pharmaceutical Proteins, Drug Delivery Tech-nology, Apr. 2007, vol. 7, No. 4, pp. 47-53.
Kuriowa et al., Sequential Targeting of the Genes Encoding Immunoglobulin-μ, and Prion Protein in Cattle; (2004) Nat Genet. 36, 775-780.
Altschul, S.F. et al. Nucleic Acids Res vol. 25, pp. 3389-3402; Jun./Jul. 1997.
Cai et al. Genomics vol. 29, 1995, pp. 413-425.
Doetschman et al. Nature vol. 330, 1987, pp. 576-578.
Joyner et al. Nature vol. 338, 1989, pp. 153-156.
Karlin et al. Proc. Natl. Acad. Sci. USA vol. 87, pp. 2264-2268.
Kim; Smithies Nucleic Acids Res. vol. 16, 1988, pp. 8887-8903.
Kucherlapati et al. Mol. Cell. Bio. vol. 5, 1985, pp. 714-720.
Kucherlapati et al. Proc. Natl. Acad. Sci. USA vol. 81, 1984, pp. 3153-3157.
Mansour et al. Nature vol. 336, 1988, pp. 348-352.
Nandi et al. Proc. Natl. Acad. Sci. USA vol. 85, 1988, pp. 3845-3849.
Kaster et al.; Nucleic Acids Research vol. 11, 1983, pp. 6895-6911.
Song, K-Y. et al. Proc. Nat'l Acad. Sci. U.S.A. vol. 84, 1987, pp. 6820-6824.
Thomas; Capecchi Cell vol. 51, 1987, pp. 503-512.
Wake et al. Mol. Cell. Bio. vol. 8, 1985, pp. 2080-2089.
Kuroiwa, Yoshimi et al.; Nature Biotechnology. vol. 27, No. 2. Feb. 2009.
Matsushita, Hiroaki, et al.; Plos One. vol. 9, Issue 3. Mar. 2014.

* cited by examiner

Graphic view of Human sequence AC002060 and NG_000002 with
Porcine lambda contigs that flank the JC cluster.

Aproximate scale: one block is about 1 kb

SEQUENCE LISTING

```
<160> NUMBER OF SEQ ID NOS: 50

<210> SEQ ID NO 1
<211> LENGTH: 666
<212> TYPE: DNA
<213> ORGANISM: Sus sp.
```

<400> SEQUENCE: 1
tctagaagac gctggagaga ggccagactt cctcggaaca gctcaaagag ctctgtcaaa 60
gccagatccc atcacacgtg ggcaccaata ggccatgcca gcctccaagg gccgaactgg 120
gttctccacg gcgcacatga agcctgcagc ctggcttatc ctcttccgtg gtgaagaggc 180
aggcccggga ctggacgagg ggctagcagg gtgtggtagg caccttgcgc cccccacccc 240
ggcaggaacc agagaccctg gggctgagag tgagcctcca aacaggatgc cccacccttc 300
aggccacctt tcaatccagc tacactccac ctgccattct cctctgggca cagggcccag 360
cccctggatc ttggccttgg ctcgacttgc acccacgcgc acacacacac ttcctaacgt 420
gctgtccgct cacccctccc cagcgtggtc catgggcagc acggcagtgc gcgtccggcg 480
gtagtgagtg cagaggtccc ttcccctccc ccaggagccc caggggtgtg tgcagatctg 540
ggggctcctg tcccttacac cttcatgccc ctcccctcat acccaccctc caggcgggag 600
gcagcgagac ctttgcccag ggactcagcc aacgggcaca cgggaggcca gccctcagca 660
gctggg 666

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
ggccagactt cctcggaaca gctca 25

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
ttccaggaga aggtgacgga gct 23

<210> SEQ ID NO 4
<211> LENGTH: 9175
<212> TYPE: DNA
<213> ORGANISM: Sus sp.

<400> SEQUENCE: 4
ggccagactt cctcggaaca gctcaaagag ctctgtcaaa gccagatccc atcacacgtg 60
ggcaccaata ggccatgcca gcctccaagg gccgaactgg gttctccacg gcgcacatga 120
agcctgcagc ctggcttatc ctcttccgtg gtgaagaggc aggcccggga ctggacgagg 180
ggctagcagg gtgtggtagg caccttgcgc cccccacccc ggcaggaacc agagaccctg 240
gggctgagag tgagcctcca aacaggatgc cccacccttc aggccacctt tcaatccagc 300
tacactccac ctgccattct cctctgggca cagggcccag cccctggatc ttggccttgg 360
ctcgacttgc acccacgcgc acacacacac ttcctaacgt gctgtccgct cacccctccc 420
cagcgtggtc catgggcagc acggcagtgc gcgtccggcg gtagtgagtg cagaggtccc 480
ttcccctccc ccaggagccc caggggtgtg tgcagatctg ggggctcctg tcccttacac 540
cttcatgccc ctcccctcat acccaccctc caggcgggag gcagcgagac ctttgcccag 600

-continued

```
ggactcagcc aacgggcaca cgggaggcca gccctcagca gctggctccc aaagaggagg    660
tgggaggtag gtccacagct gccacagaga gaaaccctga cggaccccac aggggccacg    720
ccagccggaa ccagctccct cgtgggtgag caatggccag ggccccgccg gccaccacgg    780
ctggccttgc gccagctgag aactcacgtc cagtgcaggg agactcaaga cagcctgtgc    840
acacagcctc ggatctgctc ccatttcaag cagaaaaagg aaaccgtgca ggcagccctc    900
agcatttcaa ggattgtagc agcggccaac tattcgtcgg cagtggccga ttagaatgac    960
cgtggagaag ggcggaaggg tctctcgtgg gctctgcggc caacaggccc tggctccacc   1020
tgcccgctgc cagcccgagg ggcttgggcc gagccaggaa ccacagtgct caccgggacc   1080
acagtgactg accaaactcc cggccagagc agccccaggc cagccgggct ctcgccctgg   1140
aggactcacc atcagatgca caagggggcg agtgtggaag agacgtgtcg cccgggccat   1200
ttgggaaggc gaagggacct tccaggtgga caggaggtgg gacgcactcc aggcaaggga   1260
ctgggtcccc aaggcctggg gaaggggtac tggcttgggg gttagcctgg ccagggaacg   1320
gggagcgggg cgggggggctg agcagggagg acctgacctc gtgggagcga ggcaagtcag   1380
gcttcaggca gcagccgcac atcccagacc aggaggctga ggcaggaggg gcttgcagcg   1440
gggcgggggc ctgcctggct ccgggggctc ctgggggacg ctggctcttg tttccgtgtc   1500
ccgcagcaca gggccagctc gctgggccta tgcttacctt gatgtctggg gccggggcgt   1560
cagggtcgtc gtctcctcag gggagagtcc cctgaggcta cgctgggggg ggactatggc   1620
agctccacca ggggcctggg gaccaggggc ctggaccagg ctgcagcccg gaggacgggc   1680
agggctctgg ctctccagca tctggccctc ggaaatggca gaacccctgg cgggtgagcg   1740
agctgagagc gggtcagaca gacaggggcc ggccggaaag gagaagttgg gggcagagcc   1800
cgccaggggc caggcccaag gttctgtgtg ccagggcctg ggtgggcaca ttggtgtggc   1860
catggctact tagattcgtg gggccagggc atcctggtca ccgtctcctc aggtgagcct   1920
ggtgtctgat gtccagctag gcgctggtgg gccgcgggtg ggcctgtctc aggctagggc   1980
aggggctggg atgtgtattt gtcaaggagg ggcaacaggg tgcagactgt gcccctggaa   2040
acttgaccac tggggcaggg gcgtcctggt cacgtctcct caggtaagac ggccctgtgc   2100
ccctctctcg cgggactgga aaaggaattt tccaagattc cttggtctgt gtggggccct   2160
ctggggcccc cgggggtggc tcccctcctg cccagatggg gcctcggcct gtggagcacg   2220
ggctgggcac acagctcgag tctagggcca cagaggcccg ggctcagggc tctgtgtggc   2280
ccggcgactg gcagggggct cgggtttttg gacacccccct aatgggggcc acagcactgt   2340
gaccatcttc acagctgggg ccgaggagtc gaggtcaccg tctcctcagg tgagtcctcg   2400
tcagccctct ctcactctct ggggggtttt gctgcatttt gtgggggaaa gaggatgcct   2460
gggtctcagg tctaaaggtc tagggccagc gccggggccc aggaaggggc cgaggggcca   2520
ggctcggctc ggccaggagc agagcttcca gacatctcgc ctcctggcgg ctgcagtcag   2580
gcctttggcc ggggggggtct cagcaccacc aggcctcttg gctcccgagg tccccggccc   2640
cggctgcctc accaggcacc gtgcgcggtg ggcccgggct cttggtcggc cacccttttct   2700
taactgggat ccgggcttag ttgtcgcaat gtgacaacgg gctcgaaagc tggggccagg   2760
ggaccctagt tacgacgcct cgggtgggtg tcccgcaccc ctccccactt tcacggcact   2820
cggcgagacc tggggagtca ggtgttgggg acactttgga ggtcaggaac gggagctggg   2880
gagagggctc tgtcagcggg gtccagagat gggccgccct ccaaggacgc cctgcgcggg   2940
gacaagggct tcttggcctg gcctggccgc ttcacttggg cgtcaggggg ggcttcccgg   3000
```

-continued

```
ggcaggcggt cagtcgaggc gggttggaat tctgagtctg ggttcggggt tcggggttcg   3060
gccttcatga acagacagcc caggcgggcc gttgtttggc ccctgggggc ctggttggaa   3120
tgcgaggtct cgggaagtca ggagggagcc tggccagcag agggttccca gccctgcggc   3180
cgagggacct ggagacgggc agggcattgg ccgtcgcagg gccaggccac accccccagg   3240
tttttgtggg gcgagcctgg agattgcacc actgtgatta ctatgctatg gatctctggg   3300
gcccaggcgt tgaagtcgtc gtgtcctcag gtaagaacgg ccctccaggg cctttaattt   3360
ctgctctcgt ctgtgggctt ttctgactct gatcctcggg aggcgtctgt gccccccccg   3420
gggatgaggc cggcttgcca ggaggggtca gggaccagga gcctgtggga agttctgacg   3480
ggggctgcag gcgggaaggg ccccaccggg gggcgagccc caggccgctg ggcggcagga   3540
gacccgtgag agtgcgcctt gaggagggtg tctgcggaac cacgaacgcc cgccgggaag   3600
ggcttgctgc aatgcggtct tcagacggga ggcgtcttct gccctcaccg tctttcaagc   3660
ccttgtgggt ctgaaagagc catgtcggag agagaaggga caggcctgtc ccgacctggc   3720
cgagagcggg cagccccggg ggagagcggg gcgatcggcc tgggctctgt gaggccaggt   3780
ccaagggagg acgtgtggtc ctcgtgacag gtgcacttgc gaaaccttag aagacggggt   3840
atgttggaag cggctcctga tgtttaagaa aagggagact gtaaagtgag cagagtcctc   3900
aagtgtgtta aggttttaaa ggtcaaagtg ttttaaacct ttgtgactgc agttagcaag   3960
cgtgcgggga gtgaatgggg tgccagggtg gccgagaggc agtacgaggg ccgtgccgtc   4020
ctctaattca gggcttagtt ttgcagaata aagtcggcct gttttctaaa agcattggtg   4080
gtgctgagct ggtggaggag gccgcgggca gccctggcca cctgcagcag gtggcaggaa   4140
gcaggtcggc caagaggcta ttttaggaag ccagaaaaca cggtcgatga atttatagct   4200
tctggtttcc aggaggtggt tggcatggc tttgcgcagc gccacagaac cgaaagtgcc   4260
cactgagaaa aaacaactcc tgcttaattt gcatttttct aaaagaagaa acagaggctg   4320
acggaaactg gaaagttcct gttttaacta ctcgaattga gttttcggtc ttagcttatc   4380
aactgctcac ttagattcat tttcaaagta aacgtttaag agccgaggca ttcctatcct   4440
cttctaaggc gttattcctg gaggctcatt caccgccagc acctccgctg cctgcaggca   4500
ttgctgtcac cgtcaccgtg acggcgcgca cgattttcag ttggcccgct tcccctcgtg   4560
attaggacag acgcgggcac tctggcccag ccgtcttggc tcagtatctg caggcgtccg   4620
tctcgggacg gagctcaggg gaagagcgtg actccagttg aacgtgatag tcggtgcgtt   4680
gagaggagac ccagtcgggt gtcgagtcag aaggggcccg gggcccgagg ccctgggcag   4740
gacggcccgt gccctgcatc acgggcccag cgtcctagag gcaggactct ggtggagagt   4800
gtgagggtgc ctggggcccc tccggagctg gggccgtgcg gtgcaggttg ggctctcggc   4860
gcggtgttgg ctgtttctgc gggatttgga ggaattcttc cagtgatggg agtcgccagt   4920
gaccgggcac caggctggta agagggaggc cgccgtcgtg gccagagcag ctgggagggt   4980
tcggtaaaag gctcgcccgt ttcctttaat gaggactttt cctggagggc atttagtcta   5040
gtcgggaccg ttttcgactc gggaagaggg atgcggagga gggcatgtgc ccaggagccg   5100
aaggcgccgc ggggagaagc ccagggctct cctgtcccca cagaggcgac gccactgccg   5160
cagacagaca gggcctttcc ctctgatgac ggcaaaggcg cctcggctct tgcggggtgc   5220
tggggggag tcgccccgaa gccgctcacc cagaggcctg aggggtgaga ctgaccgatg   5280
cctcttggcc gggcctgggg ccggaccgag ggggactccg tggaggcagg gcgatggtgg   5340
```

-continued

```
ctgcgggagg gaaccgaccc tggggccgagc ccggcttggc gattcccggg cgagggccct   5400
cagccgaggc gagtgggtcc ggcggaacca ccctttctgg ccagcgccac agggctctcg   5460
ggactgtccg gggcgacgct gggctgcccg tggcaggcct gggctgacct ggacttcacc   5520
agacagaaca gggctttcag ggctgagctg agccaggttt agcgaggcca agtggggctg   5580
aaccaggctc aactggcctg agctgggttg agctgggctg acctgggctg agctgagctg   5640
ggctgggctg ggctgggctg ggctgggctg ggctggactg gctgagctga gctgggttga   5700
gctgagctga gctggcctgg gttgagctgg gctgggttga gctgagctgg gttgagctgg   5760
gttgagctgg gttgatctga gctgagctgg gctgagctga gctaggctgg ggtgagctgg   5820
gctgagctgg tttgagttgg gttgagctga gctgagctgg gctgtgctgg ctgagctagg   5880
ctgagctagg ctaggttgag ctgggctggg ctgagctgag ctaggctggg ctgatttggg   5940
ctgagctgag ctgagctagg ctgcgttgag ctggctgggc tggattgagc tggctgagct   6000
ggctgagctg ggctgagctg gcctgggttg agctgagctg gactggtttg agctgggtcg   6060
atctgggttg agctgtcctg ggttgagctg ggctgggttg agctgagctg ggttgagctg   6120
ggctcagcag agctgggttg ggctgagctg ggttgagctg agctgggctg agctggcctg   6180
ggttgagctg ggctgagctg agctgggctg agctggcctg tgttgagctg ggctgggttg   6240
agctgggctg agctggattg agctgggttg agctgagctg ggctgggctg tgctgactga   6300
gctgggctga gctaggctgg ggtgagctgg gctgagctga tccgagctag gctgggctgg   6360
tttgggctga gctgagctga gctaggctgg attgatctgg ctgagctggg ttgagctgag   6420
ctgggctgag ctggtctgag ctggcctggg tcgagctgag ctggactggt ttgagctggg   6480
tcgatctggg ctgagctggc ctgggttgag ctgggctggg ttgagctgag ctgggttgag   6540
ctgggctgag ctgagggctg gggtgagctg ggctgaacta gcctagctag gttgggctga   6600
gctgggctgg tttgggctga gctgagctga gctaggctgc attgagcagg ctgagctggg   6660
ctgagcaggc ctggggtgag ctgggctagg tggagctgag ctgggtcgag ctgagttggg   6720
ctgagctggc ctgggttgag gtaggctgag ctgagctgag ctaggctggg ttgagctggc   6780
tgggctggtt tgcgctgggt caagctgggc cgagctggcc tgggttgagc tgggctcggt   6840
tgagctgggc tgagctgagc cgacctaggc tgggatgagc tgggctgatt tgggctgagc   6900
tgagctgagc taggctgcat tgagcaggct gagctgggcc tggagcctgg cctggggtga   6960
gctgggctga gctgcgctga gctaggctgg gttgagctgg ctgggctggt ttgcgctggg   7020
tcaagctggg ccgagctggc ctgggatgag ctgggccggt ttgggctgag ctgagctgag   7080
ctaggctgca ttgagcaggc tgagctgggc tgagctggcc tggggtgagc tgggctgagc   7140
taagctgagc tgggctggtt tgggctgagc tggctgagct gggtcctgct gagctgggct   7200
gagctgacca ggggtgagct gggctgagtt aggctgggct cagctaggct gggttgatct   7260
ggcagggctg gtttgcgctg ggtcaagctc ccgggagatg gcctgggatg agctgggctg   7320
gtttgggctg agctgagctg agctgagcta ggctgcattg agcaggctga gctgggctga   7380
gctggcctgg ggtgagctgg gctgggtgga gctgagctgg gctgaactgg gctaagctgg   7440
ctgagctgga tcgagctgag ctgggctgag ctggcctggg gttagctggg ctgagctgag   7500
ctgagctagg ctgggttgag ctggctgggc tggtttgcgc tgggtcaagc tgggccgagc   7560
tggcctgggt tgagctgggc tgggctgagc tgagctaggc tgggttgagc tgggctgggc   7620
tgagctgagc taggctgcat tgagctggct gggatggatt gagctggctg agctggctga   7680
gctggctgag ctgggctgag ctggcctggg ttgagctggg ctgggttgag ctgagctggg   7740
```

```
ctgagctggg ctcagcagag ctgggttgag ctgagctggg ttgagctggg gtgagctggg   7800

ctgagcagag ctgggttgag ctgagctggg ttgagctggg ctcgagcaga gctgggttga   7860

gctgagctgg gttgagctgg gctcagcaga gctgggttga gctgagctgg gttgagctgg   7920

gctgagctag ctgggctcag ctaggctggg ttgagctgag ctgggctgaa ctgggctgag   7980

ctgggctgaa ctgggctgag ctgggctgag ctgggctgag cagagctggg ctgagcagag   8040

ctgggttggt ctgagctggg ttgagctggg ctgagctggg ctgagcagag ttgggttgag   8100

ctgagctggg ttcagctggg ctgagctagg ctgggttgag ctgggttgag ttgggctgag   8160

ctgggctggg ttgagcggag ctgggctgaa ctgggctgag ctgggctgag cggaactggg   8220

ttgatctgaa ttgagctggg ctgagccggg ctgagccggg ctgagctggg ctaggttgag   8280

cttgggtgag cttgcctcag ctggtctgag ctaggttggg tggagctagg ctggattgag   8340

ctgggctgag ctgagctgat ctggcctcag ctgggctgag gtaggctgaa ctgggctgtg   8400

ctgggctgag ctgagctgag ccagtttgag ctgggttgag ctgggctgag ctgggctgtg   8460

ttgatctttc ctgaactggg ctgagctggg ctgagctggc ctagctggat tgaacggggg   8520

taagctgggc caggctggac tgggctgagc tgagctaggc tgagctgagt tgaattgggt   8580

taagctgggc tgagatgggc tgagctgggc tgagctgggt tgagccaggt cggactgggt   8640

taccctgggc cacactgggc tgagctgggc ggagctcgat taacctggtc aggctgagtc   8700

gggtccagca gacatgcgct ggccaggctg gcttgacctg gacacgttcg atgagctgcc   8760

ttgggatggt tcacctcagc tgagccaggt ggctccagct gggctgagct ggtgaccctg   8820

ggtgacctcg gtgaccaggt tgtcctgagt ccgggccaag ccgaggctgc atcagactcg   8880

ccagacccaa ggcctgggcc ccggctggca agccaggggc ggtgaaggct gggctggcag   8940

gactgtcccg gaaggaggtg cacgtggagc cgcccggacc ccgaccggca ggacctggaa   9000

agacgcctct cactcccctt tctcttctgt cccctctcgg gtcctcagag agccagtctg   9060

ccccgaatct ctaccccctc gtctcctgcg tcagcccccc gtccgatgag agcctggtgg   9120

ccctgggctg cctggcccgg gacttcctgc ccagctccgt caccttctcc tggaa        9175
```

<210> SEQ ID NO 5
<211> LENGTH: 9200
<212> TYPE: DNA
<213> ORGANISM: Artificial Sequence
<220> FEATURE:
<223> OTHER INFORMATION: Synthetic

<400> SEQUENCE: 5

```
ggccagactt cctcggaaca gctcaaagag ctctgtcaaa gccagatccc atcacacgtg     60

ggcaccaata ggccatgcca gcctccaagg gccgaactgg gttctccacg gcgcacatga    120

agcctgcagc ctggcttatc ctcttccgtg gtgaagaggc aggcccggga ctggacgagg    180

ggctagcagg gtgtggtagg caccttgcgc cccccacccc ggcaggaacc agagaccctg    240

gggctgagag tgagcctcca aacaggatgc cccacccttc aggccacctt tcaatccagc    300

tacactccac ctgccattct cctctgggca cagggcccag cccctggatc ttggccttgg    360

ctcgacttgc acccacgcgc acacacacac ttcctaacgt gctgtccgct cacccctccc    420

cagcgtggtc catgggcagc acggcagtgc gcgtccggcg gtagtgagtg cagaggtccc    480

ttcccctccc ccaggagccc caggggtgtg tgcagatctg gggctcctg tcccttacac     540

cttcatgccc ctcccctcat acccaccctc caggcgggag gcagcgagac ctttgcccag    600
```

```
ggactcagcc aacgggcaca cgggaggcca gccctcagca gctggctccc aaagaggagg    660
tgggaggtag gtccacagct gccacagaga gaaaccctga cggaccccac aggggccacg    720
ccagccggaa ccagctccct cgtgggtgag caatggccag ggccccgccg gccaccacgg    780
ctggccttgc gccagctgag aactcacgtc cagtgcaggg agactcaaga cagcctgtgc    840
acacagcctc ggatctgctc ccatttcaag cagaaaaagg aaaccgtgca ggcagccctc    900
agcatttcaa ggattgtagc agcggccaac tattcgtcgg cagtggccga ttagaatgac    960
cgtggagaag ggcggaaggg tctctcgtgg gctctgcggc caacaggccc tggctccacc   1020
tgcccgctgc cagcccgagg ggcttgggcc gagccaggaa ccacagtgct caccgggacc   1080
acagtgactg accaaactcc cggccagagc agccccaggc cagccgggct ctcgccctgg   1140
aggactcacc atcagatgca caagggggcg agtgtggaag agacgtgtcg cccgggccat   1200
ttgggaaggc gaagggacct tccaggtgga caggaggtgg gacgcactcc aggcaaggga   1260
ctgggtcccc aaggcctggg gaaggggtac tggcttgggg gttagcctgg ccagggaacg   1320
gggagcgggg cggggggctg agcagggagg acctgacctc gtgggagcga ggcaagtcag   1380
gcttcaggca gcagccgcac atcccagacc aggaggctga ggcaggaggg gcttgcagcg   1440
gggcgggggc ctgcctggct ccgggggctc ctgggggacg ctggctcttg tttccgtgtc   1500
ccgcagcaca gggccagctc gctgggccta tgcttacctt gatgtctggg gccggggcgt   1560
cagggtcgtc gtctcctcag gggagagtcc cctgaggcta cgctgggggg ggactatggc   1620
agctccacca ggggcctggg gaccaggggc ctggaccagg ctgcagcccg gaggacgggc   1680
agggctctgg ctctccagca tctggccctc ggaaatggca gaacccctgg cgggtgagcg   1740
agctgagagc gggtcagaca gacaggggcc ggccggaaag gagaagttgg gggcagagcc   1800
cgccaggggc caggcccaag gttctgtgtg ccagggcctg ggtgggcaca ttggtgtggc   1860
catggctact tagacgcgtg atcaagggcg aattccagca cactggcggc cgttactagt   1920
ggatcccggc gcgccctacc gggtagggga ggcgcttttc ccaaggcagt ctggagcatg   1980
cgctttagca gccccgctgg gcacttggcg ctacacaagt ggcctctggc ctcgcacaca   2040
ttccacatcc accggtaggc gccaaccggc tccgttcttt ggtggcccct tcgcgccacc   2100
ttctactcct cccctagtca ggaagttccc ccccgccccg cagctcgcgt cgtgcaggac   2160
gtgacaaatg gaagtagcac gtctcactag tctcgtgcag atggacagca ccgctgagca   2220
atggaagcgg gtaggccttt ggggcagcgg ccaatagcag ctttggctcc ttcgctttct   2280
gggctcagag gctgggaagg ggtgggtccg ggggcgggct caggggcggg ctcaggggcg   2340
gggcgggcgc ccgaaggtcc tccggaagcc cggcattctg cacgcttcaa aagcgcacgt   2400
ctgccgcgct gttctcctct tcctcatctc cgggcctttc gacctgcagc caatatggga   2460
tcggccattg aacaagatgg attgcacgca ggttctccgg ccgcttgggt ggagaggcta   2520
ttcggctatg actgggcaca acagacaatc ggctgctctg atgccgccgt gttccggctg   2580
tcagcgcagg ggcgcccggt tctttttgtc aagaccgacc tgtccggtgc cctgaatgaa   2640
ctgcaggacg aggcagcgcg gctatcgtgg ctggccacga cgggcgttcc ttgcgcagct   2700
gtgctcgacg ttgtcactga agcgggaagg gactggctgc tattgggcga agtgccgggg   2760
caggatctcc tgtcatctca ccttgctcct gccgagaaag tatccatcat ggctgatgca   2820
atgcggcggc tgcatacgct tgatccggct acctgcccat tcgaccacca agcgaaacat   2880
cgcatcgagc gagcacgtac tcggatggaa gccggtcttg tcaatcagga tgatctggac   2940
gaagagcatc aggggctcgc gccagccgaa ctgttcgcca ggctcaaggc gcgcatgccc   3000
```

gacggcgagg atctcgtcgt gacccatggc gatgcctgct tgccgaatat catggtggaa 3060
aatggccgct tttctggatt catcgactgt ggccggctgg gtgtggcgga tcgctatcag 3120
gacatagcgt tggctacccg tgatattgct gaagagcttg gcggcgaatg ggctgaccgc 3180
ttcctcgtgc tttacggtat cgccgctccc gattcgcagc gcatcgcctt ctatcgcctt 3240
cttgacgagt tcttctgagg ggatcaattc tctagatgca tgctcgagcg gccgccagtg 3300
tgatggatat ctgcagaatt cgcccttcca ggcgttgaag tcgtcgtgtc ctcaggtaag 3360
aacggccctc cagggccttt aatttctgct ctcgtctgtg ggcttttctg actctgatcc 3420
tcgggaggcg tctgtgcccc ccccggggat gaggccggct tgccaggagg ggtcagggac 3480
caggagcctg tgggaagttc tgacgggggc tgcaggcggg aagggcccca ccgggggggcg 3540 agccccaggc cgctgggcgg caggagaccc gtgagagtgc gccttgagga gggtgtctgc 3600
ggaaccacga acgcccgccg ggaagggctt gctgcaatgc ggtcttcaga cgggaggcgt 3660
cttctgccct caccgtcttt caagcccttg tgggtctgaa agagccatgt cggagagaga 3720
agggacaggc ctgtcccgac ctggccgaga gcgggcagcc ccgggggaga gcggggcgat 3780
cggcctgggc tctgtgaggc caggtccaag ggaggacgtg tggtcctcgt gacaggtgca 3840
cttgcgaaac cttagaagac ggggtatgtt ggaagcggct cctgatgttt aagaaaaggg 3900
agactgtaaa gtgagcagag tcctcaagtg tgttaaggtt ttaaaggtca aagtgtttta 3960
aacctttgtg actgcagtta gcaagcgtgc ggggagtgaa tggggtgcca gggtggccga 4020
gaggcagtac gagggccgtg ccgtcctcta attcagggct tagttttgca gaataaagtc 4080
ggcctgtttt ctaaaagcat tggtggtgct gagctggtgg aggaggccgc gggcagccct 4140
ggccacctgc agcaggtggc aggaagcagg tcggccaaga ggctatttta ggaagccaga 4200
aaacacggtc gatgaattta tagcttctgg tttccaggag gtggttgggc atggctttgc 4260
gcagcgccac agaaccgaaa gtgcccactg agaaaaaaca actcctgctt aatttgcatt 4320
tttctaaaag aagaaacaga ggctgacgga aactggaaag ttcctgtttt aactactcga 4380
attgagtttt cggtcttagc ttatcaactg ctcacttaga ttcattttca aagtaaacgt 4440
ttaagagccg aggcattcct atcctcttct aaggcgttat tcctggaggc tcattcaccg 4500
ccagcacctc cgctgcctgc aggcattgct gtcaccgtca ccgtgacggc gcgcacgatt 4560
ttcagttggc ccgcttcccc tcgtgattag gacagacgcg ggcactctgg cccagccgtc 4620
ttggctcagt atctgcaggc gtccgtctcg ggacggagct caggggaaga gcgtgactcc 4680
agttgaacgt gatagtcggt gcgttgagag gagacccagt cgggtgtcga gtcagaaggg 4740
gcccggggcc cgaggccctg ggcaggacgg cccgtgccct gcatcacggg cccagcgtcc 4800
tagaggcagg actctggtgg agagtgtgag ggtgcctggg gcccctccgg agctggggcc 4860
gtgcggtgca ggttgggctc tcggcgcggt gttggctgtt tctgcgggat ttggaggaat 4920
tcttccagtg atgggagtcg ccagtgaccg ggcaccaggc tggtaagagg gaggccgccg 4980
tcgtggccag agcagctggg agggttcggt aaaaggctcg cccgtttcct ttaatgagga 5040
cttttcctgg agggcattta gtctagtcgg gaccgttttc gactcgggaa gagggatgcg 5100
gaggagggca tgtgcccagg agccgaaggc gccgcgggga gaagcccagg gctctcctgt 5160
ccccacagag gcgacgccac tgccgcagac agacagggcc tttccctctg atgacggcaa 5220
aggcgcctcg gctcttgcgg ggtgctgggg gggagtcgcc ccgaagccgc tcacccagag 5280
gcctgagggg tgagactgac cgatgcctct tggccgggcc tggggccgga ccgaggggga 5340

-continued

```
ctccgtggag gcagggcgat ggtggctgcg ggagggaacc gaccctgggc cgagcccggc   5400
ttggcgattc ccgggcgagg gccctcagcc gaggcgagtg ggtccggcgg aaccaccctt   5460
tctggccagc gccacagggc tctcgggact gtccggggcg acgctgggct gcccgtggca   5520
ggcctgggct gacctggact tcaccagaca gaacagggct ttcagggctg agctgagcca   5580
ggtttagcga ggccaagtgg ggctgaacca ggctcaactg gcctgagctg ggttgagctg   5640
ggctgacctg ggctgagctg agctgggctg ggctgggctg ggctgggctg ggctgggctg   5700
gactggctga gctgagctgg gttgagctga gctgagctgg cctgggttga gctgggctgg   5760
gttgagctga gctgggttga gctgggttga gctgggttga tctgagctga gctgggctga   5820
gctgagctag gctggggtga gctgggctga gctggtttga gttgggttga gctgagctga   5880
gctgggctgt gctggctgag ctaggctgag ctaggctagg ttgagctggg ctgggctgag   5940
ctgagctagg ctgggctgat ttgggctgag ctgagctgag ctaggctgcg ttgagctggc   6000
tgggctggat tgagctggct gagctggctg agctgggctg agctggcctg ggttgagctg   6060
agctggactg gtttgagctg ggtcgatctg ggttgagctg tcctgggttg agctgggctg   6120
ggttgagctg agctgggttg agctgggctc agcagagctg ggttgggctg agctgggttg   6180
agctgagctg ggctgagctg gcctgggttg agctgggctg agctgagctg ggctgagctg   6240
gcctgtgttg agctgggctg ggttgagctg ggctgagctg gattgagctg ggttgagctg   6300
agctgggctg ggctgtgctg actgagctgg gctgagctag gctggggtga gctgggctga   6360
gctgatccga gctaggctgg gctggtttgg gctgagctga gctgagctag gctggattga   6420
tctggctgag ctgggttgag ctgagctggg ctgagctggt ctgagctggc ctgggtcgag   6480
ctgagctgga ctggtttgag ctgggtcgat ctgggctgag ctggcctggg ttgagctggg   6540
ctgggttgag ctgagctggg ttgagctggg ctgagctgag ggctggggtg agctgggctg   6600
aactagccta gctaggttgg gctgagctgg gctggtttgg gctgagctga gctgagctag   6660
gctgcattga gcaggctgag ctgggctgag caggcctggg gtgagctggg ctaggtggag   6720
ctgagctggg tcgagctgag ttgggctgag ctggcctggg ttgaggtagg ctgagctgag   6780
ctgagctagg ctgggttgag ctggctgggc tggtttgcgc tgggtcaagc tgggccgagc   6840
tggcctgggt tgagctgggc tcggttgagc tgggctgagc tgagccgacc taggctggga   6900
tgagctgggc tgatttgggc tgagctgagc tgagctaggc tgcattgagc aggctgagct   6960
gggcctggag cctggcctgg ggtgagctgg gctgagctgc gctgagctag gctgggttga   7020
gctggctggg ctggtttgcg ctgggtcaag ctgggccgag ctggcctggg atgagctggg   7080
ccggtttggg ctgagctgag ctgagctagg ctgcattgag caggctgagc tgggctgagc   7140
tggcctgggg tgagctgggc tgagctaagc tgagctgggc tggtttgggc tgagctggct   7200
gagctgggtc ctgctgagct gggctgagct gaccaggggt gagctgggct gagttaggct   7260
gggctcagct aggctgggtt gatctggcag ggctggtttg cgctgggtca agctcccggg   7320
agatggcctg ggatgagctg ggctggtttg ggctgagctg agctgagctg agctaggctg   7380
cattgagcag gctgagctgg gctgagctgg cctggggtga gctgggctgg gtggagctga   7440
gctgggctga actgggctaa gctggctgag ctggatcgag ctgagctggg ctgagctggc   7500
ctggggttag ctgggctgag ctgagctgag ctaggctggg ttgagctggc tgggctggtt   7560
tgcgctgggt caagctgggc cgagctggcc tgggttgagc tgggctgggc tgagctgagc   7620
taggctgggt tgagctgggc tgggctgagc tgagctaggc tgcattgagc tggctgggat   7680
ggattgagct ggctgagctg gctgagctgg ctgagctggg ctgagctggc ctgggttgag   7740
```

-continued ctgggctggg ttgagctgag ctgggctgag ctgggctcag cagagctggg ttgagctgag 7800
ctgggttgag ctggggtgag ctgggctgag cagagctggg ttgagctgag ctgggttgag 7860
ctgggctcga gcagagctgg gttgagctga gctgggttga gctgggctca gcagagctgg 7920
gttgagctga gctgggttga gctgggctga gctagctggg ctcagctagg ctgggttgag 7980
ctgagctggg ctgaactggg ctgagctggg ctgaactggg ctgagctggg ctgagctggg 8040
ctgagcagag ctgggctgag cagagctggg ttggtctgag ctgggttgag ctgggctgag 8100
ctgggctgag cagagttggg ttgagctgag ctgggttcag ctgggctgag ctaggctggg 8160
ttgagctggg ttgagttggg ctgagctggg ctgggttgag cggagctggg ctgaactggg 8220
ctgagctggg ctgagcggaa ctgggttgat ctgaattgag ctgggctgag ccgggctgag 8280
ccgggctgag ctgggctagg ttgagcttgg gtgagcttgc ctcagctggt ctgagctagg 8340
ttgggtggag ctaggctgga ttgagctggg ctgagctgag ctgatctggc ctcagctggg 8400
ctgaggtagg ctgaactggg ctgtgctggg ctgagctgag ctgagccagt ttgagctggg 8460
ttgagctggg ctgagctggg ctgtgttgat ctttcctgaa ctgggctgag ctgggctgag 8520
ctggcctagc tggattgaac gggggtaagc tgggccaggc tggactgggc tgagctgagc 8580
taggctgagc tgagttgaat tgggttaagc tgggctgaga tgggctgagc tgggctgagc 8640
tgggttgagc caggtcggac tgggttaccc tgggccacac tgggctgagc tgggcggagc 8700
tcgattaacc tggtcaggct gagtcgggtc cagcagacat gcgctggcca ggctggcttg 8760
acctggacac gttcgatgag ctgccttggg atggttcacc tcagctgagc caggtggctc 8820
cagctgggct gagctggtga ccctgggtga cctcggtgac caggttgtcc tgagtccggg 8880
ccaagccgag gctgcatcag actcgccaga cccaaggcct gggcccccggc tggcaagcca 8940 ggggcggtga aggctgggct ggcaggactg tcccggaagg aggtgcacgt ggagccgccc 9000
ggaccccgac cggcaggacc tggaaagacg cctctcactc ccctttctct tctgtcccct 9060
ctcgggtcct cagagagcca gtctgccccg aatctctacc ccctcgtctc ctgcgtcagc 9120
cccccgtccg atgagagcct ggtggccctg ggctgcctgg cccgggactt cctgcccagc 9180
tccgtcacct tctcctggaa 9200

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
tctagaagac gctggagaga ggccag 26

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
taaagcgcat gctccagact gcctt 25

<210> SEQ ID NO 8
<211> LENGTH: 22
<212> TYPE: DNA

<213> ORGANISM: Artificial Sequence
<220> FEATURE:
<223> OTHER INFORMATION: Synthetic

<400> SEQUENCE: 8
catcgccttc tatcgccttc tt 22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
aagtacttgc cgcctctcag ga 22

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
caaggagacc aagctggaac tc 22

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
tgatcaagca caccacagag acag 24

<210> SEQ ID NO 12
<211> LENGTH: 4277
<212> TYPE: DNA
<213> ORGANISM: Sus sp.

<400> SEQUENCE: 12
caaggaacca agctggaact caaacgtaag tcaatccaaa cgttccttcc ttggctgtct 60
gtgtcttacg gtctctgtgg ctctgaaatg attcatgtgc tgactctctg aaaccagact 120
gacattctcc agggcaaaac taaagcctgt catcaaactg gaaaactgag ggcacatttt 180
ctgggcagaa ctaagagtca ggcactgggt gaggaaaaac ttgttagaat gatagtttca 240
gaaacttact gggaagcaaa gcccatgttc tgaacagagc tctgctcaag ggtcaggagg 300
ggaaccagtt tttgtacagg agggaagttg agacgaaccc ctgtgtatat ggtttcggcg 360
cggggaccaa gctggagctc aaacgtaagt ggctttttcc gactgattct ttgctgtttc 420
taattgttgg ttggcttttt gtccattttt cagtgttttc atcgaattag ttgtcaggga 480
ccaaacaaat tgccttccca gattaggtac cagggagggg acattgctgc atgggagacc 540
agagggtggc taatttttaa cgtttccaag ccaaaataac tggggaaggg ggcttgctgt 600
cctgtgaggg taggttttta tagaagtgga agttaagggg aaatcgctat ggttcacttt 660
tggctcgggg accaaagtgg agcccaaaat tgagtacatt ttccatcaat tatttgtgag 720
atttttgtcc tgttgtgtca tttgtgcaag tttttgacat tttggttgaa tgagccattc 780
ccagggaccc aaaaggatga gaccgaaaag tagaaaagag ccaactttta agctgagcag 840

-continued

```
acagaccgaa ttgttgagtt tgtgaggaga gtagggtttg tagggagaaa ggggaacaga    900
tcgctggctt tttctctgaa ttagcctttc tcatgggact ggcttcagag gggtttttg     960
atgagggaag tgttctagag ccttaactgt gggttgtgtt cggtagcggg accaagctgg   1020
aaatcaaacg taagtgcact tttctactcc tttttctttc ttatacgggt gtgaaattgg   1080
ggacttttca tgtttggagt atgagttgag gtcagttctg aagagagtgg gactcatcca   1140
aaaatctgag gagtaagggt cagaacagag ttgtctcatg gaagaacaaa gacctagtta   1200
gttgatgagg cagctaaatg agtcagttga cttgggatcc aaatggccag acttcgtctg   1260
taaccaacaa tctaatgaga tgtagcagca aaaagagatt tccattgagg ggaaagtaaa   1320
attgttaata ttgtggatca cctttggtga agggacatcc gtggagattg aacgtaagta   1380
ttttttctct actaccttct gaaatttgtc taaatgccag tgttgacttt tagaggctta   1440
agtgtcagtt ttgtgaaaaa tgggtaaaca agagcatttc atatttatta tcagtttcaa   1500
aagttaaact cagctccaaa aatgaatttg tagacaaaaa gattaattta agccaaattg   1560
aatgattcaa aggaaaaaaa aattagtgta gatgaaaaag gaattcttac agctccaaag   1620
agcaaaagcg aattaatttt ctttgaactt tgccaaatct tgtaaatgat ttttgttctt   1680
tacaatttaa aaaggttaga gaaatgtatt tcttagtctg ttttctctct tctgtctgat   1740
aaattattat atgagataaa aatgaaaatt aataggatgt gctaaaaaat cagtaagaag   1800
ttagaaaaat atatgtttat gttaaagttg ccacttaatt gagaatcaga agcaatgtta   1860
tttttaaagt ctaaaatgag agataaactg tcaatactta aattctgcag agattctata   1920
tcttgacaga tatctccttt ttcaaaaatc caatttctat ggtagactaa atttgaaatg   1980
atcttcctca taatggaggg aaaagatgga ctgaccccaa aagctcagat ttaagaaaac   2040
ctgtttaagg aaagaaaata aaagaactgc atttttttaaa ggcccatgaa tttgtagaaa   2100
aataggaaat attttaataa gtgtattctt ttattttcct gttattactt gatggtgttt   2160
ttataccgcc aaggaggccg tggcaccgtc agtgtgatct gtagacccca tggcggcctt   2220
ttttcgcgat tgaatgacct tggcggtggg tccccagggc tctggtggca gcgcaccagc   2280
cgctaaaagc cgctaaaaac tgccgctaaa ggccacagca accccgcgac cgcccgttca   2340
actgtgctga cacagtgata cagataatgt cgctaacaga ggagaataga aatatgacgg   2400
gcacacgcta atgtggggaa aagagggaga agcctgattt ttattttttta gagattctag   2460
agataaaatt cccagtatta tatcctttta ataaaaaatt tctattagga gattataaag   2520
aatttaaagc tattttttta agtggggtgt aattctttca gtagtctctt gtcaaatgga   2580
tttaagtaat agaggcttaa tccaaatgag agaaatagac gcataaccct ttcaaggcaa   2640
aagctacaag agcaaaaatt gaacacagca gccagccatc tagccactca gattttgatc   2700
agttttactg agtttgaagt aaatatcatg aaggtataat tgctgataaa aaaataagat   2760
acaggtgtga cacatcttta agtttcagaa atttaatggc ttcagtagga ttatatttca   2820
cgtatacaaa gtatctaagc agataaaaat gccattaatg gaaacttaat agaaatatat   2880
ttttaaattc cttcattctg tgacagaaat tttctaatct gggtctttta atcacctacc   2940
ctttgaaaga gtttagtaat ttgctatttg ccatcgctgt ttactccagc taatttcaaa   21000
agtgatactt gagaaagatt atttttggtt tgcaaccacc tggcaggact attttagggc   3060
cattttaaaa ctcttttcaa actaagtatt ttaaactgtt ctaaaccatt tagggccttt   3120
taaaaatctt ttcatgaatt tcaaacttcg ttaaaagtta ttaaggtgtc tggcaagaac   3180
```

```
ttccttatca aatatgctaa tagtttaatc tgttaatgca ggatataaaa ttaaagtgat   3240

caaggcttga cccaaacagg agtatcttca tagcatattt cccctccttt ttttctagaa   3300

ttcatatgat tttgctgcca aggctatttt atataatctc tggaaaaaaa atagtaatga   3360

aggttaaaag agaagaaaat atcagaacat taagaattcg gtattttact aactgcttgg   3420

ttaacatgaa ggtttttatt ttattaaggt ttctatcttt ataaaaatct gttccctttt   3480

ctgctgattt ctccaagcaa aagattcttg atttgttttt taactcttac tctcccaccc   3540

aagggcctga atgcccacaa aggggacttc caggaggcca tctggcagct gctcaccgtc   3600

agaagtgaag ccagccagtt cctcctgggc aggtggccaa aattacagtt gacccctcct   3660

ggtctggctg aaccttgccc catatggtga cagccatctg gccagggccc aggtctccct   3720

ctgaagcctt tgggaggaga gggagagtgg ctggcccgat cacagatgcg gaaggggctg   3780

actcctcaac cggggtgcag actctgcagg gtgggtctgg gcccaacaca cccaaagcac   3840

gcccaggaag gaaaggcagc ttggtatcac tgcccagagc taggagaggc accgggaaaa   3900

tgatctgtcc aagacccgtt cttgcttcta aactccgagg gggtcagatg aagtggtttt   3960

gtttcttggc ctgaagcatc gtgttccctg caagaagcgg ggaacacaga ggaaggagag   4020

aaaagatgaa ctgaacaaag catgcaaggc aaaaaaggcc ttaggatggc tgcaggaagt   4080

tagttcttct gcattggctc cttactggct cgtcgatcgc ccacaaacaa cgcacccagt   4140

ggagaacttc cctgttactt aaacaccatt ctctgtgctt gcttcctcag gggctgatgc   4200

caagccatcc gtcttcatct tcccgccatc gaaggagcag ttagcgaccc caactgtctc   4260

tgtggtgtgc ttgatca                                                  4277


<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13

gatgccaagc catccgtctt catc                                            24


<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14

tgaccaaagc agtgtgacgg ttgc                                            24


<210> SEQ ID NO 15
<211> LENGTH: 2027
<212> TYPE: DNA
<213> ORGANISM: Sus sp.

<400> SEQUENCE: 15

gatgccaagc catccgtctt catcttcccg ccatcgaagg agcagttagc gaccccaact     60

gtctctgtgg tgtgcttgat caataacttc ttccccagag aaatcagtgt caagtggaaa    120

gtggatgggg tggtccaaag cagtggtcat ccggatagtg tcacagagca ggacagcaag    180

gacagcacct acagcctcag cagcaccctc tcgctgccca cgtcacagta cctaagtcat    240

aatttatatt cctgtgaggt cacccacaag accctggcct cccctctggt cacaagcttc    300
```

```
aacaggaacg agtgtgaggc ttagaggccc acaggcccct ggcctgcccc cagccccagc    360
ccccctcccc acctcaagcc tcaggcccct gccccagagg atccttggca atcccccagc    420
ccctcttccc tcctcatccc ctccccctct ttggctttaa ccgtgttaat actggggggt    480
gggggaatga ataaataaag tgaacctttg cacctgtgat ttctctctcc tgtctgattt    540
taaggttgtt aaatgttgtt ttccccatta tagttaatct tttaaggaac tacatactga    600
gttgctaaaa actacaccat cacttataaa attcacgcct tctcagttct cccctcccct    660
cctgtcctcc gtaagacagg cctccgtgaa acccataagc acttctcttt acaccctctc    720
ctgggccggg gtaggagact ttttgatgtc ccctcttcag caagcctcag aaccattttg    780
agggggacag ttcttacagt cacattcctg tgatctaatg actttagtta ccgaaaagcc    840
agtctctcaa aaagaaggga acggctagaa accaagtcat agaaatatat atgtataaaa    900
tatatatata tccatatatg taaaataaca aaataatgat aacagcatag gtcaacaggc    960
aacagggaat gttgaagtcc attctggcac ttcaatttaa gggaatagga tgccttcatt   1020
acattttaaa tacaatacac atggagagct tcctatctgc caaagaccat cctgaatgcc   1080
ttccacactc actacaaggt taaaagcatt cattacaatg ttgatcgagg agttcccgtt   1140
gtggctcagc aggttaagaa cgtgactggt atccaggagg atgcgggttt ggtccccagc   1200
ctcgctcagt ggattaagga tccagtgttg ctgcaagatc acgggctcag atcccgtgtt   1260
ctatggctat ggtgtaggct ggtagctgca tgcagcccta atttgacccc tagcctggga   1320
actgccatat gccacatgtg aggcccttaa aacctaaaag aaaaaaaaag aaaagaaata   1380
tcttacaccc aatttataga taagagagaa gctaaggtgg caggcccagg atcaaagccc   1440
tacctgccta tcttgacacc tgatacaaat tctgtcttct agggtttcca acactgcata   1500
gaacagaggg tcaaacatgc taccctccca gggactcctc ccttcaaatg acataaattt   1560
tgttgcccat ctctgggggc aaaactcaac aatcaatggc atctctagta ccaagcaagg   1620
ctcttctcat gaagcaaaac tctgaagcca gatccatcat gacccaagga agtaaagaca   1680
ggtgttactg gttgaactgt atccttcaat tcaatatgct caatttccaa ctcccagtcc   1740
ccgtaaatac aaccccottt gggaagagag tccttgcaga tgtagccacg ttaaaaagag   1800
attatacaga aaggctagtg aggatgcagt gaaacgggat ctttcataca ttgctggtgg   1860
aaatgtaaaa tgctgcaggc actctagaaa ataatttgcc agttttttga aaagctaaac   1920
aaaatagttt agttgcattc tggttattt atcccccaga aattaaaaat tatgtccgca   1980
caaaaacgtg tacataatca ttcataacag ccttgtacga aaagctt                 2027
```

<210> SEQ ID NO 16
<211> LENGTH: 3918
<212> TYPE: DNA
<213> ORGANISM: Sus sp.

<400> SEQUENCE: 16

```
ggatccttaa cccactaatc gaggatcaaa cacgcatcct catggacaat atgttgggtt     60
cttagcctgc tgagacacaa caggaactcc cctggcacca ctttagaggc cagagaaaca    120
gcacagataa aattccctgc cctcatgaag cttatagtct agctggggag atatcatagg    180
caagataaac acatacaaat acatcatctt aggtaataat atatactaag gagaaaatta    240
caggggagaa agaggacagg aattgctagg gtaggattat aagttcagat agttcatcag    300
gaacactgtt gctgagaaga taacatttag gtaaagaccg aagtagtaag gaaatggacc    360
```

-continued

```
gtgtgcctaa gtgggtaaga ccattctagg cagcaggaac agcgatgaaa gcactgaggt    420
gggtgttcac tgcacagagt tgttcactgc acagagttgt gtggggaggg gtaggtcttg    480
caggctctta tggtcacagg aagaattgtt ttactcccac cgagatgaag gttggtggat    540
tttgagcaga agaataattc tgcctggttt atatataaca ggatttccct gggtgctctg    600
atgagaataa tctgtcaggg gtgggatagg gagagatatg gcaataggag ccttggctag    660
gagcccacga caataattcc aagtgagagg tggtgctgca ttgaaagcag gactaacaag    720
acctgctgac agtgtggatg tagaaaaaga tagaggagac gaaggtgcat ctagggtttt    780
ctgcctgagg aattagaaag ataaagctaa agcttataga agatgcagcg ctctggggag    840
aaagaccagc agctcagttt tgatccatct ggaattaatt ttggcataaa gtatgaggta    900
tgtgggttaa cattatttgt ttttttttt tccatgtagc tatccaactg tcccagcatc    960
atttatttta aaagactttc ctttccccta ttggattgtt ttggcacctt cactgaagat   1020
caactgagca taaaattggg tctatttcta agctcttgat tccattccat gacctatttg   1080
ttcatcttta ccccagtaga cactgccttg atgattaaag cccctgttac catgtctgtt   1140
ttggacatgg taaatctgag atgcctatta gccaaccaag caagcacggc ccttagagag   1200
ctagatatga gagcctggaa ttcagacgag aaaggtcagt cctagagaca tacatgtagt   1260
gccatcacca tgcggatggt gttaaaagcc atcagactgc aacagactgt gagagggtac   1320
caagctagag agcatggata gagaaaccca agcactgagc tgggaggtgc tcctacatta   1380
agagattagt gagatgaagg actgagaaga ttgatcagag aagaaggaaa atcaggaaaa   1440
tggtgctgtc ctgaaaatcc aagggaagag atgttccaaa gaggagaaaa ctgatcagtt   1500
gtcagctagc gtcaattggg atgaaaatgg accattggac agagggatgt agtgggtcat   1560
gggtgaatag ataagagcag cttctataga atggcagggg caaaattctc atctgatcgg   1620
catgggttct aaagaaaacg ggaagaaaaa attgagtgca tgaccagtcc cttcaagtag   1680
agaggtggaa aagggaagga ggaaaatgag gccacgacaa catgagagaa atgacagcat   1740
ttttaaaaat tttttatttt attttattta tttatttttg ctttttaggg ctgcccctgc   1800
aacatatgga ggttcccagg ttaggggtct aatcagagct atagctgcca gcctacacca   1860
cagccatagc aatgccagat ctacatgacc tacaccacag ctcacagcaa cgccggatcc   1920
ttaacccact gagtgaggcc agagatcaaa cccatatcct tatggatact agtcaggttc   1980
attaccactg agccaaaatg ggaaatcctg agtaatgaca gcattttta atgtgccagg    2040
aagcaaaact tgccaccccg aaatgtctct caggcatgtg gattattttg agctgaaaac   2100
gattaaggcc caaaaaacac aagaagaaat gtggaccttc ccccaacagc ctaaaaaatt   2160
tagattgagg gcctgttccc agaatagagc tattgccaga cttgtctaca gaggctaagg   2220
gctaggtgtg gtggggaaac cctcagagat cagagggacg tttatgtacc aagcattgac   2280
atttccatct ccatgcgaat ggccttcttc ccctctgtag ccccaaacca ccacccccaa   2340
aatcttcttc tgtctttagc tgaagatggt gttgaaggtg atagtttcag ccactttggc   2400
gagttcctca gttgttctgg gtctttcctc cggatccaca ttattcgact gtgtttgatt   2460
ttctcctgtt tatctgtctc attggcaccc atttcattct tagaccagcc caaagaacct   2520
agaagagtga aggaaaattt cttccaccct gacaaatgct aaatgagaat caccgcagta   2580
gaggaaaatg atctggtgct gcgggagata gaagagaaaa tcgctggaga gatgtcactg   2640
agtaggtgag atgggaaagg gggggcacag gtggaggtgt tgccctcagc taggaagaca   2700
gacagttcac agaagagaag cgggtgtccg tggacatctt gcctcatgga tgaggaaacc   2760
```

gaggctaaga aagactgcaa aagaaaggta aggattgcag agaggtcgat ccatgactaa 2820
aatcacagta accaacccca aaccaccatg ttttctccta gtctggcacg tggcaggtac 2880
tgtgtaggtt ttcaatatta ttggtttgta acagtaccta ttaggcctcc atcccctcct 2940
ctaatactaa caaaagtgtg agactggtca gtgaaaaatg gtcttctttc tctatgcaat 3000
ctttctcaag aagatacata actttttatt ttatcatagg cttgaagagc aaatgagaaa 3060
cagcctccaa cctatgacac cgtaacaaag tgtttatgat cagtgaaggg caagaaacaa 3120
aacatacaca gtaaagaccc tccataatat tgtgggctgg cccaacacag gccaggttgt 3180
aaaagctttt tattctttga tagaggaatg gatagtaatg tttcaacctg gacagagatc 3240
atgttcactg aatccttcca aaaattcatg ggtagtttga attataagga aaataagact 3300
taggataaat actttgtcca gatcccagag ttaatgccaa aatcagtttt cagactccag 3360
gcagcctgat caagagccta aactttaaag acacagtccc ttaataacta ctattcacag 3420
ttgcactttc agggcgcaaa gactcattga atcctacaat agaatgagtt tagatatcaa 3480
atctctcagt aatagatgag gagactaaat agcgggcatg acctggtcac ttaaagacag 3540
aattgagatt caaggctagt gttctttcta cctgttttgt ttctacaaga tgtagcaatg 3600
cgctaattac agacctctca gggaaggaat tcacaaccct cagcaaaaac caaagacaaa 3660
tctaagacaa ctaagagtgt tggtttaatt tggaaaaata actcactaac caaacgcccc 3720
tcttagcacc ccaatgtctt ccaccatcac agtgctcagg cctcaaccat gccccaatca 3780
ccccagcccc agactggtta ttaccaagtt tcatgatgac tggcctgaga agatcaaaaa 3840
agcaatgaca tcttacaggg gactaccccg aggaccaaga tagcaactgt catagcaacc 3900
gtcacactgc tttggtca 3918

<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
ggatcaaaca cgcatcctca tggac 25

<210> SEQ ID NO 18
<211> LENGTH: 22
<212> TYPE: DNA
<213> ORGANISM: Artificial Sequence
<220> FEATURE:
<223> OTHER INFORMATION: Synthetic

<400> SEQUENCE: 18
ggtgattggg gcatggttga gg 22

<210> SEQ ID NO 19
<211> LENGTH: 3759
<212> TYPE: DNA
<213> ORGANISM: Sus sp.

<400> SEQUENCE: 19
ggatcaaaca cgcatcctca tggacaatat gttgggttct tagcctgctg agacacaaca 60
ggaactcccc tggcaccact ttagaggcca gagaaacagc acagataaaa ttccctgccc 120
tcatgaagct tatagtctag ctggggagat atcataggca agataaacac atacaaatac 180

-continued

```
atcatcttag gtaataatat atactaagga gaaaattaca ggggagaaag aggacaggaa    240
ttgctagggt aggattataa gttcagatag ttcatcagga acactgttgc tgagaagata    300
acatttaggt aaagaccgaa gtagtaagga aatggaccgt gtgcctaagt gggtaagacc    360
attctaggca gcaggaacag cgatgaaagc actgaggtgg gtgttcactg cacagagttg    420
ttcactgcac agagttgtgt ggggaggggt aggtcttgca ggctcttatg gtcacaggaa    480
gaattgtttt actcccaccg agatgaaggt tggtggattt tgagcagaag aataattctg    540
cctggtttat atataacagg atttccctgg gtgctctgat gagaataatc tgtcaggggt    600
gggataggga gagatatggc aataggagcc ttggctagga gcccacgaca ataattccaa    660
gtgagaggtg gtgctgcatt gaaagcagga ctaacaagac ctgctgacag tgtggatgta    720
gaaaaagata gaggagacga aggtgcatct agggttttct gcctgaggaa ttagaaagat    780
aaagctaaag cttatagaag atgcagcgct ctggggagaa agaccagcag ctcagttttg    840
atccatctgg aattaatttt ggcataaagt atgaggtatg tgggttaaca ttatttgttt    900
tttttttttc catgtagcta tccaactgtc ccagcatcat ttattttaaa agactttcct    960
ttcccctatt ggattgtttt ggcaccttca ctgaagatca actgagcata aaattgggtc   1020
tatttctaag ctcttgattc cattccatga cctatttgtt catctttacc ccagtagaca   1080
ctgccttgat gattaaagcc cctgttacca tgtctgtttt ggacatggta aatctgagat   1140
gcctattagc caaccaagca agcacggccc ttagagagct agatatgaga gcctggaatt   1200
cagacgagaa aggtcagtcc tagagacata catgtagtgc catcaccatg cggatggtgt   1260
taaaagccat cagactgcaa cagactgtga gagggtacca agctagagag catggataga   1320
gaaacccaag cactgagctg ggaggtgctc ctacattaag agattagtga gatgaaggac   1380
tgagaagatt gatcagagaa gaaggaaaat caggaaaatg gtgctgtcct gaaaatccaa   1440
gggaagagat gttccaaaga ggagaaaact gatcagttgt cagctagcgt caattgggat   1500
gaaaatggac cattggacag agggatgtag tgggtcatgg gtgaatagat aagagcagct   1560
tctatagaat ggcaggggca aaattctcat ctgatcggca tgggttctaa agaaaacggg   1620
aagaaaaaat tgagtgcatg accagtccct tcaagtagag aggtggaaaa gggaaggagg   1680
aaaatgaggc cacgacaaca tgagagaaat gacagcattt ttaaaaattt tttattttat   1740
tttatttatt tatttttgct ttttagggct gcccctgcaa catatggagg ttcccaggtt   1800
aggggtctaa tcagagctat agctgccagc ctacaccaca gccatagcaa tgccagatct   1860
acatgaccta caccacagct cacagcaacg ccggatcctt aacccactga gtgaggccag   1920
agatcaaacc catatcctta tggatactag tcaggttcat taccactgag ccaaaatggg   1980
aaatcctgag taatgacagc attttttaat gtgccaggaa gcaaaacttg ccaccccgaa   2040
atgtctctca ggcatgtgga ttattttgag ctgaaaacga ttaaggccca aaaaacacaa   2100
gaagaaatgt ggaccttccc ccaacagcct aaaaaattta gattgagggc ctgttcccag   2160
aatagagcta ttgccagact tgtctacaga ggctaagggc taggtgtggt ggggaaaccc   2220
tcagagatca gagggacgtt tatgtaccaa gcattgacat ttccatctcc atgcgaatgg   2280
ccttcttccc ctctgtagcc ccaaaccacc acccccaaaa tcttcttctg tctttagctg   2340
aagatggtgt tgaaggtgat agtttcagcc actttggcga gttcctcagt tgttctgggt   2400
ctttcctcct gatccacatt attcgactgt gtttgatttt ctcctgttta tctgtctcat   2460
tggcacccat ttcattctta gaccagccca aagaacctag aagagtgaag gaaaatttct   2520
tccaccctga caaatgctaa atgagaatca ccgcagtaga ggaaaatgat ctggtgctgc   2580
```

gggagataga agagaaaatc gctggagaga tgtcactgag taggtgagat gggaaagggg 2640
tgacacaggt ggaggtgttg ccctcagcta ggaagacaga cagttcacag aagagaagcg 2700
ggtgtccgtg gacatcttgc ctcatggatg aggaaaccga ggctaagaaa gactgcaaaa 2760
gaaaggtaag gattgcagag aggtcgatcc atgactaaaa tcacagtaac caaccccaaa 2820
ccaccatgtt ttctcctagt ctggcacgtg gcaggtactg tgtaggtttt caatattatt 2880
ggtttgtaac agtacctatt aggcctccat cccctcctct aatactaaca aaagtgtgag 2940
actggtcagt gaaaaatggt cttctttctc tatgaatctt tctcaagaag atacataact 3000
ttttatttta tcataggctt gaagagcaaa tgagaaacag cctccaacct atgacaccgt 3060
aacaaaatgt ttatgatcag tgaagggcaa gaaacaaaac atacacagta aagaccctcc 3120
ataatattgt gggtggccca acacaggcca ggttgtaaaa gctttttatt ctttgataga 3180
ggaatggata gtaatgtttc aacctggaca gagatcatgt tcactgaatc cttccaaaaa 3240
ttcatgggta gtttgaatta taaggaaaat aagacttagg ataaatactt tgtccaagat 3300
cccagagtta atgccaaaat cagttttcag actccaggca gcctgatcaa gagcctaaac 3360
tttaaagaca cagtccctta ataactacta ttcacagttg cactttcagg gcgcaaagac 3420
tcattgaatc ctacaataga atgagtttag atatcaaatc tctcagtaat agatgaggag 3480
actaaatagc gggcatgacc tggtcactta aagacagaat tgagattcaa ggctagtgtt 3540
ctttctacct gttttgtttc tacaagatgt agcaatgcgc taattacaga cctctcaggg 3600
aaggaattca caaccctcag caaaaaccaa agacaaatct aagacaacta agagtgttgg 3660
tttaatttgg aaaaataact cactaaccaa acgcccctct tagcacccca atgtcttcca 3720
ccatcacagt gctcaggcct caaccatgcc ccaatcacc 3759

<210> SEQ ID NO 20
<211> LENGTH: 9010
<212> TYPE: DNA
<213> ORGANISM: Sus sp.

<400> SEQUENCE: 20
ctcaaacgta agtggctttt tccgactgat tctttgctgt ttctaattgt tggttggctt 60
tttgtccatt tttcagtgtt ttcatcgaat tagttgtcag ggaccaaaca aattgccttc 120
ccagattagg taccagggag gggacattgc tgcatgggag accagagggt ggctaatttt 180
taacgtttcc aagccaaaat aactggggaa gggggcttgc tgtcctgtga gggtaggttt 240
ttatagaagt ggaagttaag gggaaatcgc tatggttcac ttttggctcg gggaccaaag 300
tggagcccaa aattgagtac attttccatc aattatttgt gagatttttg tcctgttgtg 360
tcatttgtgc aagtttttga cattttggtt gaatgagcca ttcccaggga cccaaaagga 420
tgagaccgaa aagtagaaaa gagccaactt ttaagctgag cagacagacc gaattgttga 480
gtttgtgagg agagtagggt ttgtagggag aaaggggaac agatcgctgg ctttttctct 540
gaattagcct ttctcatggg actggcttca gagggggttt ttgatgaggg aagtgttcta 600
gagccttaac tgtgggttgt gttcggtagc gggaccaagc tggaaatcaa acgtaagtgc 660
acttttctac tcctttttct ttcttatacg ggtgtgaaat tggggacttt tcatgtttgg 720
agtatgagtt gaggtcagtt ctgaagagag tgggactcat ccaaaaatct gaggagtaag 780
ggtcagaaca gagttgtctc atggaagaac aaagacctag ttagttgatg aggcagctaa 840
atgagtcagt tgacttggga tccaaatggc cagacttcgt ctgtaaccaa caatctaatg 900

-continued

```
agatgtagca gcaaaaagag atttccattg aggggaaagt aaaattgtta atattgtgga    960
tcacctttgg tgaagggaca tccgtggaga ttgaacgtaa gtattttttc tctactacct   1020
tctgaaattt gtctaaatgc cagtgttgac ttttagaggc ttaagtgtca gttttgtgaa   1080
aaatgggtaa acaagagcat ttcatattta ttatcagttt caaaagttaa actcagctcc   1140
aaaaatgaat ttgtagacaa aaagattaat ttaagccaaa ttgaatgatt caaaggaaaa   1200
aaaaattagt gtagatgaaa aaggaattct tacagctcca aagagcaaaa gcgaattaat   1260
tttctttgaa ctttgccaaa tcttgtaaat gatttttgtt ctttacaatt taaaaaggtt   1320
agagaaatgt atttcttagt ctgttttctc tcttctgtct gataaattat tatatgagat   1380
aaaaatgaaa attaatagga tgtgctaaaa aatcagtaag aagttagaaa aatatatgtt   1440
tatgttaaag ttgccactta attgagaatc agaagcaatg ttatttttaa agtctaaaat   1500
gagagataaa ctgtcaatac ttaaattctg cagagattct atatcttgac agatatctcc   1560
tttttcaaaa atccaatttc tatggtagac taaatttgaa atgatcttcc tcataatgga   1620
gggaaaagat ggactgaccc caaaagctca gatttaagaa aacctgttta aggaaagaaa   1680
ataaaagaac tgcatttttt aaaggcccat gaatttgtag aaaaatagga aatattttaa   1740
taagtgtatt cttttatttt cctgttatta cttgatggtg tttttatacc gccaaggagg   1800
ccgtggcacc gtcagtgtga tctgtagacc ccatggcggc ctttttttcgc gattgaatga   1860
ccttggcggt gggtccccag ggctctggtg gcagcgcacc agccgctaaa agccgctaaa   1920
aactgccgct aaaggccaca gcaaccccgc gaccgcccgt tcaactgtgc tgacacagtg   1980
atacagataa tgtcgctaac agaggagaat agaaatatga cgggcacacg ctaatgtggg   2040
gaaaagaggg agaagcctga tttttatttt ttagagattc tagagataaa attcccagta   2100
ttatatcctt ttaataaaaa atttctatta ggagattata aagaatttaa agctattttt   2160
ttaagtgggg tgtaattctt tcagtagtct cttgtcaaat ggatttaagt aatagaggct   2220
taatccaaat gagagaaata gacgcataac cctttcaagg caaaagctac aagagcaaaa   2280
attgaacaca gcagccagcc atctagccac tcagattttg atcagtttta ctgagtttga   2340
agtaaatatc atgaaggtat aattgctgat aaaaaaataa gatacaggtg tgacacatct   2400
ttaagtttca gaaatttaat ggcttcagta ggattatatt tcacgtatac aaagtatcta   2460
agcagataaa aatgccatta atggaaactt aatagaaata tatttttaaa ttccttcatt   2520
ctgtgacaga aattttctaa tctgggtctt ttaatcacct accctttgaa agagtttagt   2580
aatttgctat ttgccatcgc tgtttactcc agctaatttc aaaagtgata cttgagaaag   2640
attattttttg gtttgcaacc acctggcagg actattttag ggccatttta aaactctttt   2700
caaactaagt attttaaact gttctaaacc atttagggcc ttttaaaaat cttttcatga   2760
atttcaaact tcgttaaaag ttattaaggt gtctggcaag aacttcctta tcaaatatgc   2820
taatagttta atctgttaat gcaggatata aaattaaagt gatcaaggct tgacccaaac   2880
aggagtatct tcatagcata tttcccctcc tttttttcta gaattcatat gattttgctg   2940
ccaaggctat tttatataat ctctggaaaa aaaatagtaa tgaaggttaa aagagaagaa   3000
aatatcagaa cattaagaat tcggtatttt actaactgct tggttaacat gaaggttttt   3060
attttattaa ggtttctatc tttataaaaa tctgttccct tttctgctga tttctccaag   3120
caaaagattc ttgatttgtt ttttaactct tactctccca cccaagggcc tgaatgccca   3180
caaaggggac ttccaggagg ccatctggca gctgctcacc gtcagaagtg aagccagcca   3240
gttcctcctg ggcaggtggc caaaattaca gttgacccct cctggtctgg ctgaaccttg   3300
```

-continued

```
ccccatatgg tgacagccat ctggccaggg cccaggtctc cctctgaagc ctttgggagg   3360
agagggagag tggctggccc gatcacagat gcggaagggg ctgactcctc aaccggggtg   3420
cagactctgc agggtgggtc tgggcccaac acacccaaag cacgcccagg aaggaaaggc   3480
agcttggtat cactgcccag agctaggaga ggcaccggga aaatgatctg tccaagaccc   3540
gttcttgctt ctaaactccg agggggtcag atgaagtggt tttgtttctt ggcctgaagc   3600
atcgtgttcc ctgcaagaag cggggaacac agaggaagga gagaaaagat gaactgaaca   3660
aagcatgcaa ggcaaaaaag gggtctagc cgcggtctag gaagctttct agggtacctc    3720
tagggatccc ggcgcgccct accgggtagg ggaggcgctt ttcccaaggc agtctggagc   3780
atgcgcttta gcagccccgc tgggcacttg gcgctacaca agtggcctct ggcctcgcac   3840
acattccaca tccaccggta ggcgccaacc ggctccgttc tttggtggcc ccttcgcgcc   3900
accttctact cctcccctag tcaggaagtt cccccccgcc ccgcagctcg cgtcgtgcag   3960
gacgtgacaa atggaagtag cacgtctcac tagtctcgtg cagatggaca gcaccgctga   4020
gcaatggaag cgggtaggcc tttggggcag cggccaatag cagctttggc tccttcgctt   4080
tctgggctca gaggctggga aggggtgggt ccgggggcgg gctcaggggc gggctcaggg   4140
gcggggcggg cgcccgaagg tcctccggaa gcccggcatt ctgcacgctt caaaagcgca   4200
cgtctgccgc gctgttctcc tcttcctcat ctccgggcct ttcgacctgc agccaatatg   4260
ggatcggcca ttgaacaaga tggattgcac gcaggttctc cggccgcttg ggtggagagg   4320
ctattcggct atgactgggc acaacagaca atcggctgct ctgatgccgc cgtgttccgg   4380
ctgtcagcgc aggggcgccc ggttcttttt gtcaagaccg acctgtccgg tgccctgaat   4440
gaactgcagg acgaggcagc gcggctatcg tggctggcca cgacgggcgt tccttgcgca   4500
gctgtgctcg acgttgtcac tgaagcggga agggactggc tgctattggg cgaagtgccg   4560
gggcaggatc tcctgtcatc tcaccttgct cctgccgaga aagtatccat catggctgat   4620
gcaatgcggc ggctgcatac gcttgatccg gctacctgcc cattcgacca ccaagcgaaa   4680
catcgcatcg agcgagcacg tactcggatg gaagccggtc ttgtcaatca ggatgatctg   4740
gacgaagagc atcaggggct cgcgccagcc gaactgttcg ccaggctcaa ggcgcgcatg   4800
cccgacggcg aggatctcgt cgtgacccat ggcgatgcct gcttgccgaa tatcatggtg   4860
gaaaatggcc gcttttctgg attcatcgac tgtggccggc tgggtgtggc ggatcgctat   4920
caggacatag cgttggctac ccgtgatatt gctgaagagc ttggcggcga atgggctgac   4980
cgcttcctcg tgctttacgg tatcgccgct cccgattcgc agcgcatcgc cttctatcgc   5040
cttcttgacg agttcttctg aggggatcaa ttctctagag ctcgctgatc agcctcgact   5100
gtgccttcta gttgccagcc atctgttgtt tgcccctccc ccgtgccttc cttgaccctg   5160
gaaggtgcca ctcccactgt cctttcctaa taaaatgagg aaattgcatc gcattgtctg   5220
agtaggtgtc attctattct ggggggtggg gtggggcagg acagcaaggg ggaggattgg   5280
gaagacaata gcaggcatgc tggggatgcg gtgggctcta tggcttctga ggcggaaaga   5340
accagctggg ggcgcgcccc tcgagcggcc gccagtgtga tggatatctg cagaattcgc   5400
ccttggatca aacacgcatc ctcatggaca atatgttggg ttcttagcct gctgagacac   5460
aacaggaact cccctggcac cactttagag gccagagaaa cagcacagat aaaattccct   5520
gccctcatga agcttatagt ctagctgggg agatatcata ggcaagataa acacatacaa   5580
atacatcatc ttaggtaata atatatacta aggagaaaat tacaggggag aaagaggaca   5640
```

ggaattgcta gggtaggatt ataagttcag atagttcatc aggaacactg ttgctgagaa 5700
gataacattt aggtaaagac cgaagtagta aggaaatgga ccgtgtgcct aagtgggtaa 5760
gaccattcta ggcagcagga acagcgatga aagcactgag gtgggtgttc actgcacaga 5820
gttgttcact gcacagagtt gtgtggggag gggtaggtct tgcaggctct tatggtcaca 5880
ggaagaattg ttttactccc accgagatga aggttggtgg attttgagca gaagaataat 5940
tctgcctggt ttatatataa caggatttcc ctgggtgctc tgatgagaat aatctgtcag 6000
gggtgggata gggagagata tggcaatagg agccttggct aggagcccac gacaataatt 6060
ccaagtgaga ggtggtgctg cattgaaagc aggactaaca agacctgctg acagtgtgga 6120
tgtagaaaaa gatagaggag acgaaggtgc atctagggtt ttctgcctga ggaattagaa 6180
agataaagct aaagcttata gaagatgcag cgctctgggg agaaagacca gcagctcagt 6240
tttgatccat ctggaattaa ttttggcata aagtatgagg tatgtgggtt aacattattt 6300
gttttttttt tttccatgta gctatccaac tgtcccagca tcatttattt taaaagactt 6360
tcctttcccc tattggattg ttttggcacc ttcactgaag atcaactgag cataaaattg 6420
ggtctatttc taagctcttg attccattcc atgacctatt tgttcatctt taccccagta 6480
gacactgcct tgatgattaa agcccctgtt accatgtctg ttttggacat ggtaaatctg 6540
agatgcctat tagccaacca agcaagcacg gcccttagag agctagatat gagagcctgg 6600
aattcagacg agaaaggtca gtcctagaga catacatgta gtgccatcac catgcggatg 6660
gtgttaaaag ccatcagact gcaacagact gtgagagggt accaagctag agagcatgga 6720
tagagaaacc caagcactga gctgggaggt gctcctacat taagagatta gtgagatgaa 6780
ggactgagaa gattgatcag agaagaagga aaatcaggaa aatggtgctg tcctgaaaat 6840
ccaagggaag agatgttcca aagaggagaa aactgatcag ttgtcagcta gcgtcaattg 6900
ggatgaaaat ggaccattgg acagagggat gtagtgggtc atgggtgaat agataagagc 6960
agcttctata gaatggcagg ggcaaaattc tcatctgatc ggcatgggtt ctaaagaaaa 7020
cgggaagaaa aaattgagtg catgaccagt cccttcaagt agagaggtgg aaaagggaag 7080
gaggaaaatg aggccacgac aacatgagag aaatgacagc atttttaaaa attttttatt 7140
ttattttatt tatttatttt tgctttttag ggctgcccct gcaacatatg gaggttccca 7200
ggttaggggt ctaatcagag ctatagctgc cagcctacac cacagccata gcaatgccag 7260
atctacatga cctacaccac agctcacagc aacgccggat ccttaaccca ctgagtgagg 7320
ccagagatca aacccatatc cttatggata ctagtcaggt tcattaccac tgagccaaaa 7380
tgggaaatcc tgagtaatga cagcattttt taatgtgcca ggaagcaaaa cttgccaccc 7440
cgaaatgtct ctcaggcatg tggattattt tgagctgaaa acgattaagg cccaaaaaac 7500
acaagaagaa atgtggacct tcccccaaca gcctaaaaaa tttagattga gggcctgttc 7560
ccagaataga gctattgcca gacttgtcta cagaggctaa gggctaggtg tggtggggaa 7620
accctcagag atcagaggga cgtttatgta ccaagcattg acatttccat ctccatgcga 7680
atggccttct tcccctctgt agccccaaac caccaccccc aaaatcttct tctgtcttta 7740
gctgaagatg gtgttgaagg tgatagtttc agccactttg gcgagttcct cagttgttct 7800
gggtctttcc tcctgatcca cattattcga ctgtgtttga ttttctcctg tttatctgtc 7860
tcattggcac ccatttcatt cttagaccag cccaaagaac ctagaagagt gaaggaaaat 7920
ttcttccacc ctgacaaatg ctaaatgaga atcaccgcag tagaggaaaa tgatctggtg 7980
ctgcgggaga tagaagagaa aatcgctgga gagatgtcac tgagtaggtg agatgggaaa 8040

-continued

```
ggggtgacac aggtggaggt gttgccctca gctaggaaga cagacagttc acagaagaga   8100

agcgggtgtc cgtggacatc ttgcctcatg gatgaggaaa ccgaggctaa gaaagactgc   8160

aaaagaaagg taaggattgc agagaggtcg atccatgact aaaatcacag taaccaaccc   8220

caaaccacca tgttttctcc tagtctggca cgtggcaggt actgtgtagg ttttcaatat   8280

tattggtttg taacagtacc tattaggcct ccatcccctc ctctaatact aacaaaagtg   8340

tgagactggt cagtgaaaaa tggtcttctt tctctatgaa tctttctcaa gaagatacat   8400

aactttttat tttatcatag gcttgaagag caaatgagaa acagcctcca acctatgaca   8460

ccgtaacaaa atgtttatga tcagtgaagg gcaagaaaca aaacatacac agtaaagacc   8520

ctccataata ttgtgggtgg cccaacacag gccaggttgt aaaagctttt tattctttga   8580

tagaggaatg gatagtaatg tttcaacctg gacagagatc atgttcactg aatccttcca   8640

aaaattcatg ggtagtttga attataagga aaataagact taggataaat actttgtcca   8700

agatcccaga gttaatgcca aaatcagttt tcagactcca ggcagcctga tcaagagcct   8760

aaactttaaa gacacagtcc cttaataact actattcaca gttgcacttt cagggcgcaa   8820

agactcattg aatcctacaa tagaatgagt ttagatatca aatctctcag taatagatga   8880

ggagactaaa tagcgggcat gacctggtca cttaaagaca gaattgagat tcaaggctag   8940

tgttctttct acctgttttg tttctacaag atgtagcaat gcgctaatta cagacctctc   9000

agggaaggaa                                                          9010
```

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21

```
cgaacccctg tgtatatagt t                                               21
```

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22

```
gagatgagga agaggagaac a                                               21
```

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23

```
gcattgtctg agtaggtgtc att                                             23
```

<210> SEQ ID NO 24
<211> LENGTH: 22
<212> TYPE: DNA
<213> ORGANISM: Artificial Sequence
<220> FEATURE:
<223> OTHER INFORMATION: Synthetic

<400> SEQUENCE: 24
cgcttcttgc agggaacacg at 22

<210> SEQ ID NO 25
<211> LENGTH: 6772
<212> TYPE: DNA
<213> ORGANISM: Sus sp.

<400> SEQUENCE: 25
gcacatggta ggcaaaggac tttgcttctc ccagcacatc tttctgcaga gatccatgga 60
aacaagactc aactccaaag cagcaaagaa gcagcaagtt ctcaagtgat ctcctctgac 120
tccctcctcc caggctaatg aagccatgtt gcccctgggg gattaagggc aggtgtccat 180
tgtggcaccc agcccgaaga caagcaattt gatcaggttc tgagcactcc tgaatgtgga 240
ctctggaatt ttctcctcac cttgtggcat atcagcttaa gtcaagtaca agtgacaaac 300
aacataatcc taagaagaga ggaatcaagc tgaagtcaaa ggatcactgc cttggattct 360
actgtgaatg atgacctgga aaatatcctg aacaacagct tcagggtgat catcagagac 420
aaaagttcca gagccaggta gggaaaccct caagccttgc aaagagcaaa atcatgccat 480
tgggttctta acctgctgag tgatttacta tatgttactg tgggaggcaa agcgctcaaa 540
tagcctgggt aagtatgtca aataaaaagc aaaagtggtg tttcttgaaa tgttagacct 600
gaggaaggaa tattgataac ttaccaataa ttttcagaat gatttataga tgtgcactta 660
gtcagtgtct ctccaccccg cacctgacaa gcagtttaga atttattcta agaatctagg 720
tttgctgggg gctacatggg aatcagcttc agtgaagagt ttgttggaat gattcactaa 780
atttctattt tccagcataa atccaagaac ctctcagact agtttattga cactgctttt 840
cctccataat ccatctcatc tccgtccatc atggacactt tgtagaatga caggtcctgg 900
cagagactca cagatgcttc tgaaacatcc tttgccttca aagaatgaac agcacacata 960
ctaaggatct cagtgatcca caaattagtt tttgccacaa tggttcttat gataaaagtc 1020
tttcattaac agcaaattgt tttataatag ttgttctgct ttataataat tgcatgcttc 1080
actttctttt cttttctttt tttttctttt tttgcttttt agtgccgcag gtgcagcata 1140
tgaaatttcc caggctaggg gtcaaatcag aactacacct actggcctac gccacagcca 1200
cagcaactca ggatctaagc catgtcggtg acctacacta cagctcatgg caatgccaga 1260
tccttaaccc aatgagcgag gccagggatc gaacccatgt cctcatggat actagtcagg 1320
ctcattatcc gctgagccat aacaggaact cccgagtttg ctttttatca aaattggtac 1380
agccttattg tttctgaaaa ccacaaaatg aatgtattca cataatttta aaaggttaaa 1440
taatttatga tatacaagac aatagaaaga gaaaacgtca ttgcctcttt cttccacgac 1500
aacacgcctc cttaattgat ttgaagaaat aactactgag catggtttag tgtacttctt 1560
tcagcaatta gcctgtattc atagccatac atattcaatt aaaatgagat catgatatca 1620
cacaatacat accatacagc ctatagggat ttttacaatc atcttccaca tgactacata 1680
aaaacctacc taaaaaaaaa aaaaacccta cttcatcctc ctattggctg ctttgtgctc 1740
cattaaaaag ctctatcata attaggttat gatgaggatt tccattttct acctttcaag 1800
caacatttca atgcacagtc ttatatacac atttgagcct acttttcttt ttctttcttt 1860
ttttggtttt ttttttttt ttttttttgg tctttttgtc ttttctaagg ctgcatatgg 1920
aggttcccag gctagctgtc taatcagaac tatagctgct ggcctacgcc acatccacag 1980
caatacaaga tctgagccat gtctgcaact tacaccacag ctcacagcaa cggtggatcc 2040

-continued

```
ttaaaccact gagcaaggcc agggatcaaa cccataactt catggctcct agttggattt   2100
gttaaccact gagccatgat ggcaactcct gagcctactt ttctaatcat ttccaaccct   2160
aggacacttt tttaagtttc atttttctcc ccccaccccc tgttttctga agtgtgtttg   2220
cttccactgg gtgacttcac tcccaggatc tcatctgcag gatactgcag ctaagtgtat   2280
gagctctgaa tttgaatccc aactctgcca ctcaaaggga taggagtttc cgatgtggcc   2340
caatgggatc agtggcatct ctgcagtgcc aggacgcagg ttccatccct ggcccagcac   2400
agtgggttaa gaatctggca ttgctgcagc tgaggcatag atttcaattg tgcctcagat   2460
ctgatccttg gcccaaggac tgcatatgcc tcagggcaac caaaaaagag aaaagggggg   2520
tgatagcatt agtttctaga tttgggggat aattaaataa agtgatccat gtacaatgta   2580
tggcattttg taaatgctca acaaatttca actattatgg agttcccatc atggctcagt   2640
ggaagggaat ctgattagca tccatgagga cacaggtcca accccgacct tgctcagtgg   2700
gcattgctgt gagctgtggc atgggttaca gacgaagctc ggatctggca ttgctgtggc   2760
tgtggtgtaa gccagcaact acagctctca ttcagcccct agcctgggaa cctccatatg   2820
cctaaaagac aaaaaataaa atttaaatta aaaataaaga aatgttaact attatgattg   2880
gtactgcttg cattactgca aagaaagtca ctttctatac tctttaatat cttagttgac   2940
tgtgtgctca gtgaactatt ttggacactt aatttccact ctcttctatc tccaacttga   3000
caactctctt tcctctcttc tggtgagatc cactgctgac tttgctcttt aaggcaacta   3060
gaaaagtgct cagtgacaaa atcaaagaaa gttaccttaa tcttcagaat tacaatctta   3120
agttctcttg taaagcttac tatttcagtg gttagtatta ttccttggtc ccttacaact   3180
tatcagctct gatctattgc tgattttcaa ctatttattg ttggagtttt ttcctttttt   3240
ccctgttcat tctgcaaatg tttgctgagc atttgtcaag tgaagatact ggactgggcc   3300
ttccaaatat aagacaatga aacatcggga gttctcatta tggtgcagca gaaacgaatc   3360
caactaggaa atgtgaggtt gcaggttcga tccctgccct tgctcagtgg gttaaggatc   3420
cagcattacc gtgagctgtg gtgtaggttg cagacgtggc tcagatcctg cgttgctgtg   3480
gctgtggcat aggctggcag ctctagctct gattcgaccg ctagcctggg aacctccatg   3540
cgccccgagt gcagccctta aaaagcaaaa aaaaaagaaa gaaagaaaaa gacaatgaaa   3600
catcaaacag ctaacaatcc agtagggtag aaagaatctg gcaacagata agagcgatta   3660
aatgttctag gtccagtgac cttgcctctg tgctctacac agtcgtgcca cttgctgagg   3720
gagaaggtct ctcttgagtt gagtcctgaa agacattagt tgttcacaaa ctaatgccag   3780
tgagtgaagg tgtttccaag cagagggaga gtttggtaaa aagctggaag tcacagaaag   3840
actctaaaga gtttaggatg gtgggagcaa catacgctga gatggggctg gaaggttaag   3900
agggaaacaa ctatagtaag tgaagctgga ctcacagcaa agtgaggacc tcagcatcct   3960
tgatggggtt accatggaaa caccaaggca caccttgatt tccaaaacag caggcacctg   4020
attcagccca atgtgacatg gtgggtaccc ctctagctct acctgttctg tgacaactga   4080
caaccaacga agttaagtct ggattttcta ctctgctgat ccttgttttt gtttcacacg   4140
tcatctatag cttcatgcca aaatagagtt caaggtaaga cgcgggcctt ggtttgatat   4200
acatgtagtc tatcttgttt gagacaatat ggtggcaagg aagaggttca aacaggaaaa   4260
tactctctaa ttatgattaa ctgagaaaag ctaaagagtc ccataatgac actgaatgaa   4320
gttcatcatt tgcaaaagcc ttcccccccc cccaggagac tataaaaaag tgcaattttt   4380
```

-continued

```
taaatgaact tatttacaaa acagaaatag actcacagac ataggaaacg aacagatggt   4440
taccaagggt gaaagggagt aggagggata aataaggagt ctggggttag cagatacacc   4500
ccagtgtaca caaaataaac aacagggacc tactatatag cacagggaac tatatgcagt   4560
agcttacaat aacctataat ggaaaagaat gtgaaaaaga atatatgtat gcgtgtgtgt   4620
gtaactgaat cactttgctg taacctgaat ctaacataac attgtaaatc aactacagtt   4680
ttttttttt ttaagtgcag ggttttggtg ttttttttt ttcatttttg tttttgtttt   4740
tgtttttgc tttttagggc cacacccaga catatggggg ttcccaggct aggggtctaa   4800
ttagagctac agttgccggc ttgcaccaca gccacagcaa catcagatcc gagccgcact   4860
tgcgacttac accacagctc atggcaatac cagatcctta acccactgag caaggcccag   4920
ggatcgtacc cgcaacctca tggttcctag tcagattcat ttctgctgcg ctacaatggg   4980
aactccaagt gcagtttttt gtaatgtgct tgtctttctt tgtaattcat attcatccta   5040
cttcccaata aataaataaa tacataaata ataaacatac cattgtaaat caactacaat   5100
tttttttaaa tgcagggttt ttgtttttg tttttgttt tgtcttttg ccttttctag   5160
ggccgctccc atggcatatg gaggttccca ggctaggggt cgaatcggag ctgtagccac   5220
cggcctacgc cagagccaca gcaacgcggg atccgagccg cgtctgcaac ctacaccaca   5280
gctcacggca acgccggatc gttaacccac tgagcaaggg cagggatcga acctgcaacc   5340
tcatggttcc tagtcagatt cgttaactac tgagccacaa cggaaactcc taaagtgcag   5400
tttttaaatg tgcttgtctt tctttgtaat ttacactcaa cctacttccc aataaataaa   5460
taaataaaca aataaatcat agacatggtt gaattctaaa ggaagggacc atcaggcctt   5520
agacagaaat acgtcatctt ctagtatttt aaaacacact aaagaagaca aacatgctct   5580
gccagagaag cccagggcct ccacagctgc ttgcaaaggg agttaggctt cagtagctga   5640
cccaaggctc tgttcctctt cagggaaaag ggtttttgtt cagtgagaca gcagacagct   5700
gtcactgtgg tggacgttcg gccaaggaac caagctggaa ctcaaacgta agtcaatcca   5760
aacgttcctt ccttggctgt ctgtgtctta cggtctctgt ggctctgaaa tgattcatgt   5820
gctgactctc tgaaaccaga ctgacattct ccagggcaaa actaaagcct gtcatcaaac   5880
cggaaaactg agggcacatt ttctgggcag aactaagagt caggcactgg gtgaggaaaa   5940
acttgttaga atgatagttt cagaaactta ctgggaagca aagcccatgt tctgaacaga   6000
gctctgctca agggtcagga ggggaaccag tttttgtaca ggagggaagt tgagacgaac   6060
ccctgtgtat atggtttcgg cgcggggacc aagctggagc tcaaacgtaa gtggcttttt   6120
ccgactgatt ctttgctgtt tctaattgtt ggttggcttt ttgtccattt ttcagtgttt   6180
tcatcgaatt agttgtcagg gaccaaacaa attgccttcc cagattaggt accagggagg   6240
ggacattgct gcatgggaga ccagagggtg gctaattttt aacgtttcca agccaaaata   6300
actggggaag ggggcttgct gtcctgtgag ggtaggtttt tatagaagtg gaagttaagg   6360
ggaaatcgct atggttcact tttggctcgg ggaccaaagt ggagcccaaa attgagtaca   6420
ttttccatca attatttgtg agatttttgt cctgttgtgt catttgtgca agtttttgac   6480
attttggttg aatgagccat tcccagggac ccaaaaggat gagaccgaaa agtagaaaag   6540
agccaacttt taagctgagc agacagaccg aattgttgag tttgtgagga gagtagggtt   6600
tgtagggaga aaggggaaca gatcgctggc tttttctctg aattagcctt tctcatggga   6660
ctggcttcag agggggtttt tgatgaggga agtgttctag agccttaact gtgggttgtg   6720
ttcggtagcg ggaccaagct ggaaatcaaa cgtaagtgca cttttctact cc           6772
```

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
ccttcctcct gcacctgtca ac 22

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
tagacacacc agggtggcct tg 22

<210> SEQ ID NO 28
<211> LENGTH: 5918
<212> TYPE: DNA
<213> ORGANISM: Sus sp.

<400> SEQUENCE: 28
ccttcctcct gcacctgtca actcccaata aaccgtcctc cttgtcattc agaaatcatg 60
ctctccgctc acttgtgtct acccattttc gggcttgcat ggggtcatcc tcgaaggtgg 120
agagagtccc ccttggcctt ggggaagtcg agggggggcgg ggggaggcct gaggcatgtg 180
ccagcgaggg gggtcacctc cacgcccctg aggaccttct agaaccaggg gcgtggggcc 240
accgcctgag tggaaggctg tccacttttc ccccgggccc ccaggctccc tcctccgtgt 300
ggaccttgtc cacctctgac tggcccagcc actcatgcat tgtttccccg aaaccccagg 360
acgatagctc agcacgcgac agtgtccccc tctgagggcc tctgtccatt tcaggacgac 420
ccgcatgtac agcgtgacca ctctgctcac gcccactcac cacgtcctag agccccaccc 480
ccagccccat ccttaggggc acagccagct ccgaccgccc cggggacacc accctctgcc 540
ccttccccag gccctccctg tcacacgcac cacagggccc tccgtcccga gaccctgctc 600
cctcatccct cggtcccctc aggtagcctt ccacccgcgt gtgtcccgag gtcccagatg 660
cagcaaggcc cctgggacaa cgccagatct ctgctctccc cgacccctca gaagccagcc 720
cacgcctggc cccaccacca ctgcctaacg tccaagtgtc cataggcctc gggacctcca 780
agtccaggtt ctgcctctgg gattccgcca tgggtctgcc tgggaaatga tgcacttgga 840
ggagctcagc atgggatgcg ggaccttgtc tctaggcgct ccctcaggat cccacagctg 900
ccctgtgaga cacacacaca cacacacaca cacacacaca cacacacaca cacacaaaca 960
cgcatgcacg cacgccggca cacacgctat tgcagagatg gccacggtag ctgtgcctcg 1020
aggccgagtg gagtgtctag aactctcggg ggtcccctct gcagacgaca ctgctccatc 1080
ccccccgtgc cctgaagggc tcctcactct cccatcagga tctctccaag ctgctgacct 1140
ggagaggaag gggcctggga caggcgggga cactcagacc tccctgctgc ccctcctctg 1200
cctgggcttg gacggctccc cccttcccac gggtgaaggt gcaggtgggg agagggcacc 1260
cccctcagcc tcccagaccc agaccagccc ccgtggcagg ggcagcctgt gagcctccag 1320
ccagatgcag gtggcctggg gtggggggtg gagggggcgg gaggtttatg tttgaggctg 1380

-continued

```
tatcactgtg taatattttc ggcggtggga cccatctgac cgtcctcggt gagtctcccc   1440
ttttctctcc tccttgggga tccgagtgaa atctgggtcg atcttctctc cgttctcctc   1500
cgactggggc tgaggtctga acctcggtgg ggtccgaaga ggaggcccct aggccaggct   1560
cctcagcccc tccagcccga ccggccctct tgacacaggg tccagctaag ggcagacatg   1620
gaggctgcta gtccagggcc aggctctgag acccaagggc gctgcccaag gaacccttgc   1680
cccagggacc ctgggagcaa agctcctcac tcagagcctg cagccctggg gtctgaggac   1740
aaggagggac tgaggactgg gcgtggggag ttcaggcggg gacaccaggt ccagggaggt   1800
gacaaaggcg ctgggagggg gcggacggtg ccggggactc ctcctgggcc ctgtgggctc   1860
ggggtccttg tgaggaccct gagggactga ggggcccctg ggcctaggga cttgcagtga   1920
gggaggcagg gagtgtccct tgagaacgtg gcctccgcgg gctgggtccc cctcgtgctc   1980
ccagccggga ggacacccca gagcaagcgc cccaggtggg cggggagggt ctcctcacag   2040
gggcagctga cagatagagg cccccgccag gcagatgctt gatcctggca gttatactgg   2100
gttcgcacaa ctttccctga acaaggggcc ctccgaacag acacagacgc aacccagtcg   2160
acccaggctc agcacagaaa atgcactgac acccaaaacc ctcatctggg ggcctggccg   2220
gcatcccgcc ccaggaccca aggcccctgc cccctggcag ccctggacac ggtcctctgt   2280
gggcggtggg gtcggggctg tggtgacggt ggcatcgggg agcctgtgcc ccctccctga   2340
aagggcggag aggctcaaga ggggacagaa atgtcctccc ctaggaagac ctcggacggg   2400
ggcggggggg tggtctccga cagacagatg cccgggaccg acagacctgc cgagggaaga   2460
gggcacctcg gtcgggttag gctccaggca gcacgaggga gcgaggctgg gagggtgagg   2520
acatgggagc ctgaggagga gctggagact tcagcaggcc cccagctccg ggcttcgggc   2580
tctgagatgc tcggacgcaa ggtgagtgac cccacctgtg gctgacctga cctcaggggg   2640
acaaggctca gcctgggact ctgtgtcccc atcgcctgca caggggattc ccctgatgga   2700
cactgagcca acgacctccc gtctctcccc gacccccagg tcagcccaag gccactccca   2760
cggtcaacct cttcccgccc tcctctgagg agctcggcac caacaaggcc accctggtgt   2820
gtctaataag tgacttctac ccgggcgccg tgacggtgac ctggaaggca ggcggcacca   2880
ccgtcaccca gggcgtggag accaccaagc cctcgaaaca gagcaacaac aagtacgcgg   2940
ccagcagcta cctggccctg tccgccagtg actggaaatc ttccagcggc ttcacctgcc   3000
aggtcaccca cgaggggacc attgtggaga agacagtgac gccctccgag tgcgcctagg   3060
tccctgggcc cccaccctca ggggcctgga gccacaggac ccccgcgagg gtctccccgc   3120
gaccctggtc cagcccagcc cttcctcctg cacctgtcaa ctcccaataa accgtcctcc   3180
ttgtcattca gaaatcatgc tctccgctca cttgtgtcta cccattttcg ggcttgcatg   3240
gggtcatcct cgaaggtgga gagagtcccc cttggccttg gggaaatcga ggggggcggg   3300
gggaggcctg aggcatgtgc cagcgagggg ggtcacctcc acgcccctga ggaccttcta   3360
gaaccagggg cgtggggcca ccgccagagt ggaaggctgt ccacttttcc cccgggcccc   3420
caggctccct cctccgtgtg gaccttgtcc acctctgact ggcccagcca ctcatgcatt   3480
gtttccccga aaccccagga cgatagctca gcacgcgaca gtgtcccccct ctgagggcct   3540
ctgtccattt caggacgacc cgcatgtaca gcgtgaccac tctgctcacg cccactcacc   3600
acgtcctaga gccccacccc cagccccatc cttaggggca cagccagctc cgaccgcccc   3660
ggggacacca ccctctgccc cttccccagg ccctccctgt cacacgcacc acagggccct   3720
ccgtcccgag accctgctcc ctcatccctc ggtcccctca ggtagccttc cacccgcgtg   3780
```

tgtcccgagg tcccagatgc agcaaggccc ctgggacaac gccagatctc tgctctcccc 3840
gaccctcaga agccagccca cgcctggccc accaccactg cctaacgtcc aagtgtccat 3900
aggctcggga cctccaagtc caggttctgc ctctgggatt ccgccatggg tctgcctgga 3960
atgatgcact tggaggagct cagcatggga tgcggaactt gtctagcgct cctcagatcc 4020
acagctgcct gtgagacaca cacacacaca cacacacacc aaacacgcat gcacgcacgc 4080
cggcacacac gctattacag agatggccac ggtagctgtg cctcgaggcc gagtggagtg 4140
tctagaactc tcgggggtcc cctctgcaga cgacactgct ccatcccccc cgtgccctga 4200
agggctcctc actctcccat caggatctct ccaagctgct gacctggaga ggaaggggcc 4260
tgggacaggc ggggacactc agacctccct gctgcccctc ctctgcctgg gcttggacgg 4320
ctcccccctt cccacgggtg aaggtgcagg tggggagagg gcaccccccct caccctccca 4380 gacccagacc agcccccgtg gcaggggcag cctgtgagcc tccagccaga tgcaggtggc 4440
ctggggtggg gggtggaggg ggcgggaggt ttatgtttga ggctgtattc atctgtgtaa 4500
tattttcggc ggtgggaccc atctgaccgt cctcggtgag tctccccttt tctttcctcc 4560
ttggggatcc gagtgaaatc tgggtcgatc ttctctccgt tctcctccga ctggggctga 4620
ggtctgaacc tcggtggggt ccgaagagga ggcccctagg ccggctcctc agcccctcca 4680
gcccgacccg ccctcttgac acagggtcca gctaagggca gacatggctg ctagtccagg 4740
gccaggctct gagacccaag ggcgctgccc aaggaaccct tgccccaggg accctgggag 4800
caaagctcct cactcagagc ctgcagccct ggggtctgag gacaaggagg gactgaggac 4860
tgggcgtggg gagttcaggc ggggacaccg ggtccaggga ggtgacaaag gcgctgggag 4920
ggggcggacg gtgccggaga ctcctcctgg gccctgtggg ctcgtggtcc ttgtgaggac 4980
cctgagggct gaggggcccc tgggcctagg gacttgcagt gagggaggca gggagtgtcc 5040
cttgagaacg tggcctccgc gggctgggtc cccctcgtgc tcccagcagg gaggacaccc 5100
cagagcaagc gccccaggtg ggcggggagg gtctcctcac aggggcagct gacagataga 5160
cggcccccgc cagacagatg cttgatcctg gtcagtactg ggttcgccac ttccctgaac 5220
aggggccctc cgaacagaca cagacgcaga ccaggctcag cacagaaaat gcactgacac 5280
ccaaaaccct catctggggg cctggccggc atcccgcccc aggacccaag gcccctgccc 5340
cctggcagcc ctggacacgg tcctctgtgg gcggtggggt cggggctgtg gtgacggtgg 5400
catcggggag cctgtgcccc ctccctgaaa gggcggagag gctcaagagg ggacagaaat 5460
gtcctcccct aggaagacct cggacggggg cggggggggtg gtctccgaca gacagatgcc 5520
cgggaccgac agacctgccg agggaagagg gcacctcggt cgggttaggc tccaggcagc 5580
acgagggagc gaggctggga gggtgaggac atgggagcct gaggaggagc tggagacttc 5640
agcaggcccc cagctccggg cttcgggctc tgagatgctc ggacgcaagg tgagtgaccc 5700
cacctgtggc tgacctgacc tgacctcagg gggacaaggc tcagcctggg actctgtgtc 5760
cccatcgcct gcacagggga ttcccctgat ggacactgag ccaacgacct cccgtctctc 5820
cccgaccccc aggtcagccc aaggccactc ccacggtcaa cctcttcccg ccctcctctg 5880
aggagctcgg caccaacaag gccaccctgg tgtgtcta 5918

<210> SEQ ID NO 29
<211> LENGTH: 11051
<212> TYPE: DNA
<213> ORGANISM: Sus sp.

<400> SEQUENCE: 29

```
tctagaagac gctggagaga ggccagactt cctcggaaca gctcaaagag ctctgtcaaa     60
gccagatccc atcacacgtg ggcaccaata ggccatgcca gcctccaagg gccgaactgg    120
gttctccacg gcgcacatga agcctgcagc ctggcttatc ctcttccgtg gtgaagaggc    180
aggcccggga ctggacgagg ggctagcagg gtgtggtagg caccttgcgc cccccacccc    240
ggcaggaacc agagaccctg ggctgagag tgagcctcca aacaggatgc cccacccttc     300
aggccacctt tcaatccagc tacactccac ctgccattct cctctgggca cagggcccag    360
cccctggatc ttggccttgg ctcgacttgc acccacgcgc acacacacac ttcctaacgt    420
gctgtccgct caccccctccc cagcgtggtc catgggcagc acggcagtgc gcgtccggcg   480
gtagtgagtg cagaggtccc ttcccctccc ccaggagccc caggggtgtg tgcagatctg    540
ggggctcctg tcccttacac cttcatgccc ctcccctcat acccaccctc caggcgggag    600
gcagcgagac ctttgcccag ggactcagcc aacgggcaca cgggaggcca gccctcagca    660
gctggctccc aaagaggagg tgggaggtag gtccacagct gccacagaga gaaaccctga    720
cggaccccac aggggccacg ccagccggaa ccagctccct cgtgggtgag caatggccag    780
ggccccgccg gccaccacgg ctggccttgc gccagctgag aactcacgtc cagtgcaggg    840
agactcaaga cagcctgtgc acacagcctc ggatctgctc ccatttcaag cagaaaaagg    900
aaaccgtgca ggcagccctc agcatttcaa ggattgtagc agcggccaac tattcgtcgg    960
cagtggccga ttagaatgac cgtggagaag ggcggaaggg tctctcgtgg gctctgcggc   1020
caacaggccc tggctccacc tgcccgctgc cagcccgagg ggcttgggcc gagccaggaa   1080
ccacagtgct caccgggacc acagtgactg accaaactcc cggccagagc agccccaggc   1140
cagccgggct ctcgccctgg aggactcacc atcagatgca caagggggcg agtgtggaag   1200
agacgtgtcg cccgggccat ttgggaaggc gaagggacct tccaggtgga caggaggtgg   1260
gacgcactcc aggcaaggga ctgggtcccc aaggcctggg gaaggggtac tggcttgggg   1320
gttagcctgg ccagggaacg gggagcgggg cggggggctg agcagggagg acctgacctc   1380
gtgggagcga ggcaagtcag gcttcaggca gcagccgcac atcccagacc aggaggctga   1440
ggcaggaggg gcttgcagcg gggcgggggc ctgcctggct ccgggggctc ctgggggacg   1500
ctggctcttg tttccgtgtc ccgcagcaca gggccagctc gctgggccta tgcttacctt   1560
gatgtctggg gccggggcgt cagggtcgtc gtctcctcag gggagagtcc cctgaggcta   1620
cgctgggggg ggactatggc agctccacca ggggcctggg gaccaggggc ctggaccagg   1680
ctgcagcccg gaggacgggc agggctctgg ctctccagca tctggccctc ggaaatggca   1740
gaacccctgg cgggtgagcg agctgagagc gggtcagaca gacaggggcc ggccggaaag   1800
gagaagttgg gggcagagcc cgccaggggc caggcccaag gttctgtgtg ccagggcctg   1860
ggtgggcaca ttggtgtggc catggctact tagattcgtg gggccagggc atcctggtca   1920
ccgtctcctc aggtgagcct ggtgtctgat gtccagctag gcgctggtgg gccgcgggtg   1980
ggcctgtctc aggctagggc aggggctggg atgtgtattt gtcaaggagg ggcaacaggg   2040
tgcagactgt gcccctggaa acttgaccac tggggcaggg gcgtcctggt cacgtctcct   2100
caggtaagac ggccctgtgc ccctctctcg cgggactgga aaaggaattt tccaagattc   2160
cttggtctgt gtggggccct ctggggcccc cgggggtggc tcccctcctg cccagatggg   2220
gcctcggcct gtggagcacg ggctgggcac acagctcgag tctagggcca cagaggcccg   2280
ggctcagggc tctgtgtggc ccggcgactg gcagggggct cgggtttttg gacacccccct  2340
```

-continued

```
aatgggggcc acagcactgt gaccatcttc acagctgggg ccgaggagtc gaggtcaccg   2400
tctcctcagg tgagtcctcg tcagccctct ctcactctct ggggggtttt gctgcatttt   2460
gtgggggaaa gaggatgcct gggtctcagg tctaaaggtc tagggccagc gccggggccc   2520
aggaaggggc cgaggggcca ggctcggctc ggccaggagc agagcttcca gacatctcgc   2580
ctcctggcgg ctgcagtcag gcctttggcc ggggggtct cagcaccacc aggcctcttg   2640
gctcccgagg tccccggccc cggctgcctc accaggcacc gtgcgcggtg ggcccgggct   2700
cttggtcggc caccctttct taactgggat ccgggcttag ttgtcgcaat gtgacaacgg   2760
gctcgaaagc tggggccagg ggaccctagt ctacgacgcc tcgggtgggt gtcccgcacc   2820
cctccccact ttcacggcac tcggcgagac ctggggagtc aggtgttggg gacactttgg   2880
aggtcaggaa cgggagctgg ggagagggct ctgtcagcgg ggtccagaga tgggccgccc   2940
tccaaggacg ccctgcgcgg ggacaagggc ttcttggcct ggcctggccg cttcacttgg   3000
gcgtcagggg gggcttcccg gggcaggcgg tcagtcgagg cgggttggaa ttctgagtct   3060
gggttcgggg ttcggggttc ggccttcatg aacagacagc ccaggcgggc cgttgtttgg   3120
cccctggggg cctggttgga atgcgaggtc tcgggaagtc aggagggagc ctggccagca   3180
gagggttccc agccctgcgg ccgagggacc tggagacggg cagggcattg gccgtcgcag   3240
ggccaggcca caccccccag gtttttgtgg ggcgagcctg gagattgcac cactgtgatt   3300
actatgctat ggatctctgg ggcccaggcg ttgaagtcgt cgtgtcctca ggtaagaacg   3360
gccctccagg gcctttaatt tctgctctcg tctgtgggct tttctgactc tgatcctcgg   3420
gaggcgtctg tgcccccccc ggggatgagg ccggcttgcc aggaggggtc agggaccagg   3480
agcctgtggg aagttctgac gggggctgca ggcgggaagg gccccaccgg ggggcgagcc   3540
ccaggccgct gggcggcagg agacccgtga gagtgcgcct tgaggagggt gtctgcggaa   3600
ccacgaacgc ccgccgggaa gggcttgctg caatgcggtc ttcagacggg aggcgtcttc   3660
tgccctcacc gtctttcaag cccttgtggg tctgaaagag ccatgtcgga gagagaaggg   3720
acaggcctgt cccgacctgg ccgagagcgg gcagccccgg gggagagcgg ggcgatcggc   3780
ctgggctctg tgaggccagg tccaagggag gacgtgtggt cctcgtgaca ggtgcacttg   3840
cgaaacctta gaagacgggg tatgttggaa gcggctcctg atgtttaaga aaagggagac   3900
tgtaaagtga gcagagtcct caagtgtgtt aaggttttaa aggtcaaagt gttttaaacc   3960
tttgtgactg cagttagcaa gcgtgcgggg agtgaatggg gtgccagggt ggccgagagg   4020
cagtacgagg gccgtgccgt cctctaattc agggcttagt tttgcagaat aaagtcggcc   4080
tgttttctaa aagcattggt ggtgctgagc tggtggagga ggccgcgggc agccctggcc   4140
acctgcagca ggtggcagga agcaggtcgg ccaagaggct attttaggaa gccagaaaac   4200
acggtcgatg aatttatagc ttctggtttc caggaggtgg ttgggcatgg ctttgcgcag   4260
cgccacagaa ccgaaagtgc ccactgagaa aaaacaactc ctgcttaatt tgcatttttc   4320
taaaagaaga aacagaggct gacggaaact ggaaagttcc tgttttaact actcgaattg   4380
agttttcggt cttagcttat caactgctca cttagattca ttttcaaagt aaacgtttaa   4440
gagccgaggc attcctatcc tcttctaagg cgttattcct ggaggctcat tcaccgccag   4500
cacctccgct gcctgcaggc attgctgtca ccgtcaccgt gacggcgcgc acgattttca   4560
gttggcccgc ttcccctcgt gattaggaca gacgcgggca ctctggccca gccgtcttgg   4620
ctcagtatct gcaggcgtcc gtctcgggac ggagctcagg ggaagagcgt gactccagtt   4680
```

-continued gaacgtgata gtcggtgcgt tgagaggaga cccagtcggg tgtcgagtca gaaggggccc 4740
ggggcccgag gccctgggca ggacggcccg tgccctgcat cacgggccca gcgtcctaga 4800
ggcaggactc tggtggagag tgtgagggtg cctggggccc ctccggagct ggggccgtgc 4860
ggtgcaggtt gggctctcgg cgcggtgttg gctgtttctg cgggatttgg aggaattctt 4920
ccagtgatgg gagtcgccag tgaccgggca ccaggctggt aagagggagg ccgccgtcgt 4980
ggccagagca gctgggaggg ttcggtaaaa ggctcgcccg tttcctttaa tgaggacttt 5040
tcctggaggg catttagtct agtcgggacc gttttcgact cgggaagagg gatgcggagg 5100
agggcatgtg cccaggagcc gaaggcgccg cggggagaag cccagggctc tcctgtcccc 5160
acagaggcga cgccactgcc gcagacagac agggcctttc cctctgatga cggcaaaggc 5220
gcctcggctc ttgcggggtg ctggggggga gtcgccccga agccgctcac ccagaggcct 5280
gaggggtgag actgaccgat gcctcttggc cgggcctggg gccggaccga gggggactcc 5340
gtggaggcag ggcgatggtg gctgcgggag ggaaccgacc ctgggccgag cccggcttgg 5400
cgattcccgg gcgagggccc tcagccgagg cgagtgggtc cggcggaacc accctttctg 5460
gccagcgcca cagggctctc gggactgtcc ggggcgacgc tgggctgccc gtggcaggcc 5520
tgggctgacc tggacttcac cagacagaac agggctttca gggctgagct gagccaggtt 5580
tagcgaggcc aagtggggct gaaccaggct caactggcct gagctgggtt gagctgggct 5640
gacctgggct gagctgagct gggctgggct gggctgggct gggctgggct gggctggact 5700
ggctgagctg agctgggttg agctgagctg agctggcctg ggttgagctg ggctgggttg 5760
agctgagctg ggttgagctg ggttgagctg ggttgatctg agctgagctg ggctgagctg 5820
agctaggctg gggtgagctg ggctgagctg gtttgagttg ggttgagctg agctgagctg 5880
ggctgtgctg gctgagctag gctgagctag gctaggttga gctgggctgg gctgagctga 5940
gctaggctgg gctgatttgg gctgagctga gctgagctag gctgcgttga gctggctggg 6000
ctggattgag ctggctgagc tggctgagct gggctgagct ggcctgggtt gagctgagct 6060
ggactggttt gagctgggtc gatctgggtt gagctgtcct gggttgagct gggctgggtt 6120
gagctgagct gggttgagct gggctcagca gagctgggtt gggctgagct gggttgagct 6180
gagctgggct gagctggcct gggttgagct gggctgagct gagctgggct gagctggcct 6240
gtgttgagct gggctgggtt gagctgggct gagctggatt gagctgggtt gagctgagct 6300
gggctgggct gtgctgactg agctgggctg agctaggctg gggtgagctg ggctgagctg 6360
atccgagcta ggctgggctg gtttgggctg agctgagctg agctaggctg gattgatctg 6420
gctgagctgg gttgagctga gctgggctga gctggtctga gctggcctgg gtcgagctga 6480
gctggactgg tttgagctgg gtcgatctgg gctgagctgg cctgggttga gctgggctgg 6540
gttgagctga gctgggttga gctgggctga gctgagggct ggggtgagct gggctgaact 6600
agcctagcta ggttgggctg agctgggctg gtttgggctg agctgagctg agctaggctg 6660
cattgagcag gctgagctgg gctgagcagg cctggggtga gctgggctag gtggagctga 6720
gctgggtcga gctgagttgg gctgagctgg cctgggttga ggtaggctga gctgagctga 6780
gctaggctgg gttgagctgg ctgggctggt ttgcgctggg tcaagctggg ccgagctggc 6840
ctgggttgag ctgggctcgg ttgagctggg ctgagctgag ccgacctagg ctgggatgag 6900
ctgggctgat ttgggctgag ctgagctgag ctaggctgca ttgagcaggc tgagctgggc 6960
ctggagcctg gcctggggtg agctgggctg agctgcgctg agctaggctg ggttgagctg 7020
gctgggctgg tttgcgctgg gtcaagctgg gccgagctgg cctgggatga gctgggccgg 7080
tttgggctga gctgagctga gctaggctgc attgagcagg ctgagctggg ctgagctggc 7140
ctggggtgag ctgggctgag ctaagctgag ctgggctggt ttgggctgag ctggctgagc 7200
tgggtcctgc tgagctgggc tgagctgacc aggggtgagc tgggctgagt taggctgggc 7260
tcagctaggc tgggttgatc tggcagggct ggtttgcgct gggtcaagct cccgggagat 7320
ggcctgggat gagctgggct ggtttgggct gagctgagct gagctgagct aggctgcatt 7380
gagcaggctg agctgggctg agctggcctg gggtgagctg ggctgggtgg agctgagctg 7440
ggctgaactg ggctaagctg gctgagctgg atcgagctga gctgggctga gctggcctgg 7500
ggttagctgg gctgagctga gctgagctag gctgggttga gctggctggg ctggtttgcg 7560
ctgggtcaag ctgggccgag ctggcctggg ttgagctggg ctgggctgag ctgagctagg 7620
ctgggttgag ctgggctggg ctgagctgag ctaggctgca ttgagctggc tgggatggat 7680
tgagctggct gagctggctg agctggctga gctgggctga gctggcctgg gttgagctgg 7740
gctgggttga gctgagctgg gctgagctgg gctcagcaga gctgggttga gctgagctgg 7800
gttgagctgg ggtgagctgg gctgagcaga gctgggttga gctgagctgg gttgagctgg 7860
gctcgagcag agctgggttg agctgagctg ggttgagctg ggctcagcag agctgggttg 7920
agctgagctg ggttgagctg ggctgagcta gctgggctca gctaggctgg gttgagctga 7980
gctgggctga actgggctga gctgggctga actgggctga gctgggctga gctgggctga 8040
gcagagctgg gctgagcaga gctgggttgg tctgagctgg gttgagctgg gctgagctgg 8100
gctgagcaga gttgggttga gctgagctgg gttcagctgg gctgagctag gctgggttga 8160
gctgggttga gttgggctga gctgggctgg gttgagcgga gctgggctga actgggctga 8220
gctgggctga gcggaactgg gttgatctga attgagctgg gctgagccgg gctgagccgg 8280
gctgagctgg gctaggttga gcttgggtga gcttgcctca gctggtctga gctaggttgg 8340
gtggagctag gctggattga gctgggctga gctgagctga tctggcctca gctgggctga 8400
ggtaggctga actgggctgt gctgggctga gctgagctga gccagtttga gctgggttga 8460
gctgggctga gctgggctgt gttgatcttt cctgaactgg gctgagctgg gctgagctgg 8520
cctagctgga ttgaacgggg gtaagctggg ccaggctgga ctgggctgag ctgagctagg 8580
ctgagctgag ttgaattggg ttaagctggg ctgagatggg ctgagctggg ctgagctggg 8640
ttgagccagg tcggactggg ttaccctggg ccacactggg ctgagctggg cggagctcga 8700
ttaacctggt caggctgagt cgggtccagc agacatgcgc tggccaggct ggcttgacct 8760
ggacacgttc gatgagctgc cttgggatgg ttcacctcag ctgagccagg tggctccagc 8820
tgggctgagc tggtgaccct gggtgacctc ggtgaccagg ttgtcctgag tccgggccaa 8880
gccgaggctg catcagactc gccagaccca aggcctgggc cccggctggc aagccagggg 8940
cggtgaaggc tgggctggca ggactgtccc ggaaggaggt gcacgtggag ccgcccggac 9000
cccgaccggc aggacctgga aagacgcctc tcactcccct ttctcttctg tcccctctcg 9060
ggtcctcaga gagccagtct gccccgaatc tctacccccct cgtctcctgc gtcagccccc 9120
cgtccgatga gagcctggtg gccctgggct gcctggcccg ggacttcctg cccagctccg 9180
tcaccttctc ctggaactac aagaacagca gcaaggtcag cagccagaac atccaggact 9240
tcccgtccgt cctgagaggc ggcaagtact tggcctcctc ccgggtgctc ctaccctctg 9300
tgagcatccc ccaggaccca gaggccttcc tggtgtgcga ggtccagcac cccagtggca 9360
ccaagtccgt gtccatctct gggccaggtg agctgggctc cccctgtggc tgtggcgggg 9420

```
gcggggccgg gtgccgccgg cacagtgacg ccccgttcct gcctgcagtc gtagaggagc   9480
agcccccgt cttgaacatc ttcgtcccca cccgggagtc cttctccagt actccccagc   9540
gcacgtccaa gctcatctgc caggcctcag acttcagccc caagcagatc tccatggcct   9600
ggttccgtga tgggaaacgg gtggtgtctg gcgtcagcac aggccccgtg gagaccctac   9660
agtccagtcc ggtgacctac aggctccaca gcatgctgac cgtcacggag tccgagtggc   9720
tcagccagag cgtcttcacc tgccaggtgg agcacaaagg gctgaactac gagaagaacg   9780
cgtcctctct gtgcacctcc agtgagtgca gcccctcggg ccgggcggcg gggcggcggg   9840
agccacacac acaccagctg ctccctgagc cttggcttcc gggagtggcc aaggcgggga   9900
ggggctgtgc agggcagctg gagggcactg tcagctgggg cccagcaccc cctcaccccg   9960
gcagggcccg ggctccgagg ggccccgcag tcgcaggccc tgctcttggg ggaagcccta  10020
cttggcccct tcagggcgct gacgctcccc ccacccaccc ccgcctagat cccaactctc  10080
ccatcaccgt cttcgccatc gccccctcct tcgctggcat cttcctcacc aagtcggcca  10140
agctttcctg cctggtcacg ggcctcgtca ccagggagag cctcaacatc tcctggaccc  10200
gccaggacgg cgaggttctg aagaccagta tcgtcttctc tgagatctac gccaacggca  10260
ccttcggcgc caggggcgaa gcctccgtct gcgtggagga ctgggagtcg ggcgacaggt  10320
tcacgtgcac ggtgacccac acggacctgc cctcgccgct gaagcagagc gtctccaagc  10380
ccagaggtag gccctgccct gcccctgcct ccgcccggcc tgtgccttgg ccgccggggc  10440
gggagccgag cctggccgag gagcgccctc ggcccccgc ggtcccgacc cacacccctc  10500
ctgctctcct ccccagggat cgccaggcac atgccgtccg tgtacgtgct gccgccggcc  10560
ccggaggagc tgagcctgca ggagtgggcc tcggtcacct gcctggtgaa gggcttctcc  10620
ccggcggacg tgttcgtgca gtggctgcag aagggggagc ccgtgtccgc cgacaagtac  10680
gtgaccagcg cgccggtgcc cgagcccgag cccaaggccc ccgcctccta cttcgtgcag  10740
agcgtcctga cggtgagcgc caaggactgg agcgacgggg agacctacac ctgcgtcgtg  10800
ggccacgagg ccctgcccca cacggtgacc gagaggaccg tggacaagtc caccggtaaa  10860
cccaccctgt acaacgtctc cctggtcctg tccgacacgg ccagcacctg ctactgaccc  10920
cctggctgcc cgccgcggcc ggggccagag cccccgggcg accatcgctc tgtgtgggcc  10980
tgtgtgcaac ccgaccctgt cggggtgagc ggtcgcattt ctgaaaatta gaaataaaag  11040
atctcgtgcc g                                                       11051
```

<210> SEQ ID NO 30
<211> LENGTH: 12048
<212> TYPE: DNA
<213> ORGANISM: Sus sp.

<400> SEQUENCE: 30

```
gcgtccgaag tcaaaaatat ctgcagcctt catgtattca tagaaacaag gaatgtctac     60
attttccaaa gtgggaccag aatcttgggt catgtctaag gcatgtgcat ttgcacatgg    120
taggcaaagg actttgcttc tcccagcaca tctttctgca gagatccatg gaaacaagac    180
tcaactccaa agcagcaaag aagcagcaag ttctcaagtg atctcctctg actccctcct    240
cccaggctaa tgaagccatg ttgcccctgg gggattaagg gcaggtgtcc attgtggcac    300
ccagcccgaa gacaagcaat ttgatcaggt tctgagcact cctgaatgtg gactctggaa    360
ttttctcctc accttgtggc atatcagctt aagtcaagta caagtgacaa acaacataat    420
cctaagaaga gaggaatcaa gctgaagtca aaggatcact gccttggatt ctactgtgaa    480
```

-continued

```
tgatgacctg gaaaatatcc tgaacaacag cttcagggtg atcatcagag acaaaagttc    540
cagagccagg tagggaaacc ctcaagcctt gcaaagagca aaatcatgcc attgggttct    600
taacctgctg agtgatttac tatatgttac tgtgggaggc aaagcgctca aatagcctgg    660
gtaagtatgt caaataaaaa gcaaaagtgg tgtttcttga aatgttagac ctgaggaagg    720
aatattgata acttaccaat aattttcaga atgatttata gatgtgcact tagtcagtgt    780
ctctccaccc cgcacctgac aagcagttta gaatttattc taagaatcta ggtttgctgg    840
gggctacatg ggaatcagct tcagtgaaga gtttgttgga atgattcact aaattttcta    900
tttccagcat aaatccaaga acctctcaga ctagtttatt gacactgctt ttcctccata    960
atccatctca tctccgtcca tcatggacac tttgtagaat gacaggtcct ggcagagact   1020
cacagatgct tctgaaacat cctttgcctt caaagaatga acagcacaca tactaaggat   1080
ctcagtgatc cacaaattag tttttgccac aatggttctt atgataaaag tctttcatta   1140
acagcaaatt gttttataat agttgttctg ctttataata attgcatgct tcactttctt   1200
ttcttttctt ttttttcttt tttttgcttt ttagtgccgc aggtgcagca tatgaaattt   1260
cccaggctag gggtcaaatc agaactacac ctactggcct acgccacagc cacagcaact   1320
caggatctaa gccatgtcgg tgacctacac tacagctcat ggcaatgcca gatccttaac   1380
ccaatgagcg aggccaggga tcgaacccat gtcctcatgg atactagtca ggctcattat   1440
ccgctgagcc ataacaggaa ctcccgagtt tgctttttat caaaattggt acagccttat   1500
tgtttctgaa aaccacaaaa tgaatgtatt cacataattt taaaaggtta aataatttat   1560
gatatacaag acaatagaaa gagaaaacgt cattgcctct ttcttccacg acaacacgcc   1620
tccttaattg atttgaagaa ataactactg agcatggttt agtgtacttc tttcagcaat   1680
tagcctgtat tcatagccat acatattcaa ttaaaatgag atcatgatat cacacaatac   1740
ataccataca gcctataggg atttttacaa tcatcttcca catgactaca taaaaaccta   1800
cctaaaaaaa aaaaaaaccc tacttcatcc tcctattggc tgctttgtgc tccattaaaa   1860
agctctatca taattaggtt atgatgagga tttccatttt ctacctttca agcaacattt   1920
caatgcacag tcttatatac acatttgagc ctacttttct ttttctttct ttttttggtt   1980
tttttttttt tttttttttt ggtctttttg tcttttctaa ggctgcatat ggaggttccc   2040
aggctagctg tctaatcaga actatagctg ctggcctacg ccacatccac agcaatacaa   2100
gatctgagcc atgtctgcaa cttacaccac agctcacagc aacggtggat ccttaaacca   2160
ctgagcaagg ccagggatca aacccataac ttcatggctc ctagttggat ttgttaacca   2220
ctgagccatg atggcaactc ctgagcctac ttttctaatc atttccaacc ctaggacact   2280
tttttaagtt tcattttttct cccccccaccc cctgttttct gaagtgtgtt tgcttccact   2340
gggtgacttc actcccagga tctcatctgc aggatactgc agctaagtgt atgagctctg   2400
aatttgaatc ccaactctgc cactcaaagg gataggagtt tccgatgtgg cccaatggga   2460
tcagtggcat ctctgcagtg ccaggacgca ggttccatcc ctggcccagc acagtgggtt   2520
aagaatctgg cattgctgca gctgaggcat agatttcaat tgtgcctcag atctgatcct   2580
tggcccaagg actgcatatg cctcagggca accaaaaaag agaaaagggg ggtgatagca   2640
ttagtttcta gatttggggg ataattaaat aaagtgatcc atgtacaatg tatggcattt   2700
tgtaaatgct caacaaattt caactattat ggagttccca tcatggctca gtggaaggga   2760
atctgattag catccatgag gacacaggtc caaccccgac cttgctcagt gggcattgct   2820
```

gtgagctgtg gcatgggtta cagacgaagc tcggatctgg cattgctgtg gctgtggtgt 2880
aagccagcaa ctacagctct cattcagccc ctagcctggg aacctccata tgcctaaaag 2940
acaaaaaata aaatttaaat taaaaataaa gaaatgttaa ctattatgat tggtactgct 3000
tgcattactg caaagaaagt cactttctat actctttaat atcttagttg actgtgtgct 3060
cagtgaacta ttttggacac ttaatttcca ctctcttcta tctccaactt gacaactctc 3120
tttcctctct tctggtgaga tccactgctg actttgctct ttaaggcaac tagaaaagtg 3180
ctcagtgaca aaatcaaaga aagttacctt aatcttcaga attacaatct taagttctct 3240
tgtaaagctt actatttcag tggttagtat tattccttgg tcccttacaa cttatcagct 3300
ctgatctatt gctgattttc aactatttat tgttggagtt ttttcctttt ttccctgttc 3360
attctgcaaa tgtttgctga gcatttgtca agtgaagata ctggactggg ccttccaaat 3420
ataagacaat gaaacatcgg gagttctcat tatggtgcag cagaaacgaa tccaactagg 3480
aaatgtgagg ttgcaggttc gatccctgcc cttgctcagt gggttaagga tccagcatta 3540
ccgtgagctg tggtgtaggt tgcagacgtg gctcagatcc tgcgttgctg tggctgtggc 3600
ataggctggc agctctagct ctgattcgac cgctagcctg ggaacctcca tgcgccccga 3660
gtgcagccct taaaaagcaa aaaaaaaaga aagaaagaaa aagacaatga aacatcaaac 3720
agctaacaat ccagtagggt agaaagaatc tggcaacaga taagagcgat taaatgttct 3780
aggtccagtg accttgcctc tgtgctctac acagtcgtgc cacttgctga gggagaaggt 3840
ctctcttgag ttgagtcctg aaagacatta gttgttcaca aactaatgcc agtgagtgaa 3900
ggtgtttcca agcagaggga gagtttggta aaaagctgga agtcacagaa agactctaaa 3960
gagtttagga tggtgggagc aacatacgct gagatggggc tggaaggtta agagggaaac 4020
aactatagta agtgaagctg gactcacagc aaagtgagga cctcagcatc cttgatgggg 4080
ttaccatgga aacaccaagg cacaccttga tttccaaaac agcaggcacc tgattcagcc 4140
caatgtgaca tggtgggtac ccctctagct ctacctgttc tgtgacaact gacaaccaac 4200
gaagttaagt ctggattttc tactctgctg atccttgttt ttgtttcaca cgtcatctat 4260
agcttcatgc caaaatagag ttcaaggtaa gacgcgggcc ttggtttgat atacatgtag 4320
tctatcttgt ttgagacaat atggtggcaa ggaagaggtt caaacaggaa aatactctct 4380
aattatgatt aactgagaaa agctaaagag tcccataatg acactgaatg aagttcatca 4440
tttgcaaaag ccttcccccc cccccaggag actataaaaa agtgcaattt tttaaatgaa 4500
cttatttaca aaacagaaat agactcacag acataggaaa cgaacagatg gttaccaagg 4560
gtgaaaggga gtaggaggga taaataagga gtctggggtt agcagataca ccccagtgta 4620
cacaaaataa acaacaggga cctactatat agcacaggga actatatgca gtagcttaca 4680
ataacctata atggaaaaga atgtgaaaaa gaatatatgt atgcgtgtgt gtgtaactga 4740
atcactttgc tgtaacctga atctaacata acattgtaaa tcaactacag tttttttttt 4800
ttttaagtgc agggttttgg tgtttttttt ttttcatttt tgtttttgtt tttgtttttt 4860
gctttttagg gccacaccca gacatatggg ggttcccagg ctaggggtct aattagagct 4920
acagttgccg gcttgcacca cagccacagc aacatcagat ccgagccgca cttgcgactt 4980
acaccacagc tcatggcaat accagatcct taacccactg agcaaggccc agggatcgta 5040
cccgcaacct catggttcct agtcagattc atttctgctg cgctacaatg ggaactccaa 5100
gtgcagtttt ttgtaatgtg cttgtctttc tttgtaattc atattcatcc tacttcccaa 5160
taaataaata aatacataaa taataaacat accattgtaa atcaactaca atttttttta 5220
aatgcagggt ttttgttttt tgttttttgt tttgtctttt tgccttttct agggccgctc 5280
ccatggcata tggaggttcc caggctaggg gtcgaatcgg agctgtagcc accggcctac 5340
gccagagcca cagcaacgcg ggatccgagc cgcgtctgca acctacacca cagctcacgg 5400
caacgccgga tcgttaaccc actgagcaag ggcagggatc gaacctgcaa cctcatggtt 5460
cctagtcaga ttcgttaact actgagccac aacggaaact cctaaagtgc agtttttaaa 5520
tgtgcttgtc tttctttgta atttacactc aacctacttc ccaataaata aataaataaa 5580
caaataaatc atagacatgg ttgaattcta aaggaaggga ccatcaggcc ttagacagaa 5640
atacgtcatc ttctagtatt ttaaaacaca ctaaagaaga caaacatgct ctgccagaga 5700
agcccagggc ctccacagct gcttgcaaag ggagttaggc ttcagtagct gacccaaggc 5760
tctgttcctc ttcagggaaa agggtttttg ttcagtgaga cagcagacag ctgtcactgt 5820
ggtggacgtt cggccaagga accaagctgg aactcaaacg taagtcaatc caaacgttcc 5880
ttccttggct gtctgtgtct tacggtctct gtggctctga aatgattcat gtgctgactc 5940
tctgaaacca gactgacatt ctccagggca aaactaaagc ctgtcatcaa actggaaaac 6000
tgagggcaca ttttctgggc agaactaaga gtcaggcact gggtgaggaa aaacttgtta 6060
gaatgatagt ttcagaaact tactgggaag caaagcccat gttctgaaca gagctctgct 6120
caagggtcag gaggggaacc agtttttgta caggagggaa gttgagacga acccctgtgt 6180
atatggtttc ggcgcgggga ccaagctgga gctcaaacgt aagtggcttt ttccgactga 6240
ttctttgctg tttctaattg ttggttggct ttttgtccat tttcagtgt tttcatcgaa 6300
ttagttgtca gggaccaaac aaattgcctt cccagattag gtaccaggga ggggacattg 6360
ctgcatggga gaccagaggg tggctaattt ttaacgtttc caagccaaaa taactgggga 6420
agggggcttg ctgtcctgtg agggtaggtt tttatagaag tggaagttaa ggggaaatcg 6480
ctatggttca cttttggctc ggggaccaaa gtggagccca aaattgagta catttttccat 6540
caattatttg tgagattttt gtcctgttgt gtcatttgtg caagtttttg acattttggt 6600
tgaatgagcc attcccaggg acccaaaagg atgagaccga aaagtagaaa agagccaact 6660
tttaagctga gcagacagac cgaattgttg agtttgtgag gagagtaggg tttgtaggga 6720
gaaaggggaa cagatcgctg gctttttctc tgaattagcc tttctcatgg gactggcttc 6780
agagggggtt tttgatgagg gaagtgttct agagccttaa ctgtgggttg tgttcggtag 6840
cgggaccaag ctggaaatca aacgtaagtg cacttttcta ctccttttttc tttcttatac 6900
gggtgtgaaa ttggggactt ttcatgtttg gagtatgagt tgaggtcagt tctgaagaga 6960
gtgggactca tccaaaaatc tgaggagtaa gggtcagaac agagttgtct catggaagaa 7020
caaagaccta gttagttgat gaggcagcta aatgagtcag ttgacttggg atccaaatgg 7080
ccagacttcg tctgtaacca acaatctaat gagatgtagc agcaaaaaga gatttccatt 7140
gaggggaaag taaaattgtt aatattgtgg atcacctttg gtgaagggac atccgtggag 7200
attgaacgta agtatttttt ctctactacc ttctgaaatt tgtctaaatg ccagtgttga 7260
cttttagagg cttaagtgtc agttttgtga aaaatgggta aacaagagca tttcatattt 7320
attatcagtt tcaaaagtta aactcagctc caaaaatgaa tttgtagaca aaaagattaa 7380
tttaagccaa attgaatgat tcaaaggaaa aaaaaattag tgtagatgaa aaaggaattc 7440
ttacagctcc aaagagcaaa agcgaattaa ttttctttga actttgccaa atcttgtaaa 7500
tgatttttgt tctttacaat ttaaaaaggt tagagaaatg tatttcttag tctgttttct 7560

-continued

```
ctcttctgtc tgataaatta ttatatgaga taaaaatgaa aattaatagg atgtgctaaa   7620
aaatcagtaa gaagttagaa aaatatatgt ttatgttaaa gttgccactt aattgagaat   7680
cagaagcaat gttattttta aagtctaaaa tgagagataa actgtcaata cttaaattct   7740
gcagagattc tatatcttga cagatatctc ctttttcaaa aatccaattt ctatggtaga   7800
ctaaatttga aatgatcttc ctcataatgg agggaaaaga tggactgacc ccaaaagctc   7860
agatttaaag aaatctgttt aagtgaaaga aaataaaaga actgcatttt ttaaaggccc   7920
atgaatttgt agaaaaatag gaaatatttt aataagtgta ttcttttatt ttcctgttat   7980
tacttgatgg tgtttttata ccgccaagga ggccgtggca ccgtcagtgt gatctgtaga   8040
ccccatggcg gcctttttc gcgattgaat gaccttggcg gtgggtcccc agggctctgg   8100
tggcagcgca ccagccgcta aaagccgcta aaaactgccg ctaaaggcca cagcaacccc   8160
gcgaccgccc gttcaactgt gctgacacag tgatacagat aatgtcgcta acagaggaga   8220
atagaaatat gacgggcaca cgctaatgtg gggaaaagag ggagaagcct gatttttatt   8280
ttttagagat tctagagata aaattcccag tattatatcc ttttaataaa aaatttctat   8340
taggagatta taaagaattt aaagctattt ttttaagtgg ggtgtaattc tttcagtagt   8400
ctcttgtcaa atggatttaa gtaatagagg cttaatccaa atgagagaaa tagacgcata   8460
accctttcaa ggcaaaagct acaagagcaa aaattgaaca cagcagccag ccatctagcc   8520
actcagattt tgatcagttt tactgagttt gaagtaaata tcatgaaggt ataattgctg   8580
ataaaaaaat aagatacagg tgtgacacat ctttaagttt cagaaattta atggcttcag   8640
taggattata tttcacgtat acaaagtatc taagcagata aaaatgccat taatggaaac   8700
ttaatagaaa tatattttta aattccttca ttctgtgaca gaaattttct aatctgggtc   8760
ttttaatcac ctaccctttg aaagagttta gtaatttgct atttgccatc gctgtttact   8820
ccagctaatt tcaaaagtga tacttgagaa agattatttt tggtttgcaa ccacctggca   8880
ggactatttt agggccattt taaaactctt ttcaaactaa gtattttaaa ctgttctaaa   8940
ccatttaggg ccttttaaaa atcttttcat gaatttcaaa cttcgttaaa agttattaag   9000
gtgtctggca agaacttcct tatcaaatat gctaatagtt taatctgtta atgcaggata   9060
taaaattaaa gtgatcaagg cttgacccaa acaggagtat cttcatagca tatttcccct   9120
ccttttttc tagaattcat atgattttgc tgccaaggct attttatata atctctggaa   9180
aaaaaatagt aatgaaggtt aaaagagaag aaaatatcag aacattaaga attcggtatt   9240
ttactaactg cttggttaac atgaaggttt ttattttatt aaggtttcta tctttataaa   9300
aatctgttcc cttttctgct gatttctcca agcaaaagat tcttgatttg tttttaact    9360
cttactctcc cacccaaggg cctgaatgcc cacaaagggg acttccagga ggccatctgg   9420
cagctgctca ccgtcagaag tgaagccagc cagttcctcc tgggcaggtg gccaaaatta   9480
cagttgaccc ctcctggtct ggctgaacct tgccccatat ggtgacagcc atctggccag   9540
ggcccaggtc tccctctgaa gcctttggga ggagagggag agtggctggc ccgatcacag   9600
atgcggaagg ggctgactcc tcaaccgggg tgcagactct gcagggtggg tctgggccca   9660
acacacccaa agcacgccca ggaaggaaag gcagcttggt atcactgccc agagctagga   9720
gaggcaccgg gaaaatgatc tgtccaagac ccgttcttgc ttctaaactc cgagggggtc   9780
agatgaagtg gttttgtttc ttggcctgaa gcatcgtgtt ccctgcaaga agcggggaac   9840
acagaggaag gagagaaaag atgaactgaa caaagcatgc aaggcaaaaa aggccttagg   9900
atggctgcag gaagttagtt cttctgcatt ggctccttac tggctcgtcg atcgcccaca   9960
```

```
aacaacgcac ccagtggaga acttccctgt tacttaaaca ccattctctg tgcttgcttc  10020
ctcaggggct gatgccaagc catccgtctt catcttcccg ccatcgaagg agcagttagc  10080
gaccccaact gtctctgtgg tgtgcttgat caataacttc ttccccagag aaatcagtgt  10140
caagtggaaa gtggatgggg tggtccaaag cagtggtcat ccggatagtg tcacagagca  10200
ggacagcaag gacagcacct acagcctcag cagcaccctc tcgctgccca cgtcacagta  10260
cctaagtcat aatttatatt cctgtgaggt cacccacaag accctggcct cccctctggt  10320
cacaagcttc aacaggaacg agtgtgaggc ttagaggccc acaggcccct ggcctgcccc  10380
cagccccagc ccccctcccc acctcaagcc tcaggccctt gccccagagg atccttggca  10440
atcccccagc ccctcttccc tcctcatccc ctccccctct ttggctttaa ccgtgttaat  10500
actgggggt gggggaatga ataaataaag tgaacctttg cacctgtgat ttctctctcc  10560
tgtctgattt taaggttgtt aaatgttgtt ttccccatta tagttaatct tttaaggaac  10620
tacatactga gttgctaaaa actacaccat cacttataaa attcacgcct tctcagttct  10680
cccctcccct cctgtcctcc gtaagacagg cctccgtgaa acccataagc acttctcttt  10740
acaccctctc ctgggccggg gtaggagact ttttgatgtc ccctcttcag caagcctcag  10800
aaccattttg agggggacag ttcttacagt cacattcctg tgatctaatg actttagtta  10860
ccgaaaagcc agtctctcaa aaagaaggga acggctagaa accaagtcat agaaatatat  10920
atgtataaaa tatatatata tccatatatg taaaataaca aaataatgat aacagcatag  10980
gtcaacaggc aacagggaat gttgaagtcc attctggcac ttcaatttaa gggaatagga  11040
tgccttcatt acattttaaa tacaatacac atggagagct tcctatctgc caaagaccat  11100
cctgaatgcc ttccacactc actacaaggt taaaagcatt cattacaatg ttgatcgagg  11160
agttcccgtt gtggctcagc aggttaagaa cgtgactggt atccaggagg atgcgggttt  11220
ggtccccagc ctcgctcagt ggattaagga tccagtgttg ctgcaagatc acgggctcag  11280
atcccgtgtt ctatggctat ggtgtaggct ggtagctgca tgcagcccta atttgacccc  11340
tagcctggga actgccatat gccacatgtg aggcccttaa aacctaaaag aaaaaaaaag  11400
aaaagaaata tcttacaccc aatttataga taagagagaa gctaaggtgg caggcccagg  11460
atcaaagccc tacctgccta tcttgacacc tgatacaaat tctgtcttct agggtttcca  11520
acactgcata gaacagaggg tcaaacatgc taccctccca gggactcctc ccttcaaatg  11580
acataaattt tgttgcccat ctctgggggc aaaactcaac aatcaatggc atctctagta  11640
ccaagcaagg ctcttctcat gaagcaaaac tctgaagcca gatccatcat gacccaagga  11700
agtaaagaca ggtgttactg gttgaactgt atccttcaat tcaatatgct caatttccaa  11760
ctcccagtcc ccgtaaatac aaccccccttt gggaagagag tccttgcaga tgtagccacg  11820
ttaaaaagag attatacaga aaggctagtg aggatgcagt gaaacgggat ctttcataca  11880
ttgctggtgg aaatgtaaaa tgctgcaggc actctagaaa ataatttgcc agttttttga  11940
aaagctaaac aaaatagttt agttgcattc tgggttattt atcccccaga aattaaaaat  12000
tatgtccgca caaaaacgtg tacataatca ttcataacag ccttgtac              12048
```

<210> SEQ ID NO 31
<211> LENGTH: 126068
<212> TYPE: DNA
<213> ORGANISM: Bovine sp.
<220> FEATURE:
<221> NAME/KEY: misc_feature
<222> LOCATION: (3591)..(3690)

<223> OTHER INFORMATION: n is a, c, g, or t
<220> FEATURE:
<221> NAME/KEY: misc_feature
<222> LOCATION: (6955)..(6955)
<223> OTHER INFORMATION: n is a, c, g, or t
<220> FEATURE:
<221> NAME/KEY: misc_feature
<222> LOCATION: (6967)..(6967)
<223> OTHER INFORMATION: n is a, c, g, or t
<220> FEATURE:
<221> NAME/KEY: misc_feature
<222> LOCATION: (6974)..(6974)
<223> OTHER INFORMATION: n is a, c, g, or t
<220> FEATURE:
<221> NAME/KEY: misc_feature
<222> LOCATION: (6976)..(6978)
<223> OTHER INFORMATION: n is a, c, g, or t
<220> FEATURE:
<221> NAME/KEY: misc_feature
<222> LOCATION: (6980)..(6980)
<223> OTHER INFORMATION: n is a, c, g, or t
<220> FEATURE:
<221> NAME/KEY: misc_feature
<222> LOCATION: (6985)..(6985)
<223> OTHER INFORMATION: n is a, c, g, or t
<220> FEATURE:
<221> NAME/KEY: misc_feature
<222> LOCATION: (6987)..(6988)
<223> OTHER INFORMATION: n is a, c, g, or t
<220> FEATURE:
<221> NAME/KEY: misc_feature
<222> LOCATION: (7000)..(7000)
<223> OTHER INFORMATION: n is a, c, g, or t
<220> FEATURE:
<221> NAME/KEY: misc_feature
<222> LOCATION: (7534)..(7633)
<223> OTHER INFORMATION: n is a, c, g, or t
<220> FEATURE:
<221> NAME/KEY: misc_feature
<222> LOCATION: (7842)..(7842)
<223> OTHER INFORMATION: n is a, c, g, or t
<220> FEATURE:
<221> NAME/KEY: misc_feature
<222> LOCATION: (11197)..(11197)
<223> OTHER INFORMATION: n is a, c, g, or t
<220> FEATURE:
<221> NAME/KEY: misc_feature
<222> LOCATION: (12793)..(12892)
<223> OTHER INFORMATION: n is a, c, g, or t
<220> FEATURE:
<221> NAME/KEY: misc_feature
<222> LOCATION: (18660)..(18759)
<223> OTHER INFORMATION: n is a, c, g, or t
<220> FEATURE:
<221> NAME/KEY: misc_feature
<222> LOCATION: (23231)..(23330)
<223> OTHER INFORMATION: n is a, c, g, or t
<220> FEATURE:
<221> NAME/KEY: misc_feature
<222> LOCATION: (27257)..(27356)
<223> OTHER INFORMATION: n is a, c, g, or t
<220> FEATURE:
<221> NAME/KEY: misc_feature
<222> LOCATION: (27727)..(27727)
<223> OTHER INFORMATION: n is a, c, g, or t
<220> FEATURE:
<221> NAME/KEY: misc_feature
<222> LOCATION: (32250)..(32349)
<223> OTHER INFORMATION: n is a, c, g, or t
<220> FEATURE:
<221> NAME/KEY: misc_feature
<222> LOCATION: (39216)..(39315)
<223> OTHER INFORMATION: n is a, c, g, or t
<220> FEATURE:
<221> NAME/KEY: misc_feature
<222> LOCATION: (41326)..(41425)
<223> OTHER INFORMATION: n is a, c, g, or t
<220> FEATURE:
<221> NAME/KEY: misc_feature
<222> LOCATION: (48650)..(48749)
<223> OTHER INFORMATION: n is a, c, g, or t
<220> FEATURE:
<221> NAME/KEY: misc_feature
<222> LOCATION: (55204)..(55204)
<223> OTHER INFORMATION: n is a, c, g, or t
<220> FEATURE:
<221> NAME/KEY: misc_feature
<222> LOCATION: (56436)..(56535)
<223> OTHER INFORMATION: n is a, c, g, or t
<220> FEATURE:
<221> NAME/KEY: misc_feature
<222> LOCATION: (61281)..(61281)
<223> OTHER INFORMATION: n is a, c, g, or t
<220> FEATURE:
<221> NAME/KEY: misc_feature
<222> LOCATION: (61394)..(61493)
<223> OTHER INFORMATION: n is a, c, g, or t
<220> FEATURE:
<221> NAME/KEY: misc_feature
<222> LOCATION: (68709)..(68808)
<223> OTHER INFORMATION: n is a, c, g, or t
<220> FEATURE:
<221> NAME/KEY: misc_feature
<222> LOCATION: (73149)..(73248)
<223> OTHER INFORMATION: n is a, c, g, or t
<220> FEATURE:
<221> NAME/KEY: misc_feature
<222> LOCATION: (80571)..(80670)
<223> OTHER INFORMATION: n is a, c, g, or t
<220> FEATURE:
<221> NAME/KEY: misc_feature
<222> LOCATION: (91799)..(91898)
<223> OTHER INFORMATION: n is a, c, g, or t
<220> FEATURE:
<221> NAME/KEY: misc_feature
<222> LOCATION: (106600)..(106699)
<223> OTHER INFORMATION: n is a, c, g, or t
<220> FEATURE:
<221> NAME/KEY: misc_feature
<222> LOCATION: (121987)..(121987)
<223> OTHER INFORMATION: n is a, c, g, or t
<220> FEATURE:
<221> NAME/KEY: misc_feature
<222> LOCATION: (121993)..(121993)
<223> OTHER INFORMATION: n is a, c, g, or t

<400> SEQUENCE: 31
tgggttctat gccacccagc ttggtctctg atggtcactt gaggccccca tctcatggca 60
aagagggaac tggattgcag atgagggacc gtgggcagac atcagaggga cacagaaccc 120
tcaaggctgg ggaccagagt cagagggcca ggaagggctg gggaccttgg gtctagggat 180
ccgggtcagg gactcggcaa aggtggaggg ctccccaagg cctccatggg gcggacctgc 240
agatcctggg ccggccaggg acccagggaa agtgcaaggg gaagacgggg gaggagaagg 300
tgctgaactc agaactgggg aaagagatag gaggtcagga tgcaggggac acggactcct 360
gagtctgcag gacacactcc tcagaagcag gagtccctga agaagcagag agacaggtac 420
cagggcagga aacctccaga cccaagaaga ctcagagagg aacctgagct cagatctgcg 480
gatgggggga ccgaggacag gcagacaggc tccccctcga ccagcacaga ggctccaagg 540
gacacagact tggagaccaa cggacgcctt cgggcaaagg ctcgaacaca catgtcagct 600
caaaatatac ctggactgac tcacaggagg ccagggaggc cacatcatcc actcagggga 660
cagactgcca gccccaggca gaccccatca accgtcagac gggcaggcaa ggagagtgag 720
ggtcagatgt ctgtgtggga aaccaagaac cagggagtct caggacagcg ctggcagggg 780
tccaggctca ggctttccca ggaagatggg gaggtgcctg agaaaacccc acccaccttc 840
cctggcacag gccctctggc tcacagtggt gcctggactc ggggtcctgc tgggctctca 900

-continued

```
aaggatcctg tgtcccctg tgacacagac tcaggggctc ccatgacggg caccagacct    960
ctgattgtgg tcttcttccc ctcgcccact ttgcaggtca gcccaagtcc acaccctcgg   1020
tcaccctgtt cccgccctcc aaggaggagc tcagcaccaa caaggccacc ctggtgtgtc   1080
tcatcagcga cttctacccg ggtagcgtga ccgtggtcta gaaggcagac ggcagcacca   1140
tcacccgcaa cgtggagacc acccgggcct ccaaacagag caacagcaag tacgcggcca   1200
gcagctacct gagcctgatg ggcagcgact ggaaatcgaa aggcagttac agctgcgagg   1260
tcacgcacga ggggagcacc gtgacgaaga cagtgaagcc tcagagtgtt cttagggccc   1320
tgggccccca ccccggaaag ttctacctc ccaccctggt tccccctagc ccttcctcct   1380
gcacacaatc agctcttaat aaaatgtcct cattgtcatt cagaaatgaa tgctctctgc   1440
tcatttttgt tgatacattt ggtgccctga gctcagttat cttcaaagga aacaaatcct   1500
cttagccttt gggaatcagg agagagggtg gaagcttggg ggtttgggga gggatgattt   1560
cactgtcatc cagaatcccc cagagaacat tctggaacag gggatggggc cactgcagga   1620
gtggaagtct gtccaccctc cccatcagcc gccatgcttc ctcctctgtg tggaccgtgt   1680
ccagctctga tggtcacggc aacacactct ggttgccacg ggcccagggc agtatctcgg   1740
ctccctccac tgggtgctca gcaatcacat ctggaagctg ctcctgctca agcggccctc   1800
tgtccactta gatgatgacc cccctgaagt catgcgtgtt ttggctgaaa ccccaccctg   1860
gtgattccca gtcgtcacag ccaagactcc ccccgactcg acctttccaa gggcactacc   1920
ctctgcccct cccccagggc tccccctcac agtcttcagg ggaccggcaa gcccccaacc   1980
ctggtcactc atctcacagt tcccccaggt cgccctcctc ccacttgcat ggcaggaggg   2040
tcccagctga cttcgaggtc tctgaccagc ccagctctgc tctgcgaccc cttaaaactc   2100
agcccaccac ggagcccagc accatctcag gtccaagtgg ccgttttggt tgatgggttc   2160
cgtgagctca agcccagaat caggttaggg aggtcgtggc gtggtcatct ctgaccttgg   2220
gtggtttctt aggagctcag aatgggagct gatacacgga taggctgtgc taggcactcc   2280
cacgggacca cacgtgagca ccgttagaca cacacacaca cacacacaca cacacacaca   2340
cacacacgag tcactacaaa cacggccatg ttggttggac gcatctctag gaccagaggc   2400
gcttccagaa tccgccatgg cctcactctg cggagaccac agctccatcc cctccgggct   2460
gaaaaccgtc tcctcaccct cccaccgggg tgacccccaa agctgctcac gaggagcccc   2520
cacctcctcc aggagaagtt ccctgggacc cggtgtgaca cccagccgtc cctcctgccc   2580
ctcccccgcc tggagatggc cggcgcccca tttcccaggg gtgaactcac aggacgggag   2640
gggtcgctcc cctcacccgc ccggagggtc aaccagcccc tttgaccagg aggggggcgg   2700
acctggggct ccgagtgcag ctgcaggcgg gcccccgggg gtggcggggc tggcggcagg   2760
gtttatgctg gaggctgtgt cactgtgcgt gtttgctcgg tggagggacc cagctggcca   2820
tccggggtga gtctcccctt tccagctttc cggagtcagg agtgacaaat gggtagattc   2880
ttgtgttttt cttacccatc tggggctgag gtctccgtca ccctaggcct gtaaccctcc   2940
cccttttagc ctgttccctc tgggcttctt cacgtttcct tgagggacag tttcactgtc   3000
acccagcaaa gcccagagaa tatccagatg gggcaggcaa tatgggacgg caagctagtc   3060
caccctctta ccttgggctc cccgcggcct ccggataatg tctgagctgc ctccctggat   3120
gcttcacctt ctgagactgt gaggcaagaa accccctccc caaaagggag gagacccgac   3180
cccagtgcag atgaacgtgc tgtgagggga ccctgggagt aagtggggtc tggcggggac   3240
cgtgatcatt gcagactgat gccccaggca gggtgagagg tcatggccgc cgacaccagc   3300
```

-continued

```
agctgcaggg agcacaggcc gggggcaagt catgcagaca ggacaggacg tgtgaccctg   3360
aagagtcaga gtgacacgcg ggggggggc ccggagctcc cgagattagg gcttgggtcc   3420
taacgggatc caggagggtc cacgggccca ccccagccct ctccctgcac ccaatcaact   3480
tgcaataaaa cgtcctctat tgtcttacaa aaaccctgct ctctgctcat gtttttcctt   3540
gccccgcatt taatcgtcaa cctctccagg attctggaac tggggtgggg nnnnnnnnnn   3600
nnnnnnnnnn nnnnnnnnnn nnnnnnnnnn nnnnnnnnnn nnnnnnnnnn nnnnnnnnnn   3660
nnnnnnnnnn nnnnnnnnnn nnnnnnnnnn agcttatgtg gtgggcaggg gggtagtaag   3720
atcaaaagtg cttaaattaa taaagccggc atgatatacg agtttggata aaaaatagat   3780
ggaaaagtaa gaaaggacag gaggggggtg aggcggaaga aagggggaag aaggaaaaaa   3840
aaataagaga gaggaacaaa gaaagggagg ggggccggtg atgggggtgg gatagaatat   3900
aataattgga gtaaagagta gcgggtggct gttaattccg gggggggaata gagaaaaaaa   3960
aaaaaaaatg tgcgggtggg cggtaagtat ggagatttta taaatattat gtgtggaata   4020
atgagcgggg gtggacgggc aaggcgagag taaaaagggg cgagagaaaa aaattaggat   4080
ggaatatatg gggtaaattt taaatagagg gtgatatatg ttagattgag caagatataa   4140
atatagatgg tgggggaaaa gagacaaggg tgagcgccaa aacgccctcc cgtatcattt   4200
gccttccttc ctttaccacc tcgttcaaac tctttttcga gaaccctgaa gcggtcaggc   4260
ccggggctgg gggtgggata cccggggagg ggctgcgcct cctcctttgc agagggggtc   4320
gaggagtggg agctgaggca ggagactggc aggctggaga gatggctgtt gacttcctgc   4380
ctgtttgaac tcacagtcac agtgccagac ccactgaatt gggctaaata ccatattttt   4440
ctggggagag agtgtagagc gagcgactga ggcgagctca tgtcatctac agggccgcca   4500
gctgcaggga ctttgtgtgt gtcgtgctcg ttgctcagtt gtgtccgact ctttatgact   4560
tcatggactg taacctgcca ggctcctctg tccgtggaat tctccaggca agaatactgg   4620
agtgggtagc cattctcatc tccgggggat cttcctgacc caagaatcaa acctgagtct   4680
cccgcattgc aggcagcttc tttcttgtct gagccaccag ggaagcccct taagtggagg   4740
atctaaatag agtgtttagg agtataagag aaaggaagga cgtctataca agatccttcg   4800
gttcctgtaa ctacgactcg agttaacaag ccctgtgtga gtgagttgcc agtaattatt   4860
gctaacctgt ttctttcact cactgagcca ggtatcctgt gagacggcat acttacctcc   4920
tcttctgcat tcctcgggat ggagctgtgc ggtggcctct aggactacca catcgaccag   4980
gtcagaccca gggacagagg attgctgaga tgcactgaga agtttgtcag cctaggtctt   5040
cacccacaca gactgtgctg tcgtctacca cgtaattctt cctgtccaaa gaactggtta   5100
aacgctcctg aagcgtattc tggtctgctt caaaaagtgc ctctttcctt tataagttcc   5160
gccaatcctg gactttgtcc caggccagtc tactttattt gtgggaaagg tttttttggt   5220
ctttttttgtt ttaaactctg cagaaattgc ttacactttt ggtgtgcaat ggctcactct   5280
tacggttcta gctgtattca aaggggttgc ttttctttgt ttttaaagct ttttgaacgt   5340
ggaccatttt taaagtcttt attaaacgtc taacatcgtt tctggtttat tttctggtgg   5400
tctggccatg aggcctacgg gtcttagctc ccctaccagg gtccaaccca catcccttgc   5460
actggacggc aaggtcttaa cctttgaacc accagagagc ttctgaaagg ggctgctttt   5520
ctccaatcct ctttgctccc tgcctgctgg tagggattca gcacccctgc aatagccctg   5580
tctgttctta ggggctcagt agcctttctg cctgggtgtg gagctggggt tgtaagagag   5640
```

-continued

```
cttcatggat ttggacacga cctacgactc agaggtaaga ctccatctta gcgctgtaat   5700
gacctctttc caacaaccac ccccaccacc ctggaccact gatcaggaga gatgattctc   5760
tctcttatca tcaacgtggt cagtcccaaa cttgcacccg gcctgtcata gatgtagcag   5820
gtaagcaata aatatttgtt gaatgttaag tgaattgaaa taacataagt gaaaaagaaa   5880
acacttaaaa acatgtgttt ttataattac acagtaaaca tataatcatt gtagaaaaaa   5940
atcgaaagag tggcgggggc caagtgaaaa ccaccatccc tggtatgtcc acccgcccgg   6000
gtagccccag gtaagaggtg cggacacgga tggccctgta gacacagaga cacacgctca   6060
tatgctgggt cttgtcttgt gacctcttgg ggatgatgtt attttcacga tgccattcaa   6120
accttctacc acaccatttt tagagggtcg ttcatcgtaa atcagttcac tgctttgttt   6180
tctgattttg aaagtgtcac attcttcgag aaatgagaag gaacaggcgc gcataaggaa   6240
gaaagtaaac acgtggcctt gcttccaggg ggcactcagc gtgttggtgt gcacgctggc   6300
agtcttttct ctgtgacagt catggccttt tcccaaaggt gggctcagat aagaccgcct   6360
cccatcccct gtccctgtcc ccgtccccta cggtggaacc cacccacggc acgtctccga   6420
ggccctttgg ggctgtggac gttaggctgt gtggacatgc tgctggtggg gacccagggc   6480
tgggcagcac gttgtccctg ggtcccgggc cagtgaggag ctcccaagga gcagggctgc   6540
tgggccaaag ggcagtgcgt cccgaggcca tggacaaggg gatacatttc ctgctgaagg   6600
gctggactgc gtctccctgg ggccccttgg agtcatgggc agtggggagg cctctgctca   6660
ccccgttgcc cacccatggc tcagtctgca gccaggagcg cctggggctg ggacgccgag   6720
gccggagccc ctccctgctg tgctgacggg ctcggtgacc ctgccgcccc ctccctgggg   6780
ccctgctgac cgcgggggcc accccggcca gttctgagat tcccctgggg tccagccctc   6840
caggatccca ggacccagga tggcaaggat gttgaggagg cagctagggg gcagcatcag   6900
gcccagaccg gggctgggca ggggctgggc gcaggcgggt ggggggggtct gcacnccccc   6960
acctgcnagc tgcncnnncn tttgntnncg tcctccctgn tcctggtctg tcccgcccgg   7020
ggggcccccc ctggtcttgt ttgttccccc tccccgtccc ttccccccctt tttccgtcct   7080
cctcccttct tttattcgcc ccttgtggtc gttttttttc cgtccctctt ttgttttttt   7140
gtctttttct ttttccccct cttctccctt gctctctttt tcattcgtcg gtttttctgc   7200
tcccttccct ctcccccccg ctttttttcc ctgtctgctt tttgtgttct ccctctctac   7260
ccccccctgca gcctattttt tttatatatc catttccccc tagtatttgg cccccgctta   7320
cttctcccta atttttattt tcctttcttt aactaaaatc accgtgtggt tataagtttt   7380
aacctttttt gcaccgccca caatgcaatc ttcacgcacg cccccccccgt cagcctcctt   7440
aaataccttt gcctactgcc cccctccttg tataataacg cgtcacgtgg tcaaccatta   7500
tcacctctcc accaccttac cacattttcc ttcnnnnnnn nnnnnnnnnn nnnnnnnnnn   7560
nnnnnnnnnn nnnnnnnnnn nnnnnnnnnn nnnnnnnnnn nnnnnnnnnn nnnnnnnnnn   7620
nnnnnnnnnn nnntgaaaaa agaaaaggct gggcaggttt taatatgggg gggttggagt   7680
ggaatgaaaa tgcattggag tggttgcaac aaatggaaag gtctcaggag cgctcctccc   7740
ccatcaggag ctggaaagaa gtggaagcaa agcaaggaat tcgtgtgatg gccagaggtc   7800
aggggcaggg agctgcaaag actgccggct gtttgtgact gnccgtctcc gggtgcattt   7860
gttagcaggg aggcattaca ctcatgtctt ggtttgctaa ctaattctta ctattgttta   7920
gttgcaaggt catgtctgac tctttgcaac ccagggactg cagcccgcca ggctcctctg   7980
tccatgggat ttcgcaggca agaatactgg aggtggtagc cattttcttc accatgggat   8040
```

cttcccgagc cagaaatgga acccgagtcg cctcctgtgc atggggtctg ctgcctaaca 8100
ggcagatatt tgacgtctga gccaacaggg aggacagacg gtaattatac caaccattga 8160
aagaggaatt acacactaat ctttatcaaa atctttcaaa cagtagagga gaaaggatac 8220
tctctagttt attccataaa gttggaatta cgcttatcaa taaagacatt acaagaaaag 8280
aaagtgaagc cccaaatgcc ttataaatat acaagaaaaa atcttttaag atattagcca 8340
acttaatcaa caaaaaatgt atcaaaagtc caagtaacat tcaccccagg aatgcaagtg 8400
tggttcagcc taagacaatc agtcatgagt ataccacgga aacaaattaa agagaaaaga 8460
cattaaatct cacaaatggt gcagaaaaag atttggcaat atcgaacatc ttttcatgac 8520
caaaggaaaa aaaagaaaca aaacaccaga aaattctgtg tagaaagaat atatctcaac 8580
ccaatgaagg gcatttatga aaaacccaca gcatacatca cactccatga gaaagactga 8640
aagctttccc cactgccatt gaactctgtc ctggaaattc tagtcacagc gacagaacaa 8700
gagaaagaaa taacggccgt ctaaactggt aggaagaaat caaagcgtct ctattctctg 8760
ggcgcataat acaatataga caaatttcta aagtccacaa aaattcctag agctcataat 8820
gaatccagaa atgcgtcagg gctcaagatt cagatgcaaa aatcgtctgg gttttgatgc 8880
accaacaaac aattccatta acaataatac caaggaatta atttaactta gaagagaaaa 8940
gacctgttta cagagagtta taaaacattt ggtgatgaaa ttaaataaga gtaaatcata 9000
tagaaacacc gttcgtgttt tggagaccta atgtcataaa cgtggcaaca cagagacgcc 9060
tcacggggaa ccctgagcct ccttctccaa acaggcctgc tcatcatttc acaggtaacc 9120
tgagacccta aagcttgact ctgaggcact ttgagggcat gaagagagca gtagctcctc 9180
ccatgggacc gacagtcaag gcccagggaa tgaccacctg gacagatgac ttcccggcct 9240
catcagcagt cggtgcagag tggccaccag ggggcagcag agagtcgctc aacactgcac 9300
ctggagatga ggcaacctgg gcatcaggtg cccatgcagg ggctggatac ccacacctca 9360
cacctgagga caggggccgg ctttctgtgg tgtcgccctc tcaggatgca cagactccac 9420
cctcttcgct tgcattgaca gcctctgtcc ttcctggagg acaagctcca ccttccccat 9480
ctctccccag ggggctgggg ccaacagtgt tctctcttgt ccactccagg aacacagagc 9540
caagagattt atttgtctta attagaaaaa ctatttgtat tcctgcattt ccccagtaac 9600
tgaaggcaac tttaaaaaat gtatttcctg gacttccctg gtgggccagt ggctagactc 9660
tgagctccca gtgcatgggg cctgggttca atccctgctc aggaaactac atcccacagg 9720
ctgcaaataa gatcctgcat gccacccgat gcaggcaaag aaacaagtgt tcggtatgca 9780
tgtatttcac gtgaggtgtt tctataattt acagccagta ttctgtctta cacttagtca 9840
ttcctttgag cacatgatcg gtcgatggcc cagaccacac acaggaatac tgaggcccag 9900
cacccaccgg ctgcccagaa cctcatggcc aagggtggac acttacagga cctcagggga 9960
cctttaagaa cgccccgtgc tcttggcagc ggagcagtgt taagcatggc tctgtccctc 10020
gggagctgtg tctgggctgc gtgcatcacc tgtggtgtgg gcctggtgag ggtcaccgtc 10080
caggggccct cgagggtcag aagaaccttc ccttaaaagt tctagaggtg gagctagaac 10140
cagacccaca tgtgaactgc acccaaaaac agtgaaggat gagacacttc aaagtcctgg 10200
gtgaaattaa gggccttccc ctgaaccagg atggagcaga ggaaggactt ggcttccagg 10260
aaaccctgac gtctccaccg tgactctggc cggggtcatg gcagggccca ggatcctttg 10320
gtgcaaagga ctcagggttc ctggaaaata cagtctccac ctctgagccc tcagtgagaa 10380

-continued

```
gggcttctct cccaggagtg gggcaaggac ccagattggg gtggagctgt ccccccagac  10440
cctgagacca gcaggtgcag gagcagcccc gggctgaggg gagtgtgagg gacgttcccc  10500
ccgctctcaa ccgctgtagc cctgggctga gcctctccga ccacggctgc aggcagcccc  10560
caccccaccc cccgaccctg gctcggactg atttgtatcc ccagcagcaa ggggataaga  10620
caggcctggg aggagccctg cccagcctgg gtttggcgag cagactcagg gcgcctccac  10680
catggcctgg accccctcct cctcggcctc ctggctcact gcacaggtga gccccagggt  10740
ccacccaccc cagcccagaa ctcggggaca ggcctggccc tgactctgag ctcagtggga  10800
tctgcccgtg agggcaggag gctcctgggg ctgctgcagg gtgggcagct ggaggggctg  10860
aaatccccct ctgtgctcac tgctaggtca gccctgaggg ctgtgcctgc cagggaaagg  10920
ggggtctcct ttactcagag actccatcca ccaggcacat gagccggggg tgctgagact  10980
gacggggagg gtgtccctgg gggccagaga atctttggca cttaatctgc atcaggcagg  11040
gggcttctgt tcctaggttc ttcacgtcca gctacctctc ctttcctctc ctgcaggcgc  11100
tgtgtcctcc tacgagctga ctcagtcacc cccggcatcg atgtccccag gacagacggc  11160
caggatcacg tgttgggggc ccagcgttgg aggtganaat gttgagtggc accagcagaa  11220
gccaggccag gcctgtgcgc tggtctccta tggtgacgat aaccgaccca cgggggtccc  11280
tgaccagttc tctggcgcca actcagggaa catggccacc ctgcccatca gcggggcccg  11340
ggccaaggat gaggccgact attactgtca gctgtgggac agcagcagta acaatcctca  11400
cagtgacaca ggcagacggg aagggagatg caaacccccct gcctggcccg cgcggcccag  11460
cctcctcgga gcagctgcag gtcccgctga ggcccggtgc cctctgtgct cagggcctct  11520
gttcatcttg ctgagcagcg gcaagtgggc attggttcca agtcctgggg gcatatcagc  11580
acccttgagc cagagggtta ggggttaggg ttagggttag gctgtcctga gtcctaggac  11640
agccgtgtcc cctgtccatg ctcagcttct ctcaggactg gtgggaagat tccagaacca  11700
ggcaggaaac cgtcagtcgc ttgtggccgc tgagtcaggc agccattctg gtcagcctac  11760
cggatcgtcc agcactgaga cccggggcct ccctggaggg caggaggtgg gactgcagcc  11820
cggcccccac accgtcaccc caaaccctcg gagaaccgcg ctccccagga cgcctgcccc  11880
tttgcaacct gacatccgaa cattttcatc agaacttctg caaaatattc acaccgctcc  11940
tttatgcaca ttcctcagaa gctaaaagtt atcatggctt gctaaccact ctccttaaat  12000
attcttctct aacgtccatc ttccctgctc cttagacgcg ttttcattcc acatgtctta  12060
ctgcctttgg tctgctcgtg tattttcttt tttttttttt ttttattgga atatatttgc  12120
gttacaatgt tgaatttgaa ttggtttctg ttgtacaaca atgtgaatta gttatacatg  12180
tcctgaggag gggcggctgc gtgggtgcag gagggccgag aggagctact ccacgttcaa  12240
ggtcaggagg ggcggccgtg aggagatacc cctcgtccaa ggtaagagaa acccaagtaa  12300
gacggtaggt gttgcgagag ggcatcagag ggcagacaca ctgaaaccat aatcacagaa  12360
actagccaat gtgatcacac ggaccacagc ctggtctaac tcagtgaaac taagccatgc  12420
ccatggggcc aaccaagatg ggcgggtcat gtgcccatgg ggccaaccaa gatgggcggg  12480
tcatggtgaa gaggtctgat ggaatgtggt ccactggaga agggaaaggc aaaccacttc  12540
agtattcttg ccttgagagc cccatgaaca gtatgaaaag gcaaaatgat aggatactga  12600
aagaggaact ccccaggtca gtaggtgccc aatatgctac tggagatcag tggagaaata  12660
actccagaaa gaatgaaggg atggagccaa agcaaaaaca atacccagtt gtggatgtga  12720
ctggtgatag aagcaagggc caatgatgta aagagcaata ttgcatagga acctggaatg  12780
```

```
ttaagtccaa gannnnnnnn nnnnnnnnnn nnnnnnnnnn nnnnnnnnnn nnnnnnnnnn  12840
nnnnnnnnnn nnnnnnnnnn nnnnnnnnnn nnnnnnnnnn nnnnnnnnnn nnagaatttt  12900
gagcattact ttactagcgt gtgagacgag tgcaattgtg cggtagtttg agcattcttt  12960
ggcattgcct ttctttggga ttggaatgaa aactgacctg ttccaggcct gtggccactg  13020
ctgagttttc caaatttgct ggcgtattga gtgcatcact ttaacagcat catcttttag  13080
gatttgaaat agctcaactg gaattctatc actttagcta attccattca ttagctttgt  13140
ttgtagtgat gcttcctaag gcccccctgg ctttatcttc ctggatgtct ggctctggtg  13200
agtgatcaca ccgctgtgat tatctgggtc atgaaggtct ttttgtatag ttcttcttag  13260
gaacagatat tatgatctcc atccttgcat ctcgttatat ctagagaagc actgactccc  13320
ttcatggtga cgtcagatcc tcatgactaa caaatggcct tttgtaagat gagtgcctca  13380
tggtattgag ctcccccgtc accaagacct tatgactgac ctcccccact gccccaggtg  13440
cctctcgaag cgtctgagat gccgcctccc aggctgcact cctcattttg cccccaataa  13500
aacttaactt gcagctctcc agctgtgcat ctgtgtttag ttgacagtac aaatataatg  13560
gaaaatttaa attaaatata atctatgggg agaaatccaa acatcttatg agggagagag  13620
agggagagaa aggaaagaag aagaagcagg aggaggagga gagtagagaa acaggggggag  13680
ggcggcaggg agacagaggg gaggacaccg aggggaaagg gaggaaggcg agtgcagtga  13740
gagagaggcc agagttcatc agagtctgga ctcgcagccc aatcccacgg gtgtgtcccg  13800
aagcagggga gagcctgagc caggcggaga cagagctgtg tctccagtcc tcgtggccgt  13860
gacctggagc tgtgtggtca gccccccctga ccccagcctg gccctgctgg tggtcggagg  13920
cagtgatcct ggacacagtg tctgagcgtc tgtctgaaat ccctgtggag gcgccactca  13980
ggacggacct cgcctggccc cacctggatc tgcaggtcca ggcccgagtg gggcttcctg  14040
cctggaactg agcagctgga ggggcgtctg caccccagca gtggagcggc cccaggggcg  14100
ctcagagctg ccgggggggac acagagcttg tctgagaccc agggctcgtc tccgaggggt  14160
cccctaaggt gtcttctggc cagggtcaga gccgggatga gcacaggtct gagtcagact  14220
ttcagagctg gtggctgcat ccctggggac agagggctgg gtcctaacct gggggtcaga  14280
gggcaggacg ggagcccagc tgacccctgg ggactggcct cctctgtggt ctcccctggg  14340
cagtcacagc ttccccggac gtggactctg aggaggacag ctggggcctg gctgtcagga  14400
gggggttcga gaggccacac tcagaggagg agaccctggc ctgcttgggt tgtgactgag  14460
tttttggggt cctctaggag actctggccc tgcaggccct gcaaggtcat ctctagtgga  14520
gcaggactcc acaagattga tgaactgaat cctctaggag aggtgtggtt gtgagggggc  14580
agcattctag aaccaacagc gtgtgcaggt agctggcacc gggtctagtg gcggcgggca  14640
gggcactcag ggccgactag gggtctgggg gattcaatgg tgcccacagc actgggtctt  14700
ccatcagaat cccagacttc acaaggcagt ttcggggatt aggtcaggac gtgagggcca  14760
cagagaggtg gtgatggcct agacaagtcc ttcacagaga gagctccagg ggccatgata  14820
agatggatgg gtctgtattg tcagtttccc cacatcaaca ccgtggtccc gccagcccat  14880
aatgctctgt ggatgcccct gtgcagagcc tacctggagg cccgggaggc ggggccgcct  14940
gggggctcag ctccggggta accgggccag gcctgtccct gctgtgtcca cagtcctccc  15000
ggggttggag gagagtgtga gcaggacagg agggtttgtg tctcacttcc ctggctgtct  15060
gtgtcactgg gaacattgta actgccactg gcccacgaca gacagtaata gtcggcttca  15120
```

-continued

```
tcctcggcac ggaccccact gatggtcaag atggctgttt tgccggagct ggagccagag  15180
aactggtcag ggatccctga gcgccgctta ctgtctttat aaatgaccag cttaggggcc  15240
tggcccggct tctgctggta ccactgagta tattgttcat ccagcagctc cccgagcag  15300
gtgatcttgg ccgtctgtcc caaggccact gacactgaag tcaactgtgt cagttcatag  15360
gagaccacgg agcctggaag agaggaggga gaggggatga gaaggaagga ctccttcccc  15420
aagtgagaag ggcgcctccc ctgaggttgt gtctgggctg agctctgggt ttgaggcagg  15480
ctcagtcctg agtgctgggg gaccagggcc ggggtgcagt gctgggggc cgcacctgtg  15540
cagagagtga ggaggggcag caggagaggg gtccaggcca tggtggacgt gccccgagct  15600
ctgcctctga gcccccagca gtgctgggct ctctgagacc ctttattccc tctcagagct  15660
ttgcaggggc cagtgagggt ttgggtttat gcaaattcac cccccggggg cccctcactc  15720
agaggcgggg tcaccacacc atcagccctg tctgtcccca gcttcctcct cggcttctca  15780
cgtctgcaca tcagacttgt cctcagggac tgaggtcact gtcaccttcc ctgtgtctga  15840
ccacatgacc actgtcccaa gcccccctgc ctgtggtcct gggctcccca gtggggcggt  15900
cagcttggca gcgtcctggc cgtggactgc ggcatggtgt cctggggttc actgtgtatg  15960
tgaccctcag aggtggtcac tagttctgag ggatggcct gtccagtcct gacttcctgc  16020
caagcgctgc tccctggaca cctgtggacg cacagggctg gttcccctga agccccgctt  16080
gggcagccca gcctctgacc tgctgctcct ggccgcgctc tgctgccccc tgctggctac  16140
cccatgtgct gcctctagca gagctgtgat ttctcagcat aactgattac tgtctccagt  16200
actttcatgt ccctgtgacg ggctgagtta gcatttctca cactagagaa ccacagtcct  16260
cctgtgtaaa gtgatcacac tcctctctgt gggacttttg taaaagattc tgcagccagg  16320
agtcatgggt ggtcttagct gagaaatgct ggatcagaga gacctgataa ccgatgtgaa  16380
gaggggaacc tggaagatct tcagttcagt tcatttcagt cattcagttg tgtccgactg  16440
tttgggatcc catggactgc cacacgccag tcctccctgt ccatcaccaa cttctgaagc  16500
ttgttcaaac tcatgtccat caagttggag atgcctttca accatctcat cctctgtcat  16560
cccctctcc tcccgccttc aatcttccct agcattaggg tcttttccgt gagtcagttc  16620
ttcgcatcag gtggccaagt tttggagttt cagtttcagc atcagtcctt tcaatgaata  16680
gtaaggactg atttccttta ggatggactg gtttgatatc cttgcagttc aagggactct  16740
caagagtctt ctccaacact gcagttaaaa gccatcaatt cttcggtgct cagctttctt  16800
tttggtacaa ctctcacatt catacatgac taccgaaaat acattagtcg tgtagaacca  16860
gtttggggct tcccacgtgg ctctagtggt aaagaatatg cctgccaact cagaagatgt  16920
aagagatgcg gttcaatctc tgggtcggga agatcccctg gagaagggca tgacaaccca  16980
ctccagtatt tttgcctgga gaatcccatg gacagagaag cctggtggac tgcagtccat  17040
ggagtctcac agagtcagac acgactgaag caacttagct acttggaaaa gagcatgcac  17100
gaagctgtct aaaaaacagg tcaagaagtc ttgtgttttg aaggtttact gagaaagttg  17160
atgcactgct ccaacacttc ctctcagttg aaaagatcag aagcgttaga tcaaatggtg  17220
gtcaatacct tggatgcgct ccaacaggtt atatctgcag atggaaatga aggcagttta  17280
tggggtaact ggaggacaag atgagatcat acacttggaa cactgtctgg catcaaaggc  17340
gtgtacagta aacattagct gttattagca aaataaattc agcttgaatc acccaaatca  17400
gatggcattc ttaaagccac tgagtggtaa aatcaggggt gtgcagccaa aacgtccatt  17460
ttgactcatt atgatttcca tgtcacaaga ctagaaagtc actttctcct cagcagaaga  17520
```

```
gaaggtagaa cattttaacc tttttttgga gtgtcaaggg aattttgttt acactgtaaa  17580
gtcagtgaaa atattgaagc ttttcatttg tggaaaatat taaatatgta aaattgaaat  17640
tttaaaattt attcctgggt agttttgttt ttccagtagt catgcatgga tgtgagagtt  17700
ggactataaa gaaagctgag cgctgaagaa ttaatgcttt tgaactgtgg cactggagaa  17760
gactcttgag agtcccttgg tctgcaagga gatcaaacca gtccatccta aaggaaatca  17820
gtcctgaata ttcactggaa ggactgatgc tgaagctgaa actccaatac tttggccacc  17880
tgatgtgaag aactgactca tatgaaaaga ctcagatgct gggaaagatt gaaggtggga  17940
ggagaagggg acgacagagg atgagatggc tgaatggcat caccgactcg atggacatga  18000
gtctgaataa gctctgggag ttgttgatgg acagggaggc cctggagtgc tgcagtccat  18060
gggattgcaa agagttggac atgactgagt gactgaactg aactgagttt ggtaacagat  18120
atgagaatta tataatttaa atctaaactc ttggtatttc tttctttggc ggttccaaaa  18180
gagctgtccc ttctgttaac tatataaatc ctttttgaga attactaaat tgataatgtt  18240
cacaagttat ccaatttctc attactctta gttgtcagta taagaaatcc catttgattt  18300
atcatgttat agtatctgca actctaatag ttcagttctg acaaattttt attttattta  18360
aaaatattgg catacagtaa aatttcaaac aatatacaat tctccctttc agtttaaaaa  18420
acaaaacaaa acaaaagtaa tattagttaa aaaaatccgg gaagaatcca agcatttaaa  18480
attgcatcac atttctatgc tagacaagct gatataaagt tataattaat aaaggattgg  18540
actattaaac tctttacata tgaggtaaca tggctctcta gcaaaacatt taaaaatatg  18600
ttgtgggtaa attattgttg tccttaaaga aataaaaaga cataagcgta agcaattggn  18660
nnnnnnnnnn nnnnnnnnnn nnnnnnnnnn nnnnnnnnnn nnnnnnnnnn nnnnnnnnnn  18720
nnnnnnnnnn nnnnnnnnnn nnnnnnnnnn nnnnnnnnna aaatggataa gggggggagga  18780
catgggtagg ggagcgcgat ggaggaagta aggtggtcga gggagttggg gggggaataa  18840
gtgggtaaaa gggaagcggg cggaaggagg gggaagcagg agagaggggt gggcgtcaga  18900
tcggggggag gggtatgagg gagagggaat ggtagacggg gggtgggaag cataaaggaa  18960
aagatagggg ggggaaaagt tagaagaaga atgaggggat aggcggaaag ggaagagaaa  19020
tgggagaaga acagaaaaat agggggaggg ggggcgtaaa gagggggggg gagggcaggt  19080
gtggagatga cagatacggg gaatgccccg gtataaaaga gtatatggcg tggggcgaga  19140
aggctgtcat cctgtgggag gggggacgcg gagaaccctt cgggctatag ggaggattcg  19200
gggggatcgt tcgggaaggc agtcagcaca gcacccacca agggtgcagg gatggatctg  19260
gggtcccaaa gaagaggccc aatcccgcgt cttggcagca aggagccctg gagactggga  19320
agtgtccagg acactgaccc aggggttcga ggaacccaga agtgtgtctg tgaagatgtg  19380
ttttgtgggg ggacaggtcc agagctttga gcagaaaagc ggccatggcc tgtggagggc  19440
caaccacgct gatctttttt aaaaggtttt tgttttgatg tggaccattt ttaaagtctt  19500
cattgaattt gctacaatat tgtttctggt ttatgctctg gtttcttcgg ctgcaaggtt  19560
tgtgtgatcg tatctcctca accaggactg aacccacagc ccctgcactg gaaggcgaag  19620
tcttaaccca gatcgccagg aacgtccctc ccctcactga tctaatccaa gaccctcatt  19680
aaggaaaaac cgagattcaa agctccccca ggaggactcg gtggggagga gagagccaag  19740
cactcagcac tcagtccagc acggcgccct ccctgtccag ggcgagggct cggccgaagg  19800
accaccggag accctgtcgg attcaccagt aggattgtga ggaatttcaa cttacttttt  19860
```

-continued

```
aaatctgtct ctcaaggctg ttacaagcgg actttaccag taacttaaaa gttgaaaggg  19920
acttcccagg cggcacttgc ggtgaagaac ccgccggctg gttttaggag acataagaga  19980
tgtgggttag atccctggtt caggaggatt cccctggaga aggaaatggc aacccactcc  20040
agtattcttg cctggaaagc ctcacggaca gaggaggctg gcgggctaca gtccacgggg  20100
tcgcacacga ctgaatcgac ttagcttcaa gttgagacag gaagaggcag tgactggtgg  20160
caaaacaccg cacccatgct cccaggggac ctgcagcgct ctggttcatg agctgtgcta  20220
acaaaaatca acccaacgag aggcccagac agagggaagc tgagttcatc aaacacgggc  20280
atgatgtgga ggagataatc caggaaggga cctgccaagc ccatgacaga ccggtgtcct  20340
gtctgagggc cgtcctggca gagcagtgca gggccctccg agaccgcccg agctccagac  20400
ccggctgggg gctacagggt ggggctgagc tgcaaggact ctgctgtgag ccccacgtca  20460
gggaggatca ccttgtttgt tttctgagtt tctcttaaaa tagcctttat gggtcctggt  20520
ctttggtttt aaaataacaa ctgttctccg taaacaacgt gaaaaaaaac aaacaggagg  20580
aaaacaacgc agcccgggca tttcacccgg aagagccgcc tctaacactt tgacgggttg  20640
ccttctattt taaccctgtt ttcattgtaa actgtaaaaa ccacatcata aataaattaa  20700
aggtctctgt gaagtttaaa aagtaagcat ggcggtggcg atggctgtgc cacaccgtga  20760
acgctcgttt caaaacggta aattctaggg accccctggt ggtccagtgg gtgagatttt  20820
gcttccattg caggagccgt gggtttgatc cctggttggg gaactaagat cccacatgct  20880
gtatggagtg gccaaaaaga attttttgta aatggtgagt tttaggtgac gtgaatttcc  20940
cattgatgca cttcacaggc tcagatgcag ccaggccctc aggaagcccg agtccaccgg  21000
tcctttactt ttccttagag ttttatggct tctgtttctg cccttaaacc caccatgttt  21060
caacctcatc tgattttgga ctttataata aagttaggct gtgtttcagg aaactttgct  21120
cagtattctg taataatcta aatggaaaga atttgaaaaa agagcagaca cttgtacatg  21180
cataactgaa tcactttggt gtacacctga aactcgagtg cagccgctca gtcgtgtccg  21240
accctgcgac cccacggact gcagcacgcg ggcttccctg cccatcacca actcccggag  21300
ttcactcaaa cacatgtccg tcgactcggt gatgccgtcc aaccgtctca tcctctgtcg  21360
tccccttctc ctcccgcctt caatcttttc cagcatcagg gtcttttcaa atgagtcagt  21420
tcttcacacc aggtggccag agtattggag tttcagcttc agcatcagcc cttccaacga  21480
ccccccatac ctgaagctaa cacagtgcta atccactgtg ctgcaacatg aaagaaaaac  21540
acattttta agtttaggct gtgtgtgtct tccttctctc aacactgcgt ctgaccccac  21600
ccacactgcc cagcactgca ttccccgtgg acaggaggcc ccctgcccca cagctgcgtg  21660
ccggccggtc actgccgagc agacctgccc gcccagagtg gggcccctgg cactggggac  21720
aaggcagggg cctctccagg gccggtcact gtccactgtt cctactggtt ttgttttcaa  21780
aagtggaggc agcgtaatat ttccctgatt ataaaaagaa gtacacaggt tctccacaaa  21840
taaaacaggg gaaaagtata aagaatggaa gttcccagca cagcctggag atcacgccgg  21900
gtgcacctgg ggtgtccttc caggctggac ctcacatttc acgcagacat cagaaggctg  21960
cgagatctac ccagaaggct gggtagatgg gggataggtc agtgacaaac agtagacaga  22020
gagatataca gacagatgat ggatagacag acgctaagac accgagcgag gggacagacg  22080
gatggaagac accatccttt gtcactgacc acacacccac atgggtgtgg tgagccggct  22140
gtcatacttg tgaacctgct gctctcacaa caccagctgg gtccctccag ccccagcgtc  22200
ccacacagca gactcccggc tccatcccca ggcaggaatc ccaccaccaa ctggggtgga  22260
```

-continued

```
ccctccccgc aggaaggtcg tgctgtctaa ggccttgaga gcaagttaca gacctacttc  22320
tgggaagaca gcgcacaacc gcctaccccg cagagcccag gaggacccct gagtcctagg  22380
gaagggacca cgcggcctgg acggggagcg gccccaggac gctgccccca acctgtccca  22440
cctcactcct gctctgctct gaggcggggc gcagagaggg gccctgaggc ctcttcccag  22500
ttcttgggag cacccactgg gcctgaacca ggccagaagc cccctcctca aggtgtcccc  22560
agaccactcc cctccacctc cggttgctct gtctcctggc agcagggagc cccagtgaga  22620
agagacagct ccaggctgtg atcttggccc ctggctgctc tggcagtgtg gggggtgggg  22680
gtcgctggga ggccatgagt gctgggggtc ggggctgtga aagcacctcg aggtcagtgg  22740
gctgttggtc gggctctgcg aggtccgcac gggtagagct gtgccaggac acaggaggcc  22800
tggtcagtgg tcccaagagt cagggccaaa ggaaggggtt cgggcccctc tggttcctca  22860
gcttctgagg ccggggaccc cagtctggcc ttggtagggg ggcgattgga gggtacaacg  22920
atccaaaaga aaacacacat ctacgaggga agagtcctga ggaggagaga gctacacaga  22980
gggtctgcac actgcggaca ctgcttggag tctgagagct cgagtgcggg gcacagtgag  23040
cgaagggagg acggaacctc caaggacacc ggacgccgat ggccagagac acacgcacgt  23100
cccatgaggg ccggctgctc agacgcaggg gagctcctca ttaaggcctc tcgctgaata  23160
gtgaggagaa ctggccccgt gtgtggggaa acttagccca gaagaaacgc tgccctggcc  23220
ccaaggatca nnnnnnnnnn nnnnnnnnnn nnnnnnnnnn nnnnnnnnnn nnnnnnnnnn  23280
nnnnnnnnnn nnnnnnnnnn nnnnnnnnnn nnnnnnnnnn nnnnnnnnnn tgccctttgc  23340
ctccagggag ggaggaagcg tggatcttgg gtttgccttg ggtttaaagg atccacccac  23400
tccctttta gccactccct gtgctggcaa tttcttaaga ctggaggtcg caaagagttg  23460
gacacactga gcgagtgaac tgcactgagc ctaagaaaag tctttgaatt cctccaaaca  23520
aaacacactt gtcttgggta ctttccttgg ttttgttaca aatgtctggt ccctctgttc  23580
tcctggccag ctcctgggtg tcattttgac ctgacgaagt caaagggagc ctggaccctc  23640
aaaatctgta ggacccagca cccctccatt acacctctgt tcccccgcga acgggcacgt  23700
gtttcgccgt ctggcgtaat gtgtaagcga cggtgtgata ctcgggagtc ttactctgtt  23760
tctttttctt ctggggtgac accaccatcc gcacgactct gtctgaatgt gaacatttgg  23820
gtgatttgat gtggcccaga ctcccccaac gaatgtacct tcaggttggt tttcttcttt  23880
tatattttgc ttttgtgaat agacacagga tcccatcagt tgtatgtagt gagaaagtaa  23940
aaacccactc agccttagct ggatggagat ctagtagtaa gatagcacgt tagccggaaa  24000
tggaaatttc agccagaatc tgaaaagcgt gtcctggaag gagaagaggg actcaggccc  24060
gagcacactg ctccacgctg gagcctcagg ctctgacagc tgtacctgcc ggggtcttca  24120
tgggacaggc catgcaggcc acgatcccgt tgagaagttt cttgcctttc catcacattg  24180
gcaattgcac gctttgctct tgcttctaca tggagtttta cttttatccc agacagtttg  24240
gtttcttctc tgattttcgc caattgtaca gatcgttaca gtatttctta accacataga  24300
attcggcagg gggggtgggg ggacagggta gggtggggtg agagtgaggg gagggggctg  24360
caccgagcag catctggggt cgtagctccc tgacggggat agacctcgtg cccctgcagt  24420
gacagcacag agtcctcctc tctgaactgc cagggacgct cctgcaattg acttaatgaa  24480
aggcatctaa ttaggaattt tggggtgaca ttttacattt aagtgtgtga gcagtgatta  24540
tagttcatat cattttatag tttcgtgatt ttactagctt aaagggtttt tggggtttct  24600
```

```
ttttgtttta aaagctaaaa tctgtttttt aattccatgg aatacaaaaa aaaaaagtct  24660
gtagaatatt ttaaagagtg aaggctttgt tcggaatgtg agcgctttgc tccactgaac  24720
cgaacggtaa taacatttgt agaagagacg cagagtgaaa ggtacctctt tttattgagt  24780
gacatgacag cacccatcgc gtgagttatt ggctggagtt tagagacagg ccatgttggg  24840
ctaaactcct tattgctgtt ctcagccttt gagtaataat cagaagcttt ctctgaagag  24900
agtggggtca gctgtcagac tcctaggtgt ctacctgcag cagggctggg attaaatgca  24960
gcagccagta gatacgggat ggggcaagag gtcaccttgt ccctttgttg ctgctgggag  25020
agaggcttgt cctggtgcca gtggggccaa agctgtgact ttgtgaccac aggatgtctc  25080
tgaccctgcc ttgggttccc tgagggtgga gggacagcag ggtctccccg gttccttggc  25140
cggagaagga ccccccaccc cttgctctct gacatccccc caggacttgc cccggagtag  25200
gttcttcagg atgggcatcc gggccccacc ctgactcctg gagctggccg gctagagctt  25260
gctgcagaat gaggccttgg ccattgcggc cctgaaggag ctgcccgtca agctcttccc  25320
gaggctgttt acggcggcct ttgccaggag gcacacccat gccgtgaagg cgatggtgca  25380
ggcctggccc ttcccctacc tcccgatggg ggccctgatg aaggactacc agcctcatct  25440
ggagaccttc caggctgtac ttgatggcct ggacctcctg cttgctgagg aggtccgccg  25500
taggtaaggt cgacctggca gactggtggg gcctggggtg tgagcaagat gcagccaggc  25560
caggaagatg aggggtcacc tggaacaggg cgttgggtgt acaggactgg ttgaggctca  25620
gaggggacaa aaggcacgtg ggcctccccc ccagtgtccc ttaaagtggg aaccaagggg  25680
gccccggaag ccggaggagc tgtggtgtgt ggagtgcaga gccctcgcgg ggtcctgatg  25740
cccgtcggac tctgcacagc tcagcgtgtg ccccgcggcc cggtaggcgg tggaagctgc  25800
aggtgctgga cttgcgccgg aacgcccacc agggacttct ggaccttgtg gtccggcatc  25860
aaggccagcg tgtgctcact gctggagccc gagtcagccc agcccatgca gaagaggagc  25920
agggtagagg gttccagggg tgggggctga agcctgtgcc gggccctttg gaggtgctgg  25980
tcgacctgtg cctcaaggag gacacgctgg acgagaccct ctgctacctg ctgaagaagg  26040
ccaagcagag gaggagcctg ctgcacctgc gctgccagaa gctgaggatc ttcgccatgc  26100
ccatgcagag catcaggagg atcctgaggc tggtgcagct ggactccatc caggacctgg  26160
aggtgaactg cacctggaag ctggctgggc cggatgggca acctgcgcgg ctgctgctgt  26220
cgtgcatgcg cctgttgccg cgcaccgccc ccgaccggga ggagcactgc gttggccagc  26280
tcaccgccca gttcctgagc ctgccccacc tgcaggagct ctacctggac tccatctcct  26340
tcctcaaggg cccgctgcac caggtgctca ggtgaggcgt ggcgccagct ccaaagacca  26400
gagcaggcct ctcttgtttc gtgcccgctg gggacattgc cagggtgccc ggccactcgg  26460
aagtcctcac gatgccaccg ctctgaccct gggcatcttg tcaggtcact tccctggtta  26520
gggtcagagg cgtggcctag gttaaatgct gtcaaagggg actcctttct gggagtccgc  26580
atagtggggg cttggtgtga tgcccttggg aattctttcc gagagagtga tgtcttagct  26640
gagataatga cagataacta agcgagaagg acggtccatc aggtgtgagg tttgaagtcc  26700
aaagctctgt ctctccctcc cacctgcccc ttctgtcctg agctgtttta ggctccaggt  26760
gagctgtggg aagtgggtga ttctggagat gacaagaagg gatcaggagg ggaaaattgt  26820
ggctcctaag cagtccagag aagagaaaaa gtcaaataag cattattgtt aaagtggctc  26880
cagtctcttt aagtccaaat tataattata attttcctct aagacttctg aatacatagg  26940
aaatcctcag taacaggtta ttgctctgcc ttgaacacag tgataaaagc tgggaggatg  27000
```

-continued cagcctaatc tgtctgtgtg aatgagttgt attgattccc tttttggcag ctgcaaactc 27060
caagcattag gaataaatat gttcactgag aaccccgaag aaagaaagaa agaaaaaaaa 27120
aaagaattgt aggtgttgat ggacggtttg tggcccctga atatctgggg gatgttcacc 27180
cagggatcac gtgtaactgc tgggaccccc agccccatgt ccactgcatc cagcctgctg 27240
ttgaattccg cggatcnnnn nnnnnnnnnn nnnnnnnnnn nnnnnnnnnn nnnnnnnnnn 27300
nnnnnnnnnn nnnnnnnnnn nnnnnnnnnn nnnnnnnnnn nnnnnnnnnn nnnnnncaat 27360
tcgagctcgg taccccaaag gtccgtctag tcaaggctat ggtttttcca gtggtcatgt 27420
atggatgtga gagttggact gtgaagaaag ctgagtgcca aagaattatt cttttgtact 27480
gggtgttgga gaagactctt gagagtccct tgaactgcaa ggagatccaa ccagtccgtt 27540
ctaaaggaga tcagtcctga atgttcattg gaaggactga tgctgaagct gaaactccaa 27600
tactttggcc acctgacgtg aagagttgac tcattggaaa agaccatgat gctgagagga 27660
attgggggca ggaggagaag gggacgacag aggatgagat ggctggatgg catcaccaac 27720
tcgatgngac atgagtttgg ttaaactcca ggagttggtg atggacttgg aggcctggtg 27780
tgctgggatt catggggtcg cagagtcgga catgactgag cgactgaact gaactgaact 27840
gagctgaaga gctcacctgt accagagctc ctcaggtcct cctgcaggcc tggctgtaat 27900
ggcccccagg tcaccgtcct gcctccttca tcccatcctt tcacgacagg ctgggagtgg 27960
ggtgaggtga gttgtcttgt atctagaatt tctgcatgcg accctcagag tgcaatttag 28020
ctccagagaa ctgagctcca agagttcatt ttttcctttt cttctttatg atactaccct 28080
cttctgagca gagacctcat gtcagggaga aggggactct gccttcctca gccttttgtt 28140
cctccaagac ccacacgggg agggtcgcct gcttcactga gccggaaggt tcaattgctc 28200
atgtcctcca gaaacacccc cccccccaga gacccccaga aataagtgga acagcacctt 28260
gtttcccaga caagtgggac acacgttatg aaccacctca gtgattaaaa tagtaacctc 28320
tgtgtatgtg tatttactgg agaaggaaac ggcaacctac tccactattc ctgcctagaa 28380
aattccatgg gagagaagcc aggcaggcta cagtccacgg ggtcacagag actgaacata 28440
cacaagcaca tggaagtgta ttttgcagta tttttaaatt tgttcagttc aacatggagt 28500
acaagaattc aaatcgtgaa gtcaattgac caagaaacca gaagaaatca ctgtgttgtg 28560
atctctgtgg aggtaacatg ggtacctgtg ctctgaccct cacagcctct ggctctctct 28620
ctacatgtac atacacatat atttccatgt atgtatgtat tcggaagatt tcacatacgt 28680
ctcaccagtc cacagccccc gcgttccctg atgcccagaa catctgtgat agctgtgagt 28740
attgtcacca gataagatct tccaggttcc tgcactcaca ttggttatca ggtctctctg 28800
atccagcatt tctcagctaa gattccttgt gactcctggc tgcagaatct tctgcaaaag 28860
tcccacagag aggagtgtga tcactgtaca caggagggcc gtggttctct agtgtgagaa 28920
aagctaactc agcccgtcac agggacgtga atgtacctga gacagtaatc agttatgctg 28980
agaaatcaca gctctgctag aggcagcaca tggggtagcc agcagggggc agcagagcac 29040
ggccaggagc cgcaggtcag aggctgggct gcccaagcgg ggcttcaggg gaaccagccc 29100
tgcgggtcca caggtgtcca gggagcagcg cttggcagga agtcaggacc ggacaggcca 29160
tcccctcagg actagtgacc acctctgagg gtcacatcca cagtgaaccc cagagcacca 29220
tgcctcagtc cacggccagg acgctgccag gctgaccgcc ccactgggga gtccagggga 29280
gaccacaggc cgggggcctt gggacagtga tcatgtggtc agacacagag aaggtgacag 29340

-continued

```
tgacctcagt ccctgaggac aagtctgatg tgcagacgtg agaagccgag gaggaagctg  29400
gggacagaca gggctgatgg tgtggtgacc ccgcctctca gtgaggggcc cccgggggtg  29460
aatttgcata aacccaagcc ctcactgccc ccacaaagct ctgagaggga ataaaggggc  29520
tcggagagcc cagcactgct gcgggctcag aggcagagct cggggcgcgt ccaccatggc  29580
ctgggcccct ctcgtactgc ccctcctcac tctctgcgca ggtgcggccc cccagcctcg  29640
gtccccaagt gaccaggcct caggctggcc tgtcagctca gcacaggggc tgctgcaggg  29700
aatcggggcc gctgggagga gacgctcttc ccacactccc cttcctctcc tctcttctag  29760
gtcacctggc ttcttctcag ctgactcagc cgcctgcggt gtccgtgtcc ttgggacaga  29820
cggccagcat cacctgccag ggagacgact tagaaagcta ttatgctcac tggtaccagc  29880
agaagccaag ccaggccccc tgtgctggtc atttatgagt ctagtgagag accctcaggg  29940
atccctgacc ggttctctgg ctccagctca gggaacacgg ccaccctgac catcagcggg  30000
gcccagactg aggacgaggc cgactattac tgtcagtcat atgacagcag cggtgatcct  30060
cacagtgaca cagacagacg gggaagtgag acacaaacct tccagtcctg ctcacgctct  30120
cctccagccc cgggaggact gtgggcacag cagggacagg cctggcccgg ttcccccgga  30180
gctgagcccc caggcggccc cgcctcccgg ccctccaggc aggctctgca caggggcgtt  30240
agcagtggac gatgggctgg caggccctgc tgtgtcgggg tctgggctgt ggagtgacct  30300
ggagaacgga ggcctggatg aggactaaca gagggacaga gactcagtgc taatggcccc  30360
tgggtgtcca tgtgatgctg gctggaccct cagcagccaa aatctcctgg attgacccca  30420
gaacttccca gatccagatc cacgtggctt tagaaaggct taggaggtga acaagtgggg  30480
tgagggctac catggtgacc tggaccagaa ctcctgagac ccatggcacc ccactccagt  30540
actcttccct ggaaaatccc atggacggag gagcctggaa ggcttcagcc catggggtcg  30600
ctaagagtca gacacgactg agcgacgtca ctttcccttt tcactttcat gcattggaga  30660
aggaaatggc aacccagtcc agtgttcctg cctggaaaat cccagggaca ggggagcctg  30720
gtgggctgcc atccatgggg ccacacagag tcagacacga ctgaagcaac ttagcagcag  30780
cagcagcagc ccaataaaac tcagcttaag taatggcatc taaatggacc ctattgccaa  30840
ataaggtcca ctcgcgtgca ctctgtttag gacttcagtt cctgattgtg gagggttccc  30900
acaagacgtg tgtgtatatt ggtgttgccg gaaaacagtg tcaatgtgag catcccagac  30960
tcatcaccct cctactccca ctattccatt gtctctgcag gtattaagca taaaggttaa  31020
gggtcttatt agatggaaga ggagtgaata ctcgtctgtg cttaacacat accaagtacc  31080
atcaaggtcc ttcctattta ttaacgtgtg ttttaatcag aaatatgcta tgtagaagca  31140
tccggacgat agcccatgtt acagacgggg aagctgaggc atgaagttct cagcaccttg  31200
tttcacgtca gacctgaaac ggggcagagc cggcagcaaa caaggttcct cttcccaagc  31260
gcccgctctt cacccgcttc ctatggcttc tcactgtgct tcctaaacta agctctcccc  31320
aaccctgtgg agacaggatt agagacttta ggagaaaaga ccaggaacat cccacacccg  31380
acccgagtga gccactaaga caaggctttg taaggacaga accagcaggt gtcctcagcg  31440
agccagggag agacctcgca ccaaaaacaa tattgtagca tcctgaccct ggacttctga  31500
cctccagaaa tgtgaaaaag aaacgtgtgg ggtttaatca actcaccggt gttatttggt  31560
tatgactgcc tgagttaaga aggagttggg aacacttgag tgtaggtgtt tatggaacat  31620
aagtcttgtt tctctgaaat aaattcccaa gggtataatt cctaggttgt agggtaactg  31680
ccacaaatct aggcagctta ttaaaaaaca aagatatcac tttgccagca aaggttcata  31740
```

-continued

```
tagtcaaatt atggttttta tagtagtcat gtatggatgt aaaagttgga tcataaagaa  31800
ggctgagcac cagagaattg atcccttcaa atcgtggtgc tggagaagac tcttgagagt  31860
cccttggaca gcaaggagat ccaaccagtc aatcctaaag gaaatgaact gtgaatattc  31920
actggaagga ctgatgctga agctgaagat ccaatacttt ggccacctga tgcgaagagt  31980
tgactcattg gaaaagaccc tgatgctgga aagcttgagg gcaggaggag aagagggcgg  32040
cagaggatga gacggttgga tggcatcact gactcaatgg acatgagttt gagccaactc  32100
tgggagacag tgaaggatag ggaaggctgg cgtggtacag tgcatgcggt cacaaagagt  32160
ctgacacatc ttagtgactc aacaacgaca gcaacacagg catcacacgc ttagtgtgat  32220
aagcggcaga actgttttcc aggggtccgn nnnnnnnnnn nnnnnnnnnn nnnnnnnnnn  32280
nnnnnnnnnn nnnnnnnnnn nnnnnnnnnn nnnnnnnnnn nnnnnnnnnn nnnnnnnnnn  32340
nnnnnnnnng tacgattcga gctcggaccc tgacattgtg agtcacgtca tgagcagctg  32400
ttttccggtc ttcagggatt gtggacgatt tctgtttggg tttgctcatg ataatttagt  32460
tacagcttag gttctttctt tccaggccac gagcgacatg ttttcaggtg agatgacgtg  32520
gtgggggatg ggcggccaag cccccactgg ggggggaggg attctgttgt gggcaggagt  32580
tggcagcatc cctgaactga tgacctgcga tccaggtgac aagaaccggg ggatattatt  32640
cctctgcctt ctcatgtcat gtcctcggtt cttcatgatg aaaacatatg acaatacagg  32700
ggagttagat ttgggcgggc acaactctgg gtgggggacc cggtggcatt gtgcccagca  32760
gggccatcaa gatgagggcg acctgggtgg tccccttctc ccctggggtc ttagttttcc  32820
cctcatggaa atgggatcag gcagcagcca tggaacaccg cgaccgtggc ttctctcacc  32880
tcctcgtctg tgattttggg tcgggatacc aggcatgaag acctggggcg gggggacatc  32940
actcctctgc agcagggagg ccgcagagtc ctccgtccat gaggacttcg tccctgggct  33000
gaccctgcgg actgctggag gctgaagctg gaggcacagg cgggctgcga ggccagggtc  33060
ctgaggacga cagagccagt ggggctgcag ctctgagcag atggcccctc gccccgggcc  33120
ctgagcttgt gtgtccagct gcaggttcgc tcaggtgagc cactacgtta tgggggaggc  33180
gccctgggca gggatcgggg gtgctgactc ctccgagatt ccgaccttct gggagcactc  33240
tggccacact ctaagcctgg caagagctgg gttcatcagt ctaactctcc tcctgaagtc  33300
caatggactc tctccatgcg gcagtcactg gatggcctct ttatccccga tggtgtcctt  33360
ttccgctgac ctggctctcc tgaccacctc ccagcccccc accatacagg aagatggcac  33420
ctggtccctg cagagctaag tccacccctg gcctggcttc agatgcctac agtcctcctg  33480
cgggaggccc cgctccccac taggccccaa gcctgccgtg tgagtctcag tctcacctgg  33540
aaccctcctc atttctcccc agtcctcagc tcccaacccc agaggtatcc cctgcccctt  33600
tcaaggccct tgtcccttcc tggggggatg gggtgtatgg gagggcaagc ctgatccccc  33660
gagcctgtgc cgctgacaat gtccgtctct ggatcatcgc tcccctggct ctcagagctc  33720
cctggtccct ggggatgggt tgcggtgatg acaagtggat ggactctcag gtcacacctg  33780
tcccttccct aaggaactga ccccttaaccc cgacactcgg ccagacccag aaagcacttc  33840
agacatgtcg gctgataaat gagaaggtct ttattcagga gaaacaggaa cagggaggga  33900
ggagaggccc ctggtgtgag gcgacctggg taggggctca ggggtccatg gagaggtggg  33960
ggagggggtg tgggccagag ggcccccgag ggtgggggtc cagggcccta agaacacgct  34020
gaggtcttca ctgtcttcgt cacggtgctc ccctcgtgcg tgacctcgca gctgtaactg  34080
```

-continued cctttcgatt tccagtcgct gcccgtcagg ctcagtagct gctggccgcg tatttgctgt 34140
tgctctgttt ggaggcccgg gtggtctcca cgttgcgggt gatggtgctg ccgtctgcct 34200
tccaggccac ggtcacgcta cccgggtaga agtcgctgat gagacacacc agggtggcct 34260
tgttggcgct gagctcctcg gtggggggcg ggaacagggt gaccgagggt gcggacttgg 34320
gctgacccgt gtggacagag gagagggtgt aagacgccgg ggaggttctg accttgtccc 34380
cacggtagcc ctgtttgcct tctctgtgcc ctccgaccct tgccctcagc ccctgggcgg 34440
cagacagccc ctcagaagcc attgcaatcc actctccaag tgaccagcca aacgtggcct 34500
cagagtcccc ggctgcgacc agggctgctc tcctccgtcc tcctggcccc gggagtctgt 34560
gtctgctctt ggcactgacc ccttgagccc tcagcccctg ccagacccct ccgtgacctt 34620
ccgctcatgc agcccaggtg cctcctccgt gaacccgggt ccccccgccc acctgccagg 34680
acggtcctga tgggagatgt ggggacaagc gtgctagggt catgtgcgga gccgggcccg 34740
ggcctccctc tcctcgccca gcccagcctc agctctcctg gccaaagccc ggggctcctc 34800
tgaggtcctg cctgtctacc gtccgccctg cctgagtgca gggcccctcg cctcacctgc 34860
cttcagggga cggtgccccc acacagcacc tccaaagacc ccgattctgt gggagtcaga 34920
gccctgttca tatctcctaa gtccaatgct cgcttcgagg ccagcggagg ccgaccctcg 34980
gacaggtgtg acccctgggt cccaggggat caggtctccc agactgacga gtttctgccc 35040
catgggaccc gctcctttct gaccgctgtc ctgagatcct ctggtcagct tgccccgtct 35100
cagctgtgtc cacccggccc ctcagcccag agcgggcgag acccctctct ctctgccctc 35160
cagggccttc cctcaggctg ccctctgtgt tcctggggcc tggtcatagc ccccgccgag 35220
cccccaagct cctgtctggc ctcccggctg gggcatggag ctcacagcac agagcccggg 35280
gcttggagat gcccctagtc agcaccagcc tctggcccgc accccagcgt ctgccctgca 35340
agaggggaac aagtccctgc attcctggac caaacaccag ccccggcgcc ccgactggcc 35400
ccattggacg gtcggccact ggatgctcct gctggttacc ccaagaccaa cccgcctccc 35460
ctcccggccc cacggagaaa ggtggggatc ggcccttaag gccgggggga cagagaggaa 35520
gctgccccca gagcaagaga agtgactttc ccgagagagc agagggtgag agaggctggg 35580
gtagggtgag agccacttac ccaggacggt gacccaggtc ccgccgccta agacaaaata 35640
cagagactaa gtctcggacc aaaacccgcc gggacagcgc ctggggcctg tcccccgggg 35700
gggctgggcc gagcgggaac ctgctgggcg tgacgggcgc agggctgcag ccggtggggc 35760
tgtgtcctcc gctgaggggt gttgtggagc cagccttcca gaggccaggg gaccttgtgt 35820
cctggaggtg ccctgtgccc agccccctgg ccgaggcagc agccacacac gcccttgggg 35880
tcacccagtg ccccctcact cggaggctgt cctggccacc actgacgcct tagcgctgag 35940
ggagacgtgg agcgccgcgt ctgtgcgggg cggcagagga gtaccggcct ggcttggacc 36000
tgcccagccg ctcctggcct cactgtaagg cctctgggtg ttccttcccc acagtcctca 36060
cagtccagcc aggcagcttc cttcctgggg ctgtggacac cgggctattc ctcaggcccc 36120
aagtggggaa ccctgccctt tttctccacc cacggagatg cagttcagtt tgttctcttc 36180
aatgaacatt ctctgctgtc agatcactgt ctttctgtac atctgtttgt ccatccatcg 36240
atccaacatc catccatcca tccatcaccc agccatccat ctgtcatcca acatccatcc 36300
ttccatccat tgtccatcca tctgtccatc ttgcatctgt ctgtccaaca gtggccatca 36360
agcacccgtc tgccaagccc tgtgtcacac gctgggactt ggtgggggga gccctcgccc 36420
tcccaccctc ccatctctcc tgaaacttct ggggtcaagt ctaacaaggt cccatcccgt 36480
ctagtctgag gtccccccgc agcctcctct tccactctct ctgcttctga cccacactgt 36540
gcactcggac gaccacccag ggcccttgca tccctgtttc cttcctgacc tctttttttt 36600
ggctctggat ttatacacat tctgcctcct ggaggcgtct cagcttgagt gtcccacaga 36660
cgcctcagac tcagcatctt ccatcgaaac tgctcccagg tccttgcaga cctggtcccc 36720
cacattgttc tcaattcggt agatttctcc acaagccaga ggcctggact catcccataa 36780
tgcctgcccc tcattgagtc agcctctgtg tcctaccata accaaacatc cccttaaaaa 36840
tctcagaaga acaaaaaaag cacccagatg gcactgtcag agtttatgat gacaagaatc 36900
ctcagttcag ttcagtcact cagtcgtgtc cgactctttg cgaccccatg aatcgcagca 36960
cgccaggcct ccctgtccat caccaactcc cggagttcac tcagactcac gtccattgag 37020
tcagtgatgc catccagcca tctcatcctc tctcgtcccc ttctcctcct gcccccaatc 37080
cctcccagca tcagagtttt ttccaatgag tcaactcttc gcgtgaggtg accaaagtac 37140
tggagtttca gcttcagcat cattccttcc aaagaaatcc cagggctgat ctccttcaga 37200
atggactggt tggatctcct tacagtccaa gggactctca agagtcttct ccaacaccac 37260
agttcaaaag cctcaattct ttggcgctca gccttcttca cagtccaact ctcacatcca 37320
tacatgacca caggaaaaac cataaccttg actagatgga cctttgttgg caaagtaatg 37380
tctctgcttt ttaatatgct atctaggttg ctcataactt tccttccaag aagtaagtgt 37440
cttttaattt catggctgca atcaacatct gcagtgattt tggagcccca aaaaataaag 37500
tctgccactg tttccactgt ttccccatct atttcccatg aagtgatggg accagatgcc 37560
atgatctttg ttttctgaat gttgagcttt aagccaactt ttcactctcc actttcactt 37620
tcatcaagag gctttttagt tcctcttcac tttctgccat aagggtggtg tcatctgcat 37680
atctgaggtt attgatattt ctcctggcaa tcttgattcc agtttgtgtt tcttccagtc 37740
cagtgtttct catgatgtac tctgcatata agttaaataa gcagggtgat aatatacagc 37800
cttgacgtac tccttttcct atttggaacc agtctgttgt tccatgtcca gttctaactg 37860
ttgcttcctg acctgcatac agatttctca agaggcaggt caggtggtct ggtattccca 37920
tctctttcag aattttccac agttgattgt gatccacaca gtcaaaggct ttggcatagt 37980
caataaagca gaaatagatg tttttctgaa actctcttgc tttttccatg atccagcaga 38040
tgttggcaat ttgatctctg gttcctctgc cttttctaaa accagcttga acatcaggaa 38100
gttcacggtt catgtattgc tgaagcctgg cttggagaat tttgagcatt cctttgctag 38160
cgtgtgagat gagtgcaatt gtgcggcagt ttgagcattc tttggcattg cctttctttg 38220
ggattggaat gaaaactgac ctgttccagg cctgtggcca ctgttgagtt ttcccaattt 38280
gctggcatat tgagtgcagc actttcacag catcatcttt caggatttga aatcgctcca 38340
ctggaattcc atcacctcca ctagctttgt ttgtagtgat gctctctaag gcccacttga 38400
cttcacattc caggatgtct ggctctagat gagtgatcac accatcgtga ttatctgggt 38460
cgtgaagatc ttttttgtac agttcttctg tgtattcttg ccacctcttc ttaatatctt 38520
ctgcttctgt taggcccata ccgtttctgt cctcgcctat cgagccctcg cctccctacg 38580
tagagactct aagcaggaag gtgacccgtg ctgcactggg tccagcatgc ttttaattca 38640
gcagtggaac ttctgggtca tgattgtgtt taagggatgc gcatacgatt tttgaagcaa 38700
aatttaacag gacagcagtg taaagtcagt acttatttct gattaaagaa agcaaatatc 38760
cagcctgtta ctaagttaat taactaaaga aacatcttca acttaataaa cagtatctcc 38820

-continued

```
tgaaacttac agcatgcttc acatttaaag gcaaaaccat tttagaggcc agggttccca  38880
cgcttacgtt tattatttaa tatatgctac agattcaagc ccatgacaca aaatgggggg  38940
aagagtgtga gtgttaggaa aaatgagata aaattggttt ttgcaggtga tgggctagtt  39000
tactttaaaa aaaaaaacaa aacaagctca agatgaactg aaggactatt agaactggta  39060
caagagttaa cctgtgatcg aatacaagca ggctgggcaa aactcagcag gttttcttct  39120
atacaggcag taatgattga gaatacgaaa cggcggaagc gcttacaacc tcgataacag  39180
ttctattaaa agccctagga atgaacttaa cacggnnnnn nnnnnnnnnn nnnnnnnnnn  39240
nnnnnnnnnn nnnnnnnnnn nnnnnnnnnn nnnnnnnnnn nnnnnnnnnn nnnnnnnnnn  39300
nnnnnnnnnn nnnnngctcc ccccaccctc ccctcctccc cccccaccac cagtgcccca  39360
ggtctcgtgc ccagagagct gaagatgcca gcaggcccgc tgcctgcctc gctcgcgtgg  39420
cccgggctcg ctgccggtct gcctgcccag cacacagatg cagccccagc tctcgctgcc  39480
acccgcctcc cccaggcagg actctcccac aacaccaagg gcgtctctgg gttcaggatg  39540
gccctcgttg aggtgtaaag tgcttcccgg ggctgagacg aatgggccgg agatccaaac  39600
gaggccaagg ccgccacggc gcctggcgca gggcacccat ggtgcagagc ggcccagctc  39660
cctccctccc tccctccctc cctgcttctt tatgctcccg gctatgtcta tttttactct  39720
gcaatttaga aatgataccg aaggacaaac accgttcccc ctgtgtgtct gctctaaacc  39780
ctttatctac ttatctatta gcgtgtccaa gttttgctgc taagtgaatg aaggaacact  39840
acccacaagc agcaacgtcc ccacgaccct cgcctgttca actgggaatg taaatgtgct  39900
ttcaaaggac ctaagtttct atgttcaaaa ccgttgtgtg tttcttttgg gagtgaacct  39960
aggccactcg ttgttctgcc tttcaaagca ttcttaacaa ctctccagaa cccagggctt  40020
ggcttacgtt tccagaaatt ccaaagacag acacttggaa acctgatgaa gaaggcctgt  40080
gagcacagca ggggccgggg tacctgaggt aggtgggggg ctcggtgctg atggacacgg  40140
ccttgtactt ctcatcgttg ccgtccagga tctcctccac ctcggaggct ttcagcaggg  40200
tcacgctggt ggccagggtc gtgtatccat gatctgcaac cagagacggg gctgcggtca  40260
gcccgcgggc gggcagcagg caggagcagc caggagacgc agcacaccga ggtcctcaca  40320
tgcaggaggt gggggaagcg gctgtggacc tcacgactgc ccgatgtggg cctcttccaa  40380
agggccggcc tggaccctgg ctttctccag aggccctgct gggccgtccg cacaggctcc  40440
agccacaggg cctcttggga caggagggct ccagagtgag ccggccggcg ggaagaggtc  40500
tgacaccgct gcagtccaca acacgaagcg aggtggagat gggatgaggg atgagaaaca  40560
cttttctttt aaaacaagag cccagagagt tggaaagagc tgctgcacac gcaacatgaa  40620
ctcctggccc cggtgccagc ggcgctggga gcccgagttc tcggcaatcc gaccacagct  40680
tgcctaggga gccgggtgga gacggagggt taggggaagg cggctcccca gggagcgcga  40740
ggcccggggt cgccaaggct cgccaggggc aagcgcagct aggggcgcag ggttagtgac  40800
cggcactgca cccggcgcag gagggccagg gaggggctga aaggtcacag cagtgtgtgg  40860
acaagaggct ccggctcctg cgttaaaaga acgcggtgga cagaccacga cagcgccacg  40920
gacacactca taccggacgg actgcggagt gcacgcgcgc gcacacacac acacacacca  40980
cacacacaca cacacggccc gggacacact cataccggac ggactgcgga gtgcacgcgc  41040
acacacacac ccaccacaca cacacccacc acacacacac ccaccacaca cacacacaca  41100
cacacacacc cccacacaca cccacacaca cccacacaca cccacacaca cacacccaca  41160
cacacacaca cacacacaca cacacacacg gcccggtggc cccaggcgca cacagcacgg  41220
```

```
agcaaacatg cacagagcac agagcgagcg ctagcggacc ggctgccaga ccaggcgcca  41280
cgcgatggat tgggggcggg gacggggagg ggcgggagca aacggnnnnn nnnnnnnnnn  41340
nnnnnnnnnn nnnnnnnnnn nnnnnnnnnn nnnnnnnnnn nnnnnnnnnn nnnnnnnnnn  41400
nnnnnnnnnn nnnnnnnnnn nnnnngtatt aaagaagccg ggagcgagaa tatgacggca  41460
agaggatgta ggtgggggcg gggcaagagt aaagagagcg gacggtagag ggatgcgat  41520
tgtgatgcgg aagcgagacg aggagtgatg ccgtattaga ttgatagcaa gaggaacagt  41580
aggagggggg ggggagagga gggggaggtg gggggtggtg ggtgggaagg gaactttaaa  41640
aaaaagaggg gagagttgga ggggggaata aacgggcggt aaaaaagaac aatttgaaat  41700
taccagggtg gggcggccag gggggtgatt cattcttgga gggggcaaca tatggggggt  41760
ggctgtcgcg gattaggaga aaataaatat caggggtgat taagtgtttg gcgttgggga  41820
ataatgaagt aagaatcaaa tatgaatcgc gttggcatcg ttagccatcg ggggaaacat  41880
ttcccatgca aggaacaagg atgtgagaat gcgtccgtct gaaccaccgt cccggggtcc  41940
cagtaggact cgccgagctg atagttgccg gagcaacagt taagggagca gaagctgcta  42000
caaaaccacc acctgccaaa gtagggtctc caattacgga gtgcgcctcc tgggtgtcgg  42060
tccaaacctt tggaaaggac ctggaaataa gtgctaccca ccagatatta atataaaccc  42120
acctggccag gagaggcagg cgctgctggc acaggaagtg tccccagact cagtcatcaa  42180
ggtaaataat attttgggac ctccctggaa atccagtggt taggactctg cggttcaatc  42240
cctggtcggg gaactaagat cccacaagtc acaagacatg gccaaattta aaaaagaaaa  42300
aaagagagag aaatatttag tgcaataggt tttagaattg aaattaagct cctgcccacc  42360
cccaccccc aatctggatg aataaagcat tgaaatagta agtgaagtca ggctctgaca  42420
tgcactgatg tgactcacct taagcaaccc ccaccctagg actggtcggg gttccaggag  42480
tttcaggggt gccaggaaga tggagtccag cccctgccct ctccccccac cacgtcctcc  42540
actggagccg cctaccccac ctcccacccc tccgcaccct gctacccccc acccctgccc  42600
ccaggtctcc cctgtcctgt gtctgagctc cacactttct gggcagtgtc tccctctaca  42660
gctggtttct gctgcccgct accgggcccg tcccctctgt tcagttcagt tcagtcgctc  42720
agtcatgtct gactctttgt gaccccatgg actgcagcac accaggcctc cctggccatc  42780
accaaccccc agaacttact caaactcatg tccatcgagc cagtgatgcc atccaaccat  42840
ctcatcctct gtcgacccct tctcctggcc tcaatctttc ccagcatcag ggtcttttcc  42900
aatgagtcag ttctttgcat caggtagcca aagtattgga gtttcagctt cagcatcatt  42960
tcttccaatg aatattcagg actcatttcc tttgggatga actggttgga tctccttgca  43020
gtccaaggga ctctcaagag tcttctccaa caccacagtt caaaagcatc aattcttcag  43080
tgctcagctc tctttatagt ccaactctca catccatacg tgaccactgg aaaaaccata  43140
gcctcgacta gatggaactt tgtgggcaaa gtaatgtctc tgcttttgaa tatgctgtct  43200
aggttggtca taacttttct tccaaggagc aagcgtcttt taatttcatg gctgcagtca  43260
ccatctgcag tgatttttgg agcccaagaa aataaagtct gtcactgttt ccactgtttc  43320
cccgtctatt taacggaggg aaatttccca gagcccccag gttccaggct gggccccacc  43380
ccactcccat gtcccagaga gcctggtcct cccaggctcc cggctggcgc tggtaagtcc  43440
caggatatag tctttacatc aagttgctgt gtgtcttagg aaagaaactc tccctctctg  43500
tgcctctgtt ccctcatccg cagaagtgac tgccaggtcg gggagtctgt gacgtctcca  43560
```

-continued

```
gaagccggag gattttctcc ccatttgctg aaagagagct cggggtgggg gaagcttctg  43620
cacccctagg atcaccagag gagccagggt cttcagggtt cccggggacc cctcagtggg  43680
ggctcaggaa ccacagagcc agaccctgat tccaaaaacc tggtcacacc tccagatgac  43740
cctttgtccc ttggctccgc ctcaaatgct ccaagcccca acagtgaagc gcttaagaga  43800
aggatccacc aggcttgagt ttggggagga gggaagtggg gagctggggg agggcctggg  43860
cctgggagac aggaatccac catggcttca ggcagggtct ctggggcctg cggggtggag  43920
agcgggcagg agcagacaga ggtgactgga cacgacacac ccctccactc caagggaggt  43980
gggcaggggc ggggcacaga ggaacaagag accctgagaa ggggtccacc gagcagactg  44040
ctggacccag acatctctga gccagctgga atccagctct aagccatgct cagcccaggc  44100
agggtatagg gcaggactga gtggagtggc cagagctgca gctgcatggg ctgggaaggc  44160
cctgcccgtc ccctgagggt cccccagggt ctagccagac tccaatttcc gaccgcagca  44220
cacacaggag gaagtggtcg gggtggagtt ggcccagagg tctgggcagg tgcagggtgg  44280
gggaaggggg gcagctggag tcacccgctg aattcaggga cagtcccttt ttctccctga  44340
aacctggggc tgtcccgggg gccaccgcag cctccaggca gcggggggac ccagccccca  44400
atatgtgaga agagcaggtc ccaggctgga gagagcgaag caccatggtg gggagaagtt  44460
agactggatc ggggccccta ggggctcccc cggacctgca cggcagccgt cagggcaccc  44520
gcaccccatt gctgttcagt gctggccagt gtccaaggcc agggatgtgt gtgtgtgtgt  44580
gtgcgtgcgt gcgtgcgtgt gtgtgtgcgt gtgtgcgcgt gcgtgcgtgt gtgtgtgtgt  44640
gcgtgcgtgt gcgtgcgtag acgtgtgcgt gcgtgcgtgc gtgcgtgcgt gtgtgtgcgc  44700
acgcgcgcag cccagcctca gcactggacc aggcagcctg ggattcctcc aaaactgcct  44760
tgtgagtttg gtcaaaccgt gaggctctga tcaccgccat ccattcgccc cctcctgccc  44820
ccctcatcac cgtggttgtt gtcattatcg agagctgtgg agggtctggg aggtcatccc  44880
acctgccagc taaaccgtga ggctgccgca atcgcactga tgcgggcaga cccgagacgc  44940
tgtgccggag acgaaggcca gcttgtcacc ccgccagagc ggcagtcggg ccacaagcat  45000
catccaagca gtggttctct gagcccgacg gggtgatgca aaggagccag gagacacctg  45060
cgcgtccaag ctgggggacc ccaggtctgt tatgccggac agtaaacacg ttcagctccg  45120
gagggagagg gttcccctac cttccagggt ttctcattcc acaaacatcc aaagacaatc  45180
cataccgaag gcgatccgtg cctttgctcc tgagacgtgc ggaagcacag agatccacag  45240
acactgtctc ccaggatcct atgtatgtaa aggaaccgaa gtcccaggct gtgtgtctgg  45300
taccacatcc cacggaacag gctggactga ttttcaccaa atgtagcaga aacgttaagg  45360
agtatcagct tcaaaatatg agggccagac atgtctgaga agtcccttcc agaaaagtcc  45420
ctttggggtc cttccccaga gttgctgaaa cagagaaccg gaagggctgc agagctgaac  45480
ttaaacaact ggatcgcaaa ggtccgtctc atcagagcga tggtttttcc agtggtcatg  45540
tatggatgag agagttggac cataaagaaa gctgagcgcc gaagaatcga tgcttttgaa  45600
ctctggtgtt ggagaagact cttgagagtc ccttggactg caaggagatc caaccagtca  45660
atcctaaagg aaatcaatcc tgaatattca tgggaaggac tgatgctgaa gctgaaactc  45720
caatactttg gccacttgat gcaaagaact gactcactgg aaaaaccctg atgctgggaa  45780
aggttgaagg caggaggaga aggggtcgac agaggatgag atggttgggt ggcatcaccc  45840
acccatggac tcaatggaca tgggtttgag taaactctgg gagttggtga tggacagaga  45900
atcctggcat gctgcggtcc atggggtcat agagagtcag acacaactga gcgactgaca  45960
```

```
gaactgaagc aactggcaag ccggagggta ggtgccggct gcgatgagcg ggaacgtgca  46020
acctgccacg tggagctctt cctacaccca gagtcctgac ggcactggga ccctagccct  46080
ccacggcctc tccagggcca cgagacaccc tcacagagca gagaagcgga acagagctgg  46140
tgtgcagaac caggccccgg gggtggggcg gggctggtgg gcaggcttta gtgagaagcc  46200
cttgagccct ggaaccagag cagagcagaa cagttggcag aggccccccct gggagaggcc  46260
ccccgcccag agtaccggcc ctgggccctg ggggagaggg cggtgctggg ggcagggaca  46320
gaaggcccag gcagaggatg ggccccgtgg gacggggcgc accaaaacag cccctgccag  46380
caaggggaag ctggggcact ttcgaccccc tccaaggagg agcccacacc agcgcatctg  46440
cccaaggtgc ccttggccct gggggcacat gaggcccagg ccaggccagg gggcccatga  46500
ggcccccagg ggtcagtgca gtgtccccag gcagccctgg cctctcatcc tgctgggcct  46560
ggcctcttat cccgtgggcg cccacggcct gctgccccccg acagcggcgc ctcagagcac  46620
agccccccgc atggaagccc cgtcaggaaa gagcccttgg agcctgcagg acaggtaagg  46680
gccgagggag tcatggtgca gggaagtggg gcttcccttc gatgggaccc aggggtgaat  46740
gaccgcaggg gcggggaacg agaagggaaa ccagctggag agaaggagcc tgggcagacg  46800
tggctgcacg cacagcgctg accctgggcc cagtgtgcct ttgtgttggg ttttattttt  46860
aattttgtat tgagatgcta tttatctcgt ggagcttttg ccgccctgag attttgtacc  46920
cgtggctggt gtccctcttg cctcaccccg gcctctgtag cagggcagac acggcgcaac  46980
ggggcagggc gtgcccagga ggcactgtca ttttgggggc agcggcccca caaggcaggt  47040
ctgccttcct cccctcttac aggcagcgac agaggtccag agaggtgagg caagctgccc  47100
aatgtcacac agcacacggg cgcagtccca ggactgtaga aatcccggga ctagacaggc  47160
accagagtgt cctgtgtttt taaaaaaacg gcccaagaga agaggcaagt ctgcaaggcg  47220
tcccgggaag gcagcagggg cttggctcgg tctcccccaa ggaggccagc tcctcagcga  47280
ggttcctaag tgtctaacgg agccaagcct gaaccaaggg ggtcacgtgc agctatggga  47340
cactgacctg ggatgggggga gctccaggca aagggagtag ggaggccaag gaggagagag  47400
gggtgcacag gcctgcaggg agcttccaga gctggggaaa acggggttca gaccacgggg  47460
tcatgtccac ccctccttta tcctgggatc cggggcaggt attgagggat ttatgtgcgg  47520
ggctgtcagg gtccagttcg tgctgtggaa aaattgtttc agatcagaga ccagcgtgag  47580
gtcaggttag aggatggaga agaagctgtg aaaaggtgat ggagagcggg gggacggtcc  47640
tcggtgatca ggcaccgaga tcgcccatgg aatccgcagg cgaatttaca gtgacgtcgt  47700
cagagggctg tcggggagga acaggcactg tcatgaactg gctacaaaaa tctaaaatgt  47760
gcaccctttt cggcaatatg cagcaagtca taaaagaaaa cgcatttctt taaaattgcg  47820
taattccgct tttaggaatt catctggggg cgggggaaca atcaaaaaga tgtgaccaaa  47880
ggtttacaag ccaggaagtc aactcgttaa tgatgggaga aaaccggaaa taacctgaat  47940
atccaacaga aagggtgtga tgaagcgcag catggcacat ccaccgcaag gaatcctaac  48000
acaaacttcc aaaacaatat ttctgacgtt gggtttttaa agcatgcgtg cactttcaaa  48060
agcttgtcag aaaacataga aatatgccaa taatgtgtct ctagccaaat tttttaattt  48120
ttgctttata attttataaa gttataattg tatgaaatat aatgataaaa ttataaacta  48180
taaaaaagtt atgaaaatgt tcacaagaag atatacatgt aattttatct tctacaatac  48240
tttttaatac cagaataacg tgcttttaaa aaagattgag cacagaagcg tataaagtaa  48300
```

-continued

```
aaattgagag tttctgctca ccaaccacac gtcttacctt aaaacccatt ctccagcgag  48360
agacagtgtc atgtgggtct gtacacttct ggcctttctc ctaggcatgt atgtccctga  48420
aaactcacac acacggctaa tggtgctggg attttagttt tcaaaacgga ctcatactct  48480
gcctatgagc ctgcaactat ttattcagtc tgttgagatt ttctatatca gcccacatgg  48540
atcccgcatg ttctctgaat ggctctgtat gaattcaaag tttggaagaa gcagcgtgtc  48600
tttaatcatt cgcctattaa tggacgtttg gggtgtttcc actacaaaan nnnnnnnnnn  48660
nnnnnnnnnn nnnnnnnnnn nnnnnnnnnn nnnnnnnnnn nnnnnnnnnn nnnnnnnnnn  48720
nnnnnnnnnn nnnnnnnnnn nnnnnnnnng atacaattcg agctcggtac cctggcttga  48780
actatatgaa cagagaacga tgagaacagt ttctcaaact tggaacagtt aacattttgg  48840
gctaaatgat tctttttgt gtggagttgg cctatgaata gaggatatta gcagcatcat  48900
ttaaccttta ctcactacat acctgtagca actacatcct ctccatttgt gtcaatcaaa  48960
actgtctccg gacatggaca agtgtgcccc tgggatgggt ggaatgacct tttgttaaga  49020
accactgggt cagagattca tagattttg tcttgttgac tttttaaaaa tacatcttgg  49080
tttttatttt attggtttct gctcttatct ttatgattac cttcctttta cttggggctt  49140
ccctgataga ttttcccttc tggctcagct ggtaaagaat ctgcctgcaa tgcaggagac  49200
ctgggttcag tccctgggtt gggaggatcc cctggagagg agaagggcta cccaccccag  49260
tattctggcc tggaggattc catggagtgt atagtccatg gggtcgcaga gtcggacatg  49320
actgagtgac tttcacacac acatatgtcc ctggtagctc agctagtaaa gaatcccacc  49380
cgcaatgcag gagaccccgg tccaattcct gggtccggaa gattcccttt tgtttactcc  49440
ataagatctt atctggggac aaaactaaca gctatgccag accttctgga catcagggaa  49500
cgtgaggggt gtggactgga cagatgtgtg tgttctccca aacacaaaca tacatctgta  49560
tacatgtaca tggagagagg gggagggagg ctgtgagtct ccaggggacc gtgcaaccat  49620
gtgacattca tggaggcgtt tgcgggtgat cactacacag tttcttcttc tggtttcttg  49680
gtcaattgac ttcacaattc caattcctat acttcatttt agactgaggg aattttacac  49740
tattgtaaga catatgtata catgagttat gttcagcgcc atgagggctc attttgtgtg  49800
tccactttgc ctggaaacaa agttggactg atttacttct aggggtgcct gggggtgttt  49860
ctggaggaca ggagcatttg aacccaaggg ctcggtgaag catgagcctc tctgcaggtg  49920
gacccaggag gaacgcaagg ccgaggaagg cagactctcc tcctccctaa cccgaggtct  49980
ctgctcagaa aagggacaat ataatgacta gaagaaaaga aagaacatca gctgtgggag  50040
gtttgttctc tggagcagat tcacacgttg aggctcatgt gcaggaattc taggtgaaac  50100
agagcagtca cccatgtgtg ttggaaaatt ttaaattaca tttgcagtta cgactttgtt  50160
taagccagac agggtagcac agcaaagtca ccatgtggtc acctgtgttt tgtaaaggag  50220
agagaacttg ctggcacatt caggaaaggc cgtgtctcag ctttggaggc acactgagag  50280
gccacaagca gatggtgagg accagggtct cgggcagagg gatcaattca ctgctcttca  50340
cttttgccac atctgtgtgc tgtccatcct ggccagagta gttcagtctt cagatgctgg  50400
agttcccatt ggtagaaatc caatctgggt catttttaaa cctctcttgg ttctacttaa  50460
tggttttaaa atctctttgg ctcaagaaaa aaaataaaca taattttaaa gggtggtttg  50520
gggccttgac tataaagtac attatctggg ccatttcaga gcatggttga attaatacat  50580
ttcgtgctta ctatagctcc tattttcttg attctttaca ggtaattttt gttaggaatc  50640
gggtactgtg aatattttct tgttgaatac gggatctttg tattttttcc taattttttt  50700
```

-continued

```
tttttttca tttttggttt taccttcagg aaagtcacta ggactcagga aagtcctttg  50760
tccgcctgtt atttcagtct cttacctggg gccagggcag cgtttcctct gggctaagtt  50820
tccccacaac cggggccagt tctcctcact cttcaccctg aggccttaat gaggagctcc  50880
cctgcgtctg agcagccggc cctcctgtga cgtgcgtgtg tctctggcca tcggcgtccg  50940
gtgtccttgg aggttccgtc ctcccttcgc tcactgtgcc ccgcactcga gctctcaggc  51000
tccaagcagt gtccgcagtg tgcagaccct ctgtgtagct ctctcctcct caggactctt  51060
ccctctagat gtgtgttttc ttttggctcc ttggacctcc gctctgaacg caggcctggt  51120
gctgagtgtg atctctggag ggaagcctgg gaggctggac gggtccgccc tgcggtgtgg  51180
tgacaggtgt gggctcgggg cggggcctgc acgtcgtcct gacccgagcc gggactgggc  51240
tccgggcctc aggcatcact gactgaatct ccctcacaga ggggtcaggg cctgggcggg  51300
ggaaccgtct ctgcaatgac agcccctccc agggagggca cagcggggag ctgccgaggc  51360
tccagcccta gtgggaggtc ggggagccca ggggagcggc ctgacggccc cacaccggcc  51420
cagggctggt tcgttctgtt tctcgagctc aacagaagct ccgaggagct gggcagttct  51480
ctgaattcgt cccggagttt tggctgctga gtgtcctgtc agcaccgtat ggacatccag  51540
agtccattag cagtggtctc tgtccctctg tctgtccttc atcaggctct ttgtccaggt  51600
caccacacgg ccaacaccag gacagtctgg tcccgccagc ccatcgtccc tgcggacgcc  51660
cctgtgcagc ctgccgaagg gccgggaggc cgggggaacc gggccaggcc tgtccctgct  51720
gtgtccacag tcctcccggg gctggaggag agcgtgagca ggacgggagg gtttgtgtct  51780
cacttccccg tctgtctgtg tcactgtgag gattatcact gctgtcagct gactgacagt  51840
aatagtcggc ctcgtcctcg gtctgggccc cgctgatggt cagcgtggct gttttgcctg  51900
agctggagcc agagaaccgg tcagagatcc ctgagggccg ctcactatct ttataaatga  51960
ccctcacagg gccctggccc ggcttctgct ggtaccactg agtatattgt tcatccagca  52020
ggtcccccga gcaggtgatc ttggccgtct gtcccaaggc cactgacact gaagtcggct  52080
gggtcagttc ataggagacc acggagccgg aagagaggag ggagagggga tgagaaagaa  52140
ggaccccttc cccgggcatc ccaccctgag gcggtgcctg gagtgcactc tgggttcggg  52200
gcaggcccca gcccagggtc ctgtgtggcc ggagcctgcg ggcagggccg gggggccgca  52260
cctgtgcaga gagtgaggag gggcagcagg agaggggtcc aggccatggt ggatgcgccc  52320
cgagctctgc ctctgagccc gcagcagcac tgggctctct gagacccttt attccctctc  52380
agagctttgc aggggccagt gagggtttgg gtttatgcaa attcaccccc gggggcccct  52440
cactgagagg cggggtcacc acaccatcag ccctgtctgt ccccagcttc ctcctcggct  52500
tctcacgtct gcacatcaga cttgtcctca gggactgagg tcactgtcac cttccccgtc  52560
tctgaccaca tgaccactgt cccaagcccc ccggcctgtg gtctcccctg gactccccag  52620
tggggcggtc agcctggcag catcctggcc gtggactgag gcatggtgct ctggggttca  52680
ctgtggatgt gaccctcaga ggtggtcact agtcctgagg ggatggcctg tccagtcctg  52740
acttcctgcc aagcgctgct ccttggacag ctgtggaccc gcagggctgc ttcccctgaa  52800
gctccccttg ggcagcccag cctctgacct gctgctcctg gccacgctct gctgcccccct  52860
gctggtggag gacgatcagg gcagcggctc ccctcccgca ggtcacccca aggcccctgt  52920
cagcagagag ggtgtggacc tgggagtcca gccctgcctg gcccagcact agaggccgcc  52980
tgcaccggga agttgctgtg ctgtgaccct gtctcagggc ggagatgacc gcgccgtccc  53040
```

tttggtttgt tagtggagtg gagggtccgg gatgactcta gccgtaaact gccaggctcc 53100
gtagcaacct gtgcgatgcc cccggggacc cagggctcct tgtgctggtg taccaaggtt 53160
ggcactagtc ccaccccagg agggcacttc gctgatggtg ttcctggcag ttgagtgcat 53220
ttgagaactt acatcatttt catcatcaca tcttcatcac cagtatcatc accaccatca 53280
ccattccatc atctcttctc tctttttctt ttatgtcatc tcacaatctc acacccctca 53340
agagtttgca ttggtagcat atttacttta gcacagtgtg cctcttttta ggaaactggg 53400
ggtctcctgc tgatacccct gggaacccat ccagaaattg tactgatggc tgaacccctg 53460
cgtttggatt cttgccgagg agaccctagg gcctcaaagt tctctgaatc actcccatag 53520
ttaacaacac tcattgggcc tttttatact ttaatttgga aaaatatcct tgaagttagt 53580
acctacctcc acattttaca gcaggtaaag ctgcttcgca tttgagagca agtccccaga 53640
tcaataaaga gaatgggatg aacccaggat ggggcccagg ggtcctggat tcagactcca 53700
gccgtttagg acagaacttg actaggtacg aagtgagcgg ggtggggggg caatctgggg 53760
ggaactgtgg cacccccagg gctcggggcc atccccacca catcctggct ttcatcagta 53820
gccccctcag cctgcgtgtg gaggaggcca gggaagctat ggtccaggtc atgctggaga 53880
atatgtgggg ctggggtgct gctgggtcct aggggtctgg ccaggtcctg ctgcctctgc 53940
tgggcagtga taattggtcc tcatcctcct gagaagtcac gagtgacagg tgtctcatgg 54000
ccaagctatt ggaggaggca gtgagcactc ccacccctgc agacatctct ggaggcatca 54060
gtggtcctgt aggtggtcct ggggcttggg ccgggggacc tgagattcag ccattgactc 54120
tcagaggggc cagctgtggg tgcagcggca gggctgggcg gtggaggata cctcaccaga 54180
gccaaaataa gagatcaccc aacggataga aattgactca caccctttgg tctggcacat 54240
tctgtcttga aatttcttgt ggacaggaca cagtccctgg ataaagggat ttctatcttg 54300
cgtgtgcaat agagctgtcg acacgcttgg ctgggacatg taatcctttg aacatggtat 54360
taaattctgt tcactaacat ctgaaaggat ttttgcatca ataaacctaa ggtatattgc 54420
cctgtcattt ccttgtcttg tagtgtctct gagtaggctg gaaggggtaa ccagcttcac 54480
aaatcgagtt aggaaattcc cttattcttc cactgtctaa tagactttca taagattagt 54540
gttaattcct ctttaaatcg ctgctataat catcactgtg gccaccggta ctgaattttt 54600
tgttaggatg atttttaaac aagcatttta atgatttttc cttttatttt cggctgtgct 54660
gggtctcgtt gctgtgtgcc ggcgttctct cgctgtggcc agtgggggcg ctgctctcgc 54720
gttgcgaagc tcgggcttct gactgcagtg gcttctctcg ttgcagagcg cgggctccag 54780
ggcgctcagg ctcgcgtggc tgcggcacgt gggctcagta gtcctggggc acaggtgcag 54840
cagcctctca ggacgttttg ttcccagatg gtgggtcggt cgaaccggtg tcccctgcgt 54900
tgcaaggtgg attcttcacc gctggaccac cagcgacgtt ccctggaggt ttttaattat 54960
ggatttaagc tctcattaga tgtctcctca catttcctat ttctttttga gtcagtttga 55020
tactttgttt gtgtctgtaa gtttgtccat tttatccaag tcatctaatg tgttgataga 55080
caattattgg ttagtcatct aattgttggt ttacaatttt gagagcattg tcctgcaatt 55140
ccttctatct gcaagattgg taataatatc tcccaagagg agtcacaaac tgaaatgaga 55200
ttanatacag gctttttttt taaaagaatg aacttatgtt gttgcctttc tcatagatct 55260
tacttcttag catgactgta cttactgact ggggcgtttt catgtctgtg tggagagcta 55320
ccattagtac ttcttatcgc ccaaagacat cgggctcctg ggcacagtga aaacactcct 55380
ttctgtggct attttgcaaa atatggccta gcctagcgtc ataagggatc acagctgaca 55440
actgctggaa cagagggaca tgcgaagcaa cgtgagggct ggaacctgga gggtcctctc 55500
tggggacagt ttaaccagct ataatggaca ttccagcatc tgggacatgg agctgtgaac 55560
tggaccaatg actgtcattt ttggaagaga aatcccagga gagaagggtc caggggaatc 55620
tgaggccgca tgcagtgcct caggacaggg gacaccttct ccagcagagc aggggggccc 55680
gcccaggccg cctgcagtga ttccaccagg aggagatgca tccctgcaga cctctgacag 55740
cacggccctc tcctgagaca cagggtcaca cccggggccc tggaaccctt tgagacccta 55800
aacctttcct ttcctgacca ccctgacagc agtctagctc agaacagaca tcttcatttt 55860
cagcaggaaa atccttttcc tcgtttgagg gagcgactgg caccggagga gctgagtctt 55920
ttaaacacag gctgcctgaa cctcagggat gacctgcagc tgctcagagg aggctggagt 55980
gtgatagctc actctaatgt tactaaaagg aacatattgg acaccccctc tctgaaaaat 56040
ttccctcctg cctctcatct cttagtccac tttatcgccg ttttactgct tttctattta 56100
ctactcttaa cgccaaccta tcttatttcc cctcccagtt taacacggtt ttccctccac 56160
ccgctctctt taatctcaga agattctgcc tattcctcta ttatcacacg cccctacttt 56220
ttattttttt tcttacccgc cttttattcc ctcccctcct cactctctat ttaattacat 56280
cttaactaca ccgcctgcgc tatcttcgaa tgtatccaaa tatttttccc ttatataaca 56340
ctccaggccg agcggctaac ttattataat ttctttatag cgcctaccta atttcccttt 56400
atttctaatt atctatatat acccatgcaa tttcgnnnnn nnnnnnnnnn nnnnnnnnnn 56460
nnnnnnnnnn nnnnnnnnnn nnnnnnnnnn nnnnnnnnnn nnnnnnnnnn nnnnnnnnnn 56520
nnnnnnnnnn nnnnntgggt gtacgttata gagtaaacgc gcatgaagaa gtgggtcaat 56580
ctatggctgt gagaggcaga aaataatatt atcatatata atttatgtta taacacactg 56640
aggtggtggg ctcgtagaat agtgcggacg gggagaaagg tgggaaggag aagacacaag 56700
agagagatgt tcgcctcgcg ggatggatgg gcggagggat agaagaataa aaagaggaga 56760
ggtatagagg ggggcggggg gcataacgtg tggtggggta aatagtaggc ggtaattatg 56820
aaaaaaagaa agacgggggg ggcggtaaca tagaatacgc aaaaaagtca tatactgaac 56880
ggggattagg gagaagaggt ggggggcgtg gggtgcgggg gaaagaggtg tgtgtataat 56940
tggtatggag tgttatttga atatatatta atgtaatagg gagtgtaatt agtgaaattg 57000
tgggagtatt atattggggt gtgggggaca tggcaaagtg atgatcggga taaaaaaagt 57060
aaagcaagag gggaggggaa aataaggggg gggagaaggt cgaagaaaat aagaggaaga 57120
agaaagaacg gggtggcgg gcgggggggg cgccgctctt gtatctggct tttttgttgt 57180
gtcggtggtt gttcgcgtct tgttgggtcc ggggcgggtg tgcggaaaaa aaaaaaggcg 57240
ggaggcccgg ggcccggtca cgcggcaccc ccgcgggtcc ctggcttctc cttcggcagc 57300
tccgggggtc ggtgagcctg cgccctccgg gccgccggcc cgagctgtgt gcgccctgga 57360
gaatcggagc cgctgtggca gcacgcggag ggcgcgcgca agggccacgg gacggacctt 57420
caaaggccgc ggcggagcgc ggcaagccga accgagggcg gtctggcgat cggccgagcc 57480
ctgctccccc ctcccgcgtg gccccagggt cgcgggtgga ctggggcggg tacaaagcac 57540
tcacccccgt cccgccccca gaaagcctcc caggactctc acagagcacc cgccaggagg 57600
catccggttc ccccctcggc tcagttcagt tgctcagtcg tgtccaactc tttgcgaccc 57660
catggactgc agcaccccaa gcttccctgt ccatcaccaa ctcccggagt ttactcaaac 57720
tcatctattg agtcagtgat gccatccaac cgtctcatcc tctgttgtcc ccttctcctc 57780
ccactttcaa tctttcccag catcagggtc ttttcttatg agccagttct tcacatcagg 57840
tggtcagagt attggagttt cagcttcagc atcagtcctt ccaatgaaca ctcaggactg 57900
atttccttta ggatggactg gctggatgca gcgccagaca ccgaccgcgt ttaccccgtg 57960
tgtcctttcc aatggctgtc ccctgcgggc ctaggggcat tggtgcgggt ttgaatcctg 58020
tggccttgaa ttttacgcct tagttccagg tccagggcag ggccatccgg attcaggatg 58080
cttcccagcc cttcaggaat ggcaggtttt catggtcctt tctgagtgag ttctgagtgg 58140
tcatattggt gcccttggca gggagggctc ctgactttcc tatcttcaca tcactgtccc 58200
caacccccaa gagaggcctc ttggcccagg gactgcaggg aggatgaagt caggagcaga 58260
agcatggggt agggggctca ggtgggcaga ggaggcccct ctgtgaggag gaacggcaag 58320
cgaggaggga acaggggcac cggcagtgcc tggcaagctg ggtgatgtca cgactacgtc 58380
ccgaccacac agtcctctca gccagcccga gaagcagggc cctcccctga cccccatctg 58440
ggcctgggct tcagttttct cctccctgca atggggtgac tgtttgcctc caggagaggg 58500
gagcatgtaa aggtggccac tctcttctgg cagacatgcc aggcctgggc cagcctccac 58560
ccctttgctc ctgcagcccc tgctgacctg ctcctgtttg ccacaccggc ccctcctggg 58620
ctgatcaggg ccccccctcct gcaggaagcc ctctgggaca agcccagctt gctgtaactg 58680
tggctttcca ctgtgacctg caacgtggga ggctgttact taaaactccc atgactggtg 58740
gattgccggt ccccagaaca aggccacgca tccctggagg ccctcgagac catttaaggt 58800
agttaaacat ttttacttta tgcattttca tgtgtatcag aaagaaaaaa aatgtatcat 58860
cagttcatca aatccatgat ttcttgacca atattgctaa gatgaggctg aaataggcat 58920
ttccattttt aaaaaactga atcactctga agaaacagat ggcaggcttc cctggtggtc 58980
cggtggttaa cagtccatgc ttccagtgct gggggcatgg gttcgatccc tgaaaatttt 59040
aaaaaggaag aaaaagatgg ctcccccgtc cctgggattc tccaggcaag aacactggag 59100
tgggttgcca tttccttctc cagtgcatga aagggaaaag ggaaagtgaa gtcgctcagt 59160
cgtgtgcgac tcttagcaac cccatggact gcagcctacc agactcctcc gtccatggga 59220
ttttccaggc aagagtactg gagtggggtg ccattgcctt ctccaggcaa acggcctgct 59280
actgctactg ctgctaaatc gcttcagtcg tgtccaactc tgtgcgaccc catagacggc 59340
agcccaccag gctcccccgt ccctgggatt ctccaggcaa gaacactgga gtggggtgcc 59400
attgccttca gcctgctgct gctgctgcta agtcgcttca gtcgtgtccg actctgtgtg 59460
accgcataga cggcagccca ccaggctccc ccgtccctgg gattctccag gcaagaacac 59520
tggagtgggt tgccatttcc ttctccaatg catgaaagtg aaaagttaaa gtgaaattgc 59580
tcagtcgtgt ccgactctta gtgacccaat ggactgcagc ctaccagggt cctccatcca 59640
tgggattttc caggcaagag tactggagtg gggtgccatt cggcctaggg agtgagaaat 59700
cacggctgtc ttccctcttc tcgccctcta ggggtctctg tggagcctcc ctggagaggc 59760
cgcggcggct ccggggactg gagggggagg gggggttgag tcagccggtg gccctcccct 59820
cgctgcccgt ctcctccctt tttaggcaca agctgggcgc cctttttagg cgcagcctca 59880
ccctgcgggc cactgcccgt gtttcggctc cccggagata aaacagattg cctgcacccc 59940
gggtcatcac aaggattgta tgaccgtttc ccagtgtgct caccaccctc cctctgattc 60000
tcagagacgc gccctcgcct caggaggctg ctcatcccag gccaaggggc ggcgtggggt 60060
ccccagcgcc ccgcacagac actgccttct gaccacctcc tcccaacagc ttacctgcca 60120
agaaggcctc ctgacccctc atcctgcccg gtggtttgga gaaagcctca tctggcccct 60180

```
ccttctcggg gcctcagttt ccccctctgt gaactggcgg attctgccaa gctgacgtcc  60240
tggccagccg cctccccgtg gccagtgtcc cccgggacac agctgaatgt ccctgctcgg  60300
gatgcacctt cccaagttgg cctgtcagga ggcgggggcg agcagggaaa cccgactcct  60360
ctcagacggc ccatcgcatt ggggacgctg aggcccggag cagcggcacc ctcctggcca  60420
gggtcattct cccgccccgc cccgtccctc cgggcctccg agaccgcagc ccggcccgcc  60480
ccgggaagga ccggatccgc gggccgggcc accccccttc cctggccgcg ggcgcggggc  60540
gagtgcagaa caaaagcggg gggcggggcc ggggcggggg cggggcggag gatataaggg  60600
gcggcggccg gcggcacccc agcaggccct gcacccccgg gggggatggc tcgggccgcc  60660
ggcctccgcg gggcggcctc gcgcgccttt ttgtttttgg tgagggtgat gggggcggtc  60720
gcggggtact attttttcat ttataattgg gtattagcta gcgagtggaa ccacaccctt  60780
attccactat agccaatttt tgcgggggca tcttacatta cagactcgcc cgcctcttat  60840
ttcggtacag catatcagat cgtctcttta ctcagacact agtgattatt gtctatagta  60900
cacaaaaaga acggttgtgt cggcgtaatg gttgcatttt ccctcctcgt ttctcctgac  60960
cacctcaatt acaccaacac tctactattt aaatcacgta ttgtacgcca ccctccgccc  61020
gcgaactaaa agaatgtgca gatattctga agataaaatc gttcattgtt acgccccgcg  61080
cgcttcgcgt atattactct tagaacttct tattcgcccg agcagttatt caccccccgc  61140
aactagatgt cgccttaata tttgttctaa ccgttttgga ttctaacgat aggcgggaaa  61200
ggtagacatt cgaccgctac gacaactaaa atcgacgagc acaggctatt tatatcgcga  61260
ccacacgcgc gcggtataca naccgtaaaa ttatctaaca tcgagagtaa gggcacagag  61320
cgaaatacaa gcggcgtggt gggaggtgtg tctgtagtga attcgcacct cgcgccgccg  61380
cctctgtgcg tcgnnnnnnn nnnnnnnnnn nnnnnnnnnn nnnnnnnnnn nnnnnnnnnn  61440
nnnnnnnnnn nnnnnnnnnn nnnnnnnnnn nnnnnnnnnn nnnnnnnnnn nnngatataa  61500
tattaataaa cagcggatag atgtgtgtaa gggaggaggt gcataagaga ttaaagagag  61560
gcgggcggag agaaatagag tagaggagga tgagagaaaa aagaaagcaa gcgtaggtac  61620
aacggcgggt gggtagtatg ataaagtgag tgtatatatt tgagtaaagg aagggtagat  61680
ggagtataaa gaagtaagga gaggagaggg cggcggagag agagagtgca aagaaaataa  61740
gtgggcaaag gcggggtggg tgagaagcag tagaagagaa gatagagaag ggggaaaaag  61800
aggaaaatga ggattagaac aagtaggaca ggatagatgt gaaaaatgag atcaggtcaa  61860
ggtggagaaa aagtagaaac tggggcgtga ttgtaaaaaa gggaggccgc gatggggcag  61920
caccataagc gaagagatga attaatgaaa gcaaggcagg gagaatcaaa tgagttgggt  61980
ggaggaagga ggctgtgact tccttcgctg ccggaaagag aactagaata gcctcgggct  62040
gtggggggag gtaaagataa agtgacttct gggccctggg ggaggcccag gagtttctac  62100
cgagctgagc tgggtgcctc tcccaaatgc ccaaccccct gagagtcgac gggagagcac  62160
agcctggcca aacctgggca gggcacacgt gtccttcacc ccacagtggt cacgagccca  62220
gcgtggtccc tgcgtctggc gggaaacaca gaccctcaca ccccacacaa gggtccggcc  62280
gctttcaaat aacagcagcc gtgccctctg ggccggtgac ccggacacag agagatgaag  62340
tccgcatctc tcagagtgcg ctgtcctccg cccggtcagg cccgggtccc ctgcttctct  62400
gaggtcacca ggagggattg catgtgggtc tcagggacac aggttcagtg atgtgacaga  62460
gggtagtggg tcccagcagg gccggtcttt ggacccgttt ttctgaaaag ccagttggcg  62520
```

acctggggtc acagcaaagc tgatcctgtt tggccaggag tctcccagtg acggcctccc 62580
ccagaacatc gggcccagtg ggggctccag ggggtagact tgcctcccag ctcacgcccg 62640
tgtcttgaca agtccatgat ttggtaaaat taatttgtgt tggatggagt tgatttagtg 62700
gtgtgtgagt ttctgtggcg cagcaaagtc aatcagttac gcatacacat gtatccagct 62760
cttcctacga ttctgttccc atataggtca ttatggggtg tcaggtagag cttcctgtgc 62820
tacgcagtac ggccttattc agttcagctc agtcgtgtcc gactccttgt gaccccatgg 62880
actgcagcac gccaggctcc cctgtccatc accaactcct ggagcttatt caaactcatg 62940
tccatcgagc cggtgatgcc atccaaccat ctcatcctct gtcgttccct ctcctcctgc 63000
cttcagtctt tcccagcacc ccctagagaa gggaatggca aaccacttcg gtattcttgc 63060
cctgagaacc ccatgaacag tacggaaagt ccttattagt tttctatttt atatatagca 63120
gtgcacacgt gtcagcccca atctcgcaat ttatcacccc cctccgccgc cgattggtag 63180
tcatgtttgt tttctacatc tgcgactcta tttctgtttt gtaaacaagt tcatttacac 63240
cactttttta gattctgcac atacgtggca agcccacagc aaacatgctc aatggtgaaa 63300
gactgaaagc atttcctcta agatcaaaaa caagacgagg atgtccactc actccgtttt 63360
tactcaacac agccctgaac gtcctagcca tggcaatcag agaagagaaa gaaattaagg 63420
aatccaaatt ggaaaagaag aagtaaaact cactctttgc aaatgacatg acacttatac 63480
ccagaaaatc ctagagatgc taccagataa ctattagagc tcatcagtga atttgttgca 63540
ggatacaaaa ttaatacaca gaaatctcct gcattcctat agactgacaa caaaagatct 63600
gagagagaaa ttaaggaaac catcccacgg catgaaaaag agtaaaatac ctaggaataa 63660
agctacctaa agaggcaaaa gacctgtact cagaaaacta taaaatactg acaaaggaaa 63720
tcagacgaca cagagagaga gagataccac gctcttggat gagaagaatc gatagtgtga 63780
caatgactat actacccaga gaaacataca gattcagtac aacccctatc aaattcccaa 63840
tggcattttt cacagaatca gaattagaac aaaaagtttt acaagtttca gggaaacaag 63900
aaagatccta aagagccaga gcaatcttga gaaagaaaaa tggagctgga agagtcaggc 63960
tccctgagtt ctgactgtgt atacaaagct ggcatgattt ttaacagcag gggtgtaaat 64020
gaacttgttc acaaaacaga tggtggggtg ggcttccctg gtggctcagc tggtaaagaa 64080
tcctcctgca acgcaggaga cctgggttcg atccctaggc tgggaagatc ccctggagaa 64140
gggaaaggct acccactcca gtattctggc ctggaaaatt ccaaggacca tatagtccat 64200
gggtttgcaa agagtcggac acgactgagc gacttccaat cctggaaacg tcccattgtg 64260
gacggtgaac tggggttgtc caagctcagg gtaaccgttt gctgagtgac tgacactcct 64320
tctcatgggt taaaatgtgg ggcccaaggc caggaccaga ccccgcagtc agccaggcag 64380
accctgtgca gccccagcga gtgtgtggcc gccgtggagt tcctggcccc catgggcctc 64440
gactggagcc cctggagtga gcccattccc tcccagcccg tgagaggctg ggtgcagccc 64500
taaccatttc ccacccagtg acagatccgc ctgtgtggaa acctgctctt gtccccaggg 64560
aacctggcag gactcaggga gaatgtctca gggcggccac agatcagggg ctggggggc 64620
agggctgggt ccagcagagg ccctgtgccc actccccgga aagagcagct gatggtcagc 64680
atgacccacc agggcaccga cgcgtgcttg cacacaggcc gccccctcat ggtgacactc 64740
ttttcctgtg gccacatctc gccccctcag gtccctcctg ctccccagct cctggcctgg 64800
gaacctcttc cccgccccgg ggacgtcagg gctggtgtcc actgagcatc ccatgcccgg 64860
gactgtgctg atcaccagca cctgcacccc ctctcgggtc tcaccaggat gggcaactcc 64920

```
tgcccatcca gcacccagcc tcctgggtac acatcggggg aggagggaga agcctgggcc  64980
agacccccag tgggctccct aaggaggaca gaaaggctgc cgtgggccag ccgagagcag  65040
ctctctgaga gacgtgggac cccagaccac ctgtgagcca cccgcagtgt ctctgctcac  65100
acgggccacc agcccagcac tagtgtggac gagggtgagt gggtgaggcc caggtgcacc  65160
agggcaagtg ggtgaggccc gagtggacag ggtgagtggg tgaggcccag gtagaccagg  65220
gcccatgtgg gtgaggcccg ggtggaccag agtgagcggg tgaggcccag gtggacaggg  65280
cgagcgggtg aggcccaggt ggacagggcg agcgggtgag gcccgggtgg acagggcgag  65340
cgggtgaggc ccgggtggac agggcgagcg ggtgaggccc gggtggacag ggcgagtggg  65400
tgaggcccgg gtggaccagg gcgagtgggt gaggcccggg tggacagggc gagtgggtga  65460
ggcccgggtg gaccagggcg agtgggtgag gcccaggtgg acagggtgag tgggtgaggc  65520
ccaggtagac cagggcccag agcaaagccc cggctcagca gtgatttcct gagcgcccac  65580
tgcttgcagg gacctcagcg atggtaaggc agccctgttg gggctcccg actggggaca  65640
gcatgcagag agcgagtggt cccctggaga aacagccagg gcatggccgg gcgccctgcc  65700
aggctgcccc aggggccaca gctgagcccc gaggcggcca ggggccggga cagccctgat  65760
tctgggttgg gggctggggg ccagagtgcc ctctgtgcag ctgggccggt gacagtggcg  65820
cctcgctccc tgggggcccg ggagggacgg tcaggtggaa aatggacgtt tgcgggtctc  65880
tggggttgac agttgtcgcc attggcactg ggctgttggg gcccagcagc ctcaggccag  65940
cacccccggg gctccccacg ggccccgcac cctcacccca cgcagctggc ctggcgaaac  66000
caagaggccc tgacgcccga aatagccagg aaaccccgac cgaccgccca gccctggcag  66060
caggtgcctc cctctccccg gggtgggggg aggggttgct ccagttctgg aagcttccac  66120
cagcccagct ggagaaaggc ccacatccca gcacccaggc cgcccaggcc cctgtgtcca  66180
ggcctggccg cctgagacca cgtccgtcag aagcggcatc tcttatccca cgatcctgtg  66240
tctgggatcc tggaggtcat ggcccctctc ggggccccag gagcccatct aagtgccagg  66300
ctcagagctg aggctgccgc gggacacaga ggagctgggg ctggcctagg gcaccgcggt  66360
cacacttccc ctgccgcccc tcacttggga ctctttgcgg ggagggactg agccaagtat  66420
ggggatgggg agaaaaatgg ggaccctcac gatcactgcc ctgggagccc tggtgcgtct  66480
ggagtaacaa tgcggtgact cgaagcacag ctgttcccca cgaggcctca cagggtcctt  66540
ctccagggga cgggacctca gatggccagt cactcatcca ttccccacga ggcctcacag  66600
ggtccttctc caggggacgg gacctcagat ggccagtcac tcatccattc cccatgaggt  66660
ctcacagggt ccttctccag gggacgggac ctcagatggc cagtcactca tccattcccc  66720
acgaggcctc acagggtcct tctccagggg acgggacccc agatgggcca gtcactcatc  66780
catccgtctg tgcacccatc cgtccaacca tcacccttcc ctccatccat ctgaaagctt  66840
ccctgaggcc tccccgggga cccagcctgc atgcggccct cagctgctca tcccaggcca  66900
gtcaggcccg gcacagtcaa ggccaaagtc agacctggaa ggtgcctgct tcaccacggg  66960
aggagggggg ctgtggacac agggcgcccc atgccctgcc cagcctgccc cccgtgctcg  67020
gccgagatgc tgagggcaac ggggggcag gaggtgggac agacaggcca gcgtgggggg  67080
ccagctgccg cctggctgcg ggtgagcaga ctgccccct caccccaggt acaggtctcc  67140
ctgatgtccc ctgccctccc tgcctccctg tccggctcca atcagagagg tcccggcatt  67200
ccagggctcc gtggtcctca tgggaataaa aggtggggaa caagtacccg gcacgctctc  67260
```

ctgagcccac ccccaaacac acacaaaaaa atccctccac cggtgggact tcaccagctc 67320
gttctcaggg gagctgccag ggggtccccc agccccagga agccaggggc caggcctgca 67380
agtccacagc cataacacca tgtcagctga cacagagaga cagtgtctgg tggacaggtg 67440
cccccacctg cgagcctgga gagtgtggcc ctcgcctgcc ccagccgcgg tcagtcggct 67500
cagcaaccgc tgtccactcc cagcgccctg gcctcccctg tgggcccagg tcaagtcctg 67560
ggggtgaagc taagtcaggg agcctcatcc atgcccagcc cggagcccac agcgccatca 67620
agaaatgctt cttccctcca tcaggaaaca ttagtgggaa agacaagagc tggggggttc 67680
tggggtcctg ggggatcaga tgaaggggtc tgggagcagc agcagcctca ggcaccccaa 67740
aacaaggccc aggagctgga ctcccagggc tgaggggcag agggaaggaa ggcctcctgg 67800
ggggttggca tgagcaaagg cacccaggtg ggggctgagc acccctcggc tggcacacac 67860
aggcccccac tgcagtacct tccccctcgg agaccctggg ctcccgtctc ccgcctggcc 67920
tgccatcctg ctcaccaccc agaaatccct gagtgcggtg ccatgtgact gggccctgcc 67980
ctggggagga aggagattca gacagacagg atgccagggc agagaggggc gagcagagga 68040
tgctgggagg gggcccgggg aggcctgggg ggcagggggg caggagttct ccagggtgga 68100
cggcgctgtg ctatgctcgg tgagcacaga ggcccccgggt gtcccaggcc tgggaaccca 68160
gcagaggggc agggacgggg ctcaaaggac ccaaaggccg agccctgacc agacctgtgg 68220
gtccagaagg cagctgcgcc ctgaggccac tgagtggccc cgtgtcccga accaccgctg 68280
aaacatggga cacacgttcc caggcggagc cactcctgcc ttccgggagg ctcccagcgg 68340
gctcatcgct ccatcccaca gggagggaaa ccgaggccca gatgacgaac atcccggcga 68400
gcaggtcaaa gccagcccct ggggtcccct ctcccggcct ggggcctccc ctctgcaggg 68460
tgggaaaccg aggccacaca ggggctccat ggggctgccc tctgccaggc cctggacacc 68520
ccgcgggtga cccccgcctc tatcatccca gccctgccag gccctggaca ccccgtggat 68580
gacccccgcc tctatcatcc cagccctggg ggacagatgg gaggcccaag cgtggacccc 68640
ctggccaccc cctaccccac agccgggagg agccgggagc tggtggccaa gggcctagag 68700
gagccagann nnnnnnnnnn nnnnnnnnnn nnnnnnnnnn nnnnnnnnnn nnnnnnnnnn 68760
nnnnnnnnnn nnnnnnnnnn nnnnnnnnnn nnnnnnnnnn nnnnnnnnca atatagaggg 68820
ggtgggataa agggtaatat gatgtttagg tagttagagt taaattagaa gggtttggat 68880
aaagattaat aaaattacaa gcgtacatat cgtgtgagtg tgggtgataa tatttgtgta 68940
tgtggggaat agaagtgagt gtgagtagta ttcaagatgt aagtgtgcga atacaggtct 69000
gagcgatttg aatggaagtg aaaaaaagcg tgtgtgtgga ggaggcggga gaggaagata 69060
gtgtggggga agaaaagaag gctagtgggt aaagaaatat cagtaggcgg ttgacgaaag 69120
aagaactagg aagaattaat ataaaaataa agggaggatt aaaaaataaa gagggaggag 69180
gtaacggaaa tagttagtta agaaaagaat ggagagtgga ggtaagataa ataagggagt 69240
aatgggagtg aggaggaata aataaaaaaa tggtgaggga aaatagagta gaatgagaac 69300
aagaatgaaa aagggagtga agggggtgaa aaaaagtgaa gttgaaaaaa gaggaaaaaa 69360
aaggagaaga taaaaaaata aaataaaaaa aggaaaaaaa agaaaaaaag aaagaagggt 69420
taaaggacga aaagaaggga agagaaaaaa aatagtttaa gtgggggagg gtaaaaaaga 69480
attaataaag taaatatggt tgtggtcgaa aaaaaaaaaa aaattgttgt gttgatgaga 69540
agaaaagaaa aaagaagaaa gggaaaagca aaaagaaagg agagaaaaag acaaccccac 69600
cgcccgggcg catggagggt gaggatggcg cacgcccgcg gatggcacag catcacagca 69660
atcctaaaac gttttcagac cggtgcatct tcaccgcgcg cgcgccccgc ccggccctcc 69720
tcccgccctg accgcggacc cccacccgca ccggggagcc tacccccacc ccggggacgc 69780
tccgccacgc taaggtcagg actgccgtga agacgcgccg gggtgaaaac gttttatctt 69840
catgacataa gcgagtggtt ttgaaacagg tttacaaacc ctcgtgaaga cgcaccctta 69900
gcgttaggtt ttgttttttt accatgtgac gatgcaacta ttttcttcct ctcttccaca 69960
gtggctagtc gcctccagag cgaggggtat ctcttgtaca gagaccctcg gaacatccgg 70020
aggtagtttc ccacctaggg gtaaagcgag aaggctcatt acgagggccg gggctcctcg 70080
gggaagggca gggccctggc gcagaggctc tgccacctca gtgacacgca gaccacgcgc 70140
ggcctgcagg cgccgggctc tgaaagcagg caaagcccga tctgctgaca tcaggggttc 70200
cgcagcagcg aaggtctggc ccgcacctgg cccactggca gggggtaagc tctgcctccc 70260
gacgacagca ccaagttcag gaagggccac gcagacactg gtgagacacg gccccccccgg 70320
agctgcccga gaagctctga ctttgcacta aagatctctg gcgcggtcca aaaatgtaag 70380
gcctctcttc cttttatctt aagactttga tatttttacg atgtaataaa taccaagaag 70440
ggcttttaat ttcagacaga tgtaggataa tttcccccgt agcccttgct gctttgttta 70500
gtaacgaaac tcaaaccaga aataccaaag gaattttcca aagagtttca aaagcgctta 70560
tcagcaatca ctagactgct gcatacatca tcactgcccc aaacaatagc ctgcctgtgc 70620
cagttactca aagtactact tacttgacga aaacaaatct agtcctaacg tttttacaaa 70680
gaaactccac tcttccgcca acttttcaga aacaaccact cgatcacgtg gcaggggacc 70740
gtggctggac tgggtgctgg ctccttctgt gaccaggcaa cactgccccc ttctcggcct 70800
ccctacgcct cttgacaaat gttcatcagc tgtaaagttc accccacgag ggacccactt 70860
ctgctatttc ccacgtacct accccattat aggagttttc tttgtgacag tttctgcatt 70920
tttcatggat ttagaggttt acataatcag ggctgctgaa cagcatgaga gacgtggcca 70980
caaggtccct cctgcacctt gccgcagggg cagggcgagt tatctggctt gagcgtggtt 71040
accatcaggg ggtaaacaca gtttccagga cgtttttgac aagacactga cccggatgcc 71100
cccactacca ccgtgcaggt cctgcaggcc tcccagcctc ccaggccctt cccgaggtcc 71160
cttcggaact taggggactc ggtctgcccc cctgggtttt ccctgcacca gcttttgccc 71220
cctctggacc caggtttccc aaatggaaaa cgaaggtgtg ggtatggaag ctccctgggc 71280
tcctctcagc tgtgcctctg catggtgatg acggctgccc atcggggggg gcaggactgg 71340
ggcagctgcg gacaccctcc caaggctgct acccccgagt ggtgtggggc gctgtgggca 71400
cgctctgctc agcgcacctc ctggaaacca gcgcctgccg tctgcccggg gcaaccggcc 71460
cgggagccaa gcaccactgc cgtcagagga gctgctggct gtgagtggac gccagtctag 71520
ctctgaaccc tgcccaggcc tcctgaggtc tgaacattgt aaaatcaggc cccggacggc 71580
aactgcctct ccctcctgcc gtctggtctc cataaactgc atctcaggac aaatcttctc 71640
actcaccagg gctgaaacag aagactgcag ctatctttct caaatctaag gtgtgctaca 71700
gggcaagtcg cagaaactgt ctggcctaag catctcatca gatgcctgag acaagagctg 71760
tggacgccaa gctggagcca gagctcctcg cgttctgccc acctggcacc gcgttccacc 71820
cagtaaacgc aggcttgatt ttcaaaagta ccaccgactc agagccaatg ctaaaccgac 71880
cacttttcct gcccattaga ttgggtgaag gtttctttaa tcaatctgcc agtcaccaca 71940
tgccgcctct gtgcccacag gctggcgaag acctttctga gctacggcat gtggcaggca 72000

```
gcggcacctc tcttcagtac ggccagctgt caaggggagc gtttctgtga tgatgtgaaa  72060
atacattgca tccggccccg tgtttcatga acacgggtga ggaaaggaaa cacacaaagt  72120
tctgatgcga ctgacagcac gggtctcata actcaataca agtcagacaa accacaggga  72180
gtcacaggga atcccaatag cctcatctag tgtgaccatc atgaggctta atttattcag  72240
tgtattcaat cataaagagg gggaaaaatt gtaaaaaaaa aaaaaaagaa agagtgaaat  72300
gtgtaatact gaaaactgtt gctaggagaa gcaagcattg gcgtttgtaa ctgctttgac  72360
tccccaagac ccacactcgc ctcgctacaa aagggaggca ctgctgctca gtacttgcac  72420
acccgaactg cggatttgta atttaaaaat gtgtgtgtgg acacagcaca agccagagac  72480
tgccaaaggt tgagggacac tggaagaact taatatactt ggtgcatgct gccagtgaca  72540
gtcagtcacc agctgattca atagagtgcc gaaaggtcac cttttaggta aggatgaagg  72600
ggttctgggc tcgtttactt gcactaactc agagttagtc cgagatatcc gaagtgccag  72660
gtgcctccca tttgctgatg gatctagctc agggacggct gggccctagc catccaaaaa  72720
tcaagcattg ttctcccaac ctgtcttctc gctgataatg gaaggtcaga acgcccaccc  72780
gcccacctca aagtcaaaga acaccaagcg ggtgagtccc cactaagctc ggtgtttcca  72840
atcagcggtt tcaggattcc agctggggca atgagggagg gagcgtgcga gggatccaac  72900
acctcgcccc gtgcgcagca agggataacc caacaccccg tttctgtacg tccggctgga  72960
gttgtggaac tcagcgcgga cccggggcca ccgcgacccc cgggaccctg gccgcgcggc  73020
gcatccccgc tgccgggaca cgggtaagcg tccccaaact gccggacgcg gggcggggcc  73080
ttctccgcca cgccccgata ggccacgccc aaggacaagg atggtcgtgc ccagacggcc  73140
ggggcgggnn nnnnnnnnnn nnnnnnnnnn nnnnnnnnnn nnnnnnnnnn nnnnnnnnnn  73200
nnnnnnnnnn nnnnnnnnnn nnnnnnnnnn nnnnnnnnnn nnnnnnnncg gagggggggg  73260
ggcggggcgg gggctgccgc cgcgcgtata ggacggtggt cgcccggcct ggggtccggc  73320
cgggaatgac cccgcctctc cccgcatccc gcagccgccc cgccgcgccc tctgccgcgc  73380
acccgcctgc gcacccgccg ccctcggccg cggccccggc ccccgccccg tcgggccagc  73440
ccggcctgat ggcgcagatg gcgaccaccg ccgccggagt ggccgtgggc tcggctgtgg  73500
gccacgtcgt gggcagcgct ctgaccggag ccttcagtgg ggggagctca gagcccgccc  73560
agcctgcggc ccagcaggtg agcaagggct caggggaaac tgaggcccga cacagagccg  73620
cagcaagaag gatcctactg gtcactcggc tgttggcctg gggtcatcac aggcgggctc  73680
tcccaaccca tcccctgagg ccaaggtccc tagaaccccg tgggcagaca ccaaccagcc  73740
ctttaaatat ggggaaacca aggtgcttag gggtcagaga tagccctagg tcgcccaacc  73800
ctagtagaag ggagggctgt tggagttcct gagtgcccgc tctcccaccc cccgggaggc  73860
cccttcctga gcccaagggt gactggtagt cagtgacttt gggcctgccg acctgtaccc  73920
cactgggcac cccaccagtc ctgagccaca tttgggctta gtgacggggt cagggatcat  73980
gaggatcaat gtggctgagc caggaaggtg ttagaacctg tcggcctgga gttcatacca  74040
gcactgccct gggcttttct agacccatgt cccgcctcct gccccacctg cccctgttcc  74100
cgcaccccac cagcagcggc aggggcttcg agagggctgt gggctcaccc tatttcaggg  74160
atggagccgc taagacctgg ggcacactgc ccgctaggga cccctgaggc accagggccg  74220
ggggctctgc ggaggggcag ccgccacccc cagctttgga gtcctctccc gggtgcccag  74280
cccgagctga tccggctgcc tcccacgctg tgccccaggg cccggagcgc gccgccccgc  74340
agcccctgca gatggggccc tgtgcctatg agatcaggca gttcctggac tgctccacca  74400
```

cccagagcga cctgaccctg tgtgagggct tcagcgaggc cctgaagcag tgcaagtaca 74460
accacggtga gcggctgctg cccgactggc gccagggtgg gaagggcggt ccacggctcc 74520
cactccttcg gggtgctccc gctattccca ggtgctcctg cacttcccat gtgctcccga 74580
ttctccctgg tgctccctct cctcctggct gctcctttgc ctcccaggtg ctcccacttc 74640
tccctggtgc tcctgctcct cccggcggct cctgtacctt cggcctgacc tcctccctct 74700
acaggtctga gctccctgcc ctaagagacc agagcagatt gggtggccag ccctgcaccc 74760
acctgcaccc ccctcccacc gacagccgga ccatgacgtc agattgtacc caccgagctg 74820
ggacccagag tgaggagggg gtccctcacc ccacagatga cctgagatga aaacgtgcaa 74880
ttaaaagcct ttattttagc cgaacctgct gtgtctcctc ttgttggact gtctgcgggg 74940
ggcggggggg agggagatgg aagtcccact gcggggtggg gtgccacccc ttcagctgct 75000
gccccctgtg gggagggtga ccttgtcatc ctgcgtaatc cgacgggcag cgcagaccgg 75060
atggtgaggc actaactgct gacctcaagc ctcaagggcg tccgactccg gccagctgga 75120
gaccctggag gagcgtgccg cctccttctc gtctctgggg gcccctcggt ggcctcacgc 75180
tctgtcggtc accttgcccc tcttgctgat gcaatttccc cgtaattgca gattcagcag 75240
gaggaatgct tcgggccttt gcacctgacc gcatgagcag aggtcacggc cagccccctt 75300
ggatctcagt ccagctcggc cgcttggccg tgacgttcca ggtcacaggg cctgccggca 75360
cagaggagca ggcccttcag tgccgtcgag cactcggagc tgctgcctcc gctgagttca 75420
ctcagtgtct acgcacagag cgcccactgt gtaccaggcc ctattccacg ttccccagtc 75480
accgagcccc cagggctggt ggggacctgc cctcgggtac actgtgtccc gtcacgtggc 75540
tttacgtgtg tctctgaggg aggctggcat tgcggtccac ctctcagcac aaacatctgt 75600
cccctgggaa gggggtccca tttctgggtg cgagcagccc cctggggtcc gtgtctcctc 75660
cttacctggc tcaaggcccc ggctcctggg tcctggacag cagggagccc acccctcggg 75720
gctgtggagg gggaccttgc ttctggaggc cacgccgagg gcccaggcgc cgcctccggc 75780
cgtcgccctg agggagcagg cccgacgcca gcgcggctcc tctgtgaggc ccgggaaacc 75840
ctgcctgagg gtgcgggtgg gcaggtgccc ctgcccccag gctctcctgt gtgagtgaca 75900
ctcaccagcc agctctggat gccacccatc cgggttctcc aggaggcact catagcgggt 75960
ggggtcccct ccctcccccc tctgtggagg gagggagtct gatcactggg aggctggtgg 76020
tccgtacccg cccccccgac tctggacgtg tttactaccc ccgcctgggc tcaggacagg 76080
gcattggatg ggaaggacag ggctgggtcc tggccaggct gggggctctg cagggcatgg 76140
gtgcccctgt ctcttcttat attccaacgt cactgcaggg gggcgcaaat cttggacccc 76200
acttactgat gatctgcatc aggacatagg tccccccctcc tgcagcgggg ggctggccac 76260
ggagggcgct ggggaaggcc cctcctccag cccctcggcg aggctcacca ggtgcccatc 76320
ctcagccagc agggcgacgc tcgctgggag ggcggagagg gaggcagggc agggctggta 76380
cgacccccgc tggggcgggg gggccctcag ccggtcctcc agcacccttg ctgccccccc 76440
tcaccgtcag gggg cacctg gccgctctgc ctcaggtggg cggtgagggt cccaaggcca 76500
caccaggtgt tcaccagctc ccagcagctg gctgtgggag aggggcagag gtgggcgcat 76560
ggcacccgcc ttccccccag accaggatgc tctgccttcc tcccgcccat ctccccagac 76620
atctgaagga ctcttgcctc caccatgcag ccccgcctcc accagaagct caggttcccc 76680
gcccccccctc cccgaagctg caggacccct gaccagcgaa gagatgggac agttggaaca 76740

```
cacgctcccc cagcagcggc acagcagctg tgtggcccag aagagcccgc ctgtttccct  76800
caagcaactc cccatggatg tcatcccatg gacacccccct tccccacacc gcctcctcgt  76860
tctccccctc caaggcagag ggaacgcacc cccacctgtc tgctaggaca ggggacccca  76920
cttacctccg aacatcacct tgataaacat ggccgtggtg gggacagatc cctccgaccc  76980
ccaacttccg acctggggaa ggagctgggg tggagctcga ctgcagggtg gggccctgtg  77040
ggaggtgtac gggtggagag ggtgatgggt gggtgggctc aagcggagct ccttgctcag  77100
tccaggcggt ccctgcagct agtccaggat cctcagcctt ctccccctca ctggatcagg  77160
gaagactgag gttccctccc ctgccccccc acccagcttc caagctggtc tctgtggcag  77220
tgggagctgc caagaggtct gagcggccag tatccgggta acggggtttg tggagggtcc  77280
gggcattccc ggtgcagggc tctagtgggg gctggagcct cgggcccaga gctgtccaga  77340
gaccagtgcc ctcccaccgc cgccgcccgc aaggagagac agagctccca ggcggggagt  77400
cggaggttcc tggaggggga gcatcctcaa ctctgcaggc cccccttccca ggcgcactcc  77460
cggcctcccc gtcttctgtc ccctgctctt gttgaagtat gattggcata cagttcacag  77520
ccactcttcg gagtgttctc cacactaagg atacagaaca tgtccctcgt ccccccaaac  77580
tcccagccag gctgtcacga agagggaggc ggccgacggg gcagggcctt gcactcctgc  77640
gtgtggggtc cacaggggtc gtccccgtgt cggtggcccc ttcctctcac gccaggaggg  77700
tccccttgcc tggaggtgcc gtggatccgc tcgctgcctg ctctttgggt tgtttcccgc  77760
atggggtgat gatgaagagg ccagtacaga cactcgccag caggtctctg ggtgaacagg  77820
catttatttc tctttcctga gggcagatcc tgggagtggg gtgccggacc gtccggggag  77880
agtatgcttc tgtttctaag aagctgccgt gttctccagt gtgctgcacc atgtcacggc  77940
ccctctgtgc gtctggactc aggagacctc cttctcagcg gccctccccc ccaggtggtc  78000
aggccatctg tgcccttctg gggcagagc tcagcgccgg aggcgggagg aggcccagat  78060
cccagcgcag cccaccagcg ttgctctgct tccctcggca ttcatagctg gagaaagggc  78120
aaggagcacc ggctgaagcc ccacctggag gacgcacttc gatggcagca ggtgctcaga  78180
ggtggccccg ggcagcattc cccagacgca caggccagtg ctttcttccc aggacaccac  78240
tgtgtctggg gacccgagtc ctgcagcacg gtcgggagcg gctgtgccca gattccggcc  78300
tgcacccttg gctccagcca ccacccctgt ttgtcaaggg gtttttgtct ttcgagccgc  78360
cgaggaggga gtcttttgtc tgcagtgtca cagaagtgcc ataaagaggg gcccacagtg  78420
ggagctttat aacattggtg cggagggctg taacaggtca gggaggcact tgagggagcc  78480
ttctagggcg atggagatgt tctaaaattt ggtctgggta caggctacag agatgtgtgg  78540
gtgtgtgtgt gtgtgtgtgt aaaaccctcg agccacacgt gtgaggtctg tgcatgtgac  78600
cgtacacagg agacctcggt ggaaagcagc cacctgctct gactgcacct gtggatttcc  78660
agctcctgcc ctcaggcggc cctgcggggc ccactggctg acggggagac ggcaccgccc  78720
tcccccgctg tcagggtggg ggggctgacg atttgcatgt cgtgtcaggg tccagcggcc  78780
tcccttgcgt ggaggtcccg aagcacctgg agcgccgccc gcagaacagc ggactcctgc  78840
ctgcctccct gcctctggcc atggcctgcc cgcctctggc cctctttctg ctcggggccc  78900
tcctggcagg tgagccctcc caaggcctgg ctcacctagg ggtgtgtaag acagcacggg  78960
gctctagaag taaatcgcgg ggaagtaaat cgtagtgggc aggggggatg gtttccgaag  79020
gggccctgag ggggacagga gacctggcct cagtttcccc actggtgagt gaccagatag  79080
ccagggtacc tttggactct gactctgggg ggctctcaga gactggtctc ctactcagtt  79140
```

-continued

```
tttcagaggg gaagctggtg tggccttgtc actgccctgc agggcctcag ggacaagcta  79200
tccctgagga ggtctccagc agtcagtggc cggaggctga gccgatggat atagtaacag  79260
cccaggcggc ctcttggggg tggtcagcct gtagccaggt tttggacgag ccgaagtgac  79320
ctaagtgatg gggtctgca gagcaaggga tgagggtggg cagcaggagg acccagagcc  79380
caccagccca ccctctgaat tctggaccct tagctgcatg tggctccttg ggaagacggg  79440
gcttaagggt tgcccgctct gtggcccaca cagtgctgat tccacagcac tggctgtgag  79500
cttttgggag cagattctcc cggggagtct gacccaggct ttgtggggca ggggctggag  79560
ggaaggggcc caggccagac ctgagtgtgt gtctctcagc ctcccagcca gccctgacca  79620
agccagaagc actgctggtc ttcccaggac aagtggccca actgtcctgc acgatcagcc  79680
cccattacgc catcgtcggg gacctcggcg tgtcctggta tcagcagcga gcaggcagcg  79740
ccccccgcct gctcctctac taccgctcag aggagcacca acaccgggcc cccggcattc  79800
cggaccgctt ctctgcagct gcggatgcag cccacaacac ctgcatcctg accatcagcc  79860
ccgtgcagcc cgaagatgac gccgattatt actgctttgt gggtgactta ttctaggggt  79920
gtgggatgag tgtcttccgt ctgcctgcca cttctactcc tgaccttggg accctctctc  79980
tgagcctcag ttttcctcct ctgtgaaatg ggttaataac actcaccatg tcaacaataa  80040
ctgctctgag ggttatgaga tccctgtggc tcggggtgtg gggtaggga tggtcctggg  80100
gattactgca gaagaggaag cacctgagac ccttggcgtg gggcccagcc tccccaccag  80160
cccccagggg cccagactgg tggctcttgc cttcctgtga cgggaggagc tggagtgaga  80220
gaaaaaggaa ccagcctttg ctggtcccgg ctctgcatgg ctggttgggt tccaacactc  80280
aacgagggga ctggaccggg tcttcgggag cccctgccta ctcctgggtg gggcaagggg  80340
gcaggtgtga gtgtgtgtgt ggggtgcaga cactcagagg cacctgaagg caggtgggca  80400
gagggcaggg gaggcatggg cagcagccct cctggggtag agaggcaggc ttgccaccag  80460
aagcagaact tagccctggg agggggggtgg gggggttgaa gaacacagct ctcttctctc  80520
ccggttcctc taagaggcgc cacatgaaca gggggactac ccatcagatg nnnnnnnnnn  80580
nnnnnnnnnn nnnnnnnnnn nnnnnnnnnn nnnnnnnnnn nnnnnnnnnn nnnnnnnnnn  80640
nnnnnnnnnn nnnnnnnnnn nnnnnnnnnn agagggtggg tgggtggaat ttaatatagt  80700
ggtgcgcgtg gagcgtgggc ggcgcattta aggcggtcat ctaaaatagt ggataggggg  80760
tggtgtgaca ataacgggtg gtggatgtgg tttacggggg gtgcaatagt tctgagtttg  80820
ttagtgtctt cttgatgggg ttgcggcgtg tggacctacg ccttgagtat gtgggggggg  80880
aaaagcagtg agggtagtag ggatgggaaa tattggtgga ggttctttgt tggtgtattt  80940
tttggtatta tgttgggtgg tggagtggtg ggttgggtgt aatttcgctt gcgttatgtg  81000
tttttttct ttttcgtgtc gtgggttggg ttggttggtg ctttgtggtg gtggtgggtt  81060
gtggtataaa aaaaaatgtg tggttgtgct cagcttagcc ctataacggt cggctttgtt  81120
tcttgtttgt tctgtgggcg tgagcggatg gctcgggcct ccgtgctccg cggcgcggcc  81180
tcgcgcgccc tcctgctccc gctgctgctg ctgctgctgc tcccgccgcc gccgctgctg  81240
ctggcccggg ccccgcggcc gccggtgagt gcccgccgtc ctccagcccc cccgccccgc  81300
cccgccctcc acgccgaggg gcgccggctc gcagagctgg atccaagggg gtgcccggga  81360
gtggcccggc gcggcccgtt accccgaaac gctgtctggg tgccccgggg gtgtggtgga  81420
tagtgagctt cccgtccctg gaagtatgca agtgaagccg gcgccgggat cgctcgggct  81480
```

ggctggtgag cgggcgggac tcggtcgggc gctagacgca cgccgccagc cccccagctc 81540
ccagacctgc ccactccgcg cccgcccggc cgcgatcccg ggtgtgtgtg tgtgttgcag 81600
gggagggaca gcgggagtgg ctacagggct cccgactcac cgcagggaca aagacccgcg 81660
ggtccccagc tggcgtcagc cgccaggtgt gtggcctcgg tgagcacacc tccaggcggg 81720
agggttgagg gaagcgctgt ggggagggca tgcggggtct gagcctggaa gagacggatg 81780
ctaccgcctg ggacctgtga gtggcgggat tgggaggcta tggaatcagg aggcagccta 81840
agcgtgagag ctccggtgtg gcctggcggg ggtggtaggg gggggacgcc cctgtgtgtg 81900
ccagcctgcg tgtgccctaa aggctgcgcc ctccccccact gctggggctt cgggggacca 81960
gtcacagcct aggctactgc aggcgcacag ctccccggga gcccggccca cgcgggtgtg 82020
ccgctgagcc tccagcctgt cggggcaggg gtggggggca gggatggggt cgttagcggg 82080
gttgggggca gacgcccagg cagactctct gggcacagct ccggtgacaa gggaggtctg 82140
gcaagcctgg gccccttctg tccagccacg ccagctctgc cctggccagt cttgcccccct 82200
ggcagtgctg gggatggaag ggggagcggg tacctcagtc tgggggccct gcctcctccc 82260
cagccccgcc cggcccccta ggcctagggg cagagtctag gggtcaccct ggggagctgc 82320
tgaatccgcg ggtttaggaa ccggagggac ctgggctttt gaaccacgtg gccctaggtg 82380
agccctccgg cgcctcggta gccctcaccc ccagccttgt ccaggtgggc gggtgggagg 82440
cgacagtgcc cactgctggg ctgaacagcg tctgcaggga ggccaggaga gctgggcaca 82500
cggacacgtt ccatcacctg gagctgccac tgtgccactt gtgcggggtc aggcggggtc 82560
tgagccgggc tgtcatctgt cacgccacag atatgcaggg ggcactcggg gtcgcctcgg 82620
acatgcttat ccctggacgg ctgttggcag ggccgggaag gctctgtaaa tatttatcca 82680
tcccagctca cagctttcag ggttgatgaa agccccgccg cccgcccact gtgggggacc 82740
ccgccttccc ttctggagcc agcggggtga gggggtgggg gagatggacc tgcctgccca 82800
ggagcaggcg gtgtgactct ggcaggtcac ttgacctctc tgagcctcag ggagggcccg 82860
ggatggtgtg cggatgctct ctgccttcct cccagcctga ccagtgtcct cccctcgggg 82920
tcgcctcctg cccaccgcag agggggtggc tatggggacc tgggccgatg gcaggcaggc 82980
cggagagggc atgcccggct cagccgtgcc cagcacttcc cagtccaggg gcccccgcca 83040
ctcccagccg ctggctgcct cccattttcc cgattgcagg ttggccccga ggctgaccgg 83100
agcctctggc tcagctggga gactgaattc cccaagcaat tcctcaagga tgtgtgaggc 83160
tgtggtgtgg tgcctatccg ggagaggtgg ggtgagcgga ctgggcacct ccgcccaggg 83220
caggcccagg gagacgctgg ctgacgagca ggcaggcctg caaggaggac gagcagccat 83280
ctcaggaatg tgggttttgg agacaagcca cagctggggg ggtggggggg ccatgggtgg 83340
ggaggcctga tccccaggtc taggtccagc tctgggctcc ctcgccgtgt gaccctgggc 83400
caagacctgg acctctctgg gccccgtctc ttcccctggg aggtggggcg atgcctgctc 83460
cccaatcccc cagggctgtg gatgaggcag acgaggtgtg tgctcatccc cacctcactg 83520
ccttccagca gccccgggcg gggggggtgg tggggactgg cgcacccagg tgaggatcag 83580
gccttggagc tagggagggc cccccagccc caggccagaa aggacacggg gagacagaat 83640
gcaggagggc ggcagagcag gggccagcgg tggggaaact gaggccaaga gcctgtggac 83700
gatgtgctcc aggaaaggac ctcgctgcct ggggcctgga tcctagagcc tccaggagcg 83760
gtgaccatga cgtgggcagg gaaccggagg ccccggcttg caggtggacc cggcgcgagt 83820
cactcttcct ctctggccct gagagcttcc ttccagctgc cgctcctgtg ttctaatgtc 83880

-continued

```
aagtctggag gcctgggggg caggtggggg ctgactgcca ggtgggggag ggcaggaatt  83940
tggcagagca gcgtcccaga gtgggagaag ccagcccatg gaggggactc tctccatgcc  84000
tgctgcccca aagggcgtta tagagagagg tcggttaccc cttcgccatg gccccgttcc  84060
cattgaacag atgggaaagt ggaggctgag agaaggctgt gacttgccca gggtctccgt  84120
ggcatggaac tgggcctgct gagtctcagg ccggggatct cgctgctgca ctgagcacgc  84180
caggatgcag gggtctgggc ctggacctag cgcctcgtgg gggcaagaga ggaaggcacg  84240
ctgggcctgc ctgtcaccct ccaccccacc gtggcttgtt gctcaggcct tcctgggggc  84300
agaggagagg ggagatttca ctcgctggca ggctaggccc tgggctctct ggggctccgg  84360
gggaacaatg cagccctggt ctttctgagg agggtccttg gacctccacc agggttgagg  84420
aaaggatttc tgttcctcct ggaggtcacg gagccgacat ggggaggagc aggggcaggc  84480
ccggggccca catcctcagt gtgagacctg gacgtgtgtc ctcccacctg acgctggggg  84540
tggggggtgg gggccggggg ggatccagtg aaccctgccc ccaaattgtc tggaagacag  84600
cgggtacttg gtcatttccc cttcctcctc ttcgtttgcc ctggtgggga cagtccctcc  84660
cctggggaag ggggacccca gcctgaagaa cagagcagag ctggggtcag gggtgtgctg  84720
ggagcgcaga gagcctcctg ctctgcctgc tggtcattcc tggtggctct ggagtcggca  84780
gctggtgggg agcggctggg gtgctcgtct gagctctggg gtgcccaggg cctgggagag  84840
ttgccagagg ctgaggccga gggtggggcc ctggcggccc ggctcctgcc ccaaatatgg  84900
ctcgggaagg ccacagcggc actgagcaga caggccgggc cagacgggcg ctgaggctcc  84960
cggcctctcc cccagctccg ctgtgaccct cacctgcggc ccggggtgcc agggcccccg  85020
cttggttctg ccgtgtcttt gcaggctgat cccacgggct ctccctgcct ctctgagctt  85080
ccgccttttc caggcagggg aaccgcgacc tccaggctgg gacgcgggga gggtgtatgc  85140
gccaggtcag aatcacccct ccaccgggag agcgtggtcc aggggccctg gcagggtggg  85200
gaccgagcat ctgggaactg ccagccaccc ccacccatgc agaggggaca tacagaccac  85260
acggaggctg tgcctccgct gcagcaactg gagaacaccc agccgcggcc aaacataaat  85320
aactaaataa taaaagtttt aaagatcgtt acttaaaaaa acaagtgtgc cccagtgatc  85380
ggaccccagt tcccggtgcc ctgagtggtg ccggccctgt gctgagcatg gcctggttgg  85440
ttcaccccca gatccacact aaagggtggg atcaccccta ctagtcaggt gagcagatgc  85500
agggggggag ggcggcagcc cctccatgct ggtgggtggc cgtggtgggt gtcctgggca  85560
ggagccagct cacggagctg gagaggacag acctgggggg ttgggggcgc ccaggaagaa  85620
acgcaggggg agaggtgtct gccgggggtg ggggtccctt cgaggctgtg cgtgaagagg  85680
gcaggcgggc ctgcagcccc acctacccgt ccccggccca aacggcggga gtaagtgacc  85740
ctgggcacct ggggccctcc aggaggggc gggaggcctt gggatcagca tctggacgcc  85800
agtcagcccg cgccagagcg ccatgctccc cgacggcctc cgctggagtg aggctgcgct  85860
gacacccaca ccgctgaccc gggcctctct cccgctcagg atgccccccg ccgccacccc  85920
gtgagcagag ggccacagcc ctggcccgac gcccctcccg acagtgacgc ccccgccctg  85980
gccacccagg aggccctccc gcttgctggc cgccccagac ctccccgctg cggcgtgcct  86040
gacctgcccg atgggccgag tgcccgcaac cgacagaagc ggttcgtgct gtcgggcggg  86100
cgctgggaga agacggacct cacctacagg tagggccagt ggccacgagc tggcctttga  86160
tctccacctg ctgtctgaga cacgctggag ctgggggag ggcagatccc tatggccaac  86220
```

aggctggagt gtcccccaac tcccgtgccc actgctcaac accccaaacc cacacttaga 86280
tgcactccca tgccctccct tgggagcacg gtctccacac ccacctggcc accccacaca 86340
cccgtggggc acggccgtta gtcacccacg caacctctgc gggcaccgtg ctgcgggcca 86400
ggccctggga ctctcagtga gggaggcaga cacggcccct cctccggggg agcgaggtgc 86460
tccccacgcc cggttcagct ctagcaccgc actcgggacc ctcacaggga gggacccact 86520
ggggcaggcc aggtgacggc tcgggtgacc tcggcccctg gcgctgagac tacacttcct 86580
gcagtgggcg gcgaagatgg gtgtggtgtc ccacgtcgtt gcagcgggga ctcctggggc 86640
ctcggaagtg tcctgggcgg ggagcctggg gagcaggaag ggcaggtctt ggggtccaag 86700
gcctccccac ggtcaggtct gggagggggc ctcggggctc ttgggtcctt tccgcccagt 86760
gcagaccctc gcggccacct aagggcacac agaccacaca aagctgtgcc catgcagtgt 86820
ggggagtggt gcgcaccctc agagcacact gggcccacat cacgcacgcc tgcccccctca 86880 ctgtgcatcc ggggaaactc ctggccccga cagccagcgg ggctgacgct accccgtgag 86940
ccagacccag gcccccctca ccgcccctgt cctccccagg atcctccggt tcccatggca 87000
gctgctgcgg gaacaggtgc ggcagacggt ggcggaggcc ctccaggtgt ggagcgatgt 87060
cacaccgctc accttcaccg aggtgcacga gggccgcgcc gacatcgtga tcgacttcac 87120
caggtgagcg ggggcctgag ggcacccccca ccctgggaag gaaacccatc tgccggcagc 87180
cactgactct gcccctaccc accccccgac aggtactggc acggggacaa tctgcccttt 87240
gatggacctg ggggcatcct ggcccacgcc ttcttcccca agacccaccg agaaggggat 87300
gtccacttcg actatgatga gacctggacc atcggggaca accagggtag gggctggggc 87360
cccactttcc ggaggggccc tgtcgaggcc ccggagccgg gcccgggctc tgcgtccgct 87420
ggggagctcg cgcattgccg ggctgtctcc ctcttccagg cacggatctc ctgcaggtgg 87480
cggcacacga gtttggccac gtgctcgggc tgcagcacac gacagctgcg aaggccctga 87540
tgtccccctt ctacaccttc cgctacccac tgagcctcag cccagacgac cgcaggggca 87600
tccagcagct gtacggccgg cctcagctag ctcccacgtc caggcctccg gacctgggcc 87660
ctggcaccgg ggcggacacc aacgagatcg cgccgctgga ggtgaggccc tgctccccct 87720
gcccacggct gcctctgcag ctccaacatg ggctcctcct aacccttcgc tctcacccca 87780
gccggacgcc ccaccggatg cctgccaggt ctcctttgac gcagccgcca ccatccgtgg 87840
cgagctcttc ttcttcaagg caggctttgt gtggcggctg cgcgggggcc ggctgcagcc 87900
tggctaccct gcgctggcct ctcgccactg gcaggggctg cccagccctg tggatgcagc 87960
cttcgaggac gcccagggcc acatctggtt cttccaaggt gagtgggagc cgggtcacac 88020
tcaggagact gcagggagcc aggaacgtca tggccaaggg tagggacaga cagacgtgat 88080
gagcagatgg acagacggag ggggtcccgg agttttgggg cccaggaaga gcgtgactca 88140
ctcctctggg cacagctggg aggcttcctg gaggaggcgg ttctcgaagc gggagtagga 88200
taaaaggtat tgcaccccat gaagcacgtg tgatccttgc ccctagagac aaggctctgg 88260
ggctcagagg tggtgaagtg acccacatga gggcacagct tggagaatgt cgggagggat 88320
gtgagctcag tgtgccagag atgggagcct ggagcatgcc aaggggcagg gcctgctgcc 88380
tgagagctgg cactggggtg ggcagccaag tgcagggatg gagcgggcgc ccaggtggcc 88440
tctttgctgc tcagaacgac ctttcccatg tatacctccc agcgccgctg gcattgccca 88500
gtgtccttct tgggggcagg agtaccaagc aggcattatt actggccttt tgtgttttat 88560
ggacaacgaa actgaggctg ggaaggtccg aggtggtgtt ggtggcggaa ggtggccgct 88620
gggcagccct gttgcagcac acaccccca cccaccgttt ctccaacagg agctcagtac 88680
tgggtgtatg acggtgagaa gccggtcctg ggccccgcgc ccctctccga gctgggcctg 88740
caggggtccc cgatccatgc cgccctggtg tggggctccg agaagaacaa gatctacttc 88800
ttccgaagtg gggactactg gcgcttccag cccagcgccc gccgcgtgga cagccctgtg 88860
ccgcgccggg tcaccgactg gcgaggggtg ccctcggaga tcgacgcggc cttccaggat 88920
gctgaaggtg tgcagggggc aggccctctg cccagccccc tcccattccg cccctcctcc 88980
tgccaaggac tgtgctaact ccctgtgctc catctttgtg gctgtgggca ccaggcacgg 89040
catggagact gaggcccgtg cccaggtccc ttggatgtgg ctagtgaaat cagtccgagg 89100
ctccagcctc tgtcaggctg ggtggcagct cagaccagac cctgagggca ggcagaaggg 89160
ctcgcccaag ggtagaaaga ccctggggct tccttggtgg ctcagacagt aaagcgtctg 89220
cctgcaatgc gggagacctg gattcgatcc ctgggtcagg gagatcccct ggagaaggaa 89280
atggcaatgc cctccggtac tgttgcctgg aaaattccat ggacagagca gcctggaagc 89340
tccatggggt cgcgaagagt cagacacaat ggagcgactt cactgtctta agggccacct 89400
gaggtcctca ggtttcaagg aacccagcag tggccaaggc ctgtgcccat ccctctgtcc 89460
acttaccagg ccctgaccct cctgtctcct caggcttcgc ctacttcctg cgtggccgcc 89520
tctactggaa gtttgacccc gtgaaggtga aagccctgga gggcttcccc cggctcgtgg 89580
gccccgactt cttcagctgt actgaggctg ccaacacttt ccgctgatca ccgcctggct 89640
gtcctcaggc cctgacacct ccacacagga gaccgtggcc gtgcctgtgg ctgtaggtac 89700
caggcagggc acggagtcgc ggctgctatg gggcaaggc agggcgctgc caccaggact 89760
gcagggaggg ccacgcgggt cgtggccact gccagcgact gtctgagact gggcaggggg 89820
gctctggcat ggaggctgag ggtggtcttg ggctggctcc acgcagcctg tgcaggtcac 89880
atggaaccca gctgcccatg gtctccatcc acacccctca gggtcgggcc tcagcagggc 89940
tgggggagct ggagccctca ccgtcctcgc tgtggggtcc catagggggc tggcacgtgg 90000
gtgtcagggt cctgcgcctc ctgcctccca caggggttgg ctctgcgtag gtgctgcctt 90060
ccagtttggt ggttctggag acctattccc caagatcctg gccaaaaggc caggtcagct 90120
ggtgggggtg cttcctgcca gagaccctgc accctggggg ccccagcata cctcagtcct 90180
atcacgggtc agatcctcca aagccatgta aatgtgtaca gtgtgtataa agctgttttg 90240
tttttcattt tttaaccgac tgtcattaaa cacggtcgtt ttctacctgc ctgctggggt 90300
gtctctgtga gtgcaaggcc agtatagggt ggaactggac cagggagttg ggaggcttgg 90360
ctggggaccc gctcagtccc ctggtcctca gggctgggtg ttggttcagg gctcccctg 90420
ctccatctca tcctgcttga atgcctacag tggcttcaca gtctgctccc catctcccca 90480
gcggcctctc agaccgtcgt ccaccaagtg ctgctcacgt tttccgatcc agccactgtc 90540
aggacacaga accgaactca aggttactgt ggctgactcc tcactctctg gggtctactt 90600
gcctgccacc ctcagagagc caaggatccg cctgtgatgc aggagtgagt gaagtcgctc 90660
agccgagtcc gactctttgc aaccccatag gactgtagcc taccaggctc ctctgtctat 90720
gggattttc aggcaagagt gctggagtgg gttgccattt ccttctccag gggatcttcc 90780
caaccctggt ctcccgcata gcaggcagac tctttactgt ctgagccacc aggcaatgca 90840
ggagacctag gttcagtctc tgggtgggga agatcccctg gagaagggaa tgacaacctg 90900
cttcagtatt cttgattggg gaatcccatg gacaaaggag cctggaggcc tacagcccat 90960

-continued

```
agggtgcaaa gagacacgac tgagcaagtc acacacacag agccctacgt ggatgctcat  91020
agcggcacct catagctgcc atgtatcagg tgttggcatg ggcagccatc agcagggggc  91080
catttctgac ccactgcctt gttccaccgg atacacgggt gccttcctgt gtgtcgggcc  91140
cactcggctg tcagcgccca agggcagggc tgtcgggagg cacagggcac agagttaagg  91200
aggggatggg gacgttagct cctccccagc tctcagcgga tgcagcaggc aaaacaaacg  91260
ctaggaatcc tgccaaaccc ggtagtctct gcccatgctc gccccatccc cagagccaca  91320
agaacgggag ctggggggtg gcccggagct gggatactgg tccctgggcc cgcccatgtg  91380
ctcggccgca cagcgtcctc cgggcgggga aactgaggca cgggcgcctc cggcttcctc  91440
cccgccttcc gggcctcgcc tcgttcctcc tcaccagggc agtattccag ccccggctgt  91500
gagacggaga agggcgccgt tcgagtcagg gccgcggctg ttatttctgc cggtgagcgg  91560
ccttccctgg tacctccact tgagaggcgg ccgggaaggc cgagaaacgg gccgaggctc  91620
ctttaagggg cccgtggggg cgcgcccggc ccttttgtcc gggtggcggc ggcggcgacg  91680
cgcgcgtcag cgtcaacgcc cgcgcctgcg cactgagggc ggcctgcttg tcgtctgcgg  91740
cggcggcggc ggcggcggcg gaggaggcga accccatctg gcttggcaag agactgagnn  91800
nnnnnnnnnn nnnnnnnnnn nnnnnnnnnn nnnnnnnnnn nnnnnnnnnn nnnnnnnnnn  91860
nnnnnnnnnn nnnnnnnnnn nnnnnnnnnn nnnnnnnnct gcaggtgccg gcggtgacgc  91920
ggacgtacac cgcggcctgc gtcctcacca ccgccgccgt ggtaaccgcc cccgggggtt  91980
gccaaggtta cgattggacc ctccccgccc cgaccctgct cccctagggt gggtgggtcg  92040
gggggcagtt tctaagatct cctggttccg cagcagctgg aactcctcag tcccttccag  92100
ctctacttca acccgcacct cgtgttccgg aagttccagg tgaggccgcc ccgccccttg  92160
cacttgctgg cccaacccct cccgcccagc gctggcctga ccgcccccca ccccgcccac  92220
cccacgcagg tttggaggct catcaccaac ttcctcttct tcgggcccct gggattcagc  92280
ttcttcttca acatgctctt cgtgtatcct gcgccgtggt ggaagcggga ggagggcggg  92340
gcgggggacc gggcgggagg cagcgggccc cgggaagctg agaccctcca aggggcacgc  92400
ttcctatacc aaagccgcag gttccgctac tgccgcatgc tggaggaggg ctccttccgc  92460
ggccgcacgg ccgacttcgt cttcatgttt ctcttcgggg gcgtcctgat gactgtatcc  92520
ttcccgggct cggggaccta tgggtccggg cctctgctgg ccctgaggcc ctgcttgagc  92580
gcatgccaca gagggagagt tgcgaccccg agctgagggt gtttttgagc gtacatcacg  92640
tgctcagctg caggtgcccc tgtcgaactc cagggctaca cccaaaatac cacagggcag  92700
ggtgcccagg ggctgagtcc tgaatgcagg tagccaggag gatctagggc tgggcccggg  92760
ggctggggtg aagtggagag gcagggccga tcagggggcc cctggaggcc accgtttggt  92820
cttagagtgg gaagcgaaac caacctgctt gagggtttca ggggtttagg aagtcagagg  92880
ggccctgggc agggcacaag accttgactc tggcccagct actggggctc ctgggtagcc  92940
tcttcttcct gggccaggcc ctcacggcca tgctggtgta cgtgtggagc cgccgcagcc  93000
ctggggtgag ggtcaacttc tttggcctcc tcaccttcca ggcgccgttc ctgccctggg  93060
cgctcatggg cttttcaatg ctgctgggca actccatcct ggtggacctg ctgggtgagc  93120
ctgctgtcca gggagcctgc cccaagctgg gtgtgctggg ccagagccct ggtcctctcc  93180
ccgcccccac ccctcttccc cactcctggc gcccccatcc ttccagcccc tccaacaagt  93240
cagcctatag gttttactta ttcgagcctg acccatttgc tgacgcttgt gtggggcccg  93300
acccggtagg gatgggtggc tcagggtgcc tgctcacagc tccacttctt ctgacgtcct  93360
```

```
caggcctgac ctcctcccag gttctgccta ctctgggcca agcctggccc cacgctgggc  93420
tggctggccg tgcagggcat cagaccccca tgctttgggg gcttcagggc tgtggagggt  93480
ggcctcggca ttggcgcctc tcccacaggg attgcggtgg gccacgtcta ctacttcctg  93540
gaggacgtct tccccaacca gcctggaggc aagaggctgc tgctgacccc cagcttcctg  93600
tgagtgctga cagccttccc cacccccttc cccagatggc tctctacccc atgagggggg  93660
gggaccctgc cagctgccgc tcagcgtggg ctcctcccca caggaaactg ctactggatg  93720
ccccagagga ggaccccaat tacctgcccc tccccgagga gcagccagga cccctgcagc  93780
agtgaggacg acctcaccca gagccgggtc ccccaccccc acccctggcc tgcaacgcag  93840
ctccctgtcc tggaggccgg gcctgggccc agggccccccg ccctgaataa acaagtgacc  93900
tgcagcctgt tcgccacagc actggctctc ctgccgcggc cagcctctcc acgcggggca  93960
ggtgctgctg gccgagagcc agggccacca agcctgacgt gctctccgac ccagaacatt  94020
ggcacagctg gaggcccaga gagggtccag aacctgccca ctcgccagca gaactctgag  94080
cacagagggc agccctgctg gggttctcat ccctgccctg cctgtgccgt aattcagctt  94140
ccactgatgg ggctcacatc tcaggggcgg ggctgggact gggatgctgg gttgtgctga  94200
gctttggccg tgggggccct cctgtcccga actagcaacc cccaagggga cctctgcttc  94260
atttcccagc caggccactg aaggacgggc caggtgcaga agagggccag gccctttctg  94320
tgactccgaa gcctcaagtg tcagtgtttg cagagtccag tggctgaggc agaggcctct  94380
gggaagctct gcccctgccg tttgcagctg aggccggcag gagcctcacc tggtccccag  94440
ctcacgggca ttggaggacc agtccgcacg gtggtttact cctgggtcgg caccagccgc  94500
cgccggctgt ccctttcaca gaggataaaa gtactcgctc tggagttgga ctttaatgtt  94560
gtcatgaaac ctctggccca gcagcgggct ccgcagtggg tggcaggtga aggcccctcc  94620
ccgggcctct ccaggcaggt gccgcctggc cagcagggaa ggcaggcagt gtcatccccc  94680
actggctctg gggctcaggc tacctcctgc tgtggccgga acatctcccc cagtggtgga  94740
gcccagtgtc cgtgaggcca gctgggcctg aaaccttcct ctctgaagcc ccgctgtccc  94800
cttgccctgt atggagggca gaggctggag cgcaagttcc taggatgtgc ttgcgagacc  94860
cccgagccca ggggcgaggc ccatctcagc ccacccccga actggaaacc cttggagctc  94920
tgcccctcgt ggtgtgaggc ccctgctatg cgaccctcag ccctgccagc aacggaaggt  94980
gcagggcccg ggcccacggg cttaacgcaa ctgggcctgg gtcacctgcg gggcctggtc  95040
ccaggaggaa gacccaggtg ccaccctcct gggtgccacg tccaggtcac gtggggaccc  95100
gtccatgtca cagaagatgc agggtcaccc ggtgagctgg cgccgggccc tgccagagca  95160
ccagccgcgg gtggaggtgg gccccagctc tcctgtcagg cacgtggtgc tgggaggtgc  95220
ggccggagca gtgcccacca gctgcagcag gacaggtggg cacaggccca ccagcagtgc  95280
ccgcacggga tgggcccctg caagggccag agaagccacg ctcctggctg gggctgggc  95340
tgggactgac aggtggccct gccctctgcg ccccactact tcccagccac ccgggactcc  95400
aaggacttgc tgagctgggc aggtgggacg ccgaggggag tcaaactgct cgtgggggca  95460
ggaggggcgg tccacagggc tgagccctga gctgaaccct ggccctgctc gtggttgtgg  95520
gggtgggggg gtccagtggc gccctagccc tgctgaggcc cagctgggac gtgcgcgccg  95580
gagggcgagg ggccagccca tgccatgctg tcccccgttc tcagctccat gctaccactt  95640
tgaagaaaca gaacctgttg ccttttttatt tagaaagtgt tgcttgccct gcctggggct  95700
```

-continued tctatacaaa aaacaaacac agctcaacgt ggcctctcct gaccagagac gggcggtggg 95760
gactggggct cagcagacgg aatgtgtccc cggcggcggg agaccaggag gcccctggcc 95820
cgctcctcag gacggctggg ctgtccccac ctggtcccct ccgagccaga agatggagga 95880
gaggtgggct gatctccaga tgctccctgg gagccaagcg ccacggggtg gtcaccaggc 95940
cggggccgtg ttggccagac gcctcatccg cctgtgggag ggggagggca gcaacccccg 96000
gatctctcag gcaaccgagt gaggaggcag gagcccccag cccctccctc ggccgctctg 96060
ctgcgtgggg ccctgaagtc gtcctctgtc tcgccccccct ccccagggag agtgagcctg 96120
ttctgggctg tggtcagacc tgcccgaggg ccagcctcgc ccggggccct gtcctgcctg 96180
gaaggggctg gggcagcacc ttgtgttccg gtcctggtcc cggatcttct tctccatctc 96240
tgcatccgtc agggtctcca gcagcgggca ccactggtca gcgtcgcctg tgttccggat 96300
ggcaatctcc accgtgggca gggggttctc actgtggagg acgagagagg tagacggctc 96360
acagagcagc tgcaggagag gcccctagaa agcagtgtcc accccgctgc gggcagacag 96420
gacatggagc ctggtttctg cacccggctc ccgacacagg gcggccgggc acgctgccaa 96480
catggcatct ccgggtctgc atgtggggag gggtccacag gacagtgctg caggtccagc 96540
cattcccagt ggacttgctg ggaggaggag ggccgtccgc cccgctcagt gtccaggaga 96600
aaggagagca aaggagtcca tccacccagg agtggagtcc cagggcccct gccctgacca 96660
gcctgcaggg ggcccctcgg cccacatcac aggggcccag aatccataag ccctgactgc 96720
tccaccccgg ggcccctcaa agacgcgcct agactccgtc cgagggccac ctgcacaccc 96780
tctggcgaag tggactcagg gctgggggtc agcctcggtg aggccgcaaa ggctggggac 96840
tcctggccga gctgctgcct ctgccaggag ccaggcccag cctgccggcg agcctcagcc 96900
acgccctcac ccaccctgcc cgcggcgcca cgctggcctc cgggtcctct cctctggcct 96960
cctgctgggc cactggtgct cagccccagc agtcggcctg ccaggagccc tgcagagtca 97020
gcccccagag ggaggagggg gcccggggga acagcacagg aacaaacaga cccctggcct 97080
tagttttagc tcctcatctg gaaaatgggg acagtgtcct tgctgcgagg ggtttcagag 97140
gaccactgcc atgcaacacc cagcacacac ccactgcgtg ggggctcggg cccgagccgg 97200
tgcccccgag tcccaggctg gtggctgggc cgccccagcc accctgccga cagctgcttc 97260
ccagccgggc ggtgctgcgg cagtccagaa gccagcactg cagacccaaa tgtcactcct 97320
cacgttgcgg gctcccagct gccttccttg gggcagcag acacgaaagt caccaagccc 97380
acgccgacgg gagcaaacac gtcttcctct taaacaagtg cgggtcccgg aggccctgtg 97440
tttacctccc tgtggctccg ggaagattgc atcccagggg gttgttctaa accaagggct 97500
gctcgggcca ggcctggaag gaggggcctg gagccaggag cccaccctta cgggcattcg 97560
gcttcctggg tctcaaggcc ggctgggacc ctgcattccc accacccgcc aggtgcaagc 97620
agggaggccg tgtcggagga ggcagagggc ctggagggtc gtcttcgacg tgacctcact 97680
tttacaacct cacaggtgcg gcaggccagc tgggaggcat ggctgtgccc tcctggtaga 97740
tgagaacaag actgcaggga gtgatccccc tgaacttccc caaccaggag gagacaaaac 97800
tcggtgtcgc cctcctgctt aagatcaact gactctggac aaggggccca gcccacccga 97860
tggggaaagg gcagtccttc caacaagcgg tgctgggacg ggacccggca ggccatggtt 97920
tctcagctat gacaccagca gcacaagcac cccgagaaaa acagctaagc tgggcactgt 97980
cacacaagtg aactccaaac ccaagaaaac cacaaaaagc ctgcggatct tcagatatgt 98040
gggaagggac ctgtatctgg aatgtataac gaactcctga aaagtgaaag tgttagtcac 98100

```
tcagtctgtt cagctctttg caaccccatg gacggtagcc tgccaggctc ctctgcccat  98160
gggattctct aggcaagaat actggagtgg gttgccatgc cttcctccag ggatcttcc  98220
caacccaggg attgaacctg tgtctctctt gcactggcag gcgggttctt taccagtagc  98280
gccacctgag tagaaacact ccaggtgccc tgagtgtcag agcaggaggg actcggccca  98340
ggcctgtgag gggaccctct ccgagtcccc tgctgcacag cagtgagagg tgcgttctga  98400
gtcagcctcc agggatgagg gacttggtgt cgacatcact cccaggacct caggatctgc  98460
tctgggaagc gaggctcccc aggctggccc caggcccgct ggcctcagct cgtgagccgt  98520
gcgtggacag gtgccatgag caggcctccc acgggactcg gggcgcggcc tggaccccgg  98580
ggctgccagt ggtcgcgggg ggccccgtgt ggcggctgtt ccctctcttg ctccgagtcc  98640
taggaacatg gtgggcgctg cctcctgggg tttctggaga agcagctgag atgcaaacag  98700
ccccacgcgc tccctcagct gttccctgtc acgggtggcc ccttggtgac ggcctccatg  98760
cagggacggt gacagctcga gcagccgcgt aaaaccacac ggggacggtg gcagctcgag  98820
cagccgcgta aagcctgaca tccaatttgg aagcctcccg cagtggaaga ggggcccggg  98880
gacggggctg cccggggcga gctccaccgg gtcgggggtc acgaggagcc cacccgcgtc  98940
cccgccacca gcacctggga ccagataccc tccccgctct gagggcggcc tgaacgccgc  99000
cccctcccac gggggcgccc accgcctgct cgtggactga acaagaggcg gcagtggcct  99060
ccagaccccc tcgggggagg gcagacctgt ccgagactga gcacaagtcc agggaatgag  99120
caagggtctc agtaatgtcc ccaccgggac gggacgggag gaggcgacag aggccgctga  99180
ggtgcggggc agccctcagt agctggcatc aaggccccag gcagtcccgg ggcatccccg  99240
cagggggcgg gggcgaccac cggcccgagc ccaggcagtc ccggggcatc cctgcagcgg  99300
gcgggggcga ccaccggccc gagccctacc tgaaggcgta ggtcttctga tgccagctca  99360
gctgtccccg gatgctgtag gcgatggtgg tgacgaactc cccgcccagc cccagctcgg  99420
agcacagctt cagagcgaac ttctcgggcg agttctcctt ctccgacatg tcccactcga  99480
actggtccac caaggagatg ttccccacgt ggatgttcag ctggcccggg agcacagaca  99540
tgagccagag cggccccctc tggggccagg ccgcaccctc accacccctt ctccccggaa  99600
catccccgcc tcgttcttgg ccgcgcccct gtgctgctac ttggggtaag gaaaacaacc  99660
cccatctctc tgaaaagggt taactagcga ggaagatgcg ctggtaactg gaaaactccc  99720
tacaaagaaa gcttggatct gatggcttca ctggtgaatt ccaccaaaca tttcaagcac  99780
taacaccaat ccttatcaaa tcctgccaaa aaactgaaaa ggaaggaaca catcataact  99840
ccctgccttg ataccaaagc cagacaaaga tactacgaga aaggaaaggt gcagaccggc  99900
acttactgtg gacattgatg tgaaacctca gcagacacga gcaaaactac attcaccagc  99960
acgtcagaag aatcacacac cgttataaat gatgggatga tgacacaacc acattataaa 100020
cggtggggct tactctggtg atgtaaggac ggctcagtaa gaaaaccggt caatgccatg 100080
aaccacttga acagagtgaa ggacaaaaac cacacagtca tcttgataat tggaggaaaa 100140
tcattagaca aacttcaacg tgctttcacg ataaaagcac tcagtaaact aagatcagat 100200
ggaaaccaca tcaacaagat taattcagtc aaaaaattca ctgcaagtat cacccacaat 100260
ggcagaagac tggtaacttt tcctctaaga tcaggaacga gccaaagata cccagtcttg 100320
ccacttttgt tcaatatagc gttggaattt ctactcagtg cagtgcagtc gctcagtcgt 100380
gtccgactct tttcgacccc atggatcaca gcacgccagg cctccctgtc catcaccaac 100440
```

```
tcccggagtt cacccaaact catgtgcact gagtcagtga tgccatccag ccatctcatc 100500
ctctgtcgtc cccttctcct cctgcctcca atcccttcca gcagttaggc aagaaaaata 100560
aatcaaaggt atccacctgg aatggaagaa gtaaaactat ctctggtccg agatgttaca 100620
atcttatatg cagagtttaa gatgctaaca aaatactatt agaactaatg aatgaattca 100680
gcaaggtacc aggatacaaa gtcaacgtgc aaaaatcagc cgcatttcta catgctaaca 100740
ctgcacaatc tgaagaagaa aggatgaaca aattacaata acataaaaaa gaataaaatc 100800
cttagaaatt aacttgatca aagagatgta caatgaacaa tataaaacat actgaaagaa 100860
attgaagata taaataaatg gaaaaacatc ctatgtccat ggattggaag acttaaaatt 100920
attaagctgt caaggctatg gtttttccag tggtcatgta tggatgtgag agttggacta 100980
taaagaaagc tgagcaccga agaagtgatg cttttgaact gtggtgttgg agaagactct 101040
tgagaggtcc ttggactgca aggagatcca accagtccat cctaaaggag atcagtcctg 101100
ggtgttcatt ggaaggactg atgttaaagc tgaaactcca atactttggc cacctgatgc 101160
gaagagctga ctcatttgaa aagaccctga tgctgggtaa gattgagggc gggaggggaa 101220
ggggacaaca gaggatgaga tggttggatg gcatcaccga ctcaatggac atgggtttgg 101280
gtggactctg gaagttggtg atggacaggg aggcctggcg tgctgcggtt catggggttg 101340
tgaggagtcg gacacgactg agcgactgaa ctgaactgaa catgaatacc caaagcaatc 101400
tacaaagcca aatgtaatcc ctatcaaaat cccaatagca tttctgcaga aacaggaaaa 101460
aaaatcttaa aattcatatg gaatctaagg aaaagcaaag gatgtctggt caaaacaatg 101520
acgaaaagaa caacaaagct ggaagactca cacttcctga tttcagaact tactgcaaag 101580
atacaataat gaaaacactg tgggactaac gtaaaagcag acacgtgggc caacgggaca 101640
gcccagaaat aaactctcaa ataagcagtc aaatgatttt caacagagat gccaagacca 101700
ctcagtgaag gaaagtgttt gcaaccaacg gttttgggaa aaaagaaccc acatgcgaaa 101760
gaatgaagtg ggaccccttac ccagccccat ctacagaaat caactcaaaa cagacagaac 101820
atatggctca agccataaaa cgctcagaaa aacagagcaa agctttatga tgttggattt 101880
ggcggtgatt tctcagatat gacgtcaaag gcataggtga taagcgaaaa aataaactgg 101940
acttcaccaa aatacaacac ttctatgcat ccaaggacac taccgacagc ataacaaggc 102000
agcccaggga aaggaggaaa catccgcaaa tcacagcatc tgggaacaga ccgctgcctg 102060
tgagatacag ggaaccgata aaaacaagaa aacagcaaaa cccggactca aaaatgggaa 102120
ggactccagc agacacagga gacagacaag ccgccagcag gtcactaatc agcaagcaag 102180
gcccgcaaag gcccgtatcc aaggctgtgg tttttccagt ggtcatgtag gaaagagagc 102240
tggatcgtaa gaaagctgag cgctgaagaa ttgattgaac tgtggtgttg gagaagactc 102300
ttgagagtcc cttggactgc aagatcaaac cagtccattc tgaaggagat cagtcccgaa 102360
tagtcactga aggactgatg ctgtagctcc aatactttgg ccacctgatt cgaagaactg 102420
actcattggc aaagaccctg atgctgggaa agattgaagg caggaggaga aggggacgac 102480
agaggatgag atggttggat ggcatcactg actccatgga catgagcttg ggcaagctcc 102540
gggagagagt gaaggacagg gaagcctggc gtgctgcagc ccgtgggtcc caaatctttg 102600
gaccaagcga ctgaacaata acaaatcaac agggaaatgc aaatcaaaac cacagtgaga 102660
tactgtccac caccaggcag gcgttcttca gcggggttcg gggcaggtgg tgccctcttc 102720
tctcgtaacg cccccaggac cgcgggggct gctgagacag catggggtgt gcttggccta 102780
gcctgcccat gacaagagtg gcagtgtgct cgcctcactg cgcccttccc tgctctgccc 102840
```

accagctggg ccacccctgg gaccacccag cttccgctcc gtggacggca aggccgcagc 102900
agcgcccgga cacgcccaga acgtggtgcc ctcctcagaa gtcggcctgt gcccttcctg 102960
ggacaagccg cccaagagac agtcttccag agccctgccc cacaacacgg accccagaca 103020
ggctcctgtg gaggcctcca cgcacctccg cacctcgcaa gccccgagga caaggcaggc 103080
ccgctgcggg tgaggagccg cctaccttga taatgacgcg ctggtctgac tggtcttcca 103140
ggatgctgtc cgtggggtag gactcgatct gctgtctgat ggcagaggca atggctggca 103200
cgaatgtcag tgggttcaga tccaggtcgt cacagagaat ctctgagaac atctccgggg 103260
tcatcagctt ctctgaaacg atgacggagc gggggaaccc ccagtggacc acagggccta 103320
cggtcagcgt gctcagcccc ggcctccccc agccttgcct cctctgccac cgcccccccg 103380
ggtgacgaca ggaccccctg gcagcacgca gacagagctg agtgcacgcc agccagggcg 103440
gcggacggac cattcatgtt ccaggtaaag gcatcccgca gcttctgccc gtcaatctcc 103500
atgtccagtc ggatggggac cagcacctcg ggctgggacg cgttctcgtg gatcacggct 103560
gggtcgtggt cgtcgaagct ggaaggggag cggccgcgtg ctcagcaaag cgggctgggc 103620
ccctgtgccc agggcctccc tctctgcacc actggtcgct gagacctgcc cagagaggac 103680
ctgtccacta cgggccgggc cggcagaaac agggctggcg ggggtccacg cggggcggga 103740
ggggagctgc cgactcggca gcgggacaag ctcagaggtt ccctgcagga agagaggttt 103800
aagccccaga gcaggcagga ttctcccagc agctgtgggg aagaaagggt atgtccagaa 103860
gaagaaaccc tggaacaaag gccgaggggc aggagggttg aggagctgct tggagagcag 103920
tgaagggggg ctgggcggct ggggggtgct ggggagcctc ggtggccaag cacccagggc 103980
tccccacctg cagcctggac cccgagggag ccccagagga cggagagcaa ggcagctccg 104040
cactcacacc tgccctttag gatggggaag agggaagaga cgggggctgc ggggggcaag 104100
gaaaccaggc acgccccgct tagacccggg ggcgagaacc actttccaag aacgcagggg 104160
cgccaatgat gaacaatggg tagcagcccg caggcgggag gcccggtggc cgaggcccct 104220
caccagagcg ggaaggtccg cttcttgtcg cggcccatgc ggttcctgtt gatggtggtg 104280
gagcagggca cggcgtccag gtggtgcgag ctgttgggca gggtgggcac ccactggctg 104340
ttcctcttgg ccttctgttc cctgggagac acagacgccc gtccgctcag cctatgggcc 104400
aaaagccgcc ccccagccgc caggttgtgg ccagtggacg cccgccatgc ccctctgggc 104460
ccaggccccc atggggacct ctgtgcgccc agctccgcgg tggttattcc ccaggctcca 104520
agcggcacct gctcggggtc accagtttta ggggaggagg agagggcagg ggccccagcc 104580
cagtctgtga gctgtcaccc ccaggctcca agcggcacct gctcggggtc accagtttta 104640
ggggaggagg agagggcagg ggccccagcc cagtctgtga gctgtcaccc ccaggctcca 104700
agcggcacct gctcggggtc accagtttta ggggaggagg agagggcagg ggccccagcc 104760
cagtctgtga gctgtcaccc ccaggctcca agcggcacct gctcggggtc accagtttta 104820
ggggaggagg agagggcagg ggccccagcc cagtctgtga gctgtcaccc gtgctatgtg 104880
ctgggctggg cactcaggaa agagggtcag ggttcacggg ggggtggcgc gcagatttcc 104940
aggagagccc cgagggcagc agagaggagg ctcaggtcaa tggttgggca gggggccagg 105000
gctggagaca cagagagggt cccgattcgg gggggtgccc tcagcaggtg gctgggagtc 105060
cctgggggtt tgcacacttt cgatcaggct gttatttcag acgcttggtc cagcctgaga 105120
caggtaatgc ctctggcctc cgggccttca gggatggaaa gatactctag aaagcgggac 105180
tcaaagtaac tcaaggaact cgcgtcccac agtggggagc ccttctctcc aatttacatg 105240
gggcgtttac tacgaggaaa ataccgaagg ccgttttgag ctgaggctcc cgggccgggc 105300
tgtccgtttg tgagactgct cgtcacccct gggccacatc cctggtggcc aagggggcaa 105360
tcagtgcggt gactgcacga cacacctctg cagccctgcc ccacagctgt caccatcggt 105420
gacgtccacc ccctggagaa cctgaccact gcccggtttc ccgctaaaac agcgcccttc 105480
caggatgggg ggcagaggga gaggccttgg ccttttcact cctcttctgc agcgggggcc 105540
cctcgcaccc cagtgcccgg gcccaggagc gccccttggg gtggggcagg gagggatcca 105600
cacaccaagg ggagccagga cccccccaaa tctgctgccc tgccctgata cccgagacct 105660
ggggaaacgg gggactgggg ctgatgcggg caggaccaag aactgaggcg gtgagacggg 105720
gtccccacca caggccatct ggctggcagt ttctactccg ggcctgcagg ccaagaggga 105780
aaaggtgccc cactcagatc aggcgcctcc cgtccccagg gagggcctac aaggtcagat 105840
cctttgtaac ttccacgggc aaaactggct tgctgggcct gtgcgggccg catgggcgtg 105900
gaccaccaca cctttcccca ctgagtctcc agccggagct gtcacccagg tccccccagg 105960
ccagccccac cccgccacct tgcagtagcc tctcgtatcc aggccgaggc tgcccggtcg 106020
acccctcctg cctgatggcc tcaagtggac aatgcgagtc acgttgcagc acgtgagtgg 106080
gacgggcagc gccacgcggg gtccgggcat ccgagtccca ccactcagcc tcccttccgc 106140
tgcagagagg tctgtccaag agccctgggg gccatccagc ccctgtccga cctggccggt 106200
gtggaagagg gggtgtgcca cccctcctgg ggggctggct gggcgctggg caggcccctc 106260
ctaagagtgg agcccactgg tggttttcct gcagccccac ctccacacag cagttctcac 106320
tgcccagtaa caggaggcta ctggcctagc tctctccctc gtgtgatgga ctcaaccagg 106380
agcgttcacg gccccacaca gggttctcgg ctgctgcatg aggatctcaa agccccatcc 106440
acgtgcatgt aatctcctcc ggtaacttct ctagggaagc ccggctatcc tgccatcctc 106500
accgcaccac cagggcgaga aaagccatct ccagcgctca catccacaat gggccaggcc 106560
gtgagcacac caccttcttc gggaggttgt gggggcgggn nnnnnnnnnn nnnnnnnnnn 106620
nnnnnnnnnn nnnnnnnnnn nnnnnnnnnn nnnnnnnnnn nnnnnnnnnn nnnnnnnnnn 106680
nnnnnnnnnn nnnnnnnnng cgcgcccccc ccccccgcgg cgccggcacc ccgggcggcg 106740
gcccccggcg ctgggagcag gtgcggggcc gcggccgctc gtgagcctcc agcccggagg 106800
acgggccccg ggggccggcc cggtgcccag gccctgggag ccccggaggc cagagtgcca 106860
gagggccgga ggacccggga aggcccgaga gaggtgggaa gcacggggtt ccagccctag 106920
gccatttcag ccccaaagcc atcggtgaaa ccattgctgg ccccagataa aagcgtcgcc 106980
aactttttca ccccggcgga gactttagcg ggtagctgcc ccctaggggg aatggaaaaa 107040
ccaggattta ccaggtgggt ggaggtcaca actgcccaga tcctgagaaa gaggggtcag 107100
tggggcggga agattagtgg ggagaggagc tttcagaacc caagggaatg aaacgaggct 107160
tgaggttggt tatccagcag ccgccccctg ccccgtgagt gagcgaaggc tgggcccctt 107220
attgtcacat cttccagctc ttcgctagaa aacctagagt tttaaatact gtggcagctg 107280
agtcaaacaa taaggaaaag cccgactctt tgagagccag gcacaaggcg tctgtgacag 107340
ggtctccagg ctgcccattt gcagtctctg aaacggaggg tttttcgaga aggaggtctt 107400
ggggtgcctg ccagaattgg agggggggc gcgggaagtg aggacccaga agagagggct 107460
tggcccgctg caaggaggtc actggacact ggagctgaag cgccagccga aactggaaac 107520
tcgaaatctg tctccgtgcc agccacaagg cctatgattt tccttggcga cgttcagcat 107580

-continued cttaggagga gctggcgggg gaggcgggta gttcgtgggc ggttgcagca gggcaggaag 107640
gtgaggaacc tgaggctggt cagagagctg gttggagtga tgcccatcgg tggacccgct 107700
ggagaaggcc tgagtagaga aggtctaagc ttaacgggga aggggtgggc cagggtggaa 107760
atggggtggg aagtttgagg agggggagca gtggagatgg gggttgtgag gaatgggagt 107820
gagcttagac gtcttgagga tactgcagtt ctgtgctttt tttcacacct ggctgaaaat 107880
tcactgaaaa caaaacaacc cttgctctgt gacagcctag aggggtggga gggaggctta 107940
agagggaggg gacgtgcgtg tgcctatggg cgattcatgt gggtgtacgg cagaaagcaa 108000
cacagtatgt aattaccctc caattaaaga tcaagtacaa cttaaaaacc ccaaacacaa 108060
cattgtaagt cagctagact ccagtaaaca tttcagtaag aagattcaac tgggaatgag 108120
ttccgccgtg actatcctga tgaatttccc gtgtcttctt gaggccattc ctctttgaac 108180
ttccgtgttt ggggaagcgt gcctttgtat ggagtcctga ggagtaaatg agacgggctt 108240
gtagaaggcc tagtagtgcc ttgcacgcgg cagatgctca ataacctcga gttgtcacca 108300
ttatggtacc tcaagagtct ccttggagct tgcacggttt ctgaatgggg tcctgcgggg 108360
ctcccttggg gctcccacat ggggttgggg ggctgagtgg ggtgtccccg ctccttgctt 108420
gtcccctgtg gaacaccccc ttccacccga gcagctctgc ttttgtctct tgtgtttgtt 108480
tatatctcct agattgttgt tcagtcgctc agtcgtgtcc aactctccga ccccatggac 108540
tgcagcacac caggccttct gccttcacca tctcccggag cttgctcaaa ctcctgtcca 108600
ttgagttgct gatgccgtcc aaccatctcg tcctctgtcg tccccttctc cttttgacct 108660
cagtctttcc cagcatcagg gtcttttcca atgagtcagc tctttgactc aggtggccaa 108720
gtattggagc ttcagcttca ttatcagtcc ttccaatgaa tattcagggt tgatttcttt 108780
taggattgag tgacttgatc tccttgcagt ccaagggact ctcaagagtc ttcaacacca 108840
cagttcaaaa gcatcagttc ttcggcactc agccttcttt atgatccaac gcccacatcg 108900
gtacatgact actggaaaaa ctttggctca gagataattg acttgattga atacaaagtt 108960
ctttggcaaa aaataaaagt gtggcaagca gtactgacac aaaagcaagt ggcttttcct 109020
ccgttgagtc atttatttat tcagtgggtg tgtgcgtgta gagacggagc ggctgtgctg 109080
ggagctgggg cttccacttc agaggagccc cggacctgcc ctcggggagt tcacaggcag 109140
tgctgcgggg ggtcctgcca ggacgcctgc cctgcgagtg cccagtgctg tgatggatgc 109200
gtgtcccgca tctgcggcca ctggggccac gtgcccgaga ttgtccgggt ctgagggtgc 109260
agagaagagg aggcatttgg actgagtctg gaaaaatgag catgtggcca cgtgagaagc 109320
cagtggtgag gggaccagtc aggcggagga aagagcggct catacgagtt gtggagctgg 109380
aagcatgagg gtgtgtggaa gcagaggccg gggacagggc cgcagggccg gccatggagg 109440
gcgtgggctg ctgcaggctc ctgagaaggg ggacgctgcc atcatgaccg ggtttaggtg 109500
tttgaccctg gtgtccacgt agaggacaga tgtgtggggg gggagctgga gatgggcatc 109560
catcgggagt cagcctggag agaggcagag accccgtcag tgggccctca ggacgtggat 109620
ggggcggatg ttgggaagat ctgactcctg ggttccggct ggggctccgg gctggagggg 109680
tgccgcccac cgagcacagg aggcaaacag atgccctctc ccagcaagac cccagcccca 109740
gcaccctccg gggccggact ccgcccctct tccagaatgg ctcccttgct gtcctcgccc 109800
atctttccgg tgccctgagc ctctagagtc tggacaccag cgtccgcctt gcgcttgttt 109860
ctgggaagtc tctggcttgt ctctgactca cccaggaccg tcttcgaggg caaggttgtg 109920

-continued tccttggttc catctgcttt ggggtccggc tcctcgctgc ttgacctgct gatgtgacag 109980
tgtctcttgt tttcttttca gaatccgaga gcagctgtgt gtgtcccaga cagacccagc 110040
cgctgggatg acgggcccct ctgtggagat ccccccggcc gccaagctgg gtgaggcttt 110100
cgtgtttgcc ggcgggctgg acatgcaggc agacctgttc gcggaggagg acctgggggc 110160
cccctttctt caggggaggg ctctggagca gatggccgtc atctacaagg agatccctct 110220
cggggagcaa ggcagggagc aggacgatta ccggggggac ttcgatctgt gctccagccc 110280
tgttccgcct cagagcgtcc ccccgggaga cagggcccag gacgatgagc tgttcggccc 110340
gaccttcctc cagaaaccag acccgactgc gtaccggatc acgggcagcg gggaagccgc 110400
cgatccgcct gccagggagg cggtgggcag gggtgacttg gggctgcagg ggccgcccag 110460
gaccgcgcag cccgccaagc cctacgcgtg tcgggagtgc ggcaaggcct tcagccagag 110520
ctcgcacctg ctccggcacc tggtgattca caccggggag aagccgtatg agtgcggcga 110580
gtgcggcaag gccttcagcc agagctcgca cctgctccgg caccaggcca tccacaccgg 110640
ggagaagccg tacgagtgcg gcgagtgcgg caaggccttc cggcagagct cggccctggc 110700
gcagcacgcg aagacgcaca gcgggaggcg gccgtacgtc tgccgcgagt gcggcaagga 110760
cttcagccgc agctccagcc tgcgcaagca cgagcgcatc cacaccgggg agaagcccta 110820
cgcgtgccag gagtgcggca aggccttcaa ccagagctcg ggcctgagcc agcaccgcaa 110880
gatccactcg ctgcagaggc cgcacgcctg cgagctgtgc gggaaggcct tctgccaccg 110940
ctcgcacctg ctgcggcacc agcgcgtcca cacgggcaag aagccgtacg cctgcgcgga 111000
ctgcggcaag gccttcagcc agagctccaa cctcatcgag caccgcaaga cgcacacggg 111060
cgagaggccc taccggtgcc acaagtgcgg caaggccttc agccagagct cggcgctcat 111120
cgagcaccag cgcacccaca cgggcgagag gccttacgag tgcggccagt gcggcaaggc 111180
cttccgccac agctcggcgc tcatccagca ccagcgcacg cacacgggcc gcaagcccta 111240
cgtgtgcaac gagtgcggca aggccttccg ccaccgctcg gcgctcatcg agcactacaa 111300
gacgcacacg cgcgagcggc cctacgagtg caaccgctgc ggcaaggcct tccggggcag 111360
ctcgcacctc ctccgccacc agaaggtcca cgcggcggac aagctctagg gtccgcccgg 111420
ggcgagggca cgccggccct ggcgcccccg gcccagcggg tggacctggg gggccagccg 111480
gacggcggaa tcccggccgg ctcttctctg ccgtgacccc ggggggttgg ttttgccctc 111540
cattcgcttt ttctaaagtg cagacgaata cacgtcagag ggacgaagtg gggttaagcc 111600
cccgggagac gtccggcgag ctctaacgtc agacacttga agaagtgaag cggactcgca 111660
gcccgtacag cccggggaag atgagtccaa agtcgagggt caccttggcc actgcagggt 111720
cgctcggcgg tggggcggag cggtgcaggg agggctcctc ctgggcttgg ggtggcaggc 111780
gaggaccccg cgcctctcag ccctcggcct gggttggctg agggcgggcc tggctgtagg 111840
ccctccagcg gaggtggagg cgctgcccgg ctcagccagg cacaggaccc tgccacgagg 111900
agtagccctc cgccagaccc ggcgtccagg ctggggcgcc tgcggggcct ccgttctgtg 111960
gctgggcagc ctgcgccctg tccagggatg aaggggttcc ggtctgaagg gctgggttca 112020
gggtccagct ctggcccctc ctgccttggt gtcctggagg aagccccaag gctccgtttc 112080
cctctccagg aggtggggac gttgggaatg ccacattccc ctggggggtg tgtgtgtgtg 112140
ttcaaggctc ccattcagac tgggactggg cactcacgag ctttggcaac tggcaactga 112200
ggacggagac ccagggtgac accccacctc ctgctgcggc ccccccggca ggggagacac 112260
aggcccgtct ggttcccaag atggcagggc ccctccccct ccagcttgtg ccctgggtgt 112320
ggtgcctggg gctacagcga ccctttccgg ttccccgggc cagttcagct gggcatcctc 112380
agggcggggc tctgagggtg ccatgtttcc agagctcctc ctcctcccac cagtagcagg 112440
cgggcggcca gctcccaggc agccccctgg catcgcctag gtgcacacct gcccgctgtg 112500
acccagcaag gcttgaaggt ggccatccca gttaagtccc ctgcccctgg cccaggaatg 112560
ggctcgggca gggccgcatc tggctgcccc agaagcgtct gtccctggcc tctgggagtt 112620
ggcggtggtc tctggtactg tccctcgcag ggccccttag cactgctcgg ggaggaggtg 112680
ggctgaactg attttgaagt tttacatgtc tgcggccgca gtcctacgag cccgtcaggg 112740
tcatgctggt tatttcagca gatggggctt ggctcggcag ctaggatggt cctgaataaa 112800
aatgggaagg ccagagctgt tcctccatca gcaggcttgg cagctgggga cgttgaaagg 112860
acaggtctgc tggtctgggg agaccagctc tgtgcagccc ctgctgtccg tgggggtact 112920
aaaccagccc ctgtgtgcgc ccatctgagt ggcagcccgc ctggaggatc gcccatcact 112980
tgtgagaatt gagagaatgc tgacaccccc gcttggtgca gggggacagg gccccctaag 113040
atctacctcc ttgccccacc cccgggaccc cctcagcctt ggccaggact gtccttactg 113100
ggcagggcag tcatccactt ccaacctttg ccgtctcctc cgcgcgctgt gctcccagcc 113160
aaattgtttt attttttcc aagcatcact ttgcacacgt caccactctc cttaaaacca 113220
cccttccgga gtctcctgct cgtaaatcgc cggtttcagc caacctgggt cgccccccaa 113280
gcccagcaag cctgctgagc cccgcgcctc ccagctactt cacgctcgcc tcaagcttct 113340
aaacgcggac cttctccccc ccaccccat ccctttcttt tctgatttat gtaacacggc 113400
aggtaagact cctctcctga agggttgaca gactcacaca aaaccgtggt cagaccaggc 113460
aagtgctttt tttcagaagt gtgagcggaa cctagtcttc agctcatgct ctttccttgt 113520
tttcttatgt gttctaagtc ctttgacttg ggctcccaga cagcgacgtt gtaagaggcc 113580
gtcctggtag catttgaatt gtcctcgagt ttcgttgtcg gattttgttt tattgtctta 113640
gttttccctt cttttagcag acgttgttga ctgtcgtaaa gctccagttc ttggttctgt 113700
ttactaatca aattgttttg tcaaagtaca tgtattctgc tcttttcttt atcttttttg 113760
ttgcttaata ttaacacttt acatttctaa gattaattat ttaggtaatt aataattttt 113820
aacatttcta gtaaacgtgg gtacttgggt ctgtgtttgt tttcttgtag ttacagcttt 113880
ttctgctcta tactgttgac gtctgggttt ttttttgctc ttaggaattt ccctttgacc 113940
ccattattat tattttaatt agtatttttt aataattaaa aattagtgtt tttaaattaa 114000
ccctaatcct aaccccagtg atgactgctt cagtcattgc tgttacttat tatgtgctgg 114060
tgtcaggatt tttaagtgtc catagacatt ctctgagcct gaatatatta tcagttttat 114120
acagcatttg tgtactctca agaaacgtgt tttcactctg tcagttcggt ttgttacctc 114180
agtctttatg ttattttgct ccagtccgca cttgctctaa cttgtcttcc cttcgaggtg 114240
tgaggacgcc tggcagccgg tgagcatgcc ggggtccggg gtcgtgggcc caggcgccca 114300
gcaaagccct gtgggtgtgt gcacggctgg gctgctccgg gaggaagcct gtggccccac 114360
ggtagttagg agcgctggtt tacctggtca caccacggtc tggttttgtg tgcttttccc 114420
tgacgtgttt ctgttttgcc ttggtttcta ttctgtttta tgagtgccgt ttacgctttg 114480
ttagtcatgc cgttatctcg atagacaggg tgtacgtgat caagtgatta ccgtatttgg 114540
agcagatgtc tatttaacag agatgaactg agaacctgtg cctttgcatg ccctctttgc 114600
ctcttttaat gcttctagct tcaacttctc ttttccaaac attataatgg aaaccccttg 114660

```
cttttttttt tttaatttgc atttgcatga gagtttattt agctcggcat tttattttta 114720
aaatttgtgt atatattttt gctatatatc tgtaacttat aaacagcaaa ttattggatt 114780
ttgctttctg attctttctg taattcttct tacataagaa gttctcctat gagtaacatt 114840
gctgtttaga gtgaggcatg atttatttcc agcttagtat gtattgggtc ggttaacccc 114900
caaaggtcat gctcatcccc gccccatctc tgtgagttat tgtccgagtg tggagcgccc 114960
tgtctaggcc gacgagagac ccaccatcgg gcacacctgc ccctcctggt ctggtcagtg 115020
ccgggctctg tcctgagtcc actcctgatg tcacaggctg gtgcttcagc gacctcggct 115080
gtgacacgga gggtgtgatg gcactgccca gccccatggg gcttggagga ctaaaggatg 115140
cacacctgcc tggcagactg agggcacagg tgtttctcac actgtcagcg ttttgaaata 115200
ttcctttgat tttctaccct aactcccaaa ggccgttcaa cataagctag aatgctacgt 115260
ggtgcttgat tacattttag aaaagtttca gcaaatacca cgagatgcag caaagaacta 115320
gacctcacag atcaggccgc ctgcataagg gagcccacac agtcgtggga gacggggacc 115380
ctctcccacg tcctgtctgt cccaggatgg tcccctcacc cgccccctct ctcccctcgc 115440
cctcctgtgg tgggggccgg ccaccatcac agctgcagag cctcaagaag gggtcgcccc 115500
tggccactcc cgtggcagga gggacacgag ggcaggagct taccgcgggt gcagtggtct 115560
cggatcagct cagctggccg ctgcggggtc ggggggacag ttcagtggga ggcaggagcc 115620
cccactacag ctgccaggac ttctcagagg tgacaagggg gttcagtcac ctcagcccag 115680
gtggaaacca aatggcctct tgcgcggctc ctggggccac gcggaggttc gctgggatca 115740
caggtatctg gatgtgtgcg ccatggacat gcaccacctt cggggggtaa ggggtgggga 115800
aaggcagccc ctttcttttg ggggaccccc tcttcagtgt ctgataacca ggaaaccaaa 115860
tcagaaggtg gtctgggggt gctgagcagg gtgtctccta caccacaggc cacacactca 115920
cacagcctcc aggactccag tggggctgag cgctggagac tcacccacgt ttgctacccc 115980
cccacccaag gccatcccag aacagctgcc tgcgtcctca cggctggccc ctcccctctg 116040
gtctaaccca gtgtgggtgg gccggcctgg ggtctccacc tgcctcctgc tgttccctgg 116100
gctgctggct gtctgcagat gcggggccct ggcccggaga agccccatca gagcccagag 116160
gacgggagtg gagcggggag gtgagccccg gagtctcgag gggccagagg caaaatactg 116220
ggctgtgtcc ctggaaggca gtttcccatg aaaccttcaa tataggccgc cccagacgat 116280
cagcctcatc tgctacgtgg attcctcccc gtagcgaatg gtgattgggt tctacatgga 116340
cccgggactt ctgtttgaat tataatcttt cccccactgc ccctccaggg atctggaaaa 116400
tggaggcctg ggctagacgg aagcttcctc caagattctt tattgaaggg attcgaagag 116460
aaacaggtgg tcagtaatct gtgggggatg gaggggtgag cgctacgtgt aacggtttta 116520
ctgttgctac gggaccagtt ttgatgtctt tccccttcaa gaagcagacc caaacaccga 116580
gatgctgagg ttagcagcac agagcgggtt catccacaag gcaaccaggc agggagacca 116640
gagacgctct ggaatctgcc tccctatggg cacgggctgg gtgctcacgg atgaagacca 116700
agcagcaggt ggcgtggggc gtggggagcc tgcggaaagc gatggacaag gtgcgggacc 116760
gcggtccgcg cggtggaccc aagctccgcc tctgcgctgc agcgcgagct gggggcggag 116820
cttccaggga cccgcgaccg cgcccagtgg gagggtccgc ggtccaccca gtcctaacag 116880
ctcagctcca gctagacgcc gctgagtccg gctttctaga gagcaacccc ggcgggtatt 116940
ttatggttct ggcttcctga ttggaggaca cgcgagtctt agaacaccct tgattagtgc 117000
gggcaggcgg aatggatttg actgatcacg atctgcagtt tcaccatctc aggggccgcc 117060
```

ctcaccccca cctatcctgc caaagggggg gcctcggtgc tgagatcggg gccacacgtg 117120
cactagacgg tcggtcagcg ctgctgctga gcggacccgg ggccatcctc acaccgccac 117180
tggcccctgt gctcaataaa aggaaggaaa gcgggaaaag cgctttctgg ccgcggtggc 117240
ctcgcgcgtt cctccatcgc catctgctgg cagagcccgg catggcaccc gctgcacaga 117300
aacctcggtg tccgtttggg tgccccatcc ttgaccccga gagagcaccc tccgtccaaa 117360
atgaaaaaca gctgctccca agagtcatta taatcacagc caattgtgtt aattcgtcct 117420
cggatccact cacagttcca cggaacattc tgctaacctc tgacaactcc tacataaagc 117480
aatactgaga agaaaagaac gtggttgata aatacaaagg catacaacaa taaggagcaa 117540
agaaaaaaga cagtcctcgc agttctgttt tgttcatctc tcatgagtag gatggcagat 117600
aaaacacaga atgcccagtg aataatttta gtctaagtat gtccccaata ctgcctaatc 117660
ttcaaatcta accttatttt taaaatatat attttttgct ggtcactcat cagttcatgc 117720
accaaagcct ttgtttcttg actcctaact ttttgacccc tctggggtga ggagcacccc 117780
taacctcgag agcccatcac acagtcccct tgggactaga cccttctttg cccatcacag 117840
ctgaccggaa gggccagccc atggccagcg ctcgcgcccc ctggcggaca gactctgcgc 117900
ggcagccccg ggagcccagg tgcgaccccg cggtctctgg cgccctctag tgtggaaaga 117960
tctcctcctg gtgttcccag tcattgggct gtattttatt agagaagatg ctcgcgtgac 118020
gatgatgatg gtcctttacc gggaggcacg tttggggcgc gtcggctcag gggccgagct 118080
attagcctgc atcgcgccca caggcatcgc gtccccctga gccgggtcag ctgtgggctg 118140
tcctgacacg ggtttccccc agtctctggc ccgctgtccc tcccaggtca gtgtccagcg 118200
ttgcccttct ggttgtggac ttgtgcagcg gtctcagcag atggaggggc gaccctaaag 118260
gatgtattga ggcatctcag cactgtcctc cgcccaggtt tgctggtcag cagtgaagtg 118320
accgggaaaa ggggctgtct tggggtcctt tcagaggcct gggttagacc aaagttttct 118380
agaagattca ccattgcagg gagtcaaaga caaaactagg gtggtcagca atctgtgggg 118440
gattcggcgg tgagggaatt ctgaatgcta catgtaatgg ttttactatt gttagggaac 118500
atttttcccc cctacaaaca gcaggccaaa atactgagat gtcaggtttg catcaaagag 118560
cgggttcatc cacaaggcaa ccagagaacg ctctggaatc tgcctccctg cgggcacagg 118620
ctgggtgctc acggatgaag accaagcagc aggtggcgtg gggagtgggg agcctgggga 118680
aagcgatgga caaggtgcga ggacctccgg cgcgagctgg aggcggagct tccagggaca 118740
cgcggccacg cccagtggga gggtcagcgg tccatccagt cctaacagct cagctccaac 118800
tagacgctgc tgagtctggc tttctagaga acactccggg cgggtatttt attgttttgg 118860
cttcgtgact ggaggacgtt caagtcttaa aacacccttg attagtgcgg ggaggcggaa 118920
tggatttgac tgatcacgac ccgcagtttc accatctcag gggccgccct cacccccctcc 118980
taccctacca aaggtggggg catcggtgct gagatctggg gtgacacata aaatcaggtg 119040
aagtcttagg acagggggcc gattccaggt cctagggtgc agaaaaaacc tacctggccc 119100
cgggctagac agcgtggagg gcgtggcccg ggctggtgca cagaagtggc ccccaactgg 119160
tcagaaggtg tgggagccca gggctggtct actgcagaag ggtcgcctg gtggacagag 119220
tggggcctga gtgcctgctg aactggtccg tcagggctgc tgagcagaca cgggccatca 119280
tcactggctc ctgtgctcga tagaagggag ggaaaccagg aaagcaaagg cgctttatgg 119340
ccgcttttgt gtttcgcgtt cctctagcac cgtctgccgg cagaacgcgg cattacatcc 119400

-continued gctggccaaa cctcggggtc cggcttggat gtccccatcc ttgtctcgga gatctcacct 119460
ctcagcagtt cccctgggga caatgtcgag aagatgcgac cttgacccgg agctcggtgg 119520
agagggtgcc ctgggttctt tccgcagttg cttggagtgg aggtgcctca tgttgggctg 119580
ggaacgggag gaaggaaaca ggtcatgatt gagatgctct agacagactg tccctgctct 119640
tgccaaattt cagaagattg tctttaataa atattccatt ttttgtatgc ccttaggtct 119700
atttccagac actttaaata tattgaaaga ctttaaatat ttatataaaa atattattta 119760
tagactgtat aaaaggaaca gttagaactg gacttggaac aacagactgg ttccaaatag 119820
gaaaaggagt acgtcaaggc tgtatattgt caccctgctt atttaactta tatgcagagt 119880
acatcatgag aaacgctggg ctggaagaaa cacaagctgg aatcaagatt gccgggagaa 119940
atatcaataa cctcagatat gcagatgaca ccacccttat ggcagaaagt gaagaggaac 120000
tcaaaagcct cttgatgaag gtgaaagagg agagcgaaaa agttggctta aagctcaaca 120060
tttagaaaac gaagatcatg gcatctggtc ccatcacttc atggaaatag atggggaaac 120120
agttgagaca gtgtcagact ttatttttgg gggctccaat gaaattaaaa gacgcttact 120180
tcttggaagg aaagttatga ccaacctaga cagcatatta aaaagcagag acactacttt 120240
gccagcaaag gtccgtctag tcaaggctat ggtttttcca gtggtcatgt atggatgtga 120300
gagttggact gtgaagaagg ctgagcaccg aagaagtgat gcttttgaac tgtggtgttg 120360
gagaagactc ttgagaggcc cttggactgc aaggagatcc aaccagtcca tcgtaaagga 120420
gatcaccccc tgggtggtca ttggaaggac tgatgttgaa gctgaaactc cagtactttg 120480
gctacctaat gcgaagagct gactcattgg aaaagaccct gatgctggga aagattgaag 120540
gtgggaggag aaggggacaa cagaggatga gatggttgga ttgcatcact gactcgatgg 120600
acgtgagtct gagtgaagtc tgggagttgg tgatggccag ggaggccctg gcgtgctggc 120660
ggttcatggg gtcgcaaaga gtcggccatg actgagtgac tgaactgaac tgatccagaa 120720
atttaaaatt aatatataaa ccaaatccat gcagacaatt ataagcatat attataaatg 120780
cataattata agcaagtata tgttatattt ataatagttt ataatgtatt tataagcaag 120840
tatatattat tataagcata attgtaagta gaagtaactt tgggctttcc tggtggctca 120900
gacagtaaag aatctgcctg cagtacagga gaccgggttc gatccctggt ttggggaaat 120960
tccctggaga agggaatggc aaccaactcc aacatgtttg cctggagaat tccatggaca 121020
gaggagcccg gaaggttgca gtccatgggg ttgcaaagag ctggatacaa cagagtgact 121080
aacacatgta tataaataaa tttacctata tattgtatat atatttataa acatattcag 121140
atattataaa taattagaaa catattatac atgtatttaa atactgttat aaacataaat 121200
ttaaaaaata attttcagcc ctttggcttg ggggtgtgtt tgtggacgtc tttgtgctac 121260
tgttcctgaa gtggagctct cccctcccaa accagctttt gaaatgactg ggaaagcaat 121320
ggaatacata agcatcagga agatagcaac agagctgtca ttcttcacag agggtgtgct 121380
tgagtgtgta gcaagtcccg cagaatgtag acagattaat atagtctatt aaaaatagtg 121440
tagcaaattt acgaggtgcg atttcaagta taaagactta ctgggtctct cagttcagtt 121500
cagtcgcttg gttgtgtccg actctttttg accccatgga ccgcagcacg ccaggcctcc 121560
ctgtccatca ccaactcctg gagttcactc aaactcatgt ccatcgagtc ggtgatgcca 121620
tccaaccatc tcatcctctg gcgtcccctt ctcctcccac cttcaatctt tcccagcatc 121680
agggtctttc ccagtgagtc agttctttgc atcaggtggc cagagtagtg gagtttcagc 121740
ttcagcatcg gtccttccaa tgaatattct ggactgattt cctttaggat tgactggttg 121800
gatctccttg cagttcaagg gactctcaag agtcttctcc aacagcacag tctatgaata 121860
gaatagcaaa tgaatagaga ataacattta cgaggatata ttttaccatt gcataaaata 121920
tatcagcttg tagagaacag acttgttccc aggggagagg gtgggtaggg atggagtggg 121980
agtttgngat cancagaagc gagctgttat atagaagatg gataaaaagg atacacaaca 122040
atgtcctact gtgtggcacc gggacctata ttcagtagct tgtgagaaac cataatcgac 122100
aagactgagg aaaagtatat atatatgtat gtacttgagt tgctttgctg tacagaagaa 122160
attaacacaa cattgtaaat cgatatttca atagaatcca cccccccaaa tatataagtt 122220
tcctggagat ggagacggca acccactcca tttcttgcac ccaatattct tgcctggagg 122280
atcccatgga tagaggatcg caaagactcg gacataaccc agcgactaac actttccctt 122340
tcaaatgtgt aggtttacta gcgtgaatct acagagatgc ccaagacatt cgtttatgag 122400
gaaaactcca cacgcagctt cactgagaat tattaaacct attaaaggga gagagcgcca 122460
ggatattcat ggattgaaag attcgatgtg gtcaagttgc cagttttccc caaactgatt 122520
ggtaaattcc ccaggagctg gctcaaggcg caaaattccc tttacctttt tttaagagac 122580
gaagccaagg agccgattct ggttgagaga cgctcaggtc ctcctgcggg agagcagccc 122640
tcttcctccc ggtcgcctgg gcagtttcga ggccacgacc agaaggactt ggctccctgt 122700
gtcgcgcact cagaagtctc cctctccgtc ccaaggactc agaagctggg cgtcctgccc 122760
gcagcagagg aggcagcctg gaggggcccc gcgggcacag cggtccgggt ttcagccgag 122820
ttgcccgccc cgcccctcta cctgggcgct gccgcccggc tccggggccg gccgtgccct 122880
ccgtggccgc aaggcgtcgc tgtccccccg ctggaagtgc tgacccggag gaagggggccc 122940
agacggaggg actcggagcc tccgagtgac accctgggac tccgagcgct ggagcctggc 123000
gtcaccccag gcaggggcag tgggggcccg gggcggggtc aggggcctcc cccggttctc 123060
atttgacacc gcgggggtgc gctgggcaca gtgtccaggg gccacgttcc gagcaggggc 123120
gcgatgcagg cccgggcgcg gcctgtcccg ggcgcgagtc cagctgcttt gcagaggtgg 123180
cggcaggtcg cagtgaccct cacagagacg ccccactctg cggctccagg tgggcctgtg 123240
ccccccagaa gtgctgacct gtgcaccggg aaggcacagg gccccccagc catgtctgcg 123300
atggaagagc cggaaccgcg ccatgcccgt cctcgctgac cggcaggcac ccgccgtgtg 123360
tccacacgct gagccatctg gctccccttg cttgacatac acccaggacc tgagtgtgca 123420
ggaagttaga aggggcaggt gtggtgacac gatgccatcc agcatcacct gagaacctgg 123480
acaaacctca ggggcccagc ctgctctgtg aggccccgag ggccggcccc tccccggacc 123540
cctgccttga atccggccac actgcccgcc ttcctgctcc tgcggcttgt cagacacgcc 123600
tgagcccagg gcctgtgcac tcgctgtccc ttctgccagg actgctcctc cccaggctct 123660
tgctggggct ccccttcttc attcgggggt ggcctctctt gttcagtggc tcagctgtgc 123720
ccagtctttg caaccccatg gactgcagca cgccaggctt ccctgtcctt cactagctcc 123780
tggagtttgc tcaaactcat gtccattgag tcagtgatgc tatccaacca tctcatcctt 123840
tgctgcccac ttcttctcct gctctcaatc tttcccagca tcagggtctt ttccaatgag 123900
ttagctctct gcatcaggag gccaaagtat tggagcttca gcatcagtcc ttccagtgaa 123960
tatgcgaggt tgatttccct tagaattgac tggttggatc tccttcctgt ccagagaact 124020
ctcaagagtc ttctccagca ccacagtcgg agagcatcag ttcttcagtg atcaggtttc 124080
tttatagccc agctctcaca tcggtacatg actattggaa aacccatagc tttgattaga 124140
tggaccttca ttggcaaagt gatgggcctt cattggccct gctttttaat acaccatcta 124200
ggtttgtcgt agctttcctt ccaaagagca aacatctttt aatttcctgg ctgcagtaac 124260
catccatagt gattttggag cccaagaaaa taaaatctgc cactgtttcc actttttccc 124320
cttctatttg ctatgaagtg aggggactgg atgccatgat cttagtttaa accagcagtt 124380
gtcaccccga ccgcttcctt tcctaaagag ctcatcacac ctcccactgg aatgcaatgt 124440
gttgcctgtc cgcctgcttc acctcctggg actttgctgc aggtcttggt ctctgaggcc 124500
cctgccgtat ccccagggcc cagagcagtg ctgggcttcg agtccgatca gggactatgt 124560
gtgtggactg gatggtgctt gcttcttctg ggaacgaga gacctgggcc tggggaacga 124620
ggggacctgg tgtgaccgga tctcctccct cgggagagga gccaagcgag tggacacagg 124680
tcagtgtgtc ttgctcctgt gtggcaggtg tcccgtctgt gtctgtcatc ttggcatttc 124740
ggtgtttctg tgaacccagc ccctcccctc ctgataccc atcccatcag cacagaggag 124800
actgggcttg gggactctct ggtcctgaga ttcctctccg catgtgactc ccccctcctg 124860
gggggagcag gcaccgtgtg tgaggagggt ggaagctttt caagaccccc agcttttctg 124920
tcccaggggg ctctggcagg gccttgggag ctggaatgag ctggaatctg ggccagtggg 124980
ggtttccctg gtggtaaaga acccgcctgc ccatgcacga ggcataagag acgcgggttc 125040
gatcactggg tcgggaagat cccctacagg agggcatggc aacccactcc agtattcttt 125100
cctgaagaat cccttggaca gaggagcctg gtgggctaca gtctctgggg tggcaaggag 125160
tcggacacga ctgaagcgac ttaccatgca cgcacgcggg gtcaggggtc agggccgcgc 125220
tgcttacctg ctgtgtgacc ttagccaggt cacaccccc aggctgtgaa agagaacagt 125280
cttcccagac tcgggcatcc aggtctttac agacgtgcct gtgagctttg tgactctggc 125340
tctgtggccg ctagagggcg ctgtccgccg ggccctatgt gcgtgcacgc atgtgagcat 125400
gttcgcatac gtgtgtgcat ctgtcggggg cgcacggtgc ggggacacgg gcacgcggtc 125460
aggaacgcag cccggacacc tccacgtggc ccgcgagtac cgtcaggtgg gggctgtggc 125520
tccgctgtgt gggtgacccg ccctcccccc gcgaacgtgg tgcatagtga ccgcctggct 125580
gggctcctga gctcagccat cctgccccc gggtcagctc ccgacaggcc cagctctagg 125640
ccccaggcgt ggaccgaggc ccccaggccc cggcctgtga gatgggacct ccgtctgggg 125700
ggctcattct gctcccggag gcctggcagg cccctcctct ttggcattgc ataccctcgc 125760
attggggtgg gtaagcacag taccccatgc ctgtggcccc gtgggagcgg cctgctcagg 125820
gaggccggag cctcagctac agggctgtca caccgggctg cagaggaaga agacgggagc 125880
gaggcctaca ggaacctagc caggccctgg cccactgagc cgacaggagc ctggccagag 125940
gcctgcacag gacggggtgg cggggggggt ggggtggggt gctgggcccc gtggccttga 126000
ctgcagaccc cgagggctcc tcagcttaga acggccaagc ctgagtcttg ggggtgcagg 126060
tcaggggg 126068

<210> SEQ ID NO 32
<211> LENGTH: 10012
<212> TYPE: DNA
<213> ORGANISM: Sus sp.

<400> SEQUENCE: 32
gccacgccca ctccatcatg cggggagggg atgggcagac cctccagaaa gaagctccct 60
ggggtgcagg ttaacagctt tcccagacac agccagtact agagtgaggt gaataagaca 120
tcctccttgc ttgtgaaatt taggaagtgc ccccaaacat cagtcattaa gataaataat 180

-continued

```
attgaatgca cttttttttt tttatttttt ttttttgctt tttagggcct aatctgcagc    240
atatggaagt tcccaggcta caagtcgaac cagagctgca gctgccagcc tacatcacag    300
ccacagcaac accagatccg agccacatct gtgactaaca ctgcagttca cagcaacgcc    360
agatccttaa cccattgagt gaggccaggg atcaaaccca catcctcatg gatactagtc    420
tggttcgtaa accactgagc cacaagggga actcctgaat gcaatatttt tgaaaattga    480
aattaaatct gtcactcttt cacttaagag tcccccttaga ttggggaaaa tttaaatatc    540
tgtcatctta gtgcatcttt gctcatatga tgtgaataaa atcccaaaat ccatatgaat    600
gaagcatcaa aatgtacatg aagtcagcct gaccctgcac tgccctcact tgcctcatgt    660
accccccacc tcaaaggaag atgcagaaag gagtccagcc cctacaccgc cacctgcccc    720
caccactgga gcccctcagg tctcccacct cctttctga gcttcagtct tcctgtggca    780
ttgcctacct ctacagctgc cccctactag gccctccccc tggggctgag ctccaggcac    840
tggactggga aagttagagg ttaaagcatg gaaaattccc aaagccacca gttccaggct    900
gccccccacc ccaccgccac gtccaaaaag gggcatcttc ccagatctct ggctggtatt    960
ggtaggaccc aggacatagt ctttatacca attctgctgt gtgtcttagg aaagaaactc   1020
tccctctctg tgcttcagtt tcctcatcaa taaaaggagc aggccaggtt ggagggtctg   1080
tgacgtctgc tgaagcagca ggattctctc tccttttgct ggaggagaac tgatccttca   1140
cccccaggat caacagagaa gccaaggtct tcagccttcc tggggacccc tcagagggaa   1200
ctcagggcca cagagccaga ccctgatgcc agaacctttg tcatatgccc agacggagac   1260
ttcatccccc tcctcctcag accctccagg ccccaacagt gagatgctga agatattaag   1320
agaagggcaa gtcagcttaa gtttgggggt agaggggaac agggagtgag gagatctggc   1380
ctgagagata ggagccctgg tggccacagg aggactcttt gggtcctgtc ggatggacac   1440
agggcggccc gggggcatgt tggagcccgg ctggttctta ccagaggcag gggcaccct   1500
ctgacacggg agcagggcat gttccataca tgacacaccc ctctgctcca gggcaggtgg   1560
gtggcggcac agaggagcca gggactctga gcaaggggtc caccagtggg gcagttggat   1620
ccagacttct ctgggccagc gagagtctag ccctcagccg ttctctgtcc aggagggggg   1680
tggggcaggc ctgggcggcc agagctcatc cctcaagggt tcccagggtc ctgccagacc   1740
cagatttccg accgcagcca ccacaagagg atgtggtctg ctgtggcagc tgccaagacc   1800
ttgcagcagg tgcagggtgg gggggtgggg gcacctgggg gcagctgggg tcactgagtt   1860
cagggaaaac ccctttttc ccctaaacct ggggccatcc ctaggggaaa ccacaacttc   1920
tgagccctgg gcagtggctg ctgggaggga agagcttcat cctggaccct ggggggggaac  1980
ccagctccaa aggtgcaagg ggcccaggtc caaggctaga gtgggccaag caccgcaatg   2040
gccagggagt gggggaggtg gagctggact ggatcagggc ctccttggga ctccctacac   2100
cctgtgtgac atgttaggt acccacaccc catcaccagt cagggcctgg cccatctcca   2160
gggccaggga tgtgcatgta agtgtgtgtg agtgtgtgtg tgtggtgtag tacacccctt   2220
ggcatccggt tccgaggcct tgggttcctc caaagttgct ctctgaatta ggtcaaactg   2280
tgaggtcctg atcgccatca tcaacttcgt tctccccacc tcccatcatt atcaagagct   2340
ggggagggtc tgggatttct tcccacccac aagccaaaag ataagcctgc tggtgatggc   2400
agaagacaca ggatcctggg tcagagacaa aggccagtgt gtcacagcga gagaggcagc   2460
cggactatca gctgtcacag agaggcctta gtccgctgaa ctcaggcccc agtgactcct   2520
```

-continued gttccactgg gcactggccc ccctccacag cgcccccagg ccccagggag aggcgtcaca 2580
gcttagagat ggccctgctg aacagggaac aagaacaggt gtgccccatc cagcgcccca 2640
ggggtgggac aggtgggctg gatttggtgt gaagcccttg agccctggaa cccaaccaca 2700
gcagggcagt tggtagatgc catttgggga gaggccccag gagtaagggc catgggccct 2760
tgagggggcc aggagctgag gacagggaca gagacggccc aggcagagga cagggccatg 2820
aggggtgcac tgagatggcc actgccagca ggggcagctg ccaacccgtc cagggaactt 2880
attcagcagt cagctggagg tgccattgac cctgagggca gatgaagccc aggccaggct 2940
aggtgggctg tgaagacccc aggggacaga gctctgtccc tgggcagcac tggcctctca 3000
ttctgcaggg cttgacggga tcccaaggcc tgctgcccct gatggtagtg gcagtaccgc 3060
ccagagcagg accccagcat ggaaacccca acgggacgca gcctgcggag cccacaaaac 3120
cagtaaggag ccgaagcagt catggcacgg ggagtgtgga cttccctttg atggggccca 3180
ggcatgaagg acagaatggg acagcggcca tgagcagaaa atcagccgga ggggatgggc 3240
ctaggcagac gctggcttta tttgaagtgt tggcattttg tctggtgtgt attgttggta 3300
ttgattttat tttagtatgt cagtgacata ctgacatatt atgtaacgac atattattat 3360
gtgttttaag aagcactcca agggaacagg ctgtctgtaa tgtgtccaga gaagagagca 3420
agagcttggc tcagtctccc ccaaggaggt cagttcctca acaggggtcc taaatgtttc 3480
ctggagccag gcctgaatca agggggtcat atctacacgt ggggcagacc catggaccat 3540
tttcggagca ataagatggc agggaggata ccaagctggt cttacagatc cagggctttg 3600
acctgtgacg cgggcgctcc tccaggcaaa gggagaagcc agcaggaagc tttcagaact 3660
ggggagaaca gggtgcagac ctccagggtc ttgtacaacg caccctttat cctggggtcc 3720
aggaggggtc actgagggat ttaagtgggg gaccatcaga accaggtttg tgttttggaa 3780
aaatggctcc aaagcagaga ccagtgtgag gccagattag atgatgaaga agaggcagtg 3840
gaaagtcgat gggtggccag gtagcaagag ggcctatgga gttggcaagt gaatttaaag 3900
tggtggcacc agagggcaga tggggaggag caggcactgt catggactgt ctatagaaat 3960
ctaaaatgta taccctttt agcaatatgc agtgagtcat aaaagaacac atatatattt 4020
aaattgtgta attccacttc taaggattca tcccaagggg ggaaaataat caaagatgta 4080
accaaaggtt tacaaacaag aactcatcat taatcttcct tgttgttatt tcaacgatat 4140
tattattatt actattatta ttattattat tttgtctttt tgcattttct agggccactc 4200
ccacggcata gagaggttcc caggctaggg gtcaaatcgg agctacagct gccggcctac 4260
gccagagcca cagcaacgca ggatctgagc cacagcaatg caggatctac accacagctc 4320
atggtaacgc tggatcctta acccaatgag tgaggccagg gatcgaacct gtaacttcat 4380
ggttcctagt cggattcatt aaccactgag ccacgacagg aactccaaca ttattaatga 4440
tgggagaaaa ctggaagtaa cctaaatatc cagcagaaag ggtgtggcca aatacagcat 4500
ggagtagcca tcataaggaa tcttacacaa gcctccaaaa ttgtgtttct gaaattgggt 4560
ttaaagtacg tttgcatttt aaaaagcctg ccagaaaata cagaaaaatg tctgtgatat 4620
gtctctggct gataggattt tgcttagttt taattttggc tttataattt tctatagtta 4680
tgaaaatgtt cacaagaaga tatatttcat tttagcttct aaaataatta taacacagaa 4740
gtaatttgtg ctttaaaaaa atattcaaca cagaagtata taaagtaaaa attgaggagt 4800
tcccatcgtg gctcagtgat taacaaaccc aactagtatc catgaggata tggatttgat 4860
ccctggcctt gctcagtggg ttgaggatcc agtgttgctg tgagctgtgg tgtaggttgc 4920

-continued

```
agacacagca ctctggcgtt gctgtgactc tggcgtaggc cggcagctac agctccattt   4980
ggacccttag cctgggaacc tccatatgcc tgagatacgg ccctaaaaag tcaaaagcca   5040
aaaaaatagt aaaaattgag tgtttctact taccacccct gcccacatct tatgctaaaa   5100
cccgttctcc agagacaaac atcgtcaggt gggtctatat atttccagcc ctcctcctgt   5160
gtgtgtatgt ccgtaaaaca cacacacaca cacacacacg cacacacaca cacacgtatc   5220
taattagcat tggtattagt ttttcaaaag ggaggtcatg ctctaccttt taggcggcaa   5280
atagattatt taaacaaatc tgttgacatt ttctatatca acccataaga tctcccatgt   5340
tcttggaaag gctttgtaag acatcaacat ctgggtaaac cagcatggtt tttagggggt   5400
tgtgtggatt tttttcatat tttttagggc acacctgcag catatggagg ttcccaggct   5460
aggggttgaa tcagagctgt agctgccggc ctacaccaca gccacagcaa cgccagatcc   5520
ttaacccact gagaaaggcc agggattgaa cctgcatcct catggatgct ggtcagattt   5580
atttctgctg agccacaaca ggaactccct gaaccagaat gcttttaacc attccacttt   5640
gcatggacat ttagattgtt tccatttaaa aatacaaatt acaaggagtt cccgtcgtgg   5700
ctcagtggta acgaattgga ctaggaacca tgaggtttcg ggttcgatcc ctggccttgc   5760
tcggtgggtt aaggatccag cattgatgtg agatatggtg taggtcgcag acgtggctcg   5820
gatcccacgt tgctgtggct ctggcgtagg ccggcaacaa cagctccgat tcgaccccta   5880
gcctgggaac ctccatgtgc cacaggagca gccctagaaa aggcaaaaag acaaaaaaat   5940
aaaaaattaa aatgaaaaaa taaaataaaa atacaaatta caagagacgg ctacaaggaa   6000
atccccaagt gtgtgcaaat gccatatatg tataaaatgt actagtgtct cctcgcggga   6060
aagttgccta aaagtgggtt ggctggacag agaggacagg ctttgacatt ctcataggta   6120
gtagcaatgg gcttctcaaa atgctgttcc agtttacact caccatagca aatgacagtg   6180
cctcttcctc tccacccttg ccaataatgt gacaggtgga tctttttcta ttttgtgtat   6240
ctgacaagca aaaaatgaga acaggagttc ctgtcgtggt gcagtggaga caaatctgac   6300
taggaaccat gaaatttcgg gttcaatccc tggcctcact cagtaggtaa aggatccagg   6360
gttgcagtga gctgtggggt aggtcgcaga cacagtgcaa atttggccct gttgtggctg   6420
tggtgtaggc cggcagctat agctccaatt ggacccctag cctgggaacc tccttatgcc   6480
gtgggtgagg ccctaaaaaa aagagtgcaa aaaaaaaaaa taagaacaaa aatgatcatc   6540
gtttaattct ttatttgatc attggtgaaa cttattttcc ttttatattt ttattgactg   6600
attttatttc tcctatgaat ttaccggtca tagttttgcc tgggtgtttt tactccggtt   6660
ttagttttgg ttggttgtat tttcttagag agctatagaa actcttcatc tatttggaat   6720
agtaattcct cattaagtat ttgtgctgca aaaaattttc cctgatctgt tttatgcttt   6780
tgtttgtggg gtctttcacg agaaagcctt tttagttttt acacctcagc ttggttgttt   6840
ttcttgattg tgtctgtaat ctgcggccaa cataggaaac acatttttac tttagtgttt   6900
ttttcctatt ttcttcaagt acgtccattg ttttggtgtc tgattttact ttgcctgggg   6960
tttgtttttg tgtggcagga atataaactt atgtattttc caaatggaga gccaatggtt   7020
gtatatttgt tgaattcaaa tgcaacttta tcaaacacca aatcatcgat ttatcacaac   7080
tcttctctgg tttattgatc taatgatcaa ttcctgttcc acgctgtttt aattatttta   7140
gctttgtgga ttttggtgcc tggtagagaa caaagcctcc attattttca ttcaaaatag   7200
tcccgtctat tatctgccat tgttgtagta ttagacttta aaatcaattt actgattttc   7260
```

-continued

```
aaaagttatt cctttggtga tgtggaatac tttatacttc ataaggtaca tggattcatt   7320
tgtggggaat tgatgtcttt gctattgtgg ccatttgtca agttgtgtaa tattttaccc   7380
atgccaactt tgcatattgt atgtgagttt attcccaggg tttttaatag gatgtttatt   7440
gaagttgtca gtgtttccac aatttcatcg cctcagtgct tactgtttgc ataaaaggaa   7500
acctactcac ttttgcctat tgctcttgta ttcaatcatt ttagttaact cttgtgttaa   7560
ttttgagagt ttttcagctg actgtctggg gttttcttta atagactagc cctttgtctg   7620
taaagaataa ttttatcgaa tttttcttaa cactcacact ctccccaccc ccaccccgc    7680
tcatctcctt tcattgggtc aaatctgtag aatacaataa aagtaagagt gggaacctta   7740
gcctttaagt cgattttgcc tttaaatgtg aatgttgcta tgtttcggga cattctcttt   7800
atcaagttgc ggatgtttcc ttagataatt aacttaataa aagactggat gtttgctttc   7860
ttcaaatcag aattgtgttg aatttatatt gctattctgt ttaattttgt ttcaaaaaat   7920
ttacatgcac accttaaaga taaccatgac caaatagtcc tcctgctgag agaaaatgtt   7980
ggccccaatg ccacaggtta cctcccgact cagataaact acaatgggag ataaaatcag   8040
atttggcaaa gcctgtggat tcttgccata actctcagag catgacttgg gtgtttttc    8100
cttttctaag tattttaatg gtatttttgt gttacaatag gaaatctagg acacagagag   8160
tgattcaatg aggggaacgc attctgggat gactctaggc ctctggtttg gggagagctc   8220
tattgaagta aagacaatga gaggaagcaa gtttgcaggg aactgtgagg aatttagatg   8280
gggaatgttg ggtttgaggt ttctataggg cacgcaagca gagatgcact caggaggaag   8340
aaggagcata aatctagagg caaaaagaga ggtcaggact ggaaatagag atgcgagaca   8400
ccagggtggc agtcagagag cacagtgtgg gtcagaagac agtggaagaa cacaaggac    8460
agagagggat ctccaacttc actgggatga gggccttgtt ggccttgacc tgagagattt   8520
ccaggagttg agggtgggaa ggagagggct cctgcacatg tcctgacatg aaacggtgcc   8580
cagcatatgg gtgcttggaa gacattgttg gacagatgga tggatgatgg atgatggatg   8640
aatggatgga tggaagatga tggataaatg gatgatggat ggatggacag aaggacaaag   8700
agatggacag aaagacagtg atctgagaga gcagagaagg cttcatgaaa ggacaggaac   8760
tgaactgtct cagtgggtgg agacaatggt gtagggggtt tccacatgga ggcaccaggg   8820
gtcaggaata atctagtgtc cacaggccca ggaaggaagc tgtctgcagg aaattgtggg   8880
gaagaacctc agagtcctta aatgaggtca ggagtggtca ggagggtctg atcaggtaag   8940
gactcatgtc catcatcaca tggtcaccta agggcatgta gctctcagca tctccatcag   9000
gacagtctca gaatgggggc ggggtcacac actgggtgac tcaaggcgtg ggtcatgcct   9060
gcctcggacg tgggcctggg catggggaca cctccagacc atgggcccgc ccagggctgc   9120
actggcctct ggtgggctag ctacccgtcc aagcaacaca ggacacagcc ctacctgctg   9180
caaccctgtg cccgaaacgc ccatctggtt cctgctccag cccggcccca gggaacagga   9240
ctcaggtgct agcccaatgg ggttttgttc gagcctcagt cagcgtggta tttctccggc   9300
agcgagactc agttcaccgc cttaggttaa gtggttctca tgaatttcct agcagtcctg   9360
cactctgcta tgccgggaaa gtcacttttg tcgctggggg ctgtttcccc gtgcccttgg   9420
agaatcaagg attgcccaac tttctctgtg gggaggtgg  ctggtcttgg ggtgaccagc   9480
aggaagggcc ccaaaagcag gagcagctgc ctccagaata caactgtcgg ctacagctca   9540
aacaggaggc ctggactggg gtttaaccac cagggcggca cgaaggagcg aggctgggag   9600
ggtgaggaca tgggagcctg aggaggagct ggagacttca gcaggccccc agctccgggc   9660
```

ttcgggctct gagatgctcg gacgcaaggt gagtgacccc acctgtggct gacctgacct 9720
cagggggaca aggctcagcc tgagactctg tgtccccatc gcctgcacag gggattcccc 9780
tgatggacac tgagccaacg acctcccgtc tctccccgac ccccaggtca gcccaaggcc 9840
gcccccacgg tcaacctctt cccgccctcc tctgaggagc tcggcaccaa caaggccacc 9900
ctggtgtgtc taataagtga cttctacccg aagggcgaat tccagcacac tggcggccgt 9960
tactagtgga tccgagctcg gtaccaagct tgatgcatag cttgagtatc ta 10012

<210> SEQ ID NO 33
<211> LENGTH: 4614
<212> TYPE: DNA
<213> ORGANISM: Sus sp.

<400> SEQUENCE: 33
agatctttaa accaccgagc aaggccaggg atcgaacccg catcctcatg aatcctagtt 60
gggttcgtta accgctgaac cacaatggga actcctgtct ttcacattta attcacaacc 120
tctccaggat tctgggggtg ggtggggaat cctaggtacc cactgggaaa gtaatccaag 180
gggagaggct cacggactct agggatcggc ggaggaggga aggtatctcc caggaaactg 240
gccaggacac attggtcctc cgccctcccc ttcctcccac tcctcctcca gacaggactg 300
tgcccacccc ctgccacctt tctggccaga actgtccatg gcaggtgacc ttcacatgag 360
cccttcctcc ctgcctgccc tagtgggacc ctccatacct ccccctggac cccgttgtcc 420
tttctttcca gtgtggccct gagcataact gatgccatca tgggctgctg acccacccgg 480
gactgtgttg tgcagtgagt cacttctctg tcatcagggc tttgtaattg atagatagtg 540
tttcatcatc attaggaccg ggtggcctct atgctctgtt agtctccaaa cactgatgaa 600
aaccttcgtt ggcatagtcc cagcttcctg ttgcccatcc ataaatcttg acttagggat 660
gcacatcctg tctccaagca accacccctc ccctaggcta actataaaac tgtcccaatg 720
gcccttgtgt ggtgcagagt tcatgcttcc agatcatttc tctgctagat ccatatctca 780
ccttgtaagt catcctataa taaactgatc cattgattat ttgcttctgt tttttccatc 840
tcaaaacagc ttctcagttc agttcgaatt ttttattccc tccatccacc catactttcc 900
tcagcctggg gaacccttgc ccccagtccc atgcccttcc tccctctctg cccagctcag 960
cacctgccca ccctcaccct tcctgtcact ccctaggact ggaccatcca ctggggccag 1020
gacactccag cagccttggc ttcatgggct ctgaaatcca tggcccatct ctattcctca 1080
ctggatggca ggttcagaga tgtgaaaggt ctaggaggaa gccaggaagg aaactgttgc 1140
atgaaaggcc ggcctgatgg ttcagtactt aaataatatg agctctgagc tccccaggaa 1200
ccaaagcatg gagggagtat gtgcctcaga atctctctga gattcagcaa agcctttgct 1260
agagggaaaa tagtggctca accttgaggg ccagcatctt gcaccacagt taaaagtggg 1320
tatttgtttt acctgaggcc tcagcattat gggaaccggg ctctgacaca aacacaggtg 1380
cagcccggca gcctcagaac acagcaacga ccacaagctg ggacagctgc ccctgaacgg 1440
ggagtccacc atgcttctgt ctcgggtacc accaggtcac catccctggg ggaggtagtt 1500
ccatagcagt agtcccctga tttcgcccct cgggcgtgta gccaggcaag ctcctgcctc 1560
tggacccagg gtggaccctt gctccccact accctgcaca tgccagacag tcaagaccac 1620
tcccacctct gtctgaggcc cccttgggtg tcccagggcc cccgagctgt cctctactca 1680
tggttcttcc acctgggtac aaaagaggcg agggacactt ttctcaggtt tgcggctcag 1740

-continued

```
aaaggtacct tcctagggtt tgtccactgg gagtcacctc ccttgcatct caatgtcagt   1800
ggggaaaact gggtcccatg gggggattag tgccactgtg aggcccctga agtctggggc   1860
ctctagacac tatgatgatg agggatgtgg tgaaaaaccc caccccagcc cttcttgccg   1920
ggaccctggg ctgtggctcc cccattgcac ttggggtcag aggggtggat ggtggctatg   1980
gtcaggcatg tttcccatga gctgggggca ccctgggtga ctttctcctg tgaatcctga   2040
attagcagct ataacaaatt gcccaaactc ttaggcttaa aacaacacac atttattcct   2100
ctgggtccca gggtcagaag tccaaaatga gtcctatagg ctaaatttga ggtgtctctg   2160
ggttgagctc ctcctggaag ccttttccag cctctagagt cccaagtcct tggctctggg   2220
cccctccctc aagcttcaaa gccacagaag cttctaatct ctctcccttc ccctctgacc   2280
tctgctccca tcctcatacc ctgtcccctc actctgaccc tcctgcctcc ctctttccct   2340
tataaagacc ctgcatgggg ccacggagat aatccagggt aatcgcccct cttccagccc   2400
ttaactccat cccatctgca aaatccctgt caccccataa tggacctact gatggtctgg   2460
gggttaggac gtggacaact tggggcctta ttcatctgat cacaactcca gttcccagac   2520
ccccagaccc ccgggcatta gggaaacttc tcccagttcc tctccctctg tgtcctgccc   2580
agtctccagg atgggccact cccgagggcc cttcagctca ggctcccccct cctttctccc   2640
tggcctcttg tggccccatc tcctcctccg ctcacaggga gagaactttg atttcagctt   2700
tggctctggg gctttgcttc cttctggcca ttggctgaag ggcgggtttc tccaggtctt   2760
acctgtcagt catcaaaccg cccttggagg aagaccctaa tatgatcctt accctacaga   2820
tggagactcg aggcccagag atcctgagtg acctgctcac attcacagca gggactgaac   2880
cccagtcacc tacccaactc cagggctcag cgcttttttt tttttttttc tttttgcctt   2940
ttcgagggcc gctcccgcaa catatggaga tttccaggct aggggtctaa ttggagcagt   3000
cgacactggc ctaagccaaa gccacagcaa caagggcaag ccgcttctgc agcctatacc   3060
acagctcacg gcaatgccgg atccttaacc cactgagcaa agccagggat tgaacctgca   3120
acctcatgtt tcctagtcaa atttgttaac cactgaccca tgacgggaac tcccagggct   3180
cagctcttga ctccaggttc gcagctgccc tcaaagcaat gcaaccctgg ctggccccgc   3240
ctcatgcatc cggcctcctc cccaaagagc tctgagccca cctgggccta ggtcctcctc   3300
cctgggactc atggcctaag ggtacagagt tactggggct gatgaaggga ccaatgggga   3360
caggggcctc aaatcaaagt ggctgtctct ctcatgtccc ttcctctcct cagggtccaa   3420
aatcagggtc agggccccag ggcaggggct gagagggcct ctttctgaag gccctgtctc   3480
agtgcaggtt atgggggtct gggggagggt caatgcaggg ctcacccttc agtgccccaa   3540
agcctagaga gtgagtgcct gccagtggct tcccaggccc aatcccttga ctgcctggga   3600
atgctcaaat gcaggaactg tcacaacacc ttcagtcagg ggctgctctg ggaggaaaaa   3660
cactcagaat tgggggttca gggaaggccc agtgccaagc atagcaggag ctcaggtggc   3720
tgcagatggt gtgaacccca ggagcaggat ggccggcact ccccccagac cctccagagc   3780
cccaggttgg ctgccctctt cactgccgac acccctgggt ccacttctgc cctttcccac   3840
ctaaaacctt tagggctccc actttctccc aaatgtgaga catcaccacg gctcccaggg   3900
agtgtccaga agggcatctg gctgagaggt cctgacatct gggagcctca ggccccacaa   3960
tggacagacg ccctgccagg atgctgctgc agggctgtta gctaggcggg gtggagatgg   4020
ggtactttgc ctctcagagg ccccggcccc accatgaaac ctcagtgaca ccccatttcc   4080
ctgagttcac atacctgtat cctactccag tcaccttccc cacgaacccc tgggagccca   4140
```

```
ggatgatgct ggggctggag ccacgaccag cccacgagtg atccagctct gccaatcagc   4200

agtcatttcc caagtgttcc agccctgcca ggtcccacta cagcagtaat ggaggcccca   4260

gacaccagtc cagcagttag agggctggac tagcaccagc tttcaagcct cagcatctca   4320

aggtgaatgg ccagtgcccc tccccgtggc catcacagga tcgcagatat gaccctaggg   4380

gaagaaatat cctgggagta aggaagtgcc catactcaag gatggcccct ctgtgaccta   4440

acctgtccct gaggattgta cttccaggcg ttaaaacagt agaacgcctg cctgtgaacc   4500

cccgccaagg gactgcttgg ggaggccccc taaaccagaa cacaggcact ccagcaggac   4560

ctctgaactc tgaccaccct cagcaagtgg caccccccgc agcttccaag gcac         4614
```

<210> SEQ ID NO 34
<211> LENGTH: 1151
<212> TYPE: DNA
<213> ORGANISM: Sus sp.

<400> SEQUENCE: 34

```
aacaagatgc taccccacca acaaaattca ccggagaaga caaggacagg gggttcctgg     60

ggtcctgaca gggtcaccaa agagggttct ggggcagcag caactccagc cgcctcagaa    120

cagagcctgg aagctgtacc ctcagagcag aggcggagag agaaagggcc tcttggtggg    180

tcagcaggag cagaggctca gaggtggggg ttgcagcccc cccttcaaca ggccaacaca    240

gtgaagcagc tgacccctcc accttggaga ccccagactc ctgtctccca cgccaccttg    300

gtttttaagg taatttttat tttatatcag agtatggttg acttacaatg ttgtgttggt    360

ttcaggtgta cagcagagtg attcacttct acatagactc atatctattc tttctcagat    420

tcttttccca tataggttat tacagaatat tgagtagatc cctgctgatt acccattttt    480

ataattgtat atgttaatcc caaactccta atttatccct ccccagacta tgattcttta    540

tatctctatc tgtttcctaa tctgtctcct ctaagtcacc ctaggagagc agaggggtca    600

cgtctgtcct gtcctggccc agccacctct ctccacccag gaatcccttg catttggtgc    660

caagggcccg gccccgccct aaagagaaag gagaacggga tgtggacagg acaccgggca    720

gagagggaca agcagaggat gccagggtag ggaggtctcc agggtggatg gtggtctgtc    780

cgcaggcagg atgaggcagg aagggtgtgg atgtactcgg tgaggctggc gcatggcctg    840

gagtgtcctg agccctggga ggcctcagcc ctggatcaga tctgtgattc caaagggcca    900

ctgcatccag agaccgttga gtggcccatt gtcctgaacc atttatagaa cacaggacaa    960

gcggtacctg actaagctgc tcacagattc catgaggctg atgccagggt tgtcacccca   1020

tctcacaggc agggaaactg atgcatatac tgcagagcca ggcagaggcc ctcccagtgc   1080

cccctcccag cctgtggccc ccctccagtg gctggacact gaggccacac tggggcaccc   1140

tgtggagatc t                                                        1151
```

<210> SEQ ID NO 35
<211> LENGTH: 630
<212> TYPE: DNA
<213> ORGANISM: Sus sp.

<400> SEQUENCE: 35

```
agatctggcc aggccagaga agcccatgtg gtgacctccc tccatcactc cacgccctga     60

cctgccaggg agcagaaagt aggcccaggg tggacccggt ggccacctgc caccccatgg    120

ctgggagaag ggagggcctg ggcaaagggc ctgggaagcc tgtggtggga ccccagaccc    180
```

cagggtggac agggagggtc ccacacccac agccatttgc ttccctctgt gggttcagtg 240
tcctcatctc atctgtgggg agggggctga taatgaatct cccccattgg ggtgggcttg 300
gggattaaag ggccagtgtc tgtgatatgc ctggaccata gtgaccctca ccctccccag 360
ccattgctgt caccttccgg gctcttgccc aggcctgcct gacatgctgt gtgaccctgg 420
gcaagatgat ccccctttct gggccccagc cttcctctct gctccggaag tgcttcctgg 480
ggaaacctgt gggctggatc ctataggaaa cctgtccaat tcctggatgc acagaggggc 540
agggaggccc tgggcctgga ggggcaggga ggctcgaggt gggagcaggg taggggccag 600
tccagggcaa ggaggtgggt gggtagggtg 630

<210> SEQ ID NO 36
<211> LENGTH: 947
<212> TYPE: DNA
<213> ORGANISM: Sus sp.

<400> SEQUENCE: 36
gatctgtgtt ccatctcaga gctatcttag cagagaggtg caggggcctc cagggccacc 60
aaagtccagg ctcagccaga ggcaatgggg tatcgatgag ctacaggaca caggcgtcag 120
cccagtgtca gggagaatca ccttgtttgt tttctgagtt cctcttaaaa tagagttaat 180
tggtcttggc cttacggttt acaataacaa ctgcaccctg taaacaacgt gaagagtaca 240
gaacaacaaa tgggggaaaa catatttcac ctgaaagagc caccgctcat attttgatgg 300
atttccttct agtttaatcc tgttttaatt gtaaactgtt aaaacaaaca taaataaaga 360
aaatgcatct gtaaagttta aaagtcatat ctatggtgat ggttgcaaaa cactgtgaat 420
gttcactttg aaatcgtgaa ctctacgtga tatgcatgtc ccgttaatta acctcacagg 480
ctcagaatgt ggttcattat ttctttaatt ttcctttaat tttatgtcct ctgtgtgtgc 540
ccttaaacca actacttttc agctctgcct gtttttgacc ttcacataga tgacatttgt 600
gagtgttttc tttctcaaca ctgggtctga tacccaccca cgctgtctgc tgtcactgcg 660
gacgtggagg gccaccaccc agctatggcc ccagccaggc caacactgga tgaatctgcc 720
cccagagcag ggccaccaac actggaggtg cagagagggt ttcttcaggg ccatcattat 780
ccaaggcatt gtttctactg taagctttca aaatgcttcc cctgattatt aaaagaaata 840
ataagatggg gggaaagtac aagaagggaa gtttccagcc cagcctgaag atcgtgctgg 900
ttgtatctgg agcctgtctt cctgacaggc ctctattccc agagtta 947

<210> SEQ ID NO 37
<211> LENGTH: 2067
<212> TYPE: DNA
<213> ORGANISM: Sus sp.

<400> SEQUENCE: 37
ggatcctagg gaagggaggg cgggggcctg gacaaagggg gcctaaagga cattctcacc 60
tatcccactg gacccctgct gtgctctgag ggagggagca gagaggggt ctgaggcctt 120 ttcccagctc ctctgagtcc ctcctccgag cacctggacg gaagcccctc ctcagggagt 180
cctcagaccc ctcccctcca gccaggttgg cctgtgtgga gtccccagta agaatagaat 240
gctcagggct tcgagctgag ccctggctac ttgggggggt gctggggatt gggggtgctg 300
ggcggggagc tggggtgtca ctagatgcca gtaggctgtg ggctcgggtc tggggggtct 360
gcacatgtgc agctgtggga aggccctatt ggtggtaccc tcagacacat atggcccctc 420
aatttctgag accagagacc ccagtctggc cttcccagaa cagctgcccc tggtggggga 480

```
gatgtagggg ggccttcagc ccaggacccc caacggcagg gcctgaggcc cccatcccct    540

tgtcctgggc ccagagcctc agctatcagg cctatcagag atcctggctg cccagctcag    600

gttccccagg agccagaggg aggccagggg ttactaggaa atccggaaag ggtctttgag    660

gctgggcccc accctctcag ctttcacagg agaaacagag gcccacaggg ggcaaaggac    720

ttgccagact cacaatgagc ccagcagctg gactcaaggc ccagtgttcg gccccacaac    780

agcactcacg tgcccttgat cgtgaggggc cccctctcag ccaggcattc agacctgtga    840

cctgcatcta agattcagca tcagccattc tgagctgaag agccctcagg gtctgcagtc    900

aaggccacag ggccagacct ccaacggcca gacatcccag ccagattcct ttctggtcaa    960

tgggccccag tctggcttgg ctcctgcagg cccagtgccg ccttcttccc ctgggcctgt   1020

ggagtccagc ctttcagttt cccacccaca tcctcagcca caatccaggc tcagaggcaa   1080

tgtccgtggg cagcccctgt gtgacccctc tgtgggtgat cctcagtcct acccttagca   1140

gacagcgcat gaggggccct cttgaacctg agggatactc catgtcggag gggagaagct   1200

ggccttcccc acccccactt ccaggccttg gggagcagag aaagacccca gacctgggtc   1260

ccttctaaca ggccaggccc cagcccagct ctccaccagc cccaggggcc tcgggtccac   1320

gcctggggac tggagggtgg gcctgtcagg cgctgaccca gaggcaggac agccaagttc   1380

aggatcccag ccaggtggtc cccgtgcacc atgcaggggt gtcacccaca caggggtgtt   1440

gccaccctca cctgactgtc ctcatgggcc acatggaggt atcctgggtt cattactggt   1500

caacataccc gtgtccctgc agtgccccct ctggcgcacg cgtgcacgcg cacacgcaca   1560

cactcataca gaggctccag ccaacagtgc cctctagtag gcactgctgt cacttctcta   1620

aaaggtcgca atcatacttg taaagaccca agattgttca gaaatcccag atggagaagt   1680

ctggaaagat ctttttctcc tttcacgggc tggggaaatg tgacctggcc aaggtcacac   1740

agcaagtggt ggaaccctgg cccctgattc cagctcattc cagttcccaa ggccctgcca   1800

gagcccagag gctgggccct ctggggcaga ggagctgggg tcctcccccc tacacagagc   1860

acacagcccc gcaagagaga agagacacct tggggagagg aatctccaga ccagagatcc   1920

cagtatgggt ctcctctatg ctgacgggat gggatgtcaa gaggggaggg ggctgggctt   1980

tagggaaaca cacaaaaatc gctgagaaca ctgacaggtg cgacacaccc accccctaatg   2040

ctaacctgtg gcccattact cagatct                                        2067
```

<210> SEQ ID NO 38
<211> LENGTH: 4898
<212> TYPE: DNA
<213> ORGANISM: Sus sp.

<400> SEQUENCE: 38

```
gatcttctcc taagaccaag gaaaactggt cataccaggt ccacttgtcc cctgtggcca     60

ttgtccctcc ttccccagaa gaaacaagca ctttccactc cacaagtagc tcctgatcag    120

cttggaagcc cggtgctgct ctgggccctg gggacacggc aggggcatca gagaccaaat    180

cctggaacaa agttccagtg ggtgaggcag gccggacaag caacacgtta taccataata    240

tgaggcaaaa tataatgtga gttctttatg aaaggaaggg gttgcaggtg caactgttgg    300

cttaggtgga tggtcacccc tgaatggagg agggggttcc cagggcatgt gcctggggag    360

aagggctcct ggcaggaggg acagcaagtg caagggccct gtgatcaaat gtgcctggca    420

agttgcagga acagctagaa ggccagcaag gttggaacca aggaaggggt caggggaggg    480
```

-continued

```
gcagggccct cagggccttg cccagcagcc tgagcatctg gagatttgtc caaagtttca    540
aatgtacctg ggcaacctca tgcccatata ccattcctaa cttctgcact taacatctct    600
aggactggga cccagccagt caagcggggg gacccagaga gctccggtgt gaacaccgag    660
gtgctggtgg gtctgcgtgt gtggacatag ggcagtcccg gtccttcctt cactaacacg    720
gcccgggaag ccctgtgcct ccctggtgcg cgggtcggcg cttccggagg gtacaggccc    780
acctggagcc cgggcacagt gcatgcaagt cgggttcacg gcaacctgag ctggctctgc    840
agggcagtgg gactcacagc caggggtaca gggcagaccg gtcctgcctc tgcgcccctc    900
cctggcctgt ggcccctgga cgtgatcccc aacagttagc atgccccgcc ggtgctgaga    960
acctggacga ggtccgcagg cgtcactggg cggtcactga gcccgcccca ggcccccctct   1020
gccccttcct ggggtgaccg tggactcctg gatgaccctg gaccctagac ttcccagggt   1080
gtctcgcgga ggttcctcag ccaggatctc tgcgtctcct ccttccatag aggggacggc   1140
gccccccttgt ggccaaggag gggacggtgg gtcccggagc tggggcggag aacacaggga   1200
gcccctccca gaccccgctc tgggcagaac ctgggaaggg atgtggccat cgggggatcc   1260
ctccaggcca tctcctcaga tgggggctgg tcgactagct tctgagtcct ccaaggaacc   1320
gggtccttct agtcatgact ctgcccagat gaagaaggag agcacttctc tccatcagga   1380
ggatctgagc ttctcttaat tagaatcagc tccttggctt ctacccctta aaaaaaggta   1440
cagaaacttt gcaccttgat ccagtatcag gggaatttat caatcaatgt gggagaaatt   1500
ggcatcttta ccacactgaa tctttcaatc catgaatatc ctctctctct tccatgcata   1560
ggttttaata attctcaatg gagtttaatg taagttttcc tcatagacaa ttgcctttgg   1620
acatctcttt agactcatct ctagtaaact gatattctta atgcaattat aaaatgtatc   1680
ctgcttaatg ttattttcta ttcatttgct gttatataga gatacaatga gtttccacat   1740
ttgaaactgg atctggtaaa ttggctaccc tttttttata gattctatta atttttatac   1800
attctgtggg acttgctaca tacttaatca tgtcacctgt gaagaatgac aatttggttg   1860
ctaccctccc aattcttata tgtctcattt ctttccctct gctggtactc tggcagcagc   1920
agggaagata atgggcctcc ttatcttgtc acaaaaggat gtttttaaag atttcgttat   1980
aaaacataac gctttctggt tttctttaaa gattctctca ccagcttaag aaaattttct   2040
tatactctgt atgataaatg ggtttttgac aatcatttgt tgcattttac ctagtgtttt   2100
ctctgcatct ttatatgctt tttctccttt aatcctgaaa attgtttcga tttttctaac   2160
attgaaccaa tcttacattc ctggaatgga tggaccagac tagtccacat gtttattctg   2220
cccaatggct agattttgtg ttcaatattt tgttcagaat gtttgcatct atattcttga   2280
gtgagacaga gctgcccttg ttaggtttca caaccgaggt tgtgttagct tcataaaatg   2340
agacgtttat tctctaaaag aattgtttcg cttctctgga tgaatttgtg taaggttaga   2400
attgcttacc agtgaagatc tcggggccag ttcttcttta ggggaagatt ttcaacaatt   2460
aagctcaatg cctttagaag aactgagagt ttctattatt tcttgagtta aatatatgta   2520
tttaattaga ctttctagga atagtctcat ttcatctcaa ataattgaca tatgctatta   2580
aagcagattc tcatgaacca ttgtaggtat tccaggtcta gaaaaatgtt cccctttgca   2640
tccctaatgt gtttaatttt caccttcttt cttttgttct tgagaaattc accaaatcat   2700
tttcaatttc agtcatatcc caaagcaacc aactctctac cttcttgttt tatcatccct   2760
gctggatttt tgttatctac ttcttcagta tttgttcttc cctttcttct attcctcatt   2820
ccatttttcc cttgttttct aactttctga gatatatgct tagttccttc atttgaagcc   2880
```

```
tttttatttt cttttttttt ttttggtctt tttgtctttt gttgttgttg ttgtgctatt   2940

tcttgggccg ctcccgcggc atatggaggt tcccaggcta ggagtcgaat cggagctgta   3000

gccaccggcc tacgccagag ccacagcaat gcgggatccg agccgcgtct gcaacctaca   3060

ccacagctca tggcaacgcc ggatcgttaa cccactgagc aagggcagga accgaacccg   3120

caacctcatg gttcctagtc ggattcgtaa ccactgtgcc acaacaggaa ctccgccttt   3180

ttattttcta taaaaatttc tatgtacatt ttaaggttat aggtttcctt ctatgtaccc   3240

cattggctgt atcctcaggg ttctgtggag tgatttcatt attgttcaag ttcaatatgt   3300

cttctgattt tccaatttga atacctctct aaatcagtag gtgaatattt ctttttcttt   3360

ttcttttctt ttcttctttt tttttttctt tcagccaggt ccatggcatg cagaaattcc   3420

caggccagga atcaaactct caccatggca gtgacaatgt cggatccttt acccactagg   3480

ccaccaggga actctgggag catatgtttt tatttcccga catctgagga tgcctagtat   3540

gtcttcatta ttgatttcta gtttgccact gatttctagt attttgctca tagagtgtat   3600

gctcaatggt tttggtcatt tgaaatgtat ttagtcctgc tttatgaccc agtatgtggt   3660

cagttttgtc aatgttcctt ttctgcttga agagaaccta catgctgtaa ctctgggtgc   3720

atgttctgta tataagtcta taggctgagc cgggggagcc ttctaatctg ccgttatctt   3780

cttcgagtta ttctaggtac tatttcttag ccataaacct ttaaattctg atatcaatat   3840

aatgacccca gcccgcttag ggtcggcact tcatgttatc tttttccatc catttaatcc   3900

ctccccactg ttttggccac acccgtggga tatgggagtt cctgggccaa ggatcagatc   3960

tgagccgcag ctgccaccta tgccacagca gcagcaatga tggatcttta acccactgca   4020

ccacactggg gattgaaccc aagcctcagc agcaacccaa gctactgcag agacaacacc   4080

agatccttaa cctgctgtgc catagcggga atttccatcc atttactttc aagccagctg   4140

aataacctag cccaccatgc ctggacatgg gtgctctgct tcaaatgatt ttgttcagtc   4200

agcatccatc tctgaaatgt gtgccaagca tttatatgca tgcaagagtc atgttggcac   4260

ttctatcatt tccaacagtt cagtagcctt tgtatcatga catttcttgg ccttttctct   4320

acaatatttg aggctgagca gactggccgt gcccctgtcc atgcttccag agcctgtgtg   4380

cagacttctg ctctagacag agacagctaa ccatcctgca gtgcccagaa aacccaactc   4440

aaagaccctc aagtaaggaa ggatttattg gctcacgtaa tctggaatcc aggcatgggg   4500

tattcagggc cacctgaacc agaggccctg gccctgttct ctaagcttct tcctgccctg   4560

ccctcgttct ggaagtgacc ctgaaggaca gcaatgaagg gcagctcccc cagggacaga   4620

tgactgagag gtccatttca agtccaactt ggcctagatt gagaggcagc aagaaatatg   4680

gacctacagt gagtcacagg atttaccagt ggtttggctg ggttgtcagt gttacaggct   4740

aaacatttgg gtccctccaa aattaacatg ttgccactct aaccaccaaa atcatggtat   4800

ttgggggtgg ggcccttgga ggtaattagg tttagaaaga atgaagaggg ggcccttgtg   4860

atgggactag tgcctttata gagagagaag agagaggg                           4898
```

<210> SEQ ID NO 39
<211> LENGTH: 1913
<212> TYPE: DNA
<213> ORGANISM: Sus sp.

<400> SEQUENCE: 39

```
cacctcatcc ccaaccacct ggatggtggc aagtggcagg ctgagaggct gcatatgagc     60
```

tcatcaagag ggtccccacc ccacagaggc tgacccagct gccactgcca cctagtggct 120
gatcggccaa gagcaggagc cccaggggca gctccattcc ctggggcggc cagggaacca 180
cctggtggta ggacaattcc attgcacctc atccatcagg aaaaggtttg ccttccctgg 240
cagtaatgca tcttcccata acatggtccc tggcctcttg gaatggcttg gccaccgtca 300
tggcctcacc cacaaagcct tgtgtctcag caaggaactt attccacagc aaaggacttg 360
cagcctggaa tgaactggtc tgactacata ccccattgcc cagaagtagg tggtctattg 420
caaagtggag tggcttaccc aagactcagt tgtgcccaag ttgagagata gcatcctaaa 480
atatgggctt atgtctcact ggctgaggtt tattctttga atcaaagaca attatatggt 540
gtggtccccc cagagataga atacatgagt ctgggaatca agggatagaa gtaagaagag 600
attttgtcac cattaatccc aataactcgc ccaaagaata tttgctttct gtcctggcag 660
ctctgctgct ttggcaataa cttcctagaa tataatgtct ccaccagggg actccacaac 720
ggttccattg atttgaagcc aatgggcaga ggaggggctg ccttactggt cggactggtc 780
agccctgatt actaaggaga aatcaggcaa cttcaacaaa actaaggcag gggggacttt 840
gtctagaacc caaagcacta agcatcttag tactttttag ttctcagagc ctccaagaac 900
aaagatttag cccctcagca ccaccaggta aagaacaggt aaatccagct gaggacaaga 960
gaaatattga atggatagag gaagaaagaa attatagata tcaactatgg cctcatgact 1020
agagtctcca gattaagcgg aataaaaata cagatgatta gatctgaaca tcaggccaaa 1080
caacgaacaa cagtttaagt gcgacctagg caatatttgg gacatactta tactaaaatt 1140
ttttcgctat ttgagcatcc tgtattttat ctggcaactt tattcatccc tagcgaaaaa 1200
ggaactgtgg taacttagtg tatttttact ttgctcatta ttgtgtatat acctacttgt 1260
atttatcaat catatttact ctgttctcag tattacttta tatagcagtt ggtggtgatg 1320
gttagcaaca tattcagtgg aactgtgact gaatttgagg agaaattaac agagttggct 1380
gtggctacaa taacccttcg ggacatgtgt cccctcattt tggggagatg gttagatctc 1440
tgggtaaatg ttagggcatc tgagccagaa accaagattt tgccagctgg tgcaatgtca 1500
gattttacca gcagagggtg ccagaggaat gcggcaaaac ccgagtgcca gaaagcacct 1560
ccctgttttc cagcttttct tcctttttat ttattttatt tacggcccag gagtccgtaa 1620
tagcgctgag gatggcccag gctcttctca gcagccctga ctgactagtt cagcaatgcg 1680
ctcaggcccc atctggccac cgggcagcct cttctgtggt agctccagcc tcagccagtg 1740
caaaaggcta ccctacactg gcgccacttc tacaatcagc actggccaca ccctccacgc 1800
catccggcac ggagccaggt gatctgccgg ccagattgca gttcgtgctg cctgagtcca 1860
ggtgattaca ctggctgcat cttttctttc tggaccattc attccatttt ttt 1913

<210> SEQ ID NO 40
<211> LENGTH: 394
<212> TYPE: DNA
<213> ORGANISM: Artificial Sequence
<220> FEATURE:
<223> OTHER INFORMATION: Synthetic

<400> SEQUENCE: 40
ctctgcactc actaccgccg gacgcgcact gccgtgctgc ccatggacca cgctggggag 60
gggtgagcgg acagcacgtt aggaagtgtg tgtgtgcgcg tgggtgcaag tcgagccaag 120
gccaagatcc aggggctggg ccctgtgccc agaggagaat ggcaggtgga gtgtagctgg 180
attgaaaggt ggcctgaagg gtggggcatc ctgtttggag gctcactctc agccccaggg 240
tctctggttc ctgccggggt ggggggcgca aggtgcctac cacaccctgc tagcccctcg 300
tccagtcccg ggcctgcctc ttcaccacgg aagaggataa gccaggctgc aggcttcatg 360
tgcgccgtgg agaacccagt tcggcccttg gagg 394

<210> SEQ ID NO 41
<211> LENGTH: 333
<212> TYPE: DNA
<213> ORGANISM: Artificial Sequence
<220> FEATURE:
<223> OTHER INFORMATION: Synthetic

<400> SEQUENCE: 41
ggctgaagtc tgaggcctgg cagatgagct tggacgtgcg ctggggagta ctggagaagg 60
actcccgggt ggggacgaag atgttcaaga cggggggctg ctcctctacg actgcaggca 120
ggaacggggc gtcactgtgc cggcggcacc cggccccgcc cccgccacag ccacaggggg 180
agcccagctc acctggccca gagatggaca cggacttggt gccactgggg tgctggacct 240
cgcacaccag gaaggcctct gggtcctggg ggatgctcac agagggtagg agcacccggg 300
aggaggccaa gtacttgccg cctctcagga cgg 333

<210> SEQ ID NO 42
<211> LENGTH: 399
<212> TYPE: DNA
<213> ORGANISM: Artificial Sequence
<220> FEATURE:
<223> OTHER INFORMATION: Synthetic

<400> SEQUENCE: 42
gaagtgaagc cagccagttc ctcctgggca ggtggccaaa attacagttg acccctcctg 60
gtctggctga accttgcccc atatggtgac agccatctgg ccagggccca ggtctccctc 120
tgaagccttt gggaggagag ggagagtggc tggcccgatc acagatgcgg aaggggctga 180
ctcctcaacc ggggtgcaga ctctgcaggg tgggtctggg cccaacacac ccaaagcacg 240
cccaggaagg aaaggcagct tggtatcact gcccagagct aggagaggca ccgggaaaat 300
gatctgtcca agacccgttc ttgcttctaa actccgaggg ggtcagatga agtggttttg 360
tttcttggcc tgaagcatcg tgttccctgc aagaagcgg 399

<210> SEQ ID NO 43
<211> LENGTH: 23
<212> TYPE: DNA
<213> ORGANISM: Artificial Sequence
<220> FEATURE:
<223> OTHER INFORMATION: Synthetic primer

<400> SEQUENCE: 43
gtctttggtt tttgctgagg gtt 23

<210> SEQ ID NO 44
<211> LENGTH: 12673
<212> TYPE: DNA
<213> ORGANISM: Artificial Sequence
<220> FEATURE:
<223> OTHER INFORMATION: Synthetic

<400> SEQUENCE: 44
taaacaaata ggggttccgc gcacatttcc ccgaaaagtg ccacctgacg tcgctgagca 60
ggccctggcc tccctggccg agggcggttt gcgtattaga ggcctaaatg gccgaattca 120

-continued

```
gcggataaca atttcacaca ggaaacagct atgaccatga ttatctagta actataacgg    180
tcctaaggta gcgagcgatc gcttaattaa cctgcaggga tatcccatgg gggccgccag    240
tgtgatggat atctgcagaa ttcgcccttg atattaagag aagggcaagt cagcttaagt    300
ttgggggtag aggggaacag ggagtgagga gatctggcct gagagatagg agccctggtg    360
gccacaggag gactctttgg gtcctgtcgg atggacacag ggcggcccgg gggcatgttg    420
gagcccggct ggttcttacc agaggcaggg ggcaccctct gacacgggag cagggcatgt    480
tccatacatg acacacccct ctgctccagg gcaggtgggt ggcggcacag aggagccagg    540
gactctgagc aaggggtcca ccagtggggc agttggatcc agacttctct gggccagcga    600
gagtctagcc ctcagccgtt ctctgtccag gagggggggtg gggcaggcct gggcggccag    660
agctcatccc tcaagggttc ccagggtcct gccagaccca gatttccgac cgcagccacc    720
acaagaggat gtggtctgct gtggcagctg ccaagacctt gcagcaggtg cagggtgggg    780
gggtgggggc acctgggggc agctggggtc actgagttca gggaaaaccc ctttttttccc    840
ctaaacctgg ggccatccct aggggaaacc acaacttctg agccctgggc agtggctgct    900
gggagggaag agcttcatcc tggaccctgg gggggaaccc agctccaaag gtgcaagggg    960
cccaggtcca aggctagagt gggccaagca ccgcaatggc cagggagtgg gggaggtgga   1020
gctggactgg atcagggcct ccttgggact ccctacaccc tgtgtgacat gttagggtac   1080
ccacacccca tcaccagtca gggcctggcc catctccagg gccagggatg tgcatgtaag   1140
tgtgtgtgag tgtgtgtgtg tggtgtagta cacccccttgg catccggttc cgaggccttg   1200
ggttcctcca aagttgctct ctgaattagg tcaaactgtg aggtcctgat cgccatcatc   1260
aacttcgttc tccccacctc ccatcattat caagagctgg ggagggtctg ggatttcttc   1320
ccacccacaa gccaaaagat aagcctgctg gtgatggcag aagacacagg atcctgggtc   1380
agagacaaag gccagtgtgt cacagcgaga gaggcagccg gactatcagc tgtcacagag   1440
aggccttagt ccgctgaact caggccccag tgactcctgt tccactgggc actggccccc   1500
ctccacagcg cccccaggcc ccagggagag gcgtcacagc ttagagatgg ccctgctgaa   1560
cagggaacaa gaacaggtgt gccccatcca gcgccccagg ggtgggacag gtgggctgga   1620
tttggtgtga agcccttgag ccctggaacc caaccacagc agggcagttg gtagatgcca   1680
tttggggaga ggccccagga gtaagggcca tgggcccttg agggggccag gagctgagga   1740
cagggacaga gacggcccag gcagaggaca gggccatgag gggtgcactg agatggccac   1800
tgccagcagg ggcagctgcc aacccgtcca gggaacttat tcagcagtca gctggaggtg   1860
ccattgaccc tgagggcaga tgaagcccag gccaggctag gtgggctgtg aagaccccag   1920
gggacagagc tctgtccctg ggcagcactg gcctctcatt ctgcagggct tgacgggatc   1980
ccaaggcctg ctgcccctga tggtagtggc agtaccgccc agagcaggac cccagcatgg   2040
aaaccccaac gggacgcagc ctgcggagcc cacaaaacca gtaaggagcc gaagcagtca   2100
tggcacgggg agtgtggact tccctttgat ggggcccagg catgaaggac agaatgggac   2160
agcggccatg agcagaaaat cagccggagg ggatgggcct aggcagacgc tggctttatt   2220
tgaagtgttg gcattttgtc tggtgtgtat tgttggtatt gattttattt tagtatgtca   2280
gtgacatact gacatattat gtaacgacat attattatgt gttttaagaa gcactccaag   2340
ggaacaggct gtctgtaatg tgtccagaga agagagcaag agcttggctc agtctccccc   2400
aaggaggtca gttcctcaac aggggtccta aatgtttcct ggagccaggc ctgaatcaag   2460
ggggtcatat ctacacgtgg ggcagaccca tggaccattt tcggagcaat aagatggcag   2520
```

-continued

```
ggaggatacc aagctggtct tacagatcca gggctttgac ctgtgacgcg ggcgctcctc   2580
caggcaaagg gagaagccag caggaagctt tcagaactgg ggagaacagg gtgcagacct   2640
ccagggtctt gtacaacgca ccctttatcc tggggtccag gaggggtcac tgagggattt   2700
aagtggggga ccatcagaac caggtttgtg ttttggaaaa atggctccaa agcagagacc   2760
agtgtgaggc cagattagat gatgaagaag aggcagtgga aagtcgatgg gtggccaggt   2820
agcaagaggg cctatggagt tggcaagtga atttaaagtg gtggcaccag agggcagatg   2880
gggaggagca ggcactgtca tggactgtct atagaaatct aaaatgtata cccttttag    2940
caatatgcag tgagtcataa aagaacacat atatatttcc tttggccggc cggcgcgcca   3000
cgcgtataac ttcgtatagc atacattata cgaagttatc ttaagggcta tggcagggcc   3060
tgccgccccg acgttggctg cgagccctgg gccttcaccc gaacttgggg ggtggggtgg   3120
ggaaaaggaa gaaacgcggg cgtattggcc ccaatggggt ctcggtgggg tatcgacaga   3180
gtgccagccc tgggaccgaa ccccgcgttt atgaacaaac gacccaacac cgtgcgtttt   3240
attctgtctt tttattgccg tcatagcgcg ggttccttcc ggtattgtct ccttccgtgt   3300
ttcactcgag ttagaagaac tcgtcaagaa ggcgatagaa ggcgatgcgc tgcgaatcgg   3360
gagcggcgat accgtaaagc acgaggaagc ggtcagccca ttcgccgcca agctcttcag   3420
caatatcacg ggtagccaac gctatgtcct gatagcggtc cgccacaccc agccggccac   3480
agtcgatgaa tccagaaaag cggccatttt ccaccatgat attcggcaag caggcatcgc   3540
catgggtcac gacgagatcc tcgccgtcgg gcatgcgcgc cttgagcctg gcgaacagtt   3600
cggctggcgc gagcccctga tgctcttcgt ccagatcatc ctgatcgaca agaccggctt   3660
ccatccgagt acgtgctcgc tcgatgcgat gtttcgcttg gtggtcgaat gggcaggtag   3720
ccggatcaag cgtatgcagc cgccgcattg catcagccat gatggatact ttctcggcag   3780
gagcaaggtg agatgacagg agatcctgcc ccggcacttc gcccaatagc agccagtccc   3840
ttcccgcttc agtgacaacg tcgagcacag ctgcgcaagg aacgcccgtc gtggccagcc   3900
acgatagccg cgctgcctcg tcctgcagtt cattcagggc accggacagg tcggtcttga   3960
caaaaagaac cgggcgcccc tgcgctgaca gccggaacac ggcggcatca gagcagccga   4020
ttgtctgttg tgcccagtca tagccgaata gcctctccac ccaagcggcc ggagaacctg   4080
cgtgcaatcc atcttgttca atggccgatc ccattccaga tctgttagcc tcccccatct   4140
cccgtgcaaa cgtgcgcgcc aggtcgcaga tcgtcggtat ggagcctggg gtggtgacgt   4200
gggtctggat catcccggag gtaagttgca gcagggcgtc ccggcagccg gcgggcgatt   4260
ggtcgtaatc caggataaag acgtgcatgg gacggaggcg tttggtcaag acgtccaagg   4320
cccaggcaaa cacgttgtac aggtcgccgt tgggggccag caactcgggg gcccgaaaca   4380
gggtaaataa cgtgtccccg atatggggtc gtgggcccgc gttgctctgg ggctcggcac   4440
cctggggcgg cacggccgtc cccgaaagct gtccccaatc ctcccgccac gacccgccgc   4500
cctgcagata ccgcaccgta ttggcaagca gcccgtaaac gcggcgaatc gcggccagca   4560
tagccaggtc aagccgctcg ccggggcgct ggcgtttggc caggcggtcg atgtgtctgt   4620
cctccggaag ggcccccaac acgatgtttg tgccgggcaa ggtcggcggg atgagggcca   4680
cgaacgccag cacggcctgg ggggtcatgc tgcccataag gtatcgcgcg gccgggtagc   4740
acaggagggc ggcgatggga tggcggtcga agatgagggt gagggccggg ggcggggcat   4800
gtgagctccc agcctccccc ccgatatgag gagccagaac ggcgtcggtc acggcataag   4860
```

-continued

```
gcatgcccat tgttatctgg gcgcttgtca ttaccaccgc cgcgtccccg gccgatatct   4920
caccctggtc aaggcggtgt tgtgtggtgt agatgttcgc gattgtctcg gaagcccccca  4980
gcacccgcca gtaagtcatc ggctcgggta cgtagacgat atcgtcgcgc gaacccaggg   5040
ccaccagcag ttgcgtggtg gtggttttcc ccatcccgtg gggaccgtct atataaaccc   5100
gcagtagcgt gggcattttc tgctccgggc ggacttccgt ggcttcttgc tgccggcgag   5160
ggcgcaacgc cgtacgtcgg ttgctatggc cgcgagaacg cgcagcctgg tcgaacgcag   5220
acgcgtgctg atggccgggg tacgaagcca tggtggctct agaggtcgaa aggcccggag   5280
atgaggaaga ggagaacagc gcggcagacg tgcgcttttg aagcgtgcag aatgccgggc   5340
ttccggagga ccttcgggcg cccgccccgc ccctgagccc gcccctgagc ccgcccccgg   5400
acccacccct tcccagcctc tgagcccaga aagcgaagga gccaaagctg ctattggccg   5460
ctgccccaaa ggcctacccg cttccattgc tcagcggtgc tgtccatctg cacgagacta   5520
gtgagacgtg ctacttccat ttgtcacgtc ctgcacgacg cgagctgcgg ggcgggggg    5580
aacttcctga ctaggggagg agtagaaggt ggcgcgaagg ggccaccaaa gaacggagcc   5640
ggttggcgcc taccggtgga tgtggaatgt gtgcgaggcc agaggccact tgtgtagcgc   5700
caagtgccca gcggggctgc taaagcgcat gctccagact gccttgggaa aagcgcctcc   5760
cctacccggt agggatccgc gttacataac ttacggtaaa tggcccgcct ggctgaccgc   5820
ccaacgaccc ccgcccattg acgtcaataa tgacgtatgt tcccatagta acgccaatag   5880
ggactttcca ttgacgtcaa tgggtggagt atttacggta aactgcccac ttggcagtac   5940
atcaagtgta tcatatgcca agtacgcccc ctattgacgt caatgacggt aaatggcccg   6000
cctggcatta tgcccagtac atgaccttat gggactttcc tacttggcag tacatctacg   6060
tattagtcat cgctattacc atggtgatgc ggttttggca gtacatcaat gggcgtggat   6120
agcggtttga ctcacgggga tttccaagtc tccaccccat tgacgtcaat gggagtttgt   6180
tttggcacca aaatcaacgg ttaacaagct tataacttcg tatagcatac attatacgaa   6240
gttattacgt agcggccgcg tcgacgataa attgtgtaat tccacttcta aggattcatc   6300
ccaagggggg aaaataatca aagatgtaac caaaggttta caaacaagaa ctcatcatta   6360
atcttccttg ttgttatttc aacgatatta ttattattac tattattatt attattattt   6420
tgtctttttg cattttctag ggccactccc acggcataga gaggttccca ggctaggggt   6480
caaatcggag ctacagctgc cggcctacgc cagagccaca gcaacgcagg atctgagcca   6540
cagcaatgca ggatctacac cacagctcat ggtaacgctg gatccttaac ccaatgagtg   6600
aggccaggga tcgaacctgt aacttcatgg ttcctagtcg gattcattaa ccactgagcc   6660
acgacaggaa ctccaacatt attaatgatg ggagaaaact ggaagtaacc taaatatcca   6720
gcagaaaggg tgtggccaaa tacagcatgg agtagccatc ataaggaatc ttacacaagc   6780
ctccaaaatt gtgtttctga aattgggttt aaagtacgtt tgcattttaa aaagcctgcc   6840
agaaaataca gaaaaatgtc tgtgatatgt ctctggctga taggattttg cttagtttta   6900
attttggctt tataattttc tatagttatg aaaatgttca caagaagata tatttcattt   6960
tagcttctaa aataattata acacagaagt aatttgtgct ttaaaaaaat attcaacaca   7020
gaagtatata aagtaaaaat tgaggagttc ccatcgtggc tcagtgatta acaaacccaa   7080
ctagtatcca tgaggatatg gatttgatcc ctggccttgc tcagtgggtt gaggatccag   7140
tgttgctgtg agctgtggtg taggttgcag acacagcact ctggcgttgc tgtgactctg   7200
gcgtaggccg gcagctacag ctccatttgg acccttagcc tgggaacctc catatgcctg   7260
```

```
agatacggcc ctaaaaagtc aaaagccaaa aaaatagtaa aaattgagtg tttctactta   7320
ccacccctgc ccacatctta tgctaaaacc cgttctccag agacaaacat cgtcaggtgg   7380
gtctatatat ttccagccct cctcctgtgt gtgtatgtcc gtaaaacaca cacacacaca   7440
cacacacgca cacacacaca cacgtatcta attagcattg gtattagttt ttcaaaaggg   7500
aggtcatgct ctacctttta ggcggcaaat agattattta aacaaatctg ttgacatttt   7560
ctatatcaac ccataagatc tcccatgttc ttggaaaggc tttgtaagac atcaacatct   7620
gggtaaacca gcatggtttt taggggggttg tgtggatttt tttcatattt tttagggcac   7680
acctgcagca tatggaggtt cccaggctag gggttgaatc agagctgtag ctgccggcct   7740
acaccacagc cacagcaacg ccagatcctt aacccactga gaaaggccag ggattgaacc   7800
tgcatcctca tggatgctgg tcagatttat ttctgctgag ccacaacagg aactccctga   7860
accagaatgc ttttaaccat tccactttgc atggacattt agattgtttc catttaaaaa   7920
tacaaattac aaggagttcc cgtcgtggct cagtggtaac gaattggact aggaaccatg   7980
aggtttcggg ttcgatccct ggccttgctc ggtgggttaa ggatccagca ttgatgtgag   8040
atatggtgta ggtcgcagac gtggctcgga tcccacgttg ctgtggctct ggcgtaggcc   8100
ggcaacaaca gctccgattc gacccctagc ctgggaacct ccatgtgcca caggagcagc   8160
cctagaaaag gcaaaaagac aaaaaaataa aaaattaaaa tgaaaaaata aaataaaaat   8220
acaaattaca agagacggct acaaggaaat ccccaagtgt gtgcaaatgc catatatgta   8280
taaaatgtac tagtgtctcc tcgcgggaaa gttgcctaaa agtgggttgg ctggacagag   8340
aggacaggct ttgacattct cataggtagt agcaatgggc ttctcaaaat gctgttccag   8400
tttacactca ccatagcaaa tgacagtgcc tcttcctctc caccccttgcc aataatgtga   8460
caggtggatc tttttctatt ttgtgtatct gacaagcaaa aaatgagaac aggagttcct   8520
gtcgtggtgc agtggagaca aatctgacta ggaaccatga aatttcgggt tcaatccctg   8580
gcctcactca gtaggtaaag gatccagggt tgcagtgagc tgtggggtag gtcgcagaca   8640
cagtgcaaat ttggccctgt tgtggctgtg gtgtaggccg gcagctatag ctccaattgg   8700
acccctagcc tgggaacctc cttatgccgt gggtgaggcc ctaaaaaaaa gagtgcaaaa   8760
aaaaaaaata agaacaaaaa tgatcatcgt ttaattcttt atttgatcat tggtgaaact   8820
tattttcctt ttatatttt attgactgat tttatttctc ctatgaattt accggtcata   8880
gttttgcctg ggtgttttta ctccggtttt agttttggtt ggttgtattt tcttagagag   8940
ctatagaaac tcttcatcta tttggaatag taattcctca ttaagtattt gtgctgcaaa   9000
aaattttccc tgatctgttt tatgcttttg tttgtggggt ctttcacgag aaagcctttt   9060
tagtttttac acctcagctt ggttgttttt cttgattgtg tctgtaatct gcggccaaca   9120
taggaaacac atttttactt tagtgttttt ttcctatttt cttcaagtac gtccattgtt   9180
ttggtgtctg attttacttt gcctggggtt tgtttttgtg tggcaggaat ataaacttat   9240
gtattttcca aatggagagc caatggttgt atatttgttg aattcaaatg caactttatc   9300
aaacaccaaa tcatcgattt atcacaactc ttctctggtt tattgatcta atgatcaatt   9360
cctgttccac gctgttttaa ttattttagc tttgtggatt ttggtgcctg gtagagaaca   9420
aagcctccat tattttcatt caaaatagtc ccgtctatta tctgccattg ttgtagtatt   9480
agactttaaa atcaatttac tgattttcaa aagttattcc tttggtgatg tggaatactt   9540
tatacttcat aaggtacatg gattcatttg tggggaattg atgtctttgc tattgtggcc   9600
```

-continued

```
atttgtcaag ttgtgtaata ttttacccat gccaactttg catattgtat gtgagtttat   9660
tcccagggtt tttaatagga tgtttattga agttgtcagt gtttccacaa tttcatcgcc   9720
tcagtgctta ctgtttgcat aaaaggaaac ctactcactt ttgcctattg ctcttgtatt   9780
caatcatttt agttaactct tgtgttaatt ttgagagttt ttcagctgac tgtctggggt   9840
tttctttaat agactagccc tttgtctgta aagaataatt ttatcgaatt tttcttaaca   9900
ctcacactct ccccaccccc acccccgctc atctcctttc attgggtcaa atctgtagaa   9960
tacaataaaa gtaagagtgg gaaccttagc ctttaagtcg attttgcctt taaatgtgaa  10020
tgttgctatg tttcgggaca ttctctttat caagttgcgg atgtttcctt agataattaa  10080
cttaataaaa gactggatgt ttgctttctt caaatcagaa ttgtgttgaa tttatattgc  10140
tattctgttt aattttgttt caaaaaattt acatgcacac cttaaagata accatgacca  10200
aatagtcctc ctgctgagag aaaatgttgg ccccaatgcc acaggttacc tcccgactca  10260
gataaactac aatgggagat aaaatcagat ttggcaaagc ctgtggattc ttgccataac  10320
tctcagagca tgacttgggt gttttttcct tttctaagta ttttaatggt atttttgtgt  10380
tacaatagga aatctaggac acagagagtg attcaatgag gggaacgcat tctgggatga  10440
ctctaggcct ctggtttggg gagagctcta ttgaagtaaa gacaatgaga ggaagcaagt  10500
ttgcagggaa ctgtgaggaa tttagatggg gaatgttggg tttgaggttt ctatagggca  10560
cgcaagcaga gatgcactca ggaggaagaa ggagcataaa tctagtggcg ctgccggcaa  10620
gcttgctgga ggaggccaat tgggagctgc tggaatgcat ggaggcggcg ctctcgaggc  10680
tggaggaggc cagctgattt aaatcggtcc gcgtacgatg catattaccc tgttatccct  10740
accgcggtta ctggccgtcg ttttacaacg tcgtgactgg gaaaaccctg gcgatgctct  10800
tctcccggtg aaaacctctg acacatggct cttctaaatc cggagtttaa acgcttcctt  10860
catgtgagca aaaggccagc aaaaggccag gaaccgtaaa aaggccgcgt tgctggcgtt  10920
tttccatagg ctccgccccc ctgacgagca tcacaaaaat cgacgctcaa gtcagaggtg  10980
gcgaaacccg acaggactat aaagatacca ggcgtttccc cctggaagct ccctcgtgcg  11040
ctctcctgtt ccgaccctgc cgcttaccgg atacctgtcc gcctttctcc cttcgggaag  11100
cgtggcgctt tctcatagct cacgctgtag gtatctcagt tcggtgtagg tcgttcgctc  11160
caagctgggc tgtgtgcacg aaccccccgt tcagcccgac cgctgcgcct tatccggtaa  11220
ctatcgtctt gagtccaacc cggtaagaca cgacttatcg ccactggcag cagccactgg  11280
taacaggatt agcagagcga ggtatgtagg cggtgctaca gagttcttga agtggtggcc  11340
taactacggc tacactagaa ggacagtatt tggtatctgc gctctgctga agccagttac  11400
cttcggaaaa agagttggta gctcttgatc cggcaaacaa accaccgctg gtagcggtgg  11460
tttttttgtt tgcaagcagc agattacgcg cagaaaaaaa ggatctcaag aagatccttt  11520
gatcttttct acggggtctg acgctcagtg gaacgaaaac tcacgttaag ggattttggt  11580
catgcctagg tggcaaacag ctattatggg tattatgggt ctaccggtgc atgagattat  11640
caaaaaggat cttcacctag atccttttaa attaaaaatg aagttttaaa tcaatctaaa  11700
gtatatatga gtaaacttgg tctgacagtt accaatgctt aatcagtgag gcacctatct  11760
cagcgatctg tctatttcgt tcatccatag ttgcctgact ccccgtcgtg tagataacta  11820
cgatacggga gggcttacca tctggcccca gtgctgcaat gataccgcga gacccacgct  11880
caccggctcc agatttatca gcaataaacc agccagccgg aagggccgag cgcagaagtg  11940
gtcctgcaac tttatccgcc tccatccagt ctattaattg ttgccgggaa gctagagtaa  12000
```

gtagttcgcc agttaatagt ttgcgcaacg ttgttgccat tgctacaggc atcgtggtgt 12060
cacgctcgtc gtttggtatg gcttcattca gctccggttc ccaacgatca aggcgagtta 12120
catgatcccc catgttgtgc aaaaaagcgg ttagctcctt cggtcctccg atcgttgtca 12180
gaagtaagtt ggccgcagtg ttatcactca tggttatggc agcactgcat aattctctta 12240
ctgtcatgcc atccgtaaga tgcttttctg tgactggtga gtactcaacc aagtcattct 12300
gagaatagtg tatgcggcga ccgagttgct cttgcccggc gtcaatacgg gataataccg 12360
cgccacatag cagaacttta aaagtgctca tcattggaaa acgttcttcg gggcgaaaac 12420
tctcaaggat cttaccgctg ttgagatcca gttcgatgta acccactcgt gcacccaact 12480
gatcttcagc atcttttact ttcaccagcg tttctgggtg agcaaaaaca ggaaggcaaa 12540
atgccgcaaa aaagggaata agggcgacac ggaaatgttg aatactcata ctcttccttt 12600
ttcaatatta ttgaagcatt tatcagggtt attgtctcgg gagcggatac atatttgaat 12660
gtatttagaa aaa 12673

<210> SEQ ID NO 45
<211> LENGTH: 12263
<212> TYPE: DNA
<213> ORGANISM: Artificial Sequence
<220> FEATURE:
<223> OTHER INFORMATION: Synthetic

<400> SEQUENCE: 45
taaacaaata ggggttccgc gcacatttcc ccgaaaagtg ccacctgacg tcgctgagca 60
ggccctggcc tccctggccg agggcggttt gcgtattaga ggcctaaatg gccgaattca 120
gcggataaca atttcacaca ggaaacagct atgaccatga ttatctagta actataacgg 180
tcctaaggta gcgagcgatc gcttaattaa cctgcaggga taaccactga cccatgacgg 240
gaactcccag ggctcagctc ttgactccag gttcgcagct gccctcaaag caatgcaacc 300
ctggctggcc ccgcctcatg catccggcct cctccccaaa gagctctgag cccacctggg 360
cctaggtcct cctccctggg actcatggcc taagggtaca gagttactgg ggctgatgaa 420
gggaccaatg gggacagggg cctcaaatca aagtggctgt ctctctcatg tcccttcctc 480
tcctcagggt ccaaaatcag ggtcagggcc ccagggcagg ggctgagagg gcctctttct 540
gaaggccctg tctcagtgca ggttatgggg gtctgggga gggtcaatgc agggctcacc 600
cttcagtgcc ccaaagccta gagagtgagt gcctgccagt ggcttcccag gcccaatccc 660
ttgactgcct gggaatgctc aaatgcagga actgtcacaa caccttcagt caggggctgc 720
tctgggagga aaaacactca gaattggggg ttcagggaag gcccagtgcc aagcatagca 780
ggagctcagg tggctgcaga tggtgtgaac cccaggagca ggatggccgg cactcccccc 840
agaccctcca gagccccagg ttggctgccc tcttcactgc cgacacccct gggtccactt 900
ctgccctttc ccacctaaaa cctttagggc tcccactttc tcccaaatgt gagacatcac 960
cacggctccc agggagtgtc cagaagggca tctggctgag aggtcctgac atctgggagc 1020
ctcaggcccc acaatggaca gacgccctgc caggatgctg ctgcagggct gttagctagg 1080
cggggtggag atggggtact ttgcctctca gaggccccgg ccccaccatg aaacctcagt 1140
gacaccccat ttccctgagt tcacatacct gtatcctact ccagtcacct tccccacgaa 1200
cccctgggag cccaggatga tgctggggct ggagccacga ccagcccacg agtgatccag 1260
ctctgccaat cagcagtcat ttcccaagtg ttccagccct gccaggtccc actacagcag 1320

-continued

```
taatggaggc cccagacacc agtccagcag ttagagggct ggactagcac cagctttcaa   1380
gcctcagcat ctcaaggtga atggccagtg cccctccccg tggccatcac aggatcgcag   1440
atatgaccct aggggaagaa atatcctggg agtaaggaag tgcccatact caaggatggc   1500
ccctctgtga cctaacctgt ccctgaggat tgtacttcca ggcgttaaaa cagtagaacg   1560
cctgcctgtg aacccccgcc aagggactgc ttggggaggc cccctaaacc agaacacagg   1620
cactccagca ggacctctga actctgacca ccctcagcaa gtgggcaccc cccgcagctt   1680
ccaaggcacc ccagggctca ccacagcggc ccctcctggc agcccctcac ccaggcccag   1740
accctctaag atggcacatc taagccaatc cacctccttg tcattcctcc tgtccccacc   1800
caggaccctt ctcagatgaa accttcgctc cagccgctgg gccctctctc ctgcccctct   1860
ggcagttctc cagggactcc gcctcccact ctctgtctct ccctgcactc ctaggaacaa   1920
gcgacctcca ggaagcccag tccaattatc ccctctgtgt cctccccaat ctctgcctct   1980
gggtggattt gagcaccaca tcctgttctc ttcgacctga aactccttgg ccccggtgtc   2040
cgctctcctg ggccctcttt tctctcctcc cctcttccgt gccccgtttg tttggtgtta   2100
caggcaggcc ccggggagcc gtccctccag ctgctcttcc ttgtctgtct caggagccag   2160
aaactggcag catctaaaaa gggctcctgt ttcttcatct gcccagcctc ctagcccaac   2220
cagggctctg gcctcactcc agagggtggg ctccagaggg caggggttgc accctcttag   2280
tgcctcagag gctcagctgg gtgcaggatg ggggggccct cagggagccc ctcagtgact   2340
gctgatcact tactgcagga ctgttcccag ctcttcccaa tcattggaat gacaatacct   2400
agttctgctc catcatagtg atgcaggaaa aatgttactg aaatcctggt tcttgtttag   2460
caatcgaaga atgaattccg cgaacacaca ggcagcaagc aagcgaagcc tttattaaag   2520
gaaagcagat agctcccagg gctgcaggga gcggggagaa gagctcccca ctctctattg   2580
tcctataggg ctttttaccc cttaaagttg gggggataca aaaaaaatag aagaaaaagg   2640
gagttcccgt cagggcacag cagaaacaaa tccaactagg aaccatgagg ttgggggttc   2700
gattcctggc ctctctcagt gggttaagga tgcagcgttg ccgtgagcta tgatacaggt   2760
cacagatgca gctcagatct actagtcaat tgacaggcgc cggagcagga gctaggcctt   2820
tggccggccg gcgcgccaga tctcttaagg gctatggcag ggcctgccgc cccgacgttg   2880
gctgcgagcc ctgggccttc acccgaactt ggggggtggg gtggggaaaa ggaagaaacg   2940
cgggcgtatt ggccccaatg gggtctcggt ggggtatcga cagagtgcca gccctgggac   3000
cgaaccccgc gtttatgaac aaacgaccca acaccgtgcg ttttattctg tctttttatt   3060
gccgtcatag cgcgggttcc ttccggtatt gtctccttcc gtgtttcact cgagttagaa   3120
gaactcgtca agaaggcgat agaaggcgat gcgctgcgaa tcgggagcgg cgataccgta   3180
aagcacgagg aagcggtcag cccattcgcc gccaagctct tcagcaatat cacgggtagc   3240
caacgctatg tcctgatagc ggtccgccac acccagccgg ccacagtcga tgaatccaga   3300
aaagcggcca ttttccacca tgatattcgg caagcaggca tcgccatggg tcacgacgag   3360
atcctcgccg tcgggcatgc gcgccttgag cctggcgaac agttcggctg gcgcgagccc   3420
ctgatgctct tcgtccagat catcctgatc gacaagaccg gcttccatcc gagtacgtgc   3480
tcgctcgatg cgatgtttcg cttggtggtc gaatgggcag gtagccggat caagcgtatg   3540
cagccgccgc attgcatcag ccatgatgga tactttctcg gcaggagcaa ggtgagatga   3600
caggagatcc tgccccggca cttcgcccaa tagcagccag tcccttcccg cttcagtgac   3660
aacgtcgagc acagctgcgc aaggaacgcc cgtcgtggcc agccacgata gccgcgctgc   3720
```

-continued

```
ctcgtcctgc agttcattca gggcaccgga caggtcggtc ttgacaaaaa gaaccgggcg   3780
cccctgcgct gacagccgga acacggcggc atcagagcag ccgattgtct gttgtgccca   3840
gtcatagccg aatagcctct ccacccaagc ggccggagaa cctgcgtgca atccatcttg   3900
ttcaatggcc gatcccattc cagatctgtt agcctccccc atctcccgtg caaacgtgcg   3960
cgccaggtcg cagatcgtcg gtatggagcc tggggtggtg acgtgggtct ggatcatccc   4020
ggaggtaagt tgcagcaggg cgtcccggca gccggcgggc gattggtcgt aatccaggat   4080
aaagacgtgc atgggacgga ggcgtttggt caagacgtcc aaggcccagg caaacacgtt   4140
gtacaggtcg ccgttggggg ccagcaactc gggggcccga aacagggtaa ataacgtgtc   4200
cccgatatgg ggtcgtgggc ccgcgttgct ctggggctcg gcaccctggg gcggcacggc   4260
cgtccccgaa agctgtcccc aatcctcccg ccacgacccg ccgccctgca gataccgcac   4320
cgtattggca agcagcccgt aaacgcggcg aatcgcggcc agcatagcca ggtcaagccg   4380
ctcgccgggg cgctggcgtt tggccaggcg gtcgatgtgt ctgtcctccg gaagggcccc   4440
caacacgatg tttgtgccgg gcaaggtcgg cgggatgagg gccacgaacg ccagcacggc   4500
ctgggggggtc atgctgccca taaggtatcg cgcggccggg tagcacagga gggcggcgat   4560
gggatggcgg tcgaagatga gggtgagggc cgggggcggg gcatgtgagc tcccagcctc   4620
ccccccgata tgaggagcca gaacggcgtc ggtcacggca taaggcatgc ccattgttat   4680
ctgggcgctt gtcattacca ccgccgcgtc cccggccgat atctcaccct ggtcaaggcg   4740
gtgttgtgtg gtgtagatgt tcgcgattgt ctcggaagcc cccagcaccc gccagtaagt   4800
catcggctcg ggtacgtaga cgatatcgtc gcgcgaaccc agggccacca gcagttgcgt   4860
ggtggtggtt ttccccatcc cgtggggacc gtctatataa acccgcagta gcgtgggcat   4920
tttctgctcc gggcggactt ccgtggcttc ttgctgccgg cgagggcgca acgccgtacg   4980
tcggttgcta tggccgcgag aacgcgcagc ctggtcgaac gcagacgcgt gctgatggcc   5040
ggggtacgaa gccatggtgg ctctagaggt cgaaaggccc ggagatgagg aagaggagaa   5100
cagcgcggca gacgtgcgct tttgaagcgt gcagaatgcc gggcttccgg aggaccttcg   5160
ggcgcccgcc ccgcccctga gcccgcccct gagcccgccc ccggacccac cccttcccag   5220
cctctgagcc cagaaagcga aggagccaaa gctgctattg gccgctgccc caaaggccta   5280
cccgcttcca ttgctcagcg gtgctgtcca tctgcacgag actagtgaga cgtgctactt   5340
ccatttgtca cgtcctgcac gacgcgagct gcggggcggg ggggaacttc ctgactaggg   5400
gaggagtaga aggtggcgcg aaggggccac caaagaacgg agccggttgg cgcctaccgg   5460
tggatgtgga atgtgtgcga ggccagaggc cacttgtgta gcgccaagtg cccagcgggg   5520
ctgctaaagc gcatgctcca gactgccttg ggaaaagcgc ctcccctacc cggtagggat   5580
ccgcgttaca taacttacgg taaatggccc gcctggctga ccgcccaacg acccccgccc   5640
attgacgtca ataatgacgt atgttcccat agtaacgcca atagggactt tccattgacg   5700
tcaatgggtg gagtatttac ggtaaactgc ccacttggca gtacatcaag tgtatcatat   5760
gccaagtacg ccccctattg acgtcaatga cggtaaatgg cccgcctggc attatgccca   5820
gtacatgacc ttatgggact ttcctacttg gcagtacatc tacgtattag tcatcgctat   5880
taccatggtg atgcggtttt ggcagtacat caatgggcgt ggatagcggt ttgactcacg   5940
gggatttcca agtctccacc ccattgacgt caatgggagt ttgttttggc accaaaatca   6000
acggttaaca agcttataac ttcgtatagc atacattata cgaagttatt acgtagcggc   6060
```

-continued

```
cgcgtcgacg atatcgctgc cggagccccc ggggccgctg ccggaagatc tggcattgct   6120
gtgactgtgg tgtaggccgg cagctggagc tctgattaga cccctcacct gggaatctcc   6180
atatgctgca cgtgcggccc taaaaagaca aaagacaaaa aaaaaaaaaa aaaaaaaaaa   6240
tcaaaaaaaa acataggggg ttaccaacgt ggggtccaga aagatgtggt tttctcccat   6300
tggccttgcc cagttaccta tatcagtcct tgtccaacag ggttttagg ggtggaaatg    6360
ccccataaat tttacggttt ctttgccctt ctcttccttt agactgagtc accattgctc   6420
tcattccttt tctatcagtt gaggagtggg ttagagatta aggtccatgt ggtggaggta   6480
cacttcttat agtaaacaag gcctatgggg aattactctc tggagccctt aaaccacaaa   6540
tgataatcca tgccacatca aagatgcatc gaagcccatg ctcctacact gactacctga   6600
gttagcattc tgcctcaaca ggactgacca tccccagctc tggggcagat atcctctctc   6660
tgccacaagg gcagtgaccc ccatgctgtc tgagggtcac gctttacccc ccccccaccc   6720
ctgccgtgac cccccagacc accccaggag gtgggcacta atatccctca ttaccccata   6780
gatgaggaaa cagaggttcc cccggggtcc cacaggtgct cagggtcaca tgcaccgtgg   6840
gcacccaggc cccatcccaa ggccaccctc cctcctcagg aagctgtgct gcgctgggcc   6900
agaaggtact gcacacgact cctcagcctc cggtggtggg aggcagcctc aagcctctga   6960
gtggggggc acccgggctc ctcaatctat actgactcct gggggtggga gaaggggagg    7020
gggagctgtg gcctctgagt ccactaagca aatcagggtg ggcaatgcgg gcccatttca   7080
aggaggagag aaccgaggct ctgacagcag gccgggggtc cagggacctg cccagggtca   7140
taggctgaac tgctggctga cctgccttgg gttctttcct tggctcctca gccctgtgtg   7200
atgtgacagg tcattcattc actcactcgc tcattcattc agcaaaccct cagtgagccc   7260
tgctgggagc aggtgctagg ggcaaggaga caggacctct tgccctggaa cagctgaagc   7320
actgggggac aggcagtggc agggaggtgc gtgatcaccg ctgaccccat tccatcctcc   7380
agcccccagg tcagtttcca cccaccattg accccaccat gtcctccatc cccaaggtca   7440
gtttcccgcc caaggagcat ctccttacac actagggaca aaatttcacg gctgtcactg   7500
ggcatctctc cacgctcatc acagccctct agcagccttg aagtcctgta gagcccttcc   7560
catttcacag aagggacaag actatgaggg ccacaccgtg agccatgagc cttaggctgt   7620
gagccgggac agcccctgca ggactggtgg cctcagggca ctgggtgggg agggtgcaca   7680
gtgggtgggc cccttgtgga atagagagga gtgtcaggtc aggggagggg gcttggcctg   7740
gccctggcct gcctggtgtg caaccctagg cagcccctcc ttcccaggcc tcctacttcc   7800
tggaggccaa gcctcaggga ggtaattgag tcaggtgggg gaggggggt tgtggctttc    7860
ttcacagcag aaaaacagag cccacaatag tgtccactga gacagagggg tcctggggga   7920
ggggaggggt gggaggtgac tgctgagccc tgtgggaggg agggagcaac tactgagctg   7980
agctgggtga ctctcccatc tgccccgccc cctgtggggc cagcagagtc accgagagaa   8040
catgacccag ccaggcctgg acagggggac acccatgtcc tttaccccac agggttcact   8100
gagcctatct gccccaagcc tgtgtctccc tgggacggag accctcactc ccaaccacaa   8160
aggtctaaac tcaagttccc aacagccttg aaaatacagc ttccgggggc ctccaaggag   8220
cagtcagccg tccactgcca ggctcgctgg ctcagtgaca caggacacat cctgatgacg   8280
gtccacctgt ctccaagcag gttctcctct gccgatgggg caacgagctc ctcctgtggc   8340
tccctggctg gatgcgtggg aggcggggtg ggggggcagg cggtgttcct ggccgcacac   8400
aaggagcacc cccaccagca tccgaagacg gggcccggt ctttccccaa aacactgctt    8460
```

-continued

```
gcgggagact ttgtgacgtt tccaggggcc atgctccctt cgggcagctt gggggacttc   8520
tgctcctatg tggtcacctg cagggactcc ccccaggcct tggggacaaa caaagtgatg   8580
agagggaggg ttagtgggtc ggggcagggc cagtctttgg accggtttat ctgaaaagcc   8640
agttggtcac cgggaaccac agcaaaccta aacccatttg gccaggcatc tcccagggac   8700
agtctccccc aggatgcggg gcccaggggg gctccagggg tgacctgcgt cctggatttc   8760
cctgatgctc ccagttcgtg cctctgtcca agcatgattt ttaatagtgc cccttccact   8820
cccagaaatg tccaagtgtg ggcaataaat tctggtcacc tgagctcagt gtaactgttt   8880
gctgaatgac acttactgta acaggttaaa atgggaggcc caaggccacg cagagccatc   8940
gaaggctctg tgtgtcccag ccctgataga agcatcagga tggggactgt ggcctcacca   9000
ggggccacat ccaggcggtc accatggggt tcctggtctc cgtgggcctt gactggagcc   9060
cctggtgtga gctcacccca tcccagcctg tgagaggcct ggatgtgggc ctgacatcat   9120
ttcccaccca gtgacagcac tgcatgtgat ggggcctctg ggcagccttt ttcccggggg   9180
aaactggcag gaatcaggac caccaggaca ggggtcaggg gagaggcgat gctgggcacc   9240
agagcctgga ccaccctcgg gttctcagcg atgggcaacc cctgccaccc agggccccgc   9300
cttcctgggg agacatcggg gtttccaggc catcctggga ggagggtggg agcctcagct   9360
agaccccagc tggcttgccc ccccatgccc cggccaagag agggtcttgg agggaagggg   9420
gaccccagac cagcctggcg agcccatcct cagggtctct ggtcagacag gggctcagct   9480
gagctccagg gtagaccaag gccctgcgtg gatgaggcca gtgtggtcac tgcccagagc   9540
aaagccacct ctcagcagcc ctttcctgag caccttctgt gtgcggggac atcagcagtg   9600
gcaacacagc catgctgggg actcagggct agagacaggg gaccagccta tggagagtgg   9660
gtagtgtcct gcagggcagg cttgtgccct ggagaaaaca aaccagggtg aggccaggga   9720
cgctggccgg gttcacaggg tgatggctga gcacagagtg ccaggggctg gactgtcctg   9780
actctgggtt ggtggctgag ggcctgtgtc cctctatgcc tctgggttgg tgataatgga   9840
aacttgctcc ctggagagac aggacgaatg gttgatggga aatgaatgtt tgcttgtcac   9900
ttggttgact gttgttgccg ttagcattgg gcttcttggg ccaggcagcc tcaggccagc   9960
actgctgggc tccccacagg cccgacaccc tcagccctgt gcagctggcc tggcgaaacc  10020
aagaggccct gatgcccaaa atagccggga aaccccaacc agcccagccc tggcagcagg  10080
tgcctcccat ttgcctgggc tgggggaggg gtggctctgg ttctggaagt ttctgccagt  10140
ccagctggag aagggacctg tatcccagca cccaggccgc ccaagcccct gcaccagggc  10200
ctgggccagg cagagttgac atcaatcaat tgggagctgc tggaatgcat ggaggcggcg  10260
ctctcgaggc tggaggaggc cagctgattt aaatcggtcc gcgtacgatg catattaccc  10320
tgttatccct accgcggtta ctggccgtcg ttttacaacg tcgtgactgg gaaaaccctg  10380
gcgatgctct tctcccggtg aaaacctctg acacatggct cttctaaatc cggagtttaa  10440
acgcttcctt catgtgagca aaaggccagc aaaaggccag gaaccgtaaa aaggccgcgt  10500
tgctggcgtt tttccatagg ctccgccccc ctgacgagca tcacaaaaat cgacgctcaa  10560
gtcagaggtg gcgaaacccg acaggactat aaagatacca ggcgtttccc cctggaagct  10620
ccctcgtgcg ctctcctgtt ccgaccctgc cgcttaccgg atacctgtcc gcctttctcc  10680
cttcgggaag cgtggcgctt tctcatagct cacgctgtag gtatctcagt tcggtgtagg  10740
tcgttcgctc caagctgggc tgtgtgcacg aaccccccgt tcagcccgac cgctgcgcct  10800
```

tatccggtaa ctatcgtctt gagtccaacc cggtaagaca cgacttatcg ccactggcag 10860
cagccactgg taacaggatt agcagagcga ggtatgtagg cggtgctaca gagttcttga 10920
agtggtggcc taactacggc tacactagaa ggacagtatt tggtatctgc gctctgctga 10980
agccagttac cttcggaaaa agagttggta gctcttgatc cggcaaacaa accaccgctg 11040
gtagcggtgg tttttttgtt tgcaagcagc agattacgcg cagaaaaaaa ggatctcaag 11100
aagatccttt gatcttttct acggggtctg acgctcagtg gaacgaaaac tcacgttaag 11160
ggattttggt catgcctagg tggcaaacag ctattatggg tattatgggt ctaccggtgc 11220
atgagattat caaaaaggat cttcacctag atccttttaa attaaaaatg aagttttaaa 11280
tcaatctaaa gtatatatga gtaaacttgg tctgacagtt accaatgctt aatcagtgag 11340
gcacctatct cagcgatctg tctatttcgt tcatccatag ttgcctgact ccccgtcgtg 11400
tagataacta cgatacggga gggcttacca tctggcccca gtgctgcaat gataccgcga 11460
gacccacgct caccggctcc agatttatca gcaataaacc agccagccgg aagggccgag 11520
cgcagaagtg gtcctgcaac tttatccgcc tccatccagt ctattaattg ttgccgggaa 11580
gctagagtaa gtagttcgcc agttaatagt ttgcgcaacg ttgttgccat tgctacaggc 11640
atcgtggtgt cacgctcgtc gtttggtatg gcttcattca gctccggttc ccaacgatca 11700
aggcgagtta catgatcccc catgttgtgc aaaaaagcgg ttagctcctt cggtcctccg 11760
atcgttgtca gaagtaagtt ggccgcagtg ttatcactca tggttatggc agcactgcat 11820
aattctctta ctgtcatgcc atccgtaaga tgcttttctg tgactggtga gtactcaacc 11880
aagtcattct gagaatagtg tatgcggcga ccgagttgct cttgcccggc gtcaatacgg 11940
gataataccg cgccacatag cagaacttta aaagtgctca tcattggaaa acgttcttcg 12000
gggcgaaaac tctcaaggat cttaccgctg ttgagatcca gttcgatgta acccactcgt 12060
gcacccaact gatcttcagc atcttttact ttcaccagcg tttctgggtg agcaaaaaca 12120
ggaaggcaaa atgccgcaaa aaagggaata agggcgacac ggaaatgttg aatactcata 12180
ctcttccttt ttcaatatta ttgaagcatt tatcagggtt attgtctcgg gagcggatac 12240
atatttgaat gtatttagaa aaa 12263

<210> SEQ ID NO 46
<211> LENGTH: 12639
<212> TYPE: DNA
<213> ORGANISM: Artificial Sequence
<220> FEATURE:
<223> OTHER INFORMATION: Synthetic

<400> SEQUENCE: 46
taaacaaata ggggttccgc gcacatttcc ccgaaaagtg ccacctgacg tcgctgagca 60
ggccctggcc tccctggccg agggcggttt gcgtattaga ggcctaaatg gccgaattca 120
gcggataaca atttcacaca ggaaacagct atgaccatga ttatctagta actataacgg 180
tcctaaggta gcgagcgatc gcttaattaa cctgcaggga tatcccatgg gggccgccag 240
tgtgatggat atctgcagaa ttcgcccttg atattaagag aagggcaagt cagcttaagt 300
ttgggggtag aggggaacag ggagtgagga gatctggcct gagagatagg agccctggtg 360
gccacaggag gactctttgg gtcctgtcgg atggacacag ggcggcccgg gggcatgttg 420
gagcccggct ggttcttacc agaggcaggg ggcaccctct gacacgggag cagggcatgt 480
tccatacatg acacacccct ctgctccagg gcaggtgggt ggcggcacag aggagccagg 540
gactctgagc aaggggtcca ccagtggggc agttggatcc agacttctct gggccagcga 600

```
gagtctagcc ctcagccgtt ctctgtccag gagggggggtg gggcaggcct gggcggccag    660
agctcatccc tcaagggttc ccagggtcct gccagaccca gatttccgac cgcagccacc    720
acaagaggat gtggtctgct gtggcagctg ccaagacctt gcagcaggtg cagggtgggg    780
gggtgggggc acctgggggc agctggggtc actgagttca gggaaaaccc ctttttttccc   840
ctaaacctgg ggccatccct aggggaaacc acaacttctg agccctgggc agtggctgct    900
gggagggaag agcttcatcc tggaccctgg gggggaaccc agctccaaag gtgcaagggg    960
cccaggtcca aggctagagt gggccaagca ccgcaatggc cagggagtgg gggaggtgga   1020
gctggactgg atcagggcct ccttgggact ccctacaccc tgtgtgacat gttagggtac   1080
ccacacccca tcaccagtca gggcctggcc catctccagg gccagggatg tgcatgtaag   1140
tgtgtgtgag tgtgtgtgtg tggtgtagta cacccccttgg catccggttc cgaggccttg  1200
ggttcctcca aagttgctct ctgaattagg tcaaactgtg aggtcctgat cgccatcatc   1260
aacttcgttc tccccacctc ccatcattat caagagctgg ggagggtctg ggatttcttc   1320
ccacccacaa gccaaaagat aagcctgctg gtgatggcag aagacacagg atcctgggtc   1380
agagacaaag gccagtgtgt cacagcgaga gaggcagccg gactatcagc tgtcacagag   1440
aggccttagt ccgctgaact caggccccag tgactcctgt tccactgggc actggccccc   1500
ctccacagcg cccccaggcc ccagggagag gcgtcacagc ttagagatgg ccctgctgaa   1560
cagggaacaa gaacaggtgt gccccatcca gcgccccagg ggtgggacag gtgggctgga   1620
tttggtgtga agcccttgag ccctggaacc caaccacagc agggcagttg gtagatgcca   1680
tttggggaga ggccccagga gtaagggcca tgggcccttg agggggccag gagctgagga   1740
cagggacaga gacggcccag gcagaggaca gggccatgag gggtgcactg agatggccac   1800
tgccagcagg ggcagctgcc aacccgtcca gggaacttat tcagcagtca gctggaggtg   1860
ccattgaccc tgagggcaga tgaagcccag gccaggctag gtgggctgtg aagaccccag   1920
gggacagagc tctgtccctg ggcagcactg gcctctcatt ctgcagggct tgacgggatc   1980
ccaaggcctg ctgcccctga tggtagtggc agtaccgccc agagcaggac cccagcatgg   2040
aaaccccaac gggacgcagc ctgcggagcc cacaaaacca gtaaggagcc gaagcagtca   2100
tggcacgggg agtgtggact tccctttgat ggggcccagg catgaaggac agaatgggac   2160
agcggccatg agcagaaaat cagccggagg ggatgggcct aggcagacgc tggctttatt   2220
tgaagtgttg gcattttgtc tggtgtgtat tgttggtatt gattttattt tagtatgtca   2280
gtgacatact gacatattat gtaacgacat attattatgt gttttaagaa gcactccaag   2340
ggaacaggct gtctgtaatg tgtccagaga agagagcaag agcttggctc agtctccccc   2400
aaggaggtca gttcctcaac aggggtccta aatgtttcct ggagccaggc ctgaatcaag   2460
ggggtcatat ctacacgtgg ggcagaccca tggaccattt tcggagcaat aagatggcag   2520
ggaggatacc aagctggtct tacagatcca gggctttgac ctgtgacgcg ggcgctcctc   2580
caggcaaagg gagaagccag caggaagctt tcagaactgg ggagaacagg gtgcagacct   2640
ccagggtctt gtacaacgca ccctttatcc tggggtccag gaggggtcac tgagggattt   2700
aagtggggga ccatcagaac caggtttgtg ttttggaaaa atggctccaa agcagagacc   2760
agtgtgaggc cagattagat gatgaagaag aggcagtgga aagtcgatgg gtggccaggt   2820
agcaagaggg cctatggagt tggcaagtga atttaaagtg gtggcaccag agggcagatg   2880
gggaggagca ggcactgtca tggactgtct atagaaatct aaaatgtata cccttttttag  2940
```

-continued

```
caatatgcag tgagtcataa aagaacacat atatatttcc tttggccggc cggcgcgcca   3000
cgcgtataac ttcgtatagc atacattata cgaagttatc ttaagggcta tggcagggcc   3060
tgccgccccg acgttggctg cgagccctgg gccttcaccc gaacttgggg ggtggggtgg   3120
ggaaaaggaa gaaacgcggg cgtattggcc ccaatggggt ctcggtgggg tatcgacaga   3180
gtgccagccc tgggaccgaa ccccgcgttt atgaacaaac gacccaacac cgtgcgtttt   3240
attctgtctt tttattgccg tcatagcgcg ggttccttcc ggtattgtct ccttccgtgt   3300
ttcactcgag ttagaagaac tcgtcaagaa ggcgatagaa ggcgatgcgc tgcgaatcgg   3360
gagcggcgat accgtaaagc acgaggaagc ggtcagccca ttcgccgcca agctcttcag   3420
caatatcacg ggtagccaac gctatgtcct gatagcggtc cgccacaccc agccggccac   3480
agtcgatgaa tccagaaaag cggccatttt ccaccatgat attcggcaag caggcatcgc   3540
catgggtcac gacgagatcc tcgccgtcgg gcatgcgcgc cttgagcctg gcgaacagtt   3600
cggctggcgc gagcccctga tgctcttcgt ccagatcatc ctgatcgaca agaccggctt   3660
ccatccgagt acgtgctcgc tcgatgcgat gtttcgcttg gtggtcgaat gggcaggtag   3720
ccggatcaag cgtatgcagc cgccgcattg catcagccat gatggatact ttctcggcag   3780
gagcaaggtg agatgacagg agatcctgcc ccggcacttc gcccaatagc agccagtccc   3840
ttcccgcttc agtgacaacg tcgagcacag ctgcgcaagg aacgcccgtc gtggccagcc   3900
acgatagccg cgctgcctcg tcctgcagtt cattcagggc accggacagg tcggtcttga   3960
caaaaagaac cgggcgcccc tgcgctgaca gccggaacac ggcggcatca gagcagccga   4020
ttgtctgttg tgcccagtca tagccgaata gcctctccac ccaagcggcc ggagaacctg   4080
cgtgcaatcc atcttgttca atggccgatc ccattccaga tctgttagcc tcccccatct   4140
cccgtgcaaa cgtgcgcgcc aggtcgcaga tcgtcggtat ggagcctggg gtggtgacgt   4200
gggtctggat catcccggag gtaagttgca gcagggcgtc ccggcagccg gcgggcgatt   4260
ggtcgtaatc caggataaag acgtgcatgg gacggaggcg tttggtcaag acgtccaagg   4320
cccaggcaaa cacgttgtac aggtcgccgt tgggggccag caactcgggg gcccgaaaca   4380
gggtaaataa cgtgtccccg atatggggtc gtgggcccgc gttgctctgg ggctcggcac   4440
cctggggcgg cacggccgtc cccgaaagct gtccccaatc ctcccgccac gacccgccgc   4500
cctgcagata ccgcaccgta ttggcaagca gcccgtaaac gcggcgaatc gcggccagca   4560
tagccaggtc aagccgctcg ccggggcgct ggcgtttggc caggcggtcg atgtgtctgt   4620
cctccggaag ggcccccaac acgatgtttg tgccgggcaa ggtcggcggg atgagggcca   4680
cgaacgccag cacggcctgg ggggtcatgc tgcccataag gtatcgcgcg gccgggtagc   4740
acaggagggc ggcgatggga tggcggtcga agatgagggt gagggccggg ggcggggcat   4800
gtgagctccc agcctccccc ccgatatgag gagccagaac ggcgtcggtc acggcataag   4860
gcatgcccat tgttatctgg gcgcttgtca ttaccaccgc cgcgtccccg gccgatatct   4920
caccctggtc aaggcggtgt tgtgtggtgt agatgttcgc gattgtctcg gaagccccca   4980
gcacccgcca gtaagtcatc ggctcgggta cgtagacgat atcgtcgcgc gaacccaggg   5040
ccaccagcag ttgcgtggtg gtggttttcc ccatcccgtg gggaccgtct atataaaccc   5100
gcagtagcgt gggcattttc tgctccgggc ggacttccgt ggcttcttgc tgccggcgag   5160
ggcgcaacgc cgtacgtcgg ttgctatggc cgcgagaacg cgcagcctgg tcgaacgcag   5220
acgcgtgctg atggccgggg tacgaagcca tggtggctct agaggtcgaa aggcccggag   5280
atgaggaaga ggagaacagc gcggcagacg tgcgcttttg aagcgtgcag aatgccgggc   5340
```

-continued

```
ttccggagga ccttcgggcg cccgccccgc ccctgagccc gcccctgagc ccgcccccgg   5400

acccacccct tcccagcctc tgagcccaga aagcgaagga gccaaagctg ctattggccg   5460

ctgccccaaa ggcctacccg cttccattgc tcagcggtgc tgtccatctg cacgagacta   5520

gtgagacgtg ctacttccat ttgtcacgtc ctgcacgacg cgagctgcgg ggcggggggg   5580

aacttcctga ctaggggagg agtagaaggt ggcgcgaagg ggccaccaaa gaacggagcc   5640

ggttggcgcc taccggtgga tgtggaatgt gtgcgaggcc agaggccact tgtgtagcgc   5700

caagtgccca gcggggctgc taaagcgcat gctccagact gccttgggaa aagcgcctcc   5760

cctacccggt agggatccgc gttacataac ttacggtaaa tggcccgcct ggctgaccgc   5820

ccaacgaccc ccgcccattg acgtcaataa tgacgtatgt tcccatagta acgccaatag   5880

ggactttcca ttgacgtcaa tgggtggagt atttacggta aactgcccac ttggcagtac   5940

atcaagtgta tcatatgcca agtacgcccc ctattgacgt caatgacggt aaatggcccg   6000

cctggcatta tgcccagtac atgaccttat gggactttcc tacttggcag tacatctacg   6060

tattagtcat cgctattacc atggtgatgc ggttttggca gtacatcaat gggcgtggat   6120

agcggtttga ctcacgggga tttccaagtc tccaccccat tgacgtcaat gggagtttgt   6180

tttggcacca aaatcaacgg ttaacaagct tagatctgcg gccgcgtcga cgataaattg   6240

tgtaattcca cttctaagga ttcatcccaa gggggaaaa taatcaaaga tgtaaccaaa   6300

ggtttacaaa caagaactca tcattaatct tccttgttgt tatttcaacg atattattat   6360

tattactatt attattatta ttattttgtc tttttgcatt ttctagggcc actcccacgg   6420

catagagagg ttcccaggct aggggtcaaa tcggagctac agctgccggc ctacgccaga   6480

gccacagcaa cgcaggatct gagccacagc aatgcaggat ctacaccaca gctcatggta   6540

acgctggatc cttaacccaa tgagtgaggc cagggatcga acctgtaact tcatggttcc   6600

tagtcggatt cattaaccac tgagccacga caggaactcc aacattatta atgatgggag   6660

aaaactggaa gtaacctaaa tatccagcag aaagggtgtg gccaaataca gcatggagta   6720

gccatcataa ggaatcttac acaagcctcc aaaattgtgt ttctgaaatt gggtttaaag   6780

tacgtttgca ttttaaaaag cctgccagaa aatacagaaa aatgtctgtg atatgtctct   6840

ggctgatagg attttgctta gttttaattt tggctttata attttctata gttatgaaaa   6900

tgttcacaag aagatatatt tcattttagc ttctaaaata attataacac agaagtaatt   6960

tgtgctttaa aaaaatattc aacacagaag tatataaagt aaaaattgag gagttcccat   7020

cgtggctcag tgattaacaa acccaactag tatccatgag gatatggatt tgatccctgg   7080

ccttgctcag tgggttgagg atccagtgtt gctgtgagct gtggtgtagg ttgcagacac   7140

agcactctgg cgttgctgtg actctggcgt aggccggcag ctacagctcc atttggaccc   7200

ttagcctggg aacctccata tgcctgagat acggccctaa aaagtcaaaa gccaaaaaaa   7260

tagtaaaaat tgagtgtttc tacttaccac ccctgcccac atcttatgct aaaacccgtt   7320

ctccagagac aaacatcgtc aggtgggtct atatatttcc agccctcctc ctgtgtgtgt   7380

atgtccgtaa aacacacaca cacacacaca cacgcacaca cacacacacg tatctaatta   7440

gcattggtat tagtttttca aaagggaggt catgctctac cttttaggcg gcaaatagat   7500

tatttaaaca aatctgttga cattttctat atcaacccat aagatctccc atgttcttgg   7560

aaaggctttg taagacatca acatctgggt aaaccagcat ggtttttagg gggttgtgtg   7620

gatttttttc atattttta gggcacacct gcagcatatg gaggttccca ggctaggggt   7680
```

-continued

```
tgaatcagag ctgtagctgc cggcctacac cacagccaca gcaacgccag atccttaacc   7740
cactgagaaa ggccagggat tgaacctgca tcctcatgga tgctggtcag atttatttct   7800
gctgagccac aacaggaact ccctgaacca gaatgctttt aaccattcca ctttgcatgg   7860
acatttagat tgtttccatt taaaaataca aattacaagg agttcccgtc gtggctcagt   7920
ggtaacgaat tggactagga accatgaggt ttcgggttcg atccctggcc ttgctcggtg   7980
ggttaaggat ccagcattga tgtgagatat ggtgtaggtc gcagacgtgg ctcggatccc   8040
acgttgctgt ggctctggcg taggccggca acaacagctc cgattcgacc cctagcctgg   8100
gaacctccat gtgccacagg agcagcccta gaaaaggcaa aaagacaaaa aaataaaaaa   8160
ttaaaatgaa aaaataaaat aaaaatacaa attacaagag acggctacaa ggaaatcccc   8220
aagtgtgtgc aaatgccata tatgtataaa atgtactagt gtctcctcgc gggaaagttg   8280
cctaaaagtg ggttggctgg acagagagga caggctttga cattctcata ggtagtagca   8340
atgggcttct caaaatgctg ttccagttta cactcaccat agcaaatgac agtgcctctt   8400
cctctccacc cttgccaata atgtgacagg tggatctttt tctattttgt gtatctgaca   8460
agcaaaaaat gagaacagga gttcctgtcg tggtgcagtg gagacaaatc tgactaggaa   8520
ccatgaaatt tcgggttcaa tccctggcct cactcagtag gtaaaggatc caggggttgca   8580
gtgagctgtg gggtaggtcg cagacacagt gcaaatttgg ccctgttgtg gctgtggtgt   8640
aggccggcag ctatagctcc aattggaccc ctagcctggg aacctcctta tgccgtgggt   8700
gaggccctaa aaaaaagagt gcaaaaaaaa aaaataagaa caaaaatgat catcgtttaa   8760
ttctttattt gatcattggt gaaacttatt ttccttttat atttttattg actgatttta   8820
tttctcctat gaatttaccg gtcatagttt tgcctgggtg tttttactcc ggttttagtt   8880
ttggttggtt gtattttctt agagagctat agaaactctt catctatttg gaatagtaat   8940
tcctcattaa gtatttgtgc tgcaaaaaat tttccctgat ctgttttatg cttttgtttg   9000
tggggtcttt cacgagaaag cctttttagt ttttacacct cagcttggtt gtttttcttg   9060
attgtgtctg taatctgcgg ccaacatagg aaacacattt ttactttagt gtttttttcc   9120
tattttcttc aagtacgtcc attgttttgg tgtctgattt tactttgcct ggggtttgtt   9180
tttgtgtggc aggaatataa acttatgtat tttccaaatg gagagccaat ggttgtatat   9240
ttgttgaatt caaatgcaac tttatcaaac accaaatcat cgatttatca caactcttct   9300
ctggtttatt gatctaatga tcaattcctg ttccacgctg ttttaattat tttagctttg   9360
tggattttgg tgcctggtag agaacaaagc ctccattatt ttcattcaaa atagtcccgt   9420
ctattatctg ccattgttgt agtattagac tttaaaatca atttactgat tttcaaaagt   9480
tattcctttg gtgatgtgga atactttata cttcataagg tacatggatt catttgtggg   9540
gaattgatgt ctttgctatt gtggccattt gtcaagttgt gtaatatttt acccatgcca   9600
actttgcata ttgtatgtga gtttattccc agggttttta ataggatgtt tattgaagtt   9660
gtcagtgttt ccacaatttc atcgcctcag tgcttactgt ttgcataaaa ggaaacctac   9720
tcacttttgc ctattgctct tgtattcaat cattttagtt aactcttgtg ttaattttga   9780
gagtttttca gctgactgtc tggggttttc tttaatagac tagccctttg tctgtaaaga   9840
ataattttat cgaatttttc ttaacactca cactctcccc acccccaccc ccgctcatct   9900
cctttcattg ggtcaaatct gtagaataca ataaaagtaa gagtgggaac cttagccttt   9960
aagtcgattt tgcctttaaa tgtgaatgtt gctatgtttc gggacattct ctttatcaag  10020
ttgcggatgt ttccttagat aattaactta ataaaagact ggatgtttgc tttcttcaaa  10080
```

-continued

```
tcagaattgt gttgaattta tattgctatt ctgtttaatt ttgtttcaaa aaatttacat  10140
gcacacctta aagataacca tgaccaaata gtcctcctgc tgagagaaaa tgttggcccc  10200
aatgccacag gttacctccc gactcagata aactacaatg ggagataaaa tcagatttgg  10260
caaagcctgt ggattcttgc cataactctc agagcatgac ttgggtgttt tttccttttc  10320
taagtatttt aatggtattt ttgtgttaca ataggaaatc taggacacag agagtgattc  10380
aatgagggga acgcattctg ggatgactct aggcctctgg tttggggaga gctctattga  10440
agtaaagaca atgagaggaa gcaagtttgc agggaactgt gaggaattta gatggggaat  10500
gttgggtttg aggtttctat agggcacgca agcagagatg cactcaggag gaagaaggag  10560
cataaatcta gtggcgctgc cggcaagctt gctggaggag gccaattggg agctgctgga  10620
atgcatggag gcggcgctct cgaggctgga ggaggccagc tgatttaaat cggtccgcgt  10680
acgatgcata ttaccctgtt atccctaccg cggttactgg ccgtcgtttt acaacgtcgt  10740
gactgggaaa accctggcga tgctcttctc ccggtgaaaa cctctgacac atggctcttc  10800
taaatccgga gtttaaacgc ttccttcatg tgagcaaaag gccagcaaaa ggccaggaac  10860
cgtaaaaagg ccgcgttgct ggcgtttttc cataggctcc gcccccctga cgagcatcac  10920
aaaaatcgac gctcaagtca gaggtggcga aacccgacag gactataaag ataccaggcg  10980
tttccccctg gaagctccct cgtgcgctct cctgttccga ccctgccgct taccggatac  11040
ctgtccgcct ttctcccttc gggaagcgtg gcgctttctc atagctcacg ctgtaggtat  11100
ctcagttcgg tgtaggtcgt tcgctccaag ctgggctgtg tgcacgaacc ccccgttcag  11160
cccgaccgct gcgccttatc cggtaactat cgtcttgagt ccaacccggt aagacacgac  11220
ttatcgccac tggcagcagc cactggtaac aggattagca gagcgaggta tgtaggcggt  11280
gctacagagt tcttgaagtg gtggcctaac tacggctaca ctagaaggac agtatttggt  11340
atctgcgctc tgctgaagcc agttaccttc ggaaaaagag ttggtagctc ttgatccggc  11400
aaacaaacca ccgctggtag cggtggtttt tttgtttgca agcagcagat tacgcgcaga  11460
aaaaaaggat ctcaagaaga tcctttgatc ttttctacgg ggtctgacgc tcagtggaac  11520
gaaaactcac gttaagggat tttggtcatg cctaggtggc aaacagctat tatgggtatt  11580
atgggtctac cggtgcatga gattatcaaa aaggatcttc acctagatcc ttttaaatta  11640
aaaatgaagt tttaaatcaa tctaaagtat atatgagtaa acttggtctg acagttacca  11700
atgcttaatc agtgaggcac ctatctcagc gatctgtcta tttcgttcat ccatagttgc  11760
ctgactcccc gtcgtgtaga taactacgat acgggagggc ttaccatctg gccccagtgc  11820
tgcaatgata ccgcgagacc cacgctcacc ggctccagat ttatcagcaa taaaccagcc  11880
agccggaagg gccgagcgca gaagtggtcc tgcaacttta tccgcctcca tccagtctat  11940
taattgttgc cgggaagcta gagtaagtag ttcgccagtt aatagtttgc gcaacgttgt  12000
tgccattgct acaggcatcg tggtgtcacg ctcgtcgttt ggtatggctt cattcagctc  12060
cggttcccaa cgatcaaggc gagttacatg atcccccatg ttgtgcaaaa aagcggttag  12120
ctccttcggt cctccgatcg ttgtcagaag taagttggcc gcagtgttat cactcatggt  12180
tatggcagca ctgcataatt ctcttactgt catgccatcc gtaagatgct tttctgtgac  12240
tggtgagtac tcaaccaagt cattctgaga atagtgtatg cggcgaccga gttgctcttg  12300
cccggcgtca atacgggata ataccgcgcc acatagcaga actttaaaag tgctcatcat  12360
tggaaaacgt tcttcggggc gaaaactctc aaggatctta ccgctgttga gatccagttc  12420
```

```
gatgtaaccc actcgtgcac ccaactgatc ttcagcatct tttactttca ccagcgtttc  12480

tgggtgagca aaaacaggaa ggcaaaatgc cgcaaaaaag ggaataaggg cgacacggaa  12540

atgttgaata ctcatactct tcctttttca atattattga agcatttatc agggttattg  12600

tctcgggagc ggatacatat ttgaatgtat ttagaaaaa                         12639
```

<210> SEQ ID NO 47
<211> LENGTH: 12297
<212> TYPE: DNA
<213> ORGANISM: Artificial Sequence
<220> FEATURE:
<223> OTHER INFORMATION: Synthetic

<400> SEQUENCE: 47

```
taaacaaata ggggttccgc gcacatttcc ccgaaaagtg ccacctgacg tcgctgagca     60

ggccctggcc tccctggccg agggcggttt gcgtattaga ggcctaaatg gccgaattca    120

gcggataaca atttcacaca ggaaacagct atgaccatga ttatctagta actataacgg    180

tcctaaggta gcgagcgatc gcttaattaa cctgcaggga taaccactga cccatgacgg    240

gaactcccag ggctcagctc ttgactccag gttcgcagct gccctcaaag caatgcaacc    300

ctggctggcc ccgcctcatg catccggcct cctccccaaa gagctctgag cccacctggg    360

cctaggtcct cctccctggg actcatggcc taagggtaca gagttactgg ggctgatgaa    420

gggaccaatg ggacaggggg cctcaaatca aagtggctgt ctctctcatg tcccttcctc    480

tcctcagggt ccaaaatcag ggtcagggcc ccagggcagg ggctgagagg gcctctttct    540

gaaggccctg tctcagtgca ggttatgggg gtctgggga gggtcaatgc agggctcacc    600

cttcagtgcc ccaaagccta gagagtgagt gcctgccagt ggcttcccag gcccaatccc    660

ttgactgcct gggaatgctc aaatgcagga actgtcacaa caccttcagt caggggctgc    720

tctgggagga aaaacactca gaattggggg ttcagggaag gcccagtgcc aagcatagca    780

ggagctcagg tggctgcaga tggtgtgaac cccaggagca ggatggccgg cactcccccc    840

agaccctcca gagccccagg ttggctgccc tcttcactgc cgacacccct gggtccactt    900

ctgccctttc ccacctaaaa cctttagggc tcccactttc tcccaaatgt gagacatcac    960

cacggctccc agggagtgtc cagaagggca tctggctgag aggtcctgac atctgggagc   1020

ctcaggcccc acaatggaca gacgccctgc caggatgctg ctgcagggct gttagctagg   1080

cggggtggag atggggtact ttgcctctca gaggccccgg ccccaccatg aaacctcagt   1140

gacaccccat ttccctgagt tcacatacct gtatcctact ccagtcacct tccccacgaa   1200

cccctgggag cccaggatga tgctggggct ggagccacga ccagcccacg agtgatccag   1260

ctctgccaat cagcagtcat ttcccaagtg ttccagccct gccaggtccc actacagcag   1320

taatggaggc cccagacacc agtccagcag ttagagggct ggactagcac cagctttcaa   1380

gcctcagcat ctcaaggtga atggccagtg cccctccccg tggccatcac aggatcgcag   1440

atatgaccct aggggaagaa atatcctggg agtaaggaag tgcccatact caaggatggc   1500

ccctctgtga cctaacctgt ccctgaggat tgtacttcca ggcgttaaaa cagtagaacg   1560

cctgcctgtg aacccccgcc aagggactgc ttggggaggc cccctaaacc agaacacagg   1620

cactccagca ggacctctga actctgacca ccctcagcaa gtgggcaccc cccgcagctt   1680

ccaaggcacc ccagggctca ccacagcggc ccctcctggc agcccctcac ccaggcccag   1740

accctctaag atggcacatc taagccaatc cacctccttg tcattcctcc tgtccccacc   1800

caggaccctt ctcagatgaa accttcgctc cagccgctgg gccctctctc ctgcccctct   1860
```

-continued

```
ggcagttctc cagggactcc gcctcccact ctctgtctct ccctgcactc ctaggaacaa   1920
gcgacctcca ggaagcccag tccaattatc ccctctgtgt cctccccaat ctctgcctct   1980
gggtggattt gagcaccaca tcctgttctc ttcgacctga aactccttgg ccccggtgtc   2040
cgctctcctg ggccctcttt tctctcctcc cctcttccgt gccccgtttg tttggtgtta   2100
caggcaggcc ccggggagcc gtccctccag ctgctcttcc ttgtctgtct caggagccag   2160
aaactggcag catctaaaaa gggctcctgt ttcttcatct gcccagcctc ctagcccaac   2220
cagggctctg gcctcactcc agagggtggg ctccagaggg caggggttgc accctcttag   2280
tgcctcagag gctcagctgg gtgcaggatg ggggggccct cagggagccc ctcagtgact   2340
gctgatcact tactgcagga ctgttcccag ctcttcccaa tcattggaat gacaatacct   2400
agttctgctc catcatagtg atgcaggaaa aatgttactg aaatcctggt tcttgtttag   2460
caatcgaaga atgaattccg cgaacacaca ggcagcaagc aagcgaagcc tttattaaag   2520
gaaagcagat agctcccagg gctgcaggga gcggggagaa gagctcccca ctctctattg   2580
tcctataggg ctttttaccc cttaaagttg gggggataca aaaaaaatag aagaaaaagg   2640
gagttcccgt cagggcacag cagaaacaaa tccaactagg aaccatgagg ttgggggttc   2700
gattcctggc ctctctcagt gggttaagga tgcagcgttg ccgtgagcta tgatacaggt   2760
cacagatgca gctcagatct actagtcaat tgacaggcgc cggagcagga gctaggcctt   2820
tggccggccg gcgcgccacg cgtataactt cgtatagcat acattatacg aagttatctt   2880
aagggctatg gcagggcctg ccgccccgac gttggctgcg agccctgggc cttcacccga   2940
acttgggggg tggggtgggg aaaaggaaga aacgcgggcg tattggcccc aatggggtct   3000
cggtggggta tcgacagagt gccagccctg ggaccgaacc ccgcgtttat gaacaaacga   3060
cccaacaccg tgcgttttat tctgtctttt tattgccgtc atagcgcggg ttccttccgg   3120
tattgtctcc ttccgtgttt cactcgagtt agaagaactc gtcaagaagg cgatagaagg   3180
cgatgcgctg cgaatcggga gcggcgatac cgtaaagcac gaggaagcgg tcagcccatt   3240
cgccgccaag ctcttcagca atatcacggg tagccaacgc tatgtcctga tagcggtccg   3300
ccacacccag ccggccacag tcgatgaatc cagaaaagcg gccattttcc accatgatat   3360
tcggcaagca ggcatcgcca tgggtcacga cgagatcctc gccgtcgggc atgcgcgcct   3420
tgagcctggc gaacagttcg gctggcgcga gcccctgatg ctcttcgtcc agatcatcct   3480
gatcgacaag accggcttcc atccgagtac gtgctcgctc gatgcgatgt ttcgcttggt   3540
ggtcgaatgg gcaggtagcc ggatcaagcg tatgcagccg ccgcattgca tcagccatga   3600
tggatacttt ctcggcagga gcaaggtgag atgacaggag atcctgcccc ggcacttcgc   3660
ccaatagcag ccagtccctt cccgcttcag tgacaacgtc gagcacagct gcgcaaggaa   3720
cgcccgtcgt ggccagccac gatagccgcg ctgcctcgtc ctgcagttca ttcagggcac   3780
cggacaggtc ggtcttgaca aaaagaaccg ggcgcccctg cgctgacagc cggaacacgg   3840
cggcatcaga gcagccgatt gtctgttgtg cccagtcata gccgaatagc ctctccaccc   3900
aagcggccgg agaacctgcg tgcaatccat cttgttcaat ggccgatccc attccagatc   3960
tgttagcctc ccccatctcc cgtgcaaacg tgcgcgccag gtcgcagatc gtcggtatgg   4020
agcctggggt ggtgacgtgg gtctggatca tcccggaggt aagttgcagc agggcgtccc   4080
ggcagccggc gggcgattgg tcgtaatcca ggataaagac gtgcatggga cggaggcgtt   4140
tggtcaagac gtccaaggcc caggcaaaca cgttgtacag gtcgccgttg gggccagca    4200
```

```
actcgggggc ccgaaacagg gtaaataacg tgtccccgat atggggtcgt gggcccgcgt   4260
tgctctgggg ctcggcaccc tggggcggca cggccgtccc cgaaagctgt ccccaatcct   4320
cccgccacga cccgccgccc tgcagatacc gcaccgtatt ggcaagcagc ccgtaaacgc   4380
ggcgaatcgc ggccagcata gccaggtcaa gccgctcgcc ggggcgctgg cgtttggcca   4440
ggcggtcgat gtgtctgtcc tccggaaggg cccccaacac gatgtttgtg ccgggcaagg   4500
tcggcgggat gagggccacg aacgccagca cggcctgggg ggtcatgctg cccataaggt   4560
atcgcgcggc cgggtagcac aggagggcgg cgatgggatg gcggtcgaag atgagggtga   4620
gggccggggg cggggcatgt gagctcccag cctccccccc gatatgagga gccagaacgg   4680
cgtcggtcac ggcataaggc atgcccattg ttatctgggc gcttgtcatt accaccgccg   4740
cgtccccggc cgatatctca ccctggtcaa ggcggtgttg tgtggtgtag atgttcgcga   4800
ttgtctcgga agcccccagc acccgccagt aagtcatcgg ctcgggtacg tagacgatat   4860
cgtcgcgcga acccagggcc accagcagtt gcgtggtggt ggttttcccc atcccgtggg   4920
gaccgtctat ataaacccgc agtagcgtgg gcattttctg ctccgggcgg acttccgtgg   4980
cttcttgctg ccggcgaggg cgcaacgccg tacgtcggtt gctatggccg cgagaacgcg   5040
cagcctggtc gaacgcagac gcgtgctgat ggccggggta cgaagccatg gtggctctag   5100
aggtcgaaag gcccggagat gaggaagagg agaacagcgc ggcagacgtg cgcttttgaa   5160
gcgtgcagaa tgccgggctt ccggaggacc ttcgggcgcc cgccccgccc ctgagcccgc   5220
ccctgagccc gcccccggac ccaccccttc ccagcctctg agcccagaaa gcgaaggagc   5280
caaagctgct attggccgct gccccaaagg cctacccgct tccattgctc agcggtgctg   5340
tccatctgca cgagactagt gagacgtgct acttccattt gtcacgtcct gcacgacgcg   5400
agctgcgggg cggggggga cttcctgact aggggaggag tagaaggtgg cgcgaagggg   5460
ccaccaaaga acggagccgg ttggcgccta ccggtggatg tggaatgtgt gcgaggccag   5520
aggccacttg tgtagcgcca agtgcccagc ggggctgcta aagcgcatgc tccagactgc   5580
cttgggaaaa gcgcctcccc tacccggtag ggatccgcgt tacataactt acggtaaatg   5640
gcccgcctgg ctgaccgccc aacgaccccc gcccattgac gtcaataatg acgtatgttc   5700
ccatagtaac gccaataggg actttccatt gacgtcaatg ggtggagtat ttacggtaaa   5760
ctgcccactt ggcagtacat caagtgtatc atatgccaag tacgccccct attgacgtca   5820
atgacggtaa atggcccgcc tggcattatg cccagtacat gaccttatgg gactttccta   5880
cttggcagta catctacgta ttagtcatcg ctattaccat ggtgatgcgg ttttggcagt   5940
acatcaatgg gcgtggatag cggtttgact cacggggatt tccaagtctc caccccattg   6000
acgtcaatgg gagtttgttt tggcaccaaa atcaacggtt aacaagctta taacttcgta   6060
tagcatacat tatacgaagt tattacgtag cggccgcgtc gacgatatcg ctgccggagc   6120
cccggggcc gctgccggaa gatctggcat tgctgtgact gtggtgtagg ccggcagctg   6180
gagctctgat tagacccctc acctgggaat ctccatatgc tgcacgtgcg gccctaaaaa   6240
gacaaaagac aaaaaaaaaa aaaaaaaaaa aaaatcaaaa aaaaacatag gggttacca   6300
acgtggggtc cagaaagatg tggttttctc ccattggcct tgcccagtta cctatatcag   6360
tccttgtcca acaggggttt taggggtgga aatgccccat aaattttacg gtttctttgc   6420
ccttctcttc ctttagactg agtcaccatt gctctcattc cttttctatc agttgaggag   6480
tgggttagag attaaggtcc atgtggtgga ggtacacttc ttatagtaaa caaggcctat   6540
ggggaattac tctctggagc ccttaaacca caaatgataa tccatgccac atcaaagatg   6600
```

-continued

```
catcgaagcc catgctccta cactgactac ctgagttagc attctgcctc aacaggactg   6660
accatcccca gctctggggc agatatcctc tctctgccac aagggcagtg acccccatgc   6720
tgtctgaggg tcacgcttta cccccccccc acccctgccg tgacccccca gaccacccca   6780
ggaggtgggc actaatatcc ctcattaccc catagatgag gaaacagagg ttcccccggg   6840
gtcccacagg tgctcagggt cacatgcacc gtgggcaccc aggccccatc ccaaggccac   6900
cctccctcct caggaagctg tgctgcgctg ggccagaagg tactgcacac gactcctcag   6960
cctccggtgg tgggaggcag cctcaagcct ctgagtgggg gggcacccgg gctcctcaat   7020
ctatactgac tcctgggggt gggagaaggg gagggggagc tgtggcctct gagtccacta   7080
agcaaatcag ggtgggcaat gcgggcccat ttcaaggagg agagaaccga ggctctgaca   7140
gcaggccggg ggtccaggga cctgcccagg gtcataggct gaactgctgg ctgacctgcc   7200
ttgggttctt tccttggctc ctcagccctg tgtgatgtga caggtcattc attcactcac   7260
tcgctcattc attcagcaaa ccctcagtga gccctgctgg gagcaggtgc taggggcaag   7320
gagacaggac ctcttgccct ggaacagctg aagcactggg ggacaggcag tggcagggag   7380
gtgcgtgatc accgctgacc ccattccatc ctccagcccc caggtcagtt tccacccacc   7440
attgacccca ccatgtcctc catccccaag gtcagtttcc cgcccaagga gcatctcctt   7500
acacactagg gacaaaattt cacggctgtc actgggcatc tctccacgct catcacagcc   7560
ctctagcagc cttgaagtcc tgtagagccc ttcccatttc acagaaggga caagactatg   7620
agggccacac cgtgagccat gagccttagg ctgtgagccg ggacagcccc tgcaggactg   7680
gtggcctcag ggcactgggt ggggagggtg cacagtgggt gggccccttg tggaatagag   7740
aggagtgtca ggtcagggga gggggcttgg cctggccctg gcctgcctgg tgtgcaaccc   7800
taggcagccc ctccttccca ggcctcctac ttcctggagg ccaagcctca gggaggtaat   7860
tgagtcaggt gggggagggg gggttgtggc tttcttcaca gcagaaaaac agagcccaca   7920
atagtgtcca ctgagacaga ggggtcctgg gggaggggag gggtgggagg tgactgctga   7980
gccctgtggg agggagggag caactactga gctgagctgg gtgactctcc catctgcccc   8040
gccccctgtg gggccagcag agtcaccgag agaacatgac ccagccaggc ctggacaggg   8100
ggacacccat gtcctttacc ccacagggtt cactgagcct atctgcccca agcctgtgtc   8160
tccctgggac ggagaccctc actcccaacc acaaaggtct aaactcaagt tcccaacagc   8220
cttgaaaata cagcttccgg gggcctccaa ggagcagtca gccgtccact gccaggctcg   8280
ctggctcagt gacacaggac acatcctgat gacggtccac ctgtctccaa gcaggttctc   8340
ctctgccgat ggggcaacga gctcctcctg tggctccctg gctggatgcg tgggaggcgg   8400
ggtggggggg caggcggtgt tcctggccgc acacaaggag cacccccacc agcatccgaa   8460
gacgggggcc cggtctttcc ccaaaacact gcttgcggga gactttgtga cgtttccagg   8520
ggccatgctc ccttcgggca gcttggggga cttctgctcc tatgtggtca cctgcaggga   8580
ctccccccag gccttgggga caaacaaagt gatgagaggg agggttagtg ggtcggggca   8640
gggccagtct ttggaccggt ttatctgaaa agccagttgg tcaccgggaa ccacagcaaa   8700
cctaaaccca tttggccagg catctcccag ggacagtctc ccccaggatg cggggcccag   8760
gggggctcca ggggtgacct gcgtcctgga tttccctgat gctcccagtt cgtgcctctg   8820
tccaagcatg atttttaata gtgccccttc cactcccaga aatgtccaag tgtgggcaat   8880
aaattctggt cacctgagct cagtgtaact gtttgctgaa tgacacttac tgtaacaggt   8940
```

-continued

```
taaaatggga ggcccaaggc cacgcagagc catcgaaggc tctgtgtgtc ccagccctga   9000
tagaagcatc aggatgggga ctgtggcctc accaggggcc acatccaggc ggtcaccatg   9060
gggttcctgg tctccgtggg ccttgactgg agcccctggt gtgagctcac cccatcccag   9120
cctgtgagag gcctggatgt gggcctgaca tcatttccca cccagtgaca gcactgcatg   9180
tgatggggcc tctgggcagc ctttttcccg ggggaaactg gcaggaatca ggaccaccag   9240
gacaggggtc aggggagagg cgatgctggg caccagagcc tggaccaccc tcgggttctc   9300
agcgatgggc aacccctgcc acccagggcc ccgccttcct ggggagacat cggggtttcc   9360
aggccatcct gggaggaggg tgggagcctc agctagaccc cagctggctt gccccccat   9420
gccccggcca agagagggtc ttggagggaa gggggacccc agaccagcct ggcgagccca   9480
tcctcagggt ctctggtcag acaggggctc agctgagctc cagggtagac caaggccctg   9540
cgtggatgag gccagtgtgg tcactgccca gagcaaagcc acctctcagc agccctttcc   9600
tgagcacctt ctgtgtgcgg ggacatcagc agtggcaaca cagccatgct ggggactcag   9660
ggctagagac aggggaccag cctatggaga gtgggtagtg tcctgcaggg caggcttgtg   9720
ccctggagaa aacaaaccag ggtgaggcca gggacgctgg ccgggttcac agggtgatgg   9780
ctgagcacag agtgccaggg gctggactgt cctgactctg ggttggtggc tgagggcctg   9840
tgtccctcta tgcctctggg ttggtgataa tggaaacttg ctccctggag agacaggacg   9900
aatggttgat gggaaatgaa tgtttgcttg tcacttggtt gactgttgtt gccgttagca   9960
ttgggcttct tgggccaggc agcctcaggc cagcactgct gggctcccca caggcccgac  10020
accctcagcc ctgtgcagct ggcctggcga aaccaagagg ccctgatgcc caaaatagcc  10080
gggaaacccc aaccagccca gccctggcag caggtgcctc ccatttgcct gggctggggg  10140
aggggtggct ctggttctgg aagtttctgc cagtccagct ggagaaggga cctgtatccc  10200
agcacccagg ccgcccaagc ccctgcacca gggcctgggc caggcagagt tgacatcaat  10260
caattgggag ctgctggaat gcatggaggc ggcgctctcg aggctggagg aggccagctg  10320
atttaaatcg gtccgcgtac gatgcatatt accctgttat ccctaccgcg gttactggcc  10380
gtcgttttac aacgtcgtga ctgggaaaac cctggcgatg ctcttctccc ggtgaaaacc  10440
tctgacacat ggctcttcta aatccggagt ttaaacgctt ccttcatgtg agcaaaaggc  10500
cagcaaaagg ccaggaaccg taaaaaggcc gcgttgctgg cgtttttcca taggctccgc  10560
ccccctgacg agcatcacaa aaatcgacgc tcaagtcaga ggtggcgaaa cccgacagga  10620
ctataaagat accaggcgtt tccccctgga agctccctcg tgcgctctcc tgttccgacc  10680
ctgccgctta ccggatacct gtccgccttt ctcccttcgg gaagcgtggc gctttctcat  10740
agctcacgct gtaggtatct cagttcggtg taggtcgttc gctccaagct gggctgtgtg  10800
cacgaacccc ccgttcagcc cgaccgctgc gccttatccg gtaactatcg tcttgagtcc  10860
aacccggtaa gacacgactt atcgccactg gcagcagcca ctggtaacag gattagcaga  10920
gcgaggtatg taggcggtgc tacagagttc ttgaagtggt ggcctaacta cggctacact  10980
agaaggacag tatttggtat ctgcgctctg ctgaagccag ttaccttcgg aaaaagagtt  11040
ggtagctctt gatccggcaa acaaaccacc gctggtagcg gtggtttttt tgtttgcaag  11100
cagcagatta cgcgcagaaa aaaaggatct caagaagatc ctttgatctt ttctacgggg  11160
tctgacgctc agtggaacga aaactcacgt taagggattt tggtcatgcc taggtggcaa  11220
acagctatta tgggtattat gggtctaccg gtgcatgaga ttatcaaaaa ggatcttcac  11280
ctagatcctt ttaaattaaa aatgaagttt taaatcaatc taaagtatat atgagtaaac  11340
```

ttggtctgac agttaccaat gcttaatcag tgaggcacct atctcagcga tctgtctatt 11400
tcgttcatcc atagttgcct gactccccgt cgtgtagata actacgatac gggagggctt 11460
accatctggc cccagtgctg caatgatacc gcgagaccca cgctcaccgg ctccagattt 11520
atcagcaata aaccagccag ccggaagggc cgagcgcaga agtggtcctg caactttatc 11580
cgcctccatc cagtctatta attgttgccg ggaagctaga gtaagtagtt cgccagttaa 11640
tagtttgcgc aacgttgttg ccattgctac aggcatcgtg gtgtcacgct cgtcgtttgg 11700
tatggcttca ttcagctccg gttcccaacg atcaaggcga gttacatgat cccccatgtt 11760
gtgcaaaaaa gcggttagct ccttcggtcc tccgatcgtt gtcagaagta agttggccgc 11820
agtgttatca ctcatggtta tggcagcact gcataattct cttactgtca tgccatccgt 11880
aagatgcttt tctgtgactg gtgagtactc aaccaagtca ttctgagaat agtgtatgcg 11940
gcgaccgagt tgctcttgcc cggcgtcaat acgggataat accgcgccac atagcagaac 12000
tttaaaagtg ctcatcattg gaaaacgttc ttcggggcga aaactctcaa ggatcttacc 12060
gctgttgaga tccagttcga tgtaacccac tcgtgcaccc aactgatctt cagcatcttt 12120
tactttcacc agcgtttctg ggtgagcaaa aacaggaagg caaaatgccg caaaaaaggg 12180
aataagggcg acacggaaat gttgaatact catactcttc ctttttcaat attattgaag 12240
catttatcag ggttattgtc tcgggagcgg atacatattt gaatgtattt agaaaaa 12297

<210> SEQ ID NO 48
<211> LENGTH: 12163
<212> TYPE: DNA
<213> ORGANISM: Artificial Sequence
<220> FEATURE:
<223> OTHER INFORMATION: Synthetic

<400> SEQUENCE: 48
gcaaaaggcc aggaaccgta aaaaggccgc gttgctggcg tttttccata ggctccgccc 60
ccctgacgag catcacaaaa atcgacgctc aagtcagagg tggcgaaacc cgacaggact 120
ataaagatac caggcgtttc cccctggaag ctccctcgtg cgctctcctg ttccgaccct 180
gccgcttacc ggatacctgt ccgcctttct cccttcggga agcgtggcgc tttctcaatg 240
ctcacgctgt aggtatctca gttcggtgta ggtcgttcgc tccaagctgg gctgtgtgca 300
cgaacccccc gttcagcccg accgctgcgc cttatccggt aactatcgtc ttgagtccaa 360
cccggtaaga cacgacttat cgccactggc agcagccact ggtaacagga ttagcagagc 420
gaggtatgta ggcggtgcta cagagttctt gaagtggtgg cctaactacg gctacactag 480
aaggacagta tttggtatct gcgctctgct gaagccagtt accttcggaa aaagagttgg 540
tagctcttga tccggcaaac aaaccaccgc tggtagcggt ggtttttttg tttgcaagca 600
gcagattacg cgcagaaaaa aaggatctca agaagatcct ttgatctttt ctacggggtc 660
tgacgctcag tggaacgaaa actcacgtta agggattttg gtcatgagat tatcaaaaag 720
gatcttcacc tagatccttt taaattaaaa atgaagtttt aaatcaatct aaagtatata 780
tgagtaaact tggtctgaca gttaccaatg cttaatcagt gaggcaccta tctcagcgat 840
ctgtctattt cgttcatcca tagttgcctg actccccgtc gtgtagataa ctacgatacg 900
ggagggctta ccatctggcc ccagtgctgc aatgataccg cgagacccac gctcaccggc 960
tccagattta tcagcaataa accagccagc cggaagggcc gagcgcagaa gtggtcctgc 1020
aactttatcc gcctccatcc agtctattaa ttgttgccgg gaagctagag taagtagttc 1080

-continued

```
gccagttaat agtttgcgca acgttgttgc cattgctaca ggcatcgtgg tgtcacgctc   1140
gtcgtttggt atggcttcat tcagctccgg ttcccaacga tcaaggcgag ttacatgatc   1200
ccccatgttg tgcaaaaaag cggttagctc cttcggtcct ccgatcgttg tcagaagtaa   1260
gttggccgca gtgttatcac tcatggttat ggcagcactg cataattctc ttactgtcat   1320
gccatccgta agatgctttt ctgtgactgg tgagtactca accaagtcat tctgagaata   1380
gtgtatgcgg cgaccgagtt gctcttgccc ggcgtcaata cgggataata ccgcgccaca   1440
tagcagaact ttaaaagtgc tcatcattgg aaaacgttct tcggggcgaa aactctcaag   1500
gatcttaccg ctgttgagat ccagttcgat gtaacccact cgtgcaccca actgatcttc   1560
agcatctttt actttcacca gcgtttctgg gtgagcaaaa acaggaaggc aaaatgccgc   1620
aaaaaaggga ataagggcga cacggaaatg ttgaatactc atactcttcc tttttcaata   1680
ttattgaagc atttatcagg gttattgtct catgagcgga tacatatttg aatgtattta   1740
gaaaaataaa caaatagggg ttccgcgcac atttccccga aaagtgccac ctgacgtcaa   1800
acagctatga ccatggcggc cgcgtcgaca gggtgtggcc aaatacagca tggagtagcc   1860
atcataagga atcttacaca agcctccaaa attgtgtttc tgaaattggg tttaaagtac   1920
gtttgcattt taaaaagcct gccagaaaat acagaaaaat gtctgtgata tgtctctggc   1980
tgataggatt ttgcttagtt ttaattttgg ctttataatt ttctatagtt atgaaaatgt   2040
tcacaagaag atatatttca ttttagcttc taaaataatt ataacacaga agtaatttgt   2100
gctttaaaaa aatattcaac acagaagtat ataaagtaaa aattgaggag ttcccatcgt   2160
ggctcagtga ttaacaaacc caactagtat ccatgaggat atggatttga tccctggcct   2220
tgctcagtgg gttgaggatc cagtgttgct gtgagctgtg gtgtaggttg cagacacagc   2280
actctggcgt tgctgtgact ctggcgtagg ccggcagcta cagctccatt tggaccctta   2340
gcctgggaac ctccatatgc ctgagatacg gccctaaaaa gtcaaaagcc aaaaaaatag   2400
taaaaattga gtgtttctac ttaccacccc tgcccacatc ttatgctaaa acccgttctc   2460
cagagacaaa catcgtcagg tgggtctata tatttccagc cctcctcctg tgtgtgtatg   2520
tccgtaaaac acacacacac acacacacac gcacacacac acacacgtat ctaattagca   2580
ttggtattag tttttcaaaa gggaggtcat gctctacctt ttaggcggca aatagattat   2640
ttaaacaaat ctgttgacat tttctatatc aacccataag atctcccatg ttcttggaaa   2700
ggctttgtaa gacatcaaca tctgggtaaa ccagcatggt ttttaggggg ttgtgtggat   2760
ttttttcata ttttttaggg cacacctgca gcatatggag gttcccaggc taggggttga   2820
atcagagctg tagctgccgg cctacaccac agccacagca acgccagatc cttaacccac   2880
tgagaaaggc cagggattga acctgcatcc tcatggatgc tggtcagatt tatttctgct   2940
gagccacaac aggaactccc tgaaccagaa tgcttttaac cattccactt tgcatggaca   3000
tttagattgt ttccatttaa aaatacaaat tacaaggagt tcccgtcgtg gctcagtggt   3060
aacgaattgg actaggaacc atgaggtttc gggttcgatc cctggccttg ctcggtgggt   3120
taaggatcca gcattgatgt gagatatggt gtaggtcgca gacgtggctc ggatcccacg   3180
ttgctgtggc tctggcgtag gccggcaaca acagctccga ttcgacccct agcctgggaa   3240
cctccatgtg ccacaggagc agccctagaa aaggcaaaaa gacaaaaaaa taaaaaatta   3300
aaatgaaaaa ataaaataaa aatacaaatt acaagagacg gctacaagga aatccccaag   3360
tgtgtgcaaa tgccatatat gtataaaatg tactagtgtc tcctcgcggg aaagttgcct   3420
aaaagtgggt tggctggaca gagaggacag gctttgacat tctcataggt agtagcaatg   3480
```

-continued

```
ggcttctcaa aatgctgttc cagtttacac tcaccatagc aaatgacagt gcctcttcct   3540
ctccaccctt gccaataatg tgacaggtgg atctttttct attttgtgta tctgacaagc   3600
aaaaaatgag aacaggagtt cctgtcgtgg tgcagtggag acaaatctga ctaggaacca   3660
tgaaatttcg ggttcaatcc ctggcctcac tcagtaggta aaggatccag ggttgcagtg   3720
agctgtgggg taggtcgcag acacagtgca aatttggccc tgttgtggct gtggtgtagg   3780
ccggcagcta tagctccaat tggaccccta gcctgggaac ctccttatgc cgtgggtgag   3840
gccctaaaaa aaagagtgca aaaaaaaaaa ataagaacaa aaatgatcat cgtttaattc   3900
tttatttgat cattggtgaa acttatttc ctttatatt tttattgact gattttattt   3960
ctcctatgaa tttaccggtc atagttttgc ctgggtgttt ttactccggt tttagttttg   4020
gttggttgta ttttcttaga gagctataga aactcttcat ctatttggaa tagtaattcc   4080
tcattaagta tttgtgctgc aaaaaatttt ccctgatctg ttttatgctt ttgtttgtgg   4140
ggtctttcac gagaaagcct ttttagtttt tacacctcag cttggttgtt tttcttgatt   4200
gtgtctgtaa tctgcggcca acataggaaa cacattttta ctttagtgtt tttttcctat   4260
tttcttcaag tacgtccatt gttttggtgt ctgattttac tttgcctggg gtttgttttt   4320
gtgtggcagg aatataaact tatgtatttt ccaaatggag agccaatggt tgtatatttg   4380
ttgaattcaa atgcaacttt atcaaacacc aaatcatcga tttatcacaa ctcttctctg   4440
gtttattgat ctaatgatca attcctgttc cacgctgttt taattatttt agctttgtgg   4500
attttggtgc ctggtagaga acaaagcctc cattattttc attcaaaata gtcccgtcta   4560
ttatctgcca ttgttgtagt attagacttt aaaatcaatt tactgatttt caaaagttat   4620
tcctttggtg atgtggaata ctttatactt cataaggtac atggattcat ttgtggggaa   4680
ttgatgtctt tgctattgtg gccatttgtc aagttgtgta atattttacc catgccaact   4740
ttgcatattg tatgtgagtt tattcccagg gtttttaata ggatgtttat tgaagttgtc   4800
agtgtttcca caatttcatc gcctcagtgc ttactgtttg cataaaagga aacctactca   4860
cttttgccta ttgctcttgt attcaatcat tttagttaac tcttgtgtta attttgagag   4920
tttttcagct gactgtctgg ggttttcttt aatagactag ccctttgtct gtaaagaata   4980
attttatcga atttttctta acactcacac tctccccacc cccaccccg ctcatctcct   5040
ttcattgggt caaatctgta gaatacaata aaagtaagag tgggaacctt agcctttaag   5100
tcgattttgc ctttaaatgt gaatgttgct atgtttcggg acattctctt tatcaagttg   5160
cggatgtttc cttagataat taacttaata aaagactgga tgtttgcttt cttcaaatca   5220
gaattgtgtt gaatttatat tgctattctg tttaattttg tttcaaaaaa tttacatgca   5280
caccttaaag ataaccatga ccaaatagtc ctcctgctga gagaaaatgt tggccccaat   5340
gccacaggtt acctcccgac tcagataaac tacaatggga gataaaatca gatttggcaa   5400
agcctgtgga ttcttgccat aactctcaga gcatgacttg ggtgtttttt ccttttctaa   5460
gtattttaat ggtattttg tgttacaata ggaaatctag gacacagaga gtgattcaat   5520
gaggggaacg cattctggga tgactctagg cctctggttt ggggagagct ctattgaagt   5580
aaagacaatg agaggaagca agtttgcagg gaactgtgag gaatttagat ggggaatgtt   5640
gggtttgagg tttctatagg gcacgcaagc agagatgcac tcaggaggaa gaaggagcat   5700
aaatctagag gcaaaaagag aggtcaggac tggaaataga gatgcgagac accagggtgg   5760
cagtcagaga gcacagtgtg ggtcagaaga cagtggaaga acacaaggga cagagaggga   5820
```

-continued

```
tctccaactt cactgggatg agggccttgt tggccttgac ctgagagatt tccaggagtt   5880
gagggtggga aggagccgcg gtctaggaag ctttctaggg tacctctagg gatccgaaca   5940
atggaagtcc gagctcatcg ctaataactt cgtatagcat acattatacg aagttatatt   6000
cgatgcggcc gcaaggggtt cgcgtcagcg ggtgttggcg ggtgtcgggg ctggcttaac   6060
tatgcggcat cagagcagag atcccggcgc gccctaccgg gtaggggagg cgcttttccc   6120
aaggcagtct ggagcatgcg ctttagcagc cccgctgggc acttggcgct acacaagtgg   6180
cctctggcct cgcacacatt ccacatccac cggtaggcgc caaccggctc cgttctttgg   6240
tggccccttc gcgccacctt ctactcctcc cctagtcagg aagttccccc ccgccccgca   6300
gctcgcgtcg tgcaggacgt gacaaatgga agtagcacgt ctcactagtc tcgtgcagat   6360
ggacagcacc gctgagcaat ggaagcgggt aggcctttgg ggcagcggcc aatagcagct   6420
ttggctcctt cgctttctgg gctcagaggc tgggaagggg tgggtccggg ggcgggctca   6480
ggggcgggct caggggcggg gcgggcgccc gaaggtcctc cggaagcccg gcattctgca   6540
cgcttcaaaa gcgcacgtct gccgcgctgt tctcctcttc ctcatctccg ggcctttcga   6600
cctgcagcca atatgggatc ggccattgaa caagatggat tgcacgcagg ttctccggcc   6660
gcttgggtgg agaggctatt cggctatgac tgggcacaac agacaatcgg ctgctctgat   6720
gccgccgtgt tccggctgtc agcgcagggg cgcccggttc tttttgtcaa gaccgacctg   6780
tccggtgccc tgaatgaact gcaggacgag gcagcgcggc tatcgtggct ggccacgacg   6840
ggcgttcctt gcgcagctgt gctcgacgtt gtcactgaag cgggaaggga ctggctgcta   6900
ttgggcgaag tgccggggca ggatctcctg tcatctcacc ttgctcctgc cgagaaagta   6960
tccatcatgg ctgatgcaat gcggcggctg catacgcttg atccggctac ctgcccattc   7020
gaccaccaag cgaaacatcg catcgagcga gcacgtactc ggatggaagc cggtcttgtc   7080
aatcaggatg atctggacga agagcatcag gggctcgcgc cagccgaact gttcgccagg   7140
ctcaaggcgc gcatgcccga cggcgaggat ctcgtcgtga cccatggcga tgcctgcttg   7200
ccgaatatca tggtggaaaa tggccgcttt tctggattca tcgactgtgg ccggctgggt   7260
gtggcggatc gctatcagga catagcgttg gctacccgtg atattgctga agagcttggc   7320
ggcgaatggg ctgaccgctt cctcgtgctt tacggtatcg ccgctcccga ttcgcagcgc   7380
atcgccttct atcgccttct tgacgagttc ttctgagggg atcaattctc tagtgaacaa   7440
tggaagtccg agctcatcgc taataacttc gtatagcata cattatacga agttatattc   7500
gatgcggccg caaggggttc gcgtcagcgg gtgttggcgg gtgtcggggc tggcttaact   7560
atgcggcatc agagcagtct agagctcgct gatcagcctc gactgtgcct tctagttgcc   7620
agccatctgt tgtttgcccc tcccccgtgc cttccttgac cctggaaggt gccactccca   7680
ctgtcctttc ctaataaaat gaggaaattg catcgcattg tctgagtagg tgtcattcta   7740
ttctgggggg tggggtgggg caggacagca agggggagga ttgggaagac aatagcaggc   7800
atgctgggga tgcggtgggc tctatggctt ctgaggcgga aagaaccagc tgggggcgcg   7860
cccctcgagg ggaaggtatc tcccaggaaa ctggccagga cacattggtc ctccgccctc   7920
cccttcctcc cactcctcct ccagacagga ctgtgcccac cccctgccac ctttctggcc   7980
agaactgtcc atggcaggtg accttcacat gagcccttcc tccctgcctg ccctagtggg   8040
accctccata cctccccctg gaccccgttg tcctttcttt ccagtgtggc cctgagcata   8100
actgatgcca tcatgggctg ctgacccacc cgggactgtg ttgtgcagtg agtcacttct   8160
ctgtcatcag ggctttgtaa ttgatagata gtgtttcatc atcattagga ccgggtggcc   8220
```

-continued

```
tctatgctct gttagtctcc aaacactgat gaaaaccttc gttggcatag tcccagcttc   8280
ctgttgccca tccataaatc ttgacttagg gatgcacatc ctgtctccaa gcaaccaccc   8340
ctcccctagg ctaactataa aactgtccca atggcccttg tgtggtgcag agttcatgct   8400
tccagatcat ttctctgcta gatccatatc tcaccttgta agtcatccta taataaactg   8460
atccattgat tatttgcttc tgttttttcc atctcaaaac agcttctcag ttcagttcga   8520
atttttatt ccctccatcc acccatactt tcctcagcct ggggaaccct tgcccccagt   8580
cccatgccct tcctccctct ctgcccagct cagcacctgc ccaccctcac ccttcctgtc   8640
actccctagg actggaccat ccactggggc caggacactc cagcagcctt ggcttcatgg   8700
gctctgaaat ccatggccca tctctattcc tcactggatg gcaggttcag agatgtgaaa   8760
ggtctaggag gaagccagga aggaaactgt tgcatgaaag gccggcctga tggttcagta   8820
cttaaataat atgagctctg agctccccag gaaccaaagc atggagggag tatgtgcctc   8880
agaatctctc tgagattcag caaagccttt gctagaggga aaatagtggc tcaaccttga   8940
gggccagcat cttgcaccac agttaaaagt gggtatttgt tttacctgag gcctcagcat   9000
tatgggaacc gggctctgac acaaacacag gtgcagcccg gcagcctcag aacacagcaa   9060
cgaccacaag ctgggacagc tgcccctgaa cggggagtcc accatgcttc tgtctcgggt   9120
accaccaggt caccatccct gggggaggta gttccatagc agtagtcccc tgatttcgcc   9180
cctcgggcgt gtagccaggc aagctcctgc ctctggaccc agggtggacc cttgctcccc   9240
actaccctgc acatgccaga cagtcaagac cactcccacc tctgtctgag gccccccttgg   9300
gtgtcccagg gcccccgagc tgtcctctac tcatggttct tccacctggg tacaaaagag   9360
gcgagggaca cttttctcag gtttgcggct cagaaaggta ccttcctagg gtttgtccac   9420
tgggagtcac ctcccttgca tctcaatgtc agtggggaaa actgggtccc atgggggat   9480
tagtgccact gtgaggcccc tgaagtctgg ggcctctaga cactatgatg atgagggatg   9540
tggtgaaaaa ccccaccccca gcccttcttg ccgggaccct gggctgtggc tcccccattg   9600
cacttggggt cagaggggtg gatggtggct atggtcaggc atgtttccca tgagctgggg   9660
gcaccctggg tgactttctc ctgtgaatcc tgaattagca gctataacaa attgcccaaa   9720
ctcttaggct taaaacaaca cacatttatt cctctgggtc ccagggtcag aagtccaaaa   9780
tgagtcctat aggctaaatt tgaggtgtct ctgggttgag ctcctcctgg aagccttttc   9840
cagcctctag agtcccaagt ccttggctct gggcccctcc ctcaagcttc aaagccacag   9900
aagcttctaa tctctctccc ttcccctctg acctctgctc ccatcctcat accctgtccc   9960
ctcactctga ccctcctgcc tccctctttc ccttataaag accctgcatg gggccacgga  10020
gataatccag ggtaatcgcc cctcttccag cccttaactc catcccatct gcaaaatccc  10080
tgtcacccca taatggacct acagatctcc tagagttaac actggccgtc gttttaccgg  10140
tccgtagtca ggtttagttc gtccggcggc gccagaaatc cgcgcggtgg tttttggggg  10200
tcgggggtgt ttggcagcca cagacgcccg gtgttcgtgt cgcgccagta catgcggtcc  10260
atgcccaggc catccaaaaa ccatgggtct gtctgctcag tccagtcgtg gactgacccc  10320
acgcaacgcc caaaataata acccccacga accataaacc attccccatg gggaccccg   10380
tccctaaccc acggggcccg tggctatggc aggcctgccg cccgacgttg gctgcgagcc  10440
ctgggccttc acccgaactt ggggggtggg gtggggaaaa ggaagaaacg cgggcgtatt  10500
ggccccaatg ggtctcggt ggggtatcga cagagtgcca gccctgggac cgaaccccgc  10560
```

-continued

```
gtttatgaac aaacgaccca acacccgtgc gttttattct gtctttttat tgccgacata  10620

gcgcgggttc cttccggtat tgtctccttc cgtgtttcag ttagcctccc ccatctcccg  10680

tgcaaacgtg cgcgccaggt cgcagatcgt cggtatggag cctggggtgg tgacgtgggt  10740

ctggatcatc ccggaggtaa gttgcagcag ggcgtcccgg cagccggcgg gcgattggtc  10800

gtaatccagg ataaagacgt gcatgggacg gaggcgtttg gccaagacgt ccaaggccca  10860

ggcaaacacg ttgtacaggt cgccgttggg ggccagcaac tcgggggccc gaaacagggt  10920

aaataacgtg tccccgatat ggggtcgtgg gcccgcgttg ctctggggct cggcaccctg  10980

gggcggcacg gccgtccccg aaagctgtcc ccaatcctcc cgccacgacc cgccgccctg  11040

cagataccgc accgtattgg caagcagccc gtaaacgcgg cgaatcgcgg tcagcatagc  11100

caggtcaagc cgctcgccgg ggcgctggcg tttggccagg cggtcgatgt gtctgtcctc  11160

cggaagggcc cccaacacga tgtttgtgcc gggcaaggtc ggcgggatga gggccacgaa  11220

cgccagcacg gcctgggggg tcatgctgcc cataaggtat cgcgcggccg ggtagcacag  11280

gagggcggcg atgggatggc ggtcgaagat gagggtgagg gccgggggcg gggcatgtga  11340

gctcccagcc tcccccccga tatgaggagc cagaacggcg tcggtcacgg tataaggcat  11400

gcccattgtt atctgggcgc ttgtcattac caccgccgcg tccccggccg atatctcacc  11460

ctggtcaagg cggtgttgtg tggtgtagat gttcgcgatt gtctcggaag cccccagcac  11520

ccgccagtaa gtcatcggct cgggtacgta gacgatatcg tcgcgcgaac ccagggccac  11580

cagcagttgc gtggtggtgg ttttccccat cccgtgggga ccgtctatat aaacccgcag  11640

tagcgtgggc attttctgct ccgggcggac ttccgtggct tcttgctgcc ggcgagggcg  11700

caacgccgta cgtcggttgc tatggccgcg agaacgcgca gcctggtcga acgcagacgc  11760

gtgctgatgg ccggggtacg aagccatacg cgcttctaca aggcgctggc cgaagaggtg  11820

cgggagtttc acgccaccaa gatgtgcggc acgctgttga cgctgttaag cgggtcgctg  11880

cagggtcgct cggtgttcga ggccacacgc gtcaccttaa tatgcgaagt ggacctggga  11940

ccgcgccgcc ccgactgcat ctgcgtgttc caattcgcca atgacaagac gctgggcggg  12000

gtttgctcga cattgggtgg aaacattcca ggcctgggtg gagaggcttt ttgcttcctc  12060

ttgcaaaacc acactgctcg acattgggtg gaaacattcc aggcctgggt ggagaggctt  12120

tttgcttcct cttgaaaacc acactgctcg actctacggt ccg                    12163
```

<210> SEQ ID NO 49
<211> LENGTH: 4066
<212> TYPE: DNA
<213> ORGANISM: Artificial Sequence
<220> FEATURE:
<223> OTHER INFORMATION: Synthetic

<400> SEQUENCE: 49

```
agggtgtggc caaatacagc atggagtagc catcataagg aatcttacac aagcctccaa     60

aattgtgttt ctgaaattgg gtttaaagta cgtttgcatt ttaaaaagcc tgccagaaaa    120

tacagaaaaa tgtctgtgat atgtctctgg ctgataggat tttgcttagt tttaattttg    180

gctttataat tttctatagt tatgaaaatg ttcacaagaa gatatatttc attttagctt    240

ctaaaataat tataacacag aagtaatttg tgctttaaaa aaatattcaa cacagaagta    300

tataaagtaa aaattgagga gttcccatcg tggctcagtg attaacaaac ccaactagta    360

tccatgagga tatggatttg atccctggcc ttgctcagtg ggttgaggat ccagtgttgc    420

tgtgagctgt ggtgtaggtt gcagacacag cactctggcg ttgctgtgac tctggcgtag    480
```

-continued

```
gccggcagct acagctccat ttggaccctt agcctgggaa cctccatatg cctgagatac    540
ggccctaaaa agtcaaaagc caaaaaaata gtaaaaattg agtgtttcta cttaccaccc    600
ctgcccacat cttatgctaa aacccgttct ccagagacaa acatcgtcag gtgggtctat    660
atatttccag ccctcctcct gtgtgtgtat gtccgtaaaa cacacacaca cacacacaca    720
cgcacacaca cacacacgta tctaattagc attggtatta gtttttcaaa agggaggtca    780
tgctctacct tttaggcggc aaatagatta tttaaacaaa tctgttgaca ttttctatat    840
caacccataa gatctcccat gttcttggaa aggctttgta agacatcaac atctgggtaa    900
accagcatgg tttttagggg gttgtgtgga tttttttcat attttttagg gcacacctgc    960
agcatatgga ggttcccagg ctaggggttg aatcagagct gtagctgccg gcctacacca   1020
cagccacagc aacgccagat ccttaaccca ctgagaaagg ccagggattg aacctgcatc   1080
ctcatggatg ctggtcagat ttatttctgc tgagccacaa caggaactcc ctgaaccaga   1140
atgcttttaa ccattccact ttgcatggac atttagattg tttccattta aaaatacaaa   1200
ttacaaggag ttcccgtcgt ggctcagtgg taacgaattg gactaggaac catgaggttt   1260
cgggttcgat ccctggcctt gctcggtggg ttaaggatcc agcattgatg tgagatatgg   1320
tgtaggtcgc agacgtggct cggatcccac gttgctgtgg ctctggcgta ggccggcaac   1380
aacagctccg attcgacccc tagcctggga acctccatgt gccacaggag cagccctaga   1440
aaaggcaaaa agacaaaaaa ataaaaaatt aaaatgaaaa aataaaataa aaatacaaat   1500
tacaagagac ggctacaagg aaatccccaa gtgtgtgcaa atgccatata tgtataaaat   1560
gtactagtgt ctcctcgcgg gaaagttgcc taaaagtggg ttggctggac agagaggaca   1620
ggctttgaca ttctcatagg tagtagcaat gggcttctca aaatgctgtt ccagtttaca   1680
ctcaccatag caaatgacag tgcctcttcc tctccaccct tgccaataat gtgacaggtg   1740
gatctttttc tattttgtgt atctgacaag caaaaaatga gaacaggagt tcctgtcgtg   1800
gtgcagtgga gacaaatctg actaggaacc atgaaatttc gggttcaatc cctggcctca   1860
ctcagtaggt aaaggatcca gggttgcagt gagctgtggg gtaggtcgca gacacagtgc   1920
aaatttggcc ctgttgtggc tgtggtgtag gccggcagct atagctccaa ttggacccct   1980
agcctgggaa cctccttatg ccgtgggtga ggccctaaaa aaaagagtgc aaaaaaaaaa   2040
aataagaaca aaaatgatca tcgtttaatt ctttatttga tcattggtga aacttatttt   2100
ccttttatat ttttattgac tgattttatt tctcctatga atttaccggt catagttttg   2160
cctgggtgtt tttactccgg ttttagtttt ggttggttgt attttcttag agagctatag   2220
aaactcttca tctatttgga atagtaattc ctcattaagt atttgtgctg caaaaaattt   2280
tccctgatct gttttatgct tttgtttgtg gggtctttca cgagaaagcc tttttagttt   2340
ttacacctca gcttggttgt ttttcttgat tgtgtctgta atctgcggcc aacataggaa   2400
acacattttt actttagtgt ttttttccta ttttcttcaa gtacgtccat tgttttggtg   2460
tctgatttta ctttgcctgg ggtttgtttt tgtgtggcag gaatataaac ttatgtattt   2520
tccaaatgga gagccaatgg ttgtatattt gttgaattca aatgcaactt tatcaaacac   2580
caaatcatcg atttatcaca actcttctct ggtttattga tctaatgatc aattcctgtt   2640
ccacgctgtt ttaattattt tagctttgtg gattttggtg cctggtagag aacaaagcct   2700
ccattatttt cattcaaaat agtcccgtct attatctgcc attgttgtag tattagactt   2760
taaaatcaat ttactgattt tcaaaagtta ttcctttggt gatgtggaat actttatact   2820
```

tcataaggta catggattca tttgtgggga attgatgtct ttgctattgt ggccatttgt 2880
caagttgtgt aatattttac ccatgccaac tttgcatatt gtatgtgagt ttattcccag 2940
ggtttttaat aggatgttta ttgaagttgt cagtgtttcc acaatttcat cgcctcagtg 3000
cttactgttt gcataaaagg aaacctactc acttttgcct attgctcttg tattcaatca 3060
ttttagttaa ctcttgtgtt aattttgaga gtttttcagc tgactgtctg ggttttctt 3120 taatagacta gccctttgtc tgtaaagaat aattttatcg aatttttctt aacactcaca 3180
ctctccccac ccccaccccc gctcatctcc tttcattggg tcaaatctgt agaatacaat 3240
aaaagtaaga gtgggaacct tagcctttaa gtcgattttg cctttaaatg tgaatgttgc 3300
tatgtttcgg gacattctct ttatcaagtt gcggatgttt ccttagataa ttaacttaat 3360
aaaagactgg atgtttgctt tcttcaaatc agaattgtgt tgaatttata ttgctattct 3420
gtttaatttt gtttcaaaaa atttacatgc acaccttaaa gataaccatg accaaatagt 3480
cctcctgctg agagaaaatg ttggccccaa tgccacaggt tacctcccga ctcagataaa 3540
ctacaatggg agataaaatc agatttggca aagcctgtgg attcttgcca taactctcag 3600
agcatgactt gggtgttttt tccttttcta agtattttaa tggtattttt gtgttacaat 3660
aggaaatcta ggacacagag agtgattcaa tgaggggaac gcattctggg atgactctag 3720
gcctctggtt tggggagagc tctattgaag taaagacaat gagaggaagc aagtttgcag 3780
ggaactgtga ggaatttaga tggggaatgt tgggtttgag gtttctatag ggcacgcaag 3840
cagagatgca ctcaggagga agaaggagca taaatctaga ggcaaaaaga gaggtcagga 3900
ctggaaatag agatgcgaga caccagggtg gcagtcagag agcacagtgt gggtcagaag 3960
acagtggaag aacacaaggg acagagaggg atctccaact tcactgggat gagggccttg 4020
ttggccttga cctgagagat ttccaggagt tgagggtggg aaggag 4066

<210> SEQ ID NO 50
<211> LENGTH: 2233
<212> TYPE: DNA
<213> ORGANISM: Artificial Sequence
<220> FEATURE:
<223> OTHER INFORMATION: Synthetic

<400> SEQUENCE: 50
gggaaggtat ctcccaggaa actggccagg acacattggt cctccgccct ccccttcctc 60
ccactcctcc tccagacagg actgtgccca ccccctgcca cctttctggc cagaactgtc 120
catggcaggt gaccttcaca tgagcccttc ctccctgcct gccctagtgg gaccctccat 180
acctccccct ggaccccgtt gtcctttctt tccagtgtgg ccctgagcat aactgatgcc 240
atcatgggct gctgacccac ccgggactgt gttgtgcagt gagtcacttc tctgtcatca 300
gggctttgta attgatagat agtgtttcat catcattagg accgggtggc ctctatgctc 360
tgttagtctc caaacactga tgaaaacctt cgttggcata gtcccagctt cctgttgccc 420
atccataaat cttgacttag ggatgcacat cctgtctcca agcaaccacc cctcccctag 480
gctaactata aaactgtccc aatggccctt gtgtggtgca gagttcatgc ttccagatca 540
tttctctgct agatccatat ctcaccttgt aagtcatcct ataataaact gatccattga 600
ttatttgctt ctgtttttc catctcaaaa cagcttctca gttcagttcg aattttttat 660
tccctccatc cacccatact ttcctcagcc tggggaaccc ttgcccccag tcccatgccc 720
ttcctccctc tctgcccagc tcagcacctg cccaccctca cccttcctgt cactccctag 780
gactggacca tccactgggg ccaggacact ccagcagcct tggcttcatg ggctctgaaa 840

```
tccatggccc atctctattc ctcactggat ggcaggttca gagatgtgaa aggtctagga    900

ggaagccagg aaggaaactg ttgcatgaaa ggccggcctg atggttcagt acttaaataa    960

tatgagctct gagctcccca ggaaccaaag catggaggga gtatgtgcct cagaatctct   1020

ctgagattca gcaaagcctt tgctagaggg aaaatagtgg ctcaaccttg agggccagca   1080

tcttgcacca cagttaaaag tgggtatttg ttttacctga ggcctcagca ttatgggaac   1140

cgggctctga cacaaacaca ggtgcagccc ggcagcctca gaacacagca acgaccacaa   1200

gctgggacag ctgcccctga acggggagtc caccatgctt ctgtctcggg taccaccagg   1260

tcaccatccc tgggggaggt agttccatag cagtagtccc ctgatttcgc ccctcgggcg   1320

tgtagccagg caagctcctg cctctggacc cagggtggac ccttgctccc cactaccctg   1380

cacatgccag acagtcaaga ccactcccac ctctgtctga ggccccttg ggtgtcccag    1440

ggcccccgag ctgtcctcta ctcatggttc ttccacctgg gtacaaaaga ggcgagggac   1500

acttttctca ggtttgcggc tcagaaaggt accttcctag ggtttgtcca ctgggagtca   1560

cctcccttgc atctcaatgt cagtggggaa aactgggtcc catgggggga ttagtgccac   1620

tgtgaggccc ctgaagtctg gggcctctag acactatgat gatgagggat gtggtgaaaa   1680

accccacccc agcccttctt gccgggaccc tgggctgtgg ctcccccatt gcacttgggg   1740

tcagaggggt ggatggtggc tatggtcagg catgtttccc atgagctggg ggcaccctgg   1800

gtgactttct cctgtgaatc ctgaattagc agctataaca aattgcccaa actcttaggc   1860

ttaaaacaac acacatttat tcctctgggt cccagggtca gaagtccaaa atgagtccta   1920

taggctaaat ttgaggtgtc tctgggttga gctcctcctg gaagcctttt ccagcctcta   1980

gagtcccaag tccttggctc tgggcccctc cctcaagctt caaagccaca gaagcttcta   2040

atctctctcc cttcccctct gacctctgct cccatcctca taccctgtcc cctcactctg   2100

accctcctgc ctccctcttt cccttataaa gaccctgcat ggggccacgg agataatcca   2160

gggtaatcgc ccctcttcca gcccttaact ccatcccatc tgcaaaatcc ctgtcacccc   2220

ataatggacc tac                                                      2233
```

UNGULATES WITH GENETICALLY MODIFIED IMMUNE SYSTEMS

This application is a continuation of pending prior application U.S. Non-provisional application Ser. No. 11/789,961, filed on Apr. 26, 2007, which is a continuation-in-part of U.S. Non-provisional application Ser. No. 11/257,817, filed on Oct. 24, 2005, which claims the benefit of U.S. Provisional Application No. 60/621,433, filed on Oct. 22, 2004. This application also claims the benefit of U.S. Provisional Patent Application No. 60/794,963, filed on Apr. 26, 2006. The contents of the foregoing U.S. patent applications are hereby incorporated by reference in their entireties.

FIELD OF THE INVENTION

The present invention provides ungulate animals, tissue and organs as well as cells and cell lines derived from such animals, tissue and organs, which lack expression of functional endogenous immunoglobulin loci. The present invention also provides ungulate animals, tissue and organs as well as cells and cell lines derived from such animals, tissue and organs, which express xenogenous, such as human, immunoglobulin loci. The present invention further provides ungulate, such as porcine genomic DNA sequence of porcine heavy and light chain immunogobulins. Such animals, tissues, organs and cells can be used in research and medical therapy. In addition, methods are provided to prepare such animals, organs, tissues, and cells.

BACKGROUND OF THE INVENTION

An antigen is an agent or substance that can be recognized by the body as 'foreign'. Often it is only one relatively small chemical group of a larger foreign substance which acts as the antigen, for example a component of the cell wall of a bacterium. Most antigens are proteins, though carbohydrates can act as weak antigens. Bacteria, viruses and other microorganisms commonly contain many antigens, as do pollens, dust mites, molds, foods, and other substances. The body reacts to antigens by making antibodies. Antibodies (also called immunoglobulins (Igs)) are proteins that are manufactured by cells of the immune system that bind to an antigen or foreign protein. Antibodies circulate in the serum of blood to detect foreign antigens and constitute the gamma globulin part of the blood proteins. These antibodies interact chemically with the antigen in a highly specific manner, like two pieces of a jigsaw puzzle, forming an antigen/antibody complex, or immune complex. This binding neutralizes or brings about the destruction of the antigen.

When a vertebrate first encounters an antigen, it exhibits a primary humoral immune response. If the animal encounters the same antigen after a few days the immune response is more rapid and has a greater magnitude. The initial encounter causes specific immune cell (B-cell) clones to proliferate and differentiate. The progeny lymphocytes include not only effector cells (antibody producing cells) but also clones of memory cells, which retain the capacity to produce both effector and memory cells upon subsequent stimulation by the original antigen. The effector cells live for only a few days. The memory cells live for a lifetime and can be reactivated by a second stimulation with the same antigen. Thus, when an antigen is encountered a second time, its memory cells quickly produce effector cells which rapidly produce massive quantities of antibodies.

By exploiting the unique ability of antibodies to interact with antigens in a highly specific manner, antibodies have been developed as molecules that can be manufactured and used for both diagnostic and therapeutic applications. Because of their unique ability to bind to antigenic epitopes, polyclonal and monoclonal antibodies can be used to identify molecules carrying that epitope or can be directed, by themselves or in conjunction with another moiety, to a specific site for diagnosis or therapy. Polyclonal and monoclonal antibodies can be generated against practically any pathogen or biological target. The term polyclonal antibody refers to immune sera that usually contain pathogen-specific antibodies of various isotypes and specificities. In contrast, monoclonal antibodies consist of a single immunoglobulin type, representing one isotype with one specificity.

In 1890, Shibasaburo Kitazato and Emil Behring conducted the fundamental experiment that demonstrated immunity can be transmitted from one animal to another by transferring the serum from an immune animal to a non-immune animal. This landmark experiment laid the foundation for the introduction of passive immunization into clinical practice. However, wide scale serum therapy was largely abandoned in the 1940s because of the toxicity associated with the administration of heterologous sera and the introduction of effective antimicrobial chemotherapy. Currently, such polyclonal antibody therapy is indicated to treat infectious diseases in relatively few situations, such as replacement therapy in immunoglobulin-deficient patients, post-exposure prophylaxis against several viruses (e.g., rabies, measles, hepatitis A and B, varicella), and toxin neutralization (diphtheria, tetanus, and botulism). Despite the limited use of serum therapy, in the United States, more than 16 metric tons of human antibodies are required each year for intravenous antibody therapy. Comparable levels of use exist in the economies of most highly industrialized countries, and the demand can be expected to grow rapidly in developing countries. Currently, human antibody for passive immunization is obtained from the pooled serum of donors. Thus, there is an inherent limitation in the amount of human antibody available for therapeutic and prophylactic therapies.

The use of antibodies for passive immunization against biological warfare agents represents a very promising defense strategy. The final line of defense against such agents is the immune system of the exposed individual. Current defense strategies against biological weapons include such measures as enhanced epidemiologic surveillance, vaccination, and use of antimicrobial agents. Since the potential threat of biological warfare and bioterrorism is inversely proportional to the number of immune persons in the targeted population, biological agents are potential weapons only against populations with a substantial proportion of susceptible persons.

Vaccination can reduce the susceptibility of a population against specific threats; provided that a safe vaccine exists that can induce a protective response. Unfortunately, inducing a protective response by vaccination may take longer than the time between exposure and onset of disease. Moreover, many vaccines require multiple doses to achieve a protective immune response, which would limit their usefulness in an emergency to provide rapid prophylaxis after an attack. In addition, not all vaccine recipients mount a protective response, even after receiving the recommended immunization schedule.

Drugs can provide protection when administered after exposure to certain agents, but none are available against many potential agents of biological warfare. Currently, no small-molecule drugs are available that prevent disease following exposure to preformed toxins. The only currently available intervention that could provide a state of immediate immunity is passive immunization with protective antibody (Arturo Casadevall "Passive Antibody Administration (Immediate Immunity) as a Specific Defense Against Biological Weapons" from Emerging Infectious Diseases, Posted Sep. 12, 2002).

In addition to providing protective immunity, modern antibody-based therapies constitute a potentially useful option against newly emergent pathogenic bacteria, fungi, virus and parasites (A. Casadevall and M. D. Scharff, Clinical Infectious Diseases 1995; 150). Therapies of patients with malignancies and cancer (C. Botti et al, Leukemia 1997; Suppl 2:S55-59; B. Bodey, S. E. Siegel, and H. E. Kaiser, Anticancer Res 1996; 16(2):661), therapy of steroid resistant rejection of transplanted organs as well as autoimmune diseases can also be achieved through the use of monoclonal or polyclonal antibody preparations (N. Bonnefoy-Berard and J. P. Revillard, J Heart Lung Transplant 1996; 15(5):435-442; C. Colby, et al Ann Pharmacother 1996; 30(10):1164-1174; M. J. Dugan, et al, Ann Hematol 1997; 75(1-2):41 2; W. Cendrowski, Boll Ist Sieroter Milan 1997; 58(4):339-343; L. K. Kastrukoff, et al Can J Neurol Sci 1978; 5(2):175178; J. E. Walker et al J Neurol Sci 1976; 29(2-4):303309).

Recent advances in the technology of antibody production provide the means to generate human antibody reagents, while avoiding the toxicities associated with human serum therapy. The advantages of antibody-based therapies include versatility, low toxicity, pathogen specificity, enhancement of immune function, and favorable pharmacokinetics.

The clinical use of monoclonal antibody therapeutics has just recently emerged. Monoclonal antibodies have now been approved as therapies in transplantation, cancer, infectious disease, cardiovascular disease and inflammation. In many more monoclonal antibodies are in late stage clinical trials to treat a broad range of disease indications. As a result, monoclonal antibodies represent one of the largest classes of drugs currently in development.

Despite the recent popularity of monoclonal antibodies as therapeutics, there are some obstacles for their use. For example, many therapeutic applications for monoclonal antibodies require repeated administrations, especially for chronic diseases such as autoimmunity or cancer. Because mice are convenient for immunization and recognize most human antigens as foreign, monoclonal antibodies against human targets with therapeutic potential have typically been of murine origin. However, murine monoclonal antibodies have inherent disadvantages as human therapeutics. For example, they require more frequent dosing to maintain a therapeutic level of monoclonal antibodies because of a shorter circulating half-life in humans than human antibodies. More critically, repeated administration of murine immunoglobulin creates the likelihood that the human immune system will recognize the mouse protein as foreign, generating a human anti-mouse antibody response, which can cause a severe allergic reaction. This possibility of reduced efficacy and safety has lead to the development of a number of technologies for reducing the immunogenicity of murine monoclonal antibodies.

Polyclonal antibodies are highly potent against multiple antigenic targets. They have the unique ability to target and kill a plurality of "evolving targets" linked with complex diseases. Also, of all drug classes, polyclonals have the highest probability of retaining activity in the event of antigen mutation. In addition, while monoclonals have limited therapeutic activity against infectious agents, polyclonals can both neutralize toxins and direct immune responses to eliminate pathogens, as well as biological warfare agents.

The development of polyclonal and monoclonal antibody production platforms to meet future demand for production capacity represents a promising area that is currently the subject of much research. One especially promising strategy is the introduction of human immunoglobulin genes into mice or large domestic animals. An extension of this technology would include inactivation of their endogenous immunoglobulin genes. Large animals, such as sheep, pigs and cattle, are all currently used in the production of plasma derived products, such as hyperimmune serum and clotting factors, for human use. This would support the use of human polyclonal antibodies from such species on the grounds of safety and ethics. Each of these species naturally produces considerable quantities of antibody in both serum and milk.

Arrangement of Genes Encoding Immunoglobulins

Antibody molecules are assembled from combinations of variable gene elements, and the possibilities resulting from combining the many variable gene elements in the germline enable the host to synthesize antibodies to an extraordinarily large number of antigens. Each antibody molecule consists of two classes of polypeptide chains, light (L) chains (that can be either kappa (κ) L-chain or lambda (λ) L-chain) and heavy (H) chains. The heavy and light chains join together to define a binding region for the epitope. A single antibody molecule has two identical copies of the L chain and two of the H chain. Each of the chains is comprised of a variable region (V) and a constant region (C). The variable region constitutes the antigen-binding site of the molecule. To achieve diverse antigen recognition, the DNA that encodes the variable region undergoes gene rearrangement. The constant region amino acid sequence is specific for a particular isotype of the antibody, as well as the host which produces the antibody, and thus does not undergo rearrangement.

The mechanism of DNA rearrangement is similar for the variable region of both the heavy- and light-chain loci, although only one joining event is needed to generate a light-chain gene whereas two are needed to generate a complete heavy-chain gene. The most common mode of rearrangement involves the looping-out and deletion of the DNA between two gene segments. This occurs when the coding sequences of the two gene segments are in the same orientation in the DNA. A second mode of recombination can occur between two gene segments that have opposite transcriptional orientations. This mode of recombination is less common, although such rearrangements can account for up to half of all $V_κ$ to $J_κ$ joins; the transcriptional orientation of half of the human $V_κ$ gene segments is opposite to that of the $J_κ$ gene segments.

The DNA sequence encoding a complete V region is generated by the somatic recombination of separate gene segments. The V region, or V domain, of an immunoglobulin heavy or light chain is encoded by more than one gene segment. For the light chain, the V domain is encoded by two separate DNA segments. The first segment encodes the first 95-101 amino acids of the light chain and is termed a V gene segment because it encodes most of the V domain. The second segment encodes the remainder of the V domain (up to 13 amino acids) and is termed a joining or J gene segment. The joining of a V and a J gene segment creates a continuous exon that encodes the whole of the light-chain V region. To make a complete immunoglobulin light-chain messenger RNA, the V-region exon is joined to the C-region sequence by RNA splicing after transcription.

A heavy-chain V region is encoded in three gene segments. In addition to the V and J gene segments (denoted $V_H$ and $J_H$ to distinguish them from the light-chain $V_L$ and $J_L$), there is a third gene segment called the diversity or $D_H$ gene segment, which lies between the $V_H$ and $J_H$ gene segments. The process of recombination that generates a complete heavy-chain V region occurs in two separate stages. In the first, a $D_H$ gene segment is joined to a $J_H$ gene segment; then a $V_H$ gene segment rearranges to $DJ_H$ to make a complete $V_H$-region exon. As with the light-chain genes, RNA splicing joins the assembled V-region sequence to the neighboring C-region gene.

Diversification of the antibody repertoire occurs in two stages: primarily by rearrangement ("V(D)J recombination") of Ig V, D and J gene segments in precursor B cells resident in the bone marrow, and then by somatic mutation and class switch recombination of these rearranged Ig genes when mature B cells are activated. Immunoglobulin somatic mutation and class switching are central to the maturation of the immune response and the generation of a "memory" response.

The genomic loci of antibodies are very large and they are located on different chromosomes. The immunoglobulin gene segments are organized into three clusters or genetic loci: the κ, λ, and heavy-chain loci. Each is organized slightly differently. For example, in humans, immunoglobulin genes are organized as follows. The λ light-chain locus is located on chromosome 22 and a cluster of $V_\lambda$ gene segments is followed by four sets of $J_\lambda$ gene segments each linked to a single $C_\lambda$ gene. The κ light-chain locus is on chromosome 2 and the cluster of $V_\kappa$, gene segments is followed by a cluster of $J_\kappa$ gene segments, and then by a single $C_\kappa$ gene. The organization of the heavy-chain locus, on chromosome 14, resembles that of the κ locus, with separate clusters of $V_H$, $D_H$, and $J_H$ gene segments and of $C_H$ genes. The heavy-chain locus differs in one important way: instead of a single C-region, it contains a series of C regions arrayed one after the other, each of which corresponds to a different isotype. There are five immunoglobulin heavy chain isotypes: IgM, IgG, IgA, IgE and IgD. Generally, a cell expresses only one at a time, beginning with IgM. The expression of other isotypes, such as IgG, can occur through isotype switching.

The joining of various V, D and J genes is an entirely random event that results in approximately 50,000 different possible combinations for VDJ(H) and approximately 1,000 for VJ(L). Subsequent random pairing of H and L chains brings the total number of antibody specificities to about $10^7$ possibilities. Diversity is further increased by the imprecise joining of different genetic segments. Rearrangements occur on both DNA strands, but only one strand is transcribed (due to allelic exclusion). Only one rearrangement occurs in the life of a B cell because of irreversible deletions in DNA. Consequently, each mature B cell maintains one immunologic specificity and is maintained in the progeny or clone. This constitutes the molecular basis of the clonal selection; i.e., each antigenic determinant triggers the response of the pre-existing clone of B lymphocytes bearing the specific receptor molecule. The primary repertoire of B cells, which is established by V(D)J recombination, is primarily controlled by two closely linked genes, recombination activating gene (RAG)-1 and RAG-2.

Over the last decade, considerable diversity among vertebrates in both Ig gene diversity and antibody repertoire development has been revealed. Rodents and humans have five heavy chain classes, IgM, IgD, IgG, IgE and IgA, and each have four subclasses of IgG and one or two subclasses of IgA, while rabbits have a single IgG heavy chain gene but 13 genes for different IgA subclasses (Burnett, R. C et al. *EMBO J.* 8:4047; Honjo, In Honjo, T, Alt. F. W. T. H. eds, *Immunoglobulin Genes* p. 123 Academic Press, New York). Swine have at least six IgG subclasses (Kacskovics, I et al. 1994 *J Immunol* 153:3565), but no IgD (Butler et al. 1996 Inter. Immunol 8:1897-1904). A gene encoding IgD has only been described in rodents and primates. Diversity in the mechanism of repertoire development is exemplified by contrasting the pattern seen in rodents and primates with that reported for chickens, rabbits, swine and the domesticated Bovidae. Whereas the former group have a large number of $V_H$ genes belonging to seven to 10 families (Rathbun, G. In Hongo, T. Alt. F. W. and Rabbitts, T. H., eds, *Immunoglobulin Genes*, p. 63, Academic press New York), the $V_H$ genes of each member of the latter group belong to a single $V_H$ gene family (Sun, J. et al. 1994 *J. Immunol.* 1553:56118; Dufour, V et al. 1996*, J Immunol.* 156:2163). With the exception of the rabbit, this family is composed of less than 25 genes. Whereas rodents and primates can utilize four to six $J_H$ segments, only a single $J_H$ is available for repertoire development in the chicken (Reynaud et al. 1989 Adv. Immunol. 57:353). Similarly, Butler et al. (1996 Inter. Immunol 8:1897-1904) hypothesized that swine may resemble the chicken in having only a single $J_H$ gene. These species generally have fewer V, D and J genes; in the pig and cow a single VH gene family exists, consisting of less than 20 gene segments (Butler et al, Advances in Swine in Biomedical Research, eds: Tumbleson and Schook, 1996; Sinclair et al, J. Immunol. 159: 3883, 1997). Together with lower numbers of J and D gene segments, this results in significantly less diversity being generated by gene rearrangement. However, there does appear to be greater numbers of light chain genes in these species. Similar to humans and mice, these species express a single κ light chain but multiple λ light chain genes. However, these do not seem to affect the restricted diversity that is achieved by rearrangement.

Since combinatorial joining of more than 100 $V_H$, 20-30 $D_H$ and four to six $J_H$ gene segments is a major mechanism of generating the antibody repertoire in humans, species with fewer $V_H$, $D_H$ or $J_H$ segments must either generate a smaller repertoire or use alternative mechanisms for repertoire development. Ruminants, pigs, rabbits and chickens, utilize several mechanisms to generate antibody diversity. In these species there appears to be an important secondary repertoire development, which occurs in highly specialized lymphoid tissue such as ileal Peyer's patches (Binns and Licence, Adv. Exp. Med. Biol. 186: 661, 1985). Secondary repertoire development occurs in these species by a process of somatic mutation which is a random and not fully understood process. The mechanism for this repertoire diversification appears to be templated mutation, or gene conversion (Sun et al, J. Immunol. 153: 5618, 1994) and somatic hypermutation.

Gene conversion is important for antibody diversification in some higher vertebrates, such as chickens, rabbits and cows. In mice, however, conversion events appear to be infrequent among endogenous antibody genes. Gene conversion is a distinct diversifying mechanism characterized by transfers of homologous sequences from a donor antibody V gene segment to an acceptor V gene segment. If donor and acceptor segments have numerous sequence differences then gene conversion can introduce a set of sequence changes into a V region by a single event. Depending on the species, gene conversion events can occur before and/or after antigen exposure during B cell differentiation (Tsai et al. International Immunology, Vol. 14, No. 1, 55-64, January 2002).

Somatic hypermutation achieves diversification of antibody genes in all higher vertebrate species. It is typified by the introduction of single point mutations into antibody V(D)J segments. Generally, hypermutation appears to be activated in B cells by antigenic stimulation.

Production of Animals with Humanized Immune Systems

In order to reduce the immunogenicity of antibodies generated in mice for human therapeutics, various attempts have been made to replace murine protein sequences with human protein sequences in a process now known as humanization. Transgenic mice have been constructed which have had their own immunoglobulin genes functionally replaced with human immunoglobulin genes so that they produce human antibodies upon immunization. Elimination of mouse antibody production was achieved by inactivation of mouse Ig genes in embryonic stem (ES) cells by using gene-targeting technology to delete crucial cis-acting sequences involved in the process of mouse Ig gene rearrangement and expression. B cell development in these mutant mice could be restored by the introduction of megabase-sized YACs containing a human germline-configuration H- and κ L-chain minilocus transgene. The expression of fully human antibody in these transgenic mice was predominant, at a level of several 100 μg/l of blood. This level of expression is several hundred-fold higher than that detected in wild-type mice expressing the human Ig gene, indicating the importance of inactivating the endogenous mouse Ig genes in order to enhance human antibody production by mice.

The first humanization attempts utilized molecular biology techniques to construct recombinant antibodies. For example, the complementarity determining regions (CDR) from a mouse antibody specific for a hapten were grafted onto a human antibody framework, effecting a CDR replacement. The new antibody retained the binding specificity conveyed by the CDR sequences (P. T. Jones et al. Nature 321: 522-525 (1986)). The next level of humanization involved combining an entire mouse VH region with a human constant region such as $gamma_1$ (S. L. Morrison et al., Proc. Natl. Acad. Sci., 81, pp. 6851-6855 (1984)). However, these chimeric antibodies, which still contain greater than 30% xenogeneic sequences, are sometimes only marginally less immunogenic than totally xenogeneic antibodies (M. Bruggemann et al., J. Exp. Med., 170, pp. 2153-2157 (1989)).

Subsequently, attempts were carried out to introduce human immunoglobulin genes into the mouse, thus creating transgenic mice capable of responding to antigens with antibodies having human sequences (Bruggemann et al. Proc. Nat'l. Acad. Sci. USA 86:6709-6713 (1989)). Due to the large size of human immunoglobulin genomic loci, these attempts were thought to be limited by the amount of DNA, which could be stably maintained by available cloning vehicles. As a result, many investigators concentrated on producing mini-loci containing limited numbers of V region genes and having altered spatial distances between genes as compared to the natural or germline configuration (See, for example, U.S. Pat. No. 5,569,825). These studies indicated that producing human sequence antibodies in mice was possible, but serious obstacles remained regarding obtaining sufficient diversity of binding specificities and effector functions (isotypes) from these transgenic animals to meet the growing demand for antibody therapeutics.

In order to provide additional diversity, work has been conducted to add large germline fragments of the human Ig locus into transgenic mammals. For example, a majority of the human V, D, and J region genes arranged with the same spacing found in the unrearranged germline of the human genome and the human Cμ and Cδ constant regions was introduced into mice using yeast artificial chromosome (YAC) cloning vectors (See, for example, WO 94/02602). A 22 kb DNA fragment comprising sequences encoding a human gamma-2 constant region and the upstream sequences required for class-switch recombination was latter appended to the foregoing transgene. In addition, a portion of a human kappa locus comprising Vκ, Jκ and Cκ region genes, also arranged with substantially the same spacing found in the unrearranged germline of the human genome, was introduced into mice using YACS. Gene targeting was used to inactivate the murine IgH & kappa light chain immunoglobulin gene loci and such knockout strains were bred with the above transgenic strains to generate a line of mice having the human V, D, J, Cμ, Cδ and $C\gamma_2$ constant regions as well as the human Vκ, Jκ and Cκ region genes all on an inactivated murine immunoglobulin background (See, for example, PCT patent application WO 94/02602 to Kucherlapati et al.; see also Mendez et al., Nature Genetics 15:146-156 (1997)).

Yeast artificial chromosomes as cloning vectors in combination with gene targeting of endogenous loci and breeding of transgenic mouse strains provided one solution to the problem of antibody diversity. Several advantages were obtained by this approach. One advantage was that YACs can be used to transfer hundreds of kilobases of DNA into a host cell. Therefore, use of YAC cloning vehicles allows inclusion of substantial portions of the entire human Ig heavy and light chain regions into a transgenic mouse thus approaching the level of potential diversity available in the human. Another advantage of this approach is that the large number of V genes has been shown to restore full B cell development in mice deficient in murine immunoglobulin production. This ensures that these reconstituted mice are provided with the requisite cells for mounting a robust human antibody response to any given immunogen. (See, for example, WO 94/02602; L. Green and A. Jakobovits, J. Exp. Med. 188:483-495 (1998)). A further advantage is that sequences can be deleted or inserted onto the YAC by utilizing high frequency homologous recombination in yeast. This provides for facile engineering of the YAC transgenes.

In addition, Green et al. Nature Genetics 7:13-21 (1994) describe the generation of YACs containing 245 kb and 190 kb-sized germline configuration fragments of the human heavy chain locus and kappa light chain locus, respectively, which contained core variable and constant region sequences. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See, for example, Mendez et al. Nature Genetics 15:146-156 (1997), Green and Jakobovits J. Exp. Med. 188:483-495 (1998), European Patent No. EP 0 463 151 B1, PCT Publication Nos. WO 94/02602, WO 96/34096 and WO 98/24893.

Several strategies exist for the generation of mammals that produce human antibodies. In particular, there is the "minilocus" approach that is typified by work of GenPharm International, Inc. and the Medical Research Council, YAC introduction of large and substantially germline fragments of the Ig loci that is typified by work of Abgenix, Inc. (formerly Cell Genesys). The introduction of entire or substantially entire loci through the use microcell fusion as typified by work of Kirin Beer Kabushiki Kaisha.

In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (such as a gamma constant region) are formed into a construct for insertion into an animal. See, for example, U.S. Pat. Nos. 5,545,807, 5,545,806, 5,625,825, 5,625,126, 5,633,425, 5,661,016, 5,770,429, 5,789,650, 5,814,318, 5,591,669, 5,612,205, 5,721,367, 5,789,215, 5,643,763; European Patent No. 0 546 073; PCT Publication Nos. WO 92/03918, WO 92/22645, WO 92/22647, WO 92/22670, WO 93/12227, WO 94/00569, WO 94/25585, WO 96/14436, WO 97/13852, and WO 98/24884; Taylor et al. Nucleic Acids Research 20:6287-6295 (1992), Chen et al. International Immunology 5:647-656 (1993), Tuaillon et al. J. Immunol. 154:6453-6465 (1995), Choi et al. Nature Genetics 4:117-123 (1993), Lonberg et al. Nature 368:856-859 (1994), Taylor et al. International Immunology 6:579-591 (1994), Tuaillon et al. J. Immunol. 154:6453-6465 (1995), and Fishwild et al. Nature Biotech. 14:845-851 (1996).

In the microcell fusion approach, portions or whole human chromosomes can be introduced into mice (see, for example, European Patent Application No. EP 0 843 961 A1). Mice generated using this approach and containing the human Ig heavy chain locus will generally possess more than one, and potentially all, of the human constant region genes. Such mice will produce, therefore, antibodies that bind to particular antigens having a number of different constant regions.

While mice remain the most developed animal for the expression of human immunoglobulins in humans, recent technological advances have allowed for progress to begin in applying these techniques to other animals, such as cows. The general approach in mice has been to genetically modify embryonic stem cells of mice to knock-out murine immunoglobulins and then insert YACs containing human immunoglobulins into the ES cells. However, ES cells are not available for cows or other large animals such as sheep and pigs. Thus, several fundamental developments had to occur before even the possibility existed to generate large animals with immunoglobulin genes knocked-out and that express human antibody. The alternative to ES cell manipulation to create genetically modified animals is cloning using somatic cells that have been genetically modified. Cloning using genetically modified somatic cells for nuclear transfer has only recently been accomplished.

Since the announcement of Dolly's (a cloned sheep) birth from an adult somatic cell in 1997 (Wilmut, I., et al (1997) Nature 385: 810-813), ungulates, including cattle (Cibelli, J et al 1998 Science 280: 1266-1258; Kubota, C. et al. 2000 Proc. Nat'l. Acad. Sci. 97: 990-995), goats (Baguisi, A. et al., (1999) Nat. Biotechnology 17: 456-461), and pigs (Polejaeva, I. A., et al. 2000 Nature 407: 86-90; Betthauser, J. et al. 2000 Nat. Biotechnology 18: 1055-1059) have been cloned.

The next technological advance was the development of the technique to genetically modify the cells prior to nuclear transfer to produce genetically modified animals. PCT publication No. WO 00/51424 to PPL Therapeutics describes the targeted genetic modification of somatic cells for nuclear transfer.

Subsequent to these fundamental developments, single and double allele knockouts of genes and the birth of live animals with these modifications have been reported. Between 2002 and 2004, three independent groups, Immerge Biotherapeutics, Inc. in collaboration with the University of Missouri (Lai et al. (Science (2002) 295: 1089-1092) & Kolber-Simonds et al. (PNAS. (2004) 101 (19):7335-40)), Alexion Pharmaceuticals (Ramsoondar et al. (Biol Reprod (2003)69: 437-445) and Revivicor, Inc. (Dai et al. (Nature Biotechnology (2002) 20: 251-255) & Phelps et al. (Science (2003) January 17; 299(5605):411-4)) produced pigs that lacked one allele or both alleles of the alpha-1,3-GT gene via nuclear transfer from somatic cells with targeted genetic deletions. In 2003, Sedai et al. (Transplantation (2003) 76:900-902) reported the targeted disruption of one allele of the alpha-1,3-GT gene in cattle, followed by the successful nuclear transfer of the nucleus of the genetically modified cell and production of transgenic fetuses.

Thus, the feasibility of knocking-out immunoglobulin genes in large animals and inserting human immunoglobulin loci into their cells is just now beginning to be explored. However, due to the complexity and species differences of immunoglobulin genes, the genomic sequences and arrangement of Ig kappa, lambda and heavy chains remain poorly understood in most species. For example, in pigs, partial genomic sequence and organization has only been described for heavy chain constant alpha, heavy chain constant mu and heavy chain constant delta (Brown and Butler Mol Immunol. 1994 June; 31(8):633-42, Butler et al Vet Immunol Immunopathol. 1994 October; 43(1-3):5-12, and Zhao et al J Immunol. 2003 Aug. 1; 171(3):1312-8).

In cows, the immunoglobulin heavy chain locus has been mapped (Zhao et al. 2003 J. Biol. Chem. 278:35024-32) and the cDNA sequence for the bovine kappa gene is known (See, for example, U.S. Patent Publication No. 2003/0037347). Further, approximately 4.6 kb of the bovine mu heavy chain locus has been sequenced and transgenic calves with decreased expression of heavy chain immunoglobulins have been created by disrupting one or both alleles of the bovine mu heavy chain. In addition, a mammalian artificial chromosome (MAC) vector containing the entire unarranged sequences of the human Ig H-chain and κ L-chain has been introduced into cows (TC cows) with the technology of microcell-mediated chromosome transfer and nuclear transfer of bovine fetal fibroblast cells (see, for example, Kuroiwa et al. 2002 Nature Biotechnology 20:889, Kuroiwa et al. 2004 Nat Genet. June 6 Epub, U.S. Patent Publication Nos. 2003/0037347, 2003/0056237, 2004/0068760 and PCT Publication No. WO 02/07648).

While significant progress has been made in the production of bovine that express human immunoglobulin, little has been accomplished in other large animals, such as sheep, goats and pigs. Although cDNA sequence information for immunoglobulin genes of sheeps, goats and pigs is readily available in Genbank, the unique nature of immunoglobulin loci, which undergo massive rearrangements, creates the need to characterize beyond sequences known to be present in mRNAs (or cDNAs). Since immunoglobulin loci are modular and the coding regions are redundant, deletion of a known coding region does not ensure altered function of the locus. For example, if one were to delete the coding region of a heavy-chain variable region, the function of the locus would not be significantly altered because hundreds of other function variable genes remain in the locus. Therefore, one must first characterize the locus to identify a potential "Achilles heel".

Despite some advancements in expressing human antibodies in cattle, greater challenges remain for inactivation of the endogenous bovine Ig genes, increasing expression levels of the human antibodies and creating human antibody expression in other large animals, such as porcine, for which the sequence and arrangement of immunoglobulin genes are largely unknown.

It is therefore an object of the present invention to provide the arrangement of ungulate immunoglobin germline gene sequence.

It is another object of the present invention to provide novel ungulate immunoglobulin genomic sequences.

It is a further object of the present invention to provide cells, tissues and animals lacking at least one allele of a heavy and/or light chain immunoglobulin gene.

It is another object of the present invention to provide ungulates that express human immunoglobulins.

It is a still further object of the present invention to provide methods to generate cells, tissues and animals lacking at least one allele of novel ungulate immunoglobulin gene sequences and/or express human immunoglobulins.

SUMMARY OF THE INVENTION

The present invention provides for the first time ungulate immunoglobin germline gene sequence arrangement as well as novel genomic sequences thereof. In addition, novel ungulate cells, tissues and animals that lack at least one allele of a heavy or light chain immunoglobulin gene are provided. Based on this discovery, ungulates can be produced that completely lack at least one allele of a heavy and/or light chain immunoglobulin gene. In addition, these ungulates can be further modified to express xenoogenous, such as human, immunoglobulin loci or fragments thereof.

In one aspect of the present invention, a transgenic ungulate that lacks any expression of functional endogenous immunoglobulins is provided. In one embodiment, the ungulate can lack any expression of endogenous heavy and/or light chain immunoglobulins. The light chain immunoglobulin can be a kappa and/or lambda immunoglobulin. In additional embodiments, transgenic ungulates are provided that lack expression of at least one allele of an endogenous immunoglobulin wherein the immunoglobulin is selected from the group consisting of heavy chain, kappa light chain and lambda light chain or any combination thereof. In one embodiment, the expression of functional endogenous immunoglobulins can be accomplished by genetic targeting of the endogenous immunoglobulin loci to prevent expression of the endogenous immunoglobulin. In one embodiment, the genetic targeting can be accomplished via homologous recombination. In another embodiment, the transgenic ungulate can be produced via nuclear transfer.

In other embodiments, the transgenic ungulate that lacks any expression of functional endogenous immunoglobulins can be further genetically modified to express an xenogenous immunoglobulin loci. In an alternative embodiment, porcine animals are provided that contain an xenogeous immunoglobulin locus. In one embodiment, the xenogeous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In another aspect of the present invention, transgenic ungulates are provided that expresses a xenogenous immunoglobulin loci or fragment thereof, wherein the immunoglobulin can be expressed from an immunoglobulin locus that is integrated within an endogenous ungulate chromosome. In one embodiment, ungulate cells derived from the transgenic animals are provided. In one embodiment, the xenogenous immunoglobulin locus can be inherited by offspring. In another embodiment, the xenogenous immunoglobulin locus can be inherited through the male germ line by offspring. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In another aspect of the present invention, novel genomic sequences encoding the heavy chain locus of ungulate immunoglobulin are provided. In one embodiment, an isolated nucleotide sequence encoding porcine heavy chain is provided that includes at least one variable region, two diversity regions, at least four joining regions and at least one constant region, such as the mu constant region, for example, as represented in Seq ID No. 29. In another embodiment, an isolated nucleotide sequence is provided that includes at least four joining regions and at least one constant region, such as the mu constant region, of the porcine heavy chain genomic sequence, for example, as represented in Seq ID No. 4. In a further embodiment, nucleotide sequence is provided that includes 5' flanking sequence to the first joining region of the porcine heavy chain genomic sequence, for example, as represented in Seq ID No 1. Still further, nucleotide sequence is provided that includes 3' flanking sequence to the first joining region of the porcine heavy chain genomic sequence, for example, as represented in the 3' region of Seq ID No 4. In further embodiments, isolated nucleotide sequences as depicted in Seq ID Nos 1, 4 or 29 are provided. Nucleic acid sequences at least 80, 85, 90, 95, 98 or 99% homologous to Seq ID Nos 1, 4 or 29 are also provided. In addition, nucleotide sequences that contain at least 10, 15, 17, 20, 25 or 30 contiguous nucleotides of Seq ID Nos 1, 4 or 29 are provided. In one embodiment, the nucleotide sequence contains at least 17, 20, 25 or 30 contiguous nucleotides of Seq ID No 4 or residues 1-9,070 of Seq ID No 29. In another embodiment, the nucleotide sequence contains residues 9,070-11039 of Seq ID No 29. Further provided are nucleotide sequences that hybridize, optionally under stringent conditions, to Seq ID Nos 1, 4 or 29, as well as, nucleotides homologous thereto.

In another embodiment, novel genomic sequences encoding the kappa light chain locus of ungulate immunoglobulin are provided. The present invention provides the first reported genomic sequence of ungulate kappa light chain regions. In one embodiment, nucleic acid sequence is provided that encodes the porcine kappa light chain locus. In another embodiment, the nucleic acid sequence can contain at least one joining region, one constant region and/or one enhancer region of kappa light chain. In a further embodiment, the nucleotide sequence can include at least five joining regions, one constant region and one enhancer region, for example, as represented in Seq ID No. 30. In a further embodiment, an isolated nucleotide sequence is provided that contains at least one, at least two, at least three, at least four or five joining regions and 3' flanking sequence to the joining region of porcine genomic kappa light chain, for example, as represented in Seq ID No 12. In another embodiment, an isolated nucleotide sequence of porcine genomic kappa light chain is provided that contains 5' flanking sequence to the first joining region, for example, as represented in Seq ID No 25. In a further embodiment, an isolated nucleotide sequence is provided that contains 3' flanking sequence to the constant region and, optionally, the 5' portion of the enhancer region, of porcine genomic kappa light chain, for example, as represented in Seq ID Nos. 15, 16 and/or 19.

In further embodiments, isolated nucleotide sequences as depicted in Seq ID Nos 30, 12, 25, 15, 16 or 19 are provided. Nucleic acid sequences at least 80, 85, 90, 95, 98 or 99% homologous to Seq ID Nos 30, 12, 25, 15, 16 or 19 are also provided. In addition, nucleotide sequences that contain at least 10, 15, 17, 20, 25 or 30 contiguous nucleotides of Seq ID Nos 30, 12, 25, 15, 16 or 19 are provided. Further provided are nucleotide sequences that hybridizes, optionally under stringent conditions, to Seq ID Nos 30, 12, 25, 15, 16 or 19, as well as, nucleotides homologous thereto.

In another embodiment, novel genomic sequences encoding the lambda light chain locus of ungulate immunoglobulin are provided. The present invention provides the first reported genomic sequence of ungulate lambda light chain regions. In one embodiment, the porcine lambda light chain nucleotides include a concatamer of J to C units. In a specific embodiment, an isolated porcine lambda nucleotide sequence is provided, such as that depicted in Seq ID No. 28. In one embodiment, a nucleotide sequence is provided that includes 5' flanking sequence to the first lambda J/C unit of the porcine lambda light chain genomic sequence, for example, as represented by Seq ID No 32. Still further, nucleotide sequence is provided that includes 3' flanking sequence to the J/C cluster region of the porcine lambda light chain genomic sequence, for example, approximately 200 base pairs downstream of lambda J/C, such as that represented by Seq ID No 33. Alternatively, nucleotide sequence is provided that includes 3' flanking sequence to the J/C cluster region of the porcine lambda light chain genomic sequence, for example, as represented by Seq ID No 34, 35, 36, 37, 38, and/or 39.

In a further embodiment, nucleic acid sequences are provided that encode bovine lambda light chain locus, which can include at least one joining region-constant region pair and/or at least one variable region, for example, as represented by Seq ID No. 31. In further embodiments, isolated nucleotide sequences as depicted in Seq ID Nos 28, 31, 32, 33, 34, 35, 36, 37, 38, or 39 are provided. Nucleic acid sequences at least 80, 85, 90, 95, 98 or 99% homologous to Seq ID Nos 28, 31, 32, 33, 34, 35, 36, 37, 38, or 39 are also provided. In addition, nucleotide sequences that contain at least 10, 15, 17, 20, 25 or 30 contiguous nucleotides of Seq ID Nos 28, 31, 32, 33, 34, 35, 36, 37, 38, or 39 are provided. Further provided are nucleotide sequences that hybridizes, optionally under stringent conditions, to Seq ID Nos 28, 31, 32, 33, 34, 35, 36, 37, 38, or 39, as well as, nucleotides homologous thereto.

In another embodiment, nucleic acid targeting vector constructs are also provided. The targeting vectors can be designed to accomplish homologous recombination in cells. These targeting vectors can be transformed into mammalian cells to target the ungulate heavy chain, kappa light chain or lambda light chain genes via homologous recombination. In one embodiment, the targeting vectors can contain a 3' recombination arm and a 5' recombination arm (i.e. flanking sequence) that is homologous to the genomic sequence of ungulate heavy chain, kappa light chain or lambda light chain genomic sequence, for example, sequence represented by Seq ID Nos. 1, 4, 29, 30, 12, 25, 15, 16, 19, 28 or 31, as described above. The homologous DNA sequence can include at least 15 bp, 20 bp, 25 bp, 50 bp, 100 bp, 500 bp, 1 kbp, 2 kbp, 4 kbp, 5 kbp, 10 kbp, 15 kbp, 20 kbp, or 50 kbp of sequence homologous to the genomic sequence.

In one embodiment, the 5' and 3' recombination arms of the targeting vector can be designed such that they flank the 5' and 3' ends of at least one functional variable, joining, diversity, and/or constant region of the genomic sequence. The targeting of a functional region can render it inactive, which results in the inability of the cell to produce functional immunoglobulin molecules. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

In one particular embodiment, the targeting vector can contain 5' and 3' recombination arms that contain homologous sequence to the 3' and 5' flanking sequence of the J6 region of the porcine immunoglobulin heavy chain locus. Since the J6 region is the only functional joining region of the porcine immunoglobulin heavy chain locus, this will prevent the expression of a functional porcine heavy chain immunoglobulin. In a specific embodiment, the targeting vector can contain a 5' recombination arm that contains sequence homologous to genomic sequence 5' of the J6 region, including J1-4, and a 3' recombination arm that contains sequence homologous to genomic sequence 3' of the J6 region, including the mu constant region (a "J6 targeting construct"), see for example, FIG. 1. Further, this J6 targeting construct can also contain a selectable marker gene that is located between the 5' and 3' recombination arms, see for example, Seq ID No 5 and FIG. 1. In other embodiments, the targeting vector can contain a 5' recombination arm that contains sequence homologous to genomic sequence 5' of the diversity region, and a 3' recombination arm that contains sequence homologous to genomic sequence 3' of the diversity region of the porcine heavy chain locus. In a further embodiment, the targeting vector can contain a 5' recombination arm that contains sequence homologous to genomic sequence 5' of the mu constant region and a 3' recombination arm that contains sequence homologous to genomic sequence 3' of the mu constant region of the porcine heavy chain locus.

In another particular embodiment, the targeting vector can contain 5' and 3' recombination arms that contain homologous sequence to the 3' and 5' flanking sequence of the constant region of the porcine immunoglobulin kappa light chain locus. Since the present invention discovered that there is only one constant region of the porcine immunoglobulin kappa light chain locus, this will prevent the expression of a functional porcine kappa light chain immunoglobulin. In a specific embodiment, the targeting vector can contain a 5' recombination arm that contains sequence homologous to genomic sequence 5' of the constant region, optionally including the joining region, and a 3' recombination arm that contains sequence homologous to genomic sequence 3' of the constant region, optionally including at least part of the enhancer region (a "Kappa constant targeting construct"), see for example, FIG. 2. Further, this kappa constant targeting construct can also contain a selectable marker gene that is located between the 5' and 3' recombination arms, see for example, Seq ID No 20 and FIG. 2. In other embodiments, the targeting vector can contain a 5' recombination arm that contains sequence homologous to genomic sequence 5' of the joining region, and a 3' recombination arm that contains sequence homologous to genomic sequence 3' of the joining region of the porcine kappa light chain locus.

In another particular embodiment, the targeting vector can contain 5' and 3' recombination arms that contain homologous sequence to the 3' and 5' flanking sequence of the J/C region of the porcine lambda light chain. See FIG. 3. Disruption of the J/C region will prevent the expression of a functional porcine kappa light chain immunoglobulin. In one embodiment, the targeting vector can contain a 5' recombination arm that contains sequence homologous to genomic sequence 5' of the first J/C unit and a 3' recombination arm that contains sequence homologous to genomic sequence 3' of the last J/C unit. Further, this lambda light chain targeting construct can also contain a selectable marker gene that is located between the 5' and 3' recombination arms, see for example FIG. 4.

In a further embodiment, more than one targeting vector can be used to target the ungulate heavy chain, kappa light chain or lambda light chain genes via homologous recombination. For example, two targeting vectors can be used to target the gene of interest. A first targeting vector can contain 5' and 3' recombination arms that contain homologous sequence to the 5' flanking sequence of at least one functional variable, joining, diversity, and/or constant region of the genomic sequence. A second targeting vector can contain 5' and 3' recombination arms that contain homologous sequence to the 3' flanking sequence at least one functional variable, joining, diversity, and/or constant region of the genomic sequence.

In a particular embodiment, the first targeting vector can contain 5' and 3' recombination arms that contain homologous sequence to the 5' flanking sequence of the first J/C unit in the J/C cluster region. See FIG. 5. According to this embodiment, a second targeting vector can contain 5' and 3' recombination arms that contain homologous sequence to the 3' flanking sequence of the last J/C unit in the J/C cluster region. See FIG. 6.

In another embodiment, primers are provided to generate 3' and 5' sequences of a targeting vector. The oligonucleotide primers can be capable of hybridizing to porcine immunoglobulin genomic sequence, such as Seq ID Nos. 1, 4, 29, 30, 12, 25, 15, 16, 19, 28 or 31, as described above. In a particular embodiment, the primers hybridize under stringent conditions to Seq ID Nos. 1, 4, 29, 30, 12, 25, 15, 16, 19, 28 or 31, as described above. Another embodiment provides oligonucleotide probes capable of hybridizing to porcine heavy chain, kappa light chain or lambda light chain nucleic acid sequences, such as Seq ID Nos. 1, 4, 29, 30, 12, 25, 15, 16, 19, 28 or 31, as described above. The polynucleotide primers or probes can have at least 14 bases, 20 bases, 30 bases, or 50 bases which hybridize to a polynucleotide of the present invention. The probe or primer can be at least 14 nucleotides in length, and in a particular embodiment, are at least 15, 20, 25, 28, or 30 nucleotides in length.

In one embodiment, primers are provided to amplify a fragment of porcine Ig heavy-chain that includes the functional joining region (the J6 region). In one non-limiting embodiment, the amplified fragment of heavy chain can be represented by Seq ID No 4 and the primers used to amplify this fragment can be complementary to a portion of the J-region, such as, but not limited to Seq ID No 2, to produce the 5' recombination arm and complementary to a portion of Ig heavy-chain mu constant region, such as, but not limited to Seq ID No 3, to produce the 3' recombination arm. In another embodiment, regions of the porcine Ig heavy chain (such as, but not limited to Seq ID No 4) can be subcloned and assembled into a targeting vector.

In other embodiments, primers are provided to amplify a fragment of porcine Ig kappa light-chain that includes the constant region. In another embodiment, primers are provided to amplify a fragment of porcine Ig kappa light-chain that includes the J region. In one non-limiting embodiment, the primers used to amplify this fragment can be complementary to a portion of the J-region, such as, but not limited to Seq ID No 21 or 10, to produce the 5' recombination arm and complementary to genomic sequence 3' of the constant region, such as, but not limited to Seq ID No 14, 24 or 18, to produce the 3' recombination arm. In another embodiment, regions of the porcine Ig heavy chain (such as, but not limited to Seq ID No 20) can be subcloned and assembled into a targeting vector.

In another aspect of the present invention, ungulate cells lacking at least one allele of a functional region of an ungulate heavy chain, kappa light chain and/or lambda light chain locus produced according to the process, sequences and/or constructs described herein are provided. These cells can be obtained as a result of homologous recombination. Particularly, by inactivating at least one allele of an ungulate heavy chain, kappa light chain or lambda light chain gene, cells can be produced which have reduced capability for expression of ungulate antibodies. In other embodiments, mammalian cells lacking both alleles of an ungulate heavy chain, kappa light chain and/or lambda light chain gene can be produced according to the process, sequences and/or constructs described herein. In a further embodiment, porcine animals are provided in which at least one allele of an ungulate heavy chain, kappa light chain and/or lambda light chain gene is inactivated via a genetic targeting event produced according to the process, sequences and/or constructs described herein. In another aspect of the present invention, porcine animals are provided in which both alleles of an ungulate heavy chain, kappa light chain and/or lambda light chain gene are inactivated via a genetic targeting event. The gene can be targeted via homologous recombination.

In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques. Additional genes for a desired protein or regulatory sequence that modulate transcription of an existing sequence can be inserted. To achieve multiple genetic modifications of ungulate immunoglobulin genes, in one embodiment, cells can be modified sequentially to contain multiple genetic modifications. In other embodiments, animals can be bred together to produce animals that contain multiple genetic modifications of immunoglobulin genes. As an illustrative example, animals that lack expression of at least one allele of an ungulate heavy chain gene can be further genetically modified or bred with animals lacking at least one allele of a kappa light chain gene.

In embodiments of the present invention, alleles of ungulate heavy chain, kappa light chain or lambda light chain gene are rendered inactive according to the process, sequences and/or constructs described herein, such that functional ungulate immunoglobulins can no longer be produced. In one embodiment, the targeted immunoglobulin gene can be transcribed into RNA, but not translated into protein. In another embodiment, the targeted immunoglobulin gene can be transcribed in an inactive truncated form. Such a truncated RNA may either not be translated or can be translated into a nonfunctional protein. In an alternative embodiment, the targeted immunoglobulin gene can be inactivated in such a way that no transcription of the gene occurs. In a further embodiment, the targeted immunoglobulin gene can be transcribed and then translated into a nonfunctional protein.

In a further aspect of the present invention, ungulate, such as porcine or bovine, cells lacking one allele, optionally both alleles of an ungulate heavy chain, kappa light chain and/or lambda light chain gene can be used as donor cells for nuclear transfer into recipient cells to produce cloned, transgenic animals. Alternatively, ungulate heavy chain, kappa light chain and/or lambda light chain gene knockouts can be created in embryonic stem cells, which are then used to produce offspring. Offspring lacking a single allele of a functional ungulate heavy chain, kappa light chain and/or lambda light chain gene produced according to the process, sequences and/or constructs described herein can be breed to further produce offspring lacking functionality in both alleles through mendelian type inheritance.

In one aspect of the present invention, a method is provided to disrupt the expression of an ungulate immunoglobulin gene by (i) analyzing the germline configuration of the ungulate heavy chain, kappa light chain or lambda light chain genomic locus; (ii) determining the location of nucleotide sequences that flank the 5' end and the 3' end of at least one functional region of the locus; and (iii) transfecting a targeting construct containing the flanking sequence into a cell wherein, upon successful homologous recombination, at least one functional region of the immunoglobulin locus is disrupted thereby reducing or preventing the expression of the immunoglobulin gene. In one embodiment, the germline configuration of the porcine heavy chain locus is provided. The porcine heavy chain locus contains at least four variable regions, two diversity regions, six joining regions and five constant regions, for example, as illustrated in FIG. 1. In a specific embodiment, only one of the six joining regions, J6, is functional. In another embodiment, the germline configuration of the porcine kappa light chain locus is provided. The porcine kappa light chain locus contains at least six variable regions, six joining regions, one constant region and one enhancer region, for example, as illustrated in FIG. 2. In a further embodiment, the germline configuration of the porcine lambda light chain locus is provided. The porcine lambda light chain locus contains a variable region and the J/C region. See FIG. 3.

In a further aspect of the present invention, a method is provided to disrupt the expression of an ungulate lambda light chain locus by (i) analyzing the germline configuration of the ungulate lambda light chain genomic locus; (ii) determining the location of nucleotide sequences that flank the 5' end of at least one functional region of the locus; (ii) constructing a 5' targeting construct; (iv) determining the location of nucleotide sequences that flank the 3' end of at least one functional region of the locus; (v) constructing a 3' targeting construct; (vi) transfecting both the 5' and the 3' targeting constructs into a cell wherein, upon successful homologous recombination of each targeting construct, at least one functional region of the immunoglobulin locus is disrupted thereby reducing or preventing the expression of the immunoglobulin gene. See FIGS. 5 and 6.

In one embodiment, the germline configuration of the porcine lambda light chain locus is provided. The porcine lambda light chain locus contains a variable region and a J/C region. See FIG. 3.

In further aspects of the present invention provides ungulates and ungulate cells that lack at least one allele of a functional region of an ungulate heavy chain, kappa light chain and/or lambda light chain locus produced according to the processes, sequences and/or constructs described herein, which are further modified to express at least part of a human antibody (i.e. immunoglobulin (Ig)) locus. In additional embodiments, porcine animals are provided that express xenogenous immunoglobulin. This human locus can undergo rearrangement and express a diverse population of human antibody molecules in the ungulate. These cloned, transgenic ungulates provide a replenishable, theoretically infinite supply of human antibodies (such as polyclonal antibodies), which can be used for therapeutic, diagnostic, purification, and other clinically relevant purposes. In one particular embodiment, artificial chromosomes (ACs), such as yeast or mammalian artificial chromosomes (YACS or MACS) can be used to allow expression of human immunoglobulin genes into ungulate cells and animals. All or part of human immunoglobulin genes, such as the Ig heavy chain gene (human chromosome 414), Ig kappa chain gene (human chromosome #2) and/or the Ig lambda chain gene (chromosome #22) can be inserted into the artificial chromosomes, which can then be inserted into ungulate cells. In further embodiments, ungulates and ungulate cells are provided that contain either part or all of at least one human antibody gene locus, which undergoes rearrangement and expresses a diverse population of human antibody molecules.

In additional embodiments, methods of producing xenogenous antibodies are provided, wherein the method can include: (a) administering one or more antigens of interest to an ungulate whose cells comprise one or more artificial chromosomes and lack any expression of functional endogenous immunoglobulin, each artificial chromosome comprising one or more xenogenous immunoglobulin loci that undergo rearrangement, resulting in production of xenogenous antibodies against the one or more antigens; and/or (b) recovering the xenogenous antibodies from the ungulate. In one embodiment, the immunoglobulin loci can undergo rearrangement in a B cell.

In one aspect of the present invention, an ungulate, such as a pig or a cow, can be prepared by a method in accordance with any aspect of the present invention. These cloned, transgenic ungulates (e.g., porcine and bovine animals) provide a replenishable, theoretically infinite supply of human polyclonal antibodies, which can be used as therapeutics, diagnostics and for purification purposes. For example, transgenic animals produced according to the process, sequences and/or constructs described herein that produce polyclonal human antibodies in the bloodstream can be used to produce an array of different antibodies which are specific to a desired antigen. The availability of large quantities of polyclonal antibodies can also be used for treatment and prophylaxis of infectious disease, vaccination against biological warfare agents, modulation of the immune system, removal of undesired human cells such as cancer cells, and modulation of specific human molecules.

In other embodiments, animals or cells lacking expression of functional immunoglobulin, produced according to the process, sequences and/or constructs described herein, can contain additional genetic modifications to eliminate the expression of xenoantigens. Such animals can be modified to eliminate the expression of at least one allele of the alpha-1,3-galactosyltransferase gene, the CMP-Neu5Ac hydroxylase gene (see, for example, U.S. Ser. No. 10/863, 116), the iGb3 synthase gene (see, for example, U.S. Patent Application 60/517,524), and/or the Forssman synthase gene (see, for example, U.S. Patent Application 60/568,922). In additional embodiments, the animals discloses herein can also contain genetic modifications to express fucosyltransferase and/or sialyltransferase. To achieve these additional genetic modifications, in one embodiment, cells can be modified to contain multiple genetic modifications. In other embodiments, animals can be bred together to achieve multiple genetic modifications. In one specific embodiment, animals, such as pigs, lacking expression of functional immunoglobulin, produced according to the process, sequences and/or constructs described herein, can be bred with animals, such as pigs, lacking expression of alpha-1, 3-galactosyl transferase (for example, as described in WO 04/028243).

DETAILED DESCRIPTION

Figure 1:
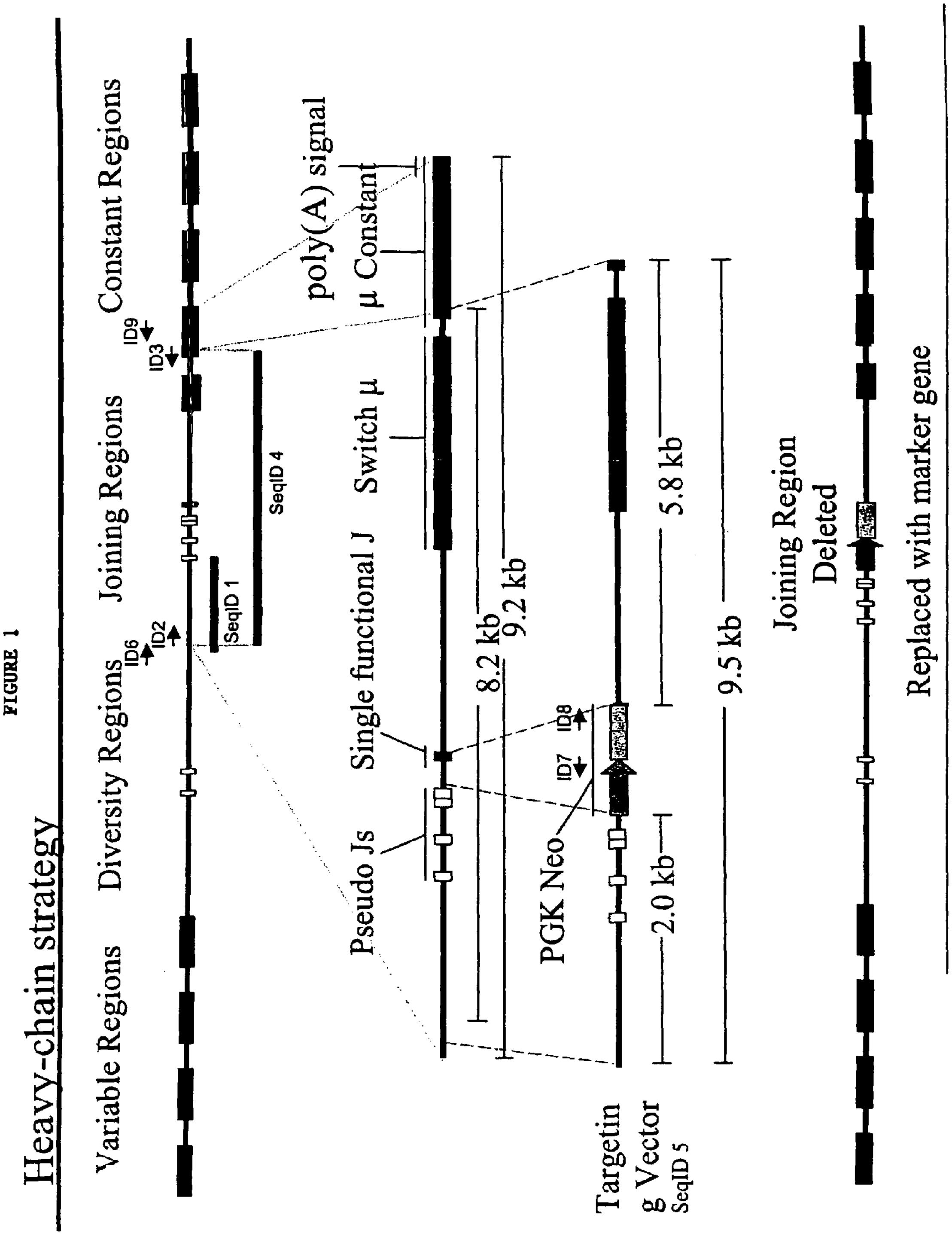
FIG. 1 illustrates the design of a targeting vector that disrupts the expression of the joining region of the porcine heavy chain immunoglobulin gene.

The present invention provides for the first time ungulate immunoglobin germline gene sequence arrangement as well as novel genomic sequences thereof. In addition, novel ungulate cells, tissues and animals that lack at least one allele of a heavy or light chain immunoglobulin gene are provided. Based on this discovery, ungulates can be produced that completely lack at least one allele of a heavy and/or light chain immunoglobulin gene. In addition, these ungulates can be further modified to express xenoogenous, such as human, immunoglobulin loci or fragments thereof.

In one aspect of the present invention, a transgenic ungulate that lacks any expression of functional endogenous immunoglobulins is provided. In one embodiment, the ungulate can lack any expression of endogenous heavy and/or light chain immunoglobulins. The light chain immunoglobulin can be a kappa and/or lambda immunoglobulin. In additional embodiments, transgenic ungulates are provided that lack expression of at least one allele of an endogenous immunoglobulin wherein the immunoglobulin is selected from the group consisting of heavy chain, kappa light chain and lambda light chain or any combination thereof. In one embodiment, the expression of functional endogenous immunoglobulins can be accomplished by genetic targeting of the endogenous immunoglobulin loci to prevent expression of the endogenous immunoglobulin. In one embodiment, the genetic targeting can be accomplished via homologous recombination. In another embodiment, the transgenic ungulate can be produced via nuclear transfer.

In other embodiments, the transgenic ungulate that lacks any expression of functional endogenous immunoglobulins can be further genetically modified to express an xenogenous immunoglobulin loci. In an alternative embodiment, porcine animals are provided that contain an xenogeous immunoglobulin locus. In one embodiment, the xenogeous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof.

In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In another aspect of the present invention, transgenic ungulates are provided that expresses a xenogenous immunoglobulin loci or fragment thereof, wherein the immunoglobulin can be expressed from an immunoglobulin locus that is integrated within an endogenous ungulate chromosome. In one embodiment, ungulate cells derived from the transgenic animals are provided. In one embodiment, the xenogenous immunoglobulin locus can be inherited by offspring. In another embodiment, the xenogenous immunoglobulin locus can be inherited through the male germ line by offspring. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

DEFINITIONS

The terms “recombinant DNA technology,” “DNA cloning,” “molecular cloning,” or “gene cloning” refer to the process of transferring a DNA sequence into a cell or organism. The transfer of a DNA fragment can be from one organism to a self-replicating genetic element (e.g., bacterial plasmid) that permits a copy of any specific part of a DNA (or RNA) sequence to be selected among many others and produced in an unlimited amount. Plasmids and other types of cloning vectors such as artificial chromosomes can be used to copy genes and other pieces of chromosomes to generate enough identical material for further study. In addition to bacterial plasmids, which can carry up to 20 kb of foreign DNA, other cloning vectors include viruses, cosmids, and artificial chromosomes (e.g., bacteria artificial chromosomes (BACs) or yeast artificial chromosomes (YACs)). When the fragment of chromosomal DNA is ultimately joined with its cloning vector in the lab, it is called a “recombinant DNA molecule.” Shortly after the recombinant plasmid is introduced into suitable host cells, the newly inserted segment will be reproduced along with the host cell DNA.

“Cosmids” are artificially constructed cloning vectors that carry up to 45 kb of foreign DNA. They can be packaged in lambda phage particles for infection into *E. coli* cells.

As used herein, the term “mammal” (as in “genetically modified (or altered) mammal”) is meant to include any non-human mammal, including but not limited to pigs, sheep, goats, cattle (bovine), deer, mules, horses, monkeys, dogs, cats, rats, mice, birds, chickens, reptiles, fish, and insects. In one embodiment of the invention, genetically altered pigs and methods of production thereof are provided.

The term “ungulate” refers to hoofed mammals. Artiodactyls are even-toed (cloven-hooved) ungulates, including antelopes, camels, cows, deer, goats, pigs, and sheep. Perissodactyls are odd toes ungulates, which include horses, zebras, rhinoceroses, and tapirs. The term ungulate as used herein refers to an adult, embryonic or fetal ungulate animal.

As used herein, the terms “porcine”, “porcine animal”, “pig” and “swine” are generic terms referring to the same type of animal without regard to gender, size, or breed.

A “homologous DNA sequence or homologous DNA” is a DNA sequence that is at least about 80%, 85%, 90%, 95%, 98% or 99% identical with a reference DNA sequence. A homologous sequence hybridizes under stringent conditions to the target sequence, stringent hybridization conditions include those that will allow hybridization occur if there is at least 85, at least 95% or 98% identity between the sequences.

An “isogenic or substantially isogenic DNA sequence” is a DNA sequence that is identical to or nearly identical to a reference DNA sequence. The term “substantially isogenic” refers to DNA that is at least about 97-99% identical with the reference DNA sequence, or at least about 99.5-99.9% identical with the reference DNA sequence, and in certain uses 100% identical with the reference DNA sequence.

“Homologous recombination” refers to the process of DNA recombination based on sequence homology.

“Gene targeting” refers to homologous recombination between two DNA sequences, one of which is located on a chromosome and the other of which is not.

“Non-homologous or random integration” refers to any process by which DNA is integrated into the genome that does not involve homologous recombination.

A “selectable marker gene” is a gene, the expression of which allows cells containing the gene to be identified. A selectable marker can be one that allows a cell to proliferate on a medium that prevents or slows the growth of cells without the gene. Examples include antibiotic resistance genes and genes which allow an organism to grow on a selected metabolite. Alternatively, the gene can facilitate visual screening of transformants by conferring on cells a phenotype that is easily identified. Such an identifiable phenotype can be, for example, the production of luminescence or the production of a colored compound, or the production of a detectable change in the medium surrounding the cell.

The term “contiguous” is used herein in its standard meaning, i.e., without interruption, or uninterrupted.

“Stringent conditions” refers to conditions that (1) employ low ionic strength and high temperature for washing, for example, 0.015 M NaCl/0.0015 M sodium citrate/0.1% SDS at 50° C., or (2) employ during hybridization a denaturing agent such as, for example, formamide. One skilled in the art can determine and vary the stringency conditions appropriately to obtain a clear and detectable hybridization signal.

For example, stringency can generally be reduced by increasing the salt content present during hybridization and washing, reducing the temperature, or a combination thereof. See, for example, Sambrook et al., Molecular Cloning: A Laboratory Manual, Cold Spring Harbour Laboratory Press, Cold Spring Harbour, N.Y., (1989).

I. Immunoglobulin Genes

In one aspect of the present invention, a transgenic ungulate that lacks any expression of functional endogenous immunoglobulins is provided. In one embodiment, the ungulate can lack any expression of endogenous heavy and/or light chain immunoglobulins. The light chain immunoglobulin can be a kappa and/or lambda immunoglobulin. In additional embodiments, transgenic ungulates are provided that lack expression of at least one allele of an endogenous immunoglobulin wherein the immunoglobulin is selected from the group consisting of heavy chain, kappa light chain and lambda light chain or any combination thereof. In one embodiment, the expression of functional endogenous immunoglobulins can be accomplished by genetic targeting of the endogenous immunoglobulin loci to prevent expression of the endogenous immunoglobulin. In one embodiment, the genetic targeting can be accomplished via homologous recombination. In another embodiment, the transgenic ungulate can be produced via nuclear transfer.

In another aspect of the present invention, a method is provided to disrupt the expression of an ungulate immunoglobulin gene by (i) analyzing the germline configuration of the ungulate heavy chain, kappa light chain or lambda light chain genomic locus; (ii) determining the location of nucleotide sequences that flank the 5' end and the 3' end of at least one functional region of the locus; and (iii) transfecting a targeting construct containing the flanking sequence into a cell wherein, upon successful homologous recombination, at least one functional region of the immunoglobulin locus is disrupted thereby reducing or preventing the expression of the immunoglobulin gene.

In one embodiment, the germline configuration of the porcine heavy chain locus is provided. The porcine heavy chain locus contains at least four variable regions, two diversity regions, six joining regions and five constant regions, for example, as illustrated in FIG. 1. In a specific embodiment, only one of the six joining regions, J6, is functional.

Figure 2:
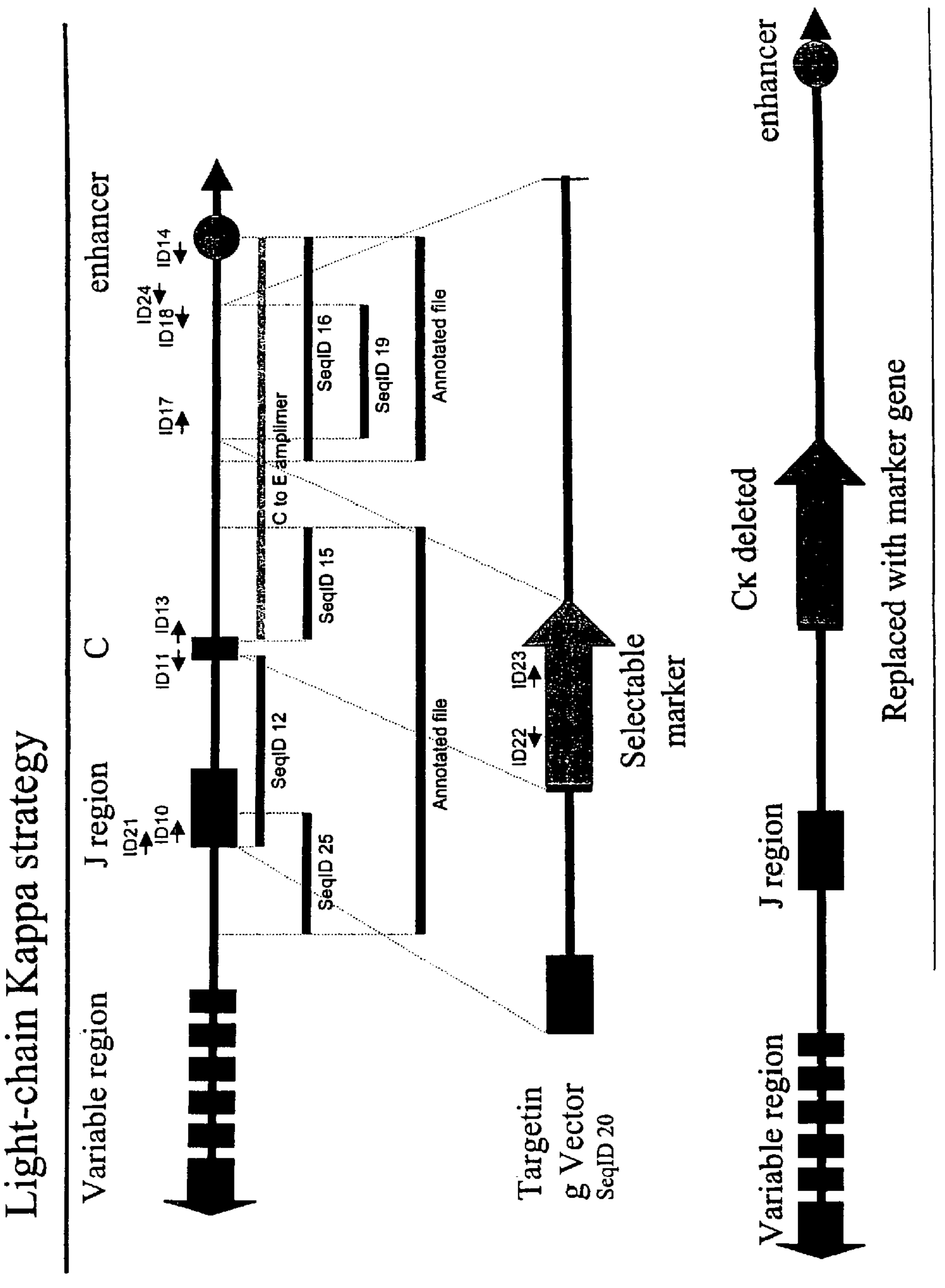
FIG. 2 illustrates the design of a targeting vector that disrupts the expression of the constant region of the porcine kappa light chain immunoglobulin gene.

In another embodiment, the germline configuration of the porcine kappa light chain locus is provided. The porcine kappa light chain locus contains at least six variable regions, six joining regions, one constant region and one enhancer region, for example, as illustrated in FIG. 2.

In a further embodiment, the germline configuration of the porcine lambda light chain locus is provided.

Isolated nucleotide sequences as depicted in Seq ID Nos 1-39 are provided. Nucleic acid sequences at least 80, 85, 90, 95, 98 or 99% homologous to any one of Seq ID Nos 1-39 are also provided. In addition, nucleotide sequences that contain at least 10, 15, 17, 20, 25 or 30 contiguous nucleotides of any one of Seq ID Nos 1-39 are provided. Further provided are nucleotide sequences that hybridize, optionally under stringent conditions, to Seq ID Nos 1-39, as well as, nucleotides homologous thereto.

Homology or identity at the nucleotide or amino acid sequence level can be determined by BLAST (Basic Local Alignment Search Tool) analysis using the algorithm employed by the programs blastp, blastn, blastx, tblastn and tblastx (see, for example, Altschul, S. F. et al (1997) Nucleic Acids Res 25:3389-3402 and Karlin et al, (1900) Proc. Natl. Acad. Sci. USA 87, 2264-2268) which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a preselected threshold of significance. See, for example, Altschul et al., (1994) (Nature Genetics 6, 119-129). The search parameters for histogram, descriptions, alignments, expect (i.e., the statistical significance threshold for reporting matches against database sequences), cutoff, matrix and filter (low co M'plexity) are at the default settings. The default scoring matrix used by blastp, blastx, tblastn, and tblastx is the BLOSUM62 matrix (Henikoff et al., (1992) Proc. Natl. Acad. Sci. USA 89, 10915-10919), which is recommended for query sequences over 85 in length (nucleotide bases or amino acids).

Porcine Heavy Chain

In another aspect of the present invention, novel genomic sequences encoding the heavy chain locus of ungulate immunoglobulin are provided. In one embodiment, an isolated nucleotide sequence encoding porcine heavy chain is provided that includes at least one variable region, two diversity regions, at least four joining regions and at least one constant region, such as the mu constant region, for example, as represented in Seq ID No. 29. In another embodiment, an isolated nucleotide sequence is provided that includes at least four joining regions and at least one constant region, such as the mu constant region, of the porcine heavy chain genomic sequence, for example, as represented in Seq ID No. 4. In a further embodiment, nucleotide sequence is provided that includes 5' flanking sequence to the first joining region of the porcine heavy chain genomic sequence, for example, as represented in Seq ID No 1. Still further, nucleotide sequence is provided that includes 3' flanking sequence to the first joining region of the porcine heavy chain genomic sequence, for example, as represented in the 3' region of Seq ID No 4. In further embodiments, isolated nucleotide sequences as depicted in Seq ID Nos 1, 4 or 29 are provided. Nucleic acid sequences at least 80, 85, 90, 95, 98 or 99% homologous to Seq ID Nos 1, 4 or 29 are also provided. Further provided are nucleotide sequences that hybridize, optionally under stringent conditions, to Seq ID Nos 1, 4 or 29, as well as, nucleotides homologous thereto.

In addition, nucleotide sequences that contain at least 10, 15, 17, 20, 25 or 30 contiguous nucleotides of Seq ID Nos 1, 4 or 29 are provided. In one embodiment, the nucleotide sequence contains at least 17, 20, 25 or 30 contiguous nucleotides of Seq ID No 4 or residues 1-9,070 of Seq ID No 29. In other embodiments, nucleotide sequences that contain at least 50, 100, 1,000, 2,500, 4,000, 4,500, 5,000, 7,000, 8,000, 8,500, 9,000, 10,000 or 15,000 contiguous nucleotides of Seq ID No. 29 are provided. In another embodiment, the nucleotide sequence contains residues 9,070-11039 of Seq ID No 29.

In further embodiments, isolated nucleotide sequences as depicted in Seq ID Nos 1, 4 or 29 are provided. Nucleic acid sequences at least 80, 85, 90, 95, 98 or 99% homologous to Seq ID Nos 1, 4 or 29 are also provided. In addition, nucleotide sequences that contain at least 10, 15, 17, 20, 25 or 30 contiguous nucleotides of Seq ID Nos 1, 4 or 29 are provided. Further provided are nucleotide sequences that hybridize, optionally under stringent conditions, to Seq ID Nos 1, 4 or 29, as well as, nucleotides homologous thereto.

In one embodiment, an isolated nucleotide sequence encoding porcine heavy chain is provided that includes at least one variable region, two diversity regions, at least four joining regions and at least one constant region, such as the mu constant region, for example, as represented in Seq ID No. 29. In Seq ID No. 29, the Diversity region of heavy chain is represented, for example, by residues 1089-1099 (D(pseudo)), the Joining region of heavy chain is represented, for example, by residues 1887-3352 (for example: J(psuedo): 1887-1931, J(psuedo): 2364-2411, J(psuedo): 2756-2804, J (functional J): 3296-3352), the recombination signals are represented, for example, by residues 3001-3261 (Nonamer), 3292-3298 (Heptamer), the Constant Region is represented by the following residues: 3353-9070 (J to C mu intron), 5522-8700 (Switch region), 9071-9388 (Mu Exon 1), 9389-9469 (Mu Intron A), 9470-9802 (Mu Exon 2), 9830-10069 (Mu Intron B), 10070-10387 (Mu Exon 3), 10388-10517 (Mu Intron C), 10815-11052 (Mu Exon 4), 11034-11039 (Poly(A) signal).

```
Seq ID No. 29 tctagaagacgctggagagaggccagacttcctcgga
acagctcaaagagctctgtcaaagccagatcccatca
cacgtgggcaccaataggccatgccagcctccaaggg
ccgaactgggttctccacggcgcacatgaagcctgca
gcctggcttatcctcttccgtggtgaagaggcaggcc
cgggactggacgaggggctagcagggtgtggtaggca
ccttgcgcccccccaccccggcaggaaccagagaccct
ggggctgagagtgagcctccaaacaggatgccccacc
cttcaggccacctttcaatccagctacactccacctg
ccattctcctctgggcacagggcccagcccctggatc
ttggccttggctcgacttgcacccacgcgcacacaca
cacttcctaacgtgctgtccgctcacccctccccagc
gtggtccatgggcagcacggcagtgcgcgtccggcgg
tagtgagtgcagaggtcccttcccctcccccaggagc
cccaggggtgtgtgcagatctgggggctcctgtccct
tacaccttcatgcccctcccctcatacccaccctcca
ggcgggaggcagcgagacctttgcccagggactcagc
caacgggcacacgggaggccagccctcagcagctggc
tcccaaagaggaggtgggaggtaggtccacagctgcc
acagagagaaaccctgacggaccccacaggggccacg
ccagccggaaccagctccctcgtgggtgagcaatggc
cagggccccgccggccaccacggctggccttgcgcca
gctgagaactcacgtccagtgcagggagactcaagac
agcctgtgcacacagcctcggatctgctcccatttca
agcagaaaaaggaaaccgtgcaggcagccctcagcat
ttcaaggattgtagcagcggccaactattcgtcggca
gtggccgattagaatgaccgtggagaagggcggaagg
gtctctcgtgggctctgcggccaacaggccctggctc
cacctgcccgctgccagcccgaggggcttgggccgag
ccaggaaccacagtgctcaccgggaccacagtgactg
```

-continued

```
accaaactcccggccagagcagccccaggccagccgg
gctctcgccctggaggactcaccatcagatgcacaag
ggggcgagtgtggaagagacgtgtcgcccgggccatt
tgggaaggcgaagggaccttccaggtggacaggaggt
gggacgcactccaggcaagggactgggtccccaaggc
ctggggaaggggtactggcttggggggttagcctggcc
agggaacggggagcggggcggggggctgagcagggag
gacctgacctcgtgggagcgaggcaagtcaggcttca
ggcagcagccgcacatcccagaccaggaggctgaggc
aggaggggcttgcagcggggcgggggcctgcctggct
ccgggggctcctgggggacgctggctcttgtttccgt
gtcccgcagcacagggccagctcgctgggcctatgct
taccttgatgtctggggccggggcgtcagggtcgtcg
tctcctcaggggagagtcccctgaggctacgctgggg
*ggggactatggcagctccaccaggggcctggggacc
aggggcctggaccaggctgcagcccggaggacgggca
gggctctggctctccagcatctggccctcggaaatgg
cagaacccctggcgggtgagcgagctgagagcgggtc
agacagacaggggccggccggaaaggagaagttgggg
gcagagcccgccaggggccaggcccaaggttctgtgt
gccagggcctgggtgggcacattggtgtggccatggc
tacttagattcgtggggccagggcatcctggtcaccg
tctcctcaggtgagcctggtgtctgatgtccagctag
gcgctggtgggccgcgggtgggcctgtctcaggctag
ggcaggggctgggatgtgtatttgtcaaggaggggca
acagggtgcagactgtgcccctggaaacttgaccact
ggggcaggggcgtcctggtcacgtctcctcaggtaag
acggccctgtgcccctctctcgcgggactggaaaagg
aattttccaagattccttggtctgtgtggggccctct
ggggcccccgggggtggctcccctcctgcccagatgg
ggcctcggcctgtggagcacgggctgggcacacagct
cgagtctagggccacagaggcccgggctcagggctct
gtgtggcccggcgactggcagggggctcgggtttttg
gacacccccctaatgggggccacagcactgtgaccatc
ttcacagctggggccgaggagtcgaggtcaccgtctc
ctcaggtgagtcctcgtcagccctctctcactctctg
gggggttttgctgcattttgtgggggaaagaggatgc
ctgggtctcaggtctaaaggtctagggccagcgccgg
ggcccaggaaggggccgaggggccaggctcggctcgg
ccaggagcagagcttccagacatctcgcctcctggcg
gctgcagtcaggcctttggccggggggtctcagcac
```

-continued caccaggcctcttggctcccgaggtccccggccccgg ctgcctcaccaggcaccgtgcgcggtgggcccgggct cttggtcggccaccctttcttaactgggatccgggct tagttgtcgcaatgtgacaacgggctcgaaagctggg gccaggggaccctagtctacgacgcctcgggtgggtg tcccgcacccctccccactttcacggcactcggcgag acctggggagtcaggtgttggggacactttggaggtc aggaacgggagctggggagagggctctgtcagcgggg tccagagatgggccgccctccaaggacgccctgcgcg gggacaagggcttcttggcctggcctggccgcttcac ttgggcgtcaggggggcttcccggggcaggcggtca gtcgaggcgggttggaattctgagtctgggttcgggg ttcggggttcggccttcatgaacagacagcccaggcg ggccgttgtttggcccctgggggcctggttggaatgc gaggtctcgggaagtcaggagggagcctggccagcag agggttcccagccctgcggccgagggacctggagacg ggcagggcattggccgtcgcagggccaggccacaccc cccaGGTTTTTGTggggcgagcctggagattgcacCA

CTGTGATTACTATGCTATGGATCTCTGGGGCCCAGGC

GTTGAAGTCGTCGTGTCCTCAGgtaagaacggccctc cagggcctttaatttctgctctcgtctgtgggctttt ctgactctgatcctcgggaggcgtctgtgccccccc ggggatgaggccggcttgccaggaggggtcagggacc aggagcctgtgggaagttctgacgggggctgcaggcg ggaagggccccaccggggggcgagccccaggccgctg ggcggcaggagacccgtgagagtgcgccttgaggagg gtgtctgcggaaccacgaacgcccgccgggaagggct tgctgcaatgcggtcttcagacgggaggcgtcttctg ccctcaccgtctttcaagcccttgtgggtctgaaaga gccatgtcggagagagaagggacaggcctgtcccgac ctggccgagagcgggcagccccgggggagagcggggc gatcggcctgggctctgtgaggccaggtccaagggag gacgtgtggtcctcgtgacaggtgcacttgcgaaacc ttagaagacggggtatgttggaagcggctcctgatgt ttaagaaaagggagactgtaaagtgagcagagtcctc aagtgtgttaaggttttaaaggtcaaagtgttttaaa cctttgtgactgcagttagcaagcgtgcggggagtga atggggtgccagggtggccgagaggcagtacgagggc cgtgccgtcctctaattcagggcttagttttgcagaa taaagtcggcctgttttctaaaagcattggtggtgct -continued gagctggtggaggaggccgcgggcagccctggccacc tgcagcaggtggcaggaagcaggtcggccaagaggct attttaggaagccagaaaacacggtcgatgaatttat agcttctggtttccaggaggtggttgggcatggcttt gcgcagcgccacagaaccgaaagtgcccactgagaaa aaacaactcctgcttaatttgcatttttctaaaagaa gaaacagaggctgacggaaactggaaagttcctgttt taactactcgaattgagttttcggtcttagcttatca actgctcacttagattcattttcaaagtaaacgttta agagccgaggcattcctatcctcttctaaggcgttat tcctggaggctcattcaccgccagcacctccgctgcc tgcaggcattgctgtcaccgtcaccgtgacggcgcgc acgattttcagttggcccgcttcccctcgtgattagg acagacgcgggcactctggcccagccgtcttggctca gtatctgcaggcgtccgtctcgggacggagctcaggg gaagagcgtgactccagttgaacgtgatagtcggtgc gttgagaggagacccagtcgggtgtcgagtcagaagg ggcccggggcccgaggccctgggcaggacggcccgtg ccctgcatcacgggcccagcgtcctagaggcaggact ctggtggagagtgtgagggtgcctggggcccctccgg agctggggccgtgcggtgcaggttgggctctcggcgc ggtgttggctgtttctgcgggatttggaggaattctt ccagtgatgggagtcgccagtgaccgggcaccaggct ggtaagagggaggccgccgtcgtggccagagcagctg ggagggttcggtaaaaggctcgcccgtttcctttaat gaggacttttcctggagggcatttagtctagtcggga ccgttttcgactcgggaagagggatgcggaggagggc atgtgcccaggagccgaaggcgccgcggggagaagcc cagggctctcctgtccccacagaggcgacgccactgc cgcagacagacagggcctttccctctgatgacggcaa aggcgcctcggctcttgcggggtgctgggggggagtc gccccgaagccgctcacccagaggcctgaggggtgag actgaccgatgcctcttggccgggcctggggccggac cgagggggactccgtggaggcagggcgatggtggctg cgggagggaaccgaccctgggccgagcccggcttggc gattcccgggcgagggccctcagccgaggcgagtggg tccggcggaaccaccctttctggccagcgccacaggg ctctcgggactgtccggggcgacgctgggctgcccgt ggcaggccTGGGCTGACCTGGACTTCACGAGACAGAA

CAGGGCTTTCAGGGCTGAGCTGAGCCAGGTTTAGCGA

GGCCAAGTGGGGCTGAACCAGGCTCAACTGGCCTGAG

-continued

CTGGGTTGAGCTGGGCTGACCTGGGCTGAGCTGAGCT

GGGCTGGGCTGGGCTGGGCTGGGCTGGGCTGGGCTGG

ACTGGCTGAGCTGAGCTGGGTTGAGCTGAGCTGAGCT

GGCCTGGGTTGAGCTGGGCTGGGTTGAGCTGAGCTGG

GTTGAGCTGGGTTGAGCTGGGTTGATCTGAGCTGAGC

TGGGCTGAGCTGAGCTAGGCTGGGGTGAGCTGGGCTG

AGCTGGTTTGAGTTGGGTTGAGCTGAGCTGAGCTGGG

CTGTGCTGGCTGAGCTAGGCTGAGCTAGGCTAGGTTG

AGCTGGGCTGGGCTGAGCTGAGCTAGGCTGGGCTGAT

TTGGGCTGAGCTGAGCTGAGCTAGGCTGCGTTGAGCT

GGCTGGGCTGGATTGAGCTGGCTGAGCTGGCTGAGCT

GGGCTGAGCTGGCCTGGGTTGAGCTGAGCTGGACTGG

TTTGAGCTGGGTCGATCTGGGTTGAGCTGTCCTGGGT

TGAGCTGGGCTGGGTTGAGCTGAGCTGGGTTGAGCTG

GGCTCAGCAGAGCTGGGTTGGGCTGAGCTGGGTTGAG

CTGAGCTGGGCTGAGCTGGCCTGGGTTGAGCTGGGCT

GAGCTGAGCTGGGCTGAGCTGGCCTGTGTTGAGCTGG

GCTGGGTTGAGCTGGGCTGAGCTGGATTGAGCTGGGT

TGAGCTGAGCTGGGCTGGGCTGTGCTGACTGAGCTGG

GCTGAGCTAGGCTGGGGTGAGCTGGGCTGAGCTGATC

CGAGCTAGGCTGGGCTGGTTTGGGCTGAGCTGAGCTG

AGCTAGGCTGGATTGATCTGGCTGAGCTGGGTTGAGC

TGAGCTGGGCTGAGCTGGTCTGAGCTGGCCTGGGTCG

AGCTGAGCTGGACTGGTTTGAGCTGGGTCGATCTGGG

CTGAGCTGGCCTGGGTTGAGCTGGGCTGGGTTGAGCT

GAGCTGGGTTGAGCTGGGCTGAGCTGAGGGCTGGGGT

GAGCTGGGCTGAACTAGCCTAGCTAGGTTGGGCTGAG

CTGGGCTGGTTTGGGCTGAGCTGAGCTGAGCTAGGCT

GCATTGAGCAGGCTGAGCTGGGCTGAGCAGGCCTGGG

GTGAGCTGGGCTAGGTGGAGCTGAGCTGGGTCGAGCT

GAGTTGGGCTGAGCTGGCCTGGGTTGAGGTAGGCTGA

GCTGAGCTGAGCTAGGCTGGGTTGAGCTGGCTGGGCT

GGTTTGCGCTGGGTCAAGCTGGGCCGAGCTGGCCTGG

GTTGAGCTGGGCTCGGTTGAGCTGGGCTGAGCTGAGC

CGACCTAGGCTGGGATGAGCTGGGCTGATTTGGGCTG

AGCTGAGCTGAGCTAGGCTGCATTGAGCAGGCTGAGC

TGGGCCTGGAGCCTGGCCTGGGGTGAGCTGGGCTGAG

CTGCGCTGAGCTAGGCTGGGTTGAGCTGGCTGGGCTG

GTTTGCGCTGGGTCAAGCTGGGCCGAGCTGGCCTGGG

ATGAGCTGGGCCGGTTTGGGCTGAGCTGAGCTGAGCT

-continued

AGGCTGCATTGAGCAGGCTGAGCTGGGCTGAGCTGGC

CTGGGGTGAGCTGGGCTGAGCTAAGCTGAGCTGGGCT

GGTTTGGGCTGAGCTGGCTGAGCTGGGTCCTGCTGAG

CTGGGCTGAGCTGACCAGGGGTGAGCTGGGCTGAGTT

AGGCTGGGCTCAGCTAGGCTGGGTTGATCTGGCAGGG

CTGGTTTGCGCTGGGTCAAGCTCCCGGGAGATGGCCT

GGGATGAGCTGGGCTGGTTTGGGCTGAGCTGAGCTGA

GCTGAGCTAGGCTGCATTGAGCAGGCTGAGCTGGGCT

GAGCTGGCCTGGGGTGAGCTGGGCTGGGTGGAGCTGA

GCTGGGCTGAACTGGGCTAAGCTGGCTGAGCTGGATC

GAGCTGAGCTGGGCTGAGCTGGCCTGGGGTTAGCTGG

GCTGAGCTGAGCTGAGCTAGGCTGGGTTGAGCTGGCT

GGGCTGGTTTGCGCTGGGTCAAGCTGGGCCGAGCTGG

CCTGGGTTGAGCTGGGCTGGGCTGAGCTGAGCTAGGC

TGGGTTGAGCTGGGCTGGGCTGAGCTGAGCTAGGCTG

CATTGAGCTGGCTGGGATGGATTGAGCTGGCTGAGCT

GGCTGAGCTGGCTGAGCTGGGCTGAGCTGGCCTGGGT

TGAGCTGGGCTGGGTTGAGCTGAGCTGGGCTGAGCTG

GGCTCAGCAGAGCTGGGTTGAGCTGAGCTGGGTTGAG

CTGGGGTGAGCTGGGCTGAGCAGAGCTGGGTTGAGCT

GAGCTGGGTTGAGCTGGGCTCGAGCAGAGCTGGGTTG

AGCTGAGCTGGGTTGAGCTGGGCTCAGCAGAGCTGGG

TTGAGCTGAGCTGGGTTGAGCTGGGCTGAGCTAGCTG

GGCTCAGCTAGGCTGGGTTGAGCTGAGCTGGGCTGAA

CTGGGCTGAGCTGGGCTGAACTGGGCTGAGCTGGGCT

GAGCTGGGCTGAGCAGAGCTGGGCTGAGCAGAGCTGG

GTTGGTCTGAGCTGGGTTGAGCTGGGCTGAGCTGGGC

TGAGCAGAGTTGGGTTGAGCTGAGCTGGGTTCAGCTG

GGCTGAGCTAGGCTGGGTTGAGCTGGGTTGAGTTGGG

CTGAGCTGGGCTGGGTTGAGCGGAGCTGGGCTGAACT

GGGCTGAGCTGGGCTGAGCGGAACTGGGTTGATCTGA

ATTGAGCTGGGCTGAGCCGGGCTGAGCCGGGCTGAGC

TGGGCTAGGTTGAGCTTGGGTGAGCTTGCCTCAGCTG

GTCTGAGCTAGGTTGGGTGGAGCTAGGCTGGATTGAG

CTGGGCTGAGCTGAGCTGATCTGGCCTCAGCTGGGCT

GAGGTAGGCTGAACTGGGCTGTGCTGGGCTGAGCTGA

GCTGAGCCAGTTTGAGCTGGGTTGAGCTGGGCTGAGC

TGGGCTGTGTTGATCTTTCCTGAACTGGGCTGAGCTG

GGCTGAGCTGGCCTAGCTGGATTGAACGGGGGTAAGC

TGGGCCAGGCTGGACTGGGCTGAGCTGAGCTAGGCTG

AGCTGAGTTGAATTGGGTTAAGCTGGGCTGAGATGGG

-continued

CTGAGCTGGGCTGAGCTGGGTTGAGCCAGGTCGGACT
GGGTTACCCTGGGCCACACTGGGCTGAGCTGGGCGGA
GCTCGattaacctggtcaggctgagtcgggtccagca
gacatgcgctggccaggctggcttgacctggacacgt
tcgatgagctgccttgggatggttcacctcagctgag
ccaggtggctccagctgggctgagctggtgaccctgg
gtgacctcggtgaccaggttgtcctgagtccgggcca
agccgaggctgcatcagactcgccagacccaaggcct
gggccccggctggcaagccaggggcggtgaaggctgg
gctggcaggactgtcccggaaggaggtgcacgtggag
ccgcccggaccccgaccggcaggacctggaaagacgc
ctctcactcccctttctcttctgtcccctctcgggtc
ctcagAGAGCCAGTCTGCCCCGAATCTCTACCCCCTC
GTCTCCTGCGTCAGCCCCCCGTCCGATGAGAGCCTGG
TGGCCCTGGGCTGCCTGGCCCGGGACTTCCTGCCCAG
CTCCGTCACCTTCTCCTGGAACTACAAGAACAGCAGC
AAGGTCAGCAGCCAGAACATCCAGGACTTCCCGTCCG
TCCTGAGAGGCGGCAAGTACTTGGCCTCCTCCCGGGT
GCTCCTACCCTCTGTGAGCATCCCCCAGGACCCAGAG
GCCTTCCTGGTGTGCGAGGTCCAGCACCCCAGTGGCA
CCAAGTCCGTGTCCATCTCTGGGCCAGgtgagctggg
ctccccctgtggctgtggcgggggcggggccgggtgc
cgccggcacagtgacgccccgttcctgcctgcagTCG
TAGAGGAGCAGCCCCCCGTCTTGAACATCTTCGTCCC
CACCCGGGAGTCCTTCTCCAGTACTCCCCAGCGCACG
TCCAAGCTCATCTGCCAGGCCTCAGACTTCAGCCCCA
AGCAGATCTCCATGGCCTGGTTCCGTGATGGGAAACG
GGTGGTGTCTGGCGTCAGCACAGGCCCCGTGGAGACC
CTACAGTCCAGTCCGGTGACCTACAGGCTCCACAGCA
TGCTGACCGTCACGGAGTCCGAGTGGCTCAGCCAGAG
CGTCTTCACCTGCCAGGTGGAGCACAAAGGGCTGAAC
TACGAGAAGAACGCGTCCTCTCTGTGCACCTCCAgtg
agtgcagcccctcgggccgggcggcggggcggcggga
gccacacacacaccagctgctccctgagccttggctt
ccgggagtggccaaggcggggaggggctgtgcagggc
agctggagggcactgtcagctggggcccagcaccccc
tcaccccggcagggcccgggctccgaggggccccgca
gtcgcaggccctgctcttgggggaagccctacttggc
cccttcagggcgctgacgctcccccacccacccccg
cctagATCCCAACTCTCCCATCACCGTCTTCGCCATC -continued GCCCCCTCCTTCGCTGGCATCTTCCTCACCAAGTCGG
CCAAGCTTTCCTGCGTGGTCACGGGCCTCGTCACCAG
GGAGAGCCTCAACATCTCCTGGACCCGCCAGGACGGC
GAGGTTCTGAAGACCAGTATCGTCTTCTCTGAGATCT
ACGCCAACGGCACCTTCGGCGCCAGGGGCGAAGCCTC
CGTCTGCGTGGAGGACTGGGAGTCGGGCGACAGGTTC
ACGTGCACGGTGACCCACACGGACCTGCCCTCGCCGC
TGAAGCAGAGCGTCTCCAAGCCCAGAGgtaggccctg
ccctgcccctgcctccgcccggcctgtgccttggccg
ccggggcgggagccgagcctggccgaggagcgccctc
ggccccccgcggtcccgacccacacccctcctgctct
cctccccagGGATCGCCAGGCACATGCCGTCCGTGTA
CGTGCTGCCGCCGGCCCCGGAGGAGCTGAGCCTGCAG
GAGTGGGCCTCGGTCACCTGCCTGGTGAAGGGCTTCT
CCCCGGCGGACGTGTTCGTGCAGTGGCTGCAGAAGGG
GGAGCCCGTGTCCGCCGACAAGTACGTGACCAGCGCG
CCGGTGCCCGAGCCCGAGCCCAAGGCCCCCGCCTCCT
ACTTCGTGCAGAGCGTCCTGACGGTGAGCGCCAAGGA
CTGGAGCGACGGGGAGACCTACACCTGCGTCGTGGGC
CACGAGGCCCTGCCCCACACGGTGACCGAGAGGACCG
TGGACAAGTCCACCGGTAAACCCACCCTGTACAACGT
CTCCCTGGTCCTGTCCGACACGGCCAGCACCTGCTAC
TGACCCCCTGGCTGCCCGCCGCGGCCGGGGCCAGAGC
CCCCGGGCGACCATCGCTCTGTGTGGGCCTGTGTGCA
ACCCGACCCTGTCGGGGTGAGCGGTCGCATTTCTGAA
AATTAGAaataaaAGATCTCGTGCCG Seq ID No. 1 TCTAgAAGACGCTGGAGAGAGGCCagACTTCCTCGGA
ACAGCTCAAAGAGCTCTGTCAAAGCCAGATCCCATCA
CACGTGGGCACCAATAGGCCATGCCAGCCTCCAAGGG
CCGAACTGGGTTCTCCACGGCGCACATGAAGCCTGCA
GCCTGGCTTATCCTCTTCCGTGGTGAAGAGGCAGGCC
CGGGACTGGACGAGGGGCTAGCAGGGTGTGGTAGGCA
CCTTGCGCCCCCCACCCCGGCAGGAACCAGAGACCCT
GGGGCTGAGAGTGAGCCTCCAAACAGGATGCCCCACC
CTTCAGGCCACCTTTCAATCCAGCTACACTCCACCTG
CCATTCTCCTCTGGGCACAGGGCCCAGCCCCTGGATC
TTGGCCTTGGCTCGACTTGCACCGACGCGCACACACA
CACTTCCTAACGTGCTGTCCGCTCACCCCTCCCCAGC
GTGGTCCATGGGCAGCACGGCAGTGCGCGTCCGGCGG
TAGTGAGTGCAGAGGTCCCTTCCCCTCCCCCAGGAGC
CCCAGGGGTGTGTGCAGATCTGGGGGCTCCTGTCCCT -continued TACACCTTCATGCCCCTCCCCTCATACCCACCCTCCA
GGCGGGAGGCAGCGAGACCTTTGCCCAGGGACTCAGC
CAACGGGCACACGGGAGGCCA GCCCTCAGCAGCTGG
G Seq ID No. 4 GGCCAGACTTCCTCGGAACAGCTCAAAGAGCTCTGTC
AAAGCCAGATCCCATCACACGTGGGCACCAATAGGCC
ATGCCAGCCTCCAAGGGCCGAACTGGGTTCTCCACGG
CGCACATGAAGCCTGCAGCCTGGCTTATCCTCTTCCG
TGGTGAAGAGGCAGGCCCGGGACTGGACGAGGGGCTA
GCAGGGTGTGGTAGGCACCTTGCGCCCCCCACCCCGG
CAGGAACCAGAGACCCTGGGGCTGAGAGTGAGCCTCC
AAACAGGATGCCCCACCCTTCAGGCCACCTTTCAATC
CAGCTACACTCCACCTGCCATTCTCCTCTGGGCACAG
GGCCCAGCCCCTGGATCTTGGCCTTGGCTCGACTTGC
ACCCACGCGCACACACACACTTCGTAACGTGCTGTCC
GCTCACCCCTCCCCAGCGTGGTCCATGGGCAGCACGG
CAGTGCGCGTCCGGCGGTAGTGAGTGCAGAGGTCCCT
TCCCCTCCCCCAGGAGCCCCAGGGGTGTGTGCAGATC
TGGGGGCTCCTGTCCCTTACACCTTCATGCCCCTCCC
CTCATACCCACCCTCCAGGCGGGAGGCAGCGAGACCT
TTGCCCAGGGACTCAGCCAACGGGCACACGGGAGGCC
AGCCCTCAGCAGCTGGCTCCCAAAGAGGAGGTGGGAG
GTAGGTCCACAGCTGCCACAGAGAGAAACCCTGACGG
ACCCCACAGGGGCCACGCCAGCCGGAACCAGCTCCCT
CGTGGGTGAGCAATGGCCAGGGCCCCGCCGGCCACCA
CGGCTGGCCTTGCGCCAGCTGAGAACTCACGTCCAGT
GCAGGGAGACTCAAGACAGCCTGTGCACACAGCCTCG
GATCTGCTCCCATTTCAAGCAGAAAAAGGAAACCGTG
CAGGCAGCCCTCAGCATTTCAAGGATTGTAGCAGCGG
CCAACTATTCGTCGGCAGTGGCCGATTAGAATGACCG
TGGAGAAGGGCGGAAGGGTCTCTCGTGGGCTCTGCGG
CCAACAGGCCCTGGCTCCACCTGCCCGCTGCCAGCCC
GAGGGGCTTGGGCCGAGCCAGGAACCACAGTGCTCAC
CGGGACCACAGTGACTGACCAAACTCCCGGCCAGAGC
AGCCCCAGGCCAGCCGGGCTCTCGCCCTGGAGGACTC
ACCATCAGATGCACAAGGGGGCGAGTGTGGAAGAGAC
GTGTCGCCCGGGCCATTTGGGAAGGCGAAGGGACCTT
CCAGGTGGACAGGAGGTGGGACGCACTCCAGGCAAGG
GACTGGGTCCCCAAGGCCTGGGGAAGGGGTACTGGCT
TGGGGGTTAGCCTGGCCAGGGAACGGGGAGCGGGGCG -continued GGGGGCTGAGCAGGGAGGACCTGACCTCGTGGGAGCG
AGGCAAGTCAGGCTTCAGGCAGCAGCCGCACATCCCA
GACCAGGAGGCTGAGGCAGGAGGGGCTTGCAGCGGGG
CGGGGGCCTGCCTGGCTCCGGGGGCTCCTGGGGGACG
CTGGCTCTTGTTTCCGTGTCCCGCAGCACAGGGCCAG
CTCGCTGGGCCTATGCTTACCTTGATGTCTGGGGCCG
GGGCGTCAGGGTCGTCGTCTCCTCAGGGGAGAGTCCC
CTGAGGCTACGCTGGGG*GGGGACTATGGCAGCTCCA
CCAGGGGCCTGGGGACCAGGGGCCTGGACCAGGCTGC
AGCCCGGAGGACGGGCAGGGCTCTGGCTCTCCAGCAT
CTGGCCCTCGGAAATGGCAGAACCCCTGGCGGGTGAG
CGAGCTGAGAGCGGGTCAGACAGACAGGGGCCGGCCG
GAAAGGAGAAGTTGGGGGCAGAGCCCGCCAGGGGCCA
GGCCCAAGGTTCTGTGTGCCAGGGCCTGGGTGGGCAC
ATTGGTGTGGCCATGGCTACTTAGATTCGTGGGGCCA
GGGCATCCTGGTCAGCGTCTCCTCAGGTGAGCCTGGT
GTCTGATGTCCAGCTAGGCGCTGGTGGGCCGCGGGTG
GGCCTGTCTCAGGCTAGGGCAGGGGCTGGGATGTGTA
TTTGTCAAGGAGGGGCAACAGGGTGCAGACTGTGCCC
CTGGAAACTTGACCACTGGGGCAGGGGCGTCCTGGTC
ACGTCTCCTCAGGTAAGACGGCCCTGTGCCCCTCTCT
CGCGGGACTGGAAAAGGAATTTTCCAAGATTCCTTGG
TCTGTGTGGGGCCCTCTGGGGCCCCCGGGGGTGGCTC
CCCTCCTGCCCAGATGGGGCCTCGGCCTGTGGAGCAC
GGGCTGGGCACACAGCTCGAGTCTAGGGCCACAGAGG
CCCGGGCTCAGGGCTCTGTGTGGCCCGGCGACTGGCA
GGGGGCTCGGGTTTTTGGACACCCCCTAATGGGGGCC
ACAGCACTGTGACCATCTTCACAGCTGGGGCCGAGGA
GTCGAGGTCACCGTCTCCTCAGGTGAGTCCTCGTCAG
CCCTCTCTCACTCTCTGGGGGGTTTTGCTGCATTTTG
TGGGGGAAAGAGGATGCCTGGGTCTCAGGTCTAAAGG
TCTAGGGCCAGCGCCGGGGCCCAGGAAGGGGCCGAGG
GGCCAGGCTCGGCTCGGCCAGGAGCAGAGCTTCCAGA
CATCTCGCCTCCTGGCGGCTGCAGTCAGGCCTTTGGC
CGGGGGGGTCTCAGCACCACCAGGCCTCTTGGCTCCC
GAGGTCCCCGGCCCCGGCTGCCTCACCAGGCACCGTG
CGCGGTGGGCCCGGGCTCTTGGTCGGCCACCCTTTCT
TAACTGGGATCCGGGCTTAGTTGTCGCAATGTGACAA
CGGGCTCGAAAGCTGGGGCCAGGGGACCCTAGT*TAC
GACGCCTCGGGTGGGTGTCCCGCACCCCTCCCCACTT
TCACGGCAGTCGGCGAGACCTGGGGAGTCAGGTGTTG -continued

GGGACACTTTGGAGGTCAGGAACGGGAGCTGGGGAGA

GGGCTCTGTCAGCGGGGTCCAGAGATGGGCCGCCCTC

CAAGGACGCCCTGCGCGGGGACAAGGGCTTCTTGGCC

TGGCCTGGCCGCTTCACTTGGGCGTCAGGGGGGGCTT

CCCGGGGCAGGCGGTCAGTCGAGGCGGGTTGGAATTC

TGAGTCTGGGTTCGGGGTTCGGGGTTCGGCCTTCATG

AACAGACAGCCCAGGCGGGCCGTTGTTTGGCCCCTGG

GGGCCTGGTTGGAATGCGAGGTCTCGGGAAGTCAGGA

GGGAGCCTGGCCAGCAGAGGGTTCCCAGCCCTGCGGC

CGAGGGACCTGGAGACGGGCAGGGCATTGGCCGTCGC

AGGGCCAGGCCACACCCCCCAGGTTTTTGTGGGGCGA

GCCTGGAGATTGCACCACTGTGATTACTATGCTATGG

ATCTCTGGGGCCCAGGCGTTGAAGTCGTCGTGTCCTC

AGGTAAGAACGGCCCTCCAGGGCCTTTAATTTCTGCT

CTCGTCTGTGGGCTTTTCTGACTCTGATCCTCGGGAG

GCGTCTGTGCCCCCCCCGGGGATGAGGCCGGCTTGCC

AGGAGGGGTCAGGGACCAGGAGCCTGTGGGAAGTTCT

GACGGGGGCTGCAGGCGGGAAGGGCCCCACCGGGGGG

CGAGCCCCAGGCCGCTGGGCGGCAGGAGACCCGTGAG

AGTGCGCCTTGAGGAGGGTGTCTGCGGAACCACGAAC

GCCCGCCGGGAAGGGCTTGCTGCAATGCGGTCTTCAG

ACGGGAGGCGTCTTCTGCCCTCACCGTCTTTCAAGCC

CTTGTGGGTCTGAAAGAGCCATGTCGGAGAGAGAAGG

GACAGGCCTGTCCCGACCTGGCCGAGAGCGGGCAGCC

CCGGGGGAGAGCGGGGCGATCGGCCTGGGCTCTGTGA

GGCCAGGTCCAAGGGAGGACGTGTGGTCCTCGTGACA

GGTGCACTTGCGAAACCTTAGAAGACGGGGTATGTTG

GAAGCGGCTCCTGATGTTTAAGAAAAGGGAGACTGTA

AAGTGAGCAGAGTCCTCAAGTGTGTTAAGGTTTTAAA

GGTCAAAGTGTTTTAAACCTTTGTGACTGCAGTTAGC

AAGCGTGCGGGGAGTGAATGGGGTGCCAGGGTGGCCG

AGAGGCAGTACGAGGGCCGTGCCGTCCTCTAATTCAG

GGCTTAGTTTTGCAGAATAAAGTCGGCCTGTTTTCTA

AAAGCATTGGTGGTGCTGAGCTGGTGGAGGAGGCCGC

GGGCAGCCCTGGCCACCTGCAGCAGGTGGCAGGAAGC

AGGTCGGCCAAGAGGCTATTTTAGGAAGCCAGAAAAC

ACGGTCGATGAATTTATAGCTTCTGGTTTCCAGGAGG

TGGTTGGGCATGGCTTTGCGCAGCGCCACAGAACCGA

AAGTGCCCACTGAGAAAAAACAACTCCTGCTTAATTT

GCATTTTTCTAAAAGAAGAAACAGAGGCTGACGGAAA

-continued

CTGGAAAGTTCCTGTTTTAACTACTCGAATTGAGTTT

TCGGTCTTAGCTTATCAACTGCTCACTTAGATTCATT

TTCAAAGTAAACGTTTAAGAGCCGAGGCATTCCTATC

CTCTTCTAAGGCGTTATTCCTGGAGGCTCATTCACCG

CCAGCACCTCCGCTGCCTGCAGGCATTGCTGTCACCG

TCACCGTGACGGCGCGCACGATTTTCAGTTGGCCCGC

TTCCCCTCGTGATTAGGACAGACGCGGGCACTCTGGC

CCAGCCGTCTTGGCTCAGTATCTGCAGGCGTCCGTCT

CGGGACGGAGCTCAGGGGAAGAGCGTGACTCCAGTTG

AACGTGATAGTCGGTGCGTTGAGAGGAGACCCAGTCG

GGTGTCGAGTCAGAAGGGGCCCGGGGCCCGAGGCCCT

GGGCAGGACGGCCCGTGCCCTGCATCACGGGCCCAGC

GTCCTAGAGGCAGGACTCTGGTGGAGAGTGTGAGGGT

GCCTGGGGCCCCTCCGGAGCTGGGGCCGTGCGGTGCA

GGTTGGGCTCTCGGCGCGGTGTTGGCTGTTTCTGCGG

GATTTGGAGGAATTCTTCCAGTGATGGGAGTCGCCAG

TGACCGGGCACCAGGCTGGTAAGAGGGAGGCCGCCGT

CGTGGCCAGAGCAGCTGGGAGGGTTCGGTAAAAGGCT

CGCCCGTTTCCTTTAATGAGGACTTTTCCTGGAGGGC

ATTTAGTCTAGTCGGGACCGTTTTCGACTCGGGAAGA

GGGATGCGGAGGAGGGCATGTGCCCAGGAGCCGAAGG

CGCCGCGGGGAGAAGCCCAGGGCTCTCCTGTCCCCAC

AGAGGCGACGCCACTGCCGCAGACAGACAGGGCCTTT

CCCTCTGATGACGGCAAAGGCGCCTCGGCTCTTGCGG

GGTGCTGGGGGGGAGTCGCCCCGAAGCCGCTCACCCA

GAGGCCTGAGGGGTGAGACTGACCGATGCCTCTTGGC

CGGGCCTGGGGCCGGACCGAGGGGGACTCCGTGGAGG

CAGGGCGATGGTGGCTGCGGGAGGGAACCGACCCTGG

GCCGAGCCCGGCTTGGCGATTCCCGGGCGAGGGCCCT

CAGCCGAGGCGAGTGGGTCCGGCGGAACCACCCTTTC

TGGCCAGCGCCACAGGGCTCTCGGGACTGTCCGGGGC

GACGCTGGGCTGCCCGTGGCAGGCCTGGGCTGACCTG

GACTTCACCAGACAGAACAGGGCTTTCAGGGCTGAGC

TGAGCCAGGTTTAGCGAGGCCAAGTGGGGCTGAACCA

GGCTCAACTGGCCTGAGCTGGGTTGAGCTGGGCTGAC

CTGGGCTGAGCTGAGCTGGGCTGGGCTGGGCTGGGCT

GGGCTGGGCTGGGCTGGACTGGCTGAGCTGAGCTGGG

TTGAGCTGAGCTGAGCTGGCCTGGGTTGAGCTGGGCT

GGGTTGAGCTGAGCTGGGTTGAGCTGGGTTGAGCTGG

GTTGATCTGAGCTGAGCTGGGCTGAGCTGAGCTAGGC

TGGGGTGAGCTGGGCTGAGCTGGTTTGAGTTGGGTTG

-continued

AGCTGAGCTGAGCTGGGCTGTGCTGGCTGAGCTAGGC
TGAGCTAGGCTAGGTTGAGCTGGGCTGGGCTGAGCTG
AGCTAGGCTGGGCTGATTTGGGCTGAGCTGAGCTGAG
CTAGGCTGCGTTGAGCTGGCTGGGCTGGATTGAGCTG
GCTGAGCTGGCTGAGCTGGGCTGAGCTGGCCTGGGTT
GAGCTGAGCTGGACTGGTTTGAGCTGGGTCGATCTGG
GTTGAGCTGTCCTGGGTTGAGCTGGGCTGGGTTGAGC
TGAGCTGGGTTGAGCTGGGCTCAGCAGAGCTGGGTTG
GGCTGAGCTGGGTTGAGCTGAGCTGGGCTGAGCTGGC
CTGGGTTGAGCTGGGCTGAGCTGAGCTGGGCTGAGCT
GGCCTGTGTTGAGCTGGGCTGGGTTGAGCTGGGCTGA
GCTGGATTGAGCTGGGTTGAGCTGAGCTGGGCTGGGC
TGTGCTGACTGAGCTGGGCTGAGCTAGGCTGGGGTGA
GCTGGGCTGAGCTGATCCGAGCTAGGCTGGGCTGGTT
TGGGCTGAGCTGAGCTGAGCTAGGCTGGATTGATCTG
GCTGAGCTGGGTTGAGCTGAGCTGGGCTGAGCTGGTC
TGAGCTGGCCTGGGTCGAGCTGAGCTGGACTGGTTTG
AGCTGGGTCGATCTGGGCTGAGCTGGCCTGGGTTGAG
CTGGGCTGGGTTGAGCTGAGCTGGGTTGAGCTGGGCT
GAGCTGAGGGCTGGGGTGAGCTGGGCTGAACTAGCCT
AGCTAGGTTGGGCTGAGCTGGGCTGGTTTGGGCTGAG
CTGAGCTGAGCTAGGCTGCATTGAGCAGGCTGAGCTG
GGCTGAGCAGGCCTGGGGTGAGCTGGGCTAGGTGGAG
CTGAGCTGGGTCGAGCTGAGTTGGGCTGAGCTGGCCT
GGGTTGAGGTAGGCTGAGCTGAGCTGAGCTAGGCTGG
GTTGAGCTGGCTGGGCTGGTTTGCGCTGGGTCAAGCT
GGGCCGAGCTGGCCTGGGTTGAGCTGGGCTCGGTTGA
GCTGGGCTGAGCTGAGCCGACCTAGGCTGGGATGAGC
TGGGCTGATTTGGGCTGAGCTGAGCTGAGCTAGGCTG
CATTGAGCAGGCTGAGCTGGGCCTGGAGCCTGGCCTG
GGGTGAGCTGGGCTGAGCTGCGCTGAGCTAGGCTGGG
TTGAGCTGGCTGGGCTGGTTTGCGCTGGGTCAAGCTG
GGCCGAGCTGGCCTGGGATGAGCTGGGCCGGTTTGGG
CTGAGCTGAGCTGAGCTAGGCTGCATTGAGCAGGCTG
AGCTGGGCTGAGCTGGCCTGGGGTGAGCTGGGCTGAG
CTAAGCTGAGCTGGGCTGGTTTGGGCTGAGCTGGCTG
AGCTGGGTCCTGCTGAGCTGGGCTGAGCTGACCAGGG
GTGAGCTGGGCTGAGTTAGGCTGGGCTCAGCTAGGCT
GGGTTGATCTGGCAGGGCTGGTTTGCGCTGGGTCAAG
CTCCCGGGAGATGGCCTGGGATGAGCTGGGCTGGTTT

-continued

GGGCTGAGCTGAGCTGAGCTGAGCTAGGCTGCATTGA
GCAGGCTGAGCTGGGCTGAGCTGGCCTGGGGTGAGCT
GGGCTGGGTGGAGCTGAGCTGGGCTGAACTGGGCTAA
GCTGGCTGAGCTGGATCGAGCTGAGCTGGGCTGAGCT
GGCCTGGGGTTAGCTGGGCTGAGCTGAGCTGAGCTAG
GCTGGGTTGAGCTGGCTGGGCTGGTTTGCGCTGGGTC
AAGCTGGGCCGAGCTGGCCTGGGTTGAGCTGGGCTGG
GCTGAGCTGAGCTAGGCTGGGTTGAGCTGGGCTGGGC
TGAGCTGAGCTAGGCTGCATTGAGCTGGCTGGGATGG
ATTGAGCTGGCTGAGCTGGCTGAGCTGGCTGAGCTGG
GCTGAGCTGGCCTGGGTTGAGCTGGGCTGGGTTGAGC
TGAGCTGGGCTGAGCTGGGCTCAGCAGAGCTGGGTTG
AGCTGAGCTGGGTTGAGCTGGGGTGAGCTGGGCTGAG
CAGAGCTGGGTTGAGCTGAGCTGGGTTGAGCTGGGCT
CGAGCAGAGCTGGGTTGAGCTGAGCTGGGTTGAGCTG
GGCTCAGCAGAGCTGGGTTGAGCTGAGCTGGGTTGAG
CTGGGCTGAGCTAGCTGGGCTCAGCTAGGCTGGGTTG
AGCTGAGCTGGGCTGAACTGGGCTGAGCTGGGCTGAA
CTGGGCTGAGCTGGGCTGAGCTGGGCTGAGCAGAGCT
GGGCTGAGCAGAGCTGGGTTGGTCTGAGCTGGGTTGA
GCTGGGCTGAGCTGGGCTGAGCAGAGTTGGGTTGAGC
TGAGCTGGGTTCAGCTGGGCTGAGCTAGGCTGGGTTG
AGCTGGGTTGAGTTGGGCTGAGCTGGGCTGGGTTGAG
CGGAGCTGGGCTGAACTGGGCTGAGCTGGGCTGAGCG
GAACTGGGTTGATCTGAATTGAGCTGGGCTGAGCCGG
GCTGAGCCGGGCTGAGCTGGGCTAGGTTGAGCTTGGG
TGAGCTTGCCTCAGCTGGTCTGAGCTAGGTTGGGTGG
AGCTAGGCTGGATTGAGCTGGGCTGAGCTGAGCTGAT
CTGGCCTCAGCTGGGCTGAGGTAGGCTGAACTGGGCT
GTGCTGGGCTGAGCTGAGCTGAGCCAGTTTGAGCTGG
GTTGAGCTGGGCTGAGCTGGGCTGTGTTGATCTTTCC
TGAACTGGGCTGAGCTGGGCTGAGCTGGCCTAGCTGG
ATTGAACGGGGGTAAGCTGGGCCAGGCTGGACTGGGC
TGAGCTGAGCTAGGCTGAGCTGAGTTGAATTGGGTTA
AGCTGGGCTGAGATGGGCTGAGCTGGGCTGAGCTGGG
TTGAGCCAGGTCGGACTGGGTTACCCTGGGCCACACT
GGGCTGAGCTGGGCGGAGCTCGATTAACCTGGTCAGG
CTGAGTCGGGTCCAGCAGACATGCGCTGGCCAGGCTG
GCTTGACCTGGACACGTTCGATGAGCTGCCTTGGGAT
GGTTCACCTCAGCTGAGCCAGGTGGCTCCAGCTGGGC
TGAGCTGGTGACCCTGGGTGACCTCGGTGACCAGGTT

-continued

```
GTCCTGAGTCCGGGCCAAGCCGAGGCTGCATCAGACT
CGCCAGACCCAAGGCCTGGGCCCCGGCTGGCAAGCCA
GGGGCGGTGAAGGCTGGGCTGGCAGGACTGTCCCGGA
AGGAGGTGCACGTGGAGCCGCCCGGACCCCGACCGGC
AGGACCTGGAAAGACGCCTCTCACTCCCCTTCTCTTC
TGTCCCCTCTCGGGTCCTCAGAGAGCCAGTCTGCCCC
GAATCTCTACCCCCTCGTCTCCTGCGTCAGCCCCCCG
TCCGATGAGAGCCTGGTGGCCCTGGGCTGCCTGGCCC
GGGACTTCCTGCCCAGCTCCGTCACCTTCTCCTGGAA
```

Porcine Kappa Light Chain

In another embodiment, novel genomic sequences encoding the kappa light chain locus of ungulate immunoglobulin are provided. The present invention provides the first reported genomic sequence of ungulate kappa light chain regions. In one embodiment, nucleic acid sequence is provided that encodes the porcine kappa light chain locus. In another embodiment, the nucleic acid sequence can contain at least one joining region, one constant region and/or one enhancer region of kappa light chain. In a further embodiment, the nucleotide sequence can include at least five joining regions, one constant region and one enhancer region, for example, as represented in Seq ID No. 30. In a further embodiment, an isolated nucleotide sequence is provided that contains at least one, at least two, at least three, at least four or five joining regions and 3' flanking sequence to the joining region of porcine genomic kappa light chain, for example, as represented in Seq ID No 12. In another embodiment, an isolated nucleotide sequence of porcine genomic kappa light chain is provided that contains 5' flanking sequence to the first joining region, for example, as represented in Seq ID No. 25. In a further embodiment, an isolated nucleotide sequence is provided that contains 3' flanking sequence to the constant region and, optionally, the 5' portion of the enhancer region, of porcine genomic kappa light chain, for example, as represented in Seq ID Nos. 15, 16 and/or 19.

In further embodiments, isolated nucleotide sequences as depicted in Seq ID Nos 30, 12, 25, 15, 16 or 19 are provided. Nucleic acid sequences at least 80, 85, 90, 95, 98 or 99% homologous to Seq ID Nos 30, 12, 25, 15, 16 or 19 are also provided. In addition, nucleotide sequences that contain at least 10, 15, 17, 20, 25 or 30 contiguous nucleotides of Seq ID Nos 30, 12, 25, 15, 16 or 19 are provided. In addition, nucleotide sequences that contain at least 10, 15, 17, 20, 25 or 30 contiguous nucleotides of Seq ID Nos 1, 4 or 29 are provided. In other embodiments, nucleotide sequences that contain at least 50, 100, 1,000, 2,500, 5,000, 7,000, 8,000, 8,500, 9,000, 10,000 or 15,000 contiguous nucleotides of Seq ID No. 30 are provided. Further provided are nucleotide sequences that hybridizes, optionally under stringent conditions, to Seq ID Nos 30, 12, 25, 15, 16 or 19, as well as, nucleotides homologous thereto.

In one embodiment, an isolated nucleotide sequence encoding kappa light chain is provided that includes at least five joining regions, one constant region and one enhancer region, for example, as represented in Seq ID No. 30. In Seq ID No. 30, the coding region of kappa light chain is represented, for example by residues 1-549 and 10026-10549, whereas the intronic sequence is represented, for example, by residues 550-10025, the Joining region of kappa light chain is represented, for example, by residues 5822-7207 (for example, J1:5822-5859, J2:6180-6218, J3:6486-6523, J4:6826-6863, J5:7170-7207), the Constant Region is represented by the following residues: 10026-10549 (C exon) and 10026-10354 (C coding), 10524-10529 (Poly(A) signal) and 11160-11264 (SINE element).

```
Seq ID No 30 GCGTCCGAAGTCAAAAATATCTGCAGCCTTCATGTAT
             TCATAGAAACAAGGAATGTCTACATTTTCCAAAGTGG
             GACCAGAATCTTGGGTCATGTCTAAGGCATGTGCATT
             TGCACATGGTAGGCAAAGGACTTTGCTTCTCCCAGCA
             CATCTTTCTGCAGAGATCCATGGAAACAAGACTCAAC
             TCCAAAGCAGCAAAGAAGCAGCAAGTTCTCAAGTGAT
             CTCCTCTGACTCCCTCCTCCCAGGCTAATGAAGCCAT
             GTTGCCCCTGGGGGATTAAGGGCAGGTGTCCATTGTG
             GCACCCAGCCCGAAGACAAGCAATTTGATCAGGTTCT
             GAGCACTCCTGAATGTGGACTCTGGAATTTTCTCCTC
             ACCTTGTGGCATATCAGCTTAAGTCAAGTACAAGTGA
             CAAACAACATAATCCTAAGAAGAGAGGAATCAAGCTG
             AAGTCAAAGGATCACTGCCTTGGATTCTACTGTGAAT
             GATGACCTGGAAAATATCCTGAACAACAGCTTCAGGG
             TGATCATCAGAGACAAAAGTTCCAGAGCCAGgtaggg
             aaaccctcaagccttgcaaagagcaaaatcatgccat
             tgggttcttaacctgctgagtgatttactatatgtta
             ctgtgggaggcaaagcgctcaaatagcctgggtaagt
             atgtcaaataaaaagcaaaagtggtgtttcttgaaat
             gttagacctgaggaaggaatattgataacttaccaat
             aattttcagaatgatttatagatgtgcacttagtcag
             tgtctctccaccccgcacctgacaagcagtttagaat
             ttattctaagaatctaggtttgctgggggctacatgg
             gaatcagcttcagtgaagagtttgttggaatgattca
             ctaaattttctatttccagcataaatccaagaacctc
             tcagactagtttattgacactgcttttcctccataat
             ccatctcatctccgtccatcatggacactttgtagaa
             tgacaggtcctggcagagactcacagatgcttctgaa
             acatcctttgccttcaaagaatgaacagcacacatac
             taaggatctcagtgatccacaaattagtttttgccac
             aatggttcttatgataaaagtctttcattaacagcaa
             attgttttataatagttgttctgctttataataattg
             catgcttcactttcttttcttttcttttttttttcttt
             ttttgctttttagtgccgcaggtgcagcatatgaaat
             ttcccaggctaggggtcaaatcagaactacacctact
             ggcctacgccacagccacagcaactcaggatctaagc
```

-continued catgtcggtgacctacactacagctcatggcaatgcc
agatccttaacccaatgagcgaggccagggatcgaac
ccatgtcctcatggatactagtcaggctcattatccg
ctgagccataacaggaactcccgagtttgctttttat
caaaattggtacagccttattgtttctgaaaaccaca
aaatgaatgtattcacataattttaaaaggttaaata
atttatgatatacaagacaatagaaagagaaaacgtc
attgcctctttcttccacgacaacacgcctccttaat
tgatttgaagaaataactactgagcatggtttagtgt
acttctttcagcaattagcctgtattcatagccatac
atattcaattaaaatgagatcatgatatcacacaata
cataccatacagcctatagggattttacaatcatct
tccacatgactacataaaaacctacctaaaaaaaaaa
aaaaccctacttcatcctcctattggctgctttgtgc
tccattaaaaagctctatcataattaggttatgatga
ggatttccattttctacctttcaagcaacatttcaat
gcacagtcttatatacacatttgagcctacttttctt
tttctttctttttttggttttttttttttttttttt
ttggtctttttgtcttttctaaggctgcatatggagg
ttcccaggctagctgtctaatcagaactatagctgct
ggcctacgccacatccacagcaatacaagatctgagc
catgtctgcaacttacaccacagctcacagcaacggt
ggatccttaaaccactgagcaaggccagggatcaaac
ccataacttcatggctcctagttggatttgttaacca
ctgagccatgatggcaactcctgagcctacttttcta
atcatttccaaccctaggacactttttaagtttcat
ttttctcccccccacccccctgttttctgaagtgtgttt
gcttccactgggtgacttcactcccaggatctcatct
gcaggatactgcagctaagtgtatgagctctgaattt
gaatcccaactctgccactcaaagggataggagtttc
cgatgtggcccaatgggatcagtggcatctctgcagt
gccaggacgcaggttccatccctggcccagcacagtg
ggttaagaatctggcattgctgcagctgaggcataga
tttcaattgtgcctcagatctgatccttggcccaagg
actgcatatgcctcagggcaaccaaaaaagagaaaag
gggggtgatagcattagtttctagatttgggggataa
ttaaataaagtgatccatgtacaatgtatggcatttt
gtaaatgctcaacaaatttcaactattatggagttcc
catcatggctcagtggaagggaatctgattagcatcc
atgaggacacaggtccaaccccgaccttgctcagtgg -continued gcattgctgtgagctgtggcatgggttacagacgaag
ctcggatctggcattgctgtggctgtggtgtaagcca
gcaactacagctctcattcagcccctagcctgggaac
ctccatatgcctaaaagacaaaaaataaaatttaaat
taaaaataaagaaatgttaactattatgattggtact
gcttgcattactgcaaagaaagtcactttctatactc
tttaatatcttagttgactgtgtgctcagtgaactat
tttggacacttaatttccactctcttctatctccaac
ttgacaactctctttcctctcttctggtgagatccac
tgctgactttgctctttaaggcaactagaaaagtgct
cagtgacaaaatcaaagaaagttaccttaatcttcag
aattacaatcttaagttctcttgtaaagcttactatt
tcagtggttagtattattccttggtcccttacaactt
atcagctctgatctattgctgattttcaactatttat
tgttggagtttttttcctttttttccctgttcattctgc
aaatgtttgctgagcatttgtcaagtgaagatactgg
actgggccttccaaatataagacaatgaaacatcggg
agttctcattatggtgcagcagaaacgaatccaacta
ggaaatgtgaggttgcaggttcgatccctgcccttgc
tcagtgggttaaggatccagcattaccgtgagctgtg
gtgtaggttgcagacgtggctcagatcctgcgttgct
gtggctgtggcataggctggcagctctagctctgatt
cgaccgctagcctgggaacctccatgcgccccgagtg
cagcccttaaaaagcaaaaaaaaaagaaagaaagaaa
aagacaatgaaacatcaaacagctaacaatccagtag
ggtagaaagaatctggcaacagataagagcgattaaa
tgttctaggtccagtgaccttgcctctgtgctctaca
cagtcgtgccacttgctgagggagaaggtctctcttg
agttgagtcctgaaagacattagttgttcacaaacta
atgccagtgagtgaaggtgtttccaagcagagggaga
gtttggtaaaaagctggaagtcacagaaagactctaa
agagtttaggatggtgggagcaacatacgctgagatg
gggctggaaggttaagagggaaacaactatagtaagt
gaagctggactcacagcaaagtgaggacctcagcatc
cttgatggggttaccatggaaacaccaaggcacacct
tgatttccaaaacagcaggcacctgattcagcccaat
gtgacatggtgggtacccctctagctctacctgttct
gtgacaactgacaaccaacgaagttaagtctggattt
tctactctgctgatccttgtttttgtttcacacgtca
tctatagcttcatgccaaaatagagttcaaggtaaga
cgcgggccttggtttgatatacatgtagtctatcttg -continued tttgagacaatatggtggcaaggaagaggttcaaaca
ggaaaatactctctaattatgattaactgagaaaagc
taaagagtcccataatgacactgaatgaagttcatca
tttgcaaaagccttcccccccccccaggagactataa
aaaagtgcaatttttaaatgaacttatttacaaaac
agaaatagactcacagacataggaaacgaacagatgg
ttaccaagggtgaaagggagtaggagggataaataag
gagtctggggttagcagatacaccccagtgtacacaa
aataaacaacagggacctactatatagcacagggaac
tatatgcagtagcttacaataacctataatggaaaag
aatgtgaaaaagaatatatgtatgcgtgtgtgtgtaa
ctgaatcactttgctgtaacctgaatctaacataaca
ttgtaaatcaactacagttttttttttttttaagtgc
agggttttggtgttttttttttttcattttgttttt
gtttttgtttttttgctttttagggccacacccagaca
tatgggggttcccaggctaggggtctaattagagcta
cagttgccggcttgcaccacagccacagcaacatcag
atccgagccgcacttgcgacttacaccacagctcatg
gcaataccagatccttaacccactgagcaaggcccag
ggatcgtacccgcaacctcatggttcctagtcagatt
catttctgctgcgctacaatgggaactccaagtgcag
ttttttgtaatgtgcttgtctttctttgtaattcata
ttcatcctacttcccaataaataaataaatacataaa
taataaacataccattgtaaatcaactacaattttttt
ttaaatgcagggttttttgtttttttgtttttttgttttg
tctttttgccttttctagggccgctcccatggcatat
ggaggttcccaggctaggggtcgaatcggagctgtag
ccaccggcctacgccagagccacagcaacgcgggatc
cgagccgcgtctgcaacctacaccacagctcacggca
acgccggatcgttaacccactgagcaagggcagggat
cgaacctgcaacctcatggttcctagtcagattcgtt
aactactgagccacaacggaaactcctaaagtgcagt
ttttaaatgtgcttgtctttctttgtaatttacactc
aacctacttcccaataaataaataaataaacaaataa
atcatagacatggttgaattctaaaggaagggaccat
caggccttagacagaaatacgtcatcttctagtattt
taaaacacactaaagaagacaaacatgctctgccaga
gaagcccagggcctccacagctgcttgcaaagggagt
taggcttcagtagctgacccaaggctctgttcctctt
cagggaaaagggtttttgttcagtgagacagcagaca -continued gctgtcactgtgGTGGACGTTCGGCCAAGGAACCAAG
CTGGAACTCAAACgtaagtcaatccaaacgttccttc
cttggctgtctgtgtcttacggtctctgtggctctga
aatgattcatgtgctgactctctgaaaccagactgac
attctccagggcaaaactaaagcctgtcatcaaactg
gaaaactgagggcacattttctgggcagaactaagag
tcaggcactgggtgaggaaaaacttgttagaatgata
gtttcagaaacttactgggaagcaaagcccatgttct
gaacagagctctgctcaagggtcaggaggggaaccag
tttttgtacaggagggaagttgagacgaacccctgtg
TATATGGTTTCGGCGCGGGGACCAAGCTGGAGCTCAA
ACgtaagtggctttttccgactgattctttgctgttt
ctaattgttggttggctttttgtccatttttcagtgt
tttcatcgaattagttgtcagggaccaaacaaattgc
cttcccagattaggtaccagggaggggacattgctgc
atgggagaccagagggtggctaatttttaacgtttcc
aagccaaaataactggggaagggggcttgctgtcctg
tgagggtaggtttttatagaagtggaagttaaggggga
aatcgctatgGTTCACTTTTGGCTCGGGGACCAAAGT
GGAGCCCAAAAttgagtacattttccatcaattattt
gtgagatttttgtcctgttgtgtcatttgtgcaagtt
tttgacattttggttgaatgagccattcccagggacc
caaaaggatgagaccgaaaagtagaaaagagccaact
tttaagctgagcagacagaccgaattgttgagtttgt
gaggagagtagggtttgtagggagaaaggggaacaga
tcgctggctttttctctgaattagcctttctcatggg
actggcttcagaggggggtttttgatgagggaagtgtt
ctagagccttaactgtgGGTTGTGTTCGGTAGCGGGA
CCAAGCTGGAAATCAAACgtaagtgcacttttctact
ccttttttctttcttatacgggtgtgaaattggggact
tttcatgtttggagtatgagttgaggtcagttctgaa
gagagtgggactcatccaaaaatctgaggagtaaggg
tcagaacagagttgtctcatggaagaacaaagaccta
gttagttgatgaggcagctaaatgagtcagttgactt
gggatccaaatggccagacttcgtctgtaaccaacaa
tctaatgagatgtagcagcaaaaagagatttccattg
aggggaaagtaaaattgttaatattgtgGATCACCTT
TGGTGAAGGGACATCCGTGGAGATTGAACgtaagtat
tttttctctactaccttctgaaatttgtctaaatgcc
agtgttgacttttagaggcttaagtgtcagttttgtg
aaaaatgggtaaacaagagcatttcatatttattatc -continued agtttcaaaagttaaactcagctccaaaaatgaattt gtagacaaaaagattaatttaagccaaattgaatgat tcaaaggaaaaaaaaattagtgtagatgaaaaaggaa ttcttacagctccaaagagcaaaagcgaattaatttt ctttgaactttgccaaatcttgtaaatgatttttgtt ctttacaatttaaaaaggttagagaaatgtatttctt agtctgttttctctcttctgtctgataaattattata tgagataaaaatgaaaattaataggatgtgctaaaaa atcagtaagaagttagaaaaatatatgtttatgttaa agttgccacttaattgagaatcagaagcaatgttatt tttaaagtctaaaatgagagataaactgtcaatactt aaattctgcagagattctatatcttgacagatatctc ctttttcaaaaatccaatttctatggtagactaaatt tgaaatgatcttcctcataatggagggaaaagatgga ctgaccccaaaagctcagatttaaagaaatctgttta agtgaaagaaaataaaagaactgcatttttttaaaggc ccatgaatttgtagaaaaataggaaatattttaataa gtgtattcttttattttcctgttattacttgatggtg tttttataccgccaaggaggccgtggcaccgtcagtg tgatctgtagaccccatggcggcctttttttcgcgatt gaatgaccttggcggtgggtccccagggctctggtgg cagcgcaccagccgctaaaagccgctaaaaactgccg ctaaaggccacagcaaccccgcgaccgcccgttcaac tgtgctgacacagtgatacagataatgtcgctaacag aggagaatagaaatatgacgggcacacgctaatgtgg ggaaaagagggagaagcctgatttttatttttttagag attctagagataaaattcccagtattatatcctttta ataaaaaatttctattaggagattataaagaatttaa agctattttttttaagtggggtgtaattctttcagtag tctcttgtcaaatggatttaagtaatagaggcttaat ccaaatgagagaaatagacgcataaccctttcaaggc aaaagctacaagagcaaaaaattgaacacagcagccag ccatctagccactcagattttgatcagttttactgag tttgaagtaaatatcatgaaggtataattgctgataa aaaaataagatacaggtgtgacacatctttaagtttc agaaatttaatggcttcagtaggattatatttcacgt atacaaagtatctaagcagataaaaatgccattaatg gaaacttaatagaaatatatttttaaattccttcatt ctgtgacagaaattttctaatctgggtcttttaatca cctaccctttgaaagagtttagtaatttgctatttgc -continued catcgctgtttactccagctaatttcaaaagtgatac ttgagaaagattattttggtttgcaaccacctggca ggactattttagggccattttaaaactcttttcaaac taagtattttaaactgttctaaaccatttagggcctt ttaaaaatcttttcatgaatttcaaacttcgttaaaa gttattaaggtgtctggcaagaacttccttatcaaat atgctaatagtttaatctgttaatgcaggatataaaa ttaaagtgatcaaggcttgacccaaacaggagtatct tcatagcatatttcccctcctttttttctagaattca tatgattttgctgccaaggctattttatataatctct ggaaaaaaaatagtaatgaaggttaaaagagaagaaa atatcagaacattaagaattcggtattttactaactg cttggttaacatgaaggtttttattttattaaggttt ctatctttataaaaatctgttccctttttctgctgatt tctccaagcaaaagattcttgatttgtttttttaactc ttactctcccacccaagggcctgaatgcccacaaagg ggacttccaggaggccatctggcagctgctcaccgtc agaagtgaagccagccagttcctcctgggcaggtggc caaaattacagttgacccctcctggtctggctgaacc ttgccccatatggtgacagccatctggccagggccca ggtctccctctgaagcctttgggaggagagggagagt ggctggcccgatcacagatgcggaaggggctgactcc tcaaccggggtgcagactctgcagggtgggtctgggc ccaacacacccaaagcacgcccaggaaggaaaggcag cttggtatcactgcccagagctaggagaggcaccggg aaaatgatctgtccaagacccgttcttgcttctaaac tccgagggggtcagatgaagtggttttgtttcttggc ctgaagcatcgtgttccctgcaagaagcggggaacac agaggaaggagagaaaagatgaactgaacaaagcatg caaggcaaaaaaggccttaggatggctgcaggaagtt agttcttctgcattggctccttactggctcgtcgatc gcccacaaacaacgcacccagtggagaacttccctgt tacttaaacaccattctctgtgcttgcttcctcagGG

GCTGATGCCAAGCCATCCGTCTTCATCTTCCCGCCAT

CGAAGGAGCAGTTAGCGACCCCAACTGTCTCTGTGGT

GTGCTTGATCAATAACTTCTTCCCCAGAGAAATCAGT

GTCAAGTGGAAAGTGGATGGGGTGGTCCAAAGCAGTG

GTCATCCGGATAGTGTCACAGAGCAGGACAGCAAGGA

CAGCACCTACAGCCTCAGCAGCACCCTCTCGCTGCCC

ACGTCACAGTACCTAAGTCATAATTTATATTCCTGTG

AGGTCACCCACAAGACCCTGGCCTCCCCTCTGGTCAC

-continued

AAGCTTCAACAGGAACGAGTGTGAGGCTtagAGGCCC
ACAGGCCCCTGGCCTGCCCCCAGCCCCAGCCCCCCTC
CCCACCTCAAGCCTCAGGCCCTTGCCCCAGAGGATCC
TTGGCAATCCCCCAGCCCCTCTTCCCTCCTCATCCCC
TCCCCCTCTTTGGCTTTAACCGTGTTAATACTGGGGG
GTGGGGGAATGAATAaataaaGTGAACCTTTGCACCT
GTGAtttctctctcctgtctgattttaaggttgttaa
atgttgttttccccattatagttaatcttttaaggaa
ctacatactgagttgctaaaaactacaccatcactta
taaaattcacgccttctcagttctcccctcccctcct
gtcctccgtaagacaggcctccgtgaaacccataagc
acttctctttacaccctctcctgggccggggtaggag
actttttgatgtcccctcttcagcaagcctcagaacc
attttgaggggacagttcttacagtcacat*tcctg
tgatctaatgactttagttaccgaaaagccagtctct
caaaaagaagggaacggctagaaaccaagtcatagaa
atatatatgtataaaatatatatatatccatatatgt
aaaataacaaaataatgataacagcataggtcaacag
gcaacagggaatgttgaagtccattctggcacttcaa
tttaagggaataggatgccttcattacattttaaata
caatacacatggagagcttcctatctgccaaagacca
tcctgaatgccttccacactcactacaaggttaaaag
cattcattacaatgttgatcgaggagttcccgttgtg
gctcagcaggttaagaacgtgactggtatccaggagg
atgcgggtttggtccccagcctcgctcagtggattaa
ggatccagtgttgctgcaagatcacgggctcagatcc
cgtgttctatggctatggtgtaggctggtagctgcat
gcagccctaatttgacccctagcctgggaactgccat
atgccacatgtgaggcccttaaaacctaaaagaaaaa
aaaagaaaagaaatatcttacacccaatttatagata
agagagaagctaaggtggcaggcccaggatcaaagcc
ctacctgcctatcttgacacctgatacaaattctgtc
ttctagggtttccaacactgcatagaacagagggtca
aacatgctaccctcccagggactcctcccttcaaatg
acataaattttgttgcccatctctgggggcaaaactc
aacaatcaatggcatctctagtaccaagcaaggctct
tctcatgaagcaaaactctgaagccagatccatcatg
acccaaggaagtaaagacaggtgttactggttgaact
gtatccttcaattcaatatgctcaatttccaactccc
agtccccgtaaatacaacccccttgggaagagagtc -continued cttgcagatgtagccacgttaaaaagagattatacag
aaaggctagtgaggatgcagtgaaacgggatctttca
tacattgctggtggaaatgtaaaatgctgcaggcact
ctagaaaataatttgccagtttttttgaaaagctaaac
aaaatagtttagttgcattctgggttatttatccccc
agaaattaaaaattatgtccgcacaaaaacgtgtaca
taatcattcataacagccttgtac Seq ID No. 12 caaggaaccaagctggaactcaaacgtaagtcaatcc
aaacgttccttccttggctgtctgtgtcttacggtct
ctgtggctctgaaatgattcatgtgctgactctctga
aaccagactgacattctccagggcaaaactaaagcct
gtcatcaaactggaaaactgagggcacattttctggg
cagaactaagagtcaggcactgggtgaggaaaaactt
gttagaatgatagtttcagaaacttactgggaagcaa
agcccatgttctgaacagagctctgctcaagggtcag
gaggggaaccagtttttgtacaggagggaagttgaga
cgaacccctgtgtatatggtttcggcgcggggaccaa
gctggagctcaaacgtaagtggctttttccgactgat
tctttgctgtttctaattgttggttggctttttgtcc
atttttcagtgttttcatcgaattagttgtcagggac
caaacaaattgccttcccagattaggtaccagggagg
ggacattgctgcatgggagaccagagggtggctaatt
tttaacgtttccaagccaaaataactggggaaggggg
cttgctgtcctgtgagggtaggtttttatagaagtgg
aagttaaggggaaatcgctatggttcacttttggctc
ggggaccaaagtggagcccaaaattgagtacattttc
catcaattatttgtgagatttttgtcctgttgtgtca
tttgtgcaagtttttgacattttggttgaatgagcca
ttcccagggacccaaaaggatgagaccgaaaagtaga
aaagagccaacttttaagctgagcagacagaccgaat
tgttgagtttgtgaggagagtagggtttgtagggaga
aaggggaacagatcgctggctttttctctgaattagc
ctttctcatgggactggcttcagagggggtttttgat
gagggaagtgttctagagccttaactgtgggttgtgt
tcggtagcgggaccaagctggaaatcaaacgtaagtg
cacttttctactcctttttctttcttatacgggtgtg
aaattggggacttttcatgtttggagtatgagttgag
gtcagttctgaagagagtgggactcatccaaaaatct
gaggagtaagggtcagaacagagttgtctcatggaag
aacaaagacctagttagttgatgaggcagctaaatga
gtcagttgacttgggatccaaatggccagacttcgtc -continued tgtaaccaacaatctaatgagatgtagcagcaaaaag agatttccattgaggggaaagtaaaattgttaatatt gtggatcacctttggtgaagggacatccgtggagatt gaacgtaagtatttttctctactaccttctgaaatt tgtctaaatgccagtgttgacttttagaggcttaagt gtcagttttgtgaaaaatgggtaaacaagagcatttc atatttattatcagtttcaaaagttaaactcagctcc aaaaatgaatttgtagacaaaaagattaatttaagcc aaattgaatgattcaaaggaaaaaaaaattagtgtag atgaaaaaggaattcttacagctccaaagagcaaaag cgaattaattttctttgaactttgccaaatcttgtaa atgattttgttctttacaatttaaaaaggttagaga aatgtatttcttagtctgttttctctcttctgtctga taaattattatatgagataaaaatgaaaattaatagg atgtgctaaaaaatcagtaagaagttagaaaaatata tgtttatgttaaagttgccacttaattgagaatcaga agcaatgttatttttaaagtctaaaatgagagataaa ctgtcaatacttaaattctgcagagattctatatctt gacagatatctcctttttcaaaaatccaatttctatg gtagactaaatttgaaatgatcttcctcataatggag ggaaaagatggactgaccccaaaagctcagattt*aa gaaaacctgtttaag*gaaagaaaataaaagaactgc atttttaaaggcccatgaatttgtagaaaaatagga aatattttaataagtgtattcttttattttcctgtta ttacttgatggtgtttttataccgccaaggaggccgt ggcaccgtcagtgtgatctgtagaccccatggcggcc tttttcgcgattgaatgaccttggcggtgggtcccc agggctctggtggcagcgcaccagccgctaaaagccg ctaaaaactgccgctaaaggccacagcaaccccgcga ccgcccgttcaactgtgctgacacagtgatacagata atgtcgctaacagaggagaatagaaatatgacgggca cacgctaatgtggggaaaagagggagaagcctgattt ttatttttagagattctagagataaaattcccagta ttatatccttttaataaaaaatttctattaggagatt ataaagaatttaaagctattttttaagtggggtgta attctttcagtagtctcttgtcaaatggatttaagta atagaggcttaatccaaatgagagaaatagacgcata accctttcaaggcaaaagctacaagagcaaaaattga acacagcagccagccatctagccactcagattttgat cagttttactgagtttgaagtaaatatcatgaaggta -continued taattgctgataaaaaaataagatacaggtgtgacac atctttaagtttcagaaatttaatggcttcagtagga ttatatttcacgtatacaaagtatctaagcagataaa aatgccattaatggaaacttaatagaaatatattttt aaattccttcattctgtgacagaaattttctaatctg ggtcttttaatcacctaccctttgaaagagtttagta atttgctatttgccatcgctgtttactccagctaatt tcaaaagtgatacttgagaaagattatttttggtttg caaccacctggcaggactattttagggccattttaaa actcttttcaaactaagtattttaaactgttctaaac catttagggccttttaaaaatcttttcatgaatttca aacttcgttaaaagttattaaggtgtctggcaagaac ttccttatcaaatatgctaatagtttaatctgttaat gcaggatataaaattaaagtgatcaaggcttgaccca aacaggagtatcttcatagcatatttcccctcctttt tttctagaattcatatgattttgctgccaaggctatt ttatataatctctggaaaaaaaatagtaatgaaggtt aaaagagaagaaaatatcagaacattaagaattcggt attttactaactgcttggttaacatgaaggtttttat tttattaaggtttctatctttataaaaatctgttccc ttttctgctgatttctccaagcaaaagattcttgatt tgtttttaactcttactctcccacccaagggcctga atgcccacaaaggggacttccaggaggccatctggca gctgctcaccgtcagaagtgaagccagccagttcctc ctgggcaggtggccaaaattacagttgacccctcctg gtctggctgaaccttgccccatatggtgacagccatc tggccagggcccaggtctccctctgaagcctttggga ggagagggagagtggctggcccgatcacagatgcgga aggggctgactcctcaaccggggtgcagactctgcag ggtgggtctgggcccaacacacccaaagcacgcccag gaaggaaaggcagcttggtatcactgcccagagctag gagaggcaccgggaaaatgatctgtccaagacccgtt cttgcttctaaactccgagggggtcagatgaagtggt tttgtttcttggcctgaagcatcgtgttccctgcaag aagcggggaacacagaggaaggagagaaaagatgaac tgaacaaagcatgcaaggcaaaaaaggccttaggatg gctgcaggaagttagttcttctgcattggctccttac tggctcgtcgatcgcccacaaacaacgcacccagtgg agaacttccctgttacttaaacaccattctctgtgct tgcttcctcaggggctgatgccaagccatccgtcttc atcttcccgccatcgaaggagcagttagcgacccaa -continued ctgtctctgtggtgtgcttgatca Seq ID No. 15 gatgccaagccatccgtcttcatcttcccgccatcga
aggagcagttagcgaccccaactgtctctgtggtgtg
cttgatcaataacttcttccccagagaaatcagtgtc
aagtggaaagtggatggggtggtccaaagcagtggtc
atccggatagtgtcacagagcaggacagcaaggacag
cacctacagcctcagcagcaccctctcgctgcccacg
tcacagtacctaagtcataatttatattcctgtgagg
tcacccacaagaccctggcctcccctctggtcacAAG
CTTCAACAGGAACGAGTGTGAGGCTTAGAGGCCCACA
GGCCCCTGGCCTGCCCCCAGCCCCAGCCCCCCTCCCC
ACCTCAAGCCTCAGGCCCTTGCCCCAGAGGATCCTTG
GCAATCCCCCAGCCCCTCTTCCCTCCTCATCCCCTCC
CCCTCTTTGGCTTTAACCGTGTTAATACTGGGGGGTG
GGGGAATGAATAAATAAAGTGAACCTTTGCACCTGTG
ATTTCTCTCTCCTGTCTGATTTTAAGGTTGTTAAATG
TTGTTTTCCCCATTATAGTTAATCTTTTAAGGAACTA
CATACTGAGTTGCTAAAAACTACACCATCACTTATAA
AATTCAcgCCTTCTCAGTTCTCCCCTCCCCTCCTGTC
CTCCGTAAGACAGGCCTCCGTGAAACCCATAAGCACT
TCTCTTTACACCCTCTCCTGGGCCGGGGTAGGAGACT
TTTTGATGTCCCCTcTTCAGCAAGCCTCAGAACCATT
TTGAGGGGGACAGTTCTTACAGTCACAT*TCCtGtGA
TCTAATGACTTTAGTTaCCGAAAAGCCAGTCTCTCAA
AAAGAAGGGAACGGCTAGAAACCAAGTCATAGAAATA
TATATGTATAAAATATATATATATCCATATATGTAAA
ATAACAAAATAATGATAACAGCATAGGTCAACAGGCA
ACAGGGAATGTTGAAGTCCATTCTGGCACTTCAATTT
AAGGGAATAGGATGCCTTCATTACATTTTAAATACAA
TACACATGGAGAGCTTCCTATCTGCCAAAGACCATCC
TGAATGCCTTCCACACTCACTACAAGGTTAAAAGCAT
TCATTACAATGTTGATCGAGGAGTTCCCGTTGTGGCT
CAGCAGGTTAAGAACGTGACTGGTATCCAGGAGGATG
CGGGTTTGGTCCCCAGCCTCGCTCAGTGGATTAAGGA
TCCAGTGTTGCTGCAAGATCACGGGCTCAGATCCCGT
GTTCTATGGCTATGGTGTAGGCTGGTAGCTGCATGCA
GCCCTAATTTGACCCCTAGCCTGGGAACTGCCATAtG
CCACATGTGAGGCCCTTAAAACCTAAAAGAAAAAaAA
AGAAAAGAAATATCTTACACCCAATTTATAGATAAGA
GAGAAGCTAAGGTGGCAGGCCCAGGATCAAAGCCCTA -continued CCTGCCTATCTTGACACCTGAtACAAATTCTGTCTTC
TAGGGtTTCCAACACTGCATAGAACAGAGGGTCAAAC
ATGCTACCCTCCCAGGGACTCCTCCCTTCAAATGACA
TAAATTTTGTTGCCCATCTCTGGGGGCAAAACTCAAC
AATCAATGGCATCTCTAGTACCAAGCAAGGCTCTTCT
CATGAAGCAAAACTCTGAAGCCAGATCCATCATGACC
CAAGGAAGTAAAGACAGGTGTTACTGGTTGAACTGTA
TCCTTCAATTCAATATGCTCAATTTCCAACTCCCAGT
CCCCGTAAATACAACCCCCTTTGGGAAGAGAGTCCTT
GCAGATGTAGCCACGTTAAAAAGAGATTATACAGAAA
GGCTAGTGAGGATGCAGTGAAACGGGATCTTTCATAC
ATTGCTGGTGGAAATGTAAAATGCTGCAGGCACTCTA
GAAAATAATTTGCCAGTTTTTTGAAAAGCTAAACAAA
ATAGTTTAGTTGCATTCTGGGTTATTTATCCCCCAGA
AATTAAAAATTATGTCCGCACAAAAACGTGTACATAA
TCATTCATAACAGCCTTGTACGAAAAGCTT Seq ID No. 16 GGATCCTTAACCCACTAATCGAGGATCAAACACGCAT
CCTCATGGACAATATGTTGGGTTCTTAGCCTGCTGAG
ACACAACAGGAACTCCCCTGGCACCACTTTAGAGGCC
AGAGAAACAGCACAGATAAAATTCCCTGCCCTCATGA
AGCTTATAGTCTAGCTGGGGAGATATCATAGGCAAGA
TAAACACATACAAATACATCATCTTAGGTAATAATAT
ATACTAAGGAGAAAATTACAGGGGAGAAAGAGGACAG
GAATTGCTAGGGTAGGATTATAAGTTCAGATAGTTCA
TCAGGAACACTGTTGCTGAGAAGATAACATTTAGGTA
AAGACCGAAGTAGTAAGGAAATGGACCGTGTGCCTAA
GTGGGTAAGACCATTCTAGGCAGCAGGAACAGCGATG
AAAGCACTGAGGTGGGTGTTCACTGCACAGAGTTGTT
CACTGCACAGAGTTGTGTGGGGAGGGGTAGGTCTTGC
AGGCTCTTATGGTCACAGGAAGAATTGTTTTACTCCC
ACCGAGATGAAGGTTGGTGGATTTTGAGCAGAAGAAT
AATTCTGCCTGGTTTATATATAACAGGATTTCCCTGG
GTGCTCTGATGAGAATAATCTGTCAGGGGTGGGATAG
GGAGAGATATGGCAATAGGAGCCTTGGCTAGGAGCCC
ACGACAATAATTCCAAGTGAGAGGTGGTGCTGCATTG
AAAGCAGGACTAACAAGACCTGCTGACAGTGTGGATG
TAGAAAAAGATAGAGGAGACGAAGGTGCATCTAGGGT
TTTCTGCCTGAGGAATTAGAAAGATAAAGCTAAAGCT
TATAGAAGATGCAGCGCTCTGGGGAGAAAGACCAGCA
GCTCAGTTTTGATCCATCTGGAATTAATTTTGGCATA
AAGTATGAGGTATGTGGGTTAACATTATTTGTTTTTT -continued TTTTTTCCATGTAGCTATCCAACTGTCCCAGCATCAT
TTATTTTAAAAGACTTTCCTTTCCCCTATTGGATTGT
TTTGGCACCTTCACTGAAGATCAACTGAGCATAAAAT
TGGGTCTATTTCTAAGCTCTTGATTCCATTCCATGAC
CTATTTGTTCATCTTTACCCCAGTAGACACTGCCTTG
ATGATTAAAGCCCCTGTTACCATGTCTGTTTTGGACA
TGGTAAATCTGAGATGCCTATTAGCCAACCAAGCAAG
CACGGCCCTTAGAGAGCTAGATATGAGAGCCTGGAAT
TCAGACGAGAAAGGTCAGTCCTAGAGACATACATGTA
GTGCCATCACCATGCGGATGGTGTTAAAAGCCATCAG
ACTGCAACAGACTGTGAGAGGGTACCAAGCTAGAGAG
CATGGATAGAGAAACCCAAGCACTGAGCTGGGAGGTG
CTCCTACATTAAGAGATTAGTGAGATGAAGGACTGAG
AAGATTGATCAGAGAAGAAGGAaAATCAGGAAAATGG
TGCTGTCcTGAAAATCCAAGGGAAGAGATGTTCCAAA
GAGGAGAaAACTGATCAGTTGTCAGCTAGCGTCAATT
GGGATGAAAATGGACCATTGGACAGAGGGATGTAGTG
GGTCATGGGTGAATAGATAAGAGCAGCTTCTATAGAA
TGGCAGGGGCAAAATTCTCATCTGATCGGCATGGGTT
cTAAAGAAAACGGGAAGAAAAAATTGAGTGCATGACC
AGTCCCTTCAAGTAGAGAGGTgGAAAAGGGAAGGAGG
AAAATGAGGCCACGACAACATGAGAGAAATGACAGCA
TTTTTAAAAATTTTTTATTTTATTTtATTTATTTATT
TTTGCTTTTTAGGGCTGCCCCTGCAAcatatggaggt
tcccaggttaggggtctaatcagagctatagctgcca
gcctacaccacagccatagcaatgccagatctacatg
acctacaccacagctcacagcaacgccggatccttaa
cccactgagtgaggccagagatcaaacccatatcctt
atggatactagtcaggttcattaccactgagccaaaa
tgggaaATCCTGAGTAATGACAGCATTTTTTAATGTG
CCAGGAAGCAAAACTTGCCACCCCGAAATGTCTCTCA
GGCATGTGGATTATTTTGAGCTGAAAACGATTAAGGC
CCAAAAAACACAAGAAGAAATGTGGACCTTCCCCCAA
CAGCCTAAAAAATTTAGATTGAGGGCCTGTTCCCAGA
ATAGAGCTATTGCCAGACTTGTCTACAGAGGCTAAGG
GCTAGGTGTGGTGGGGAAACCCTCAGAGATCAGAGGG
ACGTTTATGTACCAAGCATTGACATTTCCATCTCCAT
GCGAATGGCCTTCTTCCCCTCTGTAGCCCCAAACCAC
CACCCCCAAAATCTTCTTCTGTCTTTAGCTGAAGATG
GTGTTGAAGGTGATAGTTTCAGCCACTTTGGCGAGTT -continued CCTCAGTTGTTCTGGGTCTTTCCTCCGGATCCACATT
ATTCGACTGTGTTTGATTTTCTCCTGTTTATCTGTCT
CATTGGCACCCATTTCATTCTTAGACCAGCCCAAAGA
ACCTAGAAGAGTGAAGGAAAATTTCTTCCACCCTGAC
AAATGCTAAATGAGAATCACCgCAGTAGAGGAAAATG
ATCTGGTgCTGCGGGAGATAGAAGAGAAAATcGCTGG
AGAGATGTCACTGAGTAGGTGAGATGGGAAAGGGGGG
GCACAGGTGGAGGTGTTGCCCTCAGCTAGGAAGACAG
ACAGTTcacagaagagaagcgggtgtccgtGGACATC
TTGCCTCATGGATGAGGAAACCGAGGCTAAGAAAGAC
TGCAAAAGAAAGGTAAGGATTGCAGAGAGGTCGATCC
ATGACTAAAATCACAGTAACCAACCCCAAACCACCAT
GTTTTCTCCTAGTCTGGCACGTGGCAGGTACTGTGTA
GGTTTTCAATATTATTGGTTTGTAACAGTACCTATTA
GGCCTCCATCcCCTCCTCTAATACTAACAAAAGTGTG
AGACTGGTCAGTGAAAAATGGTCTTCTTTCTCTATGC
AATCTTTCTCAAGAAGATACATAACTTTTTATTTTAT
CATaGGCTTGAAGAGCAAATGAGAAACAgCCTCCAAC
CTATGACACCGTAACAAAGTGTTTATGATCAGTGAAG
GGCAAGAAACAAAACATACACaGTAAAGACCCTCCAT
AATATTGtGGGCTGGCCCAaCACAGGCCAGGTTGTAA
AAGCTTTTTATTCTTTGATAGAGGAATGGATAGTAAT
GTTTCAACCTGGACAGAGAT*CATGTTCACTGAATCC
TTCCAAAAATTCATGGGTAGTTTGAAtTATAAGGAAA
ATAAGACTTAGGATAAATACTTTgTCCA*GATCCCAG
AGTTAATgCCAAAATCAGTTTTCAGACTCCAGGCAGC
CTGATCAAGAGCCTAAACTTTAAAGACACAGTCCCTT
AATAACTACTATTCACAGTTGCACTTTCAgGGCGCAA
AGACTCATTGAATCCTACAATAGAATGAGTTTAGATA
TCAAATCTCTCAGTAATAGATGAGGAGACTAAATAGC
GGGCATGACCTGGTCACTTAAAGACAGAATTGAGATT
CAAGGCTAGTGTTCTTTCTACCTGTTTTGTTTCTACA
AGATGTAGCAATGCGCTAATTACAGACCTCTCAGGGA
AGGAATTCACAACCCTCAGCAAAAACCAAAGACAAAT
CTAAGACAACTAAGAGTGTTGGTTTAATTTGGAAAAA
TAACTCACTAACCAAACGCCCCTCTTAGCACCCCAAT
GTCTTCCACCATCACAGTGCTCAGGCCTCAACCATGC
CCCAATGACCCCAGCCCCAGACTGGTTATTACCAAGT
TTCATGATGACTGGCCTGAGAAGATCAAAAAAGCAAT
GACATCTTACAGGGGACTACCCCGAGGACCAAGATAG
CAACTGTCATAGCAACCGTCACACTGCTTTGGTCA -continued Seq ID No. 19 ggatcaaacacgcatcctcatggacaatatgttgggt tcttagcctgctgagacacaacaggaactcccctggc accactttagaggccagagaaacagcacagataaaat tccctgccctcatgaagcttatagtctagctggggag atatcataggcaagataaacacatacaaatacatcat cttaggtaataatatatactaaggagaaaattacagg ggagaaagaggacaggaattgctagggtaggattata agttcagatagttcatcaggaacactgttgctgagaa gataacatttaggtaaagaccgaagtagtaaggaaat ggaccgtgtgcctaagtgggtaagaccattctaggca gcaggaacagcgatgaaagcactgaggtgggtgttca ctgcacagagttgttcactgcacagagttgtgtgggg aggggtaggtcttgcaggctcttatggtcacaggaag aattgttttactcccaccgagatgaaggttggtggat tttgagcagaagaataattctgcctggtttatatata acaggatttccctgggtgctctgatgagaataatctg tcaggggtgggatagggagagatatggcaataggagc cttggctaggagcccacgacaataattccaagtgaga ggtggtgctgcattgaaagcaggactaacaagacctg ctgacagtgtggatgtagaaaaagatagaggagacga aggtgcatctagggttttctgcctgaggaattagaaa gataaagctaaagcttatagaagatgcagcgctctgg ggagaaagaccagcagctcagttttgatccatctgga attaattttggcataaagtatgaggtatgtgggttaa cattatttgtttttttttttccatgtagctatccaa ctgtcccagcatcatttattttaaaagactttccttt cccctattggattgttttggcaccttcactgaagatc aactgagcataaaattgggtctatttctaagctcttg attccattccatgacctatttgttcatctttacccca gtagacactgccttgatgattaaagcccctgttacca tgtctgttttggacatggtaaatctgagatgcctatt agccaaccaagcaagcacggcccttagagagctagat atgagagcctggaattcagacgagaaaggtcagtcct agagacatacatgtagtgccatcaccatgcggatggt gttaaaagccatcagactgcaacagactgtgagaggg taccaagctagagagcatggatagagaaacccaagca ctgagctgggaggtgctcctacattaagagattagtg agatgaaggactgagaagattgatcagagaagaagga aaatcaggaaaatggtgctgtcctgaaaatccaaggg aagagatgttccaaagaggagaaaactgatcagttgt -continued cagctagcgtcaattgggatgaaaatggaccattgga cagagggatgtagtgggtcatgggtgaatagataaga gcagcttctatagaatggcaggggcaaaattctcatc tgatcggcatgggttctaaagaaaacgggaagaaaaa attgagtgcatgaccagtcccttcaagtagagaggtg gaaaagggaaggaggaaaatgaggccacgacaacatg agagaaatgacagcatttttaaaaatttttttattta ttttatttatttatttttgctttttagggctgcccct gcaacatatggaggttcccaggttaggggtctaatca gagctatagctgccagcctacaccacagccatagcaa tgccagatctacatgacctacaccacagctcacagca acgccggatccttaacccactgagtgaggccagagat caaacccatatccttatggatactagtcaggttcatt accactgagccaaaatgggaaatcctgagtaatgaca gcatttttttaatgtgccaggaagcaaaacttgccacc ccgaaatgtctctcaggcatgtggattattttgagct gaaaacgattaaggcccaaaaaacacaagaagaaatg tggaccttcccccaacagcctaaaaaatttagattga gggcctgttcccagaatagagctattgccagacttgt ctacagaggctaagggctaggtgtggtggggaaaccc tcagagatcagagggacgtttatgtaccaagcattga catttccatctccatgcgaatggccttcttcccctct gtagccccaaaccaccacccccaaaatcttcttctgt ctttagctgaagatggtgttgaaggtgatagtttcag ccactttggcgagttcctcagttgttctgggtctttc ctccTgatccacattattcgactgtgtttgattttct cctgtttatctgtctcattggcacccatttcattctt agaccagcccaaagaacctagaagagtgaaggaaaat ttcttccaccctgacaaatgctaaatgagaatcaccg cagtagaggaaaatgatctggtgctgcgggagataga agagaaaatcgctggagagatgtcactgagtaggtga gatgggaaaggggtgacacaggtggaggtgttgccct cagctaggaagacagacagttcacagaagagaagcgg gtgtccgtggacatcttgcctcatggatgaggaaacc gaggctaagaaagactgcaaaagaaaggtaaggattg cagagaggtcgatccatgactaaaatcacagtaacca accccaaaccaccatgttttctcctagtctggcacgt ggcaggtactgtgtaggttttcaatattattggtttg taacagtacctattaggcctccatcccctcctctaat actaacaaaagtgtgagactggtcagtgaaaaatggt cttctttctctatgaatctttctcaagaagatacata -continued acttttttattttatcataggcttgaagagcaaatgag
aaacagcctccaacctatgacaccgtaacaaaatgtt
tatgatcagtgaagggcaagaaacaaaacatacacag
taaagaccctccataatattgtgggtggcccaacaca
ggccaggttgtaaaagctttttattctttgatagagg
aatggatagtaatgtttcaacctggacagagatcatg
ttcactgaatccttccaaaaattcatgggtagtttga
attataaggaaaataagacttaggataaatactttgt
ccaagatcccagagttaatgccaaaatcagttttcag
actccaggcagcctgatcaagagcctaaactttaaag
acacagtcccttaataactactattcacagttgcact
ttcagggcgcaaagactcattgaatcctacaatagaa
tgagtttagatatcaaatctctcagtaatagatgagg
agactaaatagcgggcatgacctggtcacttaaagac
agaattgagattcaaggctagtgttctttctacctgt
tttgtttctacaagatgtagcaatgcgctaattacag
acctctcagggaaggaattcacaaccctcagcaaaaa
ccaaagacaaatctaagacaactaagagtgttggttt
aatttggaaaaataactcactaaccaaacgcccctct
tagcaccccaatgtcttccaccatcacagtgctcagg
cctcaaccatgccccaatcacc Seq ID No.25 GCACATGGTAGGCAAAGGACTTTGCTTCTCCCAGCAC
ATCTTTCTGCAGAGATCCATGGAAACAAGACTCAACT
CCAAAGCAGCAAAGAAGCAGCAAGTTCTCAAGTGATC
TCCTCTGACTCCCTCCTCCCAGGCTAATGAAGCCATG
TTGCCCCTGGGGGATTAAGGGCAGGTGTCCATTGTGG
CACCCAGCCCGAAGACAAGCAATTTGATCAGGTTCTG
AGCACTCCTGAATGTGGACTCTGGAATTTTCTCCTCA
CCTTGTGGCATATCAGCTTAAGTCAAGTACAAGTGAC
AAACAACATAATCCTAAGAAGAGAGGAATCAAGCTGA
AGTCAAAGGATCACTGCCTTGGATTCTACTGTGAATG
ATGACCTGGAAAATATCCTGAACAACAGCTTCAGGGT
GATCATCAGAGACAAAAGTTCCAGAGCCAGGTAGGGA
AACCCTCAAGCCTTGCAAAGAGCAAAATCATGCCATT
GGGTTCTTAACCTGCTGAGTGATTTACTATATGTTAC
TGTGGGAGGCAAAGCGCTCAAATAGCCTGGGTAAGTA
TGTCAAATAAAAAGCAAAAGTGGTGTTTCTTGAAATG
TTAGACCTGAGGAAGGAATATTGATAACTTACCAATA
ATTTTCAGAATGATTTATAGATGTGCACTTAGTCAGT
GTCTCTCCACCCCGCACCTGACAAGCAGTTTAGAATT -continued TATTCTAAGAATCTAGGTTTGCTGGGGGCTACATGGG
AATCAGCTTCAGTGAAGAGTTTGTTGGAATGATTCAC
TAAATTTTCTATTTCCAGCATAAATCCAAGAACCTCT
CAGACTAGTTTATTGACACTGCTTTTCCTCCATAATC
CATCTCATCTCCGTCCATCATGGACACTTTGTAGAAT
GACAGGTCCTGGCAgAGACTCaCAGATGCTTCTGAAA
CATCCTTTGCCTTCAAAGAATGAACAGCACACATACT
AAGGATCTCAGTGATCCACAAATTAGTTTTTGCCACA
ATGGTTCTTATGATAAAAGTCTTTCATTAACAGCAAA
TTGTTTTATAATAGTTGTTCTGCTTTATAATAATTGC
ATGCTTCACTTTCTTTTCTTTTCTTTTTTTTTCTTTT
TTTGCTTTTTAGTGCCGCAGGTgcagcatatgaaatt
tcccaggctaggggtcaaatcagaactacacctactg
gcctacgccacagccacagcaactcaggatctaagcc
atgtcggtgacctacactacagctcatggcaatgcca
gatccttaacccaatgagcgaggccagggatcgaacc
catgtcctcatggatactagtcaggctcattatccgc
tgagccataacaggaactcccGAGTTTGCTTTTTATC
AAAATTGGTACAGCCTTATTGTTTCTGAAAACCACAA
AATGAATGTATTCACATAATTTTAAAAGGTTAAATAA
TTTATGATATACAAGACAATAGAAAGAGAAAACGTCA
TTGCCTCTTTCTTCCACGACAACACGCCTCCTTAATT
GATTTGAAGAAATAACTACTGAGCATGGTTTAGTGTA
CTTCTTTCAGCAATTAGCCTGTATTCATAGCCATACA
TATTCAATTAAAATGAGATCATGATATCACACAATAC
ATACCATACAGCCTATAGGGATTTTTACAATCATCTT
CCACATGACTACATAAAAACCTACCTAAAAAAAAAAA
AAACCCTACTTCATCCTCCTATTGGCTGCTTTGTGCT
CCATTAAAAAGCTCTATCATAATTAGGTTATGATGAG
GATTTCCATTTTCTACCTTTCAAGCAACATTTCAATG
CACAGTCTTATATACACATTTGAGCCTACTTTTCTTT
TTCTTTCTTTTTTTGGTTTTTTTTTTTTTTTTTTTTT
TGGTCTTTTTGTCTTTTCTAAGgctgcatatggaggt
tcccaggctagctgtctaatcagaactatagctgctg
gcctacgccacatccacagcaatacaagatctgagcc
atgtctgcaacttacaccacagctcacagcaacggtg
gatccttaaaccactgagcaaggccagggatcaaacc
catAACTTCATGGCTCCTAGTTGGATTTGTTAACCAC
TGAGCCATGATGGCAACTCCTGAGCCTACTTTTCTAA
TCATTTCCAACCCTAGGACACTTTTTTAAGTTTCATT
TTTCTCCCCCCACCCCCTGTTTTCTGAAGtGTGTTTG -continued CTTCCACTGGGTGACTTCACtCCCAGGATCTCATCTG

CAGGATACTGCAGCTAAGTGTATGAGCTCTGAATTTG

AATCCCAACTCTGCCACTCAAAGGATAGGAGTTTCC

GATGTGGCCCAATGGGATCAGTGGCATCTCTGCAGTG

CCAGGACGCaggttccatccctggcccagcacagtgg gttaagaatctggCATTGCTGCAGCTGAGGCATAGAT

TTCAATTGTGCCTCAgATCTGATCCTTGGCCCAAGGA

CTGCATATGCCTCAGGGCAACCAAAAAAGAGAAAAGG

GGGGTGATAGCATTAGTTTCTAGATTTGGGGGATAAT

TAAATAAAGTGATCCATGTACAATGTATGGCATTTTG

TAAATGCTCAACAAATTTCAACTATTATggagttccc atcatggctcagtggaagggaatctgattagcatcca tgaggacacaggtCCAACCCCGACCTTGCTCAGTGGG

CATTGCTGTGAGCTGTGGCATGGGTTACAGACGAAGC

TCGGATCTGGCATTGCTGTGGCTGTGGTGTAAGCCAg

CAActacagctctcattcagcccctagcctgggaacc tccatatgccTAAAAGACAAAAAATAAAATTTAAATT

AAAAATAAAGAAATGTTAACTATTATGATTGgTACTG

CTTGCATTACTGCAAAGAAAGTCACTTTCTATACTCT

TTAATATCTTAGTTGACTGTGTGCTCAGTGAACTATT

TTGGACACTTAATTTCCACTCTCTTCTATCTCCAACT

TGACAACTCTCTTTCCTCTCTTCTGGTGAGATCCACT

GCTGACTTTGCTCTTTAAGGCAACTAGAAAAGTGCTC

AGTGACAAAATCAAAGAAAGTTACCTTAATCTTCAGA

ATTACAATCTTAAGTTCTCTTGTAAAGCTTACTATTT

CAGTGGTTAGTATTATTCCTTGGTCCCTTACAACTTA

TCAGCTCTGATCTATTGCTGATTTTCAACTATTTATT

GTTGGAGTTTTTTCCTTTTTTCCCTGTTCATTCTGCA

AATGTTTGCTGAGCATTTGTCAAGTGAAGATACTGGA

CTGGGCCTTCCAAATATAAGACAATGAAACATCGGGA

GTTCTCATTATGGTGCAGCAGAaacgaatccaactag gaaatgtgaggttgcaggttcgatccctgcccttgct cagtgggttaaggatccagcattaccgtgagctgtgg tgtaggttgcagacgtggctcagatcctgcgttgctg tggctgtggcataggctggcagctctagctctgattc gaccgctagcctgggaacctccatGCGCCCCGAGTGC

AGCCCTTAAAAGCAAAAAAAAAAGAAAGAAAGAAAA

AGACAATGAAACATCAAACAGCTAACAATCCAGTAGG

GTAGAAAGAATCTGGCAACAGATAAGAGCGATTAAAT

GTTCTAGGTCCAGTGACCTTGCCTCTGTGCTCTACAC

-continued

AGTCGTGCCACTTGCTGAGGGAGAAGGTCTCTCTTGA

GTTGAGTCCTGAAAGACATTAGTTGTTCACAAACTAA

TGCCAGTGAGTGAAGGTGTTTCCAAGCAGAGGGAGAG

TTTGGTAAAAAGCTGGAAGTCACAGAAAGACTCTAAA

GAGTTTAGGATGGTGGGAGCAACATACGCTGAGATGG

GGCTGGAAGGTTAAGAGGGAAACAACTATAGTAAGTG

AAGCTGGACTCACAGCAAAGTGAGGACCTCAGCATCC

TTGATGGGGTTACCATGGAAACACCAAGGCACACCTT

GATTTCCAAAACAGCAGGCACCTGATTCAGCCCAATG

TGACATGGTGGGTACCCCTCTAGCTCTACCTGTTCTG

TGACAACTGACAACCAACGAAGTTAAGTCTGGATTTT

CTACTCTGCTGATCCTTGTTTTTGTTTCACACGTCAT

CTATAGCTTCATGCCAAAATAGAGTTCAAGGTAAGAC

GCGGGCCTTGGTTTGATATACATGTAGTCTATCTTGT

TTGAGACAATATGGTGGCAAGGAAGAGGTTCAAACAG

GAAAATACTCTCTAATTATGATTAACTGAGAAAAGCT

AAAGAGTCCCATAATGACACTGAATGAAGTTCATCAT

TTGCAAAAGCCTTCCCCCCCCCCCAGGAGACTATAAA

AAAGTGCAATTTTTTAAATGAACTTATTTACAAAACA

GAAATAGACTCACAGACATAGGAAACGAACAGATGGT

TACCAAGGGTGAAAGGGAGTAGGAGGGATAAATAAGG

AGTCTGGGGTTAGCAGATACACCCCAGTGTACACAAA

ATAAACAACAGGGACCTACTATATAGCACAGGGAACT

ATATGCAGTAGCTTACAATAACCTATAATGGAAAAGA

ATGTGAAAAAGAATATATGTATGCGTGTGTGTGTAAC

TGAATCACTTTGCTGTAACCTGAATCTAACATAACAT

TGTAAATCAACTACAGTTTTTTTTTTTTTTTAAGTGCA

GGGTTTTGGTGTTTTTTTTTTTTTCATTTTTGTTTTTGT

TTTTGTTTTTTGCTTTTTAGGGCCACACCCAGACAT

ATGGGGGTTCCCAGGctAGGGGTcTAaTTAGAGcTAC

AGtTGCCGGCTTGCAccacagccacagcaacatcaga tccgagccgcacttgcgacttacaccacagctcatgg caataccagatccttaacccactgagcaaggcccagg gatcgtacccgcaacctcatggttcctagtcagattc attTCTGCTGCGCTACAATGGGAACTCCAAGTGCAGT TTTTTGTAATGTGCTtGTCTTTCTTTGTAATTCATAT

TCATCCTACTTCCCAATAAATAAATAAATACATAAAT

AATAAACATACCATTGTAAATCAACTACAATTTTTTT

TAAATGCAGGGTTTTTGTTTTTTGTTTTTTGTTTTGT

CTTTTTGCCTTTTCTAgggccgctcccatggcatatg gaggttcccaggctaggggtcgaatcggagctgtagc

-continued

```
caccggcctacgccagagccacagcaacgcgggatcc
gagccgcgtctgcaacctacaccacagctcacggcaa
cgccggatcgttaacccactgagcaagggcagggatc
gaacctgcaacctcatggttcctagtcagattcgtta
actactgagccacaacggaaacTCCTAAAGTGCAGTT
TTTAAATGTGCTTGTCTTTCTTTGTAATTTACACTCA
ACCTACTTCCCAATAAATAAATAAATAAACAAATAAA
TCATAGACATGGTTGAATTCTAAAGGAAGGGACCATC
AGGCCTTAGACAGAAATACGTCATCTTCTAGTATTTT
AAAACACACTAAAGAAGACAAACATGCTCTGCCAGAG
AAGCCCAGGGCCTCCACAGCTGCTTGCAAAGGGAGTT
AGGCTTCAGTAGCTGACCCAAGGCTCTGTTCCTCTTC
AGGGAAAAGGGTTTTTGTTCAGTGAGACAGCAGACAG
CTGTCACTGTGGgtggacgttcggccaaggaaccaagc
tggaactcaaacGTAAGTCAATCCAAACGTTCCTTCC
TTGGCTGTCTGTGTCTTACGGTCTCTGTGGCTCTGAA
ATGATTCATGTGCTGACTCTCTGAAACCAGACTGACA
TTCTCCAGGGCAAAACTAAAGCCTGTCATCAAACcGG
AAAACTGAGGGCACATTTTCTGGGCAGAACTAAGAGT
CAGGCACTGGGTGAGGAAAAACTTGTTAGAATGATAG
TTTCAGAAACTTACTGGGAAGCAAAGCCCATGTTCTG
AACAGAGCTCTGCTCAAGGGTCAGGAGGGGAACCAGT
TTTTGTACAGGAGGGAAGTTGAGACGAACCCCTGTGT
Atatggtttcggcgcggggaccaagctggagctcaaa
cGTAAGTGGCTTTTTCCGACTGATTCTTTGCTGTTTC
TAATTGTTGGTTGGCTTTTTGTCCATTTTTCAGTGTT
TTCATCGAATTAGTTGTCAGGGACCAAACAAATTGCC
TTCCCAGATTAGGTACCAGGGAGGGGACATTGCTGCA
TGGGAGACCAGAGGGTGGCTAATTTTTAACGTTTCCA
AGCCAAAATAACTGGGGAAGGGGGCTTGCTGTCCTGT
GAGGGTAGGTTTTTATAGAAGTGGAAGTTAAGGGGAA
ATCGCTATGGTtcacttttggctcggggaccaaagtg
gagcccaaaattgaGTACATTTTCCATCAATTATTTG
TGAGATTTTTGTCCTGTTGTGTCATTTGTGCAAGTTT
TTGACATTTTGGTTGAATGAGCCATTCCCAGGGACCC
AAAAGGATGAGACCGAAAAGTAGAAAAGAGCCAACTT
TTAAGCTGAGCAGACAGACCGAATTGTTGAGTTTGTG
AGGAGAGTAGGGTTTGTAGGGAGAAAGGGGAACAGAT
CGCTGGCTTTTTCTCTGAATTAGCCTTTCTCATGGGA
CTGGCTTCAGAGGGGGTTTTTGATGAGGGAAGTGTTC
```

-continued

```
TAGAGCCTTAACTGTGGgttgtgttcggtagcgggac
caagctggaaatcaaaCGTAAGTGCACTTTTCTACTC
C
```

Porcine Lambda Light Chain

Figure 3:
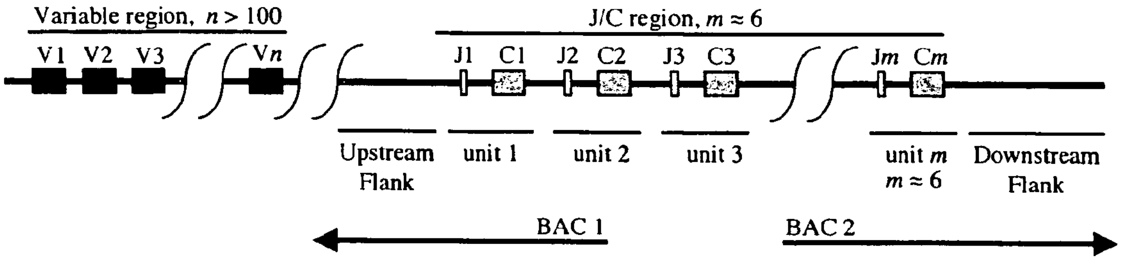
FIG. 3 illustrates the genomic organization of the porcine lambda immunoglobulin locus, including a concatamer of J-C sequences or units as well as flanking regions that include the variable region 5' to the JC cluster region. Bacterial artificial chromosomes (BAC1 and BAC2) represent fragments of the porcine immunoglobulin genome that can be obtained from BAC libraries.

In another embodiment, novel genomic sequences encoding the lambda light chain locus of ungulate immunoglobulin are provided. The present invention provides the first reported genomic sequence of ungulate lambda light chain regions. In one embodiment, the porcine lambda light chain nucleotides include a concatamer of J to C units. In a specific embodiment, an isolated porcine lambda nucleotide sequence is provided, such as that depicted in Seq ID No. 28. See FIG. 3 for a diagram of the organization of the porcine lamba immunoglobulin locus.

In one embodiment, nucleotide sequence is provided that includes 5' flanking sequence to the first lambda J/C region of the porcine lambda light chain genomic sequence, for example, as represented by Seq ID No 32.

Still further, nucleotide sequence is provided that includes 3' flanking sequence to the J/C cluster region of the porcine lambda light chain genomic sequence, for example, approximately 200 base pairs downstream of lambda J/C, such as that represented by Seq ID No 33. Alternatively, nucleotide sequence is provided that includes 3' flanking sequence to the J/C cluster region of the porcine lambda light chain genomic sequence, for example, approximately 11.8 kb downstream of the J/C cluster, near the enhancer (such as that represented by Seq ID No. 34), approximately 12 Kb downstream of lambda, including the enhancer region (such as that represented by Seq ID No. 35), approximately 17.6 Kb downstream of lambda (such as that represented by Seq ID No. 36, approximately 19.1 Kb downstream of lambda (such as that represented by Seq ID No. 37), approximately 21.3 Kb downstream of lambda (such as that represented by Seq ID No. 38), and/or approximately 27 Kb downstream of lambda (such as that represented by Seq ID No. 39).

In still further embodiments, isolated nucleotide sequences as depicted in Seq ID Nos 28, 31, 32, 33, 34, 35, 36, 37, 38, or 39 are provided. Nucleic acid sequences at least 80, 85, 90, 95, 98 or 99% homologous to Seq ID Nos 28, 31, 32, 33, 34, 35, 36, 37, 38, or 39 are also provided. In addition, nucleotide sequences that contain at least 10, 15, 17, 20, 25, 30, 40, 50, 75, 100, 150, 200, 250, 500 or 1,000 contiguous nucleotides of Seq ID Nos 28, 31, 32, 33, 34, 35, 36, 37, 38, or 39 are provided. Further provided are nucleotide sequences that hybridizes, optionally under stringent conditions, to Seq ID Nos 28, 31, 32, 33, 34, 35, 36, 37, 38, or 39, as well as, nucleotides homologous thereto.

```
Seq ID   CCTTCCTCCTGCACCTGTCAACTCCCAATAAACCGTC
No. 28
         CTCCTTGTCATTCAGAAATCATGCTCTCCGCTCACTT
         GTGTCTACCCATTTTCGGGCTTGCATGGGGTCATCCT
         CGAAGGTGGAGAGAGTCCCCCTTGGCCTTGGGGAAGT
         CGAGGGGGGCGGGGGGAGGCCTGAGGCATGTGCCAGC
         GAGGGGGGTCACCTCCACGCCCCTGAGGACCTTCTAG
         AACCAGGGGCGTGGGGCCACCGCCTGAGTGGAAGGCT
         GTCCACTTTTCCCCCGGGCCCCCAGGCTCCCTCCTCC
```

-continued

GTGTGGACCTTGTCCACCTCTGACTGGCCCAGCCACT
CATGCATTGTTTCCCCGAAACCCCAGGACGATAGCTC
AGCACGCGACAGTGTCCCCCTCTGAGGGCCTCTGTCC
ATTTCAGGACGACCCGCATGTACAGCGTGACCACTCT
GCTCACGCCCACTCACCACGTCCTAGAGCCCCACCCC
CAGCCCCATCCTTAGGGGCACAGCCAGcTCCGACCGC
CCCGGGGACACCACCCTCTGCCCCTTcCCCAGGCCCT
CCCTGTCACACGCACCACAGGGCCCTCCGTCCCGAGA
CCCTGCTCCCTCATCCCTCGGTCCCCTCAGGTAGCCT
TCCACCCGCGTGTGTCCCGAGGTCCCAGATGCAGCAA
GGCCCCTGGGACAACGCCAGATCTCTGCTCTcCCCGA
CCCCTCAGAAGCCAGCCCACGCCTGGCCCCACCACCA
CTGCCTAACgTCCAAGTGTCCATAGGCCTCGGGACCT
CCAAGTCCAGGTTCTGCCTCTGGGATTCCGCCATGGG
TCTGCCTGGGAAATGATGCACTTGGAGGAGCTCAGCA
TGGGATGCGGGACCTTGTCTCTAGGCGCTcCCTCAGG
ATCCCACAGCTGCCCTGTGAGACACACACACACACAC
ACACACACACACACACACACACACACACAAACACG
CATGCACGCACGCCGGCACACACGCTATTGCAGAGAT
GGCCACGGTAGCTGTGCCTCGAGGCCGAGTGGAGTGT
CTAGAACTCTCGGGGGTCCCCTCTGCAGACGACACTG
CTCCATCCCCCCCGTGCCCTGAAGGGCTCCTCACTCT
CCCATCAGGATCTCTCCAAGCTGCTGACCTGGAGAGG
AAGGGGCCTGGGACAGGCGGGGACACTCAGACCTCCC
TGCTGCCCCTCCTCTGCCTGGGCTTGGACGGCTCCCC
CCTTCCCACGGGTGAAGGTGCAGGTGGGGAGAGGGCA
CCCCCCTCAGCCTCCCAGACCCAGACCAGCCCCCGTG
GCAGGGGCAGCCTGTGAGCCTCCAGCCAGATGCAGGT
GGCCTGGGGTGGGGGGTGGAGGGGGCGGGAGGTTTAT
GTTTGAGGCTGTATCACTGTGTAATATTTTCGGCGGT
GGGACCCATCTGACCGTCCTCGGTGAGTCTCCCCTTT
TCTCTCCTCCTTGGGGATCCGAGTGAAATCTGGGTCG
ATCTTCTCTCCGTTCTCCTCCGACTGGGGCTGAGGTC
TGAACCTCGGTGGGGTCCGAAGAGGAGGCCCCTAGGC
CAGGCTCCTCAGCCCCTCCAGCCCGACcgGCCCTCTT
GACACAGGGTCCAGCTAAGGGCAGACATGGAGGCTGC
TAGTCCAGGGCCAGGCTCTGAGACCCAAGGGCGCTGC
CCAAGGAACCCTTGCCCCAGGGACCCTGGGAGCAAAG
CTCCTCACTCAGAGCCTGCAGCCCTGGGGTCTGAGGA
CAAGGAGGGACTGAGGACTGGGCGTGGGGAGTTCAGG

-continued

CGGGGACACCAGGTCCAGGGAGGTGACAAAGGCGCTG
GGAGGGGGCGGACGGTGCCGGGGACTCCTCCTGGGCC
CTGTGGGCTCGGGGTCCTTGTGAGGACCCTGAGGGAC
TGAGGGGCCCCTGGGCCTAGGGACTTGCAgTgAGGGA
GGCAGGGAGTGTCCCTTGAGAACGTGGCCTCCGCGGG
CTGGGTCCCCCTCGTGCTCCCAGCC*GGGAGGACACC
CCAGAGCAAGCGCCCCAGGTGGGCGGGGAGGGTCTCC
TCACAGGGGCAGCTGACAGATAGAGGCCCCCGCCAGG
CAGATGCTTGATCCTGGCAgTTATACTGGGTTC**GC
ACAACTTTCCCTGAACAAGGGGCCCTCCGAACAGACA
CAGACGCAACCCAGTCGACCcaggCTCAGCACAgAAA
ATGCACTGACACCCAAAACCCTCATCTggggGCCTGG
CCGGcAtCCCGCCCCAGGACCCAAGGCCCCTGCCCCC
TGGCAGCCCTGGACACGGTCCTCTGTGGGCGGTGGGG
TCgGGGCTGTGGTGACGGTGGCATCGGGGAGCCTGTG
CCCCCTCCCTGAAAGGGCGGAGAGGCTCAAGAGGGGA
GAGAAATGTCCTCCCCTAGGAAGACCTCGGACGGGGG
CGGGGGGGTGGTCTCCGACAGACAGATGCCCGGGACC
GACAGACCTGCCGAGGGAAGAGGGCACCTCGGTCGGG
TTAGGCTCCAGGCAGCACGAGGGAGCGAGGCTGGGAG
GGTGAGGACATGGGAGCCTGAGGAGGAGCTGGAGACT
TCAGCAGGCCCCCAGCTCCGGGCTTCGGGCTCTGAGA
TGCTCGGACGCAAGGTGAGTGACCCCACCTGTGGCTG
ACCTGACCTCAgGGgGACAAGGCTCAGCCTGGGACTC
TGTGTCCCCATCGCCTGcACAGGGGATTCCCCTGATG
GACACTGAGCCAACGACCTCCCGTCTCTCCCCGACCC
CCAGGTCAGCCCAAgGCCaCTCCCACGGTCAACCTCT
TCCCGCCCTCCTCTGAGGAGCTCGGCACCAACAAGGC
CACCCTGGTGTGTCTAATAAGTGACTTCTACCCGGGC
GCCGTGACGGTGACCTGGAAGGCAGGCGGCACCACCG
TCACCCAGGGCGTGGAGACCACCAAGCCCTCGAAACA
GAGCAACAACAAGTACGCGGCCAGCAGCTACCTGGCC
CTGTCCGCCAGTGACTGGAAATCTTCCAGCGGCTTCA
CCTGCCAGGTCACCCACGAGGGGACCATTGTGGAGAA
GACAGTGACGCCCTCCGAGTGCGCCTAGGTCCCTGGG
CCCCCACCCTCAGGGGCCTGGAGCCACAGGACCCCCG
CGAGGGTCTCCCCGCGACCCTGGTCCAGCCCAGCCCT
TCCTCCTGCACCTGTCAACTCCCAATAAACCGTCCTC
CTTGTCATTCAGAAATCATGCTCTCCCGCTCACTTGTG
TCTACCCATTTTCGGGCTTGCATGGGGTCATCCTCGA
AGGTGGAGAGAGTCCCCCTTGGCCTTGGGgAAATCGA -continued

```
GGGGGGCGGGGGGAGGCCTGAGGCATGTGCCAGCGAG
GGGGGTCACCTCCACGCCCCTGAGGACCTTCTAGAAC
CAGGGGCGTGGGGCCACCGCCAGAGTGGAAGGCTGTC
CACTTTTCCCCCGGGCCCCCAGGCTCCCTCCTCCGTG
TGGACCTTGTCCACCTCTGACTGGCCCAGCCACTCAT
GCATTGTTTCCCCGAAACCCCAGGACGATAGCTCAGC
ACGCGACAGTGTCCCCCTCTGAGGGCCTCTGTCCATT
TCAGGACGACCCGCATGTACAGCGTGACCACTCTGCT
CACGCCCACTCACCACGTCCTAGAGCCCCACCCCCAG
CCCCATCCTTAGGGGCACAGCCAGCTCCGACCGCCCC
GGGGACACCACCCTCTGCCCCTTCCCCAGGCCCTCCC
TGTCACACGCACCACAGGGCCCTCCGTCCCGAGACCC
TGCTCCCTCATCCCTCGGTCCCCTCAGGTAGCCTTCC
ACCCGCGTGTGTCCCGAGGTCCCAGATGCAGCAAGGC
CCCTGGGACAACGCCAGATCTCTGCTCTCCCCGACCC
TCAGAAGCCAGCCCACGCCTGGCCCACCACCACTGCC
TAACGTCCAAGTGTCCATAGGCTCGGGAcCTCcAaGT
CCAGGTTCTGCCTCTGGGATTCCGCCATGGGTCTGCC
TGGAATGATGCACTTGGAGgAgCTCAGcATGGGATGc
GGAACTTGTCTAGcGCTCCTCAGATCCAcAGcTGCCT
GtGAgAcacacacacacacacacacacaccAAAcaCG
cATGCACGCACGCCGGCACACACGCTATTACAGAGAT
GGCCACGGTAGCTGTGCCTCGAGGCCGAGTGGAGTGT
CTAGAACTCTCGGGGGTCCCCTCTGCAGACGACACTG
CTCCATCCCCCCCGTGCCCTGAAGGGCTCCTCACTCT
CCCATCAGGATCTCTCCAAGCTGCTGACCTGGAGAGG
AAGGGGCCTGGGACAGGCGGGGACACTCAGACCTCCC
TGCTGCCCCTCCTCTGCCTGGGCTTGGACGGCTCCCC
CCTTCCCACGGGTGAAGGTGCAGGTGGGGAGAGGGCA
CCCCCCTCACCCTCCCAGACCCAGACCAGCCCCCGTG
GCAGGGGCAGCCTGTGAGCCTCCAGCCAGATGCAGGT
GGCCTGGGGTGGGGGGTGGAGGGGGCGGGAGGTTTAT
GTTTGAGGCTGTATTCATCTGTGTAATATttTCGGCG
GTGGGACCCATCTGACCGTCCTCGGTGAGTCTCCCCT
tttctttcctccttggggatccgagtgaaATcTGGGT
CGATCTTCTCTCCGTTCTCCTCCGACTGGGGCTGAGG
TCTGAACCTCGGTgGGGTCCGAAGAGGAGGCCCCTAG
GCC*GGCTCcTCAGCCCCTCCAGCCCGACCCGCCCTC
TTGACACAGGGTCCAGCTAAGGGCAGACAT***GGCT
GCTAGTCCAGGGCCAGGCTcTGAGACCCAAGGGCGCT
```

-continued

```
GCCCAAGGAACCCTTGCCCCAGGGACCCTGGGAGCAA
AGCTCCTCACTCAGAGCCTGCAGCCCTGGgGTGTGAG
GACAAGGAGGGACTGAGGACTGGGCGTGGGGAGTTCA
CGGCgGGGACACCGGGTCAGGGAGGTGACAAAGGCGC
TGGGAGGGGGGCGGACGGTGCCGGAGACTCCTCCTGGG
CCCTGTGGGCTCGTGGTCCTTGTGAGGACCCTGAGGG
*CTGAGGGGCCCCTGGGCCTAGGGACTTGCAGTGAGG
GAGGCAGGGAGTGTCCCTTGAGAACGTGGCCTCCGCG
GGCTGGGTCCCCCTCGTGCTCCCAGCAGGGAGGACAC
CCCAGAGCAAGCGCCCCAGGTGGGCGGGGAGGGTCTC
CTCACAGGGGCAGCTGACAGATAGAC*GgccCCCGCC
AGACAGATGCTTGATCCTGGTCag***TACTGGGTTC
GCcACTTCCCTGAACAGGGGCCCTCCGAACAGACACA
GACGCAGACCaggCTCAGCACAgAAAATGCACTGACA
CCCAAAACCCTCATCTGggGGCCTGGCCGGCATCCCG
CCCCAGGACCCAAGGCCCCTGCCCCCTGGCAGCCCTG
GACACGGTCCTCTGTGGGCGGTGGGGTCgGGGCTGTG
GTGACGGTGGCATCGGGGAGCCTGTGCCCCCTCCCTG
AAAGGGCGGAGAGGCTCAAGAGGGGACAGAAATGTCC
TCCCCTAGGAAGACCTCGGACGGGGGCGGGGGGGTGG
TCTCCGACAGACAGATGCCCGGGACCGACAGACCTGC
CGAGGGAAGAGGGCACCTCGGTCGGGTTAGGCTCCAG
GCAGCACGAGGGAGCGAGGCTGGGAGGGTGAGGACAT
GGGAGCCTGAGGAGGAGCTGGAGACTTCAGCAGGCCC
CCAGCTCCGGGCTTCGGGCTCTGAGATGCTCGGACGC
AAGGTGAGTGACCCCACCTGTGGCTGACCTGACCTGA
CCtCAGGGGGACAAGGCTCAGCCTGGGACTCTGgTGTC
CCCATCGCCTGCACAGGGGATTCCCCTGATGGACACT
GAGCCAACGACCTCCCGTCTCTCCCCGACCCCCAGGT
CAGCCCAAGGCCACTCCCACGGTCAACCTCTTCCCGC
CCTCCTCTGAGGAGCTCGGCACCAACAAGGCCACCCT
GGTGTGTCTA
```

Seq ID No. 32

```
GCCACGCCCACTCCATCATGCGGGGAGGGGATGGGCA
GACCCTCCAGAAAGAAGCTCCCTGGGGTGCAGGTTAA
CAGCTTTCCCAGACACAGCCAGTACTAGAGTGAGGTG
AATAAGACATCCTCCTTGCTTGTGAAATTTAGGAAGT
GCCCCCAAACATCAGTCATTAAGATAAATAATATTGA
ATGCACTTTTTTTTTTTATTTTTTTTTTTTGCTTTT
TAGGGCCTAATCTGCAGCatatggaagttcccaggct
acaagtcgaaccagagctgcagctgccagcctacatc
```

-continued acagccacagcaacaccagatccgagccacatctgtg actaacactgcagttcacagcaacgccagatccttaa cccattgagtgaggccagggatcaaacccacatcctc atggatactagtctggttcgtaaaccactgagccaCA

AGGGGAACTCCTGAATGCAATATTTTTGAAAATTGAA

ATTAAATCTGTCACTCTTTCACTTAAGAGTCCCCTTA

GATTGGGGAAAATTTAAATATCTGTCATCTTAGTGCA

TCTTTGCTCATATGATGTGAATAAAATCCCAAAATCC

ATATGAATGAAGCATCAAAATGTACATGAAGTCAGCC

TGACCCTGCACTGCCCTCACTTGCCTCATGTACCCCC

CACCTCAAAGGAAGATGCAGAAAGGAGTCCAGCCCCT

ACACCGCCACCTGCCCCCACCACTGGAGCCCCTCAGG

TCTCCCACCTCCTTTTCTGAGCTTCAGTCTTCCTGTG

GCATTGCCTACCTCTACAGCTGCCCCCTACTAGGCCC

TCCCCCTGGGGCTGAGCTCCAGGCACTGGACTGGGAA

AGTTAGAGGTTAAAGCATGGAAAATTCCCAAAGCCAC

CAGTTCCAGGCTGCCCCCCACCCCACCGCCACGTCCA

AAAAGGGGCATCTTCCCAGATCTCTGGCTGGTATTGG

TAGGACCCAGGACATAGTCTTTATACCAATTCTGCTG

TGTGTCTTAGGAAAGAaactctccctctctgtgcttc agtttcctcatcaataaaAGGAGCAGGCCAGGTTGGA

GGGTCTGTGACGTCTGCTGAAGCAGCAGGATTCTCTC

TCCTTTTGCTGGAGGAGAACTGATCCTTCACCCCCAG

GATCAACAGAGAAGCCAAGGTCTTCAGCCTTCCTGGG

GACCCCTCAGAGGGAACTCAGGGCCACAGAGCCAGAC

CCTGATGCCAGAACCTTTGTCATATGCCCAGACGGAG

ACTTCATCCCCCTCCTCCTCAGACCCTCCAGGCCCCA

ACAGTGAGATGCTGAAGATATTAAGAGAAGGGCAAGT

CAGcTTAAGTTTGGGGGTAGAGGGGAACAGGGAGTGA

GGAGATCTGGCCTGAGAGATAGGAGCCCTGGTGGCCA

CAGGAGGACTCTTTGGGTCCTGTCGGATGGACACAGG

GCGGCCCGGGGGCATGTTGGAGCCCGGCTGGTTCTTA

CCAGAGGCAGGGGGCACCCTCTGACACGGGAGCAGGG

CATGTTCCATACATGACACACCCCTCTGCTCCAGGGC

AGGTGGGTGGCGGCACAGAGGAGCCAGGGACTCTGAG

CAAGGGGTCCACCAGTGGGGCAGTTGGATCCAGACTT

CTCTGGGCCAGCGAGAGTCTAGCCCTCAGCCGTTCTC

TGTCCAGGAGGGGGGTGGGGCAGGCCTGGGCGGCCAG

AGCTCATCCCTCAAGGGTTCCCAGGGTCCTGCCAGAC

CCAGATTTCCGACCGCAGCCACCACAAGAGGATGTGG

TCTGCTGTGGCAGCTGCCAAGACCTTGCAGCAGGTGC

-continued

AGGGTGGGGGGGTGGGGGCACCTGGGGGCAGCTGGGG

TCACTGAGTTCAGGGAAAACCCCTTTTTTCCCCTAAA

CCTGGGGCCATCCCTAGGGGAAACCACAACTTCTGAG

CCCTGGGCAGTGGCTGCTGGGAGGGAAGAGCTTCATC

CTGGACCCTGGGGGGGAACCCAGCTCCAAAGGTGCAA

GGGGCCCAGGTCCAAGGCTAGAGTGGGCCAAGCACCG

CAATGGCCAGGGAGTGGGGGAGGTGGAGCTGGACTGG

ATCAGGGCCTCCTTGGGACTCCCTACACCCTGTGTGA

CATGTTAGGGTACCCACACCCCATCACCAGTCAGGGC

CTGGCCCATCTCCAGGGCCAGGGATGTGCATGTAAGT

GTGTGTGAGTGTGTGTGTGTGGTGTAGTACACCCCTT

GGCATCCGGTTCCGAGGCCTTGGGTTCCTCCAAAGTT

GCTCTCTGAATTAGGTCAAACTGTGAGGTCCTGATCG

CCATCATCAACTTCGTTCTCCCCACCTCCCATCATTA

TCAAGAGCTGGGGAGGGTCTGGGATTTCTTCCCACCC

ACAAGCCAAAAGATAAGCCTGCTGGTGATGGCAGAAG

ACACAGGATCCTGGGTCAGAGACAAAGGCCAGTGTGT

CACAGCGAGAGAGGCAGCCGGACTATCAGCTGTCACA

GAGAGGCCTTAGTCCGCTGAACTCAGGCCCCAGTGAC

TCCTGTTCCACTGGGCACTGGCCCCCCTCCACAGCGC

CCCCAGGCCCCAGGGAGAGGCGTCACAGCTTAGAGAT

GGCCCTGCTGAACAGGGAACAAGAACAGGTGTGCCCC

ATCCAGCGCCCCAGGGGTGGGACAGGTGGGCTGGATT

TGGTGTGAAGCCCTTGAGCCCTGgAACCCAAcCACAG

CAgGGCAGTTGGTAGATGCCATTTGGGGAGAGGCCCC

AGGAGTAAGGGCCATGGGCCCTTGAGGGGGCCAGGAG

CTGAGGACAGGGACAGAGACGGCCCAGGCAGAGGACA

GGGCCATGAGGGGTGCACTGAGATGGCCACTGCCAGC

AGGGGCAGCTGCCAACCCGTCCAGGGAACTTATTCAG

CAGTCAGCTGGAGGTGCCATTGACCCTGAGGGCAGAT

GAAGCCCAGGCCAGGCTAGGTGGGCTGTGAAGACCCC

AGGGGACAGAGCTCTGTCCCTGGGCAGCACTGGCCTC

TCATTCTGCAGGGCTTGACGGGATCCCAAGGCCTGCT

GCCCCTGATGGTAGTGGCAGTACCGCCCAGAGCAGGA

CCCCAGCATGGAAACCCCAACGGGACGCAGCCTGCGG

AGCCCACAAAACCAGTAAGGAGCCGAAGCAGTCATGG

CACGGGGAGTGTGGACTTCCCTTTGATGGGGCCCAGG

CATGAAGGACAGAATGGGACAGCGGCCATGAGCAGAA

AATCAGCCGGAGGGGATGGGCCTAGGCAGACGCTGGC

TTTATTTGAAGTGTTGGCATTTTGTCTGGTGTGTATT

-continued

GTTGGTATTGATTTTATTTTAGTATGTCAGTGACATA

CTGACATATTATGTAACGACATATTATTATGTGTTTT

AAGAAGCACTCCAAGGGAACAGGCTGTCTGTAATGTG

TCCAGAGAAGAGAGCAAGAGCTTGGCTCAGTCTCCCC

CAAGGAGGTCAGTTCCTCAACAGGGGTCCTAAATGTT

TCCTGGAGCCAGGCCTGAATCAAGGGGgTCATATCTA

CACGTGGGGCAGACCCATGGACCATTTTCGGAGCAAT

AAGATGGCAGGGAGGATACCAAGCTGGTCTTACAGAT

CCAGGGCTTTGACCTGTGACGCGGGCGCTCCTCCAGG

CAAAGGGAGAAGCCAGCAGGAAGCTTTCAGAACTGGG

GAGAACAGGGTGCAGACCTCCAGGGTCTTGTACAACG

CACCCTTTATCCTGGGGTCCAGGAGGGGTCACTGAGG

GATTTAAGTGGGGGACCATCAGAACCAGGTTTGTGTT

TTGGAAAAATGGCTCCAAAGCAGAGACCAGTGTGAGG

CCAGATTAGATGATGAAGAAGAGGCAGTGGAAAGTCG

ATGGGTGGCCAGGTAGCAAGAGGGCCTATGGAGTTGG

CAAGTGAATTTAAAGTGGTGGCACCAGAGGGCAGATG

GGGAGGAGCAGGCACTGTCATGGACTGTCTATAGAAA

TCTAAAATGTATACCCTTTTTAGCAATATGCAGTGAG

TCATAAAAGAACACATATATATTTAAATTGTGTAATT

CCACTTCTAAGGATTCATCCCAAGGGGGGAAAATAAT

CAAAGATGTAACCAAAGGTTTACAAACAAGAACTCAT

CATTAATCTTCCTTGTTGTTATTTCAACGATATTATT

ATTATTACTATTATTATTATTATTATTttgtcttttt gcattttctagggccactcccacggcatagagaggtt cccaggctaggggtcaaatcggagctacagctgccgg cctacgccagagccacagcaacgcaggatctgagcca cagcaatgcaggatctacaccacagctcatggtaacg ctggatccttaacccaatgagtgaggccagggatcga acctgtaacttcatggttcctagtcggattcattaac cactgagccacgacaggaactccAACATTATTAATGA

TGGGAGAAAACTGGAAGTAACCTAAATATCCAGCAGA

AAGGGTGTGGCCAAATACAGCATGGAGTAGCCATCAT

AAGGAATCTTACACAAGCCTCCAAAATTGTGTTTCTG

AAATTGGGTTTAAAGTACGTTTGCATTTTAAAAAGCC

TGCCAGAAAATACAGAAAAATGTCTGTGATATGTCTC

TGGCTGATAGGATTTTGCTTAGTTTTAATTTTGGCTT

TATAATTTTCTATAGTTATGAAAATGTTCACAAGAAG

ATATATTTCATTTTAGCTTCTAAAATAATTATAACAC

AGAAGTAATTTGTGCTTTAAAAAAATATTCAACACAG

AAGTATATAAAGTAAAAATTGaggagttcccatcgtg

-continued gctcagtgattaacaaacccaactagtatccatgagg atatggatttgatccctggccttgctcagtgggttga ggatccagtgttgctgtgagctgtggtgtaggttgca gacacagcactctggcgttgctgtgactctggcgtag gccggcagctacagctccatttggacccttagcctgg gaacctccatatgcctgagatacggcccTAAAAAGTC

AAAAGCCAAAAAAATAGTAAAAATTGAGTGTTTCTAC

TTACCACCCCTGCCCACATCTTATGCTAAAACCCGTT

CTCCAGAGACAAACATCGTCAGGTGGGTCTATATATT

TCCAGCCCTCCTCCTGTGTGTGTATGTCCGTAAAACA

CACACACACACACACACACGCACACACACACACACGT

ATCTAATTAGCATTGGTATTAGTTTTTCAAAAGGGAG

GTCATGCTCTACCTTTTAGGCGGCAAATAGATTATTT

AAACAAATCTGTTGACATTTTCTATATCAACCCATAA

GATCTCCCATGTTCTTGGAAAGGCTTTGTAAGACATC

AACATCTGGGTAAACCAGCATGGTTTTTAGGGGGTTG

TGTGGATTTTTTTCATATTTTTTAGGGCACACCTGCA gcatatggaggttcccaggctaggggttgaatcagag ctgtagctgccggcctacaccacagccacagcaacgc cagatccttaacccactgagaaaggccagggattgaa cctgcatcctcatggATGCTGGTCAGATTTATTTCTG

CTGAGCCACAACAGGAACTCCCTGAACCAGAATGCTT

TTAACCATTCCACTTTGCATGGACATTTAGATTGTTT

CCATTTAAAAATACAAATTACAaggagttcccgtcgt ggctcagtggtaacgaattggactaggaaccatgagg tttcgggttcgatccctggccttgctcggtgggttaa ggatccagcattgatgtgagatatggtgtaggtcgca gacgtggctcggatcccacgttgctgtggctctggcg taggccggcaacaacagctccgattcgacccctagcc TGggaacctccatgtgccacaggagcagccctaGAAA

AGGCAAAAAGACAAAAAAATAAAAAATTAAAATGAAA

AAATAAAATAAAAATACAAATTACAAGAGACGGCTAC

AAGGAAATCCCCAAGTGTGTGCAAATGCCATATATGT

ATAAAATGTACTAGTGTCTCCTCGCGGGAAAGTTGCC

TAAAAGTGGGTTGGCTGGACAGAGAGGACAGGCTTTG

ACATTCTCATAGGTAGTAGCAATGGGCTTCTCAAAAT

GCTGTTCCAGTTTACACTCACCATAGCAAATGACAGT

GCCTCTTCCTCTCCACCCTTGCCAATAATGTGACAGG

TGGATCTTTTTCTATTTTGTGTATCTGACAAGCAAAA

AATGAGAACAggagttcctgtcgtggtgcagtggaga

-continued caaatctgactaggaaccatgaaatttcgggttcaat
ccctggcctcactcagtaggtaaaggatccagggttg
cagtgagctgtggggtaggtcgcagacacagtgcaaa
tttggccctgttgtggctgtggtgtaggccggcagct
atagctccaattggacccctagcctgggaacctcctt
atgccgtgggtgaggccctAAAAAAAAGAGTGCAAAA
AAAAAAAATAAGAACAAAAATGATCATCGTTTAATTC
TTTATTTGATCATTGGTGAAACTTATTTTCCTTTTAT
ATTTTTATTGACTGATTTTATTTCTCCTATGAATTTA
CCGGTCATAGTTTTGCCTGGGTGTTTTTACTCCGGTT
TTAGTTTTGGTTGGTTGTATTTTCTTAGAGAGCTATA
GAAACTCTTCATCTATTTGGAATAGTAATTCCTCATT
AAGTATTTGTGCTGCAAAAAATTTTCCCTGATCTGTT
TTATGCTTTTGTTTGTGGGGTCTTTCACGAGAAAGCC
TTTTTAGTTTTTACACCTCAGCTTGGTTGTTTTTCTT
GATTGTGTCTGTAATCTGCGGCCAACATAGGAAACAC
ATTTTTACTTTAGTGTTTTTTTCCTATTTTCTTCAAG
TACGTCCATTGTTTTGGTGTCTGATTTTACTTTGCCT
GGGGTTTGTTTTTGTGTGGCAGGAATATAAACTTATG
TATTTTCCAAATGGAGAGCCAATGGTTGTATATTTGT
TGAATTCAAATGCAACTTTATCAAACACCAAATCATC
GATTTATCACAACTCTTCTCTGGTTTATTGATCTAAT
GATCAATTCCTGTTCCACGCTGTTTTAATTATTTTAG
CTTTGTGGATTTTGGTGCCTGGTAGAGAACAAAGCCT
CCATTATTTTCATTCAAAATAGTCCCGTCTATTATCT
GCCATTGTTGTAGTATTAGACTTTAAAATCAATTTAC
TGATTTTCAAAAGTTATTCCTTTGGTGATGTGGAATA
CTTTATACTTCATAAGGTACATGGATTCATTTGTGGG
GAATTGATGTCTTTGCTATTGTGGCCATTTGTCAAGT
TGTGTAATATTTTACCCATGCCAACTTTGCATATTGT
ATGTGAGTTTATTCCCAGGGTTTTTAATAGGATGTTT
ATTGAAGTTGTCAGTGTTTCCACAATTTCATCGCCTC
AGTGCTTACTGTTTGCATAAAAGGAAACCTACTCACT
TTTGCCTATTGCTCTTGTATTCAATCATTTTAGTTAA
CTCTTGTGTTAATTTTGAGAGTTTTTCAGCTGACTGT
CTGGGGTTTTCTTTAATAGACTAGCCCTTTGTCTGTA
AAGAATAATTTTATCGAATTTTTCTTAACACTCACAC
TCTCCCCACCCCCACCCCCGCTCATCTCCTTTCATTG
GGTCAAATCTGTAGAATACAATAAAAGTAAGAGTGGG
AACCTTAGCCTTTAAGTCGATTTTGCCTTTAAATGTG
AATGTTGCTATGTTTCGGGACATTCTCTTTATCAAGT -continued TGCGGATGTTTCCTTAGATAATTAACTTAATAAAAGA
CTGGATGTTTGCTTTCTTCAAATCAGAATTGTGTTGA
ATTTATATTGCTATTCTGTTTAATTTTGTTTCAAAAA
ATTTACATGCACACCTTAAAGATAACCATGACCAAAT
AGTCCTCCTGCTGAGAGAAAATGTTGGCCCCAATGCC
ACAGGTTACCTCCCGACTCAGATAAACTACAATGGGA
GATAAAATCAGATTTGGCAAAGCCTGTGGATTCTTGC
CATAACTCTCAGAGCATGACTTGGGTGTTTTTTCCTT
TTCTAAGTATTTTAATGGTATTTTTGTGTTACAATAG
GAAATCTAGGACACAGAGAGTGATTCAATGAGGGGAA
CGCATTCTGGGATGACTCTAGGCCTCTGGTTTGGGGA
GAGCTCTATTGAAGTAAAGACAATGAGAGGAAGCAAG
TTTGCAGGGAACTGTGAGGAATTTAGATGGGGAATGT
TGGGTTTGAGGTTTCTATAGGGCACGCAAGCAGAGAT
GCACTCAGGAGGAAGAAGGAGCATAAATCTAGAGGCA
AAAAGAGAGGTCAGGACTGGAAATAGAGATGCGAGAC
ACCAGGGTGGCAGTCAGAGAGCACAGTGTGGGTCAGA
AGACAGTGGAAGAACACAAGGGACAGAGAGGGATCTC
CAACTTCACTGGGATGAGGGCCTTGTTGGCCTTGACC
TGAGAGATTTCCAGGAGTTGAGGGTGGGAAGGAGAGG
GCTCCTGCACATGTCCTGACATGAAACGGTGCCCAGC
ATATGGGTGCTTGGAAGACATTGTTGGACAGATGGAT
GGATGATGGATGATGGATGAATGGATGGATGGAAGAT
GATGGATAAATGGATGATGGATGGATGGACAGAAGGA
CAAAGAGATGGACAGAAAGACAGTGATCTGAGAGAGC
AGAGAAGGCTTCATGAAAGGACAGGAACTGAACTGTC
TCAGTGGGTGGAGACAATGGTGTAGGGGGGTTTCCACA
TGGAGGCACCAGGGGTCAGGAATAATCTAGTGTCCAC
AGGCCCAGGAAGGAAGCTGTCTGCAGGAAATTGTGGG
GAAGAACCTCAGAGTCCTTAAATGAGGTCAGGAGTGG
TCAGGAGGGTCTGATCAGGTAAGGACTCATGTCCATC
ATCACATGGTCACCTAAGGGCATGTAGCTCTCAGCAT
CTCCATCAGGACAGTCTCAGAATGGGGGCGGGGTCAC
ACACTGGGTGACTCAAGGCGTGGGTCATGCCTGCCTC
GGACGTGGGCCTGGGCATGGGGACACCTCCAGACCAT
GGGCCCGCCCAGGGCTGCACTGGcctctggtgggcta
gctacccgtccaagcaacacaggacacagccctacct
gctgcaaccctgtgcccgaaacgcccatctggttcct
gctccagcccggccccagggaacaggactcaggtgct
agcccaatggggttttgttcgagcctcagtcagcgtg -continued gTATTTCTCCGGCAGCGAGACTCAGTTCACCGCCTTA
GGttaagtggttctcatgaatttcctagcagtcctgc
actctgctatgccgggaaagtcacttttgtcgctggg
ggctgtttccccgtgcccttggagaatcaaggattgc
ccaactttctctgtgggggaggtggctggtcttgggg
tgaccagcaggaagggccccaaaagcaggagcagctg
cctccagAATACAACTGTCGGCTACAGCTCAAACAGG
AGGCCTGGACTGGGGTTTAACCACCAGGGCGGCACGA
AGGAGCGAGGCTGGGAGGGTGAGGACATGGGAGCCTG
AGGAGGAGCTGGAGACTTCAGCAGGCCCCCAGCTCCG
GGCTTCGGGCTCTGAGATGCTCGGACGCAAGGTGAGT
GACCCCACCTGTGGCTGACCTGACCTCAGGGGGACAA
GGCTCAGCCTGAGACTCTGTGTCCCCATCGCCTGCAC
AGgggattcccctgatggacactgagccaacgacctc
ccgtctctccccgacccccaggtcagcccaaggccgc
ccccacggtcaacctcttcccgccctcctctgaggag
ctcggcaccaacaaggccaccctggtgtgtctaataa
gtgacttctacccgAAGGGCGAATTCCAGCACACTGG
CGGCCGTTACTAGTGGATCCGAGCTCGGTACCAAGCT
TGATGCATAGCTTGAGTATCTA Seq ID No. 33
agatctttaaaccaccgagcaaggccagggatcgaac
ccgcatcctcatgaatcctagttgggttcgttaaccg
ctgaaccacaatgggaactcctGTCTTTCACATTTAA
TTCACAACCTCTCCAGGATTCTGGGGGTGGGTGGGGA
ATCCTAGGTACCCACTGGGAAAGTAATCCAAGGGGAG
AGGCTCACGGACTcTAGGGATCGGCGGAGGAGGGAAG
GTATCTCCCAGGAAACTGGCCAGGACACATTGGTCCT
CCGCCCTCCCCTTCCTCCCACTCCTCCTCCAGACAGG
ACTGTGCCCACCCCCTGCCACCTTTCTGGCCAGAACT
GTCCATGGCAGGTGACCTTCACATGAGCCCTTCCTCC
CTGCCTGCCCTAGTGGGACCCTCCATACCTCCCCCTG
GACCCCGTTGTCCTTTCTTTCCAGTGTGGCCCTGAGC
ATAACTGATGCCATCATGGGCTGCTGACCCACCCGGG
ACTGTGTTGTGCAGTGAGTCACTTCTCTGTCATCAGG
GCTTTGTAATTGATAGATAGTGTTTCATCATCATTAG
GACCGGGTGGCCTCTATGCTCTGTTAGTCTCCAAACA
CTGATGAAAACCTTCGTTGGCATAGTCCCAGCTTCCT
GTTGCCCATCCATAAATCTTGACTTAGGGATGCACAT
CCTGTCTCCAAGCAACCACCCCTCCCCTAGGCTAACT
ATAAAACTGTCCCAATGGCCCTTGTGTGGTGCAGAGT -continued TCATGCTTCCAGATCATTTCTCTGCTAGATCCATATC
TCACCTTGTAAGTCATCCTATAATAAACTGATCCATT
GATTATTTGCTTCTGTTTTTTCCATCTCAAAACAGCT
TCTCAGTTCAGTTCGAATTTTTTATTCCCTCCATCCA
CCCATACTTTCCTCAGCCTGGGGAACCCTTGCCCCCA
GTCCCATGCCCTTCCTCCCTCTCTGCCCAGCTCAGCA
CCTGCCCACCCTCACCCTTCCTGTCACTCCCTAGGAC
TGGACCATCCACTGGGGCCAGGACACTCCAGCAGCCT
TGGCTTCATGGGCTCTGAAATCCATGGCCCATCTCTA
TTCCTCACTGGATGGCAGGTTCAGAGATGTGAAAGGT
CTAGGAGGAAGCCAGGAAGGAAACTGTTGCATGAAAG
GCCGGCCTGATGGTTCAGTACTTAAATAATATGAGCT
CTGAGCTCCCCAGGAACCAAAGCATGGAGGGAGTATG
TGCCTCAGAATCTCTCTGAGATTCAGCAAAGCCTTTG
CTAGAGGGAAAATAGTGGCTCAACCTTGAGGGCCAGC
ATCTTGCACCACAGTTAAAAGTGGGTATTTGTTTTAC
CTGAGGCCTCAGCATTATGGGAACCGGGCTCTGACAC
AAACACAGGTGCAGCCCGGCAGCCTCAGAACACAGCA
ACGACCACAAGCTGGGACAGCTGCCCCTGAACGGGGA
GTCCACCATGCTTCTGTCTCGGGTACCACCAGGTCAC
CATCCCTGGGGGAGGTAGTTCCATAGCAGTAGTCCCC
TGATTTCGCCCCTCGGGCGTGTAGCCAGGCAAGCTCC
TGCCTCTGGACCCAGGGTGGACCCTTGCTCCCCACTA
CCCTGCACATGCCAGACAGTCAAGACCACTCCCACCT
CTGTCTGAGGCCCCCTTGGGTGTCCCAGGGCCCCCGA
GCTGTCCTCTACTCATGGTTCTTCCACCTGGGTACAA
AAGAGGCGAGGGACACTTTTCTCAGGTTTGCGGCTCA
GAAAGGTACCTTCCTAGGGTTTGTCCACTGGGAGTCA
CCTCCCTTGCATCTCAATGTCAGTGGGGAAAACTGGG
TCCCATGGGGGGATTAGTGCCACTGTGAGGCCCCTGA
AGTCTGGGGCCTCTAGACACTATGATGATGAGGGATG
TGGTGAAAAACCCCACCCCAGCCCTTCTTGCCGGGAC
CCTGGGCTGTGGCTCCCCCATTGCACTTGGGGTCAGA
GGGGTGGATGGTGGCTATGGTCAGGCATGTTTCCCAT
GAGCTGGGGGCACCCTGGGTGACTTTCTCCTGTGAAT
CCTGAATTAGCAGCTATAACAAATTGCCCAAACTCTT
AGGCTTAAAACAACACACATTTATTCCTCTGGGTCCC
AGGGTCAGAAGTCCAAAATGAGTCCTATAGGCTAAAT
TTGAGGTGTCTCTGGGTTGAGCTCCTCCTGGAAGCCT
TTTCCAGCCTCTAGAGTCCCAAGTCCTTGGCTCTGGG
CCCCTCCCTCAAGCTTCAAAGCCACAGAAGCTTCTAA -continued

TCTCTCTCCCTTCCCCTCTGACCTCTGCTCCCATCCT

CATACCCTGTCCCCTCACTCTGACCCTCCTGCCTCCC

TCTTTCCCTTATAAAGACCCTGCATGGGGCCAGGGAG

ATAATCCAGGGTAATCGCCCCTCTTCCAGCCCTTAAC

TCCATCCCATCTGCAAAATCCCTGTCACCCCATAATG

GACCTACTGATGGTCTGGGGGTTAGGACGTGGACAAC

TTGGGGCCTTATTCATCTGATCACAACTCCAGTTCCC

AGACCCCCAGACCCCCGGGCATTAGGGAAACTTCTCC

CAGTTCCTCTCCCTCTGTGTCCTGCCCAGTCTCCAGG

ATGGGCCACTCCCGAGGGCCCTTCAGCTCAGGCTCCC

CCTCCTTTCTCCCTGGCCTCTTGTGGCCCCATCTCCT

CCTCCGCTCACAGGGAGAGAACTTTGATTTCAGCTTT

GGCTCTGGGGCTTTGCTTCCTTCTGGCCATTGGCTGA

AGGGCGGGTTTCTCCAGGTCTTACCTGTCAGTCATCA

AACCGCCCTTGGAGGAAGACCCTAATATGATCCTTAC

CCTACAGATGGAGACTCGAGGCCCAGAGATCCTGAGT

GACCTGCTCACATTCACAGCAGGGACTGAACCCCAGT

CACCTACCCAACTCCAGGGCTCAGCGCTTTTTTTTTT

TTTTTTCTTTTTgccttttcgagggccgctcccgcaa catatggagatttccaggctaggggtctaattggagc agtcgacactggcctaagccaaagccacagcaacaag ggcaagccgcttctgcagcctataccacagctcacgg caatgccggatccttaacccactgagcaaagccaggg attgaacctgcaacctcatgtttcctagtcaaatttg ttaaccactgacccatgacgggaactcccAGGGCTCA

GCTCTTGACTCCAGGTTCGCAGCTGCCCTCAAAGCAA

TGCAACCCTGGCTGGCCCCGCCTCATGCATCCGGCCT

CCTCCCCAAAGAGCTCTGAGCCCACCTGGGCCTAGGT

CCTCCTCCCTGGGACTCATGGCCTAAGGGTACAGAGT

TACTGGGGCTGATGAAGGGACCAATGGGGACAGGGGC

CTCAAATCAAAGTGGCTGTCTCTCTCATGTCCCTTCC

TCTCCTCAGGGTCCAAAATCAGGGTCAGGGCCCCAGG

GCAGGGGCTGAGAGGGCCTCTTTCTGAAGGCCCTGTC

TCAGTGCAGGTTATGGGGGTCTGGGGGAGGGTCAATG

CAGGGCTCACCCTTCAGTGCCCCAAAGCCTAGAGAGT

GAGTGCCTGCCAGTGGCTTCCCAGGCCCAATCCCTTG

ACTGCCTGGGAATGCTCAAATGCAGGAACTGTCACAA

CACCTTCAGTCAGGGGCTGCTCTGGGAGGAAAAACAC

TCAGAATTGGGGGTTCAGGGAAGGCCCAGTGCCAAGC

ATAGCAGGAGCTCAGGTGGCTGCAGATGGTGTGAACC

-continued

CCAGGAGCAGGATGGCCGGCACTCCCCCCAGACCCTC

CAGAGCCCCAGGTTGGCTGCCCTCTTCACTGCCGACA

CCCCTGGGTCCACTTCTGCCCTTTCCCACCTAAAACC

TTTAGGGCTCCCACTTTCTCCCAAATGTGAGACATCA

CCACGGCTCCCAGGGAGTGTCCAGAAGGGCATCTGGC

TGAGAGGTCCTGACATCTGGGAGCCTCAGGCCCCACA

ATGGACAGACGCCCTGCCAGGATGCTGCTGCAGGGCT

GTTAGCTAGGCGGGGTGGAGATGGGGTACTTTGCCTC

TCAGAGGCCCCGGCCCCACCATGAAACCTCAGTGACA

CCCCATTTCCCTGAGTTCACATACCTGTATCCTACTC

CAGTCACCTTCCCCACGAACCCCTGGGAGCCCAGGAT

GATGCTGGGGCTGGAGCCACGACCAGCCCACGAGTGA

TCCAGCTCTGCCAATCAGCAGTCATTTCCCAAGTGTT

CCAGCCCTGCCAGGTCCCACTACAGCAGTAATGGAGG

CCCCAGACACCAGTCCAGCAGTTAGAGGGCTGGACTA

GCACCAGCTTTCAAGCCTCAGCATCTCAAGGTGAATG

GCCAGTGCCCCTCCCCGTGGCCATCACAGGATCGCAG

ATATGACCCTAGGGGAAGAAATATCCTGGGAGTAAGG

AAGTGCCCATACTCAAGGATGGCCCCTCTGTGACCTA

ACCTGTCCCTGAGGATTGTACTTCCAGGCGTTAAAAC

AGTAGAACGCCTGCCTGTGAACCCCCGCCAAGGGACT

GCTTGGGGAGGCCCCCTAAACCAGAACACAGGCACTC

CAGCAGGACCTCTGAACTCTGACCACCCTCAGCAAGT

GGCACCCCCCGCAGCTTCCAAGGCAC

Seq ID No. 34

AACAAGATGCTACCCCACCAACAAAATTCACCGGAGA

AGACAAGGACAGGGGGTTCCTGGGGTCCTGACAGGGT

CACCAAAGAGGGTTCTGGGGCAGCAGCAACTCCAGCC

GCCTCAGAACAGAGCCTGGAAGCTGTACCCTCAGAGC

AGAGGCGGAGAGAGAAAGGGCCTCTTGGTGGGTCAGC

AGGAGCAGAGGCTCAGAGGTGGGGGTTGCAGCCCCCC

CTTCAACAGGCCAACACAGTGAAGCAGCTGACCCCTC

CACCTTGGAGACCCCAGACTCCTGTCTCCCACGCCAC

CTTGGTTTTTAAGGTAATTTTTATTTTATATCAGAGT

ATGGTTGACTTACAATGTTGTGTTGGTTTCAGGTGTA

CAGCAGAGTGATTCACTTCTACATAGACTCATATCTA

TTCTTTCTCAGATTCTTTTCCCATATAGGTTATTACA

GAATATTGAGTAGATCCCTGCTGATTACCCATTTTTA

TAATTGTATATGTTAATCCCAAACTCCTAATTTATCC

CTCCCCAGACTATGATTCTTTATATCTCTATCTGTTT

CCTAATCTGTCTCCTCTAAGTCACCCTAGGAGAGCAG

-continued

AGGGGTCACGTCTGTCCTGTCCTGGCCCAGCCACCTC
TCTCCACCCAGGAATCCCTTGCATTTGGTGCCAAGGG
CCCGGCCCCGCCCTAAAGAGAAAGGAGAACGGGATGT
GGACAGGACACCGGGCAGAGAGGGACAAGCAGAGGAT
GCCAGGGTAGGGAGGTCTCCAGGGTGGATGGTGGTCT
GTCCGCAGGCAGGATGAGGCAGGAAGGGTGTGGATGT
ACTCGGTGAGGCTGGCGCATGGCCTGGAGTGTCCTGA
GCCCTGGGAGGCCTCAGCCCTGGATCAGATCTGTGAT
TCCAAAGGGCCACTGCATCCAGAGACCGTTGAGTGGC
CCATTGTCCTGAACCATTTATAGAACACAGGACAAGC
GGTACCTGACTAAGCTGCTCACAGATTCCATGAGGCT
GATGCCAGGGTTGTCACCCCATCTCACAGGCAGGGAA
ACTGATGCATATACTGCAGAGCCAGGCAGAGGCCCTC
CCAGTGCCCCCTCCCAGCCTGTGGCCCCCCTCCAGTG
GCTGGACACTGAGGCCACACTGGGGCACCCTGTGGAG
ATCt

Seq ID No. 35 AGATCTGGCCAGGCCAGAGAAGCCCATGTGGTGACCT
CCCTCCATCACTCCACGCCCTGACCTGCCAGGGAGCA
GAAAGTAGGCCCAGGGTGGACCCGGTGGCCACCTGCC
ACCCCATGGCTGGGAGAAGGGAGGGCCTGGGCAAAGG
GCCTGGGAAGCCTGTGGTGGGACCCCAGACCCCAGGG
TGGACAGGGAGGGTCCCACACCCACAGCCATTTGCTT
CCCTCTGTGGGTTCAGTGTCCTCATCTCATCTGTGGG
GAGGGGGCTGATAATGAATCTCCCCCATTGGGGTGGG
CTTGGGGATTAAAGGGCCAGTGTCTGTGATATGCCTG
GACCATAGTGACCCTCACCCTCCCCAGCCATTGCTGT
CACCTTCCGGGCTCTTGCCCAGGCCTGCCTGACATGC
TGTGTGACCCTGGGCAAGATGATCCCCCTTTCTGGGC
CCCAGCCTTCCTCTCTGCTCCGGAAGTGCTTCCTGGG
GAAACCTGTGGGCTGGATCCTATAGGAAACCTGTCCA
ATTCCTGGATGCACAGAGGGGCAGGGAGGCCCTGGGC
CTGGAGGGGCAGGGAGGCTCGAGGTGGGAGCAGGGTA
GGGGCCAGTCCAGGGCAAGGAGGTGGGTGGGTAGGGT
G

Seq ID No. 36: GATCTGTGTTCCATCTCAGAGCTATCTTAGCAGAGAG
GTGCAGGGGCCTCCAGGGCCACCAAAGTCCAGGCTCA
GCCAGAGGCAATGGGGTATCGATGAGCTACAGGACAC
AGGCGTCAGCCCAGTGTCAGGGAGAATCACCTTGTTT
GTTTTCTGAGTTCCTCTTAAAATAGAGTTAATTGGTC
TTGGCCTTACGGTTTACAATAACAACTGCACCCTGTA

-continued

AACAACGTGAAGAGTACAGAACAACAAATGGGGGAAA
ACATATTTCACCTGAAAGAGCCACCGCTCATATTTTG
ATGGATTTCCTTCTAGTTTAATCCTGTTTTAATTGTA
AACTGTTAAAACAAACATAAATAAAGAAAATGCATCT
GTAAAGTTTAAAAGTCATATCTATGGTGATGGTTGCA
AAACACTGTGAATGTTCACTTTGAAATCGTGAACTCT
ACGTGATATGCATGTCCCGTTAATTAACCTCACAGGC
TCAGAATGTGGTTCATTATTTCTTTAATTTTCCTTTA
ATTTTATGTCCTGTGTGTGTGCCCTTAAACCAACTAC
TTTTCAGCTCTGCCTGTTTTTGACCTTCACATAGATG
GACATTTGTAGTGTTTTCTTTCTCAACACTGGGTCTG
ATACCCACCCACGCTGTCTGCTGTCACTGCGGACGTG
GAGGGCCACCACCCAGCTATGGCCCCAGCCAGGCCAA
CACTGGATGAATCTGCCCCCAGAGCAGGGCCACCAAC
ACTGGAGGTGCAGAGAGGGTTTCTTCAGGGCCATCAT
TATCCAAGGCATTGTTTCTACTGTAAGCTTTCAAAAT
GCTTCCCCTGATTATTAAAAGAAATAATAAGATGGGG
GGAAAGTACAAGAAGGGAAGTTTCCAGCCCAGCCTGA
AGATCGTGCTGGTTGTATCTGGAGCCTGTCTTCCTGA
CAGGCCTCTATTCCCAGAGTTA

Seq ID No. 37: GGATCCTAGGGAAGGGAGGGCGGGGGCCTGGACAAAG
GGGGCCTAAAGGACATTCTCACCTATCCCACTGGACC
cctgctgtgctctgagggagggagcagagagggggtc
tgaggccttttcccagCTCCTCTGAGTCCCTCCTCCG
AGCACCTGGACGGAAGCCCCTCCTCAGGGAGTCCTCA
GACCCCTCCCCTCCAGCCAGGTTGGCCTGTGTGGAGT
CCCCAGTAAGAATAGAATGCTCAGGGCTTCGAGCTGA
GCCCTGGCTACTTGGGGGGGTGCTGGGGATTGGGGGT
GCTGGGCGGGGAGCTGGGGTGTCACTAGATGCCAGTA
GGCTGTGGGCTCGGGTCTGGGGGGTCTGCACATGTGC
AGCTGTGGGAAGGCCCTATTGGTGGTACCCTCAGACA
CATATGGCCCCTCAATTTCTGAGACCAGAGACCCCAG
TCTGGCCTTCCCAGAACAGCTGCCCCTGGTGGGGGAG
ATGTAGGGGGGCCTTCAGCCCAGGACCCCCAACGGCA
GGGCCTGAGGCCCCCATCCCCTTGTCCTGGGCCCAGA
GCCTCAGCTATCAGGCCTATCAGAGATCCTGGCTGCC
CAGCTCAGGTTCCCCAGGAGCCAGAGGGAGGCCAGGG
GTTACTAGGAAATCCGGAAAGGGTCTTTGAGGCTGGG
CCCCACCCTCTCAGCTTTCACAGGAGAAACAGAGGCC
CACAGGGGGCAAAGGACTTGCCAGACTCACAATGAGC -continued

CCAGCAGCTGGACTCAAGGCCCAGTGTTCGGCCCCAC

AACAGCACTCACGTGCCCTTGATCGTGAGGGGCCCCC

TCTCAGCCAGGCATTCAGACCTGTGACCTGCATCTAA

GATTCAGCATCAGCCATTCTGAGCTGAAGAGCCCTCA

GGGTCTGCAGTCAAGGCCACAGGGCCAGACCTCCAAC

GGCCAGACATCCCAGCCAGATTCCTTTCTGGTCAATG

GGCCCCAGTCTGGCTTGGCTCCTGCAGGCCCAGTGCC

GCCTTCTTCCCCTGGGCCTGTGGAGTCCAGCCTTTCA

GTTTCCCACCCACATCCTCAGCCACAATCCAGGCTCA

GAGGCAATGTCCGTGGGCAGCCCCTGTGTGACCCCTC

TGTGGGTGATCCTCAGTCCTACCCTTAGCAGACAGCG

CATGAGGGGCCCTCTTGAACCTGAGGGATACTCCATG

TCGGAGGGGAGAAGCTGGCCTTCCCCACCCCCACTTC

CAGGCCTTGGGGAGCAGAGAAAGACCCCAGACCTGGG

TCCCTTCTAACAGGCCAGGCCCCAGCCCAGCTCTCCA

CCAGCCCCAGGGGCCTCGGGTCCACGCCTGGGGACTG

GAGGGTGGGCCTGTCAGGCGCTGACCCAGAGGCAGGA

CAGCCAAGTTCAGGATCCCAGCCAGGTGGTCCCCGTG

CACCATGCAGGGGTGTCACCCACACAGGGGTGTTGCC

ACCCTCACCTGACTGTCCTCATGGGCCACATGGAGGT

ATCCTGGGTTCATTACTGGTCAACATACCCGTGTCCC

TGCAGTGCCCCCTCTGGcgcacgcgtgcacgcgcaca cgcacacactcatacaGAGGCTCCAGCCAACAGTGCC

CTCTAGTAGGCACTGCTGTCACTTCTCTAAAAGGTCG

CAATCATACTTGTAAAGACCCAAGATTGTTCAGAAAT

CCCAGATGGAGAAGTCTGGAAAGATCtTTTTCTCCTT

TCACGGGCTGGGGAAATGTGACCTGGCCAAGGTCACA

CAGCAAGTGGTGGAACCCTGGCCCCTGATTCCAGCTC

ATTCCAGTTCCCAAGGCCCTGCCAGAGCCCAGAGGCT

GGGCCCTCTGGGGCAGAGGAGCTGGGGTCCTCCCCCC

TACACAGAGCACACAGCCCCGCAAGAGAGAAGAGACA

CCTTGGGGAGAGGAATCTCCAGACCAGAGATCCCAGT

ATGGGTCTCCTCTATGCTGACGGGATGGGATGTCAAG

AGGGGAGGGGGCTGGGCTTTAGGGAAACACACAAAAA

TCGCTGAGAACACTGACAGGTGCGACACACCCACCCC

TAATGCTAACCTGTGGCCCATTACTCAgatct

Seq ID No. 38 GATCTTCTCCTAAGACCAAGGAAAACTGGTCATACCA

GGTCCACTTGTCCCCTGTGGCCATTGTCCCTCCTTCC

CCAGAAGAAACAAGCACTTTCCACTCCACAAGTAGCT

CCTGATCAGCTTGGAAGCCCGGTGCTGCTCTGGGCCC

-continued

TGGGGACACGGCAGGGGCATCAGAGACCAAATCCTGG

AACAAAGTTCCAGTGGGTGAGGCAGGCCGGACAAGCA

ACACGTTATACCATAATATGAGGCAAAATATAATGTG

AGTTCTTTATGAAAGGAAGGGGTTGCAGGTGCAACTG

TTGGCTTAGGTGGATGGTCACCCCTGAATGGAGGAGG

GGGTTCCCAGGGCATGTGCCTGGGGAGAAGGGCTCCT

GGCAGGAGGGACAGCAAGTGCAAGGGCCCTGTGATCA

AATGTGCCTGGCAAGTTGCAGGAACAGCTAGAAGGCC

AGCAAGGTTGGAACCAAGGAAGGGGTGAGGGGAGGGG

CAGGGCCCTCAGGGCCTTGCCCAGCAGCCTGAGCATC

TGGAGATTTGTCCAAAGTTTCAAATGTACCTGGGCAA

CCTCATGCCCATATACCATTCCTAACTTCTGCACTTA

ACATCTCTAGGACTGGGACCCAGCCAGTCAAGCGGGG

GGACCCAGAGAGCTCCGGTGTGAACACCGAGGTGCTG

GTGGGTCTGCGTGTGTGGACATAGGGCAGTCCCGGTC

CTTCCTTCACTAACACGGCCCGGGAAGCCCTGTGCCT

CCCTGGTGCGCGGGTCGGCGCTTCCGGAGGGTACAGG

CCCACCTGGAGCCCGGGCACAGTGCATGCAAGTCGGG

TTCACGGCAACCTGAGCTGGCTCTGCAGGGCAGTGGG

ACTCACAGCCAGGGGTACAGGGCAGACCGGTCCTGCC

TCTGCGCCCCTCCCTGGCCTGTGGCCCCTGGACGTGA

TCCCCAACAGTTAGCATGCCCCGCCGGTGCTGAGAAC

CTGGACGAGGTCCGCAGGCGTCACTGGGCGGTCACTG

AGCCCGCCCCAGGCCCCCTCTGCCCCTTCCTGGGGTG

ACCGTGGACTCCTGGATGACCCTGGACCCTAGACTTC

CCAGGGTGTCTCGCGGAGGTTCCTCAGCCAGGATCTC

TGCGTCTCCTCCTTCCATAGAGGGGACGGCGCCCCCT

TGTGGCCAAGGAGGGGACGGTGGGTCCCGGAGCTGGG

GCGGAGAACACAGGGAGCCCCTCCCAGACCCCGCTCT

GGGCAGAACCTGGGAAGGGATGTGGCCATCGGGGGAT

CCCTCCAGGCCATCTCCTCAGATGGGGGCTGGTCGAC

TAGCTTCTGAGTCCTCCAAGGAACCGGGTCCTTCTAG

TCATGACTCTGCCCAGATGAAGAAGGAGAGCACTTCT

CTCCATCAGGAGGATCTGAGCTTCTCTTAATTAGAAT

CAGCTCCTTGGCTTCTACCCCTTAAAAAAAGGTACAG

AAACTTTGCACCTTGATCCAGTATCAGGGGAATTTAT

CAATCAATGTGGGAGAAATTGGCATCTTTACCACACT

GAATCTTTCAATCCATGAATATCCTCTCTCTCTTCCA

TGCATAGGTTTTAATAATTCTCAATGGAGTTTAATGT

AAGTTTTCCTCATAGACAATTGCCTTTGGACATCTCT

-continued

TTAGACTCATCTCTAGTAAACTGATATTCTTAATGCA
ATTATAAAATGTATCCTGCTTAATGTTATTTTCTATT
CATTTGCTGTTATATAGAGATACAATGAGTTTCCACA
TTTGAAACTGGATCTGGTAAATTGGCTACCCTTTTTT
TATAGATTCTATTAATTTTTATACATTCTGTGGGACT
TGCTACATACTTAATCATGTCACCTGTGAAGAATGAC
AATTTGGTTGCTACCCTCCCAATTCTTATATGTCTCA
TTTCTTTCCCTCTGCTGGTACTCTGGCAGCAGCAGGG
AAGATAATGGGCCTCCTTATCTTGTCACAAAAGGATG
TTTTTAAAGATTTCGTTATAAAACATAACGCTTTCTG
GTTTTCTTTAAAGATTCTCTCACCAGCTTAAGAAAAT
TTTCTTATACTCTGTATGATAAATGGGTTTTTGACAA
TCATTTGTTGCATTTTACCTAGTGTTTTCTCTGCATC
TTTATATGCTTTTTCTCCTTTAATCCTGAAAATTGTT
TCGATTTTTCTAACATTGAACCAATCTTACATTCCTG
GAATGGATGGACCAGACTAGTCCACATGTTTATTCTG
CCCAATGGCTAGATTTTGTGTTCaatatttgttcag
aatgtttgcatctatattcttGAGTGAGACAGAGCTG
CCCTTGTTAGGTTTCACAACCGAGGTTGTGTTAGCTT
CATAAAATGAGACGTTTATTCTCTAAAAGAATTGTTT
CGCTTCTCTGGATGAATTTGTGTAAGGTTAGAATTGC
TTACCAGTGAagatctCGGGgCCAGTTCTTCTTTAGG
GGAAGATTTTCAACAATTAAGCTCAATGCCTTTAGAA
GAACTGAGAGTTTCTATTATTTCTTGAGTTAAATATA
TGTATTTAATTAGACTTTCTAGGAATAGTCTCATTTC
ATCTCAAATAATTGACATATGCTATTAAAGCAGATTC
TCATGAACCATTGTAGGTATTCCAGGTCTAGAAAAAT
GTTCCCCTTTGCATCCCTAATGTGTTTAATTTTCACC
TTCTTTCTTTTGTTCTTGAGAAATTCACCAAATCATT
TTCAATTTCAGTCATATCCCAAAGCAACCAACTCTCT
ACCTTCTTGTTTTATCATCCCTGCTGGATTTTTGTTA
TCTACTTCTTCAGTATTTGTTCTTCCCTTTCTTCTAT
TCCTCATTCCATTTTTCCCTTGTTTTCTAACTTTCTG
AGATATATGCTTAGTTCCTTCATTTGAAGCCTTTTTA
TTTTCTTTTTTTTTTTTTGGTCTTTTTGTCTTTtGTT
GTTGTTGTTGTGCTATTtCTTGGGCCGCTCCCGCGGC
ATATGGAGGTTCCCAGGCTAGGAGTCGAATCGGAGCT
GTAGCCACCGGCCTACGCCAGAGCCACAGCAATGCGG
GATCCGAGCCGCGTCTGCAACCTACACCACAGCTCAT
GGCAACGCCGGATCGTTAACCCACTGAGCAAGGGCAG
GAACCGAACCCGCAACCTCATGGTTCCTAGTCGGATT -continued CGTAACCACTGTGCCACAACAGGAACTCCGCCTTTTT
ATTTTCTATAAAAATTTCTATGTACATTTTAAGGTTA
TAGGTTTCCTTCTATGTACCCCATTGGCTGTATCCTC
AGGGTTCTGTGGAGTGATTTCATTATTGTTCAAGTTC
AATATGTCTTCTGATTTTCCAATTTGAATACCTCTCT
AAATCAGTAGGTGAATATTTCTTTTTCTTTTTCTTTT
CTTTTCTTCTTTTTTTTTTTCTTTCAGCCAGGTCCAT
GGCATGCAGAAATTCCCAGGCCAGGAATCAAACTCTC
ACCATGGCAGTGACAATGTCGGATCCTTTACCCACTA
GGCCACCAGGGAACTCTGGGAGCATATGTTTTTATTT
CCCGACATCTGAGGATGCCTAGTATGTCTTCATTATT
GATTTCTAGTTTGCCACTGATTTCTAGTATTTTGCTC
ATAGAGTGTATGCTCAATGGTTTTGGTCATTTGAAAT
GTATTTAGTCCTGCTTTATGACCCAGTATGTGGTCAG
TTTTGTCAATGTTCCTTTTCTGCTTGAAGAGAACCTA
CATGCTGTAACTCTGGGTGCATGTTCTGTATATAAGT
CTATAGGCTGAGCCGGGGGAGCCTTCTAATCTGCCGT
TATCTTCTTCGAGTTATTCTAGGTACTATTTCTTAGC
CATAAACCTTTAAATTCTGATATCAATATAATGACCC
CAGCCCGCTTAGGGTCGGCACTTCATGTTATCTTTTT
CCATCCATTTAATCCCTCCCCACTGTTTTGGCCACAC
CCGTGGGATATGGGAGTTCCTGGGCCAAGGATCaGAT
CTGAGCCGCAGCTGCCACCTATGCCACAGCAgcagca
atgatggatctttaacccactgcaccacactggggat
tgaacccaagcctcagcagcaacccaagctactgcag
agacaacaccagatccttaacctgctgtgccatagcg
ggaaTTTCCATCCATTTACTTTCAAGCCAGCTGAATA
ACCTAGCCCACCATGCCTGGACATGGGTGCTCTGCTT
CAAATGATTTTGTTCAGTCAGCATCCATCTCTGAAAT
GTGTGCCAAGCATTTATATGCATGCAAGAGTCATGTT
GGCACTTCTATCATTTCCAACAGTTCAGTAGCCTTTG
TATCATGACATTTCTTGGCCTTTTCTCTACAATATTT
GAGGCTGAGCAGACTGGCCGTGCCCCTGTCCATGCTT
CCAGAGCCTGTGTGCAGACTTCTGCTCTAGACAGAGA
CAGCTAACCATCCTGCAGTGCCCAGAAAACCCAACTC
AAAGACCCTCAAGTAAGGAAGGATTTATTGGCTCACG
TAATCTGGAATCCAGGCATGGGGTATTCAGGGCCACC
TGAACCAGAGGCCCTGGCCCTGTTCTCTAAGCTTCTT
CCTGCCCTGCCCTCGTTCTGGAAGTGACCCTGAAGGA
CAGCAATGAAGGGCAGCTCCCCCAGGGACAGATGACT -continued

GAGAGGTCCATTTCAAGTCCAACTTGGCCTAGATTGA

GAGGCAGCAAGAAATATGGACCTACAGTGAGTCACAG

GATTTACCAGTGGTTTGGCTGGGTTGTCAGTGTTACA

GGCTAAACATTTGGGTCCCTCCAAAATTAACATGTTG

CCACTCTAACCACCAAAATCatggtatttgggggtgg ggcccttggaggtaattaggtttagaaAGAATGAAGA

GGGGGCCCTTGTGATGGGACTAGTGCCTTTATAGAGA

GAGAAGAGAGAGGG

Seq ID No. 39

CACTCATCCCCAACCACCTGGATGGTGGCAAGTGGC

AGGCTGAGAGGCTGCATATGAGCTCATCAAGAGGGTC

CCCACCCCACAGAGGCTGACCCAGCTGCCACTGCCAC

CTAGTGGCTGATCGGCCAAGAGCAGGAGCCCCAGGGG

CAGGTCCATTCCCTGGGGCGGCCAGGGAACCACCTGG

TGGTAGGACAATTCCATTGCACCTCATCCATCAGGAA

AAGGTTTGCCTTCCCTGGCAGTAATGCATCTTCCCAT

AACATGGTCCCTGGCCTCTTGGAATGGCTTGGCCACC

GTCATGGCCTCACCCACAAAGCCTTGTGTCTCAGCAA

GGAACTTATTCCACAGCAAAGGACTTGCAGCCTGGAA

TGAACTGGTCTGACTACATACCCCATTGCCCAGAAGT

AGGTGGTCTATTGCAAAGTGGAGTGGCTTACCCAAGA

CTCAGTTGTGCCCAAGTTGAGAGATAGCATCCTAAAA

TATGGGCTTATGTCTCACTGGCTGAGGTTTATTCTTT

GAATCAAAGACAATTATATGGTGTGGTCCCCCCAGAG

ATAGAATACATGAGTCTGGGAATCAAGGGATAGAAGT

AAGAAGAGATTTTGTCACCATTAATCCCAATAACTCG

CCCAAAGAATATTTGCTTTCTGTCCTGGCAGCTCTGC

TGCTTTGGCAATAACTTCCTAGAATATAATGTCTCCA

CCAGGGGACTCCACAACGGTTCCATTGATTTGAAGCC

AATGGGCAGAGGAGGGGCTGCCTTACTGGTCGGACTG

GTCAGCCCTGATTACTAAGGAGAAATCAGGCAACTTC

AACAAAACTAAGGCAGGGGGGACTTTGTCTAGAACCC

AAAGCACTAAGCATCTTAGTACTTTTTAGTTCTCAGA

GCCTCCAAGAACAAAGATTTAGCCCCTCAGCACCACC

AGGTAAAGAACAGGTAAATCCAGCTGAGGACAAGAGA

AATATTGAATGGATAGAGGAAGAAAGAAATTATAGAT

-continued

ATCAACTATGGCCTCATGACTAGAGTCTCCAGATTAA

GCGGAATAAAAATACAGATGATTaGATCTGAACATCA

GGCCAAACAACGAACAACAGTTTAAGTGCGACCTAGG

CAATATTTGGGACATACTTATACTAAAATTTTTTCGC

TATTTGAGCATCCTGTATTTTATCTGGCAACTTTATT

CATCCCTAGCGAAAAAGGAACTGTGGTAACTTAGTGT

ATTTTTACTTTGCTCATTATTGTGTATATACCTACTT

GTATTTATCAATCATATTTACTCTGTTCTCAGTATTA

CTTTATATAGCAGTTGGTGGTGATGGTTAGCAACATA

TTCAGTGGAACTGTGACTGAATTTGAGGAGAAATTAA

CAGAGTTGGCTGTGGCTACAATAACCCTTCGGGACAT

GTGTCCCCTCATTTTGGGGAGATGGTTagatctCTGG

GTAAATGTTAGGGCATCTGAGCCAGAAACCAAGATTT

TGCCAGCTGGTGCAATGTCAGATTTTACCAGCAGAGG

GTGCCAGAGGAATGCGGCAAAACCCGAGTGCCAGAAA

GCACCTCCCTGTTTTCCAGCTTTTCTTCCTTTTTATT

TATTTTATTTACGGCCCAGGAGTCCGTAATAGCGCTG

AGGATGGCCCAGGCTCTTCTCAGCAGCCCTGACTGAC

TAGTTCAGCAATGCGCTCAGGCCCCATCTGGCCACCG

GGCAGCCTCTTCTGTGGTAGCTCCAGCCTCAGCCAGT

GCAAAAGGCTACCCTACACTGGCGCCACTTCTACAAT

CAGCACTGGCCACACCCTCCACGCCATCCGGCACGGA

GCCAGGTGATCTGCCGGCCAGATTGCAGTTCGTGCTG

CCTGAGTCCAGGTGATTACACTGGCTGCATCTTTTCT

TTCTGGACCAtTCattccatttttt

Bovine Lambda Light Chain

In a further embodiment, nucleic acid sequences are provided that encode bovine lambda light chain locus, which can include at least one joining region-constant region pair and/or at least one variable region, for example, as represented by Seq ID No. 31. In Seq ID No 31, bovine lambda C can be found at residues 993-1333, a J to C pair can be found at the complement of residues 33848-35628 where C is the complement of 33848-34328 and J is the complement of 35599-35628, V regions can be found at (or in the complement of) residues 10676-10728, 11092-11446, 15088-15381, 25239-25528, 29784-30228, and 51718-52357. Seq ID No. 31 can be found in Genbank ACCESSION No. AC117274. Further provided are vectors and/or targeting constructs that contain all or part of Seq ID No. 31, for example at least 100, 250, 500, 1000, 2000, 5000, 10000, 20000, 500000, 75000 or 100000 contiguous nucleotides of Seq ID No. 31, as well as cells and animals that contain a disrupted bovine lambda gene.

Seq ID No 31

1 tgggttctat gccacccagc ttggtctctg atggtcactt gaggccccca tctcatggca 61 aagagggaac tggattgcag atgagggacc gtgggcagac atcagaggga cacagaaccc 121 tcaaggctgg ggaccagagt cagagggcca ggaagggctg gggaccttgg gtctagggat -continued

```
 181 ccgggtcagg gactcggcaa aggtggaggg ctccccaagg cctccatggg gcggacctgc
 241 agatcctggg ccggccaggg acccagggaa agtgcaaggg gaagacgggg gaggagaagg
 301 tgctgaactc agaactgggg aaagagatag gaggtcagga tgcaggggac acggactcct
 361 gagtctgcag gacacactcc tcagaagcag gagtccctga agaagcagag agacaggtac
 421 cagggcagga aacctccaga cccaagaaga ctcagagagg aacctgagct cagatctgcg
 481 gatgggggga ccgaggacag gcagacaggc tccccctcga ccagcacaga ggctccaagg
 541 gacacagact tggagaccaa cggacgcctt cgggcaaagg ctcgaacaca catgtcagct
 601 caaaatatac ctggactgac tcacaggagg ccagggaggc cacatcatcc actcagggga
 661 cagactgcca gccccaggca gaccccatca accgtcagac gggcaggcaa ggagagtgag
 721 ggtcagatgt ctgtgtggga aaccaagaac cagggagtct caggacagcg ctggcagggg
 781 tccaggctca ggctttccca ggaagatggg gaggtgcctg agaaaacccc acccaccttc
 841 cctggcacag gccctctggc tcacagtggt gcctggactc ggggtcctgc tgggctctca
 901 aaggatcctg tgtcccccctg tgacacagac tcaggggctc ccatgacggg caccagacct
 961 ctgattgtgg tcttcttccc ctcgcccact ttgcaggtca gcccaagtcc acaccctcgg
1021 tcaccctgtt cccgccctcc aaggaggagc tcagcaccaa caaggccacc ctggtgtgtc
1081 tcatcagcga cttctacccg ggtagcgtga ccgtggtcta gaaggcagac ggcagcacca
1141 tcacccgcaa cgtggagacc acccgggcct ccaaacagag caacagcaag tacgcggcca
1201 gcagctacct gagcctgatg ggcagcgact ggaaatcgaa aggcagttac agctgcgagg
1261 tcacgcacga ggggagcacc gtgacgaaga cagtgaagcc tcagagtgtt cttagggccc
1321 tgggccccca ccccggaaag ttctaccctc ccaccctggt tccccctagc ccttcctcct
1381 gcacacaatc agctcttaat aaaatgtcct cattgtcatt cagaaatgaa tgctctctgc
1441 tcatttttgt tgatacattt ggtgccctga gctcagttat cttcaaagga aacaaatcct
1501 cttagccttt gggaatcagg agagagggtg gaagcttggg ggtttgggga gggatgattt
1561 cactgtcatc cagaatcccc cagagaacat tctggaacag gggatggggc cactgcagga
1621 gtggaagtct gtccaccctc cccatcagcc gccatgcttc ctcctctgtg tggaccgtgt
1681 ccagctctga tggtcacggc aacacactct ggttgccacg ggcccagggc agtatctcgg
1741 ctccctccac tgggtgctca gcaatcacat ctggaagctg ctcctgctca agcggccctc
1801 tgtccactta gatgatgacc cccctgaagt catgcgtgtt ttggctgaaa ccccaccctg
1861 gtgattccca gtcgtcacag ccaagactcc ccccgactcg acctttccaa gggcactacc
1921 ctctgcccct cccccagggc tccccctcac agtcttcagg ggaccggcaa gcccccaacc
1981 ctggtcactc atctcacagt tcccccaggt cgccctcctc ccacttgcat ggcaggaggg
2041 tcccagctga cttcgaggtc tctgaccagc ccagctctgc tctgcgaccc cttaaaactc
2101 agcccaccac ggagcccagc accatctcag gtccaagtgg ccgttttggt tgatgggttc
2161 cgtgagctca agcccagaat caggttaggg aggtcgtggc gtggtcatct ctgaccttgg
2221 gtggtttctt aggagctcag aatgggagct gatacacgga taggctgtgc taggcactcc
2281 cacgggacca cacgtgagca ccgttagaca cacacacaca cacacacaca cacacacaca
2341 cacacacgag tcactacaaa cacggccatg ttggttggac gcatctctag gaccagaggc
2401 gcttccagaa tccgccatgg cctcactctg cggagaccac agctccatcc cctccgggct
2461 gaaaaccgtc tcctcaccct cccaccgggg tgacccccaa agctgctcac gaggagcccc
2521 cacctcctcc aggagaagtt ccctgggacc cggtgtgaca cccagccgtc cctcctgccc
```

-continued

```
2581 ctcccccgcc tggagatggc cggcgcccca tttcccaggg gtgaactcac aggacgggag
2641 gggtcgctcc cctcacccgc ccggagggtc aaccagcccc tttgaccagg aggggggcgg
2701 acctggggct ccgagtgcag ctgcaggcgg gcccccgggg gtggcggggc tggcggcagg
2761 gtttatgctg gaggctgtgt cactgtgcgt gtttgctcgg tggagggacc cagctggcca
2821 tccggggtga gtctcccctt tccagctttc cggagtcagg agtgacaaat gggtagattc
2881 ttgtgttttt cttacccatc tggggctgag gtctccgtca ccctaggcct gtaaccctcc
2941 cccttttagc ctgttccctc tgggcttctt cacgtttcct tgagggacag tttcactgtc
3001 acccagcaaa gcccagagaa tatccagatg gggcaggcaa tatgggacgg caagctagtc
3061 caccctctta ccttgggctc cccgcggcct ccggataatg tctgagctgc ctccctggat
3121 gcttcacctt ctgagactgt gaggcaagaa accccctccc caaaagggag gagacccgac
3181 cccagtgcag atgaacgtgc tgtgagggga ccctgggagt aagtggggtc tggcggggac
3241 cgtgatcatt gcagactgat gccccaggca gggtgagagg tcatggccgc cgacaccagc
3301 agctgcaggg agcacaggcc gggggcaagt catgcagaca ggacaggacg tgtgaccctg
3361 aagagtcaga gtgacacgcg gggggggggc ccggagctcc cgagattagg gcttgggtcc
3421 taacgggatc caggagggtc cacgggccca ccccagccct ctccctgcac ccaatcaact
3481 tgcaataaaa cgtcctctat tgtcttacaa aaaccctgct ctctgctcat gtttttcctt
3541 gccccgcatt taatcgtcaa cctctccagg attctggaac tggggtgggg nnnnnnnnnn
3601 nnnnnnnnnn nnnnnnnnnn nnnnnnnnnn nnnnnnnnnn nnnnnnnnnn nnnnnnnnnn
3661 nnnnnnnnnn nnnnnnnnnn nnnnnnnnnn agcttatgtg gtgggcaggg gggtagtaag
3721 atcaaaagtg cttaaattaa taaagccggc atgatatacg agtttggata aaaaatagat
3781 ggaaaagtaa gaaaggacag gagggggggtg aggcggaaga aagggggaag aaggaaaaaa
3841 aaataagaga gaggaacaaa gaaagggagg ggggccggtg atgggggtgg gatagaatat
3901 aataattgga gtaaagagta gcgggtggct gttaattccg ggggggaata gagaaaaaaa
3961 aaaaaaaatg tgcgggtggg cggtaagtat ggagatttta taaatattat gtgtggaata
4021 atgagcgggg gtggacgggc aaggcgagag taaaaagggg cgagagaaaa aaattaggat
4081 ggaatatatg gggtaaattt taaatagagg gtgatatatg ttagattgag caagatataa
4141 atatagatgg tgggggaaaa gagacaaggg tgagcgccaa aacgccctcc cgtatcattt
4201 gccttccttc ctttaccacc tcgttcaaac tctttttcga gaaccctgaa gcggtcaggc
4261 ccggggctgg gggtgggata cccggggagg ggctgcgcct cctcctttgc agagggggtc
4321 gaggagtggg agctgaggca ggagactggc aggctggaga gatggctgtt gacttcctgc
4381 ctgtttgaac tcacagtcac agtgccagac ccactgaatt gggctaaata ccatattttt
4441 ctggggagag agtgtagagc gagcgactga ggcgagctca tgtcatctac agggccgcca
4501 gctgcaggga ctttgtgtgt gtcgtgctcg ttgctcagtt gtgtccgact ctttatgact
4561 tcatggactg taacctgcca ggctcctctg tccgtggaat tctccaggca agaatactgg
4621 agtgggtagc cattctcatc tccgggggat cttcctgacc caagaatcaa acctgagtct
4681 cccgcattgc aggcagcttc tttcttgtct gagccaccag ggaagcccct taagtggagg
4741 atctaaatag agtgtttagg agtataagag aaaggaagga cgtctataca agatccttcg
4801 gttcctgtaa ctacgactcg agttaacaag ccctgtgtga gtgagttgcc agtaattatt
4861 gctaacctgt ttctttcact cactgagcca ggtatcctgt gagacggcat acttacctcc
4921 tcttctgcat tcctcgggat ggagctgtgc ggtggcctct aggactacca catcgaccag
4981 gtcagaccca gggacagagg attgctgaga tgcactgaga agtttgtcag cctaggtctt
```

-continued 5041 cacccacaca gactgtgctg tcgtctacca cgtaattctt cctgtccaaa gaactggtta
5101 aacgctcctg aagcgtattc tggtctgctt caaaaagtgc ctctttcctt tataagttcc
5161 gccaatcctg gactttgtcc caggccagtc tactttattt gtgggaaagg tttttttggt
5221 ctttttttgtt ttaaactctg cagaaattgc ttacactttt ggtgtgcaat ggctcactct
5281 tacggttcta gctgtattca aaggggttgc ttttctttgt ttttaaagct ttttgaacgt
5341 ggaccatttt taaagtcttt attaaacgtc taacatcgtt tctggtttat tttctggtgg
5401 tctggccatg aggcctacgg gtcttagctc ccctaccagg gtccaaccca catcccttgc
5461 actggacggc aaggtcttaa cctttgaacc accagagagc ttctgaaagg ggctgctttt
5521 ctccaatcct ctttgctccc tgcctgctgg tagggattca gcacccctgc aatagccctg
5581 tctgttctta ggggctcagt agcctttctg cctgggtgtg gagctggggt tgtaagagag
5641 cttcatggat ttggacacga cctacgactc agaggtaaga ctccatctta gcgctgtaat
5701 gacctctttc caacaaccac ccccaccacc ctggaccact gatcaggaga gatgattctc
5761 tctcttatca tcaacgtggt cagtcccaaa cttgcacccg gcctgtcata gatgtagcag
5821 gtaagcaata aatatttgtt gaatgttaag tgaattgaaa taacataagt gaaaaagaaa
5881 acacttaaaa acatgtgttt ttataattac acagtaaaca tataatcatt gtagaaaaaa
5941 atcgaaagag tggcgggggc caagtgaaaa ccaccatccc tggtatgtcc acccgcccgg
6001 gtagccccag gtaagaggtg cggacacgga tggccctgta gacacagaga cacacgctca
6061 tatgctgggt cttgtcttgt gacctcttgg ggatgatgtt attttcacga tgccattcaa
6121 accttctacc acaccatttt tagagggtcg ttcatcgtaa atcagttcac tgctttgttt
6181 tctgattttg aaagtgtcac attcttcgag aaatgagaag gaacaggcgc gcataaggaa
6241 gaaagtaaac acgtggcctt gcttccaggg ggcactcagc gtgttggtgt gcacgctggc
6301 agtcttttct ctgtgacagt catggccttt tcccaaaggt gggctcagat aagaccgcct
6361 cccatcccct gtccctgtcc ccgtccccta cggtggaacc cacccacggc acgtctccga
6421 ggccctttgg ggctgtggac gttaggctgt gtggacatgc tgctggtggg gacccagggc
6481 tgggcagcac gttgtccctg ggtcccgggc cagtgaggag ctcccaagga gcagggctgc
6541 tgggccaaag ggcagtgcgt cccgaggcca tggacaaggg gatacatttc ctgctgaagg
6601 gctggactgc gtctccctgg ggccccttgg agtcatgggc agtggggagg cctctgctca
6661 ccccgttgcc cacccatggc tcagtctgca gccaggagcg cctggggctg ggacgccgag
6721 gccggagccc ctccctgctg tgctgacggg ctcggtgacc ctgccgcccc ctccctgggg
6781 ccctgctgac cgcgggggcc accccggcca gttctgagat tcccctgggg tccagccctc
6841 caggatccca ggacccagga tggcaaggat gttgaggagg cagctagggg gcagcatcag
6901 gcccagaccg gggctgggca ggggctgggc gcaggcgggt gggggggtct gcacnccccc
6961 acctgcnagc tgcncnnncn tttgntnncg tcctccctgn tcctggtctg tcccgcccgg
7021 ggggcccccc ctggtcttgt ttgttccccc tccccgtccc ttccccccttt tttccgtcct
7081 cctcccttct tttattcgcc ccttgtggtc gtttttttttc cgtccctctt ttgttttttt
7141 gtctttttct ttttccccct cttctccctt gctctctttt tcattcgtcg gtttttctgc
7201 tcccttccct ctccccccccg cttttttttcc ctgtctgctt tttgtgttct ccctctctac
7261 ccccccctgca gcctattttt tttatatatc catttccccc tagtatttgg cccccgctta
7321 cttctcccta atttttattt tcctttcttt aactaaaatc accgtgtggt tataagtttt
7381 aacctttttt gcaccgccca caatgcaatc ttcacgcacg ccccccccgt cagcctcctt -continued

```
7441 aaataccttt gcctactgcc cccctccttg tataataacg cgtcacgtgg tcaaccatta
7501 tcacctctcc accaccttac cacattttcc ttcnnnnnnn nnnnnnnnnn nnnnnnnnnn
7561 nnnnnnnnnn nnnnnnnnnn nnnnnnnnnn nnnnnnnnnn nnnnnnnnnn nnnnnnnnnn
7621 nnnnnnnnnn nnntgaaaaa agaaaaggct gggcaggttt taatatgggg gggttggagt
7681 ggaatgaaaa tgcattggag tggttgcaac aaatggaaag gtctcaggag cgctcctccc
7741 ccatcaggag ctggaaagaa gtggaagcaa agcaaggaat tcgtgtgatg gccagaggtc
7801 aggggcaggg agctgcaaag actgccggct gtttgtgact gnccgtctcc gggtgcattt
7861 gttagcaggg aggcattaca ctcatgtctt ggtttgctaa ctaattctta ctattgttta
7921 gttgcaaggt catgtctgac tctttgcaac ccagggactg cagcccgcca ggctcctctg
7981 tccatgggat ttcgcaggca agaatactgg aggtggtagc cattttcttc accatgggat
8041 cttcccgagc cagaaatgga acccgagtcg cctcctgtgc atggggtctg ctgcctaaca
8101 ggcagatatt tgacgtctga gccaacaggg aggacagacg gtaattatac caaccattga
8161 aagaggaatt acacactaat ctttatcaaa atctttcaaa cagtagagga gaaaggatac
8221 tctctagttt attccataaa gttggaatta cgcttatcaa taaagacatt acaagaaaag
8281 aaagtgaagc cccaaatgcc ttataaatat acaagaaaaa atcttttaag atattagcca
8341 acttaatcaa caaaaaatgt atcaaaagtc caagtaacat tcaccccagg aatgcaagtg
8401 tggttcagcc taagacaatc agtcatgagt ataccacgga aacaaattaa agagaaaaga
8461 cattaaatct cacaaatggt gcagaaaaag atttggcaat atcgaacatc ttttcatgac
8521 caaaggaaaa aaaagaaaca aaacaccaga aaattctgtg tagaaagaat atatctcaac
8581 ccaatgaagg gcatttatga aaaacccaca gcatacatca cactccatga gaaagactga
8641 aagctttccc cactgccatt gaactctgtc ctggaaattc tagtcacagc gacagaacaa
8701 gagaaagaaa taacggccgt ctaaactggt aggaagaaat caaagcgtct ctattctctg
8761 ggcgcataat acaatataga caaatttcta aagtccacaa aaattcctag agctcataat
8821 gaatccagaa atgcgtcagg gctcaagatt cagatgcaaa aatcgtctgg gttttgatgc
8881 accaacaaac aattccatta acaataatac caaggaatta atttaactta gaagagaaaa
8941 gacctgttta cagagagtta taaaacattt ggtgatgaaa ttaaataaga gtaaatcata
9001 tagaaacacc gttcgtgttt tggagaccta atgtcataaa cgtggcaaca cagagacgcc
9061 tcacggggaa ccctgagcct ccttctccaa acaggcctgc tcatcatttc acaggtaacc
9121 tgagacccta aagcttgact ctgaggcact ttgagggcat gaagagagca gtagctcctc
9181 ccatgggacc gacagtcaag gcccagggaa tgaccacctg gacagatgac ttcccggcct
9241 catcagcagt cggtgcagag tggccaccag ggggcagcag agagtcgctc aacactgcac
9301 ctggagatga ggcaacctgg gcatcaggtg cccatgcagg ggctggatac ccacacctca
9361 cacctgagga caggggccgg ctttctgtgg tgtcgccctc tcaggatgca cagactccac
9421 cctcttcgct tgcattgaca gcctctgtcc ttcctggagg acaagctcca ccttccccat
9481 ctctccccag ggggctgggg ccaacagtgt tctctcttgt ccactccagg aacacagagc
9541 caagagattt atttgtctta attagaaaaa ctatttgtat tcctgcattt ccccagtaac
9601 tgaaggcaac tttaaaaaat gtatttcctg gacttccctg gtgggccagt ggctagactc
9661 tgagctccca gtgcatgggg cctgggttca atccctgctc aggaaactac atcccacagg
9721 ctgcaaataa gatcctgcat gccacccgat gcaggcaaag aaacaagtgt tcggtatgca
9781 tgtatttcac gtgaggtgtt tctataattt acagccagta ttctgtctta cacttagtca
9841 ttcctttgag cacatgatcg gtcgatggcc cagaccacac acaggaatac tgaggcccag
```

-continued

```
 9901 cacccaccgg ctgcccagaa cctcatggcc aagggtggac acttacagga cctcagggga
 9961 cctttaagaa cgccccgtgc tcttggcagc ggagcagtgt taagcatggc tctgtccctc
10021 gggagctgtg tctgggctgc gtgcatcacc tgtggtgtgg gcctggtgag ggtcaccgtc
10081 caggggccct cgagggtcag aagaaccttc ccttaaaagt tctagaggtg gagctagaac
10141 cagacccaca tgtgaactgc acccaaaaac agtgaaggat gagacacttc aaagtcctgg
10201 gtgaaattaa gggccttccc ctgaaccagg atggagcaga ggaaggactt ggcttccagg
10261 aaaccctgac gtctccaccg tgactctggc cggggtcatg gcagggccca ggatcctttg
10321 gtgcaaagga ctcagggttc ctggaaaata cagtctccac ctctgagccc tcagtgagaa
10381 gggcttctct cccaggagtg gggcaaggac ccagattggg gtggagctgt ccccccagac
10441 cctgagacca gcaggtgcag gagcagcccc gggctgaggg gagtgtgagg gacgttcccc
10501 ccgctctcaa ccgctgtagc cctgggctga gcctctccga ccacggctgc aggcagcccc
10561 caccccaccc cccgaccctg gctcggactg atttgtatcc ccagcagcaa ggggataaga
10621 caggcctggg aggagccctg cccagcctgg gtttggcgag cagactcagg gcgcctccac
10681 catggcctgg accccctcct cctcggcctc ctggctcact gcacaggtga gccccagggt
10741 ccacccaccc cagcccagaa ctcggggaca ggcctggccc tgactctgag ctcagtggga
10801 tctgcccgtg agggcaggag gctcctgggg ctgctgcagg gtgggcagct ggaggggctg
10861 aaatcccccct ctgtgctcac tgctaggtca gccctgaggg ctgtgcctgc cagggaaagg
10921 ggggtctcct ttactcagag actccatcca ccaggcacat gagccggggg tgctgagact
10981 gacggggagg gtgtccctgg gggccagaga atctttggca cttaatctgc atcaggcagg
11041 gggcttctgt tcctaggttc ttcacgtcca gctacctctc ctttcctctc ctgcaggcgc
11101 tgtgtcctcc tacgagctga ctcagtcacc cccggcatcg atgtccccag gacagacggc
11161 caggatcacg tgttgggggc ccagcgttgg aggtganaat gttgagtggc accagcagaa
11221 gccaggccag gcctgtgcgc tggtctccta tggtgacgat aaccgaccca cgggggtccc
11281 tgaccagttc tctggcgcca actcagggaa catggccacc ctgcccatca gcggggcccg
11341 ggccaaggat gaggccgact attactgtca gctgtgggac agcagcagta acaatcctca
11401 cagtgacaca ggcagacggg aagggagatg caaacccccct gcctggcccg cgcggcccag
11461 cctcctcgga gcagctgcag gtcccgctga ggcccggtgc cctctgtgct cagggcctct
11521 gttcatcttg ctgagcagcg gcaagtgggc attggttcca agtcctgggg gcatatcagc
11581 acccttgagc cagagggtta ggggttaggg ttagggttag gctgtcctga gtcctaggac
11641 agccgtgtcc cctgtccatg ctcagcttct ctcaggactg gtgggaagat tccagaacca
11701 ggcaggaaac cgtcagtcgc ttgtggccgc tgagtcaggc agccattctg gtcagcctac
11761 cggatcgtcc agcactgaga cccggggcct ccctggaggg caggaggtgg gactgcagcc
11821 cggcccccac accgtcaccc caaaccctcg gagaaccgcg ctccccagga cgcctgcccc
11881 tttgcaacct gacatccgaa cattttcatc agaacttctg caaaatattc acaccgctcc
11941 tttatgcaca ttcctcagaa gctaaaagtt atcatggctt gctaaccact ctccttaaat
12001 attcttctct aacgtccatc ttccctgctc cttagacgcg ttttcattcc acatgtctta
12061 ctgcctttgg tctgctcgtg tattttcttt tttttttttt ttttattgga atatatttgc
12121 gttacaatgt tgaatttgaa ttggtttctg ttgtacaaca atgtgaatta gttatacatg
12181 tcctgaggag gggcggctgc gtgggtgcag gagggccgag aggagctact ccacgttcaa
12241 ggtcaggagg ggcggccgtg aggagatacc cctcgtccaa ggtaagagaa acccaagtaa
```

-continued 12301 gacggtaggt gttgcgagag ggcatcagag ggcagacaca ctgaaaccat aatcacagaa 12361 actagccaat gtgatcacac ggaccacagc ctggtctaac tcagtgaaac taagccatgc 12421 ccatggggcc aaccaagatg ggcgggtcat gtgcccatgg ggccaaccaa gatgggcggg 12481 tcatggtgaa gaggtctgat ggaatgtggt ccactggaga agggaaaggc aaaccacttc 12541 agtattcttg ccttgagagc cccatgaaca gtatgaaaag gcaaaatgat aggatactga 12601 aagaggaact ccccaggtca gtaggtgccc aatatgctac tggagatcag tggagaaata 12661 actccagaaa gaatgaaggg atggagccaa agcaaaaaca atacccagtt gtggatgtga 12721 ctggtgatag aagcaagggc caatgatgta aagagcaata ttgcatagga acctggaatg 12781 ttaagtccaa gannnnnnnn nnnnnnnnnn nnnnnnnnnn nnnnnnnnnn nnnnnnnnnn 12841 nnnnnnnnnn nnnnnnnnnn nnnnnnnnnn nnnnnnnnnn nnnnnnnnnn nnagaatttt 12901 gagcattact ttactagcgt gtgagacgag tgcaattgtg cggtagtttg agcattcttt 12961 ggcattgcct ttctttggga ttggaatgaa aactgacctg ttccaggcct gtggccactg 13021 ctgagttttc caaatttgct ggcgtattga gtgcatcact ttaacagcat catcttttag 13081 gatttgaaat agctcaactg gaattctatc actttagcta attccattca ttagctttgt 13141 ttgtagtgat gcttcctaag gcccccctgg ctttatcttc ctggatgtct ggctctggtg 13201 agtgatcaca ccgctgtgat tatctgggtc atgaaggtct ttttgtatag ttcttcttag 13261 gaacagatat tatgatctcc atccttgcat ctcgttatat ctagagaagc actgactccc 13321 ttcatggtga cgtcagatcc tcatgactaa caaatggcct tttgtaagat gagtgcctca 13381 tggtattgag ctcccccgtc accaagacct tatgactgac ctcccccact gccccaggtg 13441 cctctcgaag cgtctgagat gccgcctccc aggctgcact cctcattttg cccccaataa 13501 aacttaactt gcagctctcc agctgtgcat ctgtgtttag ttgacagtac aaatataatg 13561 gaaaatttaa attaaatata atctatgggg agaaatccaa acatcttatg agggagagag 13621 agggagagaa aggaaagaag aagaagcagg aggaggagga gagtagagaa acagggggag 13681 ggcggcaggg agacagaggg gaggacaccg aggggaaagg gaggaaggcg agtgcagtga 13741 gagagaggcc agagttcatc agagtctgga ctcgcagccc aatcccacgg gtgtgtcccg 13801 aagcagggga gagcctgagc caggcggaga cagagctgtg tctccagtcc tcgtggccgt 13861 gacctggagc tgtgtggtca gccccccctga ccccagcctg gccctgctgg tggtcggagg 13921 cagtgatcct ggacacagtg tctgagcgtc tgtctgaaat ccctgtggag gcgccactca 13981 ggacggacct cgcctggccc cacctggatc tgcaggtcca ggcccgagtg gggcttcctg 14041 cctggaactg agcagctgga ggggcgtctg caccccagca gtggagcggc cccaggggcg 14101 ctcagagctg ccggggggac acagagcttg tctgagaccc agggctcgtc tccgaggggt 14161 cccctaaggt gtcttctggc cagggtcaga gccgggatga gcacaggtct gagtcagact 14221 ttcagagctg gtggctgcat ccctggggac agagggctgg gtcctaacct gggggtcaga 14281 gggcaggacg ggagcccagc tgacccctgg ggactggcct cctctgtggt ctcccctggg 14341 cagtcacagc ttccccggac gtggactctg aggaggacag ctggggcctg gctgtcagga 14401 gggggttcga gaggccacac tcagaggagg agaccctggc ctgcttgggt tgtgactgag 14461 tttttggggt cctctaggag actctggccc tgcaggccct gcaaggtcat ctctagtgga 14521 gcaggactcc acaagattga tgaactgaat cctctaggag aggtgtggtt gtgagggggc 14581 agcattctag aaccaacagc gtgtgcaggt agctggcacc gggtctagtg gcggcgggca 14641 gggcactcag ggccgactag gggtctgggg gattcaatgg tgcccacagc actgggtctt 14701 ccatcagaat cccagacttc acaaggcagt ttcggggatt aggtcaggac gtgagggcca -continued 14761 cagagaggtg gtgatggcct agacaagtcc ttcacagaga gagctccagg ggccatgata 14821 agatggatgg gtctgtattg tcagtttccc cacatcaaca ccgtggtccc gccagcccat 14881 aatgctctgt ggatgcccct gtgcagagcc tacctggagg cccgggaggc ggggccgcct 14941 gggggctcag ctccggggta accgggccag gcctgtccct gctgtgtcca cagtcctccc 15001 ggggttggag gagagtgtga gcaggacagg agggtttgtg tctcacttcc ctggctgtct 15061 gtgtcactgg gaacattgta actgccactg gcccacgaca gacagtaata gtcggcttca 15121 tcctcggcac ggaccccact gatggtcaag atggctgttt tgccggagct ggagccagag 15181 aactggtcag ggatccctga gcgccgctta ctgtctttat aaatgaccag cttaggggcc 15241 tggcccggct tctgctggta ccactgagta tattgttcat ccagcagctc ccccgagcag 15301 gtgatcttgg ccgtctgtcc caaggccact gacactgaag tcaactgtgt cagttcatag 15361 gagaccacgg agcctggaag agaggaggga gaggggatga gaaggaagga ctccttcccc 15421 aagtgagaag ggcgcctccc ctgaggttgt gtctgggctg agctctgggt ttgaggcagg 15481 ctcagtcctg agtgctgggg gaccagggcc ggggtgcagt gctgggggc cgcacctgtg 15541 cagagagtga ggaggggcag caggagaggg gtccaggcca tggtggacgt gccccgagct 15601 ctgcctctga gcccccagca gtgctgggct ctctgagacc ctttattccc tctcagagct 15661 ttgcaggggc cagtgagggt ttgggtttat gcaaattcac cccccggggg cccctcactc 15721 agaggcgggg tcaccacacc atcagccctg tctgtcccca gcttcctcct cggcttctca 15781 cgtctgcaca tcagacttgt cctcagggac tgaggtcact gtcaccttcc ctgtgtctga 15841 ccacatgacc actgtcccaa gccccccctgc ctgtggtcct gggctcccca gtggggcggt 15901 cagcttggca gcgtcctggc cgtggactgc ggcatggtgt cctggggttc actgtgtatg 15961 tgaccctcag aggtggtcac tagttctgag gggatggcct gtccagtcct gacttcctgc 16021 caagcgctgc tccctggaca cctgtggacg cacagggctg gttcccctga agccccgctt 16081 gggcagccca gcctctgacc tgctgctcct ggccgcgctc tgctgccccc tgctggctac 16141 cccatgtgct gcctctagca gagctgtgat ttctcagcat aactgattac tgtctccagt 16201 actttcatgt ccctgtgacg ggctgagtta gcatttctca cactagagaa ccacagtcct 16261 cctgtgtaaa gtgatcacac tcctctctgt gggacttttg taaaagattc tgcagccagg 16321 agtcatgggt ggtcttagct gagaaatgct ggatcagaga gacctgataa ccgatgtgaa 16381 gaggggaacc tggaagatct tcagttcagt tcatttcagt cattcagttg tgtccgactg 16441 tttgggatcc catggactgc cacacgccag tcctccctgt ccatcaccaa cttctgaagc 16501 ttgttcaaac tcatgtccat caagttggag atgcctttca accatctcat cctctgtcat 16561 ccccttctcc tcccgccttc aatcttccct agcattaggg tcttttccgt gagtcagttc 16621 ttcgcatcag gtggccaagt tttggagttt cagtttcagc atcagtcctt tcaatgaata 16681 gtaaggactg atttccttta ggatggactg gtttgatatc cttgcagttc aagggactct 16741 caagagtctt ctccaacact gcagttaaaa gccatcaatt cttcggtgct cagctttctt 16801 tttggtacaa ctctcacatt catacatgac taccgaaaat acattagtcg tgtagaacca 16861 gtttggggct tcccacgtgg ctctagtggt aaagaatatg cctgccaact cagaagatgt 16921 aagagatgcg gttcaatctc tgggtcggga agatcccctg gagaagggca tgacaaccca 16981 ctccagtatt tttgcctgga gaatcccatg gacagagaag cctggtggac tgcagtccat 17041 ggagtctcac agagtcagac acgactgaag caacttagct acttggaaaa gagcatgcac 17101 gaagctgtct aaaaaaacagg tcaagaagtc ttgtgttttg aaggtttact gagaaagttg -continued 17161 atgcactgct ccaacacttc ctctcagttg aaaagatcag aagcgttaga tcaaatggtg 17221 gtcaatacct tggatgcgct ccaacaggtt atatctgcag atggaaatga aggcagttta 17281 tggggtaact ggaggacaag atgagatcat acacttggaa cactgtctgg catcaaaggc 17341 gtgtacagta aacattagct gttattagca aaataaattc agcttgaatc acccaaatca 17401 gatggcattc ttaaagccac tgagtggtaa aatcaggggt gtgcagccaa aacgtccatt 17461 ttgactcatt atgatttcca tgtcacaaga ctagaaagtc actttctcct cagcagaaga 17521 gaaggtagaa cattttaacc tttttttgga gtgtcaaggg aattttgttt acactgtaaa 17581 gtcagtgaaa atattgaagc ttttcatttg tggaaaatat taaatatgta aaattgaaat 17641 tttaaaattt attcctgggt agttttgttt ttccagtagt catgcatgga tgtgagagtt 17701 ggactataaa gaaagctgag cgctgaagaa ttaatgcttt tgaactgtgg cactggagaa 17761 gactcttgag agtcccttgg tctgcaagga gatcaaacca gtccatccta aaggaaatca 17821 gtcctgaata ttcactggaa ggactgatgc tgaagctgaa actccaatac tttggccacc 17881 tgatgtgaag aactgactca tatgaaaaga ctcagatgct gggaaagatt gaaggtggga 17941 ggagaagggg acgacagagg atgagatggc tgaatggcat caccgactcg atggacatga 18001 gtctgaataa gctctgggag ttgttgatgg acagggaggc cctggagtgc tgcagtccat 18061 gggattgcaa agagttggac atgactgagt gactgaactg aactgagttt ggtaacagat 18121 atgagaatta tataatttaa atctaaactc ttggtatttc tttctttggc ggttccaaaa 18181 gagctgtccc ttctgttaac tatataaatc ctttttgaga attactaaat tgataatgtt 18241 cacaagttat ccaatttctc attactctta gttgtcagta taagaaatcc catttgattt 18301 atcatgttat agtatctgca actctaatag ttcagttctg acaaattttt attttattta 18361 aaaatattgg catacagtaa aatttcaaac aatatacaat tctccctttc agtttaaaaa 18421 acaaaacaaa acaaaagtaa tattagttaa aaaaatccgg gaagaatcca agcatttaaa 18481 attgcatcac atttctatgc tagacaagct gatataaagt tataattaat aaaggattgg 18541 actattaaac tctttacata tgaggtaaca tggctctcta gcaaaacatt taaaaatatg 18601 ttgtgggtaa attattgttg tccttaaaga aataaaaaga cataagcgta agcaattggn 18661 nnnnnnnnnn nnnnnnnnnn nnnnnnnnnn nnnnnnnnnn nnnnnnnnnn nnnnnnnnnn 18721 nnnnnnnnnn nnnnnnnnnn nnnnnnnnnn nnnnnnnnna aaatggataa gggggggagga 18781 catgggtagg ggagcgcgat ggaggaagta aggtggtcga gggagttggg gggggaataa 18841 gtgggtaaaa gggaagcggg cggaaggagg gggaagcagg agagaggggt gggcgtcaga 18901 tcgggggggag gggtatgagg gagagggaat ggtagacggg gggtgggaag cataaaggaa 18961 aagatagggg ggggaaaagt tagaagaaga atgaggggat aggcggaaag ggaagagaaa 19021 tgggagaaga acagaaaaat agggggaggg ggggcgtaaa gagggggggg gagggcaggt 19081 gtggagatga cagatacggg gaatgccccg gtataaaaga gtatatggcg tggggcgaga 19141 aggctgtcat cctgtgggag gggggacgcg gagaaccctt cgggctatag ggaggattcg 19201 gggggatcgt tcgggaaggc agtcagcaca gcacccacca agggtgcagg gatggatctg 19261 gggtcccaaa gaagaggccc aatcccgcgt cttggcagca aggagccctg gagactggga 19321 agtgtccagg acactgaccc aggggttcga ggaacccaga agtgtgtctg tgaagatgtg 19381 ttttgtgggg ggacaggtcc agagctttga gcagaaaagc ggccatggcc tgtggagggc 19441 caaccacgct gatctttttt aaaaggtttt tgttttgatg tggaccattt ttaaagtctt 19501 cattgaattt gctacaatat tgtttctggt ttatgctctg gtttcttcgg ctgcaaggtt 19561 tgtgtgatcg tatctcctca accaggactg aacccacagc cctgcactg gaaggcgaag -continued 19621 tcttaaccca gatcgccagg aacgtccctc ccctcactga tctaatccaa gaccctcatt
19681 aaggaaaaac cgagattcaa agctccccca ggaggactcg gtggggagga gagagccaag
19741 cactcagcac tcagtccagc acggcgccct ccctgtccag ggcgagggct cggccgaagg
19801 accaccggag accctgtcgg attcaccagt aggattgtga ggaatttcaa cttacttttt
19861 aaatctgtct ctcaaggctg ttacaagcgg actttaccag taacttaaaa gttgaaaggg
19921 acttcccagg cggcacttgc ggtgaagaac ccgccggctg gttttaggag acataagaga
19981 tgtgggttag atccctggtt caggaggatt cccctggaga aggaaatggc aacccactcc
20041 agtattcttg cctggaaagc ctcacggaca gaggaggctg gcgggctaca gtccacgggg
20101 tcgcacacga ctgaatcgac ttagcttcaa gttgagacag gaagaggcag tgactggtgg
20161 caaaacaccg cacccatgct cccaggggac ctgcagcgct ctggttcatg agctgtgcta
20221 acaaaaatca acccaacgag aggcccagac agagggaagc tgagttcatc aaacacgggc
20281 atgatgtgga ggagataatc caggaaggga cctgccaagc ccatgacaga ccggtgtcct
20341 gtctgagggc cgtcctggca gagcagtgca gggccctccg agaccgcccg agctccagac
20401 ccggctgggg gctacagggt ggggctgagc tgcaaggact ctgctgtgag ccccacgtca
20461 gggaggatca ccttgtttgt tttctgagtt tctcttaaaa tagcctttat gggtcctggt
20521 ctttggtttt aaaataacaa ctgttctccg taaacaacgt gaaaaaaaac aaacaggagg
20581 aaaacaacgc agcccgggca tttcacccgg aagagccgcc tctaacactt tgacgggttg
20641 ccttctattt taaccctgtt ttcattgtaa actgtaaaaa ccacatcata aataaattaa
20701 aggtctctgt gaagtttaaa aagtaagcat ggcggtggcg atggctgtgc cacaccgtga
20761 acgctcgttt caaaacggta aattctaggg acccccctggt ggtccagtgg gtgagatttt
20821 gcttccattg caggagccgt gggtttgatc cctggttggg gaactaagat cccacatgct
20881 gtatggagtg gccaaaaaga attttttgta aatggtgagt tttaggtgac gtgaatttcc
20941 cattgatgca cttcacaggc tcagatgcag ccaggccctc aggaagcccg agtccaccgg
21001 tcctttactt ttccttagag ttttatggct tctgtttctg cccttaaacc caccatgttt
21061 caacctcatc tgattttgga ctttataata aagttaggct gtgtttcagg aaactttgct
21121 cagtattctg taataatcta aatggaaaga atttgaaaaa agagcagaca cttgtacatg
21181 cataactgaa tcactttggt gtacacctga aactcgagtg cagccgctca gtcgtgtccg
21241 accctgcgac cccacggact gcagcacgcg ggcttccctg cccatcacca actcccggag
21301 ttcactcaaa cacatgtccg tcgactcggt gatgccgtcc aaccgtctca tcctctgtcg
21361 tccccttctc ctcccgcctt caatcttttc cagcatcagg gtcttttcaa atgagtcagt
21421 tcttcacacc aggtggccag agtattggag tttcagcttc agcatcagcc cttccaacga
21481 ccccccatac ctgaagctaa cacagtgcta atccactgtg ctgcaacatg aaagaaaaac
21541 acattttta agtttaggct gtgtgtgtct tccttctctc aacactgcgt ctgaccccac
21601 ccacactgcc cagcactgca ttccccgtgg acaggaggcc ccctgcccca cagctgcgtg
21661 ccggccggtc actgccgagc agacctgccc gcccagagtg gggcccctgg cactggggac
21721 aaggcagggg cctctccagg gccggtcact gtccactgtt cctactggtt ttgttttcaa
21781 aagtggaggc agcgtaatat ttccctgatt ataaaaagaa gtacacaggt tctccacaaa
21841 taaaacaggg gaaaagtata aagaatggaa gttcccagca cagcctggag atcacgccgg
21901 gtgcacctgg ggtgtccttc caggctggac ctcacatttc acgcagacat cagaaggctg
21961 cgagatctac ccagaaggct gggtagatgg gggataggtc agtgacaaac agtagacaga -continued 22021 gagatataca gacagatgat ggatagacag acgctaagac accgagcgag gggacagacg 22081 gatggaagac accatccttt gtcactgacc acacacccac atgggtgtgg tgagccggct 22141 gtcatacttg tgaacctgct gctctcacaa caccagctgg gtccctccag ccccagcgtc 22201 ccacacagca gactcccggc tccatcccca ggcaggaatc ccaccaccaa ctggggtgga 22261 ccctccccgc aggaaggtcg tgctgtctaa ggccttgaga gcaagttaca gacctacttc 22321 tgggaagaca gcgcacaacc gcctaccccg cagagcccag gaggacccct gagtcctagg 22381 gaagggacca cgcggcctgg acggggagcg gccccaggac gctgccccca acctgtccca 22441 cctcactcct gctctgctct gaggcggggc gcagagaggg gccctgaggc ctcttcccag 22501 ttcttgggag cacccactgg gcctgaacca ggccagaagc cccctcctca aggtgtcccc 22561 agaccactcc cctccacctc cggttgctct gtctcctggc agcagggagc cccagtgaga 22621 agagacagct ccaggctgtg atcttggccc ctggctgctc tggcagtgtg gggggtgggg 22681 gtcgctggga ggccatgagt gctgggggtc ggggctgtga aagcacctcg aggtcagtgg 22741 gctgttggtc gggctctgcg aggtccgcac gggtagagct gtgccaggac acaggaggcc 22801 tggtcagtgg tcccaagagt cagggccaaa ggaaggggtt cgggcccctc tggttcctca 22861 gcttctgagg ccggggaccc cagtctggcc ttggtagggg ggcgattgga gggtacaacg 22921 atccaaaaga aaacacacat ctacgaggga agagtcctga ggaggagaga gctacacaga 22981 gggtctgcac actgcggaca ctgcttggag tctgagagct cgagtgcggg gcacagtgag 23041 cgaagggagg acggaacctc caaggacacc ggacgccgat ggccagagac acacgcacgt 23101 cccatgaggg ccggctgctc agacgcaggg gagctcctca ttaaggcctc tcgctgaata 23161 gtgaggagaa ctggccccgt gtgtggggaa acttagccca gaagaaacgc tgccctggcc 23221 ccaaggatca nnnnnnnnnn nnnnnnnnnn nnnnnnnnnn nnnnnnnnnn nnnnnnnnnn 23281 nnnnnnnnnn nnnnnnnnnn nnnnnnnnnn nnnnnnnnnn nnnnnnnnnn tgccctttgc 23341 ctccagggag ggaggaagcg tggatcttgg gtttgccttg ggtttaaagg atccacccac 23401 tccctttta gccactccct gtgctggcaa tttcttaaga ctggaggtcg caaagagttg 23461 gacacactga gcgagtgaac tgcactgagc ctaagaaaag tctttgaatt cctccaaaca 23521 aaacacactt gtcttgggta ctttccttgg ttttgttaca aatgtctggt ccctctgttc 23581 tcctggccag ctcctgggtg tcattttgac ctgacgaagt caaagggagc ctggacccctc 23641 aaaatctgta ggacccagca cccctccatt acacctctgt tcccccgcga acgggcacgt 23701 gtttcgccgt ctggcgtaat gtgtaagcga cggtgtgata ctcgggagtc ttactctgtt 23761 tctttttctt ctggggtgac accaccatcc gcacgactct gtctgaatgt gaacatttgg 23821 gtgatttgat gtggcccaga ctcccccaac gaatgtacct tcaggttggt tttcttcttt 23881 tatattttgc ttttgtgaat agacacagga tcccatcagt tgtatgtagt gagaaagtaa 23941 aaacccactc agccttagct ggatggagat ctagtagtaa gatagcacgt tagccggaaa 24001 tggaaatttc agccagaatc tgaaaagcgt gtcctggaag gagaagaggg actcaggccc 24061 gagcacactg ctccacgctg gagcctcagg ctctgacagc tgtacctgcc ggggtcttca 24121 tgggacaggc catgcaggcc acgatcccgt tgagaagttt cttgcctttc catcacattg 24181 gcaattgcac gctttgctct tgcttctaca tggagtttta cttttatccc agacagtttg 24241 gtttcttctc tgattttcgc caattgtaca gatcgttaca gtatttctta accacataga 24301 attcggcagg gggggtgggg ggacagggta gggtggggtg agagtgaggg gagggggctg 24361 caccgagcag catctggggt cgtagctccc tgacggggat agacctcgtg cccctgcagt 24421 gacagcacag agtcctcctc tctgaactgc cagggacgct cctgcaattg acttaatgaa -continued 24481 aggcatctaa ttaggaattt tggggtgaca ttttacattt aagtgtgtga gcagtgatta 24541 tagttcatat cattttatag tttcgtgatt ttactagctt aaagggtttt tggggtttct 24601 ttttgtttta aaagctaaaa tctgtttttt aattccatgg aatacaaaaa aaaaaagtct 24661 gtagaatatt ttaaagagtg aaggctttgt tcggaatgtg agcgctttgc tccactgaac 24721 cgaacggtaa taacatttgt agaagagacg cagagtgaaa ggtacctctt tttattgagt 24781 gacatgacag cacccatcgc gtgagttatt ggctggagtt tagagacagg ccatgttggg 24841 ctaaactcct tattgctgtt ctcagccttt gagtaataat cagaagcttt ctctgaagag 24901 agtggggtca gctgtcagac tcctaggtgt ctacctgcag cagggctggg attaaatgca 24961 gcagccagta gatacgggat ggggcaagag gtcaccttgt ccctttgttg ctgctgggag 25021 agaggcttgt cctggtgcca gtggggccaa agctgtgact ttgtgaccac aggatgtctc 25081 tgaccctgcc ttgggttccc tgagggtgga gggacagcag ggtctccccg gttccttggc 25141 cggagaagga ccccccaccc cttgctctct gacatccccc caggacttgc cccggagtag 25201 gttcttcagg atgggcatcc gggccccacc ctgactcctg gagctggccg gctagagctt 25261 gctgcagaat gaggccttgg ccattgcggc cctgaaggag ctgcccgtca agctcttccc 25321 gaggctgttt acggcggcct ttgccaggag gcacacccat gccgtgaagg cgatggtgca 25381 ggcctggccc ttcccctacc tcccgatggg ggccctgatg aaggactacc agcctcatct 25441 ggagaccttc caggctgtac ttgatggcct ggacctcctg cttgctgagg aggtccgccg 25501 taggtaaggt cgacctggca gactggtggg gcctggggtg tgagcaagat gcagccaggc 25561 caggaagatg aggggtcacc tgggaacagg cgttgggtgt acaggactgg ttgaggctca 25621 gaggggacaa aaggcacgtg ggcctccccc ccagtgtccc ttaaagtggg aaccaagggg 25681 gccccggaag ccggaggagc tgtggtgtgt ggagtgcaga gccctcgcgg ggtcctgatg 25741 cccgtcggac tctgcacagc tcagcgtgtg ccccgcggcc cggtaggcgg tggaagctgc 25801 aggtgctgga cttgcgccgg aacgcccacc agggacttct ggaccttgtg gtccggcatc 25861 aaggccagcg tgtgctcact gctggagccc gagtcagccc agcccatgca gaagaggagc 25921 agggtagagg gttccagggg tgggggctga agcctgtgcc gggccctttg gaggtgctgg 25981 tcgacctgtg cctcaaggag gacacgctgg acgagaccct ctgctacctg ctgaagaagg 26041 ccaagcagag gaggagcctg ctgcacctgc gctgccagaa gctgaggatc ttcgccatgc 26101 ccatgcagag catcaggagg atcctgaggc tggtgcagct ggactccatc caggacctgg 26161 aggtgaactg cacctggaag ctggctgggc cggatgggca acctgcgcgg ctgctgctgt 26221 cgtgcatgcg cctgttgccg cgcaccgccc ccgaccggga ggagcactgc gttggccagc 26281 tcaccgccca gttcctgagc ctgccccacc tgcaggagct ctacctggac tccatctcct 26341 tcctcaaggg cccgctgcac caggtgctca ggtgaggcgt ggcgccagct ccaaagacca 26401 gagcaggcct ctcttgtttc gtgcccgctg gggacattgc cagggtgccc ggccactcgg 26461 aagtcctcac gatgccaccg ctctgaccct gggcatcttg tcaggtcact tccctggtta 26521 gggtcagagg cgtggcctag gttaaatgct gtcaaagggg actcctttct gggagtccgc 26581 atagtggggg cttggtgtga tgcccttggg aattctttcc gagagagtga tgtcttagct 26641 gagataatga cagataacta agcgagaagg acggtccatc aggtgtgagg tttgaagtcc 26701 aaagctctgt ctctccctcc cacctgcccc ttctgtcctg agctgtttta ggctccaggt 26761 gagctgtggg aagtgggtga ttctggagat gacaagaagg gatcaggagg ggaaaattgt 26821 ggctcctaag cagtccagag aagagaaaaa gtcaaataag cattattgtt aaagtggctc -continued

```
26881 cagtctcttt aagtccaaat tataattata attttcctct aagacttctg aatacatagg
26941 aaatcctcag taacaggtta ttgctctgcc ttgaacacag tgataaaagc tgggaggatg
27001 cagcctaatc tgtctgtgtg aatgagttgt attgattccc tttttggcag ctgcaaactc
27061 caagcattag gaataaatat gttcactgag aaccccgaag aaagaaagaa agaaaaaaaa
27121 aaagaattgt aggtgttgat ggacggtttg tggcccctga atatctgggg gatgttcacc
27181 cagggatcac gtgtaactgc tgggaccccc agccccatgt ccactgcatc cagcctgctg
27241 ttgaattccg cggatcnnnn nnnnnnnnnn nnnnnnnnnn nnnnnnnnnn nnnnnnnnnn
27301 nnnnnnnnnn nnnnnnnnnn nnnnnnnnnn nnnnnnnnnn nnnnnnnnnn nnnnnncaat
27361 tcgagctcgg taccccaaag gtccgtctag tcaaggctat ggtttttcca gtggtcatgt
27421 atggatgtga gagttggact gtgaagaaag ctgagtgcca aagaattatt cttttgtact
27481 gggtgttgga gaagactctt gagagtccct tgaactgcaa ggagatccaa ccagtccgtt
27541 ctaaaggaga tcagtcctga atgttcattg gaaggactga tgctgaagct gaaactccaa
27601 tactttggcc acctgacgtg aagagttgac tcattggaaa agaccatgat gctgagagga
27661 attgggggca ggaggagaag gggacgacag aggatgagat ggctggatgg catcaccaac
27721 tcgatgngac atgagtttgg ttaaactcca ggagttggtg atggacttgg aggcctggtg
27781 tgctgggatt catggggtcg cagagtcgga catgactgag cgactgaact gaactgaact
27841 gagctgaaga gctcacctgt accagagctc ctcaggtcct cctgcaggcc tggctgtaat
27901 ggcccccagg tcaccgtcct gcctccttca tcccatcctt tcacgacagg ctgggagtgg
27961 ggtgaggtga gttgtcttgt atctagaatt tctgcatgcg accctcagag tgcaatttag
28021 ctccagagaa ctgagctcca agagttcatt ttttcctttt cttctttatg atactaccct
28081 cttctgagca gagacctcat gtcagggaga aggggactct gccttcctca gccttttgtt
28141 cctccaagac ccacacgggg agggtcgcct gcttcactga gccggaaggt tcaattgctc
28201 atgtcctcca gaaacacccc cccccccaga gacccccaga aataagtgga acagcacctt
28261 gtttcccaga caagtgggac acacgttatg aaccacctca gtgattaaaa tagtaacctc
28321 tgtgtatgtg tatttactgg agaaggaaac ggcaacctac tccactattc ctgcctagaa
28381 aattccatgg gagagaagcc aggcaggcta cagtccacgg ggtcacagag actgaacata
28441 cacaagcaca tggaagtgta ttttgcagta tttttaaatt tgttcagttc aacatggagt
28501 acaagaattc aaatcgtgaa gtcaattgac caagaaacca gaagaaatca ctgtgttgtg
28561 atctctgtgg aggtaacatg ggtacctgtg ctctgaccct cacagcctct ggctctctct
28621 ctacatgtac atacacatat atttccatgt atgtatgtat tcggaagatt tcacatacgt
28681 ctcaccagtc cacagccccc gcgttccctg atgcccagaa catctgtgat agctgtgagt
28741 attgtcacca gataagatct tccaggttcc tgcactcaca ttggttatca ggtctctctg
28801 atccagcatt tctcagctaa gattccttgt gactcctggc tgcagaatct tctgcaaaag
28861 tcccacagag aggagtgtga tcactgtaca caggagggcc gtggttctct agtgtgagaa
28921 aagctaactc agcccgtcac agggacgtga atgtacctga gacagtaatc agttatgctg
28981 agaaatcaca gctctgctag aggcagcaca tggggtagcc agcagggggc agcagagcac
29041 ggccaggagc cgcaggtcag aggctgggct gcccaagcgg ggcttcaggg gaaccagccc
29101 tgcgggtcca caggtgtcca gggagcagcg cttggcagga agtcaggacc ggacaggcca
29161 tcccctcagg actagtgacc acctctgagg gtcacatcca cagtgaaccc cagagcacca
29221 tgcctcagtc cacggccagg acgctgccag gctgaccgcc ccactgggga gtccagggga
29281 gaccacaggc cgggggcctt gggacagtga tcatgtggtc agacacagag aaggtgacag
```

-continued 29341 tgacctcagt ccctgaggac aagtctgatg tgcagacgtg agaagccgag gaggaagctg
29401 gggacagaca gggctgatgg tgtggtgacc ccgcctctca gtgaggggcc cccgggggtg
29461 aatttgcata aacccaagcc ctcactgccc ccacaaagct ctgagaggga ataaaggggc
29521 tcggagagcc cagcactgct gcgggctcag aggcagagct cggggcgcgt ccaccatggc
29581 ctgggcccct ctcgtactgc ccctcctcac tctctgcgca ggtgcggccc cccagcctcg
29641 gtccccaagt gaccaggcct caggctggcc tgtcagctca gcacaggggc tgctgcaggg
29701 aatcggggcc gctgggagga gacgctcttc ccacactccc cttcctctcc tctcttctag
29761 gtcacctggc ttcttctcag ctgactcagc cgcctgcggt gtccgtgtcc ttgggacaga
29821 cggccagcat cacctgccag ggagacgact tagaaagcta ttatgctcac tggtaccagc
29881 agaagccaag ccaggccccc tgtgctggtc atttatgagt ctagtgagag accctcaggg
29941 atccctgacc ggttctctgg ctccagctca gggaacacgg ccaccctgac catcagcggg
30001 gcccagactg aggacgaggc cgactattac tgtcagtcat atgacagcag cggtgatcct
30061 cacagtgaca cagacagacg gggaagtgag acacaaacct tccagtcctg ctcacgctct
30121 cctccagccc cgggaggact gtgggcacag cagggacagg cctggcccgg ttcccccgga
30181 gctgagcccc caggcggccc cgcctcccgg ccctccaggc aggctctgca caggggcgtt
30241 agcagtggac gatgggctgg caggccctgc tgtgtcgggg tctgggctgt ggagtgacct
30301 ggagaacgga ggcctggatg aggactaaca gagggacaga gactcagtgc taatggcccc
30361 tgggtgtcca tgtgatgctg gctggaccct cagcagccaa aatctcctgg attgacccca
30421 gaacttccca gatccagatc cacgtggctt tagaaaggct taggaggtga acaagtgggg
30481 tgagggctac catggtgacc tggaccagaa ctcctgagac ccatggcacc ccactccagt
30541 actcttccct ggaaaatccc atggacggag gagcctggaa ggcttcagcc catggggtcg
30601 ctaagagtca gacacgactg agcgacgtca ctttcccttt tcactttcat gcattggaga
30661 aggaaatggc aacccagtcc agtgttcctg cctggaaaat cccagggaca ggggagcctg
30721 gtgggctgcc atccatgggg ccacacagag tcagacacga ctgaagcaac ttagcagcag
30781 cagcagcagc ccaataaaac tcagcttaag taatggcatc taaatggacc ctattgccaa
30841 ataaggtcca ctcgcgtgca ctctgtttag gacttcagtt cctgattgtg gagggttccc
30901 acaagacgtg tgtgtatatt ggtgttgccg gaaaacagtg tcaatgtgag catcccagac
30961 tcatcaccct cctactccca ctattccatt gtctctgcag gtattaagca taaaggttaa
31021 gggtcttatt agatggaaga ggagtgaata ctcgtctgtg cttaacacat accaagtacc
31081 atcaaggtcc ttcctattta ttaacgtgtg ttttaatcag aaatatgcta tgtagaagca
31141 tccggacgat agcccatgtt acagacgggg aagctgaggc atgaagttct cagcaccttg
31201 tttcacgtca gacctgaaac ggggcagagc cggcagcaaa caaggttcct cttcccaagc
31261 gcccgctctt cacccgcttc ctatggcttc tcactgtgct tcctaaacta agctctcccc
31321 aaccctgtgg agacaggatt agagacttta ggagaaaaga ccaggaacat cccacacccg
31381 acccgagtga gccactaaga caaggctttg taaggacaga accagcaggt gtcctcagcg
31441 agccagggag agacctcgca ccaaaaacaa tattgtagca tcctgaccct ggacttctga
31501 cctccagaaa tgtgaaaaag aaacgtgtgg ggtttaatca actcaccggt gttatttggt
31561 tatgactgcc tgagttaaga aggagttggg aacacttgag tgtaggtgtt tatggaacat
31621 aagtcttgtt tctctgaaat aaattcccaa gggtataatt cctaggttgt agggtaactg
31681 ccacaaatct aggcagctta ttaaaaaaca aagatatcac tttgccagca aaggttcata -continued 31741 tagtcaaatt atggttttta tagtagtcat gtatggatgt aaaagttgga tcataaagaa 31801 ggctgagcac cagagaattg atcccttcaa atcgtggtgc tggagaagac tcttgagagt 31861 cccttggaca gcaaggagat ccaaccagtc aatcctaaag gaaatgaact gtgaatattc 31921 actggaagga ctgatgctga agctgaagat ccaatacttt ggccacctga tgcgaagagt 31981 tgactcattg gaaaagaccc tgatgctgga aagcttgagg gcaggaggag aagagggcgg 32041 cagaggatga gacggttgga tggcatcact gactcaatgg acatgagttt gagccaactc 32101 tgggagacag tgaaggatag ggaaggctgg cgtggtacag tgcatgcggt cacaaagagt 32161 ctgacacatc ttagtgactc aacaacgaca gcaacacagg catcacacgc ttagtgtgat 32221 aagcggcaga actgttttcc aggggtccgn nnnnnnnnnn nnnnnnnnnn nnnnnnnnnn 32281 nnnnnnnnnn nnnnnnnnnn nnnnnnnnnn nnnnnnnnnn nnnnnnnnnn nnnnnnnnnn 32341 nnnnnnnnng tacgattcga gctcggaccc tgacattgtg agtcacgtca tgagcagctg 32401 ttttccggtc ttcagggatt gtggacgatt tctgtttggg tttgctcatg ataatttagt 32461 tacagcttag gttctttctt tccaggccac gagcgacatg ttttcaggtg agatgacgtg 32521 gtgggggatg ggcggccaag cccccactgg ggggggaggg attctgttgt gggcaggagt 32581 tggcagcatc cctgaactga tgacctgcga tccaggtgac aagaaccggg ggatattatt 32641 cctctgcctt ctcatgtcat gtcctcggtt cttcatgatg aaaacatatg acaatacagg 32701 ggagttagat ttgggcgggc acaactctgg gtgggggacc cggtggcatt gtgcccagca 32761 gggccatcaa gatgagggcg acctgggtgg tccccttctc ccctggggtc ttagttttcc 32821 cctcatggaa atgggatcag gcagcagcca tggaacaccg cgaccgtggc ttctctcacc 32881 tcctcgtctg tgattttggg tcgggatacc aggcatgaag acctggggcg gggggacatc 32941 actcctctgc agcagggagg ccgcagagtc ctccgtccat gaggacttcg tccctgggct 33001 gaccctgcgg actgctggag gctgaagctg gaggcacagg cgggctgcga ggccagggtc 33061 ctgaggacga cagagccagt ggggctgcag ctctgagcag atggcccctc gccccgggcc 33121 ctgagcttgt gtgtccagct gcaggttcgc tcaggtgagc cactacgtta tgggggaggc 33181 gccctgggca gggatcgggg gtgctgactc ctccgagatt ccgaccttct gggagcactc 33241 tggccacact ctaagcctgg caagagctgg gttcatcagt ctaactctcc tcctgaagtc 33301 caatggactc tctccatgcg gcagtcactg gatggcctct ttatccccga tggtgtcctt 33361 ttccgctgac ctggctctcc tgaccacctc ccagcccccc accatacagg aagatggcac 33421 ctggtccctg cagagctaag tccacccctg gcctggcttc agatgcctac agtcctcctg 33481 cgggaggccc cgctccccac taggccccaa gcctgccgtg tgagtctcag tctcacctgg 33541 aaccctcctc atttctcccc agtcctcagc tcccaacccc agaggtatcc cctgcccctt 33601 tcaaggccct tgtcccttcc tggggggatg gggtgtatgg gagggcaagc ctgatccccc 33661 gagcctgtgc cgctgacaat gtccgtctct ggatcatcgc tcccctggct ctcagagctc 33721 cctggtccct ggggatgggt tgcggtgatg acaagtggat ggactctcag gtcacacctg 33781 tcccttccct aaggaactga cccttaaccc cgacactcgg ccagacccag aaagcacttc 33841 agacatgtcg gctgataaat gagaaggtct ttattcagga gaaacaggaa cagggaggga 33901 ggagaggccc ctggtgtgag gcgacctggg taggggctca ggggtccatg gagaggtggg 33961 ggaggggtg tgggccagag ggcccccgag ggtgggggtc cagggcccta agaacacgct 34021 gaggtcttca ctgtcttcgt cacggtgctc ccctcgtgcg tgacctcgca gctgtaactg 34081 cctttcgatt tccagtcgct gcccgtcagg ctcagtagct gctggccgcg tatttgctgt 34141 tgctctgttt ggaggcccgg gtggtctcca cgttgcgggt gatggtgctg ccgtctgcct -continued 34201 tccaggccac ggtcacgcta cccgggtaga agtcgctgat gagacacacc agggtggcct 34261 tgttggcgct gagctcctcg gtgggggcg ggaacagggt gaccgagggt gcggacttgg 34321 gctgacccgt gtggacagag gagagggtgt aagacgccgg ggaggttctg accttgtccc 34381 cacggtagcc ctgtttgcct tctctgtgcc ctccgaccct tgccctcagc ccctgggcgg 34441 cagacagccc ctcagaagcc attgcaatcc actctccaag tgaccagcca aacgtggcct 34501 cagagtcccc ggctgcgacc agggctgctc tcctccgtcc tcctggcccc gggagtctgt 34561 gtctgctctt ggcactgacc ccttgagccc tcagcccctg ccagacccct ccgtgacctt 34621 ccgctcatgc agcccaggtg cctcctccgt gaacccgggt ccccccgccc acctgccagg 34681 acggtcctga tgggagatgt ggggacaagc gtgctagggt catgtgcgga gccgggcccg 34741 ggcctccctc tcctcgccca gcccagcctc agctctcctg gccaaagccc ggggctcctc 34801 tgaggtcctg cctgtctacc gtccgccctg cctgagtgca gggcccctcg cctcacctgc 34861 cttcagggga cggtgccccc acacagcacc tccaaagacc ccgattctgt gggagtcaga 34921 gccctgttca tatctcctaa gtccaatgct cgcttcgagg ccagcggagg ccgaccctcg 34981 gacaggtgtg acccctgggt cccaggggat caggtctccc agactgacga gtttctgccc 35041 catgggaccc gctcctttct gaccgctgtc ctgagatcct ctggtcagct tgccccgtct 35101 cagctgtgtc cacccggccc ctcagcccag agcgggcgag acccctctct ctctgccctc 35161 cagggccttc cctcaggctg ccctctgtgt tcctggggcc tggtcatagc ccccgccgag 35221 cccccaagct cctgtctggc ctcccggctg gggcatggag ctcacagcac agagcccggg 35281 gcttggagat gcccctagtc agcaccagcc tctggcccgc accccagcgt ctgccctgca 35341 agaggggaac aagtccctgc attcctggac caaacaccag ccccggcgcc ccgactggcc 35401 ccattggacg gtcggccact ggatgctcct gctggttacc ccaagaccaa cccgcctccc 35461 ctcccggccc cacggagaaa ggtggggatc ggcccttaag gccgggggga cagagaggaa 35521 gctgccccca gagcaagaga agtgactttc ccgagagagc agagggtgag agaggctggg 35581 gtagggtgag agccacttac ccaggacggt gacccaggtc ccgccgccta agacaaaata 35641 cagagactaa gtctcggacc aaaacccgcc gggacagcgc ctggggcctg tcccccgggg 35701 gggctgggcc gagcgggaac ctgctgggcg tgacgggcgc agggctgcag ccggtggggc 35761 tgtgtcctcc gctgaggggt gttgtggagc cagccttcca gaggccaggg gaccttgtgt 35821 cctggaggtg ccctgtgccc agccccctgg ccgaggcagc agccacacac gcccttgggg 35881 tcacccagtg cccccctcact cggaggctgt cctggccacc actgacgcct tagcgctgag 35941 ggagacgtgg agcgccgcgt ctgtgcgggg cggcagagga gtaccggcct ggcttggacc 36001 tgcccagccg ctcctggcct cactgtaagg cctctgggtg ttccttcccc acagtcctca 36061 cagtccagcc aggcagcttc cttcctgggg ctgtggacac cgggctattc ctcaggcccc 36121 aagtggggaa ccctgccctt tttctccacc cacggagatg cagttcagtt tgttctcttc 36181 aatgaacatt ctctgctgtc agatcactgt ctttctgtac atctgtttgt ccatccatcg 36241 atccaacatc catccatcca tccatcaccc agccatccat ctgtcatcca acatccatcc 36301 ttccatccat tgtccatcca tctgtccatc ttgcatctgt ctgtccaaca gtggccatca 36361 agcacccgtc tgccaagccc tgtgtcacac gctgggactt ggtgggggga gccctcgccc 36421 tcccaccctc ccatctctcc tgaaacttct ggggtcaagt ctaacaaggt cccatcccgt 36481 ctagtctgag gtccccccgc agcctcctct tccactctct ctgcttctga cccacactgt 36541 gcactcggac gaccacccag ggcccttgca tccctgtttc cttcctgacc tcttttttttt -continued 36601 ggctctggat ttatacacat tctgcctcct ggaggcgtct cagcttgagt gtcccacaga
36661 cgcctcagac tcagcatctt ccatcgaaac tgctcccagg tccttgcaga cctggtcccc
36721 cacattgttc tcaattcggt agatttctcc acaagccaga ggcctggact catcccataa
36781 tgcctgcccc tcattgagtc agcctctgtg tcctaccata accaaacatc cccttaaaaa
36841 tctcagaaga acaaaaaaag cacccagatg gcactgtcag agtttatgat gacaagaatc
36901 ctcagttcag ttcagtcact cagtcgtgtc cgactctttg cgaccccatg aatcgcagca
36961 cgccaggcct ccctgtccat caccaactcc cggagttcac tcagactcac gtccattgag
37021 tcagtgatgc catccagcca tctcatcctc tctcgtcccc ttctcctcct gcccccaatc
37081 cctcccagca tcagagtttt ttccaatgag tcaactcttc gcgtgaggtg accaaagtac
37141 tggagtttca gcttcagcat cattccttcc aaagaaatcc cagggctgat ctccttcaga
37201 atggactggt tggatctcct tacagtccaa gggactctca agagtcttct ccaacaccac
37261 agttcaaaag cctcaattct ttggcgctca gccttcttca cagtccaact ctcacatcca
37321 tacatgacca caggaaaaac cataaccttg actagatgga cctttgttgg caaagtaatg
37381 tctctgcttt ttaatatgct atctaggttg ctcataactt tccttccaag aagtaagtgt
37441 cttttaattt catggctgca atcaacatct gcagtgattt tggagcccca aaaaataaag
37501 tctgccactg tttccactgt ttccccatct atttcccatg aagtgatggg accagatgcc
37561 atgatctttg ttttctgaat gttgagcttt aagccaactt ttcactctcc actttcactt
37621 tcatcaagag gctttttagt tcctcttcac tttctgccat aagggtggtg tcatctgcat
37681 atctgaggtt attgatattt ctcctggcaa tcttgattcc agtttgtgtt tcttccagtc
37741 cagtgtttct catgatgtac tctgcatata agttaaataa gcagggtgat aatatacagc
37801 cttgacgtac tccttttcct atttggaacc agtctgttgt tccatgtcca gttctaactg
37861 ttgcttcctg acctgcatac agatttctca agaggcaggt caggtggtct ggtattccca
37921 tctctttcag aattttccac agttgattgt gatccacaca gtcaaaggct ttggcatagt
37981 caataaagca gaaatagatg tttttctgaa actctcttgc tttttccatg atccagcaga
38041 tgttggcaat ttgatctctg gttcctctgc cttttctaaa accagcttga acatcaggaa
38101 gttcacggtt catgtattgc tgaagcctgg cttggagaat tttgagcatt cctttgctag
38161 cgtgtgagat gagtgcaatt gtgcggcagt ttgagcattc tttggcattg cctttctttg
38221 ggattggaat gaaaactgac ctgttccagg cctgtggcca ctgttgagtt ttcccaattt
38281 gctggcatat tgagtgcagc actttcacag catcatcttt caggatttga aatcgctcca
38341 ctggaattcc atcacctcca ctagctttgt ttgtagtgat gctctctaag gcccacttga
38401 cttcacattc caggatgtct ggctctagat gagtgatcac accatcgtga ttatctgggt
38461 cgtgaagatc ttttttgtac agttcttctg tgtattcttg ccacctcttc ttaatatctt
38521 ctgcttctgt taggcccata ccgtttctgt cctcgcctat cgagccctcg cctccctacg
38581 tagagactct aagcaggaag gtgacccgtg ctgcactggg tccagcatgc ttttaattca
38641 gcagtggaac ttctgggtca tgattgtgtt taagggatgc gcatacgatt tttgaagcaa
38701 aatttaacag gacagcagtg taaagtcagt acttatttct gattaaagaa agcaaatatc
38761 cagcctgtta ctaagttaat taactaaaga aacatcttca acttaataaa cagtatctcc
38821 tgaaacttac agcatgcttc acatttaaag gcaaaaccat tttagaggcc agggttccca
38881 cgcttacgtt tattatttaa tatatgctac agattcaagc ccatgacaca aaatgggggg
38941 aagagtgtga gtgttaggaa aaatgagata aaattggttt ttgcaggtga tgggctagtt
39001 tactttaaaa aaaaaaacaa aacaagctca agatgaactg aaggactatt agaactggta -continued 39061 caagagttaa cctgtgatcg aatacaagca ggctgggcaa aactcagcag gttttcttct
39121 atacaggcag taatgattga gaatacgaaa cggcggaagc gcttacaacc tcgataacag
39181 ttctattaaa agccctagga atgaacttaa cacggnnnnn nnnnnnnnnn nnnnnnnnnn
39241 nnnnnnnnnn nnnnnnnnnn nnnnnnnnnn nnnnnnnnnn nnnnnnnnnn nnnnnnnnnn
39301 nnnnnnnnnn nnnnngctcc ccccaccctc ccctcctccc cccccaccac cagtgcccca
39361 ggtctcgtgc ccagagagct gaagatgcca gcaggcccgc tgcctgcctc gctcgcgtgg
39421 cccgggctcg ctgccggtct gcctgcccag cacacagatg cagccccagc tctcgctgcc
39481 acccgcctcc cccaggcagg actctcccac aacaccaagg gcgtctctgg gttcaggatg
39541 gccctcgttg aggtgtaaag tgcttcccgg ggctgagacg aatgggccgg agatccaaac
39601 gaggccaagg ccgccacggc gcctggcgca gggcacccat ggtgcagagc ggcccagctc
39661 cctccctccc tccctccctc cctgcttctt tatgctcccg gctatgtcta tttttactct
39721 gcaatttaga aatgataccg aaggacaaac accgttcccc ctgtgtgtct gctctaaacc
39781 ctttatctac ttatctatta gcgtgtccaa gttttgctgc taagtgaatg aaggaacact
39841 acccacaagc agcaacgtcc ccacgaccct cgcctgttca actgggaatg taaatgtgct
39901 ttcaaaggac ctaagtttct atgttcaaaa ccgttgtgtg tttcttttgg gagtgaacct
39961 aggccactcg ttgttctgcc tttcaaagca ttcttaacaa ctctccagaa cccagggctt
40021 ggcttacgtt tccagaaatt ccaaagacag acacttggaa acctgatgaa gaaggcctgt
40081 gagcacagca ggggccgggg tacctgaggt aggtgggggg ctcggtgctg atggacacgg
40141 ccttgtactt ctcatcgttg ccgtccagga tctcctccac ctcggaggct ttcagcaggg
40201 tcacgctggt ggccagggtc gtgtatccat gatctgcaac cagagacggg gctgcggtca
40261 gcccgcgggc gggcagcagg caggagcagc caggagacgc agcacaccga ggtcctcaca
40321 tgcaggaggt gggggaagcg gctgtggacc tcacgactgc ccgatgtggg cctcttccaa
40381 agggccggcc tggaccctgg ctttctccag aggccctgct gggccgtccg cacaggctcc
40441 agccacaggg cctcttggga caggagggct ccagagtgag ccggccggcg ggaagaggtc
40501 tgacaccgct gcagtccaca acacgaagcg aggtggagat gggatgaggg atgagaaaca
40561 cttttctttt aaaacaagag cccagagagt tggaaagagc tgctgcacac gcaacatgaa
40621 ctcctggccc cggtgccagc ggcgctggga gcccgagttc tcggcaatcc gaccacagct
40681 tgcctaggga gccgggtgga gacggagggt taggggaagg cggctcccca gggagcgcga
40741 ggcccggggt cgccaaggct cgccaggggc aagcgcagct aggggcgcag ggttagtgac
40801 cggcactgca cccggcgcag gagggccagg gaggggctga aaggtcacag cagtgtgtgg
40861 acaagaggct ccggctcctg cgttaaaaga acgcggtgga cagaccacga cagcgccacg
40921 gacacactca taccggacgg actgcggagt gcacgcgcgc gcacacacac acacacacca
40981 cacacacaca cacacggccc gggacacact catacccggac ggactgcgga gtgcacgcgc
41041 acacacacac ccaccacaca cacacccacc acacacacac ccaccacaca cacacacaca
41101 cacacacacc cccacacaca cccacacaca cccacacaca cccacacaca cacacccaca
41161 cacacacaca cacacacaca cacacacacg gcccggtggc cccaggcgca cacagcacgg
41221 agcaaacatg cacagagcac agagcgagcg ctagcggacc ggctgccaga ccaggcgcca
41281 cgcgatggat tgggggcggg gacggggagg ggcgggagca aacggnnnnn nnnnnnnnnn
41341 nnnnnnnnnn nnnnnnnnnn nnnnnnnnnn nnnnnnnnnn nnnnnnnnnn nnnnnnnnnn
41401 nnnnnnnnnn nnnnnnnnnn nnnnngtatt aaagaagccg ggagcgagaa tatgacggca -continued

```
41461 agaggatgta ggtgggggcg gggcaagagt aaagagagcg gacggtagag gggatgcgat
41521 tgtgatgcgg aagcgagacg aggagtgatg ccgtattaga ttgatagcaa gaggaacagt
41581 aggagggggg ggggagagga gggggaggtg gggggtggtg ggtgggaagg gaactttaaa
41641 aaaaagaggg gagagttgga ggggggaata aacgggcggt aaaaaagaac aatttgaaat
41701 taccagggtg gggcggccag gggggtgatt cattcttgga gggggcaaca tatgggggt
41761 ggctgtcgcg gattaggaga aaataaatat caggggtgat taagtgtttg gcgttgggga
41821 ataatgaagt aagaatcaaa tatgaatcgc gttggcatcg ttagccatcg ggggaaacat
41881 ttcccatgca aggaacaagg atgtgagaat gcgtccgtct gaaccaccgt cccggggtcc
41941 cagtaggact cgccgagctg atagttgccg gagcaacagt taagggagca gaagctgcta
42001 caaaaccacc acctgccaaa gtagggtctc caattacgga gtgcgcctcc tgggtgtcgg
42061 tccaaacctt tggaaaggac ctggaaataa gtgctaccca ccagatatta atataaaccc
42121 acctggccag gagaggcagg cgctgctggc acaggaagtg tccccagact cagtcatcaa
42181 ggtaaataat attttgggac ctccctggaa atccagtggt taggactctg cggttcaatc
42241 cctggtcggg gaactaagat cccacaagtc acaagacatg gccaaattta aaaaagaaaa
42301 aaagagagag aaatatttag tgcaataggt tttagaattg aaattaagct cctgcccacc
42361 cccacccccc aatctggatg aataaagcat tgaaatagta agtgaagtca ggctctgaca
42421 tgcactgatg tgactcacct taagcaaccc ccaccctagg actggtcggg gttccaggag
42481 tttcaggggt gccaggaaga tggagtccag cccctgccct ctccccccac cacgtcctcc
42541 actggagccg cctaccccac ctcccacccc tccgcaccct gctacccccc accccctgccc
42601 ccaggtctcc cctgtcctgt gtctgagctc cacactttct gggcagtgtc tccctctaca
42661 gctggtttct gctgcccgct accgggcccg tcccctctgt tcagttcagt tcagtcgctc
42721 agtcatgtct gactctttgt gaccccatgg actgcagcac accaggcctc cctggccatc
42781 accaaccccc agaacttact caaactcatg tccatcgagc cagtgatgcc atccaaccat
42841 ctcatcctct gtcgacccct tctcctggcc tcaatctttc ccagcatcag ggtcttttcc
42901 aatgagtcag ttctttgcat caggtagcca aagtattgga gtttcagctt cagcatcatt
42961 tcttccaatg aatattcagg actcatttcc tttgggatga actggttgga tctccttgca
43021 gtccaaggga ctctcaagag tcttctccaa caccacagtt caaaagcatc aattcttcag
43081 tgctcagctc tctttatagt ccaactctca catccatacg tgaccactgg aaaaaccata
43141 gcctcgacta gatggaactt tgtgggcaaa gtaatgtctc tgcttttgaa tatgctgtct
43201 aggttggtca taacttttct tccaaggagc aagcgtcttt taatttcatg gctgcagtca
43261 ccatctgcag tgatttttgg agcccaagaa aataaagtct gtcactgttt ccactgtttc
43321 cccgtctatt taacggaggg aaatttccca gagcccccag gttccaggct gggccccacc
43381 ccactcccat gtcccagaga gcctggtcct cccaggctcc cggctggcgc tggtaagtcc
43441 caggatatag tctttacatc aagttgctgt gtgtcttagg aaagaaactc tccctctctg
43501 tgcctctgtt ccctcatccg cagaagtgac tgccaggtcg gggagtctgt gacgtctcca
43561 gaagccggag gattttctcc ccatttgctg aaagagagct cggggtgggg gaagcttctg
43621 cacccctagg atcaccagag gagccagggt cttcagggtt cccggggacc cctcagtggg
43681 ggctcaggaa ccacagagcc agaccctgat tccaaaaacc tggtcacacc tccagatgac
43741 cctttgtccc ttggctccgc ctcaaatgct ccaagcccca acagtgaagc gcttaagaga
43801 aggatccacc aggcttgagt ttggggagga gggaagtggg gagctggggg agggcctggg
43861 cctgggagac aggaatccac catggcttca ggcagggtct ctggggcctg cggggtggag
```

-continued 43921 agcgggcagg agcagacaga ggtgactgga cacgacacac ccctccactc caagggaggt 43981 gggcaggggc ggggcacaga ggaacaagag accctgagaa ggggtccacc gagcagactg 44041 ctggacccag acatctctga gccagctgga atccagctct aagccatgct cagcccaggc 44101 agggtatagg gcaggactga gtggagtggc cagagctgca gctgcatggg ctgggaaggc 44161 cctgcccgtc ccctgagggt cccccagggt ctagccagac tccaatttcc gaccgcagca 44221 cacacaggag gaagtggtcg gggtggagtt ggcccagagg tctgggcagg tgcagggtgg 44281 gggaaggggg gcagctggag tcacccgctg aattcaggga cagtcccttt ttctccctga 44341 aacctggggc tgtcccgggg gccaccgcag cctccaggca gcggggggac ccagccccca 44401 atatgtgaga agagcaggtc ccaggctgga gagagcgaag caccatggtg gggagaagtt 44461 agactggatc ggggccccta ggggctcccc cggacctgca cggcagccgt cagggcaccc 44521 gcaccccatt gctgttcagt gctggccagt gtccaaggcc agggatgtgt gtgtgtgtgt 44581 gtgcgtgcgt gcgtgcgtgt gtgtgtgcgt gtgtgcgcgt gcgtgcgtgt gtgtgtgtgt 44641 gcgtgcgtgt gcgtgcgtag acgtgtgcgt gcgtgcgtgc gtgcgtgcgt gtgtgtgcgc 44701 acgcgcgcag cccagcctca gcactggacc aggcagcctg ggattcctcc aaaactgcct 44761 tgtgagtttg gtcaaaccgt gaggctctga tcaccgccat ccattcgccc cctcctgccc 44821 ccctcatcac cgtggttgtt gtcattatcg agagctgtgg agggtctggg aggtcatccc 44881 acctgccagc taaaccgtga ggctgccgca atcgcactga tgcgggcaga cccgagacgc 44941 tgtgccggag acgaaggcca gcttgtcacc ccgccagagc ggcagtcggg ccacaagcat 45001 catccaagca gtggttctct gagcccgacg gggtgatgca aaggagccag gagacacctg 45061 cgcgtccaag ctgggggacc ccaggtctgt tatgccggac agtaaacacg ttcagctccg 45121 gagggagagg gttcccctac cttccagggt ttctcattcc acaaacatcc aaagacaatc 45181 cataccgaag gcgatccgtg cctttgctcc tgagacgtgc ggaagcacag agatccacag 45241 acactgtctc ccaggatcct atgtatgtaa aggaaccgaa gtcccaggct gtgtgtctgg 45301 taccacatcc cacggaacag gctggactga ttttcaccaa atgtagcaga aacgttaagg 45361 agtatcagct tcaaaatatg agggccagac atgtctgaga agtcccttcc agaaaagtcc 45421 ctttggggtc cttccccaga gttgctgaaa cagagaaccg gaagggctgc agagctgaac 45481 ttaaacaact ggatcgcaaa ggtccgtctc atcagagcga tggtttttcc agtggtcatg 45541 tatggatgag agagttggac cataaagaaa gctgagcgcc gaagaatcga tgcttttgaa 45601 ctctggtgtt ggagaagact cttgagagtc ccttggactg caaggagatc caaccagtca 45661 atcctaaagg aaatcaatcc tgaatattca tgggaaggac tgatgctgaa gctgaaactc 45721 caatactttg gccacttgat gcaaagaact gactcactgg aaaaaccctg atgctgggaa 45781 aggttgaagg caggaggaga aggggtcgac agaggatgag atggttgggt ggcatcaccc 45841 acccatggac tcaatggaca tgggtttgag taaactctgg gagttggtga tggacagaga 45901 atcctggcat gctgcggtcc atggggtcat agagagtcag acacaactga gcgactgaca 45961 gaactgaagc aactggcaag ccggagggta ggtgccggct gcgatgagcg ggaacgtgca 46021 acctgccacg tggagctctt cctacaccca gagtcctgac ggcactggga ccctagccct 46081 ccacggcctc tccagggcca cgagacaccc tcacagagca gagaagcgga acagagctgg 46141 tgtgcagaac caggccccgg gggtggggcg gggctggtgg gcaggcttta gtgagaagcc 46201 cttgagccct ggaaccagag cagagcagaa cagttggcag aggccccccct gggagaggcc 46261 ccccgcccag agtaccggcc ctgggccctg ggggagaggg cggtgctggg ggcagggaca -continued 46321 gaaggcccag gcagaggatg ggccccgtgg gacggggcgc accaaaacag cccctgccag
46381 caaggggaag ctggggcact ttcgaccccc tccaaggagg agcccacacc agcgcatctg
46441 cccaaggtgc ccttggccct gggggcacat gaggcccagg ccaggccagg gggcccatga
46501 ggcccccagg ggtcagtgca gtgtccccag gcagccctgg cctctcatcc tgctgggcct
46561 ggcctcttat cccgtgggcg cccacggcct gctgcccccg acagcggcgc ctcagagcac
46621 agccccccgc atggaagccc cgtcaggaaa gagcccttgg agcctgcagg acaggtaagg
46681 gccgagggag tcatggtgca gggaagtggg gcttcccttc gatgggaccc aggggtgaat
46741 gaccgcaggg gcggggaacg agaagggaaa ccagctggag agaaggagcc tgggcagacg
46801 tggctgcacg cacagcgctg accctgggcc cagtgtgcct ttgtgttggg ttttattttt
46861 aatttttgtat tgagatgcta tttatctcgt ggagcttttg ccgccctgag attttgtacc
46921 cgtggctggt gtccctcttg cctcaccccg gcctctgtag cagggcagac acggcgcaac
46981 ggggcagggc gtgcccagga ggcactgtca ttttgggggc agcggcccca caaggcaggt
47041 ctgccttcct cccctcttac aggcagcgac agaggtccag agaggtgagg caagctgccc
47101 aatgtcacac agcacacggg cgcagtccca ggactgtaga aatcccggga ctagacaggc
47161 accagagtgt cctgtgtttt taaaaaaacg gcccaagaga agaggcaagt ctgcaaggcg
47221 tcccgggaag gcagcagggg cttggctcgg tctcccccaa ggaggccagc tcctcagcga
47281 ggttcctaag tgtctaacgg agccaagcct gaaccaaggg ggtcacgtgc agctatggga
47341 cactgacctg ggatggggga gctccaggca aagggagtag ggaggccaag gaggagagag
47401 gggtgcacag gcctgcaggg agcttccaga gctggggaaa acggggttca gaccacgggg
47461 tcatgtccac ccctccttta tcctgggatc cggggcaggt attgagggat ttatgtgcgg
47521 ggctgtcagg gtccagttcg tgctgtggaa aaattgtttc agatcagaga ccagcgtgag
47581 gtcaggttag aggatggaga agaagctgtg aaaaggtgat ggagagcggg gggacggtcc
47641 tcggtgatca ggcaccgaga tcgcccatgg aatccgcagg cgaatttaca gtgacgtcgt
47701 cagagggctg tcggggagga acaggcactg tcatgaactg gctacaaaaa tctaaaatgt
47761 gcaccctttt cggcaatatg cagcaagtca taaaagaaaa cgcatttctt taaaattgcg
47821 taattccgct tttaggaatt catctggggg cgggggaaca atcaaaaaga tgtgaccaaa
47881 ggtttacaag ccaggaagtc aactcgttaa tgatgggaga aaaccggaaa taacctgaat
47941 atccaacaga aagggtgtga tgaagcgcag catggcacat ccaccgcaag gaatcctaac
48001 acaaacttcc aaaacaatat ttctgacgtt gggtttttaa agcatgcgtg cactttcaaa
48061 agcttgtcag aaaacataga aatatgccaa taatgtgtct ctagccaaat tttttaattt
48121 ttgctttata attttataaa gttataattg tatgaaatat aatgataaaa ttataaacta
48181 taaaaaagtt atgaaaatgt tcacaagaag atatacatgt aattttatct tctacaatac
48241 tttttaatac cagaataacg tgcttttaaa aaagattgag cacagaagcg tataaagtaa
48301 aaattgagag tttctgctca ccaaccacac gtcttacctt aaaacccatt ctccagcgag
48361 agacagtgtc atgtgggtct gtacacttct ggcctttctc ctaggcatgt atgtccctga
48421 aaactcacac acacggctaa tggtgctggg attttagttt tcaaaacgga ctcatactct
48481 gcctatgagc ctgcaactat ttattcagtc tgttgagatt ttctatatca gcccacatgg
48541 atcccgcatg ttctctgaat ggctctgtat gaattcaaag tttggaagaa gcagcgtgtc
48601 tttaatcatt cgcctattaa tggacgtttg ggtgtttcc actacaaaan nnnnnnnnnn
48661 nnnnnnnnnn nnnnnnnnnn nnnnnnnnnn nnnnnnnnnn nnnnnnnnnn nnnnnnnnnn
48721 nnnnnnnnnn nnnnnnnnnn nnnnnnnnng atacaattcg agctcggtac cctggcttga -continued 48781 actatatgaa cagagaacga tgagaacagt ttctcaaact tggaacagtt aacattttgg 48841 gctaaatgat tctttttttgt gtggagttgg cctatgaata gaggatatta gcagcatcat 48901 ttaaccttta ctcactacat acctgtagca actacatcct ctccatttgt gtcaatcaaa 48961 actgtctccg gacatggaca agtgtgcccc tgggatgggt ggaatgacct tttgttaaga 49021 accactgggt cagagattca tagatttttg tcttgttgac tttttaaaaa tacatcttgg 49081 tttttatttt attggtttct gctcttatct ttatgattac cttcctttta cttggggctt 49141 ccctgataga ttttcccttc tggctcagct ggtaaagaat ctgcctgcaa tgcaggagac 49201 ctgggttcag tccctgggtt gggaggatcc cctggagagg agaagggcta cccaccccag 49261 tattctggcc tggaggattc catggagtgt atagtccatg gggtcgcaga gtcggacatg 49321 actgagtgac tttcacacac acatatgtcc ctggtagctc agctagtaaa gaatcccacc 49381 cgcaatgcag gagaccccgg tccaattcct gggtccggaa gattcccttt tgtttactcc 49441 ataagatctt atctggggac aaaactaaca gctatgccag accttctgga catcagggaa 49501 cgtgaggggt gtggactgga cagatgtgtg tgttctccca aacacaaaca tacatctgta 49561 tacatgtaca tggagagagg gggagggagg ctgtgagtct ccaggggacc gtgcaaccat 49621 gtgacattca tggaggcgtt tgcgggtgat cactacacag tttcttcttc tggtttcttg 49681 gtcaattgac ttcacaattc caattcctat acttcatttt agactgaggg aattttacac 49741 tattgtaaga catatgtata catgagttat gttcagcgcc atgagggctc attttgtgtg 49801 tccactttgc ctggaaacaa agttggactg atttacttct aggggtgcct gggggtgttt 49861 ctggaggaca ggagcatttg aacccaaggg ctcggtgaag catgagcctc tctgcaggtg 49921 gacccaggag gaacgcaagg ccgaggaagg cagactctcc tcctccctaa cccgaggtct 49981 ctgctcagaa aagggacaat ataatgacta gaagaaaaga aagaacatca gctgtgggag 50041 gtttgttctc tggagcagat tcacacgttg aggctcatgt gcaggaattc taggtgaaac 50101 agagcagtca cccatgtgtg ttggaaaatt ttaaattaca tttgcagtta cgactttgtt 50161 taagccagac agggtagcac agcaaagtca ccatgtggtc acctgtgttt tgtaaaggag 50221 agagaacttg ctggcacatt caggaaaggc cgtgtctcag ctttggaggc acactgagag 50281 gccacaagca gatggtgagg accagggtct cgggcagagg gatcaattca ctgctcttca 50341 cttttgccac atctgtgtgc tgtccatcct ggccagagta gttcagtctt cagatgctgg 50401 agttcccatt ggtagaaatc caatctgggt catttttaaa cctctcttgg ttctacttaa 50461 tggttttaaa atctctttgg ctcaagaaaa aaaataaaca taattttaaa gggtggtttg 50521 gggccttgac tataaagtac attatctggg ccatttcaga gcatggttga attaatacat 50581 ttcgtgctta ctatagctcc tattttcttg attctttaca ggtaattttt gttaggaatc 50641 gggtactgtg aatattttct tgttgaatac gggatctttg tatttttttcc taattttttt 50701 ttttttttca tttttggttt taccttcagg aaagtcacta ggactcagga aagtcctttg 50761 tccgcctgtt atttcagtct cttacctggg gccagggcag cgtttcctct gggctaagtt 50821 tccccacaac cggggccagt tctcctcact cttcaccctg aggccttaat gaggagctcc 50881 cctgcgtctg agcagccggc cctcctgtga cgtgcgtgtg tctctggcca tcggcgtccg 50941 gtgtccttgg aggttccgtc ctcccttcgc tcactgtgcc ccgcactcga gctctcaggc 51001 tccaagcagt gtccgcagtg tgcagaccct ctgtgtagct ctctcctcct caggactctt 51061 ccctctagat gtgtgttttc ttttggctcc ttggacctcc gctctgaacg caggcctggt 51121 gctgagtgtg atctctggag ggaagcctgg gaggctggac gggtccgccc tgcggtgtgg -continued 51181 tgacaggtgt gggctcgggg cggggcctgc acgtcgtcct gacccgagcc gggactgggc 51241 tccgggcctc aggcatcact gactgaatct ccctcacaga ggggtcaggg cctgggcggg 51301 ggaaccgtct ctgcaatgac agcccctccc agggagggca cagcggggag ctgccgaggc 51361 tccagcccta gtgggaggtc ggggagccca ggggagcggc ctgacggccc cacaccggcc 51421 cagggctggt tcgttctgtt tctcgagctc aacagaagct ccgaggagct gggcagttct 51481 ctgaattcgt cccggagttt tggctgctga gtgtcctgtc agcaccgtat ggacatccag 51541 agtccattag cagtggtctc tgtccctctg tctgtccttc atcaggctct ttgtccaggt 51601 caccacacgg ccaacaccag gacagtctgg tcccgccagc ccatcgtccc tgcggacgcc 51661 cctgtgcagc ctgccgaagg gccgggaggc cgggggaacc gggccaggcc tgtccctgct 51721 gtgtccacag tcctcccggg gctggaggag agcgtgagca ggacgggagg gtttgtgtct 51781 cacttccccg tctgtctgtg tcactgtgag gattatcact gctgtcagct gactgacagt 51841 aatagtcggc ctcgtcctcg gtctgggccc cgctgatggt cagcgtggct gttttgcctg 51901 agctggagcc agagaaccgg tcagagatcc ctgagggccg ctcactatct ttataaatga 51961 ccctcacagg gccctggccc ggcttctgct ggtaccactg agtatattgt tcatccagca 52021 ggtcccccga gcaggtgatc ttggccgtct gtcccaaggc cactgacact gaagtcggct 52081 gggtcagttc ataggagacc acggagccgg aagagaggag ggagagggga tgagaaagaa 52141 ggacccctc cccgggcatc ccaccctgag gcggtgcctg gagtgcactc tgggttcggg 52201 gcaggcccca gcccagggtc ctgtgtggcc ggagcctgcg ggcagggccg gggggccgca 52261 cctgtgcaga gagtgaggag gggcagcagg agaggggtcc aggccatggt ggatgcgccc 52321 cgagctctgc ctctgagccc gcagcagcac tgggctctct gagacccttt attccctctc 52381 agagctttgc aggggccagt gagggtttgg gtttatgcaa attcaccccc gggggcccct 52441 cactgagagg cggggtcacc acaccatcag ccctgtctgt ccccagcttc ctcctcggct 52501 tctcacgtct gcacatcaga cttgtcctca gggactgagg tcactgtcac cttccccgtc 52561 tctgaccaca tgaccactgt cccaagcccc ccggcctgtg gtctcccctg gactccccag 52621 tggggcggtc agcctggcag catcctggcc gtggactgag gcatggtgct ctggggttca 52681 ctgtggatgt gaccctcaga ggtggtcact agtcctgagg ggatggcctg tccagtcctg 52741 acttcctgcc aagcgctgct ccttggacag ctgtggaccc gcagggctgc ttcccctgaa 52801 gctcccccttg ggcagcccag cctctgacct gctgctcctg gccacgctct gctgcccct 52861 gctggtggag gacgatcagg gcagcggctc ccctcccgca ggtcacccca aggcccctgt 52921 cagcagagag ggtgtggacc tgggagtcca gccctgcctg gcccagcact agaggccgcc 52981 tgcaccggga agttgctgtg ctgtgaccct gtctcagggc ggagatgacc gcgccgtccc 53041 tttggtttgt tagtggagtg gagggtccgg gatgactcta gccgtaaact gccaggctcc 53101 gtagcaacct gtgcgatgcc cccggggacc cagggctcct tgtgctggtg taccaaggtt 53161 ggcactagtc ccaccccagg agggcacttc gctgatggtg ttcctggcag ttgagtgcat 53221 ttgagaactt acatcatttt catcatcaca tcttcatcac cagtatcatc accaccatca 53281 ccattccatc atctcttctc tctttttctt ttatgtcatc tcacaatctc acacccctca 53341 agagtttgca ttggtagcat atttacttta gcacagtgtg cctcttttta ggaaactggg 53401 ggtctcctgc tgatacccct gggaacccat ccagaaattg tactgatggc tgaacccctg 53461 cgtttggatt cttgccgagg agaccctagg gcctcaaagt tctctgaatc actcccatag 53521 ttaacaacac tcattgggcc tttttatact ttaatttgga aaaatatcct tgaagttagt 53581 acctacctcc acattttaca gcaggtaaag ctgcttcgca tttgagagca agtccccaga -continued 53641 tcaataaaga gaatgggatg aacccaggat ggggcccagg ggtcctggat tcagactcca
53701 gccgtttagg acagaacttg actaggtacg aagtgagcgg ggtggggggg caatctgggg
53761 ggaactgtgg cacccccagg gctcggggcc atccccacca catcctggct ttcatcagta
53821 gccccctcag cctgcgtgtg gaggaggcca gggaagctat ggtccaggtc atgctggaga
53881 atatgtgggg ctggggtgct gctgggtcct aggggtctgg ccaggtcctg ctgcctctgc
53941 tgggcagtga taattggtcc tcatcctcct gagaagtcac gagtgacagg tgtctcatgg
54001 ccaagctatt ggaggaggca gtgagcactc ccacccctgc agacatctct ggaggcatca
54061 gtggtcctgt aggtggtcct ggggcttggg ccgggggacc tgagattcag ccattgactc
54121 tcagaggggc cagctgtggg tgcagcggca gggctgggcg gtggaggata cctcaccaga
54181 gccaaaataa gagatcaccc aacggataga aattgactca caccctttgg tctggcacat
54241 tctgtcttga aatttcttgt ggacaggaca cagtccctgg ataaagggat ttctatcttg
54301 cgtgtgcaat agagctgtcg acacgcttgg ctgggacatg taatcctttg aacatggtat
54361 taaattctgt tcactaacat ctgaaaggat ttttgcatca ataaacctaa ggtatattgc
54421 cctgtcattt ccttgtcttg tagtgtctct gagtaggctg gaaggggtaa ccagcttcac
54481 aaatcgagtt aggaaattcc cttattcttc cactgtctaa tagactttca taagattagt
54541 gttaattcct ctttaaatcg ctgctataat catcactgtg gccaccggta ctgaattttt
54601 tgttaggatg atttttaaac aagcatttta atgatttttc cttttatttt cggctgtgct
54661 gggtctcgtt gctgtgtgcc ggcgttctct cgctgtggcc agtgggggcg ctgctctcgc
54721 gttgcgaagc tcgggcttct gactgcagtg gcttctctcg ttgcagagcg cgggctccag
54781 ggcgctcagg ctcgcgtggc tgcggcacgt gggctcagta gtcctggggc acaggtgcag
54841 cagcctctca ggacgttttg ttcccagatg gtgggtcggt cgaaccggtg tcccctgcgt
54901 tgcaaggtgg attcttcacc gctggaccac cagcgacgtt ccctggaggt ttttaattat
54961 ggatttaagc tctcattaga tgtctcctca catttcctat ttctttttga gtcagtttga
55021 tactttgttt gtgtctgtaa gtttgtccat tttatccaag tcatctaatg tgttgataga
55081 caattattgg ttagtcatct aattgttggt ttacaatttt gagagcattg tcctgcaatt
55141 ccttctatct gcaagattgg taataatatc tcccaagagg agtcacaaac tgaaatgaga
55201 ttanatacag gctttttttt taaaagaatg aacttatgtt gttgcctttc tcatagatct
55261 tacttcttag catgactgta cttactgact ggggcgtttt catgtctgtg tggagagcta
55321 ccattagtac ttcttatcgc ccaaagacat cgggctcctg ggcacagtga aaacactcct
55381 ttctgtggct attttgcaaa atatggccta gcctagcgtc ataagggatc acagctgaca
55441 actgctggaa cagagggaca tgcgaagcaa cgtgagggct ggaacctgga gggtcctctc
55501 tggggacagt ttaaccagct ataatggaca ttccagcatc tgggacatgg agctgtgaac
55561 tggaccaatg actgtcattt ttggaagaga aatcccagga gagaagggtc caggggaatc
55621 tgaggccgca tgcagtgcct caggacaggg gacaccttct ccagcagagc aggggggccc
55681 gcccaggccg cctgcagtga ttccaccagg aggagatgca tccctgcaga cctctgacag
55741 cacggccctc tcctgagaca cagggtcaca cccggggccc tggaaccctt tgagacccta
55801 aacctttcct ttcctgacca ccctgacagc agtctagctc agaacagaca tcttcatttt
55861 cagcaggaaa atccttttcc tcgtttgagg gagcgactgg caccggagga gctgagtctt
55921 ttaaacacag gctgcctgaa cctcagggat gacctgcagc tgctcagagg aggctggagt
55981 gtgatagctc actctaatgt tactaaaagg aacatattgg acacccctc tctgaaaaat -continued 56041 ttccctcctg cctctcatct cttagtccac tttatcgccg ttttactgct tttctattta 56101 ctactcttaa cgccaaccta tcttatttcc cctcccagtt taacacggtt ttccctccac 56161 ccgctctctt taatctcaga agattctgcc tattcctcta ttatcacacg cccctacttt 56221 ttattttttt tcttacccgc cttttattcc ctcccctcct cactctctat ttaattacat 56281 cttaactaca ccgcctgcgc tatcttcgaa tgtatccaaa tatttttccc ttatataaca 56341 ctccaggccg agcggctaac ttattataat ttctttatag cgcctaccta atttcccttt 56401 atttctaatt atctatatat acccatgcaa tttcgnnnnn nnnnnnnnnn nnnnnnnnnn 56461 nnnnnnnnnn nnnnnnnnnn nnnnnnnnnn nnnnnnnnnn nnnnnnnnnn nnnnnnnnnn 56521 nnnnnnnnnn nnnnntgggt gtacgttata gagtaaacgc gcatgaagaa gtgggtcaat 56581 ctatggctgt gagaggcaga aaataatatt atcatatata atttatgtta taacacactg 56641 aggtggtggg ctcgtagaat agtgcggacg gggagaaagg tgggaaggag aagacacaag 56701 agagagatgt tcgcctcgcg ggatggatgg gcggagggat agaagaataa aaagaggaga 56761 ggtatagagg ggggcggggg gcataacgtg tggtggggta aatagtaggc ggtaattatg 56821 aaaaaaagaa agacgggggg ggcggtaaca tagaatacgc aaaaaagtca tatactgaac 56881 ggggattagg gagaagaggt ggggggcgtg gggtgcgggg gaaagaggtg tgtgtataat 56941 tggtatggag tgttatttga atatatatta atgtaatagg gagtgtaatt agtgaaattg 57001 tgggagtatt atattggggt gtgggggaca tggcaaagtg atgatcggga taaaaaaagt 57061 aaagcaagag gggaggggaa aataaggggg gggagaaggt cgaagaaaat aagaggaaga 57121 agaaagaacg ggggtggcgg gcgggggggg cgccgctctt gtatctggct tttttgttgt 57181 gtcggtggtt gttcgcgtct tgttgggtcc ggggcgggtg tgcggaaaaa aaaaaaggcg 57241 ggaggcccgg ggcccggtca cgcggcaccc ccgcgggtcc ctggcttctc cttcggcagc 57301 tccgggggtc ggtgagcctg cgccctccgg gccgccggcc cgagctgtgt gcgccctgga 57361 gaatcggagc cgctgtggca gcacgcggag ggcgcgcgca agggccacgg gacggacctt 57421 caaaggccgc ggcggagcgc ggcaagccga accgagggcg gtctggcgat cggccgagcc 57481 ctgctccccc ctcccgcgtg gccccagggt cgcgggtgga ctggggcggg tacaaagcac 57541 tcacccccgt cccgccccca gaaagcctcc caggactctc acagagcacc cgccaggagg 57601 catccggttc cccccctcggc tcagttcagt tgctcagtcg tgtccaactc tttgcgaccc 57661 catggactgc agcaccccaa gcttccctgt ccatcaccaa ctcccggagt ttactcaaac 57721 tcatctattg agtcagtgat gccatccaac cgtctcatcc tctgttgtcc ccttctcctc 57781 ccactttcaa tctttcccag catcagggtc ttttcttatg agccagttct tcacatcagg 57841 tggtcagagt attggagttt cagcttcagc atcagtcctt ccaatgaaca ctcaggactg 57901 atttccttta ggatggactg gctggatgca gcgccagaca ccgaccgcgt ttaccccgtg 57961 tgtcctttcc aatggctgtc ccctgcgggc ctaggggcat tggtgcgggt ttgaatcctg 58021 tggccttgaa ttttacgcct tagttccagg tccagggcag ggccatccgg attcaggatg 58081 cttcccagcc cttcaggaat ggcaggtttt catggtcctt tctgagtgag ttctgagtgg 58141 tcatattggt gcccttggca gggagggctc ctgactttcc tatcttcaca tcactgtccc 58201 caacccccaa gagaggcctc ttggcccagg gactgcaggg aggatgaagt caggagcaga 58261 agcatggggt agggggctca ggtgggcaga ggaggcccct ctgtgaggag gaacggcaag 58321 cgaggaggga acaggggcac cggcagtgcc tggcaagctg ggtgatgtca cgactacgtc 58381 ccgaccacac agtcctctca gccagcccga gaagcagggc cctcccctga cccccatctg 58441 ggcctgggct tcagttttct cctccctgca atggggtgac tgtttgcctc caggagaggg -continued 58501 gagcatgtaa aggtggccac tctcttctgg cagacatgcc aggcctgggc cagcctccac 58561 ccctttgctc ctgcagcccc tgctgacctg ctcctgtttg ccacaccggc ccctcctggg 58621 ctgatcaggg ccccccctcct gcaggaagcc ctctgggaca agcccagctt gctgtaactg 58681 tggctttcca ctgtgacctg caacgtggga ggctgttact taaaactccc atgactggtg 58741 gattgccggt ccccagaaca aggccacgca tccctggagg ccctcgagac catttaaggt 58801 agttaaacat ttttacttta tgcattttca tgtgtatcag aaagaaaaaa aatgtatcat 58861 cagttcatca aatccatgat ttcttgacca atattgctaa gatgaggctg aaataggcat 58921 ttccattttt aaaaaactga atcactctga agaaacagat ggcaggcttc cctggtggtc 58981 cggtggttaa cagtccatgc ttccagtgct gggggcatgg gttcgatccc tgaaaatttt 59041 aaaaaggaag aaaaagatgg ctccccccgtc cctgggattc tccaggcaag aacactggag 59101 tgggttgcca tttccttctc cagtgcatga aagggaaaag ggaaagtgaa gtcgctcagt 59161 cgtgtgcgac tcttagcaac cccatggact gcagcctacc agactcctcc gtccatggga 59221 ttttccaggc aagagtactg gagtggggtg ccattgcctt ctccaggcaa acggcctgct 59281 actgctactg ctgctaaatc gcttcagtcg tgtccaactc tgtgcgaccc catagacggc 59341 agcccaccag gctcccccgt ccctgggatt ctccaggcaa gaacactgga gtggggtgcc 59401 attgccttca gcctgctgct gctgctgcta agtcgcttca gtcgtgtccg actctgtgtg 59461 accgcataga cggcagccca ccaggctccc ccgtccctgg gattctccag gcaagaacac 59521 tggagtgggt tgccatttcc ttctccaatg catgaaagtg aaaagttaaa gtgaaattgc 59581 tcagtcgtgt ccgactctta gtgacccaat ggactgcagc ctaccagggt cctccatcca 59641 tgggattttc caggcaagag tactggagtg gggtgccatt cggcctaggg agtgagaaat 59701 cacggctgtc ttccctcttc tcgccctcta ggggtctctg tggagcctcc ctggagaggc 59761 cgcggcggct ccggggactg gagggggagg gggggttgag tcagccggtg gccctcccct 59821 cgctgcccgt ctcctcccttt tttaggcaca agctgggcgc cctttttagg cgcagcctca 59881 ccctgcgggc cactgcccgt gtttcggctc cccggagata aaacagattg cctgcacccc 59941 gggtcatcac aaggattgta tgaccgtttc ccagtgtgct caccaccctc cctctgattc 60001 tcagagacgc gccctcgcct caggaggctg ctcatcccag gccaaggggc ggcgtggggt 60061 ccccagcgcc ccgcacagac actgccttct gaccacctcc tcccaacagc ttacctgcca 60121 agaaggcctc ctgacccctc atcctgcccg gtggtttgga gaaagcctca tctggcccct 60181 ccttctcggg gcctcagttt ccccctctgt gaactggcgg attctgccaa gctgacgtcc 60241 tggccagccg cctccccgtg gccagtgtcc cccgggacac agctgaatgt ccctgctcgg 60301 gatgcacctt ccccaagttgg cctgtcagga ggcgggggcg agcagggaaa cccgactcct 60361 ctcagacggc ccatcgcatt ggggacgctg aggcccggag cagcggcacc ctcctggcca 60421 gggtcattct cccgccccgc cccgtccctc cgggcctccg agaccgcagc ccggcccgcc 60481 ccgggaagga ccggatccgc gggccgggcc acccccccttc cctggccgcg ggcgcggggc 60541 gagtgcagaa caaaagcggg gggcggggcc ggggcggggg cggggcggag gatataaggg 60601 gcggcggccg gcggcacccc agcaggccct gcacccccgg gggggatggc tcgggccgcc 60661 ggcctccgcg gggcggcctc gcgcgccttt ttgtttttgg tgagggtgat gggggcggtc 60721 gcggggtact attttttcat ttataattgg gtattagcta gcgagtggaa ccacaccctt 60781 attccactat agccaatttt tgcgggggca tcttacatta cagactcgcc cgcctcttat 60841 ttcggtacag catatcagat cgtctcttta ctcagacact agtgattatt gtctatagta -continued 60901 cacaaaaaga acggttgtgt cggcgtaatg gttgcatttt ccctcctcgt ttctcctgac 60961 cacctcaatt acaccaacac tctactattt aaatcacgta ttgtacgcca ccctccgccc 61021 gcgaactaaa agaatgtgca gatattctga agataaaatc gttcattgtt acgccccgcg 61081 cgcttcgcgt atattactct tagaacttct tattcgcccg agcagttatt caccccccgc 61141 aactagatgt cgccttaata tttgttctaa ccgttttgga ttctaacgat aggcgggaaa 61201 ggtagacatt cgaccgctac gacaactaaa atcgacgagc acaggctatt tatatcgcga 61261 ccacacgcgc gcggtataca naccgtaaaa ttatctaaca tcgagagtaa gggcacagag 61321 cgaaatacaa gcggcgtggt gggaggtgtg tctgtagtga attcgcacct cgcgccgccg 61381 cctctgtgcg tcgnnnnnnn nnnnnnnnnn nnnnnnnnnn nnnnnnnnnn nnnnnnnnnn 61441 nnnnnnnnnn nnnnnnnnnn nnnnnnnnnn nnnnnnnnnn nnnnnnnnnn nnngatataa 61501 tattaataaa cagcggatag atgtgtgtaa gggaggaggt gcataagaga ttaaagagag 61561 gcgggcggag agaaatagag tagaggagga tgagagaaaa aagaaagcaa gcgtaggtac 61621 aacggcgggt gggtagtatg ataaagtgag tgtatatatt tgagtaaagg aagggtagat 61681 ggagtataaa gaagtaagga gaggagaggg cggcggagag agagagtgca aagaaaataa 61741 gtgggcaaag gcggggtggg tgagaagcag tagaagagaa gatagagaag ggggaaaaag 61801 aggaaaatga ggattagaac aagtaggaca ggatagatgt gaaaaatgag atcaggtcaa 61861 ggtggagaaa aagtagaaac tggggcgtga ttgtaaaaaa gggaggccgc gatggggcag 61921 caccataagc gaagagatga attaatgaaa gcaaggcagg gagaatcaaa tgagttgggt 61981 ggaggaagga ggctgtgact tccttcgctg ccggaaagag aactagaata gcctcgggct 62041 gtgggggag gtaaagataa agtgacttct gggccctggg ggaggcccag gagtttctac 62101 cgagctgagc tgggtgcctc tcccaaatgc ccaaccccct gagagtcgac gggagagcac 62161 agcctggcca aacctgggca gggcacacgt gtccttcacc ccacagtggt cacgagccca 62221 gcgtggtccc tgcgtctggc gggaaacaca gaccctcaca ccccacacaa gggtccggcc 62281 gctttcaaat aacagcagcc gtgccctctg ggccggtgac ccggacacag agagatgaag 62341 tccgcatctc tcagagtgcg ctgtcctccg cccggtcagg cccgggtccc ctgcttctct 62401 gaggtcacca ggagggattg catgtgggtc tcagggacac aggttcagtg atgtgacaga 62461 gggtagtggg tcccagcagg gccggtcttt ggacccgttt ttctgaaaag ccagttggcg 62521 acctggggtc acagcaaagc tgatcctgtt tggccaggag tctcccagtg acggcctccc 62581 ccagaacatc gggcccagtg ggggctccag ggggtagact tgcctcccag ctcacgcccg 62641 tgtcttgaca agtccatgat ttggtaaaat taatttgtgt tggatggagt tgatttagtg 62701 gtgtgtgagt ttctgtggcg cagcaaagtc aatcagttac gcatacacat gtatccagct 62761 cttcctacga ttctgttccc atataggtca ttatggggtg tcaggtagag cttcctgtgc 62821 tacgcagtac ggccttattc agttcagctc agtcgtgtcc gactccttgt gaccccatgg 62881 actgcagcac gccaggctcc cctgtccatc accaactcct ggagcttatt caaactcatg 62941 tccatcgagc cggtgatgcc atccaaccat ctcatcctct gtcgttccct ctcctcctgc 63001 cttcagtctt tcccagcacc ccctagagaa gggaatggca aaccacttcg gtattcttgc 63061 cctgagaacc ccatgaacag tacggaaagt ccttattagt tttctatttt atatatagca 63121 gtgcacacgt gtcagcccca atctcgcaat ttatcacccc cctccgccgc cgattggtag 63181 tcatgtttgt tttctacatc tgcgactcta tttctgtttt gtaaacaagt tcatttacac 63241 cactttttta gattctgcac atacgtggca agcccacagc aaacatgctc aatggtgaaa 63301 gactgaaagc atttcctcta agatcaaaaa caagacgagg atgtccactc actccgtttt -continued 63361 tactcaacac agccctgaac gtcctagcca tggcaatcag agaagagaaa gaaattaagg 63421 aatccaaatt ggaaaagaag aagtaaaact cactctttgc aaatgacatg acacttatac 63481 ccagaaaatc ctagagatgc taccagataa ctattagagc tcatcagtga atttgttgca 63541 ggatacaaaa ttaatacaca gaaatctcct gcattcctat agactgacaa caaaagatct 63601 gagagagaaa ttaaggaaac catcccacgg catgaaaaag agtaaaatac ctaggaataa 63661 agctacctaa agaggcaaaa gacctgtact cagaaaacta taaaatactg acaaaggaaa 63721 tcagacgaca cagagagaga gagataccac gctcttggat gagaagaatc gatagtgtga 63781 caatgactat actacccaga gaaacataca gattcagtac aacccctatc aaattcccaa 63841 tggcattttt cacagaatca gaattagaac aaaaagtttt acaagtttca gggaaacaag 63901 aaagatccta aagagccaga gcaatcttga gaaagaaaaa tggagctgga agagtcaggc 63961 tccctgagtt ctgactgtgt atacaaagct ggcatgattt ttaacagcag gggtgtaaat 64021 gaacttgttc acaaaacaga tggtggggtg ggcttccctg gtggctcagc tggtaaagaa 64081 tcctcctgca acgcaggaga cctgggttcg atccctaggc tgggaagatc ccctggagaa 64141 gggaaaggct acccactcca gtattctggc ctggaaaatt ccaaggacca tatagtccat 64201 gggtttgcaa agagtcggac acgactgagc gacttccaat cctggaaacg tcccattgtg 64261 gacggtgaac tggggttgtc caagctcagg gtaaccgttt gctgagtgac tgacactcct 64321 tctcatgggt taaaatgtgg ggcccaaggc caggaccaga ccccgcagtc agccaggcag 64381 accctgtgca gccccagcga gtgtgtggcc gccgtggagt tcctggcccc catgggcctc 64441 gactggagcc cctggagtga gcccattccc tcccagcccg tgagaggctg ggtgcagccc 64501 taaccatttc ccacccagtg acagatccgc ctgtgtggaa acctgctctt gtccccaggg 64561 aacctggcag gactcaggga gaatgtctca gggcggccac agatcagggg ctgggggggc 64621 agggctgggt ccagcagagg ccctgtgccc actccccgga aagagcagct gatggtcagc 64681 atgacccacc agggcaccga cgcgtgcttg cacacaggcc gccccctcat ggtgacactc 64741 ttttcctgtg gccacatctc gccccctcag gtccctcctg ctccccagct cctggcctgg 64801 gaacctcttc cccgccccgg ggacgtcagg gctggtgtcc actgagcatc ccatgcccgg 64861 gactgtgctg atcaccagca cctgcacccc ctctcgggtc tcaccaggat gggcaactcc 64921 tgcccatcca gcacccagcc tcctgggtac acatcggggg aggagggaga agcctgggcc 64981 agacccccag tgggctccct aaggaggaca gaaaggctgc cgtgggccag ccgagagcag 65041 ctctctgaga gacgtgggac cccagaccac ctgtgagcca cccgcagtgt ctctgctcac 65101 acgggccacc agcccagcac tagtgtggac gagggtgagt gggtgaggcc caggtgcacc 65161 agggcaagtg ggtgaggccc gagtggacag ggtgagtggg tgaggcccag gtagaccagg 65221 gcccatgtgg gtgaggcccg ggtggaccag agtgagcggg tgaggcccag gtggacaggg 65281 cgagcgggtg aggcccaggt ggacagggcg agcgggtgag gcccgggtgg acagggcgag 65341 cgggtgaggc ccgggtggac agggcgagcg ggtgaggccc gggtggacag ggcgagtggg 65401 tgaggcccgg gtggaccagg gcgagtgggt gaggcccggg tggacagggc gagtgggtga 65461 ggcccgggtg gaccagggcg agtgggtgag gcccaggtgg acagggtgag tgggtgaggc 65521 ccaggtagac cagggcccag agcaaagccc cggctcagca gtgatttcct gagcgcccac 65581 tgcttgcagg gacctcagcg atggtaaggc agccctgttg ggggctcccg actggggaca 65641 gcatgcagag agcgagtggt cccctggaga aacagccagg gcatggccgg gcgccctgcc 65701 aggctgcccc aggggccaca gctgagcccc gaggcggcca ggggccggga cagccctgat -continued 65761 tctgggttgg gggctggggg ccagagtgcc ctctgtgcag ctgggccggt gacagtggcg 65821 cctcgctccc tgggggcccg ggagggacgg tcaggtggaa aatggacgtt tgcgggtctc 65881 tggggttgac agttgtcgcc attggcactg ggctgttggg gcccagcagc ctcaggccag 65941 cacccccggg gctccccacg ggccccgcac cctcacccca cgcagctggc ctggcgaaac 66001 caagaggccc tgacgcccga aatagccagg aaaccccgac cgaccgccca gccctggcag 66061 caggtgcctc cctctccccg gggtgggggg aggggttgct ccagttctgg aagcttccac 66121 cagcccagct ggagaaaggc ccacatccca gcacccaggc cgcccaggcc cctgtgtcca 66181 ggcctggccg cctgagacca cgtccgtcag aagcggcatc tcttatccca cgatcctgtg 66241 tctgggatcc tggaggtcat ggcccctctc ggggccccag gagcccatct aagtgccagg 66301 ctcagagctg aggctgccgc gggacacaga ggagctgggg ctggcctagg gcaccgcggt 66361 cacacttccc ctgccgcccc tcacttggga ctctttgcgg ggagggactg agccaagtat 66421 ggggatgggg agaaaaatgg ggaccctcac gatcactgcc ctgggagccc tggtgcgtct 66481 ggagtaacaa tgcggtgact cgaagcacag ctgttcccca cgaggcctca cagggtcctt 66541 ctccagggga cgggacctca gatggccagt cactcatcca ttccccacga ggcctcacag 66601 ggtccttctc caggggacgg gacctcagat ggccagtcac tcatccattc cccatgaggt 66661 ctcacagggt ccttctccag gggacgggac ctcagatggc cagtcactca tccattcccc 66721 acgaggcctc acagggtcct tctccagggg acgggacccc agatgggcca gtcactcatc 66781 catccgtctg tgcacccatc cgtccaacca tcacccttcc ctccatccat ctgaaagctt 66841 ccctgaggcc tccccgggga cccagcctgc atgcggccct cagctgctca tcccaggcca 66901 gtcaggcccg gcacagtcaa ggccaaagtc agacctggaa ggtgcctgct tcaccacggg 66961 aggagggggg ctgtggacac agggcgcccc atgccctgcc cagcctgccc cccgtgctcg 67021 gccgagatgc tgagggcaac ggggggggcag gaggtgggac agacaggcca gcgtgggggg 67081 ccagctgccg cctggctgcg ggtgagcaga ctgcccccct caccccaggt acaggtctcc 67141 ctgatgtccc ctgccctccc tgcctccctg tccggctcca atcagagagg tcccggcatt 67201 ccagggctcc gtggtcctca tgggaataaa aggtggggaa caagtacccg gcacgctctc 67261 ctgagcccac ccccaaacac acacaaaaaa atccctccac cggtgggact tcaccagctc 67321 gttctcaggg gagctgccag ggggtccccc agccccagga agccaggggc caggcctgca 67381 agtccacagc cataacacca tgtcagctga cacagagaga cagtgtctgg tggacaggtg 67441 cccccacctg cgagcctgga gagtgtggcc ctcgcctgcc ccagccgcgg tcagtcggct 67501 cagcaaccgc tgtccactcc cagcgccctg gcctcccctg tgggcccagg tcaagtcctg 67561 ggggtgaagc taagtcaggg agcctcatcc atgcccagcc cggagcccac agcgccatca 67621 agaaatgctt cttccctcca tcaggaaaca ttagtgggaa agacaagagc tggggggttc 67681 tggggtcctg gggggatcaga tgaaggggtc tgggagcagc agcagcctca ggcaccccaa 67741 aacaaggccc aggagctgga ctcccagggc tgaggggcag agggaaggaa ggcctcctgg 67801 ggggttggca tgagcaaagg cacccaggtg ggggctgagc accccctcggc tggcacacac 67861 aggcccccac tgcagtacct tccccctcgg agaccctggg ctcccgtctc ccgcctggcc 67921 tgccatcctg ctcaccaccc agaaatccct gagtgcggtg ccatgtgact gggccctgcc 67981 ctggggagga aggagattca gacagacagg atgccagggc agagaggggc gagcagagga 68041 tgctgggagg gggcccgggg aggcctgggg ggcagggggg caggagttct ccagggtgga 68101 cggcgctgtg ctatgctcgg tgagcacaga ggccccgggt gtcccaggcc tgggaaccca 68161 gcagaggggc agggacgggg ctcaaaggac ccaaaggccg agccctgacc agacctgtgg -continued 68221 gtccagaagg cagctgcgcc ctgaggccac tgagtggccc cgtgtcccga accaccgctg 68281 aaacatggga cacacgttcc caggcggagc cactcctgcc ttccgggagg ctcccagcgg 68341 gctcatcgct ccatcccaca gggagggaaa ccgaggccca gatgacgaac atcccggcga 68401 gcaggtcaaa gccagcccct ggggtcccct ctcccggcct ggggcctccc ctctgcaggg 68461 tgggaaaccg aggccacaca ggggctccat ggggctgccc tctgccaggc cctggacacc 68521 ccgcgggtga cccccgcctc tatcatccca gccctgccag gccctggaca ccccgtggat 68581 gacccccgcc tctatcatcc cagccctggg ggacagatgg gaggcccaag cgtggacccc 68641 ctggccaccc cctaccccac agccgggagg agccgggagc tggtggccaa gggcctagag 68701 gagccagann nnnnnnnnnn nnnnnnnnnn nnnnnnnnnn nnnnnnnnnn nnnnnnnnnn 68761 nnnnnnnnnn nnnnnnnnnn nnnnnnnnnn nnnnnnnnnn nnnnnnnnca atatagaggg 68821 ggtgggataa agggtaatat gatgtttagg tagttagagt taaattagaa gggtttggat 68881 aaagattaat aaaattacaa gcgtacatat cgtgtgagtg tgggtgataa tatttgtgta 68941 tgtggggaat agaagtgagt gtgagtagta ttcaagatgt aagtgtgcga atacaggtct 69001 gagcgatttg aatggaagtg aaaaaaagcg tgtgtgtgga ggaggcggga gaggaagata 69061 gtgtggggga agaaaagaag gctagtgggt aaagaaatat cagtaggcgg ttgacgaaag 69121 aagaactagg aagaattaat ataaaaataa agggaggatt aaaaaataaa gagggaggag 69181 gtaacggaaa tagttagtta agaaaagaat ggagagtgga ggtaagataa ataagggagt 69241 aatgggagtg aggaggaata aataaaaaaa tggtgaggga aaatagagta gaatgagaac 69301 aagaatgaaa aagggagtga agggggtgaa aaaaagtgaa gttgaaaaaa gaggaaaaaa 69361 aaggagaaga taaaaaaata aaataaaaaa aggaaaaaaa agaaaaaaag aaagaagggt 69421 taaaggacga aaagaaggga agagaaaaaa aatagtttaa gtgggggagg gtaaaaaaga 69481 attaataaag taaatatggt tgtggtcgaa aaaaaaaaaa aaattgttgt gttgatgaga 69541 agaaaagaaa aaagaagaaa gggaaaagca aaaagaaagg agagaaaaag acaaccccac 69601 cgcccgggcg catggagggt gaggatggcg cacgcccgcg gatggcacag catcacagca 69661 atcctaaaac gttttcagac cggtgcatct tcaccgcgcg cgcgccccgc ccggccctcc 69721 tcccgccctg accgcggacc cccacccgca ccggggagcc tacccccacc ccggggacgc 69781 tccgccacgc taaggtcagg actgccgtga agacgcgccg gggtgaaaac gttttatctt 69841 catgacataa gcgagtggtt ttgaaacagg tttacaaacc ctcgtgaaga cgcaccctta 69901 gcgttaggtt ttgttttttt accatgtgac gatgcaacta ttttcttcct ctcttccaca 69961 gtggctagtc gcctccagag cgaggggtat ctcttgtaca gagaccctcg gaacatccgg 70021 aggtagtttc ccacctaggg gtaaagcgag aaggctcatt acgagggccg gggctcctcg 70081 gggaagggca gggccctggc gcagaggctc tgccacctca gtgacacgca gaccacgcgc 70141 ggcctgcagg cgccgggctc tgaaagcagg caaagcccga tctgctgaca tcaggggttc 70201 cgcagcagcg aaggtctggc ccgcacctgg cccactggca gggggtaagc tctgcctccc 70261 gacgacagca ccaagttcag gaagggccac gcagacactg gtgagacacg gccccccccgg 70321 agctgcccga gaagctctga ctttgcacta aagatctctg gcgcggtcca aaaatgtaag 70381 gcctctcttc cttttatctt aagactttga tatttttacg atgtaataaa taccaagaag 70441 ggcttttaat ttcagacaga tgtaggataa tttcccccgt agcccttgct gctttgttta 70501 gtaacgaaac tcaaaccaga aataccaaag gaattttcca aagagtttca aaagcgctta 70561 tcagcaatca ctagactgct gcatacatca tcactgcccc aaacaatagc ctgcctgtgc -continued 70621 cagttactca aagtactact tacttgacga aaacaaatct agtcctaacg tttttacaaa 70681 gaaactccac tcttccgcca acttttcaga aacaaccact cgatcacgtg gcaggggacc 70741 gtggctggac tgggtgctgg ctccttctgt gaccaggcaa cactgccccc ttctcggcct 70801 ccctacgcct cttgacaaat gttcatcagc tgtaaagttc accccacgag ggacccactt 70861 ctgctatttc ccacgtacct accccattat aggagttttc tttgtgacag tttctgcatt 70921 tttcatggat ttagaggttt acataatcag ggctgctgaa cagcatgaga gacgtggcca 70981 caaggtccct cctgcacctt gccgcagggg cagggcgagt tatctggctt gagcgtggtt 71041 accatcaggg ggtaaacaca gtttccagga cgtttttgac aagacactga cccggatgcc 71101 cccactacca ccgtgcaggt cctgcaggcc tcccagcctc ccaggccctt cccgaggtcc 71161 cttcggaact taggggactc ggtctgcccc cctgggtttt ccctgcacca gcttttgccc 71221 cctctggacc caggtttccc aaatggaaaa cgaaggtgtg ggtatggaag ctccctgggc 71281 tcctctcagc tgtgcctctg catggtgatg acggctgccc atcggggggg gcaggactgg 71341 ggcagctgcg gacaccctcc caaggctgct acccccgagt ggtgtggggc gctgtgggca 71401 cgctctgctc agcgcacctc ctggaaacca gcgcctgccg tctgcccggg gcaaccggcc 71461 cgggagccaa gcaccactgc cgtcagagga gctgctggct gtgagtggac gccagtctag 71521 ctctgaaccc tgcccaggcc tcctgaggtc tgaacattgt aaaatcaggc cccggacggc 71581 aactgcctct ccctcctgcc gtctggtctc cataaactgc atctcaggac aaatcttctc 71641 actcaccagg gctgaaacag aagactgcag ctatctttct caaatctaag gtgtgctaca 71701 gggcaagtcg cagaaactgt ctggcctaag catctcatca gatgcctgag acaagagctg 71761 tggacgccaa gctggagcca gagctcctcg cgttctgccc acctggcacc gcgttccacc 71821 cagtaaacgc aggcttgatt ttcaaaagta ccaccgactc agagccaatg ctaaaccgac 71881 cacttttcct gcccattaga ttgggtgaag gtttctttaa tcaatctgcc agtcaccaca 71941 tgccgcctct gtgcccacag gctggcgaag acctttctga gctacggcat gtggcaggca 72001 gcggcacctc tcttcagtac ggccagctgt caaggggagc gtttctgtga tgatgtgaaa 72061 atacattgca tccggccccg tgtttcatga acacgggtga ggaaaggaaa cacacaaagt 72121 tctgatgcga ctgacagcac gggtctcata actcaataca agtcagacaa accacaggga 72181 gtcacaggga atcccaatag cctcatctag tgtgaccatc atgaggctta atttattcag 72241 tgtattcaat cataaagagg gggaaaaatt gtaaaaaaaa aaaaaaagaa agagtgaaat 72301 gtgtaatact gaaaactgtt gctaggagaa gcaagcattg gcgtttgtaa ctgctttgac 72361 tccccaagac ccacactcgc ctcgctacaa aagggaggca ctgctgctca gtacttgcac 72421 acccgaactg cggatttgta atttaaaaat gtgtgtgtgg acacagcaca agccagagac 72481 tgccaaaggt tgagggacac tggaagaact taatatactt ggtgcatgct gccagtgaca 72541 gtcagtcacc agctgattca atagagtgcc gaaaggtcac cttttaggta aggatgaagg 72601 ggttctgggc tcgtttactt gcactaactc agagttagtc cgagatatcc gaagtgccag 72661 gtgcctccca tttgctgatg gatctagctc agggacggct gggccctagc catccaaaaa 72721 tcaagcattg ttctcccaac ctgtcttctc gctgataatg gaaggtcaga acgcccaccc 72781 gcccacctca aagtcaaaga acaccaagcg ggtgagtccc cactaagctc ggtgtttcca 72841 atcagcggtt tcaggattcc agctggggca atgagggagg gagcgtgcga gggatccaac 72901 acctcgcccc gtgcgcagca agggataacc caacaccccg tttctgtacg tccggctgga 72961 gttgtggaac tcagcgcgga cccggggcca ccgcgacccc cgggaccctg gccgcgcggc 73021 gcatccccgc tgccgggaca cgggtaagcg tccccaaact gccggacgcg gggcggggcc -continued 73081 ttctccgcca cgccccgata ggccacgccc aaggacaagg atggtcgtgc ccagacggcc 73141 ggggcgggnn nnnnnnnnnn nnnnnnnnnn nnnnnnnnnn nnnnnnnnnn nnnnnnnnnn 73201 nnnnnnnnnn nnnnnnnnnn nnnnnnnnnn nnnnnnnnnn nnnnnnnncg gagggggggg 73261 ggcggggcgg gggctgccgc cgcgcgtata ggacggtggt cgcccggcct ggggtccggc 73321 cgggaatgac cccgcctctc cccgcatccc gcagccgccc cgccgcgccc tctgccgcgc 73381 acccgcctgc gcacccgccg ccctcggccg cggccccggc ccccgccccg tcgggccagc 73441 ccggcctgat ggcgcagatg gcgaccaccg ccgccggagt ggccgtgggc tcggctgtgg 73501 gccacgtcgt gggcagcgct ctgaccggag ccttcagtgg ggggagctca gagcccgccc 73561 agcctgcggc ccagcaggtg agcaagggct caggggaaac tgaggcccga cacagagccg 73621 cagcaagaag gatcctactg gtcactcggc tgttggcctg ggtcatcac aggcgggctc 73681 tcccaaccca tcccctgagg ccaaggtccc tagaaccccg tgggcagaca ccaaccagcc 73741 ctttaaatat ggggaaacca aggtgcttag gggtcagaga tagccctagg tcgcccaacc 73801 ctagtagaag ggagggctgt tggagttcct gagtgcccgc tctcccaccc cccgggaggc 73861 cccttcctga gcccaagggt gactggtagt cagtgacttt gggcctgccg acctgtaccc 73921 cactgggcac cccaccagtc ctgagccaca tttgggctta gtgacggggt cagggatcat 73981 gaggatcaat gtggctgagc caggaaggtg ttagaacctg tcggcctgga gttcatacca 74041 gcactgccct gggcttttct agacccatgt cccgcctcct gccccacctg cccctgttcc 74101 cgcaccccac cagcagcggc aggggcttcg agagggctgt gggctcaccc tatttcaggg 74161 atggagccgc taagacctgg ggcacactgc ccgctaggga cccctgaggc accagggccg 74221 ggggctctgc ggagggggcag ccgccacccc cagctttgga gtcctctccc gggtgcccag 74281 cccgagctga tccggctgcc tcccacgctg tgccccaggg cccggagcgc gccgccccgc 74341 agcccctgca gatggggccc tgtgcctatg agatcaggca gttcctggac tgctccacca 74401 cccagagcga cctgaccctg tgtgagggct tcagcgaggc cctgaagcag tgcaagtaca 74461 accacggtga gcggctgctg cccgactggc gccagggtgg gaagggcggt ccacggctcc 74521 cactccttcg gggtgctccc gctattccca ggtgctcctg cacttcccat gtgctcccga 74581 ttctccctgg tgctccctct cctcctggct gctcctttgc ctcccaggtg ctcccacttc 74641 tccctggtgc tcctgctcct cccggcggct cctgtacctt cggcctgacc tcctccctct 74701 acaggtctga gctccctgcc ctaagagacc agagcagatt gggtggccag ccctgcaccc 74761 acctgcaccc ccctcccacc gacagccgga ccatgacgtc agattgtacc caccgagctg 74821 ggacccagag tgaggagggg gtccctcacc ccacagatga cctgagatga aaacgtgcaa 74881 ttaaaagcct ttattttagc cgaacctgct gtgtctcctc ttgttggact gtctgcgggg 74941 ggcggggggg agggagatgg aagtcccact gcggggtggg gtgccacccc ttcagctgct 75001 gccccctgtg gggagggtga ccttgtcatc ctgcgtaatc cgacgggcag cgcagaccgg 75061 atggtgaggc actaactgct gacctcaagc ctcaagggcg tccgactccg gccagctgga 75121 gaccctggag gagcgtgccg cctccttctc gtctctgggg gcccctcggt ggcctcacgc 75181 tctgtcggtc accttgcccc tcttgctgat gcaatttccc cgtaattgca gattcagcag 75241 gaggaatgct tcgggccttt gcacctgacc gcatgagcag aggtcacggc cagcccccctt 75301 ggatctcagt ccagctcggc cgcttggccg tgacgttcca ggtcacaggg cctgccggca 75361 cagaggagca ggcccttcag tgccgtcgag cactcggagc tgctgcctcc gctgagttca 75421 ctcagtgtct acgcacagag cgcccactgt gtaccaggcc ctattccacg ttccccagtc -continued 75481 accgagcccc cagggctggt ggggacctgc cctcgggtac actgtgtccc gtcacgtggc 75541 tttacgtgtg tctctgaggg aggctggcat tgcggtccac ctctcagcac aaacatctgt 75601 cccctgggaa gggggtccca tttctgggtg cgagcagccc cctggggtcc gtgtctcctc 75661 cttacctggc tcaaggcccc ggctcctggg tcctggacag cagggagccc acccctcggg 75721 gctgtggagg gggaccttgc ttctggaggc cacgccgagg gcccaggcgc cgcctccggc 75781 cgtcgccctg agggagcagg cccgacgcca gcgcggctcc tctgtgaggc ccgggaaacc 75841 ctgcctgagg gtgcgggtgg gcaggtgccc ctgcccccag gctctcctgt gtgagtgaca 75901 ctcaccagcc agctctggat gccacccatc cgggttctcc aggaggcact catagcgggt 75961 ggggtcccct ccctcccccc tctgtggagg gagggagtct gatcactggg aggctggtgg 76021 tccgtacccg cccccccgac tctggacgtg tttactaccc ccgcctgggc tcaggacagg 76081 gcattggatg ggaaggacag ggctgggtcc tggccaggct gggggctctg cagggcatgg 76141 gtgcccctgt ctcttcttat attccaacgt cactgcaggg gggcgcaaat cttggacccc 76201 acttactgat gatctgcatc aggacatagg tccccccctcc tgcagcgggg ggctggccac 76261 ggagggcgct ggggaaggcc cctcctccag cccctcggcg aggctcacca ggtgcccatc 76321 ctcagccagc agggcgacgc tcgctgggag ggcggagagg gaggcagggc agggctggta 76381 cgacccccgc tggggcgggg gggccctcag ccggtcctcc agcacccttg ctgccccccc 76441 tcaccgtcag gggcacctg gccgctctgc ctcaggtggg cggtgagggt cccaaggcca 76501 caccaggtgt tcaccagctc ccagcagctg gctgtgggag aggggcagag gtgggcgcat 76561 ggcacccgcc ttccccccag accaggatgc tctgccttcc tcccgcccat ctccccagac 76621 atctgaagga ctcttgcctc caccatgcag ccccgcctcc accagaagct caggttcccc 76681 gcccccccctc cccgaagctg caggacccct gaccagcgaa gagatgggac agttggaaca 76741 cacgctcccc cagcagcggc acagcagctg tgtggcccag aagagcccgc ctgtttccct 76801 caagcaactc cccatggatg tcatcccatg gacacccccct tccccacacc gcctcctcgt 76861 tctccccctc caaggcagag ggaacgcacc cccacctgtc tgctaggaca ggggacccca 76921 cttacctccg aacatcacct tgataaacat ggccgtggtg gggacagatc cctccgaccc 76981 ccaacttccg acctggggaa ggagctgggg tggagctcga ctgcagggtg gggccctgtg 77041 ggaggtgtac gggtggagag ggtgatgggt gggtgggctc aagcggagct ccttgctcag 77101 tccaggcggt ccctgcagct agtccaggat cctcagcctt ctccccctca ctggatcagg 77161 gaagactgag gttccctccc ctgccccccc acccagcttc caagctggtc tctgtggcag 77221 tgggagctgc caagaggtct gagcggccag tatccgggta acggggtttg tggagggtcc 77281 gggcattccc ggtgcagggc tctagtgggg gctggagcct cgggcccaga gctgtccaga 77341 gaccagtgcc ctcccaccgc cgccgcccgc aaggagagac agagctccca ggcggggagt 77401 cggaggttcc tggagggggga gcatcctcaa ctctgcaggc cccccttccca ggcgcactcc 77461 cggcctcccc gtcttctgtc ccctgctctt gttgaagtat gattggcata cagttcacag 77521 ccactcttcg gagtgttctc cacactaagg atacagaaca tgtccctcgt cccccccaaac 77581 tcccagccag gctgtcacga agagggaggc ggccgacggg gcagggcctt gcactcctgc 77641 gtgtggggtc cacaggggtc gtccccgtgt cggtggcccc ttcctctcac gccaggaggg 77701 tccccttgcc tggaggtgcc gtggatccgc tcgctgcctg ctctttgggt tgtttcccgc 77761 atggggtgat gatgaagagg ccagtacaga cactcgccag caggtctctg ggtgaacagg 77821 catttatttc tctttcctga gggcagatcc tgggagtggg gtgccggacc gtccggggag 77881 agtatgcttc tgtttctaag aagctgccgt gttctccagt gtgctgcacc atgtcacggc -continued 77941 ccctctgtgc gtctggactc aggagacctc cttctcagcg gccctccccc ccaggtggtc 78001 aggccatctg tgcccttctg ggggcagagc tcagcgccgg aggcgggagg aggcccagat 78061 cccagcgcag cccaccagcg ttgctctgct tccctcggca ttcatagctg gagaaagggc 78121 aaggagcacc ggctgaagcc ccacctggag gacgcacttc gatggcagca ggtgctcaga 78181 ggtggccccg ggcagcattc cccagacgca caggccagtg ctttcttccc aggacaccac 78241 tgtgtctggg gacccgagtc ctgcagcacg gtcgggagcg gctgtgccca gattccggcc 78301 tgcacccttg gctccagcca ccacccctgt ttgtcaaggg gtttttgtct ttcgagccgc 78361 cgaggaggga gtcttttgtc tgcagtgtca cagaagtgcc ataaagaggg gcccacagtg 78421 ggagctttat aacattggtg cggagggctg taacaggtca gggaggcact tgagggagcc 78481 ttctagggcg atggagatgt tctaaaattt ggtctgggta caggctacag agatgtgtgg 78541 gtgtgtgtgt gtgtgtgtgt aaaaccctcg agccacacgt gtgaggtctg tgcatgtgac 78601 cgtacacagg agacctcggt ggaaagcagc cacctgctct gactgcacct gtggatttcc 78661 agctcctgcc ctcaggcggc cctgcggggc ccactggctg acggggagac ggcaccgccc 78721 tccccccgctg tcagggtggg ggggctgacg atttgcatgt cgtgtcaggg tccagcggcc 78781 tcccttgcgt ggaggtcccg aagcacctgg agcgccgccc gcagaacagc ggactcctgc 78841 ctgcctccct gcctctggcc atggcctgcc cgcctctggc cctctttctg ctcggggccc 78901 tcctggcagg tgagccctcc caaggcctgg ctcacctagg ggtgtgtaag acagcacggg 78961 gctctagaag taaatcgcgg ggaagtaaat cgtagtgggc agggggggatg gtttccgaag 79021 gggccctgag ggggacagga gacctggcct cagtttcccc actggtgagt gaccagatag 79081 ccagggtacc tttggactct gactctgggg ggctctcaga gactggtctc ctactcagtt 79141 tttcagaggg gaagctggtg tggccttgtc actgccctgc agggcctcag ggacaagcta 79201 tccctgagga ggtctccagc agtcagtggc cggaggctga gccgatggat atagtaacag 79261 cccaggcggc ctcttggggg tggtcagcct gtagccaggt tttggacgag ccgaagtgac 79321 ctaagtgatg gggtctgca gagcaaggga tgagggtggg cagcaggagg acccagagcc 79381 caccagccca ccctctgaat tctggaccct tagctgcatg tggctccttg ggaagacggg 79441 gcttaagggt tgcccgctct gtggcccaca cagtgctgat tccacagcac tggctgtgag 79501 cttttgggag cagattctcc cggggagtct gacccaggct ttgtggggca ggggctggag 79561 ggaaggggcc caggccagac ctgagtgtgt gtctctcagc ctcccagcca gccctgacca 79621 agccagaagc actgctggtc ttcccaggac aagtggccca actgtcctgc acgatcagcc 79681 cccattacgc catcgtcggg gacctcggcg tgtcctggta tcagcagcga gcaggcagcg 79741 ccccccgcct gctcctctac taccgctcag aggagcacca acaccgggcc cccggcattc 79801 cggaccgctt ctctgcagct gcggatgcag cccacaacac ctgcatcctg accatcagcc 79861 ccgtgcagcc cgaagatgac gccgattatt actgctttgt gggtgactta ttctaggggt 79921 gtgggatgag tgtcttccgt ctgcctgcca cttctactcc tgaccttggg accctctctc 79981 tgagcctcag ttttcctcct ctgtgaaatg ggttaataac actcaccatg tcaacaataa 80041 ctgctctgag ggttatgaga tccctgtggc tcggggtgtg ggggtaggga tggtcctggg 80101 gattactgca gaagaggaag cacctgagac ccttggcgtg gggcccagcc tccccaccag 80161 cccccagggg cccagactgg tggctcttgc cttcctgtga cgggaggagc tggagtgaga 80221 gaaaaaggaa ccagcctttg ctggtcccgg ctctgcatgg ctggttgggt tccaacactc 80281 aacgagggga ctggaccggg tcttcgggag cccctgccta ctcctgggtg gggcaagggg -continued 80341 gcaggtgtga gtgtgtgtgt ggggtgcaga cactcagagg cacctgaagg caggtgggca 80401 gagggcaggg gaggcatggg cagcagccct cctggggtag agaggcaggc ttgccaccag 80461 aagcagaact tagccctggg aggggggtgg gggggttgaa gaacacagct ctcttctctc 80521 ccggttcctc taagaggcgc cacatgaaca gggggactac ccatcagatg nnnnnnnnnn 80581 nnnnnnnnnn nnnnnnnnnn nnnnnnnnnn nnnnnnnnnn nnnnnnnnnn nnnnnnnnnn 80641 nnnnnnnnnn nnnnnnnnnn nnnnnnnnnn agagggtggg tgggtggaat ttaatatagt 80701 ggtgcgcgtg gagcgtgggc ggcgcattta aggcggtcat ctaaaatagt ggataggggg 80761 tggtgtgaca ataacgggtg gtggatgtgg tttacggggg gtgcaatagt tctgagtttg 80821 ttagtgtctt cttgatgggg ttgcggcgtg tggacctacg ccttgagtat gtgggggggg 80881 aaaagcagtg agggtagtag ggatgggaaa tattggtgga ggttctttgt tggtgtattt 80941 tttggtatta tgttgggtgg tggagtggtg ggttgggtgt aatttcgctt gcgttatgtg 81001 tttttttct ttttcgtgtc gtgggttggg ttggttggtg ctttgtggtg gtggtgggtt 81061 gtggtataaa aaaaaatgtg tggttgtgct cagcttagcc ctataacggt cggctttgtt 81121 tcttgtttgt tctgtgggcg tgagcggatg gctcgggcct ccgtgctccg cggcgcggcc 81181 tcgcgcgccc tcctgctccc gctgctgctg ctgctgctgc tcccgccgcc gccgctgctg 81241 ctggcccggg ccccgcggcc gccggtgagt gcccgccgtc ctccagcccc cccgccccgc 81301 cccgccctcc acgccgaggg gcgccggctc gcagagctgg atccaagggg gtgcccggga 81361 gtggcccggc gcggcccgtt accccgaaac gctgtctggg tgccccgggg gtgtggtgga 81421 tagtgagctt cccgtccctg gaagtatgca agtgaagccg gcgccgggat cgctcgggct 81481 ggctggtgag cgggcgggac tcggtcgggc gctagacgca cgccgccagc cccccagctc 81541 ccagacctgc ccactccgcg cccgcccggc cgcgatcccg ggtgtgtgtg tgtgttgcag 81601 gggagggaca gcgggagtgg ctacagggct cccgactcac cgcagggaca aagacccgcg 81661 ggtccccagc tggcgtcagc cgccaggtgt gtggcctcgg tgagcacacc tccaggcggg 81721 agggttgagg gaagcgctgt ggggagggca tgcggggtct gagcctggaa gagacggatg 81781 ctaccgcctg ggacctgtga gtggcgggat tgggaggcta tggaatcagg aggcagccta 81841 agcgtgagag ctccggtgtg gcctggcggg ggtggtaggg gggggacgcc cctgtgtgtg 81901 ccagcctgcg tgtgccctaa aggctgcgcc ctccccact gctggggctt cgggggacca 81961 gtcacagcct aggctactgc aggcgcacag ctccccggga gcccggccca cgcgggtgtg 82021 ccgctgagcc tccagcctgt cggggcaggg gtggggggca gggatggggt cgttagcggg 82081 gttgggggca gacgcccagg cagactctct gggcacagct ccggtgacaa gggaggtctg 82141 gcaagcctgg gccccttctg tccagccacg ccagctctgc cctggccagt cttgcccct 82201 ggcagtgctg gggatggaag ggggagcggg tacctcagtc tgggggccct gcctcctccc 82261 cagccccgcc cggcccccta ggcctagggg cagagtctag ggtcaccct ggggagctgc 82321 tgaatccgcg ggtttaggaa ccggagggac ctgggctttt gaaccacgtg gccctaggtg 82381 agccctccgg cgcctcggta gccctcaccc ccagccttgt ccaggtgggc gggtgggagg 82441 cgacagtgcc cactgctggg ctgaacagcg tctgcaggga ggccaggaga gctgggcaca 82501 cggacacgtt ccatcacctg gagctgccac tgtgccactt gtgcggggtc aggcggggtc 82561 tgagccgggc tgtcatctgt cacgccacag atatgcaggg ggcactcggg gtcgcctcgg 82621 acatgcttat ccctggacgg ctgttggcag ggccgggaag gctctgtaaa tatttatcca 82681 tcccagctca cagctttcag ggttgatgaa agccccgccg cccgcccact gtgggggacc 82741 ccgccttccc ttctggagcc agcggggtga gggggtgggg gagatggacc tgcctgccca -continued 82801 ggagcaggcg gtgtgactct ggcaggtcac ttgacctctc tgagcctcag ggagggcccg
82861 ggatggtgtg cggatgctct ctgccttcct cccagcctga ccagtgtcct cccctcgggg
82921 tcgcctcctg cccaccgcag agggggtggc tatggggacc tgggccgatg gcaggcaggc
82981 cggagagggc atgcccggct cagccgtgcc cagcacttcc cagtccaggg gcccccgcca
83041 ctcccagccg ctggctgcct cccattttcc cgattgcagg ttggccccga ggctgaccgg
83101 agcctctggc tcagctggga gactgaattc cccaagcaat tcctcaagga tgtgtgaggc
83161 tgtggtgtgg tgcctatccg ggagaggtgg ggtgagcgga ctgggcacct ccgcccaggg
83221 caggcccagg gagacgctgg ctgacgagca ggcaggcctg caaggaggac gagcagccat
83281 ctcaggaatg tgggttttgg agacaagcca cagctggggg ggtgggggg ccatgggtgg
83341 ggaggcctga tccccaggtc taggtccagc tctgggctcc ctcgccgtgt gaccctgggc
83401 caagacctgg acctctctgg gccccgtctc ttcccctggg aggtggggcg atgcctgctc
83461 cccaatcccc cagggctgtg gatgaggcag acgaggtgtg tgctcatccc cacctcactg
83521 ccttccagca gccccgggcg gggggggtgg tggggactgg cgcacccagg tgaggatcag
83581 gccttggagc tagggagggc cccccagccc caggccagaa aggacacggg gagacagaat
83641 gcaggagggc ggcagagcag gggccagcgg tggggaaact gaggccaaga gcctgtggac
83701 gatgtgctcc aggaaaggac ctcgctgcct ggggcctgga tcctagagcc tccaggagcg
83761 gtgaccatga cgtgggcagg gaaccggagg ccccggcttg caggtggacc cggcgcgagt
83821 cactcttcct ctctggccct gagagcttcc ttccagctgc cgctcctgtg ttctaatgtc
83881 aagtctggag gcctgggggg caggtggggg ctgactgcca ggtgggggag ggcaggaatt
83941 tggcagagca gcgtcccaga gtgggagaag ccagcccatg gaggggactc tctccatgcc
84001 tgctgcccca aagggcgtta tagagagagg tcggttaccc cttcgccatg gccccgttcc
84061 cattgaacag atgggaaagt ggaggctgag agaaggctgt gacttgccca gggtctccgt
84121 ggcatggaac tgggcctgct gagtctcagg ccggggatct cgctgctgca ctgagcacgc
84181 caggatgcag gggtctgggc ctggacctag cgcctcgtgg gggcaagaga ggaaggcacg
84241 ctgggcctgc ctgtcaccct ccaccccacc gtggcttgtt gctcaggcct tcctgggggc
84301 agaggagagg ggagatttca ctcgctggca ggctaggccc tgggctctct ggggctccgg
84361 gggaacaatg cagccctggt ctttctgagg agggtccttg gacctccacc agggttgagg
84421 aaaggatttc tgttcctcct ggaggtcacg gagccgacat ggggaggagc aggggcaggc
84481 ccggggccca catcctcagt gtgagacctg gacgtgtgtc ctcccacctg acgctggggg
84541 tggggggtgg gggccggggg ggatccagtg aaccctgccc ccaaattgtc tggaagacag
84601 cgggtacttg gtcatttccc cttcctcctc ttcgtttgcc ctggtgggga cagtccctcc
84661 cctggggaag ggggacccca gcctgaagaa cagagcagag ctggggtcag ggtgtgctg
84721 ggagcgcaga gagcctcctg ctctgcctgc tggtcattcc tggtggctct ggagtcggca
84781 gctggtgggg agcggctggg gtgctcgtct gagctctggg gtgcccaggg cctgggagag
84841 ttgccagagg ctgaggccga gggtggggcc ctggcggccc ggctcctgcc ccaaatatgg
84901 ctcgggaagg ccacagcggc actgagcaga caggccgggc cagacgggcg ctgaggctcc
84961 cggcctctcc cccagctccg ctgtgaccct cacctgcggc ccggggtgcc agggccccg
85021 cttggttctg ccgtgtcttt gcaggctgat cccacgggct ctccctgcct ctctgagctt
85081 ccgccttttc caggcagggg aaccgcgacc tccaggctgg gacgcgggga gggtgtatgc
85141 gccaggtcag aatcacccct ccaccgggag agcgtggtcc aggggccctg gcagggtggg -continued 85201 gaccgagcat ctgggaactg ccagccaccc ccacccatgc agaggggaca tacagaccac 85261 acggaggctg tgcctccgct gcagcaactg gagaacaccc agccgcggcc aaacataaat 85321 aactaaataa taaaagtttt aaagatcgtt acttaaaaaa acaagtgtgc cccagtgatc 85381 ggaccccagt tcccggtgcc ctgagtggtg ccggccctgt gctgagcatg gcctggttgg 85441 ttcaccccca gatccacact aaagggtggg atcacccccta ctagtcaggt gagcagatgc 85501 aggggggggag ggcggcagcc cctccatgct ggtgggtggc cgtggtgggt gtcctgggca 85561 ggagccagct cacggagctg gagaggacag acctgggggg ttgggggcgc ccaggaagaa 85621 acgcaggggg agaggtgtct gccgggggtg gggtcccctt cgaggctgtg cgtgaagagg 85681 gcaggcgggc ctgcagcccc acctacccgt ccccggccca aacggcggga gtaagtgacc 85741 ctgggcacct ggggccctcc aggaggggggc gggaggcctt gggatcagca tctggacgcc 85801 agtcagcccg cgccagagcg ccatgctccc cgacggcctc cgctggagtg aggctgcgct 85861 gacacccaca ccgctgaccc gggcctctct cccgctcagg atgccccccg ccgccacccc 85921 gtgagcagag ggccacagcc ctggcccgac gcccctcccg acagtgacgc ccccgccctg 85981 gccacccagg aggccctccc gcttgctggc cgccccagac ctccccgctg cggcgtgcct 86041 gacctgcccg atgggccgag tgcccgcaac cgacagaagc ggttcgtgct gtcgggcggg 86101 cgctgggaga agacggacct cacctacagg tagggccagt ggccacgagc tggcctttga 86161 tctccacctg ctgtctgaga cacgctggag ctggggggag ggcagatccc tatggccaac 86221 aggctggagt gtcccccaac tcccgtgccc actgctcaac accccaaacc cacacttaga 86281 tgcactccca tgccctccct tgggagcacg gtctccacac ccacctggcc accccacaca 86341 cccgtggggc acggccgtta gtcacccacg caacctctgc gggcaccgtg ctgcgggcca 86401 ggccctggga ctctcagtga gggaggcaga cacggcccct cctccggggg agcgaggtgc 86461 tccccacgcc cggttcagct ctagcaccgc actcgggacc ctcacaggga gggacccact 86521 ggggcaggcc aggtgacggc tcgggtgacc tcggcccctg gcgctgagac tacacttcct 86581 gcagtgggcg gcgaagatgg gtgtggtgtc ccacgtcgtt gcagcgggga ctcctggggc 86641 ctcggaagtg tcctgggcgg ggagcctggg gagcaggaag ggcaggtctt ggggtccaag 86701 gcctccccac ggtcaggtct gggagggggc ctcggggctc ttgggtcctt tccgcccagt 86761 gcagaccctc gcggccacct aagggcacac agaccacaca aagctgtgcc catgcagtgt 86821 ggggagtggt gcgcaccctc agagcacact gggcccacat cacgcacgcc tgccccctca 86881 ctgtgcatcc ggggaaactc ctggccccga cagccagcgg ggctgacgct accccgtgag 86941 ccagacccag gcccccctca ccgcccctgt cctccccagg atcctccggt tcccatggca 87001 gctgctgcgg gaacaggtgc ggcagacggt ggcggaggcc ctccaggtgt ggagcgatgt 87061 cacaccgctc accttcaccg aggtgcacga gggccgcgcc gacatcgtga tcgacttcac 87121 caggtgagcg ggggcctgag ggcacccccca ccctgggaag gaaacccatc tgccggcagc 87181 cactgactct gcccctaccc accccccgac aggtactggc acggggacaa tctgcccttt 87241 gatggacctg gggggcatcct ggcccacgcc ttcttcccca agacccaccg agaaggggat 87301 gtccacttcg actatgatga gacctggacc atcggggaca accagggtag gggctggggc 87361 cccactttcc ggagggggccc tgtcgaggcc ccggagccgg gcccgggctc tgcgtccgct 87421 ggggagctcg cgcattgccg ggctgtctcc ctcttccagg cacggatctc ctgcaggtgg 87481 cggcacacga gtttggccac gtgctcgggc tgcagcacac gacagctgcg aaggccctga 87541 tgtccccctt ctacaccttc cgctacccac tgagcctcag cccagacgac cgcaggggca 87601 tccagcagct gtacggccgg cctcagctag ctcccacgtc caggcctccg gacctgggcc -continued 87661 ctggcaccgg ggcggacacc aacgagatcg cgccgctgga ggtgaggccc tgctccccct
87721 gcccacggct gcctctgcag ctccaacatg ggctcctcct aacccttcgc tctcacccca
87781 gccggacgcc ccaccggatg cctgccaggt ctcctttgac gcagccgcca ccatccgtgg
87841 cgagctcttc ttcttcaagg caggctttgt gtggcggctg cgcgggggcc ggctgcagcc
87901 tggctaccct gcgctggcct ctcgccactg gcaggggctg cccagccctg tggatgcagc
87961 cttcgaggac gcccagggcc acatctggtt cttccaaggt gagtgggagc cgggtcacac
88021 tcaggagact gcagggagcc aggaacgtca tggccaaggg tagggacaga cagacgtgat
88081 gagcagatgg acagacggag ggggtcccgg agttttgggg cccaggaaga gcgtgactca
88141 ctcctctggg cacagctggg aggcttcctg gaggaggcgg ttctcgaagc gggagtagga
88201 taaaaggtat tgcaccccat gaagcacgtg tgatccttgc ccctagagac aaggctctgg
88261 ggctcagagg tggtgaagtg acccacatga gggcacagct tggagaatgt cgggagggat
88321 gtgagctcag tgtgccagag atgggagcct ggagcatgcc aaggggcagg gcctgctgcc
88381 tgagagctgg cactggggtg ggcagccaag tgcagggatg gagcgggcgc ccaggtggcc
88441 tctttgctgc tcagaacgac ctttcccatg tatacctccc agcgccgctg gcattgccca
88501 gtgtccttct tgggggcagg agtaccaagc aggcattatt actggccttt tgtgttttat
88561 ggacaacgaa actgaggctg ggaaggtccg aggtggtgtt ggtggcggaa ggtggccgct
88621 gggcagccct gttgcagcac acacccccca cccaccgttt ctccaacagg agctcagtac
88681 tgggtgtatg acggtgagaa gccggtcctg ggccccgcgc ccctctccga gctgggcctg
88741 caggggtccc cgatccatgc cgccctggtg tggggctccg agaagaacaa gatctacttc
88801 ttccgaagtg gggactactg gcgcttccag cccagcgccc gccgcgtgga cagccctgtg
88861 ccgcgccggg tcaccgactg gcgaggggtg ccctcggaga tcgacgcggc cttccaggat
88921 gctgaaggtg tgcagggggc aggccctctg cccagccccc tcccattccg cccctcctcc
88981 tgccaaggac tgtgctaact ccctgtgctc catctttgtg gctgtgggca ccaggcacgg
89041 catggagact gaggcccgtg cccaggtccc ttggatgtgg ctagtgaaat cagtccgagg
89101 ctccagcctc tgtcaggctg ggtggcagct cagaccagac cctgagggca ggcagaaggg
89161 ctcgcccaag ggtagaaaga ccctggggct tccttggtgg ctcagacagt aaagcgtctg
89221 cctgcaatgc gggagacctg gattcgatcc ctgggtcagg gagatcccct ggagaaggaa
89281 atggcaatgc cctccggtac tgttgcctgg aaaattccat ggacagagca gcctggaagc
89341 tccatggggt cgcgaagagt cagacacaat ggagcgactt cactgtctta agggccacct
89401 gaggtcctca ggtttcaagg aacccagcag tggccaaggc ctgtgcccat ccctctgtcc
89461 acttaccagg ccctgaccct cctgtctcct caggcttcgc ctacttcctg cgtggccgcc
89521 tctactggaa gtttgacccc gtgaaggtga aagccctgga gggcttcccc cggctcgtgg
89581 gccccgactt cttcagctgt actgaggctg ccaacacttt ccgctgatca ccgcctggct
89641 gtcctcaggc cctgacacct ccacacagga gaccgtggcc gtgcctgtgg ctgtaggtac
89701 caggcagggc acggagtcgc ggctgctatg ggggcaaggc agggcgctgc caccaggact
89761 gcagggaggg ccacgcgggt cgtggccact gccagcgact gtctgagact gggcaggggg
89821 gctctggcat ggaggctgag ggtggtcttg ggctggctcc acgcagcctg tgcaggtcac
89881 atggaaccca gctgcccatg gtctccatcc acacccctca gggtcgggcc tcagcagggc
89941 tgggggagct ggagccctca ccgtcctcgc tgtggggtcc catagggggc tggcacgtgg
90001 gtgtcagggt cctgcgcctc ctgcctccca caggggttgg ctctgcgtag gtgctgcctt -continued 90061 ccagtttggt ggttctggag acctattccc caagatcctg gccaaaaggc caggtcagct 90121 ggtgggggtg cttcctgcca gagaccctgc accctggggg ccccagcata cctcagtcct 90181 atcacgggtc agatcctcca aagccatgta aatgtgtaca gtgtgtataa agctgttttg 90241 tttttcattt tttaaccgac tgtcattaaa cacggtcgtt ttctacctgc ctgctggggt 90301 gtctctgtga gtgcaaggcc agtatagggt ggaactggac cagggagttg ggaggcttgg 90361 ctggggaccc gctcagtccc ctggtcctca gggctgggtg ttggttcagg gctccccctg 90421 ctccatctca tcctgcttga atgcctacag tggcttcaca gtctgctccc catctcccca 90481 gcggcctctc agaccgtcgt ccaccaagtg ctgctcacgt tttccgatcc agccactgtc 90541 aggacacaga accgaactca aggttactgt ggctgactcc tcactctctg ggtctactt 90601 gcctgccacc ctcagagagc caaggatccg cctgtgatgc aggagtgagt gaagtcgctc 90661 agccgagtcc gactctttgc aaccccatag gactgtagcc taccaggctc ctctgtctat 90721 gggatttttc aggcaagagt gctggagtgg gttgccattt ccttctccag gggatcttcc 90781 caaccctggt ctcccgcata gcaggcagac tctttactgt ctgagccacc aggcaatgca 90841 ggagacctag gttcagtctc tgggtgggga agatcccctg gagaagggaa tgacaacctg 90901 cttcagtatt cttgattggg gaatcccatg gacaaaggag cctggaggcc tacagcccat 90961 agggtgcaaa gagacacgac tgagcaagtc acacacacag agccctacgt ggatgctcat 91021 agcggcacct catagctgcc atgtatcagg tgttggcatg ggcagccatc agcagggggc 91081 catttctgac ccactgcctt gttccaccgg atacacgggt gccttcctgt gtgtcgggcc 91141 cactcggctg tcagcgccca agggcagggc tgtcgggagg cacagggcac agagttaagg 91201 aggggatggg gacgttagct cctccccagc tctcagcgga tgcagcaggc aaaacaaacg 91261 ctaggaatcc tgccaaaccc ggtagtctct gcccatgctc gccccatccc cagagccaca 91321 agaacgggag ctggggggtg gcccggagct gggatactgg tccctgggcc cgcccatgtg 91381 ctcggccgca cagcgtcctc cgggcgggga aactgaggca cgggcgcctc cggcttcctc 91441 cccgccttcc gggcctcgcc tcgttcctcc tcaccagggc agtattccag ccccggctgt 91501 gagacggaga agggcgccgt tcgagtcagg gccgcggctg ttatttctgc cggtgagcgg 91561 ccttccctgg tacctccact tgagaggcgg ccgggaaggc cgagaaacgg gccgaggctc 91621 ctttaagggg cccgtggggg cgcgcccggc ccttttgtcc gggtggcggc ggcggcgacg 91681 cgcgcgtcag cgtcaacgcc cgcgcctgcg cactgagggc ggcctgcttg tcgtctgcgg 91741 cggcggcggc ggcggcggcg gaggaggcga accccatctg gcttggcaag agactgagnn 91801 nnnnnnnnnn nnnnnnnnnn nnnnnnnnnn nnnnnnnnnn nnnnnnnnnn nnnnnnnnnn 91861 nnnnnnnnnn nnnnnnnnnn nnnnnnnnnn nnnnnnnnct gcaggtgccg gcggtgacgc 91921 ggacgtacac cgcggcctgc gtcctcacca ccgccgccgt ggtaaccgcc cccgggggtt 91981 gccaaggtta cgattggacc ctccccgccc cgaccctgct ccccctagggt gggtgggtcg 92041 gggggcagtt tctaagatct cctggttccg cagcagctgg aactcctcag tcccttccag 92101 ctctacttca acccgcacct cgtgttccgg aagttccagg tgaggccgcc ccgccccttg 92161 cacttgctgg cccaacccct cccgcccagc gctggcctga ccgcccccca ccccgcccac 92221 cccacgcagg tttggaggct catcaccaac ttcctcttct tcgggcccct gggattcagc 92281 ttcttcttca acatgctctt cgtgtatcct gcgccgtggt ggaagcggga ggagggcggg 92341 gcgggggacc gggcgggagg cagcgggccc cgggaagctg agaccctcca aggggcacgc 92401 ttcctatacc aaagccgcag gttccgctac tgccgcatgc tggaggaggg ctccttccgc 92461 ggccgcacgg ccgacttcgt cttcatgttt ctcttcgggg gcgtcctgat gactgtatcc -continued 92521 ttcccgggct cggggaccta tgggtccggg cctctgctgg ccctgaggcc ctgcttgagc 92581 gcatgccaca gagggagagt tgcgaccccg agctgagggt gtttttgagc gtacatcacg 92641 tgctcagctg caggtgcccc tgtcgaactc cagggctaca cccaaaatac cacagggcag 92701 ggtgcccagg ggctgagtcc tgaatgcagg tagccaggag gatctagggc tgggcccggg 92761 ggctggggtg aagtggagag gcagggccga tcagggggcc cctggaggcc accgtttggt 92821 cttagagtgg gaagcgaaac caacctgctt gagggtttca ggggtttagg aagtcagagg 92881 ggccctgggc agggcacaag accttgactc tggcccagct actggggctc ctgggtagcc 92941 tcttcttcct gggccaggcc ctcacggcca tgctggtgta cgtgtggagc cgccgcagcc 93001 ctggggtgag ggtcaacttc tttggcctcc tcaccttcca ggcgccgttc ctgccctggg 93061 cgctcatggg cttttcaatg ctgctgggca actccatcct ggtggacctg ctgggtgagc 93121 ctgctgtcca gggagcctgc cccaagctgg gtgtgctggg ccagagccct ggtcctctcc 93181 ccgcccccac ccctcttccc cactcctggc gcccccatcc ttccagcccc tccaacaagt 93241 cagcctatag gttttactta ttcgagcctg acccatttgc tgacgcttgt gtggggcccg 93301 acccggtagg gatgggtggc tcagggtgcc tgctcacagc tccacttctt ctgacgtcct 93361 caggcctgac ctcctcccag gttctgccta ctctgggcca agcctggccc cacgctgggc 93421 tggctggccg tgcagggcat cagaccccca tgctttgggg gcttcagggc tgtggagggt 93481 ggcctcggca ttggcgcctc tcccacaggg attgcggtgg gccacgtcta ctacttcctg 93541 gaggacgtct tccccaacca gcctggaggc aagaggctgc tgctgacccc cagcttcctg 93601 tgagtgctga cagccttccc cacccccttc cccagatggc tctctacccc atgagggggg 93661 gggaccctgc cagctgccgc tcagcgtggg ctcctcccca caggaaactg ctactggatg 93721 ccccagagga ggaccccaat tacctgcccc tccccgagga gcagccagga cccctgcagc 93781 agtgaggacg acctcaccca gagccgggtc ccccaccccc accccctggcc tgcaacgcag 93841 ctccctgtcc tggaggccgg gcctgggccc agggcccccg ccctgaataa acaagtgacc 93901 tgcagcctgt tcgccacagc actggctctc ctgccgcggc cagcctctcc acgcggggca 93961 ggtgctgctg gccgagagcc agggccacca agcctgacgt gctctccgac ccagaacatt 94021 ggcacagctg gaggcccaga gagggtccag aacctgccca ctcgccagca gaactctgag 94081 cacagagggc agccctgctg gggttctcat ccctgccctg cctgtgccgt aattcagctt 94141 ccactgatgg ggctcacatc tcaggggcgg ggctgggact gggatgctgg gttgtgctga 94201 gctttggccg tgggggccct cctgtcccga actagcaacc cccaagggga cctctgcttc 94261 atttcccagc caggccactg aaggacgggc caggtgcaga agagggccag gcccttctg 94321 tgactccgaa gcctcaagtg tcagtgtttg cagagtccag tggctgaggc agaggcctct 94381 gggaagctct gcccctgccg tttgcagctg aggccggcag gagcctcacc tggtccccag 94441 ctcacgggca ttggaggacc agtccgcacg gtggtttact cctgggtcgg caccagccgc 94501 cgccggctgt ccctttcaca gaggataaaa gtactcgctc tggagttgga ctttaatgtt 94561 gtcatgaaac ctctggccca gcagcgggct ccgcagtggg tggcaggtga aggcccctcc 94621 ccgggcctct ccaggcaggt gccgcctggc cagcagggaa ggcaggcagt gtcatccccc 94681 actggctctg gggctcaggc tacctcctgc tgtggccgga acatctcccc cagtggtgga 94741 gcccagtgtc cgtgaggcca gctgggcctg aaaccttcct ctctgaagcc ccgctgtccc 94801 cttgccctgt atggagggca gaggctggag cgcaagttcc taggatgtgc ttgcgagacc 94861 cccgagccca ggggcgaggc ccatctcagc ccacccccga actggaaacc cttggagctc -continued 94921 tgcccctcgt ggtgtgaggc ccctgctatg cgaccctcag ccctgccagc aacggaaggt 94981 gcagggcccg ggcccacggg cttaacgcaa ctgggcctgg gtcacctgcg gggcctggtc 95041 ccaggaggaa gacccaggtg ccaccctcct gggtgccacg tccaggtcac gtggggaccc 95101 gtccatgtca cagaagatgc agggtcaccc ggtgagctgg cgccgggccc tgccagagca 95161 ccagccgcgg gtggaggtgg gccccagctc tcctgtcagg cacgtggtgc tgggaggtgc 95221 ggccggagca gtgcccacca gctgcagcag gacaggtggg cacaggccca ccagcagtgc 95281 ccgcacggga tgggccccctg caagggccag agaagccacg ctcctggctg ggggctgggc 95341 tgggactgac aggtggccct gccctctgcg ccccactact tcccagccac ccgggactcc 95401 aaggacttgc tgagctgggc aggtgggacg ccgaggggag tcaaactgct cgtgggggca 95461 ggaggggcgg tccacagggc tgagccctga gctgaaccct ggccctgctc gtggttgtgg 95521 gggtgggggg gtccagtggc gccctagccc tgctgaggcc cagctgggac gtgcgcgccg 95581 gagggcgagg ggccagccca tgccatgctg tcccccgttc tcagctccat gctaccactt 95641 tgaagaaaca gaacctgttg cctttttatt tagaaagtgt tgcttgccct gcctggggct 95701 tctatacaaa aaacaaacac agctcaacgt ggcctctcct gaccagagac gggcggtggg 95761 gactggggct cagcagacgg aatgtgtccc cggcggcggg agaccaggag gcccctggcc 95821 cgctcctcag gacggctggg ctgtccccac ctggtcccct ccgagccaga agatggagga 95881 gaggtgggct gatctccaga tgctccctgg gagccaagcg ccacggggtg gtcaccaggc 95941 cggggccgtg ttggccagac gcctcatccg cctgtgggag ggggagggca gcaaccccccg 96001 gatctctcag gcaaccgagt gaggaggcag gagcccccag cccctccctc ggccgctctg 96061 ctgcgtgggg ccctgaagtc gtcctctgtc tcgccccccct ccccagggag agtgagcctg 96121 ttctgggctg tggtcagacc tgcccgaggg ccagcctcgc ccggggccct gtcctgcctg 96181 gaaggggctg gggcagcacc ttgtgttccg gtcctggtcc cggatcttct tctccatctc 96241 tgcatccgtc agggtctcca gcagcgggca ccactggtca gcgtcgcctg tgttccggat 96301 ggcaatctcc accgtgggca gggggttctc actgtggagg acgagagagg tagacggctc 96361 acagagcagc tgcaggagag gcccctagaa agcagtgtcc accccgctgc gggcagacag 96421 gacatggagc ctggtttctg cacccggctc ccgacacagg gcggccgggc acgctgccaa 96481 catggcatct ccgggtctgc atgtggggag gggtccacag gacagtgctg caggtccagc 96541 cattcccagt ggacttgctg ggaggaggag ggccgtccgc cccgctcagt gtccaggaga 96601 aaggagagca aaggagtcca tccacccagg agtggagtcc cagggcccct gccctgacca 96661 gcctgcaggg ggcccctcgg cccacatcac aggggcccag aatccataag ccctgactgc 96721 tccaccccgg ggcccctcaa agacgcgcct agactccgtc cgagggccac ctgcacaccc 96781 tctggcgaag tggactcagg gctgggggtc agcctcggtg aggccgcaaa ggctggggac 96841 tcctggccga gctgctgcct ctgccaggag ccaggcccag cctgccggcg agcctcagcc 96901 acgccctcac ccaccctgcc cgcggcgcca cgctggcctc cgggtcctct cctctggcct 96961 cctgctgggc cactggtgct cagccccagc agtcggcctg ccaggagccc tgcagagtca 97021 gcccccagag ggaggagggg gcccggggga acagcacagg aacaaacaga cccctggcct 97081 tagttttagc tcctcatctg gaaaatgggg acagtgtcct tgctgcgagg ggtttcagag 97141 gaccactgcc atgcaacacc cagcacacac ccactgcgtg ggggctcggg cccgagccgg 97201 tgcccccgag tcccaggctg gtggctgggc cgccccagcc accctgccga cagctgcttc 97261 ccagccgggc ggtgctgcgg cagtccagaa gccagcactg cagacccaaa tgtcactcct 97321 cacgttgcgg gctcccagct gccttccttg ggggcagcag acacgaaagt caccaagccc -continued 97381 acgccgacgg gagcaaacac gtcttcctct taaacaagtg cgggtcccgg aggccctgtg 97441 tttacctccc tgtggctccg ggaagattgc atcccagggg gttgttctaa accaagggct 97501 gctcgggcca ggcctggaag gaggggcctg gagccaggag cccaccctta cgggcattcg 97561 gcttcctggg tctcaaggcc ggctgggacc ctgcattccc accacccgcc aggtgcaagc 97621 agggaggccg tgtcggagga ggcagagggc ctggagggtc gtcttcgacg tgacctcact 97681 tttacaacct cacaggtgcg gcaggccagc tgggaggcat ggctgtgccc tcctggtaga 97741 tgagaacaag actgcaggga gtgatccccc tgaacttccc caaccaggag gagacaaaac 97801 tcggtgtcgc cctcctgctt aagatcaact gactctggac aaggggccca gcccacccga 97861 tggggaaagg gcagtccttc caacaagcgg tgctgggacg ggacccggca ggccatggtt 97921 tctcagctat gacaccagca gcacaagcac cccgagaaaa acagctaagc tgggcactgt 97981 cacacaagtg aactccaaac ccaagaaaac cacaaaaagc ctgcggatct tcagatatgt 98041 gggaagggac ctgtatctgg aatgtataac gaactcctga aaagtgaaag tgttagtcac 98101 tcagtctgtt cagctctttg caaccccatg gacggtagcc tgccaggctc ctctgcccat 98161 gggattctct aggcaagaat actggagtgg gttgccatgc cttcctccag gggatcttcc 98221 caacccaggg attgaacctg tgtctctctt gcactggcag gcgggttctt taccagtagc 98281 gccacctgag tagaaacact ccaggtgccc tgagtgtcag agcaggaggg actcggccca 98341 ggcctgtgag gggaccctct ccgagtcccc tgctgcacag cagtgagagg tgcgttctga 98401 gtcagcctcc agggatgagg gacttggtgt cgacatcact cccaggacct caggatctgc 98461 tctgggaagc gaggctcccc aggctggccc caggcccgct ggcctcagct cgtgagccgt 98521 gcgtggacag gtgccatgag caggcctccc acgggactcg gggcgcggcc tggaccccgg 98581 ggctgccagt ggtcgcgggg ggccccgtgt ggcggctgtt ccctctcttg ctccgagtcc 98641 taggaacatg gtgggcgctg cctcctgggg tttctggaga agcagctgag atgcaaacag 98701 ccccacgcgc tccctcagct gttccctgtc acgggtggcc ccttggtgac ggcctccatg 98761 cagggacggt gacagctcga gcagccgcgt aaaaccacac ggggacggtg gcagctcgag 98821 cagccgcgta aagcctgaca tccaatttgg aagcctcccg cagtggaaga ggggcccggg 98881 gacggggctg cccggggcga gctccaccgg gtcgggggtc acgaggagcc cacccgcgtc 98941 cccgccacca gcacctggga ccagataccc tccccgctct gagggcggcc tgaacgccgc 99001 cccctcccac gggggcgccc accgcctgct cgtggactga acaagaggcg gcagtggcct 99061 ccagaccccc tcgggggagg gcagacctgt ccgagactga gcacaagtcc agggaatgag 99121 caagggtctc agtaatgtcc ccaccgggac gggacgggag gaggcgacag aggccgctga 99181 ggtgcggggc agccctcagt agctggcatc aaggccccag gcagtcccgg ggcatccccg 99241 cagggggcgg gggcgaccac cggcccgagc ccaggcagtc ccggggcatc cctgcagcgg 99301 gcgggggcga ccaccggccc gagccctacc tgaaggcgta ggtcttctga tgccagctca 99361 gctgtccccg gatgctgtag gcgatggtgg tgacgaactc cccgcccagc cccagctcgg 99421 agcacagctt cagagcgaac ttctcgggcg agttctcctt ctccgacatg tcccactcga 99481 actggtccac caaggagatg ttccccacgt ggatgttcag ctggcccggg agcacagaca 99541 tgagccagag cggccccctc tggggccagg ccgcaccctc accacccctt ctccccggaa 99601 catccccgcc tcgttcttgg ccgcgcccct gtgctgctac ttggggtaag gaaaacaacc 99661 cccatctctc tgaaaagggt taactagcga ggaagatgcg ctggtaactg gaaaactccc 99721 tacaaagaaa gcttggatct gatggcttca ctggtgaatt ccaccaaaca tttcaagcac -continued

```
99781 taacaccaat ccttatcaaa tcctgccaaa aaactgaaaa ggaaggaaca catcataact

99841 ccctgccttg ataccaaagc cagacaaaga tactacgaga aaggaaaggt gcagaccggc

99901 acttactgtg gacattgatg tgaaacctca gcagacacga gcaaaactac attcaccagc

99961 acgtcagaag aatcacacac cgttataaat gatgggatga tgacacaacc acattataaa

100021 cggtggggct tactctggtg atgtaaggac ggctcagtaa gaaaaccggt caatgccatg

100081 aaccacttga acagagtgaa ggacaaaaac cacacagtca tcttgataat tggaggaaaa

100141 tcattagaca aacttcaacg tgctttcacg ataaaagcac tcagtaaact aagatcagat

100201 ggaaaccaca tcaacaagat taattcagtc aaaaaattca ctgcaagtat cacccacaat

100261 ggcagaagac tggtaacttt tcctctaaga tcaggaacga gccaaagata cccagtcttg

100321 ccacttttgt tcaatatagc gttggaattt ctactcagtg cagtgcagtc gctcagtcgt

100381 gtccgactct tttcgacccc atggatcaca gcacgccagg cctccctgtc catcaccaac

100441 tcccggagtt cacccaaact catgtgcact gagtcagtga tgccatccag ccatctcatc

100501 ctctgtcgtc cccttctcct cctgcctcca atcccttcca gcagttaggc aagaaaaata

100561 aatcaaaggt atccacctgg aatggaagaa gtaaaactat ctctggtccg agatgttaca

100621 atcttatatg cagagtttaa gatgctaaca aaatactatt agaactaatg aatgaattca

100681 gcaaggtacc aggatacaaa gtcaacgtgc aaaaatcagc cgcatttcta catgctaaca

100741 ctgcacaatc tgaagaagaa aggatgaaca aattacaata acataaaaaa gaataaaatc

100801 cttagaaatt aacttgatca aagagatgta caatgaacaa tataaaacat actgaaagaa

100861 attgaagata taaataaatg gaaaaacatc ctatgtccat ggattggaag acttaaaatt

100921 attaagctgt caaggctatg gtttttccag tggtcatgta tggatgtgag agttggacta

100981 taaagaaagc tgagcaccga agaagtgatg cttttgaact gtggtgttgg agaagactct

101041 tgagaggtcc ttggactgca aggagatcca accagtccat cctaaaggag atcagtcctg

101101 ggtgttcatt ggaaggactg atgttaaagc tgaaactcca atactttggc cacctgatgc

101161 gaagagctga ctcatttgaa aagaccctga tgctgggtaa gattgagggc gggaggggaa

101221 ggggacaaca gaggatgaga tggttggatg gcatcaccga ctcaatggac atgggtttgg

101281 gtggactctg gaagttggtg atggacaggg aggcctggcg tgctgcggtt catggggttg

101341 tgaggagtcg gacacgactg agcgactgaa ctgaactgaa catgaatacc caaagcaatc

101401 tacaaagcca aatgtaatcc ctatcaaaat cccaatagca tttctgcaga aacaggaaaa

101461 aaaatcttaa aattcatatg gaatctaagg aaaagcaaag gatgtctggt caaaacaatg

101521 acgaaaagaa caacaaagct ggaagactca cacttcctga tttcagaact tactgcaaag

101581 atacaataat gaaaacactg tgggactaac gtaaaagcag acacgtgggc caacgggaca

101641 gcccagaaat aaactctcaa ataagcagtc aaatgatttt caacagagat gccaagacca

101701 ctcagtgaag gaaagtgttt gcaaccaacg gttttgggaa aaaagaaccc acatgcgaaa

101761 gaatgaagtg ggacccttac ccagccccat ctacagaaat caactcaaaa cagacagaac

101821 atatggctca agccataaaa cgctcagaaa aacagagcaa agctttatga tgttggattt

101881 ggcggtgatt tctcagatat gacgtcaaag gcataggtga taagcgaaaa aataaactgg

101941 acttcaccaa aatacaacac ttctatgcat ccaaggacac taccgacagc ataacaaggc

102001 agcccaggga aaggaggaaa catccgcaaa tcacagcatc tgggaacaga ccgctgcctg

102061 tgagatacag ggaaccgata aaaacaagaa aacagcaaaa cccggactca aaaatgggaa

102121 ggactccagc agacacagga gacagacaag ccgccagcag gtcactaatc agcaagcaag

102181 gcccgcaaag gcccgtatcc aaggctgtgg tttttccagt ggtcatgtag gaaagagagc
```

-continued 102241 tggatcgtaa gaaagctgag cgctgaagaa ttgattgaac tgtggtgttg gagaagactc
102301 ttgagagtcc cttggactgc aagatcaaac cagtccattc tgaaggagat cagtcccgaa
102361 tagtcactga aggactgatg ctgtagctcc aatactttgg ccacctgatt cgaagaactg
102421 actcattggc aaagaccctg atgctgggaa agattgaagg caggaggaga aggggacgac
102481 agaggatgag atggttggat ggcatcactg actccatgga catgagcttg ggcaagctcc
102541 gggagagagt gaaggacagg gaagcctggc gtgctgcagc ccgtgggtcc caaatctttg
102601 gaccaagcga ctgaacaata acaaatcaac agggaaatgc aaatcaaaac cacagtgaga
102661 tactgtccac caccaggcag gcgttcttca gcggggttcg gggcaggtgg tgccctcttc
102721 tctcgtaacg cccccaggac cgcgggggct gctgagacag catggggtgt gcttggccta
102781 gcctgcccat gacaagagtg gcagtgtgct cgcctcactg cgcccttccc tgctctgccc
102841 accagctggg ccacccctgg gaccacccag cttccgctcc gtggacggca aggccgcagc
102901 agcgcccgga cacgcccaga acgtggtgcc ctcctcagaa gtcggcctgt gcccttcctg
102961 ggacaagccg cccaagagac agtcttccag agccctgccc cacaacacgg accccagaca
103021 ggctcctgtg gaggcctcca cgcacctccg cacctcgcaa gccccgagga caaggcaggc
103081 ccgctgcggg tgaggagccg cctaccttga taatgacgcg ctggtctgac tggtcttcca
103141 ggatgctgtc cgtggggtag gactcgatct gctgtctgat ggcagaggca atggctggca
103201 cgaatgtcag tgggttcaga tccaggtcgt cacagagaat ctctgagaac atctccgggg
103261 tcatcagctt ctctgaaacg atgacggagc gggggaaccc ccagtggacc acagggccta
103321 cggtcagcgt gctcagcccc ggcctccccc agccttgcct cctctgccac cgcccccccg
103381 ggtgacgaca ggacccccctg gcagcacgca gacagagctg agtgcacgcc agccagggcg
103441 gcggacggac cattcatgtt ccaggtaaag gcatcccgca gcttctgccc gtcaatctcc
103501 atgtccagtc ggatggggac cagcacctcg ggctgggacg cgttctcgtg gatcacggct
103561 gggtcgtggt cgtcgaagct ggaaggggag cggccgcgtg ctcagcaaag cgggctgggc
103621 ccctgtgccc agggcctccc tctctgcacc actggtcgct gagacctgcc cagagaggac
103681 ctgtccacta cgggccgggc cggcagaaac agggctggcg ggggtccacg cggggcggga
103741 ggggagctgc cgactcggca gcgggacaag ctcagaggtt ccctgcagga agagaggttt
103801 aagccccaga gcaggcagga ttctcccagc agctgtgggg aagaaagggt atgtccagaa
103861 gaagaaaccc tggaacaaag gccgaggggc aggagggttg aggagctgct tggagagcag
103921 tgaagggggg ctgggcggct ggggggtgct ggggagcctc ggtggccaag cacccagggc
103981 tccccacctg cagcctggac cccgagggag ccccagagga cggagagcaa ggcagctccg
104041 cactcacacc tgccctttag gatggggaag agggaagaga cgggggctgc ggggggcaag
104101 gaaaccaggc acgccccgct tagacccggg ggcgagaacc actttccaag aacgcagggg
104161 cgccaatgat gaacaatggg tagcagcccg caggcgggag gcccggtggc cgaggcccct
104221 caccagagcg ggaaggtccg cttcttgtcg cggcccatgc ggttcctgtt gatggtggtg
104281 gagcagggca cggcgtccag gtggtgcgag ctgttgggca gggtgggcac ccactggctg
104341 ttcctcttgg ccttctgttc cctgggagac acagacgccc gtccgctcag cctatgggcc
104401 aaaagccgcc ccccagccgc caggttgtgg ccagtggacg cccgccatgc ccctctgggc
104461 ccaggccccc atggggacct ctgtgcgccc agctccgcgg tggttattcc ccaggctcca
104521 agcggcacct gctcggggtc accagtttta ggggaggagg agagggcagg ggccccagcc
104581 cagtctgtga gctgtcaccc ccaggctcca agcggcacct gctcggggtc accagtttta -continued 104641 ggggaggagg agagggcagg ggccccagcc cagtctgtga gctgtcaccc ccaggctcca 104701 agcggcacct gctcggggtc accagtttta ggggaggagg agagggcagg ggccccagcc 104761 cagtctgtga gctgtcaccc ccaggctcca agcggcacct gctcggggtc accagtttta 104821 ggggaggagg agagggcagg ggccccagcc cagtctgtga gctgtcaccc gtgctatgtg 104881 ctgggctggg cactcaggaa agagggtcag ggttcacggg ggggtggcgc gcagatttcc 104941 aggagagccc cgagggcagc agagaggagg ctcaggtcaa tggttgggca gggggccagg 105001 gctggagaca cagagagggt cccgattcgg gggggtgccc tcagcaggtg gctgggagtc 105061 cctggggggtt tgcacacttt cgatcaggct gttatttcag acgcttggtc cagcctgaga 105121 caggtaatgc ctctggcctc cgggccttca gggatggaaa gatactctag aaagcgggac 105181 tcaaagtaac tcaaggaact cgcgtcccac agtggggagc ccttctctcc aatttacatg 105241 gggcgtttac tacgaggaaa ataccgaagg ccgttttgag ctgaggctcc cgggccgggc 105301 tgtccgtttg tgagactgct cgtcacccct gggccacatc cctggtggcc aagggggcaa 105361 tcagtgcggt gactgcacga cacacctctg cagccctgcc ccacagctgt caccatcggt 105421 gacgtccacc ccctggagaa cctgaccact gcccggtttc ccgctaaaac agcgcccttc 105481 caggatgggg ggcagaggga gaggccttgg ccttttcact cctcttctgc agcgggggcc 105541 cctcgcaccc cagtgcccgg gcccaggagc gccccttggg gtggggcagg gagggatcca 105601 cacaccaagg ggagccagga cccccccaaa tctgctgccc tgccctgata cccgagacct 105661 ggggaaacgg gggactgggg ctgatgcggg caggaccaag aactgaggcg gtgagacggg 105721 gtccccacca caggccatct ggctggcagt ttctactccg ggcctgcagg ccaagaggga 105781 aaaggtgccc cactcagatc aggcgcctcc cgtccccagg gagggcctac aaggtcagat 105841 cctttgtaac ttccacgggc aaaactggct tgctgggcct gtgcgggccg catgggcgtg 105901 gaccaccaca cctttcccca ctgagtctcc agccggagct gtcacccagg tccccccagg 105961 ccagccccac cccgccacct tgcagtagcc tctcgtatcc aggccgaggc tgcccggtcg 106021 acccctcctg cctgatggcc tcaagtggac aatgcgagtc acgttgcagc acgtgagtgg 106081 gacgggcagc gccacgcggg gtccgggcat ccgagtccca ccactcagcc tcccttccgc 106141 tgcagagagg tctgtccaag agccctgggg gccatccagc ccctgtccga cctggccggt 106201 gtggaagagg gggtgtgcca cccctcctgg ggggctggct gggcgctggg caggcccctc 106261 ctaagagtgg agcccactgg tggttttcct gcagccccac ctccacacag cagttctcac 106321 tgcccagtaa caggaggcta ctggcctagc tctctccctc gtgtgatgga ctcaaccagg 106381 agcgttcacg gccccacaca gggttctcgg ctgctgcatg aggatctcaa agccccatcc 106441 acgtgcatgt aatctcctcc ggtaacttct ctagggaagc ccggctatcc tgccatcctc 106501 accgcaccac cagggcgaga aaagccatct ccagcgctca catccacaat gggccaggcc 106561 gtgagcacac caccttcttc gggaggttgt gggggcgggn nnnnnnnnnn nnnnnnnnnn 106621 nnnnnnnnnn nnnnnnnnnn nnnnnnnnnn nnnnnnnnnn nnnnnnnnnn nnnnnnnnnn 106681 nnnnnnnnnn nnnnnnnnng cgcgcccccc ccccccgcgg cgccggcacc ccgggcggcg 106741 gcccccggcg ctgggagcag gtgcggggcc gcggccgctc gtgagcctcc agcccggagg 106801 acgggccccg ggggccggcc cggtgcccag gccctgggag ccccggaggc cagagtgcca 106861 gagggccgga ggacccggga aggcccgaga gaggtgggaa gcacggggtt ccagccctag 106921 gccatttcag ccccaaagcc atcggtgaaa ccattgctgg ccccagataa aagcgtcgcc 106981 aactttttca ccccggcgga gactttagcg ggtagctgcc ccctaggggg aatggaaaaa 107041 ccaggattta ccaggtgggt ggaggtcaca actgcccaga tcctgagaaa gaggggtcag -continued 107101 tggggcggga agattagtgg ggagaggagc tttcagaacc caagggaatg aaacgaggct 107161 tgaggttggt tatccagcag ccgccccctg ccccgtgagt gagcgaaggc tgggcccctt 107221 attgtcacat cttccagctc ttcgctagaa aacctagagt tttaaatact gtggcagctg 107281 agtcaaacaa taaggaaaag cccgactctt tgagagccag gcacaaggcg tctgtgacag 107341 ggtctccagg ctgcccattt gcagtctctg aaacggaggg tttttcgaga aggaggtctt 107401 ggggtgcctg ccagaattgg aggggggggc gcgggaagtg aggacccaga agagagggct 107461 tggcccgctg caaggaggtc actggacact ggagctgaag cgccagccga aactggaaac 107521 tcgaaatctg tctccgtgcc agccacaagg cctatgattt tccttggcga cgttcagcat 107581 cttaggagga gctggcgggg gaggcgggta gttcgtgggc ggttgcagca gggcaggaag 107641 gtgaggaacc tgaggctggt cagagagctg gttggagtga tgcccatcgg tggacccgct 107701 ggagaaggcc tgagtagaga aggtctaagc ttaacgggga aggggtgggc cagggtggaa 107761 atggggtggg aagtttgagg agggggagca gtggagatgg gggttgtgag gaatgggagt 107821 gagcttagac gtcttgagga tactgcagtt ctgtgctttt tttcacacct ggctgaaaat 107881 tcactgaaaa caaaacaacc cttgctctgt gacagcctag aggggtggga gggaggctta 107941 agagggaggg gacgtgcgtg tgcctatggg cgattcatgt gggtgtacgg cagaaagcaa 108001 cacagtatgt aattaccctc caattaaaga tcaagtacaa cttaaaaacc ccaaacacaa 108061 cattgtaagt cagctagact ccagtaaaca tttcagtaag aagattcaac tgggaatgag 108121 ttccgccgtg actatcctga tgaatttccc gtgtcttctt gaggccattc ctctttgaac 108181 ttccgtgttt ggggaagcgt gcctttgtat ggagtcctga ggagtaaatg agacgggctt 108241 gtagaaggcc tagtagtgcc ttgcacgcgg cagatgctca ataacctcga gttgtcacca 108301 ttatggtacc tcaagagtct ccttggagct tgcacggttt ctgaatgggg tcctgcgggg 108361 ctcccttggg gctcccacat ggggttgggg ggctgagtgg ggtgtccccg ctccttgctt 108421 gtcccctgtg gaacaccccc ttccacccga gcagctctgc ttttgtctct tgtgtttgtt 108481 tatatctcct agattgttgt tcagtcgctc agtcgtgtcc aactctccga ccccatggac 108541 tgcagcacac caggccttct gccttcacca tctcccggag cttgctcaaa ctcctgtcca 108601 ttgagttgct gatgccgtcc aaccatctcg tcctctgtcg tccccttctc cttttgacct 108661 cagtctttcc cagcatcagg gtcttttcca atgagtcagc tctttgactc aggtggccaa 108721 gtattggagc ttcagcttca ttatcagtcc ttccaatgaa tattcagggt tgatttcttt 108781 taggattgag tgacttgatc tccttgcagt ccaagggact ctcaagagtc ttcaacacca 108841 cagttcaaaa gcatcagttc ttcggcactc agccttcttt atgatccaac gcccacatcg 108901 gtacatgact actggaaaaa ctttggctca gagataattg acttgattga atacaaagtt 108961 ctttggcaaa aaataaaagt gtggcaagca gtactgacac aaaagcaagt ggcttttcct 109021 ccgttgagtc atttatttat tcagtgggtg tgtgcgtgta gagacggagc ggctgtgctg 109081 ggagctgggg cttccacttc agaggagccc cggacctgcc ctcggggagt tcacaggcag 109141 tgctgcgggg ggtcctgcca ggacgcctgc cctgcgagtg cccagtgctg tgatggatgc 109201 gtgtcccgca tctgcggcca ctggggccac gtgcccgaga ttgtccgggt ctgagggtgc 109261 agagaagagg aggcatttgg actgagtctg gaaaaatgag catgtggcca cgtgagaagc 109321 cagtggtgag gggaccagtc aggcggagga aagagcggct catacgagtt gtggagctgg 109381 aagcatgagg gtgtgtggaa gcagaggccg gggacagggc cgcagggccg gccatggagg 109441 gcgtgggctg ctgcaggctc ctgagaaggg ggacgctgcc atcatgaccg ggtttaggtg -continued

```
109501 tttgaccctg gtgtccacgt agaggacaga tgtgtggggg gggagctgga gatgggcatc
109561 catcgggagt cagcctggag agaggcagag accccgtcag tgggccctca ggacgtggat
109621 ggggcggatg ttgggaagat ctgactcctg ggttccggct ggggctccgg gctggagggg
109681 tgccgcccac cgagcacagg aggcaaacag atgccctctc ccagcaagac cccagcccca
109741 gcaccctccg gggccggact ccgcccctct tccagaatgg ctcccttgct gtcctcgccc
109801 atctttccgg tgccctgagc ctctagagtc tggacaccag cgtccgcctt gcgcttgttt
109861 ctgggaagtc tctggcttgt ctctgactca cccaggaccg tcttcgaggg caaggttgtg
109921 tccttggttc catctgcttt ggggtccggc tcctcgctgc ttgacctgct gatgtgacag
109981 tgtctcttgt tttcttttca gaatccgaga gcagctgtgt gtgtcccaga cagacccagc
110041 cgctgggatg acgggcccct ctgtggagat ccccccggcc gccaagctgg gtgaggcttt
110101 cgtgtttgcc ggcgggctgg acatgcaggc agacctgttc gcggaggagg acctgggggc
110161 ccccttttctt caggggaggg ctctggagca gatggccgtc atctacaagg agatccctct
110221 cggggagcaa ggcagggagc aggacgatta ccggggggac ttcgatctgt gctccagccc
110281 tgttccgcct cagagcgtcc ccccgggaga cagggcccag gacgatgagc tgttcggccc
110341 gaccttcctc cagaaaccag acccgactgc gtaccggatc acgggcagcg gggaagccgc
110401 cgatccgcct gccagggagg cggtgggcag gggtgacttg gggctgcagg ggccgcccag
110461 gaccgcgcag cccgccaagc cctacgcgtg tcgggagtgc ggcaaggcct tcagccagag
110521 ctcgcacctg ctccggcacc tggtgattca caccggggag aagccgtatg agtgcggcga
110581 gtgcggcaag gccttcagcc agagctcgca cctgctccgg caccaggcca tccacaccgg
110641 ggagaagccg tacgagtgcg gcgagtgcgg caaggccttc cggcagagct cggccctggc
110701 gcagcacgcg aagacgcaca gcgggaggcg gccgtacgtc tgccgcgagt gcggcaagga
110761 cttcagccgc agctccagcc tgcgcaagca cgagcgcatc cacaccgggg agaagcccta
110821 cgcgtgccag gagtgcggca aggccttcaa ccagagctcg ggcctgagcc agcaccgcaa
110881 gatccactcg ctgcagaggc cgcacgcctg cgagctgtgc gggaaggcct tctgccaccg
110941 ctcgcacctg ctgcggcacc agcgcgtcca cacgggcaag aagccgtacg cctgcgcgga
111001 ctgcggcaag gccttcagcc agagctccaa cctcatcgag caccgcaaga cgcacacggg
111061 cgagaggccc taccggtgcc acaagtgcgg caaggccttc agccagagct cggcgctcat
111121 cgagcaccag cgcacccaca cgggcgagag gccttacgag tgcggccagt gcggcaaggc
111181 cttccgccac agctcggcgc tcatccagca ccagcgcacg cacacgggcc gcaagcccta
111241 cgtgtgcaac gagtgcggca aggccttccg ccaccgctcg gcgctcatcg agcactacaa
111301 gacgcacacg cgcgagcggc cctacgagtg caaccgctgc ggcaaggcct tccggggcag
111361 ctcgcacctc ctccgccacc agaaggtcca cgcggcggac aagctctagg gtccgcccgg
111421 ggcgagggca cgccggccct ggcgccccg gcccagcggg tggacctggg gggccagccg
111481 gacggcggaa tcccggccgg ctcttctctg ccgtgacccc ggggggttgg ttttgccctc
111541 cattcgcttt ttctaaagtg cagacgaata cacgtcagag ggacgaagtg gggttaagcc
111601 cccgggagac gtccggcgag ctctaacgtc agacacttga agaagtgaag cggactcgca
111661 gcccgtacag cccggggaag atgagtccaa agtcgagggt caccttggcc actgcagggt
111721 cgctcggcgg tggggcggag cgggtgcagg agggctcctc ctgggcttgg ggtggcaggc
111781 gaggaccccg cgcctctcag ccctcggcct gggttggctg agggcgggcc tggctgtagg
111841 ccctccagcg gaggtggagg cgctgcccgg ctcagccagg cacaggaccc tgccacgagg
111901 agtagccctc cgccagaccc ggcgtccagg ctggggcgcc tgcggggcct ccgttctgtg
```

-continued 111961 gctgggcagc ctgcgccctg tccagggatg aaggggttcc ggtctgaagg gctgggttca 112021 gggtccagct ctggcccctc ctgccttggt gtcctggagg aagccccaag gctccgtttc 112081 cctctccagg aggtggggac gttgggaatg ccacattccc ctggggggtg tgtgtgtgtg 112141 ttcaaggctc ccattcagac tgggactggg cactcacgag ctttggcaac tggcaactga 112201 ggacggagac ccagggtgac accccacctc ctgctgcggc ccccccggca ggggagacac 112261 aggcccgtct ggttcccaag atggcagggc ccctccccct ccagcttgtg ccctgggtgt 112321 ggtgcctggg gctacagcga ccctttccgg ttccccgggc cagttcagct gggcatcctc 112381 agggcggggc tctgagggtg ccatgtttcc agagctcctc ctcctcccac cagtagcagg 112441 cgggcggcca gctcccaggc agccccctgg catcgcctag gtgcacacct gcccgctgtg 112501 acccagcaag gcttgaaggt ggccatccca gttaagtccc ctgcccctgg cccaggaatg 112561 ggctcgggca gggccgcatc tggctgcccc agaagcgtct gtccctggcc tctgggagtt 112621 ggcggtggtc tctggtactg tccctcgcag ggccccttag cactgctcgg ggaggaggtg 112681 ggctgaactg attttgaagt tttacatgtc tgcggccgca gtcctacgag cccgtcaggg 112741 tcatgctggt tatttcagca gatggggctt ggctcggcag ctaggatggt cctgaataaa 112801 aatgggaagg ccagagctgt tcctccatca gcaggcttgg cagctgggga cgttgaaagg 112861 acaggtctgc tggtctgggg agaccagctc tgtgcagccc ctgctgtccg tgggggtact 112921 aaaccagccc ctgtgtgcgc ccatctgagt ggcagcccgc ctggaggatc gcccatcact 112981 tgtgagaatt gagagaatgc tgacaccccc gcttggtgca gggggacagg gccccctaag 113041 atctacctcc ttgccccacc cccgggaccc cctcagcctt ggccaggact gtccttactg 113101 ggcagggcag tcatccactt ccaacctttg ccgtctcctc cgcgcgctgt gctcccagcc 113161 aaattgtttt atttttttcc aagcatcact ttgcacacgt caccactctc cttaaaacca 113221 cccttccgga gtctcctgct cgtaaatcgc cggtttcagc caacctgggt cgccccccaa 113281 gcccagcaag cctgctgagc cccgcgcctc ccagctactt cacgctcgcc tcaagcttct 113341 aaacgcggac cttctccccc ccaccccccat ccctttcttt tctgatttat gtaacacggc 113401 aggtaagact cctctcctga agggttgaca gactcacaca aaaccgtggt cagaccaggc 113461 aagtgctttt tttcagaagt gtgagcggaa cctagtcttc agctcatgct ctttccttgt 113521 tttcttatgt gttctaagtc ctttgacttg ggctcccaga cagcgacgtt gtaagaggcc 113581 gtcctggtag catttgaatt gtcctcgagt ttcgttgtcg gattttgttt tattgtctta 113641 gttttccctt cttttagcag acgttgttga ctgtcgtaaa gctccagttc ttggttctgt 113701 ttactaatca aattgttttg tcaaagtaca tgtattctgc tcttttcttt atcttttttg 113761 ttgcttaata ttaacacttt acatttctaa gattaattat ttaggtaatt aataattttt 113821 aacatttcta gtaaacgtgg gtacttgggt ctgtgtttgt tttcttgtag ttacagcttt 113881 ttctgctcta tactgttgac gtctgggttt ttttttgctc ttaggaattt ccctttgacc 113941 ccattattat tattttaatt agtatttttt aataattaaa aattagtgtt tttaaattaa 114001 ccctaatcct aaccccagtg atgactgctt cagtcattgc tgttacttat tatgtgctgg 114061 tgtcaggatt tttaagtgtc catagacatt ctctgagcct gaatatatta tcagttttat 114121 acagcatttg tgtactctca agaaacgtgt tttcactctg tcagttcggt ttgttacctc 114181 agtctttatg ttattttgct ccagtccgca cttgctctaa cttgtcttcc cttcgaggtg 114241 tgaggacgcc tggcagccgg tgagcatgcc ggggtccggg gtcgtgggcc caggcgccca 114301 gcaaagccct gtgggtgtgt gcacggctgg gctgctccgg gaggaagcct gtggccccac -continued 114361 ggtagttagg agcgctggtt tacctggtca caccacggtc tggttttgtg tgcttttccc 114421 tgacgtgttt ctgttttgcc ttggtttcta ttctgtttta tgagtgccgt ttacgctttg 114481 ttagtcatgc cgttatctcg atagacaggg tgtacgtgat caagtgatta ccgtatttgg 114541 agcagatgtc tatttaacag agatgaactg agaacctgtg cctttgcatg ccctctttgc 114601 ctcttttaat gcttctagct tcaacttctc ttttccaaac attataatgg aaaccccttg 114661 cttttttttt tttaatttgc atttgcatga gagtttattt agctcggcat tttattttta 114721 aaatttgtgt atatattttt gctatatatc tgtaacttat aaacagcaaa ttattggatt 114781 ttgctttctg attctttctg taattcttct tacataagaa gttctcctat gagtaacatt 114841 gctgtttaga gtgaggcatg atttatttcc agcttagtat gtattgggtc ggttaacccc 114901 caaaggtcat gctcatcccc gccccatctc tgtgagttat tgtccgagtg tggagcgccc 114961 tgtctaggcc gacgagagac ccaccatcgg gcacacctgc ccctcctggt ctggtcagtg 115021 ccgggctctg tcctgagtcc actcctgatg tcacaggctg gtgcttcagc gacctcggct 115081 gtgacacgga gggtgtgatg gcactgccca gccccatggg gcttggagga ctaaaggatg 115141 cacacctgcc tggcagactg agggcacagg tgtttctcac actgtcagcg ttttgaaata 115201 ttcctttgat tttctaccct aactcccaaa ggccgttcaa cataagctag aatgctacgt 115261 ggtgcttgat tacattttag aaaagtttca gcaaatacca cgagatgcag caaagaacta 115321 gacctcacag atcaggccgc ctgcataagg gagcccacac agtcgtggga gacggggacc 115381 ctctcccacg tcctgtctgt cccaggatgg tcccctcacc cgccccctct ctcccctcgc 115441 cctcctgtgg tgggggccgg ccaccatcac agctgcagag cctcaagaag gggtcgcccc 115501 tggccactcc cgtggcagga gggacacgag ggcaggagct taccgcgggt gcagtggtct 115561 cggatcagct cagctggccg ctgcggggtc gggggacag ttcagtggga ggcaggagcc 115621 cccactacag ctgccaggac ttctcagagg tgacaagggg gttcagtcac ctcagcccag 115681 gtggaaacca aatggcctct tgcgcggctc ctggggccac gcggaggttc gctgggatca 115741 caggtatctg gatgtgtgcg ccatggacat gcaccacctt cggggggtaa ggggtgggga 115801 aaggcagccc ctttcttttg ggggaccccc tcttcagtgt ctgataacca ggaaaccaaa 115861 tcagaaggtg gtctgggggt gctgagcagg gtgtctccta caccacaggc cacacactca 115921 cacagcctcc aggactccag tggggctgag cgctggagac tcacccacgt ttgctacccc 115981 cccacccaag gccatcccag aacagctgcc tgcgtcctca cggctggccc ctcccctctg 116041 gtctaaccca gtgtgggtgg gccggcctgg ggtctccacc tgcctcctgc tgttccctgg 116101 gctgctggct gtctgcagat gcggggccct ggcccggaga agccccatca gagcccagag 116161 gacgggagtg gagcggggag gtgagccccg gagtctcgag gggccagagg caaaatactg 116221 ggctgtgtcc ctggaaggca gtttcccatg aaaccttcaa tataggccgc cccagacgat 116281 cagcctcatc tgctacgtgg attcctcccc gtagcgaatg gtgattgggt tctacatgga 116341 cccgggactt ctgtttgaat tataatcttt cccccactgc ccctccaggg atctggaaaa 116401 tggaggcctg ggctagacgg aagcttcctc caagattctt tattgaaggg attcgaagag 116461 aaacaggtgg tcagtaatct gtgggggatg gaggggtgag cgctacgtgt aacggtttta 116521 ctgttgctac gggaccagtt ttgatgtctt tccccttcaa gaagcagacc caaacaccga 116581 gatgctgagg ttagcagcac agagcgggtt catccacaag gcaaccaggc agggagacca 116641 gagacgctct ggaatctgcc tccctatggg cacgggctgg gtgctcacgg atgaagacca 116701 agcagcaggt ggcgtggggc gtggggagcc tgcggaaagc gatggacaag gtgcgggacc 116761 gcggtccgcg cggtggaccc aagctccgcc tctgcgctgc agcgcgagct gggggcggag -continued 116821 cttccaggga cccgcgaccg cgcccagtgg gagggtccgc ggtccaccca gtcctaacag 116881 ctcagctcca gctagacgcc gctgagtccg gctttctaga gagcaacccc ggcgggtatt 116941 ttatggttct ggcttcctga ttggaggaca cgcgagtctt agaacaccct tgattagtgc 117001 gggcaggcgg aatggatttg actgatcacg atctgcagtt tcaccatctc aggggccgcc 117061 ctcaccccca cctatcctgc caaagggggg gcctcggtgc tgagatcggg gccacacgtg 117121 cactagacgg tcggtcagcg ctgctgctga gcggacccgg ggccatcctc acaccgccac 117181 tggcccctgt gctcaataaa aggaaggaaa gcgggaaaag cgctttctgg ccgcggtggc 117241 ctcgcgcgtt cctccatcgc catctgctgg cagagcccgg catggcaccc gctgcacaga 117301 aacctcggtg tccgtttggg tgccccatcc ttgaccccga gagagcaccc tccgtccaaa 117361 atgaaaaaca gctgctccca agagtcatta taatcacagc caattgtgtt aattcgtcct 117421 cggatccact cacagttcca cggaacattc tgctaacctc tgacaactcc tacataaagc 117481 aatactgaga agaaaagaac gtggttgata aatacaaagg catacaacaa taaggagcaa 117541 agaaaaaaga cagtcctcgc agttctgttt tgttcatctc tcatgagtag gatggcagat 117601 aaaacacaga atgcccagtg aataatttta gtctaagtat gtccccaata ctgcctaatc 117661 ttcaaatcta accttatttt taaaatatat attttttgct ggtcactcat cagttcatgc 117721 accaaagcct ttgtttcttg actcctaact ttttgacccc tctggggtga ggagcacccc 117781 taacctcgag agcccatcac acagtcccct tgggactaga cccttctttg cccatcacag 117841 ctgaccggaa gggccagccc atggccagcg ctcgcgcccc ctggcggaca gactctgcgc 117901 ggcagccccg ggagcccagg tgcgaccccg cggtctctgg cgccctctag tgtggaaaga 117961 tctcctcctg gtgttcccag tcattgggct gtattttatt agagaagatg ctcgcgtgac 118021 gatgatgatg gtcctttacc gggaggcacg tttggggcgc gtcggctcag gggccgagct 118081 attagcctgc atcgcgccca caggcatcgc gtccccctga gccgggtcag ctgtgggctg 118141 tcctgacacg ggtttccccc agtctctggc ccgctgtccc tcccaggtca gtgtccagcg 118201 ttgcccttct ggttgtggac ttgtgcagcg gtctcagcag atggaggggc gaccctaaag 118261 gatgtattga ggcatctcag cactgtcctc cgcccaggtt tgctggtcag cagtgaagtg 118321 accgggaaaa ggggctgtct tggggtcctt tcagaggcct gggttagacc aaagttttct 118381 agaagattca ccattgcagg gagtcaaaga caaaactagg gtggtcagca atctgtgggg 118441 gattcggcgg tgagggaatt ctgaatgcta catgtaatgg ttttactatt gttagggaac 118501 atttttcccc cctacaaaca gcaggccaaa atactgagat gtcaggtttg catcaaagag 118561 cgggttcatc cacaaggcaa ccagagaacg ctctggaatc tgcctccctg cgggcacagg 118621 ctgggtgctc acggatgaag accaagcagc aggtggcgtg gggagtgggg agcctgggga 118681 aagcgatgga caaggtgcga ggacctccgg cgcgagctgg aggcggagct tccagggaca 118741 cgcggccacg cccagtggga gggtcagcgg tccatccagt cctaacagct cagctccaac 118801 tagacgctgc tgagtctggc tttctagaga acactccggg cgggtatttt attgttttgg 118861 cttcgtgact ggaggacgtt caagtcttaa aacacccttg attagtgcgg ggaggcggaa 118921 tggatttgac tgatcacgac ccgcagtttc accatctcag gggccgccct cacccccctcc 118981 taccctacca aaggtggggg catcggtgct gagatctggg gtgacacata aaatcaggtg 119041 aagtcttagg acagggggcc gattccaggt cctagggtgc agaaaaaacc tacctggccc 119101 cgggctagac agcgtggagg gcgtggcccg ggctggtgca cagaagtggc ccccaactgg 119161 tcagaaggtg tgggagccca gggctggtct actgcagaag gggtcgcctg gtggacagag -continued 119221 tggggcctga gtgcctgctg aactggtccg tcagggctgc tgagcagaca cgggccatca 119281 tcactggctc ctgtgctcga tagaagggag ggaaaccagg aaagcaaagg cgctttatgg 119341 ccgcttttgt gtttcgcgtt cctctagcac cgtctgccgg cagaacgcgg cattacatcc 119401 gctggccaaa cctcggggtc cggcttggat gtccccatcc ttgtctcgga gatctcacct 119461 ctcagcagtt cccctgggga caatgtcgag aagatgcgac cttgacccgg agctcggtgg 119521 agagggtgcc ctgggttctt tccgcagttg cttggagtgg aggtgcctca tgttgggctg 119581 ggaacgggag gaaggaaaca ggtcatgatt gagatgctct agacagactg tccctgctct 119641 tgccaaattt cagaagattg tctttaataa atattccatt ttttgtatgc ccttaggtct 119701 atttccagac actttaaata tattgaaaga ctttaaatat ttatataaaa atattattta 119761 tagactgtat aaaaggaaca gttagaactg gacttggaac aacagactgg ttccaaatag 119821 gaaaaggagt acgtcaaggc tgtatattgt caccctgctt atttaactta tatgcagagt 119881 acatcatgag aaacgctggg ctggaagaaa cacaagctgg aatcaagatt gccgggagaa 119941 atatcaataa cctcagatat gcagatgaca ccacccttat ggcagaaagt gaagaggaac 120001 tcaaaagcct cttgatgaag gtgaaagagg agagcgaaaa agttggctta aagctcaaca 120061 tttagaaaac gaagatcatg gcatctggtc ccatcacttc atggaaatag atggggaaac 120121 agttgagaca gtgtcagact ttatttttgg gggctccaat gaaattaaaa gacgcttact 120181 tcttggaagg aaagttatga ccaacctaga cagcatatta aaaagcagag acactacttt 120241 gccagcaaag gtccgtctag tcaaggctat ggtttttcca gtggtcatgt atggatgtga 120301 gagttggact gtgaagaagg ctgagcaccg aagaagtgat gcttttgaac tgtggtgttg 120361 gagaagactc ttgagaggcc cttggactgc aaggagatcc aaccagtcca tcgtaaagga 120421 gatcaccccc tgggtggtca ttggaaggac tgatgttgaa gctgaaactc cagtactttg 120481 gctacctaat gcgaagagct gactcattgg aaaagaccct gatgctggga aagattgaag 120541 gtgggaggag aaggggacaa cagaggatga gatggttgga ttgcatcact gactcgatgg 120601 acgtgagtct gagtgaagtc tgggagttgg tgatggccag ggaggccctg gcgtgctggc 120661 ggttcatggg gtcgcaaaga gtcggccatg actgagtgac tgaactgaac tgatccagaa 120721 atttaaaatt aatatataaa ccaaatccat gcagacaatt ataagcatat attataaatg 120781 cataattata agcaagtata tgttatattt ataatagttt ataatgtatt tataagcaag 120841 tatatattat tataagcata attgtaagta gaagtaactt tgggctttcc tggtggctca 120901 gacagtaaag aatctgcctg cagtacagga gaccgggttc gatccctggt ttggggaaat 120961 tccctggaga agggaatggc aaccaactcc aacatgtttg cctggagaat tccatggaca 121021 gaggagcccg gaaggttgca gtccatgggg ttgcaaagag ctggatacaa cagagtgact 121081 aacacatgta tataaataaa tttacctata tattgtatat atatttataa acatattcag 121141 atattataaa taattagaaa catattatac atgtatttaa atactgttat aaacataaat 121201 ttaaaaaata attttcagcc ctttggcttg gggtgtgttt tgtggacgtc tttgtgctac 121261 tgttcctgaa gtggagctct cccctcccaa accagctttt gaaatgactg ggaaagcaat 121321 ggaatacata agcatcagga agatagcaac agagctgtca ttcttcacag agggtgtgct 121381 tgagtgtgta gcaagtcccg cagaatgtag acagattaat atagtctatt aaaaatagtg 121441 tagcaaattt acgaggtgcg atttcaagta taaagactta ctgggtctct cagttcagtt 121501 cagtcgcttg gttgtgtccg actctttttg accccatgga ccgcagcacg ccaggcctcc 121561 ctgtccatca ccaactcctg gagttcactc aaactcatgt ccatcgagtc ggtgatgcca 121621 tccaaccatc tcatcctctg gcgtcccctt ctcctcccac cttcaatctt tcccagcatc -continued 121681 agggtctttc ccagtgagtc agttctttgc atcaggtggc cagagtagtg gagtttcagc
121741 ttcagcatcg gtccttccaa tgaatattct ggactgattt cctttaggat tgactggttg
121801 gatctccttg cagttcaagg gactctcaag agtcttctcc aacagcacag tctatgaata
121861 gaatagcaaa tgaatagaga ataacattta cgaggatata ttttaccatt gcataaaata
121921 tatcagcttg tagagaacag acttgttccc aggggagagg gtgggtaggg atggagtggg
121981 agtttgngat cancagaagc gagctgttat atagaagatg gataaaaagg atacacaaca
122041 atgtcctact gtgtggcacc gggacctata ttcagtagct tgtgagaaac cataatcgac
122101 aagactgagg aaaagtatat atatatgtat gtacttgagt tgctttgctg tacagaagaa
122161 attaacacaa cattgtaaat cgatatttca atagaatcca cccccccaaa tatataagtt
122221 tcctggagat ggagacggca acccactcca tttcttgcac ccaatattct tgcctggagg
122281 atcccatgga tagaggatcg caaagactcg gacataaccc agcgactaac actttccctt
122341 tcaaatgtgt aggtttacta gcgtgaatct acagagatgc ccaagacatt cgtttatgag
122401 gaaaactcca cacgcagctt cactgagaat tattaaacct attaaaggga gagagcgcca
122461 ggatattcat ggattgaaag attcgatgtg gtcaagttgc cagttttccc caaactgatt
122521 ggtaaattcc ccaggagctg gctcaaggcg caaaattccc tttacctttt tttaagagac
122581 gaagccaagg agccgattct ggttgagaga cgctcaggtc ctcctgcggg agagcagccc
122641 tcttcctccc ggtcgcctgg gcagtttcga ggccacgacc agaaggactt ggctccctgt
122701 gtcgcgcact cagaagtctc cctctccgtc ccaaggactc agaagctggg cgtcctgccc
122761 gcagcagagg aggcagcctg gaggggcccc gcgggcacag cggtccgggt ttcagccgag
122821 ttgcccgccc cgcccctcta cctgggcgct gccgcccggc tccggggccg gccgtgccct
122881 ccgtggccgc aaggcgtcgc tgtccccccg ctggaagtgc tgacccggag gaaggggccc
122941 agacggaggg actcggagcc tccgagtgac accctgggac tccgagcgct ggagcctggc
123001 gtcaccccag gcaggggcag tgggggcccg gggcggggtc aggggcctcc cccggttctc
123061 atttgacacc gcgggggtgc gctgggcaca gtgtccaggg gccacgttcc gagcaggggc
123121 gcgatgcagg cccgggcgcg gcctgtcccg ggcgcgagtc cagctgcttt gcagaggtgg
123181 cggcaggtcg cagtgaccct cacagagacg ccccactctg cggctccagg tgggcctgtg
123241 ccccccagaa gtgctgacct gtgcaccggg aaggcacagg gccccccagc catgtctgcg
123301 atggaagagc cggaaccgcg ccatgcccgt cctcgctgac cggcaggcac ccgccgtgtg
123361 tccacacgct gagccatctg gctccccttg cttgacatac acccaggacc tgagtgtgca
123421 ggaagttaga aggggcaggt gtggtgacac gatgccatcc agcatcacct gagaacctgg
123481 acaaacctca ggggcccagc ctgctctgtg aggccccgag ggccggcccc tccccggacc
123541 cctgccttga atccggccac actgcccgcc ttcctgctcc tgcggcttgt cagacacgcc
123601 tgagcccagg gcctgtgcac tcgctgtccc ttctgccagg actgctcctc cccaggctct
123661 tgctggggct ccccttcttc attcgggggt ggcctctctt gttcagtggc tcagctgtgc
123721 ccagtctttg caaccccatg gactgcagca cgccaggctt ccctgtcctt cactagctcc
123781 tggagtttgc tcaaactcat gtccattgag tcagtgatgc tatccaacca tctcatcctt
123841 tgctgcccac ttcttctcct gctctcaatc tttcccagca tcagggtctt ttccaatgag
123901 ttagctctct gcatcaggag gccaaagtat tggagcttca gcatcagtcc ttccagtgaa
123961 tatgcgaggt tgatttccct tagaattgac tggttggatc tccttcctgt ccagagaact
124021 ctcaagagtc ttctccagca ccacagtcgg agagcatcag ttcttcagtg atcaggtttc -continued

```
124081 tttatagccc agctctcaca tcggtacatg actattggaa aacccatagc tttgattaga
124141 tggaccttca ttggcaaagt gatgggcctt cattggccct gctttttaat acaccatcta
124201 ggtttgtcgt agctttcctt ccaaagagca aacatctttt aatttcctgg ctgcagtaac
124261 catccatagt gattttggag cccaagaaaa taaaatctgc cactgtttcc actttttccc
124321 cttctatttg ctatgaagtg aggggactgg atgccatgat cttagtttaa accagcagtt
124381 gtcaccccga ccgcttcctt tcctaaagag ctcatcacac ctcccactgg aatgcaatgt
124441 gttgcctgtc cgcctgcttc acctcctggg actttgctgc aggtcttggt ctctgaggcc
124501 cctgccgtat ccccagggcc cagagcagtg ctgggcttcg agtccgatca gggactatgt
124561 gtgtggactg gatggtgctt gcttcttctg gggaacgaga gacctgggcc tggggaacga
124621 ggggacctgg tgtgaccgga tctcctccct cgggagagga gccaagcgag tggacacagg
124681 tcagtgtgtc ttgctcctgt gtggcaggtg tcccgtctgt gtctgtcatc ttggcatttc
124741 ggtgtttctg tgaacccagc ccctcccctc ctgatacccc atcccatcag cacagaggag
124801 actgggcttg gggactctct ggtcctgaga ttcctctccg catgtgactc ccccctcctg
124861 gggggagcag gcaccgtgtg tgaggagggt ggaagctttt caagaccccc agcttttctg
124921 tcccaggggg ctctggcagg gccttgggag ctggaatgag ctggaatctg ggccagtggg
124981 ggtttccctg gtggtaaaga acccgcctgc ccatgcacga ggcataagag acgcgggttc
125041 gatcactggg tcgggaagat cccctacagg agggcatggc aacccactcc agtattcttt
125101 cctgaagaat cccttggaca gaggagcctg gtgggctaca gtctctgggg tggcaaggag
125161 tcggacacga ctgaagcgac ttaccatgca cgcacgcggg gtcaggggtc agggccgcgc
125221 tgcttacctg ctgtgtgacc ttagccaggt cacacccccc aggctgtgaa agagaacagt
125281 cttcccagac tcgggcatcc aggtctttac agacgtgcct gtgagctttg tgactctggc
125341 tctgtggccg ctagagggcg ctgtccgccg ggccctatgt gcgtgcacgc atgtgagcat
125401 gttcgcatac gtgtgtgcat ctgtcggggg cgcacggtgc ggggacacgg gcacgcggtc
125461 aggaacgcag cccggacacc tccacgtggc ccgcgagtac cgtcaggtgg gggctgtggc
125521 tccgctgtgt gggtgacccg ccctcccccc gcgaacgtgg tgcatagtga ccgcctggct
125581 gggctcctga gctcagccat cctgcccccc gggtcagctc ccgacaggcc cagctctagg
125641 ccccaggcgt ggaccgaggc ccccaggccc cggcctgtga gatgggacct ccgtctgggg
125701 ggctcattct gctcccggag gcctggcagg cccctcctct ttggcattgc ataccctcgc
125761 attggggtgg gtaagcacag taccccatgc ctgtggcccc gtgggagcgg cctgctcagg
125821 gaggccggag cctcagctac agggctgtca caccgggctg cagaggaaga agacgggagc
125881 gaggcctaca ggaacctagc caggccctgg cccactgagc cgacaggagc ctggccagag
125941 gcctgcacag gacggggtgg cggggggggt ggggtggggt gctgggcccc gtggccttga
126001 ctgcagaccc cgagggctcc tcagcttaga acggccaagc ctgagtcttg gggtgcagg
126061 tcaggggg
```

Primers

In another embodiment, primers are provided to generate 3' and 5' sequences of a targeting vector. The oligonucleotide primers can be capable of hybridizing to porcine immunoglobulin genomic sequence, such as Seq ID Nos. 1, 4, 29, 30, 12, 25, 15, 16, 19, 28 or 31, as described above. In a particular embodiment, the primers hybridize under stringent conditions to Seq ID Nos. 1, 4, 29, 30, 12, 25, 15, 16, 19, 28 or 31, as described above. Another embodiment provides oligonucleotide probes capable of hybridizing to porcine heavy chain, kappa light chain or lambda light chain nucleic acid sequences, such as Seq ID Nos. 1, 4, 29, 30, 12, 25, 15, 16, 19, 28 or 31, as described above. The polynucleotide primers or probes can have at least 14 bases, 20 bases, 30 bases, or 50 bases which hybridize to a polynucleotide of the present invention. The probe or primer can be at least 14 nucleotides in length, and in a particular embodiment, are at least 15, 20, 25, 28, or 30 nucleotides in length.

In one embodiment, primers are provided to amplify a fragment of porcine Ig heavy-chain that includes the functional joining region (the J6 region). In one non-limiting embodiment, the amplified fragment of heavy chain can be represented by Seq ID No 4 and the primers used to amplify this fragment can be complementary to a portion of the J-region, such as, but not limited to Seq ID No 2, to produce the 5' recombination arm and complementary to a portion of Ig heavy-chain mu constant region, such as, but not limited to Seq ID No 3, to produce the 3' recombination arm. In another embodiment, regions of the porcine Ig heavy chain (such as, but not limited to Seq ID No 4) can be subcloned and assembled into a targeting vector.

In other embodiments, primers are provided to amplify a fragment of porcine Ig kappa light-chain that includes the constant region. In another embodiment, primers are provided to amplify a fragment of porcine Ig kappa light-chain that includes the J region. In one non-limiting embodiment, the primers used to amplify this fragment can be complementary to a portion of the J-region, such as, but not limited to Seq ID No 21 or 10, to produce the 5' recombination arm and complementary to genomic sequence 3' of the constant region, such as, but not limited to Seq ID No 14, 24 or 18, to produce the 3' recombination arm. In another embodiment, regions of the porcine Ig heavy chain (such as, but not limited to Seq ID No 20) can be subcloned and assembled into a targeting vector.

II. Genetic Targeting of the Immunoglobulin Genes

The present invention provides cells that have been genetically modified to inactivate immunoglobulin genes, for example, immunoglobulin genes described above. Animal cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts. In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

In a particular embodiment, the cells can be fibroblasts; in one specific embodiment, the cells can be fetal fibroblasts. Fibroblast cells are a suitable somatic cell type because they can be obtained from developing fetuses and adult animals in large quantities. These cells can be easily propagated in vitro with a rapid doubling time and can be clonally propagated for use in gene targeting procedures.

Targeting Constructs

Homologous Recombination

In one embodiment, immunoglobulin genes can be genetically targeted in cells through homologous recombination. Homologous recombination permits site-specific modifications in endogenous genes and thus novel alterations can be engineered into the genome. In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome).

A number of papers describe the use of homologous recombination in mammalian cells. Illustrative of these papers are Kucherlapati et al., Proc. Natl. Acad. Sci. USA 81:3153-3157, 1984; Kucherlapati et al., Mol. Cell. Bio. 5:714-720, 1985; Smithies et al, Nature 317:230-234, 1985; Wake et al., Mol. Cell. Bio. 8:2080-2089, 1985; Ayares et al., Genetics 111:375-388, 1985; Ayares et al., Mol. Cell. Bio. 7:1656-1662, 1986; Song et al., Proc. Natl. Acad. Sci. USA 84:6820-6824, 1987; Thomas et al. Cell 44:419-428, 1986; Thomas and Capecchi, Cell 51:503-512, 1987; Nandi et al., Proc. Natl. Acad. Sci. USA 85:3845-3849, 1988; and Mansour et al., Nature 336:348-352, 1988. Evans and Kaufman, Nature 294:146-154, 1981; Doetschman et al., Nature 330: 576-578, 1987; Thoma and Capecchi, Cell 51:503-512, 4987; Thompson et al., Cell 56:316-321, 1989.

The present invention can use homologous recombination to inactivate an immunoglobulin gene in cells, such as the cells described above. The DNA can comprise at least a portion of the gene(s) at the particular locus with introduction of an alteration into at least one, optionally both copies, of the native gene(s), so as to prevent expression of functional immunoglobulin. The alteration can be an insertion, deletion, replacement or combination thereof. When the alteration is introduce into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

Targeting Vectors

In another embodiment, nucleic acid targeting vector constructs are also provided. The targeting vectors can be designed to accomplish homologous recombination in cells. These targeting vectors can be transformed into mammalian cells to target the ungulate heavy chain, kappa light chain or lambda light chain genes via homologous recombination. In one embodiment, the targeting vectors can contain a 3' recombination arm and a 5' recombination arm (i.e. flanking sequence) that is homologous to the genomic sequence of ungulate heavy chain, kappa light chain or lambda light chain genomic sequence, for example, sequence represented by Seq ID Nos. 1, 4, 29, 30, 12, 25, 15, 16, 19, 28 or 31, as described above. The homologous DNA sequence can include at least 15 bp, 20 bp, 25 bp, 50 bp, 100 bp, 500 bp, 1 kbp, 2 kbp, 4 kbp, 5 kbp, 10 kbp, 15 kbp, 20 kbp, or 50 kbp of sequence, particularly contiguous sequence, homologous to the genomic sequence. The 3' and 5' recombination arms can be designed such that they flank the 3' and 5' ends of at least one functional variable, joining, diversity, and/or constant region of the genomic sequence. The targeting of a functional region can render it inactive, which results in the inability of the cell to produce functional immunoglobulin molecules. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20: 251-255, 2002; WO 00/51424.

Various constructs can be prepared for homologous recombination at a target locus. The construct can include at least 50 bp, 100 bp, 500 bp, 1 kbp, 2 kbp, 4 kbp, 5 kbp, 10 kbp, 15 kbp, 20 kbp, or 50 kbp of sequence homologous with the target locus. The sequence can include any contiguous sequence of an immunoglobulin gene.

Various considerations can be involved in determining the extent of homology of target DNA sequences, such as, for example, the size of the target locus, availability of sequences, relative efficiency of double cross-over events at the target locus and the similarity of the target sequence with other sequences.

The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). In a particular embodiment, the targeting DNA and the target DNA can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

Porcine Heavy Chain Targeting

In particular embodiments of the present invention, targeting vectors are provided to target the porcine heavy chain locus. In one particular embodiment, the targeting vector can contain 5' and 3' recombination arms that contain homologous sequence to the 3' and 5' flanking sequence of the J6 region of the porcine immunoglobulin heavy chain locus. Since the J6 region is the only functional joining region of the porcine immunoglobulin heavy chain locus, this will prevent the expression of a functional porcine heavy chain immunoglobulin. In a specific embodiment, the targeting vector can contain a 5' recombination arm that contains sequence homologous to genomic sequence 5' of the J6 region, optionally including J1-4 and a 3' recombination arm that contains sequence homologous to genomic sequence 3' of the J6 region, including the mu constant region (a "J6 targeting construct"), see for example, FIG. 1. Further, this J6 targeting construct can also contain a selectable marker gene that is located between the 5' and 3' recombination arms, see for example, Seq ID No S and FIG. 1. In other particular embodiments, the 5' targeting arm can contain sequence 5' of J1, such as depicted in Seq ID No. 1 and/or Seq ID No 4. In another embodiments, the 5' targeting arm can contain sequence 5' of J1, J2 and/or J3, for example, as depicted in approximately residues 1-300, 1-500, 1-750, 1-1000 and/or 1-1500 Seq ID No 4. In a further embodiment, the 5' targeting arm can contain sequence 5' of the constant region, for example, as depicted in approximately residues 1-300, 1-500, 1-750, 1-1000, 1-1500 and/or 1-2000 or any fragment thereof of Seq ID No 4 and/or any contiguous sequence of Seq ID No. 4 or fragment thereof. In another embodiment, the 3' targeting arm can contain sequence 3' of the constant region and/or including the constant region, for example, such as resides 7000-8000 and/or 8000-9000 or fragment thereof of Seq ID No 4. In other embodiments, targeting vector can contain any contiguous sequence or fragment thereof of Seq ID No 4. sequence In other embodiments, the targeting vector can contain a 5' recombination arm that contains sequence homologous to genomic sequence 5' of the diversity region, and a 3' recombination arm that contains sequence homologous to genomic sequence 3' of the diversity region of the porcine heavy chain locus. In a further embodiment, the targeting vector can contain a 5' recombination arm that contains sequence homologous to genomic sequence 5' of the mu constant region and a 3' recombination arm that contains sequence homologous to genomic sequence 3' of the mu constant region of the porcine heavy chain locus.

In further embodiments, the targeting vector can include, but is not limited to any of the following sequences: the Diversity region of heavy chain is represented, for example, by residues 1089-1099 of Seq ID No 29 (D(pseudo)), the Joining region of heavy chain is represented, for example, by residues 1887-3352 of Seq ID No 29 (for example: J(psuedo): 1887-1931 of Seq ID No 29, J(pseudo): 2364-2411 of Seq ID No 29, J(pseudo): 2756-2804 of Seq ID No 29, J (functional J): 3296-3352 of Seq ID No 29), the recombination signals are represented, for example, by residues 3001-3261 of Seq ID No 29 (Nonamer), 3292-3298 of Seq ID No 29 (Heptamer), the Constant Region is represented by the following residues: 3353-9070 of Seq ID No 29 (J to C mu intron), 5522-8700 of Seq ID No 29 (Switch region), 9071-9388 of Seq ID No 29 (Mu Exon 1), 9389-9469 of Seq ID No 29 (Mu Intron A), 9470-9802 of Seq ID No 29 (Mu Exon 2), 9830-10069 of Seq ID No 29 (Mu Intron B), 10070-10387 of Seq ID No 29 (Mu Exon 3), 10388-10517 of Seq ID No 29 (Mu Intron C), 10815-11052 of Seq ID No 29 (Mu Exon 4), 11034-11039 of Seq ID No 29 (Poly(A) signal) or any fragment or combination thereof. Still further, any contiguous sequence at least about 17, 20, 30, 40, 50, 100, 150, 200 or 300 nucleotides of Seq ID No 29 or fragment and/or combination thereof can be used as targeting sequence for the heavy chain targeting vector. It is understood that in general when designing a targeting construct one targeting arm will be 5' of the other targeting arm.

In other embodiments, targeting vectors designed to disrupt the expression of porcine heavy chain genes can contain recombination arms, for example, the 3' or 5' recombination arm, that target the constant region of heavy chain. In one embodiment, the recombination arm can target the mu constant region, for example, the C mu sequences described above or as disclosed in Sun & Butler Immunogenetics (1997) 46: 452-460. In another embodiment, the recombination arm can target the delta constant region, such as the sequence disclosed in Zhao et al. (2003) J immunol 171: 1312-1318, or the alpha constant region, such as the sequence disclosed in Brown & Butler (1994) Molec Immunol 31: 633-642.

```
Seq ID No. 5 GGCCAGACTTCCTCGGAACAGCTCAAAGAGCTCTGTC
             AAAGCCAGATCCCATCACACGTGGGCACCAATAGGCC
             ATGCCAGCCTGCAAGGGCCGAACTGGGTTCTCCACGG
             CGCACATGAAGCCTGCAGCCTGGCTTATCCTCTTCCG
             TGGTGAAGAGGCAGGCCCGGGACTGGACGAGGGGCTA
             GCAGGGTGTGGTAGGCACCTTGCGCCCCCCACCCCGG
             CAGGAACCAGAGACCGTGGGGCTGAGAGTGAGCCTCC
             AAACAGGATGCGCCACCCTTCAGGCCACCTTTCAATC
             CAGCTACACTCCACCTGCCATTCTGCTCTGGGCACAG
             GGCCCAGCCCCTGGATCTTGGCCTTGGCTCGACTTGC
             ACCCACGCGCACACACACACTTCCTAACGTGCTGTGC
             GCTCACGCCTCCCCAGCGTGGTCCATGGGGAGCACGG
             GAGTGCGCGTCCGGCGGTAGTGAGTGCAGAGGTCCCT
             TCCCCTCCCCCAGGAGCCCCAGGGGTGTGTGCAGATC
             TGGGGGCTCCTGTCCCTTACACCTTCATGCCCCTCCC
             CTCATAGGCACCCTCCAGGCGGGAGGGAGCGAGACCT
             TTGCGGAGGGACTCAGCCAACGGGGACACGGGAGGCC
             AGCCCTGAGGAGCTGGCTCGCAAAGAGGAGGTGGGAG
             GTAGGTCCACAGCTGCCACAGAGAGAAACCCTGACGG
             ACCCCACAGGGGCCACGGCAGCCGGAACCAGCTCCCT
             CGTGGGTGAGCAATGGCCAGGGCCCCGCCGGCCACCA
             CGGCTGGCCTTGCGCCAGCTGAGAACTCACGTCCAGT
             GCAGGGAGACTCAAGACAGCCTGTGCACACAGCCTCG
             GATCTGCTCCCATTTCAAGCAGAAAAAGGAAACCGTG
```

-continued

```
CAGGCAGCCCTCAGCATTTCAAGGATTGTAGCAGCGG
CCAACTATTCGTCGGCAGTGGCCGATTAGAATGACCG
TGGAGAAGGGCGGAAGGGTGTCTCGTGGGCTCTGCGG
CCAACAGGCCCTGGCTCCACCTGCCCGCTGCCAGCCC
GAGGGGCTTGGGCCGAGCCAGGAACCAGAGTGCTCAC
CGGGAGCACAGTGACTGACCAAACTCCCGGCCAGAGC
AGCCCCAGGCCAGCCGGGCTCTCGCCCTGGAGGACTC
ACCATCAGATGCACAAGGGGGCGAGTGTGGAAGAGAC
GTGTCGCCCGGGCCATTTGGGAAGGCGAAGGGACCTT
CCAGGTGGACAGGAGGTGGGACGCACTCCAGGCAAGG
GACTGGGTCCCCAAGGCCTGGGGAAGGGGTACTGGCT
TGGGGGTTAGCCTGGCCAGGGAACGGGGAGCGGGGCG
GGGGGCTGAGCAGGGAGGACCTGACCTCGTGGGAGCG
AGGCAAGTCAGGCTTCAGGCAGCAGCCGCACATCCCA
GACCAGGAGGCTGAGGCAGGAGGGGCTTGCAGCGGGG
CGGGGGCCTGCCTGGCTCCGGGGGCTCCTGGGGGACG
CTGGCTCTTGTTTCCGTGTCCCGCAGCAGAGGGCGAG
CTCGCTGGGCCTATGCTTACCTTGATGTCTGGGGCCG
GGGCGTCAGGGTCGTCGTCTCCTCAGGGGAGAGTCCC
CTGAGGCTACGCTGGGG*GGGGACTATGGCAGGTCCA
CGAGGGGCCTGGGGACGAGGGGCCTGGACCAGGCTGC
AGCCCGGAGGACGGGGAGGGCTCTGGCTCTCCAGCAT
CTGGCCCTCGGAAATGGCAGAACCCCTGGCGGGTGAG
CGAGCTGAGAGCGGGTCAGACAGACAGGGGCCGGCCG
GAAAGGAGAAGTTGGGGGCAGAGCCCGCCAGGGGCCA
GGCCCAAGGTTCTGTGTGCCAGGGCCTGGGTGGGGAC
ATTGGTGTGGCCATGGCTACTTAGACGCGTGATCAAG
GGCGAATTCCAGCACACTGGCGGCCGTTACTAGTgga
tcccggcgcgccctaccgggtaggggaggcgcttttc
ccaaggcagtctggagcatgcgctttagcagccccgc
tgggcacttggcgctacacaagtggcctctggcctcg
cacacattccacatccaccggtaggcgccaaccggct
ccgttctttggtggccccttcgcgccaccttctactc
ctcccctagtcaggaagttcccccccgccccgcagct
cgcgtcgtgcaggacgtgacaaatggaagtagcacgt
ctcactagtctcgtgcagatggacagcaccgctgagc
aatggaagcgggtaggcctttggggcagcggccaata
gcagctttggctccttcgctttctgggctcagaggct
gggaaggggtgggtccgggggcgggctcaggggcggg
ctcaggggcggggcgggcgcccgaaggtcctccggaa
gcccggcattctgcacgcttcaaaagcgcacgtctgc
```

-continued cgcgctgttctcctcttcctcatctccgggcctttcg
acctgcagccaatatgggatcggccattgaacaagat
ggattgcacgcaggttctccggccgcttgggtggaga
ggctattcggctatgactgggcacaacagacaatcgg
ctgctctgatgccgccgtgttccggctgtcagcgcag
gggcgcccggttctttttgtcaagaccgacctgtccg
gtgccctgaatgaactgcaggacgaggcagcgcggct
atcgtggctggccacgacgggcgttccttgcgcagct
gtgctcgacgttgtcactgaagcgggaagggactggc
tgctattgggcgaagtgccggggcaggatctcctgtc
atctcaccttgctcctgccgagaaagtatccatcatg
gctgatgcaatgcggcggctgcatacgcttgatccgg
ctacctgcccattcgaccaccaagcgaaacatcgcat
cgagcgagcacgtactcggatggaagccggtcttgtc
aatcaggatgatctggacgaagagcatcaggggctcg
cgccagccgaactgttcgccaggctcaaggcgcgcat
gcccgacggcgaggatctcgtcgtgacccatggcgat
gcctgcttgccgaatatcatggtggaaaatggccgct
tttctggattcatcgactgtggccggctgggtgtggc
ggatcgctatcaggacatagcgttggctacccgtgat
attgctgaagagcttggcggcgaatgggctgaccgct
tcctcgtgctttacggtatcgccgctcccgattcgca
gcgcatcgccttctatcgccttcttgacgagttcttc
tgaggggatcaattcTCTAGATGCATGCTCGAGCGGC
CGCCAGTGTGATGGATATCTGCAGAATTGGCCCTtCC
AGGCGTTGAAGTCGTGGTGTCCTCAGGTAAGAACGGC
CCTCCAGGGCCTTTAATTTCTGCTCTCGTCTGTGGGC
TTTTCTGACTCTGATCCTCGGGAGGCGTCTGTGCCCC
CCCCGGGGATGAGGCCGGCTTGCCAGGAGGGGTCAGG
GACCAGGAGCCTGTGGGAAGTTCTGACGGGGGCTGCA
GGCGGGAAGGGCCCCACCGGGGGGCGAGCCCCAGGGC
GCTGGGCGGCAGGAGACCCGTGAGAGTGCGCCTTGAG
GAGGGTGTCTGCGGAAGCACGAACGCCGGCCGGGAAG
GGCTTGGTGCAATGCGGTCTTCAGACGGGAGGCGTCT
TCTGCCCTCACCGTCTTTCAAGCCCTTGTGGGTCTGA
AAGAGCCATGTCGGAGAGAGAAGGGACAGGCCTGTCC
CGACCTGGCCGAGAGCGGGCAGCCCCGGGGGAGAGGG
GGGCGATCGGGGTGGGCTCTGTGAGGCCAGGTCCAAG
GGAGGACGTGTGGTCCTCGTGACAGGTGCACTTGCGA
AACCTTAGAAGACGGGGTATGTTGGAAGCGGCTCCTG -continued ATGTTTAAGAAAAGGGAGACTGTAAAGTGAGCAGAGT
CCTCAAGTGTGTTAAGGTTTTAAAGGTCAAAGTGTTT
TAAACCTTTGTGACTGCAGTTAGCAAGCGTGCGGGGA
GTGAATGGGGTGCCAGGGTGGCCGAGAGGCAGTACGA
GGGCCGTGCCGTCCTCTAATTCAGGGCTTAGTTTTGG
AGAATAAAGTCGGCCTGTTTTCTAAAAGCATTGGTGG
TGCTGAGCTGGTGGAGGAGGCCGCGGGCAGCGCTGGC
CACCTGCAGCAGGTGGCAGGAAGCAGGTCGGCCAAGA
GGCTATTTTAGGAAGCCAGAAAACACGGTCGATGAAT
TTATAGCTTCTGGTTTCCAGGAGGTGGTTGGGCATGG
CTTTGCGCAGCGCCACAGAACCGAAAGTGCCCACTGA
GAAAAAACAACTCCTGCTTAATTTGCATTTTTGTAAA
AGAAGAAACAGAGGCTGAGGGAAACTGGAAAGTTCCT
GTTTTAACTACTCGAATTGAGTTTTCGGTCTTAGCTT
ATCAAGTGCTCACTTAGATTCATTTTCAAAGTAAACG
TTTAAGAGCCGAGGCATTCCTATCCTCTTCTAAGGCG
TTATTCCTGGAGGCTCATTCACCGCCAGCACCTCCGC
TGCCTGCAGGCATTGCTGTCACCGTCACCGTGACGGC
GCGCACGATTTTCAGTTGGCCCGCTTCCCCTCGTGAT
TAGGACAGACGCGGGCACTCTGGCCCAGCCGTCTTGG
CTCAGTATGTGCAGGCGTGCGTCTCGGGACGGAGCTC
AGGGGAAGAGCGTGACTCCAGTTGAACGTGATAGTCG
GTGCGTTGAGAGGAGACCCAGTCGGGTGTCGAGTCAG
AAGGGGCCCGGGGCCCGAGGCCCTGGGCAGGACGGCC
CGTGCCCTGCATCACGGGCCCAGCGTCCTAGAGGCAG
GACTCTGGTGGAGAGTGTGAGGGTGCCTGGGGCCCCT
CCGGAGCTGGGGCCGTGCGGTGCAGGTTGGGCTCTCG
GCGCGGTGTTGGCTGTTTCTGCGGGATTTGGAGGAAT
TCTTCCAGTGATGGGAGTCGCCAGTGACCGGGCAGCA
GGCTGGTAAGAGGGAGGCCGGCGTCGTGGCCAGAGCA
GCTGGGAGGGTTCGGTAAAAGGCTCGCCCGTTTCGTT
TAATGAGGACTTTTCCTGGAGGGCATTTAGTCTAGTC
GGGACCGTTTTCGACTCGGGAAGAGGGATGCGGAGGA
GGGCATGTGCCCAGGAGCCGAAGGCGCCGCGGGGAGA
AGCCCAGGGCTCTCCTGTCCCCACAGAGGCGACGCCA
CTGCCGCAGACAGACAGGGGCTTTCCCTCTGATGACG
GGAAAGGCGCCTGGGGTCTTGCGGGGTGCTGGGGGGG
AGTCGCCCCGAAGCCGCTCAGCCAGAGGCCTGAGGGG
TGAGACTGACCGATGCCTCTTGGCCGGGCCTGGGGCC
GGACCGAGGGGGACTCCGTGGAGGCAGGGCGATGGTG
GCTGCGGGAGGGAACCGACCCTGGGCCGAGCCCGGCT -continued TGGCGATTCCCGGGCGAGGGCCCTCAGCCGAGGCGAG
TGGGTCCGGCGGAACCACCCTTTCTGGCCAGCGGGAG
AGGGCTCTCGGGACTGTCCGGGGCGACGCTGGGCTGC
CCGTGGCAGGCCTGGGCTGACCTGGACTTCACCAGAC
AGAACAGGGCTTTCAGGGCTGAGCTGAGCCAGGTTTA
GCGAGGCCAAGTGGGGCTGAACCAGGCTCAACTGGCC
TGAGCTGGGTTGAGCTGGGCTGACCTGGGCTGAGCTG
AGCTGGGCTGGGCTGGGCTGGGCTGGGGTGGGCTGGG
CTGGACTGGCTGAGCTGAGCTGGGTTGAGCTGAGCTG
AGCTGGCCTGGGTTGAGCTGGGCTGGGTTGAGCTGAG
CTGGGTTGAGCTGGGTTGAGCTGGGTTGATCTGAGCT
GAGCTGGGCTGAGCTGAGCTAGGCTGGGGTGAGCTGG
GCTGAGCTGGTTTGAGTTGGGTTGAGCTGAGCTGAGC
TGGGCTGTGCTGGCTGAGCTAGGCTGAGCTAGGCTAG
GTTGAGCTGGGCTGGGCTGAGCTGAGGTAGGCTGGGC
TGATTTGGGCTGAGCTGAGCTGAGCTAGGCTGCGTTG
AGCTGGCTGGGCTGGATTGAGCTGGCTGAGCTGGCTG
AGCTGGGCTGAGCTGGCCTGGGTTGAGCTGAGCTGGA
CTGGTTTGAGCTGGGTCGATCTGGGTTGAGCTGTCCT
GGGTTGAGCTGGGCTGGGTTGAGCTGAGCTGGGTTGA
GCTGGGCTCAGCAGAGCTGGGTTGGGCTGAGCTGGGT
TGAGCTGAGCTGGGCTGAGCTGGCCTGGGTTGAGCTG
GGCTGAGCTGAGCTGGGCTGAGCTGGCCTGTGTTGAG
CTGGGCTGGGTTGAGCTGGGCTGAGCTGGATTGAGCT
GGGTTGAGCTGAGCTGGGCTGGGCTGTGCTGACTGAG
CTGGGGTGAGCTAGGGTGGGGTGAGCTGGGCTGAGCT
GATCCGAGCTAGGCTGGGCTGGTTTGGGCTGAGCTGA
GCTGAGCTAGGCTGGATTGATCTGGCTGAGCTGGGTT
GAGCTGAGCTGGGCTGAGGTGGTCTGAGCTGGGGTGG
GTCGAGCTGAGGTGGACTGGTTTGAGCTGGGTCGATC
TGGGCTGAGCTGGCGTGGGTTGAGCTGGGCTGGGTTG
AGCTGAGCTGGGTTGAGCTGGGCTGAGCTGAGGGCTG
GGGTGAGCTGGGCTGAACTAGGGTAGCTAGGTTGGGC
TGAGCTGGGCTGGTTTGGGCTGAGCTGAGCTGAGCTA
GGCTGCATTGAGCAGGCTGAGCTGGGCTGAGCAGGCC
TGGGGTGAGCTGGGCTAGGTGGAGCTGAGCTGGGTCG
AGCTGAGTTGGGGTGAGCTGGCCTGGGTTGAGGTAGG
CTGAGCTGAGCTGAGCTAGGCTGGGTTGAGCTGGCTG
GGCTGGTTTGCGCTGGGTCAAGCTGGGCCGAGCTGGC
CTGGGTTGAGCTGGGCTCGGTTGAGCTGGGCTGAGCT -continued GAGCCGACCTAGGCTGGGATGAGCTGGGCTGATTTGG
GCTGAGCTGAGCTGAGCTAGGCTGCATTGAGCAGGCT
GAGCTGGGCCTGGAGCCTGGCCTGGGGTGAGCTGGGC
TGAGCTGCGCTGAGCTAGGCTGGGTTGAGCTGGCTGG
GCTGGTTTGCGCTGGGTCAAGCTGGGCCGAGCTGGCC
TGGGATGAGCTGGGCCGGTTTGGGCTGAGCTGAGCTG
AGCTAGGCTGCATTGAGCAGGCTGAGCTGGGCTGAGC
TGGCCTGGGGTGAGCTGGGCTGAGCTAAGCTGAGCTG
GGCTGGTTTGGGGTGAGGTGGGTGAGCTGGGTCCTGC
TGAGCTGGGCTGAGCTGACCAGGGGTGAGCTGGGCTG
AGTTAGGCTGGGCTCAGCTAGGCTGGGTTGATCTGGC
AGGGCTGGTTTGCGCTGGGTCAAGCTCCCGGGAGATG
GGCTGGGATGAGCTGGGCTGGTTTGGGCTGAGCTGAG
CTGAGCTGAGCTAGGCTGCATTGAGCAGGCTGAGCTG
GGCTGAGCTGGCCTGGGGTGAGCTGGGCTGGGTGGAG
CTGAGCTGGGCTGAACTGGGGTAAGCTGGCTGAGGTG
GATCGAGCTGAGCTGGGCTGAGCTGGCCTGGGGTTAG
CTGGGCTGAGCTGAGCTGAGCTAGGCTGGGTTGAGCT
GGCTGGGCTGGTTTGCGCTGGGTCAAGCTGGGCCGAG
CTGGCCTGGGTTGAGCTGGGCTGGGCTGAGCTGAGCT
AGGCTGGGTTGAGCTGGGCTGGGCTGAGCTGAGCTAG
GCTGCATTGAGCTGGCTGGGATGGATTGAGCTGGCTG
AGCTGGCTGAGCTGGCTGAGCTGGGCTGAGCTGGCCT
GGGTTGAGCTGGGCTGGGTTGAGCTGAGCTGGGCTGA
GCTGGGCTCAGCAGAGCTGGGTTGAGCTGAGCTGGGT
TGAGCTGGGGTGAGCTGGGCTGAGCAGAGCTGGGTTG
AGCTGAGCTGGGTTGAGCTGGGCTCGAGCAGAGCTGG
GTTGAGCTGAGCTGGGTTGAGCTGGGCTCAGCAGAGC
TGGGTTGAGCTGAGCTGGGTTGAGCTGGGCTGAGCTA
GCTGGGCTCAGCTAGGCTGGGTTGAGCTGAGCTGGGC
TGAACTGGGCTGAGCTGGGCTGAACTGGGCTGAGCTG
GGCTGAGCTGGGCTGAGCAGAGCTGGGCTGAGCAGAG
CTGGGTTGGTCTGAGCTGGGTTGAGCTGGGCTGAGCT
GGGCTGAGCAGAGTTGGGTTGAGCTGAGCTGGGTTCA
GCTGGGCTGAGCTAGGCTGGGTTGAGGTGGGTTGAGT
TGGGCTGAGCTGGGCTGGGTTGAGCGGAGCTGGGCTG
AACTGGGCTGAGCTGGGCTGAGCGGAACTGGGTTGAT
CTGAATTGAGCTGGGCTGAGCCGGGCTGAGCCGGGCT
GAGCTGGGCTAGGTTGAGCTTGGGTGAGCTTGCCTCA
GCTGGTCTGAGCTAGGTTGGGTGGAGCTAGGCTGGAT
TGAGCTGGGCTGAGGTGAGCTGATCTGGCCTCAGCTG -continued

```
GGCTGAGGTAGGCTGAACTGGGCTGTGCTGGGCTGAG
CTGAGCTGAGCCAGTTTGAGCTGGGTTGAGCTGGGCT
GAGCTGGGCTGTGTTGATCTTTCCTGAACTGGGCTGA
GCTGGGCTGAGCTOGCCTAGCTGGATTGAACGGGGGT
AAGCTGGGCCAGGCTGGACTGGGCTGAGGTGAGCTAG
GCTGAGCTGAGTTGAATTGGGTTAAGCTGGGCTGAGA
TGGGCTGAGCTGGGCTGAGCTGGGTTGAGCCAGGTCG
GACTGGGTTACCCTGGGCCACACTGGGCTGAGCTGGG
GGGAGCTCGATTAACCTGGTCAGGCTGAGTCGGGTCC
AGCAGACATGCGCTGGGCAGGCTGGCTTGACCTGGAC
ACGTTGGATGAGCTGCCTTGGGATGGTTCACCTCAGC
TGAGCCAGGTGGCTCCAGCTGGGCTGAGCTGGTGACC
CTGGGTGACCTCGGTGACCAGGTTGTCCTGAGTCCGG
GCCAAGGGGAGGCTGCATCAGACTCGCCAGACCCAAG
GCCTGGGCCCCGGCTGGCAAGCCAGGGGCGGTGAAGG
CTGGGCTGGCAGGACTGTCCCGGAAGGAGGTGCACGT
GGAGCCGCCCGGACCCCGACCGGCAGGACCTGGAAAG
ACGCCTCTCACTCCCCTTTCTCTTCTGTCCCCTCTGG
GGTCCTCAGAGAGCCAGTCTGCCCCGAATCTCTACCC
CCTCGTCTCCTGCGTGAGCCCCCCGTGCGATGAGAGC
CTGGTGGCCCTGGGCTGCCTGGCCCGGGACTTCCTGC
CCAGCTCCGTCACCTTCTCCTGGAA
```

Porcine Kappa Chain Targeting

In particular embodiments of the present invention, targeting vectors are provided to target the porcine kappa chain locus. In one particular embodiment, the targeting vector can contain 5' and 3' recombination arms that contain homologous sequence to the 3' and 5' flanking sequence of the constant region of the porcine immunoglobulin kappa chain locus. Since the present invention discovered that there is only one constant region of the porcine immunoglobulin kappa light chain locus, this will prevent the expression of a functional porcine kappa light chain immunoglobulin. In a specific embodiment, the targeting vector can contain a 5' recombination arm that contains sequence homologous to genomic sequence 5' of the constant region, optionally including the joining region, and a 3' recombination arm that contains sequence homologous to genomic sequence 3' of the constant region, optionally including at least part of the enhancer region (a "Kappa constant targeting construct"), see for example, FIG. 2. Further, this kappa constant targeting construct can also contain a selectable marker gene that is located between the 5' and 3' recombination arms, see for example, Seq ID No 20 and FIG. 2. In other embodiments, the targeting vector can contain a 5' recombination arm that contains sequence homologous to genomic sequence 5' of the joining region, and a 3' recombination arm that contains sequence homologous to genomic sequence 3' of the joining region of the porcine kappa light chain locus. In other embodiments, the 5' arm of the targeting vector can include Seq ID No 12 and/or Seq ID No 25 or any contiguous sequence or fragment thereof. In another embodiment, the 3' arm of the targeting vector can include Seq ID No 15, 16 and/or 19 or any contiguous sequence or fragment thereof.

In further embodiments, the targeting vector can include, but is not limited to any of the following sequences: the coding region of kappa light chain is represented, for example by residues 1-549 of Seq ID No 30 and 10026-10549 of Seq ID No 30, whereas the intronic sequence is represented, for example, by residues 550-10025 of Seq ID No 30, the Joining region of kappa light chain is represented, for example, by residues 5822-7207 of Seq ID No 30 (for example, J1:5822-5859 of Seq ID No 30, J2:6180-6218 of Seq ID No 30, J3:6486-6523 of Seq ID No 30, J4:6826-6863 of Seq ID No 30, J5:7170-7207 of Seq ID No 30), the Constant Region is represented by the following residues: 10026-10549 of Seq ID No 30 (C exon) and 10026-10354 of Seq ID No 30 (C coding), 10524-10529 of Seq ID No 30 (Poly(A) signal) and 11160-11264 of Seq ID No 30 (SINE element) or any fragment or combination thereof. Still further, any contiguous sequence at least about 17, 20, 30, 40, 50, 100, 150, 200 or 300 nucleotides of Seq ID No 30 or fragment and/or combination thereof can be used as targeting sequence for the heavy chain targeting vector. It is understood that in general when designing a targeting construct one targeting arm will be 5' of the other targeting arm.

```
Seq ID No. 20 ctcaaacgtaagtggctttttccgactgattctttgc
              tgtttctaattgttggttggctttttgtccatttttc
              agtgttttcatcgaattagttgtcagggaccaaacaa
              attgccttcccagattaggtaccagggaggggacatt
              gctgcatgggagaccagagggtggctaatttttaacg
              tttccaagccaaaataactggggaagggggcttgctg
              tcctgtgagggtaggtttttatagaagtggaagttaa
              ggggaaatcgctatggttcacttttggctcggggacc
              aaagtggagcccaaaattgagtacattttccatcaat
              tatttgtgagatttttgtcctgttgtgtcatttgtgc
              aagtttttgacattttggttgaatgagccattcccag
              ggacccaaaaggatgagaccgaaaagtagaaaagagc
              caacttttaagctgagcagacagaccgaattgttgag
              tttgtgaggagagtagggtttgtagggagaaagggga
              acagatcgctggctttttctctgaattagcctttctc
              atgggactggcttcagaggggggtttttgatgagggaa
              gtgttctagagccttaactgtgggttgtgttcggtag
              cgggaccaagctggaaatcaaacgtaagtgcactttt
              ctactcctttttctttcttatacgggtgtgaaattgg
              ggacttttcatgtttggagtatgagttgaggtcagtt
              ctgaagagagtgggactcatccaaaaatctgaggagt
              aagggtcagaacagagttgtctcatggaagaacaaag
              acctagttagttgatgaggcagctaaatgagtcagtt
              gacttgggatccaaatggccagacttcgtctgtaacc
              aacaatctaatgagatgtagcagcaaaaagagatttc
```

-continued cattgaggggaaagtaaaattgttaatattgtggatc
acctttggtgaagggacatccgtggagattgaacgta
agtatttttctctactaccttctgaaatttgtctaa
atgccagtgttgacttttagaggcttaagtgtcagtt
ttgtgaaaaatgggtaaacaagagcatttcatattta
ttatcagtttcaaaagttaaactcagctccaaaaatg
aatttgtagacaaaaagattaatttaagccaaattga
atgattcaaaggaaaaaaaaattagtgtagatgaaaa
aggaattcttacagctccaaagagcaaaagcgaatta
attttctttgaactttgccaaatcttgtaaatgattt
ttgttctttacaatttaaaaaggttagagaaatgtat
ttcttagtctgttttctctcttctgtctgataaatta
ttatatgagataaaaatgaaaattaataggatgtgct
aaaaaatcagtaagaagttagaaaaatatatgtttat
gttaaagttgccacttaattgagaatcagaagcaatg
ttatttttaaagtctaaaatgagagataaactgtcaa
tacttaaattctgcagagattctatatcttgacagat
atctccttttcaaaaatccaatttctatggtagact
aaatttgaaatgatcttcctcataatggagggaaaag
atggactgaccccaaaagctcagattt*aagaaaacc
tgtttaag*gaaagaaaataaaagaactgcattttt
aaaggcccatgaatttgtagaaaaataggaaatattt
taataagtgtattcttttattttcctgttattacttg
atggtgtttttataccgccaaggaggccgtggcaccg
tcagtgtgatctgtagaccccatggcggcctttttc
gcgattgaatgaccttggcggtgggtccccagggctc
tggtggcagcgcaccagccgctaaaagccgctaaaaa
ctgccgctaaaggccacagcaaccccgcgaccgcccg
ttcaactgtgctgacacagtgatacagataatgtcgc
taacagaggagaatagaaatatgacgggcacacgcta
atgtggggaaaagagggagaagcctgatttttattt
ttagagattctagagataaaattcccagtattatatc
cttttaataaaaaatttctattaggagattataaaga
atttaaagctatttttttaagtggggtgtaattcttt
cagtagtctcttgtcaaatggatttaagtaatagagg
cttaatccaaatgagagaaatagacgcataaccctt
caaggcaaaagctacaagagcaaaaattgaacacagc
agccagccatctagccactcagattttgatcagtttt
actgagtttgaagtaaatatcatgaaggtataattgc
tgataaaaaaataagatacaggtgtgacacatcttta
agtttcagaaatttaatggcttcagtaggattatatt -continued tcacgtatacaaagtatctaagcagataaaaatgcca
ttaatggaaacttaatagaaatatatttttaaattcc
ttcattctgtgacagaaattttctaatctgggtcttt
taatcacctaccctttgaaagagtttagtaatttgct
atttgccatcgctgtttactccagctaatttcaaaag
tgatacttgagaaagattatttttggtttgcaaccac
ctggcaggactattttagggccattttaaaactcttt
tcaaactaagtattttaaactgttctaaaccatttag
ggccttttaaaaatcttttcatgaatttcaaacttcg
ttaaaagttattaaggtgtctggcaagaacttcctta
tcaaatatgctaatagtttaatctgttaatgcaggat
ataaaattaaagtgatcaaggcttgacccaaacagga
gtatcttcatagcatatttcccctcctttttttctag
aattcatatgattttgctgccaaggctattttatata
atctctggaaaaaaaatagtaatgaaggttaaaagag
aagaaaatatcagaacattaagaattcggtattttac
taactgcttggttaacatgaaggtttttattttatta
aggtttctatctttataaaaatctgttcccttttctg
ctgatttctccaagcaaaagattcttgatttgttttt
taactcttactctcccacccaagggcctgaatgccca
caaaggggacttccaggaggccatctggcagctgctc
accgtcagaagtgaagccagccagttcctcctgggca
ggtggccaaaattacagttgacccctcctggtctggc
tgaaccttgccccatatggtgacagccatctggccag
ggcccaggtctccctctgaagcctttgggaggagagg
gagagtggctggcccgatcacagatgcggaaggggct
gactcctcaaccggggtgcagactctgcagggtgggt
ctgggcccaacacacccaaagcacgcccaggaaggaa
aggcagcttggtatcactgcccagagctaggagaggc
accgggaaaatgatctgtccaagacccgttcttgctt
ctaaactccgagggggtcagatgaagtggttttgttt
cttggcctgaagcatcgtgttccctgcaagaagcggg
gaacacagaggaaggagagaaaagatgaactgaacaa
agcatgcaaggcaaaaaaggGGGTCTAGCCGCGGTCT
AGGAAGCTTTCTAGGGTACCTCTAGGGATCCCGGCGC
GCCCTACCGGGTAGGGGAGGCGCTTTTCCCAAGGCAG
TCTGGAGCATGCGCTTTAGCAGCCCCGCTGGGCACTT
GGCGCTACACAAGTGGCCTCTGGCCTCGCACACATTC
CACATCCACCGGTAGGCGCCAACCGGCTCCGTTCTTT
GGTGGCCCCTTCGCGCCACCTTCTACTCCTCCCCTAG -continued TCAGGAAGTTCCCCCCCGCCCCGCAGCTCGCGTCGTG
CAGGACGTGACAAATGGAAGTAGCACGTGTCACTAGT
CTCGTGCAGATGGACAGCACCGCTGAGCAATGGAAGC
GGGTAGGCCTTTGGGGCAGCGGCCAATAGCAGCTTTG
GCTCCTTCGCTTTCTGGGCTCAGAGGCTGGGAAGGGG
TGGGTCCGGGGGCGGGGTCAGGGGCGGGCTCAGGGGC
GGGGCGGGCGCCCGAAGGTCCTCCGGAAGCCCGGCAT
TCTGCACGCTTCAAAAGCGCACGTCTGCCGCGCTGTT
CTCCTCTTCCTCATCTCCGGGCCTTTCGACCTGCAGC
CAATATGGGATCGGCCATTGAACAAGATGGATTGCAC
GCAGGTTCTCCGGCCGCTTGGGTGGAGAGGGTATTCG
GCTATGACTGGGCAGAACAGACAATCGGCTGCTCTGA
TGCCGCCGTGTTCCGGCTGTCAGCGCAGGGGCGCCCG
GTTCTTTTTGTCAAGACCGACCTGTCCGGTGCCCTGA
ATGAACTGCAGGACGAGGCAGCGCGGCTATGGTGGCT
GGCCAGGAGGGGCGTTCGTTGGGCAGCTGTGCTCGAC
GTTGTCACTGAAGCGGGAAGGGACTGGCTGCTATTGG
GCGAAGTGCCGGGGCAGGATCTCCTGTCATCTCACCT
TGCTCCTGCCGAGAAAGTATCCATGATGGCTGATGCA
ATGGGGCGGCTGCATACGGTTGATGGGGCTACCTGCC
CATTCGACCACCAAGCGAAACATCGCATCGAGCGAGC
ACGTACTCGGATGGAAGCCGGTCTTGTCAATCAGGAT
GATCTGGACGAAGAGCATCAGGGGCTCGCGCGAGCCG
AACTGTTCGCCAGGCTCAAGGCGCGCATGCCCGACGG
CGAGGATCTCGTCGTGACCCATGGCGATGCCTGCTTG
CCGAATATCATGGTGGAAAATGGCCGCTTTTCTGGAT
TCATCGACTGTGGCCGGCTGGGTGTGGGGGATCGCTA
TGAGGACATAGCGTTGGCTACCGGTGATATTGCTGAA
GAGCTTGGCGGCGAATGGGCTGACCGGTTCCTCGTGC
TTTACGGTATCGCCGCTCCCGATTCGCAGCGCATCGC
CTTCTATCGCCTTCTTGACGAGTTCTTCTGAGGGGAT
CAATTCTCTAGAGCTCGCTGATCAGCCTCGACTGTGC
CTTCTAGTTGCCAGCCATCTGTTGTTTGCCCCTCCCC
CGTGCCTTCCTTGACCCTGGAAGGTGCCACTCCCACT
GTCCTTTCCTAATAAAATGAGGAAATTGCATCGCATT
GTGTGAGTAGGTGTCATTCTATTGTGGGGGGTGGGGT
GGGGCAGGACAGCAAGGGGGAGGATTGGGAAGACAAT
AGCAGGCATGCTGGGGATGCGGTGGGCTCTATGGCTT
CTGAGGCGGAAAGAACCAGCTGGGGGCGCGGCCctcg
agcggccgccagtgtgatggatatctgcagaattcgc
ccttggatcaaacacgcatcctcatggacaatatgtt -continued gggttcttagcctgctgagacacaacaggaactcccc
tggcaccactttagaggccagagaaacagcacagata
aaattccctgccctcatgaagcttatagtctagctgg
ggagatatcataggcaagataaacacatacaaataca
tcatcttaggtaataatatatactaaggagaaaatta
caggggagaaagaggacaggaattgctagggtaggat
tataagttcagatagttcatcaggaacactgttgctg
agaagataacatttaggtaaagaccgaagtagtaagg
aaatggaccgtgtgcctaagtgggtaagaccattcta
ggcagcaggaacagcgatgaaagcactgaggtgggtg
ttcactgcacagagttgttcactgcacagagttgtgt
ggggaggggtaggtcttgcaggctcttatggtcacag
gaagaattgttttactcccaccgagatgaaggttggt
ggattttgagcagaagaataattctgcctggtttata
tataacaggatttccctgggtgctctgatgagaataa
tctgtcaggggtgggatagggagagatatggcaatag
gagccttggctaggagcccacgacaataattccaagt
gagaggtggtgctgcattgaaagcaggactaacaaga
cctgctgacagtgtggatgtagaaaaagatagaggag
acgaaggtgcatctagggttttctgcctgaggaatta
gaaagataaagctaaagcttatagaagatgcagcgct
ctggggagaaagaccagcagctcagttttgatccatc
tggaattaattttggcataaagtatgaggtatgtggg
ttaacattatttgttttttttttttccatgtagctat
ccaactgtcccagcatcatttattttaaaagactttc
ctttcccctattggattgttttggcaccttcactgaa
gatcaactgagcataaaattgggtctatttctaagct
cttgattccattccatgacctatttgttcatctttac
cccagtagacactgccttgatgattaaagcccctgtt
accatgtctgttttggacatggtaaatctgagatgcc
tattagccaaccaagcaagcacggcccttagagagct
agatatgagagcctggaattcagacgagaaaggtcag
tcctagagacatacatgtagtgccatcaccatgcgga
tggtgttaaaagccatcagactgcaacagactgtgag
agggtaccaagctagagagcatggatagagaaaccca
agcactgagctgggaggtgctcctacattaagagatt
agtgagatgaaggactgagaagattgatcagagaaga
aggaaaatcaggaaaatggtgctgtcctgaaaatcca
agggaagagatgttccaaagaggagaaaactgatcag
ttgtcagctagcgtcaattgggatgaaaatggaccat -continued tggacagagggatgtagtgggtcatgggtgaatagat
aagagcagcttctatagaatggcaggggcaaaattct
catctgatcggcatgggttctaaagaaaacgggaaga
aaaaattgagtgcatgaccagtcccttcaagtagaga
ggtggaaaagggaaggaggaaaatgaggccacgacaa
catgagagaaatgacagcatttttaaaaatttttat
tttattttatttatttattttgctttttagggctgc
ccctgcaacatatggaggttcccaggttaggggtcta
atcagagctatagctgccagcctacaccacagccata
gcaatgccagatctacatgacctacaccacagctcac
agcaacgccggatccttaacccactgagtgaggccag
agatcaaacccatatccttatggatactagtcaggtt
cattaccactgagccaaaatgggaaatcctgagtaat
gacagcatttttaatgtgccaggaagcaaaacttgc
caccccgaaatgtctctcaggcatgtggattattttg
agctgaaaacgattaaggcccaaaaaacacaagaaga
aatgtggaccttcccccaacagcctaaaaaatttaga
ttgagggcctgttcccagaatagagctattgccagac
ttgtctacagaggctaagggctaggtgtggtggggaa
accctcagagatcagagggacgtttatgtaccaagca
ttgacatttccatctccatgcgaatggccttcttccc
ctctgtagccccaaaccaccaccccccaaaatcttctt
ctgtctttagctgaagatggtgttgaaggtgatagtt
tcagccactttggcgagttcctcagttgttctgggtc
tttcctccTgatccacattattcgactgtgtttgatt
ttctcctgtttatctgtctcattggcacccatttcat
tcttagaccagcccaaagaacctagaagagtgaagga
aaatttcttccaccctgacaaatgctaaatgagaatc
accgcagtagaggaaaatgatctggtgctgcgggaga
tagaagagaaaatcgctggagagatgtcactgagtag
gtgagatgggaaaggggtgacacaggtggaggtgttg
ccctcagctaggaagacagacagttcacagaagagaa
gcgggtgtccgtggacatcttgcctcatggatgagga
aaccgaggctaagaaagactgcaaaagaaaggtaagg
attgcagagaggtcgatccatgactaaaatcacagta
accaaccccaaaccaccatgttttctcctagtctggc
acgtggcaggtactgtgtaggttttcaatattattgg
tttgtaacagtacctattaggcctccatcccctcctc
taatactaacaaaagtgtgagactggtcagtgaaaaa
tggtcttctttctctatgaatctttctcaagaagata
cataacttttatttatcatagcttgaagagcaaa -continued tgagaaacagcctccaacctatgacaccgtaacaaaa
tgtttatgatcagtgaagggcaagaaacaaaacatac
acagtaaagaccctccataatattgtgggtggcccaa
cacaggccaggttgtaaaagctttttattctttgata
gaggaatggatagtaatgtttcaacctggacagagat
catgttcactgaatccttccaaaaattcatgggtagt
ttgaattataaggaaaataagacttaggataaatact
ttgtccaagatcccagagttaatgccaaaatcagttt
tcagactccaggcagcctgatcaagagcctaaacttt
aaagacacagtcccttaataactactattcacagttg
cactttcagggcgcaaagactcattgaatcctacaat
agaatgagtttagatatcaaatctctcagtaatagat
gaggagactaaatagcgggcatgacctggtcacttaa
agacagaattgagattcaaggctagtgttctttctac
ctgttttgtttctacaagatgtagcaatgcgctaatt
acagacctctcagggaaggaa Porcine Lambda Chain Targeting In particular embodiments of the present invention, targeting vectors are provided to target the porcine lambda chain locus. In one embodiment, lambda can be targeted by designing a targeting construct that contains a 5' arm containing sequence located 5' to the first JC unit and a 3' arm containing sequence 3' to the last JC unit of the J/C cluster region, thus preventing functional expression of the lambda locus (see, FIGS. 3-4). In one embodiment, the targeting vector can contain any contiguous sequence (such as about 17, 20, 30, 40, 50, 75, 100, 200, 300 or 5000 nucleotides of contiguous sequence) or fragment thereof. Seq ID No 28. In one embodiment, the 5' targeting arm can contain Seq ID No. 32, which includes 5' flanking sequence to the first lambda J/C region of the porcine lambda light chain genomic sequence or any contiguous sequence (such as about 17, 20, 30, 40, 50, 75, 100, 200, 300 or 5000 nucleotides of contiguous sequence) or fragment thereof (see also, for example FIG. 5). In another embodiment, the 3' targeting arm can contain, but is not limited to one or more of the following: Seq ID No. 33, which includes 3' flanking sequence to the J/C cluster region of the porcine lambda light chain genomic sequence, from approximately 200 base pairs downstream of lambda J/C; Seq ID No. 34, which includes 3' flanking sequence to the J/C cluster region of the porcine lambda light chain genomic sequence, approximately 11.8 Kb downstream of the J/C cluster, near the enhancer; Seq ID No. 35, which includes approximately 12 Kb downstream of lambda, including the enhancer region; Seq ID No. 36, which includes approximately 17.6 Kb downstream of lambda; Seq ID No. 37, which includes approximately 19.1 Kb downstream of lambda; Seq ID No. 38, which includes approximately 21.3 Kb downstream of lambda; and Seq ID No. 39, which includes approximately 27 Kb downstream of lambda, or any contiguous sequence (such as about 17, 20, 30, 40, 50, 75, 100, 200, 300 or 5000 nucleotides of contiguous sequence) or fragment thereof of Seq ID Nos 32-39 (see also, for example FIG. 6). It is understood that in general when designing a targeting construct one targeting arm will be 5' of the other targeting arm.

Seq ID No. 48 (as shown in Example 4) provides a representative, non-limiting example of a targeting construct that contains a 5' arm containing sequence located 5' to the first JC unit and a 3' arm containing sequence 3' to the last JC unit of the J/C cluster region. Representative 5' and 3' arms are shown in Seq ID No. 49 and 50 (also in Example 4).

In another embodiment, lambda is targeted using two targeting vectors. The two lambda targeting vectors, i.e., a vector pair, are utilized in a two step strategy to delete the entire J/C region of porcine lambda. In the first step, a first targeting vector is inserted upstream of the J/C region (or alternatively downstream of the J/C region). If the first targeting vector is inserted upstream of the J/C region, the 5' and 3' recombination arms of the first targeted vector contain homologous sequence to the 5' flanking sequence of the first J/C unit of the J/C cluster region. See FIG. 5, which shows 7 JC units in the J/C cluster region. If the first targeting vector is inserted downstream of the J/C cluster region, the 5' and 3' recombination arms of the first targeting vector contain homologous sequence to the 3' region of the last J/C unit in the JC region.

The first-step vectors are designed with lox sites that flank a fusion gene which can provide both positive and negative selection. Selection of the targeting event utilizes the Tn5 APHII gene commonly described as Neo resistance. Once targeting events are isolated, Cre is provided transiently to facilitate deletion of the selectable marker located between two lox sites. Negative selection is then provided by the Herpes simplex thymidine kinase coding region. This step selects for targeted cells that have deleted the selectable marker and retains a single lox site upstream (alternatively downstream) of the J/C region.

Figure 6:
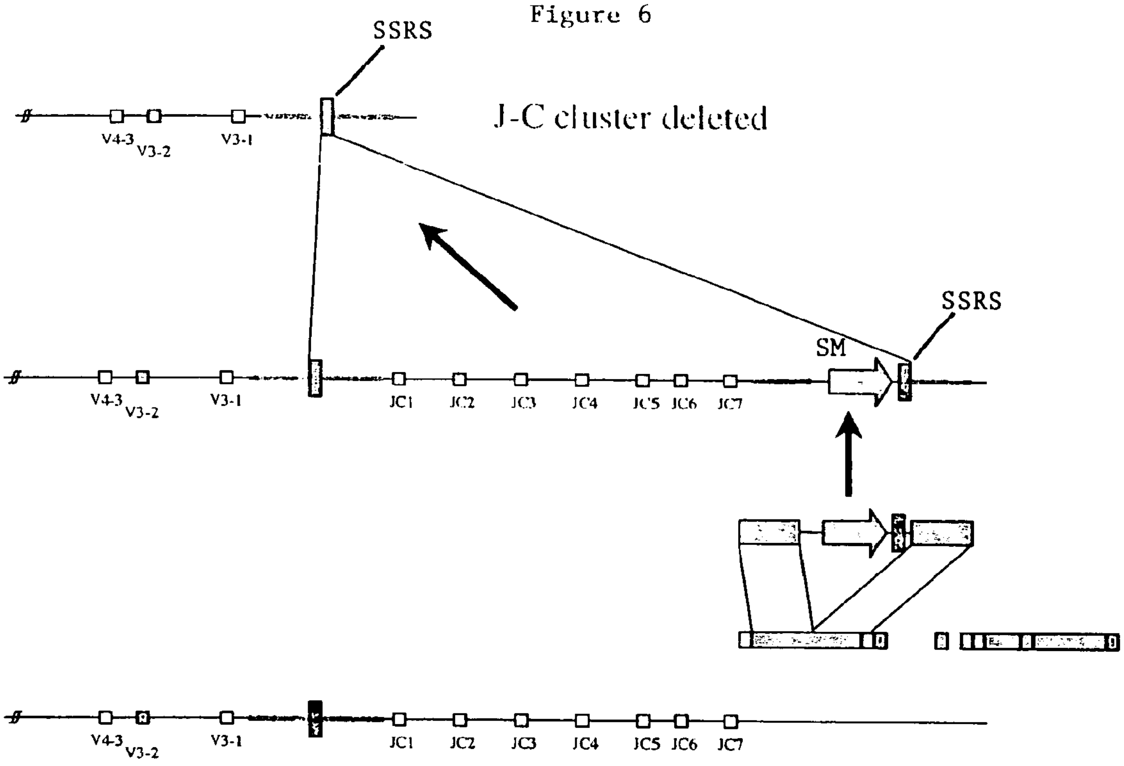
FIG. 6 illustrates a targeting strategy to insert a site specific recombinase target or recognition site into the region 3' of the JC cluster region of the porcine lambda immunoglobulin locus. "SM" stands for a selectable marker gene, which can be used in the targeting vector. "SSRRS" stands for a specific recombinase target or recognition site.

The second step is performed in the same lineage as the first step. The second targeting step also inserts a marker that provides both positive and negative selection. However, the second step inserts the marker on the opposite site of the J/C region in comparison to the first step. That is, if the first vector was inserted upstream of the J/C region, the second targeting vector is inserted downstream, and vice versa. FIG. 6 shows a second targeting vector inserted downstream of the J/C region. In addition, the second targeting vector has a single lox site that is located distally compared to the first vector. In other words, for the first strategy, the second vector has a single lox site located downstream of the marker gene (the alternative vector has the lox site upstream of the marker). After Cre mediated deletion, the region between the first targeting event (which left a lox remnant) and the second targeting event (which has a lox site outside of the marker) is deleted. Cells that have deleted the entire J/C cluster region are thus obtained.

In a representative, non-limiting example, the vector pair is Seq. ID No. 44 (step 1) and Seq. ID No. 45 (step 2).

In a further, non-limiting example, the vector pair is Seq. ID No. 46 (step 1) and Seq. ID No. 47 (step 2).

```
SEQ ID 44 taaacaaataggggttccgcgcacatttccccgaaaagtgc

          cacctgacgtcgctgagcaggccctggcctccctggccgag

          ggcggtttgcgtattagaggcctaaatggccgaattcagcg

          gataacaatttcacacaggaaacagctatgaccatgattat
```

-continued

```
ctagtaactataacggtcctaaggtagcgagcgatcgctta
attaacctgcagggatatcccatgggggccgccagtgtgat
ggatatctgcagaattcgcccttgatattaagagaagggca
agtcagcttaagtttggggtagaggggaacagggagtgag
gagatctggcctgagagataggagccctggtggccacagga
ggactctttgggtcctgtcggatggacacagggcggcccgg
gggcatgttggagcccggctggttcttaccagaggcagggg
gcaccctctgacacgggagcagggcatgttccatacatgac
acacccctctgctccagggcaggtgggtggcggcacagagg
agccagggactctgagcaaggggtccaccagtggggcagtt
ggatccagacttctctgggccagcgagagtctagccctcag
ccgttctctgtccaggagggggtggggcaggcctgggcgg
ccagagctcatccctcaagggttcccagggtcctgccagac
ccagatttccgaccgcagccaccacaagaggatgtggtctg
ctgtggcagctgccaagaccttgcagcaggtgcagggtggg
ggggtgggggcacctgggggcagctggggtcactgagttca
gggaaaaccccttttttcccctaaacctggggccatcccta
ggggaaaccacaacttctgagccctgggcagtggctgctgg
gagggaagagcttcatcctggaccctgggggggaacccagc
tccaaaggtgcaaggggcccaggtccaaggctagagtgggc
caagcaccgcaatggccagggagtgggggaggtggagctgg
actggatcagggcctccttgggactccctacaccctgtgtg
acatgttagggtacccacaccccatcaccagtcagggcctg
gcccatctccagggccagggatgtgcatgtaagtgtgtgtg
agtgtgtgtgtgtggtgtagtacaccccttggcatccggtt
ccgaggccttgggttcctccaaagttgctctctgaattagg
tcaaactgtgaggtcctgatcgccatcatcaacttcgttct
ccccacctcccatcattatcaagagctggggagggtctggg
atttcttcccacccacaagccaaaagataagcctgctggtg
atggcagaagacacaggatcctgggtcagagacaaaggcca
gtgtgtcacagcgagagaggcagccggactatcagctgtca
cagagaggccttagtccgctgaactcaggccccagtgactc
ctgttccactgggcactggccccctccacagcgcccccag
gccccagggagaggcgtcacagcttagagatggccctgctg
aacagggaacaagaacaggtgtgccccatccagcgccccag
gggtgggacaggtgggctggatttggtgtgaagcccttgag
ccctggaacccaaccacagcagggcagttggtagatgccat
ttggggagaggccccaggagtaagggccatgggcccttgag
ggggccaggagctgaggacagggacagagacggcccaggca
gaggacagggccatgaggggtgcactgagatggccactgcc
agcaggggcagctgccaacccgtccagggaacttattcagc
```

-continued agtcagctggaggtgccattgaccctgagggcagatgaagc
ccaggccaggctaggtgggctgtgaagaccccaggggacag
agctctgtccctgggcagcactggcctctcattctgcaggg
cttgacgggatcccaaggcctgctgcccctgatggtagtgg
cagtaccgcccagagcaggaccccagcatggaaaccccaac
gggacgcagcctgcggagcccacaaaaccagtaaggagccg
aagcagtcatggcacggggagtgtggacttccctttgatgg
ggcccaggcatgaaggacagaatgggacagcggccatgagc
agaaaatcagccggaggggatgggcctaggcagacgctggc
tttatttgaagtgttggcattttgtctggtgtgtattgttg
gtattgattttattttagtatgtcagtgacatactgacata
ttatgtaacgacatattattatgtgttttaagaagcactcc
aagggaacaggctgtctgtaatgtgtccagagaagagagca
agagcttggctcagtctcccccaaggaggtcagttcctcaa
caggggtcctaaatgtttcctggagccaggcctgaatcaag
ggggtcatatctacacgtggggcagacccatggaccatttt
cggagcaataagatggcagggaggataccaagctggtctta
cagatccagggctttgacctgtgacgcgggcgctcctccag
gcaaagggagaagccagcaggaagctttcagaactggggag
aacagggtgcagacctccagggtcttgtacaacgcacccctt
tatcctggggtccaggaggggtcactgagggatttaagtgg
gggaccatcagaaccaggtttgtgttttggaaaaatggctc
caaagcagagaccagtgtgaggccagattagatgatgaaga
agaggcagtggaaagtcgatgggtggccaggtagcaagagg
gcctatggagttggcaagtgaatttaaagtggtggcaccag
agggcagatggggaggagcaggcactgtcatggactgtcta
tagaaatctaaaatgtataccctttttagcaatatgcagtg
agtcataaaagaacacatatatatttcctttggccggccgg
cgcgccacgcgtataacttcgtatagcatacattatacgaa
gttatcttaagggctatggcagggcctgccgccccgacgtt
ggctgcgagccctgggccttcacccgaacttggggggtggg
gtggggaaaaggaagaaacgcgggcgtattggccccaatgg
ggtctcggtggggtatcgacagagtgccagccctgggaccg
aaccccgcgtttatgaacaaacgacccaacaccgtgcgttt
tattctgtctttttattgccgtcatagcgcgggttccttcc
ggtattgtctccttccgtgtttcactcgagttagaagaact
cgtcaagaaggcgatagaaggcgatgcgctgcgaatcggga
gcggcgataccgtaaagcacgaggaagcggtcagcccattc
gccgccaagctcttcagcaatatcacgggtagccaacgcta
tgtcctgatagcggtccgccacacccagccggccacagtcg -continued atgaatccagaaaagcggccattttccaccatgatattcgg
caagcaggcatcgccatgggtcacgacgagatcctcgccgt
cgggcatgcgcgccttgagcctggcgaacagttcggctggc
gcgagcccctgatgctcttcgtccagatcatcctgatcgac
aagaccggcttccatccgagtacgtgctcgctcgatgcgat
gtttcgcttggtggtcgaatgggcaggtagccggatcaagc
gtatgcagccgccgcattgcatcagccatgatggatacttt
ctcggcaggagcaaggtgagatgacaggagatcctgccccg
gcacttcgcccaatagcagccagtcccttcccgcttcagtg
acaacgtcgagcacagctgcgcaaggaacgcccgtcgtggc
cagccacgatagccgcgctgcctcgtcctgcagttcattca
gggcaccggacaggtcggtcttgacaaaaagaaccgggcgc
ccctgcgctgacagccggaacacggcggcatcagagcagcc
gattgtctgttgtgcccagtcatagccgaatagcctctcca
cccaagcggccggagaacctgcgtgcaatccatcttgttca
atggccgatcccattccagatctgttagcctcccccatctc
ccgtgcaaacgtgcgcgccaggtcgcagatcgtcggtatgg
agcctggggtggtgacgtgggtctggatcatcccggaggta
agttgcagcagggcgtcccggcagccggcgggcgattggtc
gtaatccaggataaagacgtgcatgggacggaggcgtttgg
tcaagacgtccaaggcccaggcaaacacgttgtacaggtcg
ccgttgggggccagcaactcgggggcccgaaacagggtaaa
taacgtgtccccgatatggggtcgtgggcccgcgttgctct
ggggctcggcaccctggggcggcacggccgtccccgaaagc
tgtccccaatcctcccgccacgacccgccgccctgcagata
ccgcaccgtattggcaagcagcccgtaaacgcggcgaatcg
cggccagcatagccaggtcaagccgctcgccggggcgctgg
cgtttggccaggcggtcgatgtgtctgtcctccggaagggc
ccccaacacgatgtttgtgccgggcaaggtcggcgggatga
gggccacgaacgccagcacggcctgggggggtcatgctgccc
ataaggtatcgcgcggccgggtagcacaggagggcggcgat
gggatggcggtcgaagatgagggtgagggccgggggcgggg
catgtgagctcccagcctcccccccgatatgaggagccaga
acggcgtcggtcacggcataaggcatgcccattgttatctg
ggcgcttgtcattaccaccgccgcgtccccggccgatatct
caccctggtcaaggcggtgttgtgtggtgtagatgttcgcg
attgtctcggaagcccccagcacccgccagtaagtcatcgg
ctcgggtacgtagacgatatcgtcgcgcgaacccagggcca
ccagcagttgcgtggtggtggttttccccatcccgtgggga
ccgtctatataaacccgcagtagcgtgggcattttctgctc
cgggcggacttccgtggcttcttgctgccggcgagggcgca -continued acgccgtacgtcggttgctatggccgcgagaacgcgcagcc
tggtcgaacgcagacgcgtgctgatggccggggtacgaagc
catggtggctctagaggtcgaaaggcccggagatgaggaag
aggagaacagcgcggcagacgtgcgcttttgaagcgtgcag
aatgccgggcttccggaggaccttcgggcgcccgccccgcc
cctgagcccgcccctgagcccgcccccggacccaccccttc
ccagcctctgagcccagaaagcgaaggagccaaagctgcta
ttggccgctgccccaaaggcctacccgcttccattgctcag
cggtgctgtccatctgcacgagactagtgagacgtgctact
tccatttgtcacgtcctgcacgacgcgagctgcggggcggg
ggggaacttcctgactaggggaggagtagaaggtggcgcga
aggggccaccaaagaacggagccggttggcgcctaccggtg
gatgtggaatgtgtgcgaggccagaggccacttgtgtagcg
ccaagtgcccagcggggctgctaaagcgcatgctccagact
gccttgggaaaagcgcctcccctacccggtagggatccgcg
ttacataacttacggtaaatggcccgcctggctgaccgccc
aacgacccccgcccattgacgtcaataatgacgtatgttcc
catagtaacgccaatagggactttccattgacgtcaatggg
tggagtatttacggtaaactgcccacttggcagtacatcaa
gtgtatcatatgccaagtacgccccctattgacgtcaatga
cggtaaatggcccgcctggcattatgcccagtacatgacct
tatgggactttcctacttggcagtacatctacgtattagtc
atcgctattaccatggtgatgcggttttggcagtacatcaa
tgggcgtggatagcggtttgactcacggggatttccaagtc
tccaccccattgacgtcaatgggagtttgttttggcaccaa
aatcaacggttaacaagcttataacttcgtatagcatacat
tatacgaagttattacgtagcggccgcgtcgacgataaatt
gtgtaattccacttctaaggattcatcccaagggggaaaa
taatcaaagatgtaaccaaaggtttacaaacaagaactcat
cattaatcttccttgttgttatttcaacgatattattatta
ttactattattattattattattttgtctttttgcattttc
tagggccactcccacggcatagagaggttcccaggctaggg
gtcaaatcggagctacagctgccggcctacgccagagccac
agcaacgcaggatctgagccacagcaatgcaggatctacac
cacagctcatggtaacgctggatccttaacccaatgagtga
ggccagggatcgaacctgtaacttcatggttcctagtcgga
ttcattaaccactgagccacgacaggaactccaacattatt
aatgatgggagaaaactggaagtaacctaaatatccagcag
aaagggtgtggccaaatacagcatggagtagccatcataag
gaatcttacacaagcctccaaaattgtgtttctgaaattgg -continued gtttaaagtacgtttgcattttaaaaagcctgccagaaaat
acagaaaaatgtctgtgatatgtctctggctgataggattt
tgcttagttttaattttggctttataatttctatagttat
gaaaatgttcacaagaagatatatttcattttagcttctaa
aataattataacacagaagtaatttgtgctttaaaaaaata
ttcaacacagaagtatataaagtaaaaattgaggagttccc
atcgtggctcagtgattaacaaacccaactagtatccatga
ggatatggatttgatccctggccttgctcagtgggttgagg
atccagtgttgctgtgagctgtggtgtaggttgcagacaca
gcactctggcgttgctgtgactctggcgtaggccggcagct
acagctccatttggacccttagcctgggaacctccatatgc
ctgagatacggccctaaaaagtcaaaagccaaaaaaatagt
aaaaattgagtgtttctacttaccacccctgcccacatctt
atgctaaaacccgttctccagagacaaacatcgtcaggtgg
gtctatatatttccagccctcctcctgtgtgtgtatgtccg
taaaacacacacacacacacacacacgcacacacacacaca
cgtatctaattagcattggtattagtttttcaaaagggagg
tcatgctctacctttttaggcggcaaatagattatttaaaca
aatctgttgacattttctatatcaacccataagatctccca
tgttcttggaaaggctttgtaagacatcaacatctgggtaa
accagcatggtttttaggggggttgtgtggatttttttcata
tttttagggcacacctgcagcatatggaggttcccaggct
aggggttgaatcagagctgtagctgccggcctacaccacag
ccacagcaacgccagatccttaacccactgagaaaggccag
ggattgaacctgcatcctcatggatgctggtcagatttatt
tctgctgagccacaacaggaactccctgaaccagaatgctt
ttaaccattccactttgcatggacatttagattgtttccat
ttaaaaatacaaattacaaggagttcccgtcgtggctcagt
ggtaacgaattggactaggaaccatgaggtttcgggttcga
tccctggccttgctcggtgggttaaggatccagcattgatg
tgagatatggtgtaggtcgcagacgtggctcggatcccacg
ttgctgtggctctggcgtaggccggcaacaacagctccgat
tcgacccctagcctgggaacctccatgtgccacaggagcag
ccctagaaaaggcaaaaagacaaaaaaataaaaaattaaaa
tgaaaaaataaaataaaaatacaaattacaagagacggcta
caaggaaatccccaagtgtgtgcaaatgccatatatgtata
aaatgtactagtgtctcctcgcgggaaagttgcctaaaagt
gggttggctggacagagaggacaggctttgacattctcata
ggtagtagcaatgggcttctcaaaatgctgttccagtttac
actcaccatagcaaatgacagtgcctcttcctctccaccct
tgccaataatgtgacaggtggatctttttctattttgtgta -continued tctgacaagcaaaaaatgagaacaggagttcctgtcgtggt gcagtggagacaaatctgactaggaaccatgaaatttcggg ttcaatccctggcctcactcagtaggtaaaggatccagggt tgcagtgagctgtggggtaggtcgcagacacagtgcaaatt tggccctgttgtggctgtggtgtaggccggcagctatagct ccaattggacccctagcctgggaacctccttatgccgtggg tgaggccctaaaaaaaagagtgcaaaaaaaaaaaataagaa caaaaatgatcatcgtttaattctttatttgatcattggtg aaacttatttcctttatatttttattgactgattttatt tctcctatgaatttaccggtcatagttttgcctgggtgttt ttactccggttttagttttggttggttgtattttcttagag agctatagaaactcttcatctatttggaatagtaattcctc attaagtatttgtgctgcaaaaaattttccctgatctgttt tatgcttttgtttgtggggtctttcacgagaaagcctttttt agtttttacacctcagcttggttgtttttcttgattgtgtc tgtaatctgcggccaacataggaaacacatttttactttag tgtttttttcctatttcttcaagtacgtccattgttttgg tgtctgattttactttgcctggggtttgtttttgtgtggca ggaatataaacttatgtattttccaaatggagagccaatgg ttgtatatttgttgaattcaaatgcaactttatcaaacacc aaatcatcgatttatcacaactcttctctggtttattgatc taatgatcaattcctgttccacgctgttttaattattttag ctttgtggattttggtgcctggtagagaacaaagcctccat tattttcattcaaaatagtcccgtctattatctgccattgt tgtagtattagactttaaaatcaatttactgattttcaaaa gttattcctttggtgatgtggaatactttatacttcataag gtacatggattcatttgtggggaattgatgtctttgctatt gtggccatttgtcaagttgtgtaatattttacccatgccaa ctttgcatattgtatgtgagtttattcccagggtttttaat aggatgtttattgaagttgtcagtgtttccacaatttcatc gcctcagtgcttactgtttgcataaaaggaaacctactcac ttttgcctattgctcttgtattcaatcattttagttaactc ttgtgttaattttgagagtttttcagctgactgtctggggt tttctttaatagactagccctttgtctgtaaagaataattt tatcgaatttttcttaacactcacactctccccaccccccac ccccgctcatctcctttcattgggtcaaatctgtagaatac aataaaagtaagagtgggaaccttagcctttaagtcgattt tgcctttaaatgtgaatgttgctatgtttcgggacattctc tttatcaagttgcggatgtttccttagataattaacttaat aaaagactggatgtttgctttcttcaaatcagaattgtgtt -continued gaatttatattgctattctgtttaattttgtttcaaaaaat ttacatgcacaccttaaagataaccatgaccaaatagtcct cctgctgagagaaaatgttggccccaatgccacaggttacc tcccgactcagataaactacaatgggagataaaatcagatt tggcaaagcctgtggattcttgccataactctcagagcatg acttgggtgtttttttccttttctaagtattttaatggtatt tttgtgttacaataggaaatctaggacacagagagtgattc aatgaggggaacgcattctgggatgactctaggcctctggt ttggggagagctctattgaagtaaagacaatgagaggaagc aagtttgcagggaactgtgaggaatttagatggggaatgtt gggtttgaggtttctatagggcacgcaagcagagatgcact caggaggaagaaggagcataaatctagtggcgctgccggca agcttgctggaggaggccaattgggagctgctggaatgcat ggaggcggcgctctcgaggctggaggaggccagctgattta aatcggtccgcgtacgatgcatattaccctgttatccctac cgcggttactggccgtcgttttacaacgtcgtgactgggaa aaccctggcgatgctcttctcccggtgaaaacctctgacac atggctcttctaaatccggagtttaaacgcttccttcatgt gagcaaaaggccagcaaaaggccaggaaccgtaaaaaggcc gcgttgctggcgtttttccataggctccgcccccctgacga gcatcacaaaaatcgacgctcaagtcagaggtggcgaaacc cgacaggactataaagataccaggcgtttccccctggaagc tccctcgtgcgctctcctgttccgaccctgccgcttaccgg atacctgtccgcctttctcccttcgggaagcgtggcgcttt ctcatagctcacgctgtaggtatctcagttcggtgtaggtc gttcgctccaagctgggctgtgtgcacgaaccccccgttca gcccgaccgctgcgccttatccggtaactatcgtcttgagt ccaacccggtaagacacgacttatcgccactggcagcagcc actggtaacaggattagcagagcgaggtatgtaggcggtgc tacagagttcttgaagtggtggcctaactacggctacacta gaaggacagtatttggtatctgcgctctgctgaagccagtt accttcggaaaaagagttggtagctcttgatccggcaaaca aaccaccgctggtagcggtggtttttttgtttgcaagcagc agattacgcgcagaaaaaaaggatctcaagaagatcctttg atcttttctacggggtctgacgctcagtggaacgaaaactc acgttaagggattttggtcatgcctaggtggcaaacagcta ttatgggtattatgggtctaccggtgcatgagattatcaaa aaggatcttcacctagatccttttaaattaaaaatgaagtt ttaaatcaatctaaagtatatatgagtaaacttggtctgac agttaccaatgcttaatcagtgaggcacctatctcagcgat ctgtctatttcgttcatccatagttgcctgactccccgtcg -continued tgtagataactacgatacgggagggcttaccatctggcccc
agtgctgcaatgataccgcgagacccacgctcaccggctcc
agatttatcagcaataaaccagccagccggaagggccgagc
gcagaagtggtcctgcaactttatccgcctccatccagtct
attaattgttgccgggaagctagagtaagtagttcgccagt
taatagtttgcgcaacgttgttgccattgctacaggcatcg
tggtgtcacgctcgtcgtttggtatggcttcattcagctcc
ggttcccaacgatcaaggcgagttacatgatcccccatgtt
gtgcaaaaaagcggttagctccttcggtcctccgatcgttg
tcagaagtaagttggccgcagtgttatcactcatggttatg
gcagcactgcataattctcttactgtcatgccatccgtaag
atgcttttctgtgactggtgagtactcaaccaagtcattct
gagaatagtgtatgcggcgaccgagttgctcttgcccggcg
tcaatacgggataataccgcgccacatagcagaactttaaa
agtgctcatcattggaaaacgttcttcggggcgaaaactct
caaggatcttaccgctgttgagatccagttcgatgtaaccc
actcgtgcacccaactgatcttcagcatcttttactttcac
cagcgtttctgggtgagcaaaaacaggaaggcaaaatgccg
caaaaaagggaataagggcgacacggaaatgttgaatactc
atactcttcctttttcaatattattgaagcatttatcaggg
ttattgtctcgggagcggatacatatttgaatgtatttaga
aaaa SEQ ID 45 taaacaaataggggttccgcgcacatttccccgaaaagtgc
cacctgacgtcgctgagcaggccctggcctccctggccgag
ggcggtttgcgtattagaggcctaaatggccgaattcagcg
gataacaatttcacacaggaaacagctatgaccatgattat
ctagtaactataacggtcctaaggtagcgagcgatcgctta
attaacctgcagggataaccactgacccatgacgggaactc
ccagggctcagctcttgactccaggttcgcagctgccctca
aagcaatgcaaccctggctggccccgcctcatgcatccggc
ctcctccccaaagagctctgagcccacctgggcctaggtcc
tcctccctgggactcatggcctaagggtacagagttactgg
ggctgatgaagggaccaatggggacaggggcctcaaatcaa
agtggctgtctctctcatgtcccttcctctcctcagggtcc
aaaatcagggtcagggccccagggcaggggctgagagggcc
tctttctgaaggccctgtctcagtgcaggttatgggggtct
gggggagggtcaatgcagggctcacccttcagtgccccaaa
gcctagagagtgagtgcctgccagtggcttcccaggcccaa
tcccttgactgcctgggaatgctcaaatgcaggaactgtca
caacaccttcagtcaggggctgctctgggaggaaaaacact -continued cagaattggggggttcagggaaggcccagtgccaagcatagc
aggagctcaggtggctgcagatggtgtgaaccccaggagca
ggatggccggcactccccccagaccctccagagccccaggt
tggctgccctcttcactgccgacacccctgggtccacttct
gccctttcccacctaaaacctttagggctcccactttctcc
caaatgtgagacatcaccacggctcccagggagtgtccaga
agggcatctggctgagaggtcctgacatctgggagcctcag
gccccacaatggacagacgccctgccaggatgctgctgcag
ggctgttagctaggcggggtggagatggggtactttgcctc
tcagaggccccggccccaccatgaaacctcagtgacacccc
atttccctgagttcacatacctgtatcctactccagtcacc
ttccccacgaacccctgggagcccaggatgatgctggggct
ggagccacgaccagcccacgagtgatccagctctgccaatc
agcagtcatttcccaagtgttccagccctgccaggtcccac
tacagcagtaatggaggccccagacaccagtccagcagtta
gagggctggactagcaccagctttcaagcctcagcatctca
aggtgaatggccagtgcccctccccgtggccatcacaggat
cgcagatatgaccctaggggaagaaatatcctgggagtaag
gaagtgcccatactcaaggatggcccctctgtgacctaacc
tgtccctgaggattgtacttccaggcgttaaaacagtagaa
cgcctgcctgtgaaccccccgccaagggactgcttggggagg
ccccctaaaccagaacacaggcactccagcaggacctctga
actctgaccaccctcagcaagtgggcacccccccgcagcttc
caaggcaccccagggctcaccacagcggcccctcctggcag
cccctcacccaggcccagaccctctaagatggcacatctaa
gccaatccacctccttgtcattcctcctgtccccacccagg
acccttctcagatgaaaccttcgctccagccgctgggccct
ctctcctgcccctctggcagttctccagggactccgcctcc
cactctctgtctctccctgcactcctaggaacaagcgacct
ccaggaagcccagtccaattatcccctctgtgtcctcccca
atctctgcctctgggtggatttgagcaccacatcctgttct
cttcgacctgaaactccttggccccggtgtccgctctcctg
ggccctcttttctctcctcccctcttccgtgccccgtttgt
ttggtgttacaggcaggccccggggagccgtccctccagct
gctcttccttgtctgtctcaggagccagaaactggcagcat
ctaaaaagggctcctgtttcttcatctgcccagcctcctag
cccaaccagggctctggcctcactccagagggtgggctcca
gagggcaggggttgcaccctcttagtgcctcagaggctcag
ctgggtgcaggatggggggggccctcagggagcccctcagtg
actgctgatcacttactgcaggactgttcccagctcttccc
aatcattggaatgacaatacctagttctgctccatcatagt -continued gatgcaggaaaaatgttactgaaatcctggttcttgtttag
caatcgaagaatgaattccgcgaacacacaggcagcaagca
agcgaagcctttattaaaggaaagcagatagctcccagggc
tgcagggagcggggagaagagctccccactctctattgtcc
tatagggctttttaccccttaaagttggggggatacaaaaa
aaatagaagaaaaagggagttcccgtcagggcacagcagaa
acaaatccaactaggaaccatgaggttgggggttcgattcc
tggcctctctcagtgggttaaggatgcagcgttgccgtgag
ctatgatacaggtcacagatgcagctcagatctactagtca
attgacaggcgccggagcaggagctaggcctttggccggcc
ggcgcgccagatctcttaagggctatggcagggcctgccgc
cccgacgttggctgcgagccctgggccttcacccgaacttg
gggggtggggtggggaaaaggaagaaacgcgggcgtattgg
ccccaatggggtctcggtggggtatcgacagagtgccagcc
ctgggaccgaaccccgcgtttatgaacaaacgacccaacac
cgtgcgttttattctgtctttttattgccgtcatagcgcgg
gttccttccggtattgtctccttccgtgtttcactcgagtt
agaagaactcgtcaagaaggcgatagaaggcgatgcgctgc
gaatcgggagcggcgataccgtaaagcacgaggaagcggtc
agcccattcgccgccaagctcttcagcaatatcacgggtag
ccaacgctatgtcctgatagcggtccgccacacccagccgg
ccacagtcgatgaatccagaaaagcggccattttccaccat
gatattcggcaagcaggcatcgccatgggtcacgacgagat
cctcgccgtcgggcatgcgcgccttgagcctggcgaacagt
tcggctggcgcgagcccctgatgctcttcgtccagatcatc
ctgatcgacaagaccggcttccatccgagtacgtgctcgct
cgatgcgatgtttcgcttggtggtcgaatgggcaggtagcc
ggatcaagcgtatgcagccgccgcattgcatcagccatgat
ggatactttctcggcaggagcaaggtgagatgacaggagat
cctgccccggcacttcgcccaatagcagccagtcccttccc
gcttcagtgacaacgtcgagcacagctgcgcaaggaacgcc
cgtcgtggccagccacgatagccgcgctgcctcgtcctgca
gttcattcagggcaccggacaggtcggtcttgacaaaaaga
accgggcgcccctgcgctgacagccggaacacggcggcatc
agagcagccgattgtctgttgtgcccagtcatagccgaata
gcctctccacccaagcggccggagaacctgcgtgcaatcca
tcttgttcaatggccgatcccattccagatctgttagcctc
ccccatctcccgtgcaaacgtgcgcgccaggtcgcagatcg
tcggtatggagcctggggtggtgacgtgggtctggatcatc
ccggaggtaagttgcagcagggcgtcccggcagccggcggg -continued cgattggtcgtaatccaggataaagacgtgcatgggacgga
ggcgtttggtcaagacgtccaaggcccaggcaaacacgttg
tacaggtcgccgttgggggccagcaactcgggggcccgaaa
cagggtaaataacgtgtccccgatatggggtcgtgggcccg
cgttgctctggggctcggcaccctggggcggcacggccgtc
cccgaaagctgtccccaatcctcccgccacgacccgccgcc
ctgcagataccgcaccgtattggcaagcagcccgtaaacgc
ggcgaatcgcggccagcatagccaggtcaagccgctcgccg
gggcgctggcgtttggccaggcggtcgatgtgtctgtcctc
cggaagggcccccaacacgatgtttgtgccgggcaaggtcg
gcgggatgagggccacgaacgccagcacggcctggggggtc
atgctgcccataaggtatcgcgcggccgggtagcacaggag
ggcggcgatgggatggcggtcgaagatgagggtgagggccg
ggggcggggcatgtgagctcccagcctcccccccgatatga
ggagccagaacggcgtcggtcacggcataaggcatgcccat
tgttatctgggcgcttgtcattaccaccgccgcgtccccgg
ccgatatctcaccctggtcaaggcggtgttgtgtggtgtag
atgttcgcgattgtctcggaagcccccagcacccgccagta
agtcatcggctcgggtacgtagacgatatcgtcgcgcgaac
ccagggccaccagcagttgcgtggtggtggttttccccatc
ccgtggggaccgtctatataaacccgcagtagcgtgggcat
tttctgctccgggcggacttccgtggcttcttgctgccggc
gagggcgcaacgccgtacgtcggttgctatggccgcgagaa
cgcgcagcctggtcgaacgcagacgcgtgctgatggccggg
gtacgaagccatggtggctctagaggtcgaaaggcccggag
atgaggaagaggagaacagcgcggcagacgtgcgcttttga
agcgtgcagaatgccgggcttccggaggaccttcgggcgcc
cgccccgcccctgagcccgcccctgagcccgcccccggacc
cacccttcccagcctctgagcccagaaagcgaaggagcca
aagctgctattggccgctgccccaaaggcctacccgcttcc
attgctcagcggtgctgtccatctgcacgagactagtgaga
cgtgctacttccatttgtcacgtcctgcacgacgcgagctg
cggggcgggggggaacttcctgactaggggaggagtagaag
gtggcgcgaaggggccaccaaagaacggagccggttggcgc
ctaccggtggatgtggaatgtgtgcgaggccagaggccact
tgtgtagcgccaagtgcccagcggggctgctaaagcgcatg
ctccagactgccttgggaaaagcgcctcccctacccggtag
ggatccgcgttacataacttacggtaaatggcccgcctggc
tgaccgcccaacgacccccgcccattgacgtcaataatgac
gtatgttcccatagtaacgccaatagggactttccattgac
gtcaatgggtggagtatttacggtaaactgcccacttggca -continued gtacatcaagtgtatcatatgccaagtacgcccctattga
cgtcaatgacggtaaatggcccgcctggcattatgcccagt
acatgaccttatgggactttcctacttggcagtacatctac
gtattagtcatcgctattaccatggtgatgcggttttggca
gtacatcaatgggcgtggatagcggtttgactcacggggat
ttccaagtctccaccccattgacgtcaatgggagtttgttt
tggcaccaaaatcaacggttaacaagcttataacttcgtat
agcatacattatacgaagttattacgtagcggccgcgtcga
cgatatcgctgccggagcccccggggccgctgccggaagat
ctggcattgctgtgactgtggtgtaggccggcagctggagc
tctgattagacccctcacctgggaatctccatatgctgcac
gtgcggccctaaaagacaaaagacaaaaaaaaaaaaaaaa
aaaaaaaatcaaaaaaaaacataggggggttaccaacgtggg
gtccagaaagatgtggttttctcccattggccttgcccagt
tacctatatcagtccttgtccaacaggggttttaggggtgg
aaatgccccataaattttacggtttctttgcccttctcttc
ctttagactgagtcaccattgctctcattccttttctatca
gttgaggagtgggttagagattaaggtccatgtggtggagg
tacacttcttatagtaaacaaggcctatggggaattactct
ctggagcccttaaaccacaaatgataatccatgccacatca
aagatgcatcgaagcccatgctcctacactgactacctgag
ttagcattctgcctcaacaggactgaccatccccagctctg
gggcagatatcctctctctgccacaagggcagtgacccccca
tgctgtctgagggtcacgctttacccccccccacccctgc
cgtgacccccccagaccaccccaggaggtgggcactaatatc
cctcattaccccatagatgaggaaacagaggttcccccggg
gtcccacaggtgctcagggtcacatgcaccgtgggcaccca
ggccccatcccaaggccaccctccctcctcaggaagctgtg
ctgcgctgggccagaaggtactgcacacgactcctcagcct
ccggtggtgggaggcagcctcaagcctctgagtgggggggc
acccgggctcctcaatctatactgactcctgggggtgggag
aaggggagggggagctgtggcctctgagtccactaagcaaa
tcagggtgggcaatgcgggcccatttcaaggaggagagaac
cgaggctctgacagcaggccgggggtccagggacctgccca
gggtcataggctgaactgctggctgacctgccttgggttct
ttccttggctcctcagccctgtgtgatgtgacaggtcattc
attcactcactcgctcattcattcagcaaaccctcagtgag
ccctgctgggagcaggtgctaggggcaaggagacaggacct
cttgccctggaacagctgaagcactgggggacaggcagtgg
cagggaggtgcgtgatcaccgctgaccccattccatcctcc -continued agcccccaggtcagtttccacccaccattgaccccaccatg
tcctccatccccaaggtcagtttcccgcccaaggagcatct
ccttacacactagggacaaaatttcacggctgtcactgggc
atctctccacgctcatcacagccctctagcagccttgaagt
cctgtagagcccttcccatttcacagaagggacaagactat
gagggccacaccgtgagccatgagccttaggctgtgagccg
ggacagcccctgcaggactggtggcctcagggcactgggtg
gggagggtgcacagtgggtgggccccttgtggaatagagag
gagtgtcaggtcaggggagggggcttggcctggccctggcc
tgcctggtgtgcaaccctaggcagcccctccttcccaggcc
tcctacttcctggaggccaagcctcagggaggtaattgagt
caggtgggggagggggggttgtggctttcttcacagcagaa
aaacagagcccacaatagtgtccactgagacagaggggtcc
tggggggaggggaggggtgggaggtgactgctgagccctgtg
ggagggagggagcaactactgagctgagctgggtgactctc
ccatctgccccgcccccctgtggggccagcagagtcaccgag
agaacatgacccagccaggcctggacaggggggacacccatg
tcctttaccccacagggttcactgagcctatctgccccaag
cctgtgtctccctgggacggagaccctcactcccaaccaca
aaggtctaaactcaagttcccaacagccttgaaaatacagc
ttccgggggcctccaaggagcagtcagccgtccactgccag
gctcgctggctcagtgacacaggacacatcctgatgacggt
ccacctgtctccaagcaggttctcctctgccgatggggcaa
cgagctcctcctgtggctccctggctggatgcgtgggaggc
ggggtggggggggcaggcggtgttcctggccgcacacaagga
gcacccccaccagcatccgaagacgggggcccggtctttcc
ccaaaacactgcttgcgggagactttgtgacgtttccaggg
gccatgctcccttcgggcagcttgggggacttctgctccta
tgtggtcacctgcagggactccccccaggccttggggacaa
acaaagtgatgagagggagggttagtgggtcggggcagggc
cagtctttggaccggtttatctgaaaagccagttggtcacc
gggaaccacagcaaacctaaacccatttggccaggcatctc
ccagggacagtctcccccaggatgcgggggcccaggggggct
ccaggggtgacctgcgtcctggatttccctgatgctcccag
ttcgtgcctctgtccaagcatgatttttaatagtgcccctt
ccactcccagaaatgtccaagtgtgggcaataaattctggt
cacctgagctcagtgtaactgtttgctgaatgacacttact
gtaacaggttaaaatgggaggcccaaggccacgcagagcca
tcgaaggctctgtgtgtcccagccctgatagaagcatcagg
atggggactgtggcctcaccaggggccacatccaggcggtc
accatggggttcctggtctccgtgggccttgactggagccc -continued ctggtgtgagctcaccccatcccagcctgtgagaggcctgg
atgtgggcctgacatcatttcccacccagtgacagcactgc
atgtgatggggcctctgggcagcctttttcccgggggaaac
tggcaggaatcaggaccaccaggacaggggtcaggggagag
gcgatgctgggcaccagagcctggaccaccctcgggttctc
agcgatgggcaacccctgccacccagggccccgccttcctg
gggagacatcggggtttccaggccatcctgggaggagggtg
ggagcctcagctagaccccagctggcttgcccccccatgcc
ccggccaagagagggtcttggagggaagggggaccccagac
cagcctggcgagcccatcctcagggtctctggtcagacagg
ggctcagctgagctccagggtagaccaaggccctgcgtgga
tgaggccagtgtggtcactgcccagagcaaagccacctctc
agcagccctttcctgagcaccttctgtgtgcggggacatca
gcagtggcaacacagccatgctggggactcagggctagaga
caggggaccagcctatggagagtgggtagtgtcctgcaggg
caggcttgtgccctggagaaaacaaaccagggtgaggccag
ggacgctggccgggttcacagggtgatggctgagcacagag
tgccaggggctggactgtcctgactctgggttggtggctga
gggcctgtgtccctctatgcctctgggttggtgataatgga
aacttgctccctggagagacaggacgaatggttgatgggaa
atgaatgtttgcttgtcacttggttgactgttgttgccgtt
agcattgggcttcttgggccaggcagcctcaggccagcact
gctgggctccccacaggcccgacaccctcagccctgtgcag
ctggcctggcgaaaccaagaggccctgatgcccaaaatagc
cgggaaaccccaaccagcccagccctggcagcaggtgcctc
ccatttgcctgggctgggggaggggtggctctggttctgga
agtttctgccagtccagctggagaagggacctgtatcccag
cacccaggccgcccaagcccctgcaccagggcctgggccag
gcagagttgacatcaatcaattgggagctgctggaatgcat
ggaggcggcgctctcgaggctggaggaggccagctgattta
aatcggtccgcgtacgatgcatattaccctgttatccctac
cgcggttactggccgtcgttttacaacgtcgtgactgggaa
aaccctggcgatgctcttctcccggtgaaaacctctgacac
atggctcttctaaatccggagtttaaacgcttccttcatgt
gagcaaaaggccagcaaaaggccaggaaccgtaaaaaggcc
gcgttgctggcgtttttccataggctccgcccccctgacga
gcatcacaaaaatcgacgctcaagtcagaggtggcgaaacc
cgacaggactataaagataccaggcgtttccccctggaagc
tccctcgtgcgctctcctgttccgaccctgccgcttaccgg
atacctgtccgcctttctcccttcgggaagcgtggcgcttt -continued ctcatagctcacgctgtaggtatctcagttcggtgtaggtc
gttcgctccaagctgggctgtgtgcacgaaccccccgttca
gcccgaccgctgcgccttatccggtaactatcgtcttgagt
ccaacccggtaagacacgacttatcgccactggcagcagcc
actggtaacaggattagcagagcgaggtatgtaggcggtgc
tacagagttcttgaagtggtggcctaactacggctacacta
gaaggacagtatttggtatctgcgctctgctgaagccagtt
accttcggaaaaagagttggtagctcttgatccggcaaaca
aaccaccgctggtagcggtggtttttttgtttgcaagcagc
agattacgcgcagaaaaaaaggatctcaagaagatcctttg
atcttttctacggggtctgacgctcagtggaacgaaaactc
acgttaagggattttggtcatgcctaggtggcaaacagcta
ttatgggtattatgggtctaccggtgcatgagattatcaaa
aaggatcttcacctagatccttttaaattaaaaatgaagtt
ttaaatcaatctaaagtatatatgagtaaacttggtctgac
agttaccaatgcttaatcagtgaggcacctatctcagcgat
ctgtctatttcgttcatccatagttgcctgactccccgtcg
tgtagataactacgatacgggagggcttaccatctggcccc
agtgctgcaatgataccgcgagacccacgctcaccggctcc
agatttatcagcaataaaccagccagccggaagggccgagc
gcagaagtggtcctgcaactttatccgcctccatccagtct
attaattgttgccgggaagctagagtaagtagttcgccagt
taatagtttgcgcaacgttgttgccattgctacaggcatcg
tggtgtcacgctcgtcgtttggtatggcttcattcagctcc
ggttcccaacgatcaaggcgagttacatgatcccccatgtt
gtgcaaaaaagcggttagctccttcggtcctccgatcgttg
tcagaagtaagttggccgcagtgttatcactcatggttatg
gcagcactgcataattctcttactgtcatgccatccgtaag
atgcttttctgtgactggtgagtactcaaccaagtcattct
gagaatagtgtatgcggcgaccgagttgctcttgcccggcg
tcaatacgggataataccgcgccacatagcagaactttaaa
agtgctcatcattggaaaacgttcttcggggcgaaaactct
caaggatcttaccgctgttgagatccagttcgatgtaaccc
actcgtgcacccaactgatcttcagcatcttttactttcac
cagcgtttctgggtgagcaaaaacaggaaggcaaaatgccg
caaaaaagggaataagggcgacacggaaatgttgaatactc
atactcttcctttttcaatattattgaagcatttatcaggg
ttattgtctcgggagcggatacatatttgaatgtatttaga
aaaa SEQ ID 46 taaacaaataggggttccgcgcacatttccccgaaaagtgc
cacctgacgtcgctgagcaggccctggcctccctggccgag -continued ggcggtttgcgtattagaggcctaaatggccgaattcagcg
gataacaatttcacacaggaaacagctatgaccatgattat
ctagtaactataacggtcctaaggtagcgagcgatcgctta
attaacctgcagggatatcccatgggggccgccagtgtgat
ggatatctgcagaattcgcccttgatattaagagaagggca
agtcagcttaagtttgggggtagaggggaacagggagtgag
gagatctggcctgagagataggagccctggtggccacagga
ggactctttgggtcctgtcggatggacacagggcggcccgg
gggcatgttggagcccggctggttcttaccagaggcagggg
gcaccctctgacacgggagcagggcatgttccatacatgac
acacccctctgctccagggcaggtgggtggcggcacagagg
agccagggactctgagcaaggggtccaccagtggggcagtt
ggatccagacttctctgggccagcgagagtctagccctcag
ccgttctctgtccaggagggggggtggggcaggcctgggcgg
ccagagctcatccctcaagggttcccagggtcctgccagac
ccagatttccgaccgcagccaccacaagaggatgtggctgc
tgtggcagctgccaagaccttgcagcaggtgcagggtgggg
gggtgggggcacctgggggcagctggggtcactgagttcag
ggaaaacccctttttccccctaaacctggggccatccctag
gggaaaccacaacttctgagccctgggcagtggctgctggg
agggaagagcttcatcctggaccctgggggggaacccagct
ccaaaggtgcaaggggcccaggtccaaggctagagtgggcc
aagcaccgcaatggccagggagtgggggaggtggagctgga
ctggatcagggcctccttgggactccctacaccctgtgtga
catgttagggtacccacaccccatcaccagtcagggcctgg
cccatctccagggccagggatgtgcatgtaagtgtgtgtga
gtgtgtgtgtgtggtgtagtacaccccttggcatccggttc
cgaggccttgggttcctccaaagttgctctctgaattaggt
caaactgtgaggtcctgatcgccatcatcaacttcgttctc
cccacctcccatcattatcaagagctggggagggtctggga
tttcttcccacccacaagccaaaagataagcctgctggtga
tggcagaagacacaggatcctgggtcagagacaaaggccag
tgtgtcacagcgagagaggcagccggactatcagctgtcac
agagaggccttagtccgctgaactcaggccccagtgactcc
tgttccactgggcactggccccctccacagcgcccccagg
ccccagggagaggcgtcacagcttagagatggccctgctga
acagggaacaagaacaggtgtgccccatccagcgccccagg
ggtgggacaggtgggctggatttggtgtgaagcccttgagc
cctggaacccaaccacagcagggcagttggtagatgccatt
tggggagaggccccaggagtaagggccatgggcccttgagg -continued gggccaggagctgaggacagggacagagacggcccaggcag
aggacagggccatgaggggtgcactgagatggccactgcca
gcaggggcagctgccaacccgtccagggaacttattcagca
gtcagctggaggtgccattgaccctgagggcagatgaagcc
caggccaggctaggtgggctgtgaagaccccaggggacaga
gctctgtccctgggcagcactggcctctcattctgcagggc
ttgacgggatcccaaggcctgctgcccctgatggtagtggc
agtaccgcccagagcaggaccccagcatggaaaccccaacg
ggacgcagcctgcggagcccacaaaaccagtaaggagccga
agcagtcatggcacggggagtgtggacttccctttgatggg
gcccaggcatgaaggacagaatgggacagcggccatgagca
gaaaatcagccggaggggatgggcctaggcagacgctggct
ttatttgaagtgttggcattttgtctggtgtgtattgttgg
tattgattttattttagtatgtcagtgacatactgacatat
tatgtaacgacatattattatgtgttttaagaagcactcca
agggaacaggctgtctgtaatgtgtccagagaagagagcaa
gagcttggctcagtctcccccaaggaggtcagttcctcaac
aggggtcctaaatgtttcctggagccaggcctgaatcaagg
gggtcatatctacacgtggggcagacccatggaccattttc
ggagcaataagatggcagggaggataccaagctggtcttac
agatccagggctttgacctgtgacgcgggcgctcctccagg
caaagggagaagccagcaggaagctttcagaactggggaga
acagggtgcagacctccagggtcttgtacaacgcaccccttt
atcctggggtccaggaggggtcactgagggatttaagtggg
ggaccatcagaaccaggtttgtgttttggaaaaatggctcc
aaagcagagaccagtgtgaggccagattagatgatgaagaa
gaggcagtggaaagtcgatgggtggccaggtagcaagaggg
cctatggagttggcaagtgaatttaaagtggtggcaccaga
gggcagatggggaggagcaggcactgtcatggactgtctat
agaaatctaaaatgtatacccttttttagcaatatgcagtga
gtcataaaagaacacatatatatttcctttggccggccggc
gcgccacgcgtataacttcgtatagcatacattatacgaag
ttatcttaagggctatggcagggcctgccgccccgacgttg
gctgcgagccctgggccttcacccgaacttggggggtgggg
tggggaaaaggaagaaacgcgggcgtattggccccaatggg
gtctcggtggggtatcgacagagtgccagccctgggaccga
accccgcgtttatgaacaaacgacccaacaccgtgcgtttt
attctgtctttttattgccgtcatagcgcgggttccttccg
gtattgtctccttccgtgtttcactcgagttagaagaactc
gtcaagaaggcgatagaaggcgatgcgctgcgaatcgggag
cggcgataccgtaaagcacgaggaagcggtcagcccattcg -continued ccgccaagctcttcagcaatatcacgggtagccaacgctat gtcctgatagcggtccgccacacccagccggccacagtcga tgaatccagaaaagcggccattttccaccatgatattcggc aagcaggcatcgccatgggtcacgacgagatcctcgccgtc gggcatgcgcgccttgagcctggcgaacagttcggctggcg cgagcccctgatgctcttcgtccagatcatcctgatcgaca agaccggcttccatccgagtacgtgctcgctcgatgcgatg tttcgcttggtggtcgaatgggcaggtagccggatcaagcg tatgcagccgccgcattgcatcagccatgatggatactttc tcggcaggagcaaggtgagatgacaggagatcctgccccgg cacttcgcccaatagcagccagtcccttcccgcttcagtga caacgtcgagcacagctgcgcaaggaacgcccgtcgtggcc agccacgatagccgcgctgcctcgtcctgcagttcattcag ggcaccggacaggtcggtcttgacaaaaagaaccgggcgcc cctgcgctgacagccggaacacggcggcatcagagcagccg attgtctgttgtgcccagtcatagccgaatagcctctccac ccaagcggccggagaacctgcgtgcaatccatcttgttcaa tggccgatcccattccagatctgttagcctcccccatctcc cgtgcaaacgtgcgcgccaggtcgcagatcgtcggtatgga gcctggggtggtgacgtgggtctggatcatcccggaggtaa gttgcagcagggcgtcccggcagccggcgggcgattggtcg taatccaggataaagacgtgcatgggacggaggcgtttggt caagacgtccaaggcccaggcaaacacgttgtacaggtcgc cgttgggggccagcaactcgggggcccgaaacagggtaaat aacgtgtccccgatatggggtcgtgggcccgcgttgctctg gggctcggcaccctggggcggcacggccgtccccgaaagct gtccccaatcctcccgccacgacccgccgccctgcagatac cgcaccgtattggcaagcagcccgtaaacgcggcgaatcgc ggccagcatagccaggtcaagccgctcgccggggcgctggc gtttggccaggcggtcgatgtgtctgtcctccggaagggcc cccaacacgatgtttgtgccgggcaaggtcggcgggatgag ggccacgaacgccagcacggcctgggggtcatgctgccca taaggtatcgcgcggccgggtagcacaggagggcggcgatg ggatggcggtcgaagatgagggtgagggccgggggcggggc atgtgagctcccagcctcccccccgatatgaggagccagaa cggcgtcggtcacggcataaggcatgcccattgttatctgg gcgcttgtcattaccaccgccgcgtccccggccgatatctc accctggtcaaggcggtgttgtgtggtgtagatgttcgcga ttgtctcggaagcccccagcacccgccagtaagtcatcggc tcgggtacgtagacgatatcgtcgcgcgaacccagggccac -continued cagcagttgcgtggtggtggttttccccatcccgtggggac cgtctatataaacccgcagtagcgtgggcattttctgctcc gggcggacttccgtggcttcttgctgccggcgagggcgcaa cgccgtacgtcggttgctatggccgcgagaacgcgcagcct ggtcgaacgcagacgcgtgctgatggccggggtacgaagcc atggtggctctagaggtcgaaaggcccggagatgaggaaga ggagaacagcgcggcagacgtgcgcttttgaagcgtgcaga atgccgggcttccggaggaccttcgggcgcccgccccgccc ctgagcccgcccctgagcccgcccccggacccaccccttcc cagcctctgagcccagaaagcgaaggagccaaagctgctat tggccgctgccccaaaggcctacccgcttccattgctcagc ggtgctgtccatctgcacgagactagtgagacgtgctactt ccatttgtcacgtcctgcacgacgcgagctgcggggcgggg gggaacttcctgactaggggaggagtagaaggtggcgcgaa ggggccaccaaagaacggagccggttggcgcctaccggtgg atgtggaatgtgtgcgaggccagaggccacttgtgtagcgc caagtgcccagcggggctgctaaagcgcatgctccagactg ccttgggaaaagcgcctcccctacccggtagggatccgcgt tacataacttacggtaaatggcccgcctggctgaccgccca acgacccccgcccattgacgtcaataatgacgtatgttccc atagtaacgccaatagggactttccattgacgtcaatgggt ggagtatttacggtaaactgcccacttggcagtacatcaag tgtatcatatgccaagtacgccccctattgacgtcaatgac ggtaaatggcccgcctggcattatgcccagtacatgacctt atgggactttcctacttggcagtacatctacgtattagtca tcgctattaccatggtgatgcggttttggcagtacatcaat gggcgtggatagcggtttgactcacggggatttccaagtct ccaccccattgacgtcaatgggagtttgttttggcaccaaa atcaacggttaacaagcttagatctgcggccgcgtcgacga taaattgtgtaattccacttctaaggattcatcccaagggg ggaaaataatcaaagatgtaaccaaaggtttacaaacaaga actcatcattaatcttccttgttgttatttcaacgatatta ttattattactattattattattattattttgtctttttgc attttctagggccactcccacggcatagagaggttcccagg ctaggggtcaaatcggagctacagctgccggcctacgccag agccacagcaacgcaggatctgagccacagcaatgcaggat ctacaccacagctcatggtaacgctggatccttaacccaat gagtgaggccagggatcgaacctgtaacttcatggttccta gtcggattcattaaccactgagccacgacaggaactccaac attattaatgatgggagaaaactggaagtaacctaaatatc cagcagaaagggtgtggccaaatacagcatggagtagccat -continued cataaggaatcttacacaagcctccaaaattgtgtttctga
aattgggtttaaagtacgtttgcattttaaaaagcctgcca
gaaaatacagaaaaatgtctgtgatatgtctctggctgata
ggattttgcttagttttaattttggctttataattttctat
agttatgaaaatgttcacaagaagatatatttcattttagc
ttctaaaataattataacacagaagtaatttgtgctttaaa
aaatattcaacacagaagtatataaaaaaattgaggagttc
ccatcgtggctcagtgattaacaaacccaactagtatccat
gaggatatggatttgatccctggccttgctcagtgggttga
ggatccagtgttgctgtgagctgtggtgtaggttgcagaca
cagcactctggcgttgctgtgactctggcgtaggccggcag
ctacagctccatttggacccttagcctgggaacctccatat
gcctgagatacggccctaaaaagtcaaaagccaaaaaaata
gtaaaaattgagtgtttctacttaccacccctgcccacatc
ttatgctaaaacccgttctccagagacaaacatcgtcaggt
gggtctatatatttccagccctcctcctgtgtgtgtatgtc
cgtaaaacacacacacacacacacacacgcacacacacaca
cacgtatctaattagcattggtattagtttttcaaaaggga
ggtcatgctctacctttaggcggcaaatagattatttaaa
caaatctgttgacattttctatatcaacccataagatctcc
catgttcttggaaaggctttgtaagacatcaacatctgggt
aaaccagcatggtttttaggggggttgtgtggatttttttca
tattttttagggcacacctgcagcatatggaggttcccagg
ctaggggttgaatcagagctgtagctgccggcctacaccac
agccacagcaacgccagatccttaacccactgagaaaggcc
agggattgaacctgcatcctcatggatgctggtcagattta
tttctgctgagccacaacaggaactccctgaaccagaatgc
ttttaaccattccactttgcatggacatttagattgtttcc
atttaaaaatacaaattacaaggagttcccgtcgtggctca
gtggtaacgaattggactaggaaccatgaggtttcgggttc
gatccctggccttgctcggtgggttaaggatccagcattga
tgtgagatatggtgtaggtcgcagacgtggctcggatccca
cgttgctgtggctctggcgtaggccggcaacaacagctccg
attcgacccctagcctgggaacctccatgtgccacaggagc
agccctagaaaaggcaaaaagacaaaaaaataaaaaattaa
aatgaaaaaataaaataaaaatacaaattacaagagacggc
tacaaggaaatccccaagtgtgtgcaaatgccatatatgta
taaaatgtactagtgtctcctcgcgggaaagttgcctaaaa
gtgggttggctggacagagaggacaggctttgacattctca
taggtagtagcaatgggcttctcaaaatgctgttccagttt -continued acactcaccatagcaaatgacagtgcctcttcctctccacc
cttgccaataatgtgacaggtggatctttttctattttgtg
tatctgacaagcaaaaaatgagaacaggagttcctgtcgtg
gtgcagtggagacaaatctgactaggaaccatgaaatttcg
ggttcaatccctggcctcactcagtaggtaaaggatccagg
gttgcagtgagctgtggggtaggtcgcagacacagtgcaaa
tttggccctgttgtggctgtggtgtaggccggcagctatag
ctccaattggacccctagcctgggaacctccttatgccgtg
ggtgaggccctaaaaaaaagagtgcaaaaaaaaaaaaataag
aacaaaaatgatcatcgtttaattctttatttgatcattgg
tgaaacttattttccttttatatttttattgactgatttta
tttctcctatgaatttaccggtcatagttttgcctgggtgt
ttttactccggttttagttttggttggttgtattttcttag
agagctatagaaactcttcatctatttggaatagtaattcc
tcattaagtatttgtgctgcaaaaaattttccctgatctgt
tttatgcttttgtttgtggggtctttcacgagaaagccttt
ttagtttttacacctcagcttggttgtttttcttgattgtg
tctgtaatctgcggccaacataggaaacacatttttacttt
agtgtttttttcctattttcttcaagtacgtccattgtttt
ggtgtctgattttactttgcctggggtttgtttttgtgtgg
caggaatataaacttatgtattttccaaatggagagccaat
ggttgtatatttgttgaattcaaatgcaactttatcaaaca
ccaaatcatcgatttatcacaactcttctctggtttattga
tctaatgatcaattcctgttccacgctgttttaattatttt
agctttgtggattttggtgcctggtagagaacaaagcctcc
attattttcattcaaaatagtcccgtctattatctgccatt
gttgtagtattagactttaaaatcaatttactgattttcaa
aagttattcctttggtgatgtggaatactttatacttcata
aggtacatggattcatttgtggggaattgatgtctttgcta
ttgtggccatttgtcaagttgtgtaatattttacccatgcc
aactttgcatattgtatgtgagtttattcccagggtttta
ataggatgtttattgaagttgtcagtgtttccacaatttca
tcgcctcagtgcttactgtttgcataaaaggaaacctactc
acttttgcctattgctcttgtattcaatcattttagttaac
tcttgtgttaattttgagagtttttcagctgactgtctggg
gttttctttaatagactagccctttgtctgtaaagaataat
tttatcgaatttttcttaacactcacactctccccaccccc
acccccgctcatctcctttcattgggtcaaatctgtagaat
acaataaaagtaagagtgggaaccttagcctttaagtcgat
tttgcctttaaatgtgaatgttgctatgtttcgggacattc
tctttatcaagttgcggatgtttccttagataattaactta -continued ataaaagactggatgtttgctttcttcaaatcagaattgtg
ttgaatttatattgctattctgtttaattttgtttcaaaaa
atttacatgcacaccttaaagataaccatgaccaaatagtc
ctcctgctgagagaaaatgttggccccaatgccacaggtta
cctcccgactcagataaactacaatgggagataaaatcaga
tttggcaaagcctgtggattcttgccataactctcagagca
tgacttgggtgttttttccttttctaagtattttaatggta
tttttgtgttacaataggaaatctaggacacagagagtgat
tcaatgaggggaacgcattctgggatgactctaggcctctg
gtttggggagagctctattgaagtaaagacaatgagaggaa
gcaagtttgcagggaactgtgaggaatttagatggggaatg
ttgggtttgaggtttctatagggcacgcaagcagagatgca
ctcaggaggaagaaggagcataaatctagtggcgctgccgg
caagcttgctggaggaggccaattgggagctgctggaatgc
atggaggcggcgctctcgaggctggaggaggccagctgatt
taaatcggtccgcgtacgatgcatattaccctgttatccct
accgcggttactggccgtcgttttacaacgtcgtgactggg
aaaaccctggcgatgctcttctcccggtgaaaacctctgac
acatggctcttctaaatccggagtttaaacgcttccttcat
gtgagcaaaaggccagcaaaaggccaggaaccgtaaaaagg
ccgcgttgctggcgtttttccataggctccgcccccctgac
gagcatcacaaaaatcgacgctcaagtcagaggtggcgaaa
cccgacaggactataaagataccaggcgtttccccctggaa
gctccctcgtgcgctctcctgttccgaccctgccgcttacc
ggatacctgtccgcctttctcccttcgggaagcgtggcgct
ttctcatagctcacgctgtaggtatctcagttcggtgtagg
tcgttcgctccaagctgggctgtgtgcacgaaccccccgtt
cagcccgaccgctgcgccttatccggtaactatcgtcttga
gtccaacccggtaagacacgacttatcgccactggcagcag
ccactggtaacaggattagcagagcgaggtatgtaggcggt
gctacagagttcttgaagtggtggcctaactacggctacac
tagaaggacagtatttggtatctgcgctctgctgaagccag
ttaccttcggaaaaagagttggtagctcttgatccggcaaa
caaaccaccgctggtagcggtggtttttttgtttgcaagca
gcagattacgcgcagaaaaaaaggatctcaagaagatcctt
tgatcttttctacggggtctgacgctcagtggaacgaaaac
tcacgttaagggattttggtcatgcctaggtggcaaacagc
tattatgggtattatgggtctaccggtgcatgagattatca
aaaaggatcttcacctagatccttttaaattaaaaatgaag
ttttaaatcaatctaaagtatatatgagtaaacttggtctg -continued acagttaccaatgcttaatcagtgaggcacctatctcagcg
atctgtctatttcgttcatccatagttgcctgactccccgt
cgtgtagataactacgatacgggagggcttaccatctggcc
ccagtgctgcaatgataccgcgagacccacgctcaccggct
ccagatttatcagcaataaaccagccagccggaagggccga
gcgcagaagtggtcctgcaactttatccgcctccatccagt
ctattaattgttgccgggaagctagagtaagtagttcgcca
gttaatagtttgcgcaacgttgttgccattgctacaggcat
cgtggtgtcacgctcgtcgtttggtatggcttcattcagct
ccggttcccaacgatcaaggcgagttacatgatcccccatg
ttgtgcaaaaaagcggttagctccttcggtcctccgatcgt
tgtcagaagtaagttggccgcagtgttatcactcatggtta
tggcagcactgcataattctcttactgtcatgccatccgta
agatgcttttctgtgactggtgagtactcaaccaagtcatt
ctgagaatagtgtatgcggcgaccgagttgctcttgcccgg
cgtcaatacgggataataccgcgccacatagcagaacttta
aaagtgctcatcattggaaaacgttcttcggggcgaaaact
ctcaaggatcttaccgctgttgagatccagttcgatgtaac
ccactcgtgcacccaactgatcttcagcatcttttacttc
accagcgtttctgggtgagcaaaaacaggaaggcaaaatgc
cgcaaaaaagggaataagggcgacacggaaatgttgaatac
tcatactcttcctttttcaatattattgaagcatttatcag
ggttattgtctcgggagcggatacatatttgaatgtattta
gaaaaa SEQ ID 47 taaacaaataggggttccgcgcacatttccccgaaaagtgc
cacctgacgtcgctgagcaggccctggcctccctggccgag
ggcggtttgcgtattagaggcctaaatggccgaattcagcg
gataacaatttcacacaggaaacagctatgaccatgattat
ctagtaactataacggtcctaaggtagcgagcgatcgctta
attaacctgcagggataaccactgacccatgacgggaactc
ccagggctcagctcttgactccaggttcgcagctgccctca
aagcaatgcaaccctggctggccccgcctcatgcatccggc
ctcctccccaaagagctctgagcccacctgggcctaggtcc
tcctccctgggactcatggcctaagggtacagagttactgg
ggctgatgaagggaccaatggggacaggggcctcaaatcaa
agtggctgtctctctcatgtcccttcctctcctcagggtcc
aaaatcagggtcagggccccagggcaggggctgagagggcc
tctttctgaaggccctgtctcagtgcaggttatgggggtct
gggggagggtcaatgcagggctcacccttcagtgccccaaa
gcctagagagtgagtgcctgccagtggcttcccaggcccaa
tcccttgactgcctgggaatgctcaaatgcaggaactgtca -continued

```
caacaccttcagtcaggggctgctctgggaggaaaaacact
cagaattgggggttcagggaaggcccagtgccaagcatagc
aggagctcaggtggctgcagatggtgtgaaccccaggagca
ggatggccggcactcccccagaccctccagagccccaggt
tggctgccctcttcactgccgacacccctgggtccacttct
gccctttcccacctaaaacctttagggctcccactttctcc
caaatgtgagacatcaccacggctcccagggagtgtccaga
agggcatctggctgagaggtcctgacatctgggagcctcag
gccccacaatggacagacgccctgccaggatgctgctgcag
ggctgttagctaggcggggtggagatggggtactttgcctc
tcagaggccccggccccaccatgaaacctcagtgacacccc
atttccctgagttcacatacctgtatcctactccagtcacc
ttccccacgaacccctgggagcccaggatgatgctggggct
ggagccacgaccagcccacgagtgatccagctctgccaatc
agcagtcatttcccaagtgttccagccctgccaggtcccac
tacagcagtaatggaggccccagacaccagtccagcagtta
gagggctggactagcaccagctttcaagcctcagcatctca
aggtgaatggccagtgcccctccccgtggccatcacaggat
cgcagatatgaccctaggggaagaaatatcctgggagtaag
gaagtgcccatactcaaggatggcccctctgtgacctaacc
tgtccctgaggattgtacttccaggcgttaaaacagtagaa
cgcctgcctgtgaaccccccgccaagggactgcttggggagg
ccccctaaaccagaacacaggcactccagcaggacctctga
actctgaccaccctcagcaagtgggcacccccccgcagcttc
caaggcaccccagggctcaccacagcggcccctcctggcag
cccctcacccaggcccagaccctctaagatggcacatctaa
gccaatccacctccttgtcattcctcctgtccccacccagg
acccttctcagatgaaaccttcgctccagccgctgggccct
ctctcctgcccctctggcagttctccagggactccgcctcc
cactctctgtctctccctgcactcctaggaacaagcgacct
ccaggaagcccagtccaattatcccctctgtgtcctcccca
atctctgcctctgggtggatttgagcaccacatcctgttct
cttcgacctgaaactccttggccccggtgtccgctctcctg
ggccctcttttctctcctcccctcttccgtgccccgtttgt
ttggtgttacaggcaggccccggggagccgtccctccagct
gctcttccttgtctgtctcaggagccagaaactggcagcat
ctaaaaagggctcctgtttcttcatctgcccagcctcctag
cccaaccagggctctggcctcactccagagggtgggctcca
gagggcaggggttgcaccctcttagtgcctcagaggctcag
ctgggtgcaggatggggggccctcagggagcccctcagtg
```

-continued

```
actgctgatcacttactgcaggactgttcccagctcttccc
aatcattggaatgacaatacctagttctgctccatcatagt
gatgcaggaaaaatgttactgaaatcctggttcttgtttag
caatcgaagaatgaattccgcgaacacacaggcagcaagca
agcgaagcctttattaaaggaaagcagatagctcccagggc
tgcagggagcggggagaagagctccccactctctattgtcc
tatagggctttttaccccttaaagttgggggatacaaaaa
aaatagaagaaaaagggagttcccgtcagggcacagcagaa
acaaatccaactaggaaccatgaggttgggggttcgattcc
tggcctctctcagtgggttaaggatgcagcgttgccgtgag
ctatgatacaggtcacagatgcagctcagatctactagtca
attgacaggcgccggagcaggagctaggcctttggccggcc
ggcgcgccacgcgtataacttcgtatagcatacattatacg
aagttatcttaagggctatggcagggcctgccgccccgacg
ttggctgcgagccctgggccttcacccgaacttgggggtg
gggtggggaaaaggaagaaacgcgggcgtattggccccaat
ggggtctcggtggggtatcgacagagtgccagccctgggac
cgaaccccgcgtttatgaacaaacgacccaacaccgtgcgt
tttattctgtctttttattgccgtcatagcgcgggttcctt
ccggtattgtctccttccgtgtttcactcgagttagaagaa
ctcgtcaagaaggcgatagaaggcgatgcgctgcgaatcgg
gagcggcgataccgtaaagcacgaggaagcggtcagcccat
tcgccgccaagctcttcagcaatatcacgggtagccaacgc
tatgtcctgatagcggtccgccacacccagccggccacagt
cgatgaatccagaaaagcggccattttccaccatgatattc
ggcaagcaggcatcgccatgggtcacgacgagatcctcgcc
gtcgggcatgcgcgccttgagcctggcgaacagttcggctg
gcgcgagcccctgatgctcttcgtccagatcatcctgatcg
acaagaccggcttccatccgagtacgtgctcgctcgatgcg
atgtttcgcttggtggtcgaatgggcaggtagccggatcaa
gcgtatgcagccgccgcattgcatcagccatgatggatact
ttctcggcaggagcaaggtgagatgacaggagatcctgccc
cggcacttcgcccaatagcagccagtcccttcccgcttcag
tgacaacgtcgagcacagctgcgcaaggaacgcccgtcgtg
gccagccacgatagccgcgctgcctcgtcctgcagttcatt
cagggcaccggacaggtcggtcttgacaaaaagaaccgggc
gcccctgcgctgacagccggaacacggcggcatcagagcag
ccgattgtctgttgtgcccagtcatagccgaatagcctctc
cacccaagcggccggagaacctgcgtgcaatccatcttgtt
caatggccgatcccattccagatctgttagcctcccccatc
tcccgtgcaaacgtgcgcgccaggtcgcagatcgtcggtat
```

-continued ggagcctggggtggtgacgtgggtctggatcatcccggagg
taagttgcagcagggcgtcccggcagccggcgggcgattgg
tcgtaatccaggataaagacgtgcatgggacggaggcgttt
ggtcaagacgtccaaggcccaggcaaacacgttgtacaggt
cgccgttgggggccagcaactcgggggcccgaaacagggta
aataacgtgtccccgatatggggtcgtgggcccgcgttgct
ctggggctcggcaccctggggcggcacggccgtccccgaaa
gctgtccccaatcctcccgccacgacccgccgccctgcaga
taccgcaccgtattggcaagcagcccgtaaacgcggcgaat
cgcggccagcatagccaggtcaagccgctcgccggggcgct
ggcgtttggccaggcggtcgatgtgtctgtcctccggaagg
gcccccaacacgatgtttgtgccgggcaaggtcggcgggat
gagggccacgaacgccagcacggcctggggggtcatgctgc
ccataaggtatcgcgcggccgggtagcacaggagggcggcg
atgggatggcggtcgaagatgagggtgagggccgggggcgg
ggcatgtgagctcccagcctcccccccgatatgaggagcca
gaacggcgtcggtcacggcataaggcatgcccattgttatc
tgggcgcttgtcattaccaccgccgcgtccccggccgatat
ctcaccctggtcaaggcggtgttgtgtggtgtagatgttcg
cgattgtctcggaagcccccagcacccgccagtaagtcatc
ggctcgggtacgtagacgatatcgtcgcgcgaacccagggc
caccagcagttgcgtggtggtggttttccccatcccgtggg
gaccgtctatataaacccgcagtagcgtgggcattttctgc
tccgggcggacttccgtggcttcttgctgccggcgagggcg
caacgccgtacgtcggttgctatggccgcgagaacgcgcag
cctggtcgaacgcagacgcgtgctgatggccggggtacgaa
gccatggtggctctagaggtcgaaaggcccggagatgagga
agaggagaacagcgcggcagacgtgcgcttttgaagcgtgc
agaatgccgggcttccggaggaccttcgggcgcccgccccg
cccctgagcccgcccctgagcccgcccccggacccacccct
tcccagcctctgagcccagaaagcgaaggagccaaagctgc
tattggccgctgccccaaaggcctacccgcttccattgctc
agcggtgctgtccatctgcacgagactagtgagacgtgcta
cttccatttgtcacgtcctgcacgacgcgagctgcggggcg
ggggggaacttcctgactaggggaggagtagaaggtggcgc
gaaggggccaccaaagaacggagccggttggcgcctaccgg
tggatgtggaatgtgtgcgaggccagaggccacttgtgtag
cgccaagtgcccagcggggctgctaaagcgcatgctccaga
ctgccttgggaaaagcgcctcccctacccggtagggatccg
cgttacataacttacggtaaatggcccgcctggctgaccgc -continued ccaacgacccccgcccattgacgtcaataatgacgtatgtt
cccatagtaacgccaatagggactttccattgacgtcaatg
ggtggagtatttacggtaaactgcccacttggcagtacatc
aagtgtatcatatgccaagtacgccccctattgacgtcaat
gacggtaaatggcccgcctggcattatgcccagtacatgac
cttatgggactttcctacttggcagtacatctacgtattag
tcatcgctattaccatggtgatgcggttttggcagtacatc
aatgggcgtggatagcggtttgactcacggggatttccaag
tctccaccccattgacgtcaatgggagtttgttttggcacc
aaaatcaacggttaacaagcttataacttcgtatagcatac
attatacgaagttattacgtagcggccgcgtcgacgatatc
gctgccggagcccccggggccgctgccggaagatctggcat
tgctgtgactgtggtgtaggccggcagctggagctctgatt
agacccctcacctgggaatctccatatgctgcacgtgcggc
cctaaaaagacaaaagacaaaaaaaaaaaaaaaaaaaaaaa
atcaaaaaaaaacatagggggttaccaacgtggggtccaga
aagatgtggttttctcccattggccttgcccagttacctat
atcagtccttgtccaacaggggttttaggggtggaaatgcc
ccataaattttacggtttctttgcccttctcttcctttaga
ctgagtcaccattgctctcattccttttctatcagttgagg
agtgggttagagattaaggtccatgtggtggaggtacactt
cttatagtaaacaaggcctatggggaattactctctggagc
ccttaaaccacaaatgataatccatgccacatcaaagatgc
atcgaagcccatgctcctacactgactacctgagttagcat
tctgcctcaacaggactgaccatccccagctctggggcaga
tatcctctctctgccacaagggcagtgacccccatgctgtc
tgagggtcacgctttaccccccccccacccctgccgtgacc
ccccagaccaccccaggaggtgggcactaatatccctcatt
accccatagatgaggaaacagaggttcccccggggtcccac
aggtgctcagggtcacatgcaccgtgggcacccaggcccca
tcccaaggccaccctccctcctcaggaagctgtgctgcgct
gggccagaaggtactgcacacgactcctcagcctccggtgg
tgggaggcagcctcaagcctctgagtgggggggcacccggg
ctcctcaatctatactgactcctggggggtgggagaaggga
gggggagctgtggcctctgagtccactaagcaaatcagggt
gggcaatgcgggcccatttcaaggaggagagaaccgaggct
ctgacagcaggccgggggtccagggacctgcccagggtcat
aggctgaactgctggctgacctgccttgggttctttccttg
gctcctcagccctgtgtgatgtgacaggtcattcattcact
cactcgctcattcattcagcaaaccctcagtgagccctgct
gggagcaggtgctaggggcaaggagacaggacctcttgccc -continued tggaacagctgaagcactgggggacaggcagtggcagggag gtgcgtgatcaccgctgaccccattccatcctccagccccc aggtcagtttccacccaccattgaccccaccatgtcctcca tccccaaggtcagtttcccgcccaaggagcatctccttaca cactagggacaaaatttcacggctgtcactgggcatctctc cacgctcatcacagccctctagcagccttgaagtcctgtag agcccttcccatttcacagaagggacaagactatgagggcc acaccgtgagccatgagccttaggctgtgagccgggacagc ccctgcaggactggtggcctcagggcactgggtggggaggg tgcacagtgggtgggccccttgtggaatagagaggagtgtc aggtcaggggagggggcttggcctggccctggcctgcctgg tgtgcaaccctaggcagcccctccttcccaggcctcctact tcctggaggccaagcctcagggaggtaattgagtcaggtgg gggagggggggttgtggctttcttcacagcagaaaaacaga gcccacaatagtgtccactgagacagaggggtcctgggga ggggaggggtgggaggtgactgctgagccctgtgggaggga gggagcaactactgagctgagctgggtgactctcccatctg ccccgccccctgtggggccagcagagtcaccgagagaacat gacccagccaggcctggacaggggacacccatgtccttta ccccacagggttcactgagcctatctgccccaagcctgtgt ctccctgggacggagaccctcactcccaaccacaaaggtct aaactcaagttcccaacagccttgaaaatacagcttccggg ggcctccaaggagcagtcagccgtccactgccaggctcgct ggctcagtgacacaggacacatcctgatgacggtccacctg tctccaagcaggttctcctctgccgatggggcaacgagctc ctcctgtggctccctggctggatgcgtgggaggcggggtgg gggggcaggcggtgttcctggccgcacacaaggagcacccc caccagcatccgaagacgggggcccggtctttccccaaaac actgcttgcgggagactttgtgacgtttccaggggccatgc tcccttcgggcagcttgggggacttctgctcctatgtggtc acctgcagggactcccccaggccttggggacaaacaaagt gatgagagggagggttagtgggtcggggcagggccagtctt tggaccggtttatctgaaaagccagttggtcaccgggaacc acagcaaacctaaacccatttggccaggcatctcccaggga cagtctcccccaggatgcggggcccaggggggctccagggg tgacctgcgtcctggatttccctgatgctcccagttcgtgc ctctgtccaagcatgatttttaatagtgccccttccactcc cagaaatgtccaagtgtgggcaataaattctggtcacctga gctcagtgtaactgtttgctgaatgacacttactgtaacag gttaaaatgggaggcccaaggccacgcagagccatcgaagg -continued ctctgtgtgtcccagccctgatagaagcatcaggatgggga ctgtggcctcaccaggggccacatccaggcggtcaccatgg ggttcctggtctccgtgggccttgactggagcccctggtgt gagctcaccccatcccagcctgtgagaggcctggatgtggg cctgacatcatttcccacccagtgacagcactgcatgtgat ggggcctctgggcagcctttttcccgggggaaactggcagg aatcaggaccaccaggacaggggtcaggggagaggcgatgc tgggcaccagagcctggaccaccctcgggttctcagcgatg ggcaacccctgccacccagggccccgccttcctggggagac atcggggtttccaggccatcctgggaggagggtgggagcct cagctagaccccagctggcttgccccccatgccccggcca agagagggtcttggagggaaggggaccccagaccagcctg gcgagcccatcctcagggtctctggtcagacaggggctcag ctgagctccagggtagaccaaggccctgcgtggatgaggcc agtgtggtcactgcccagagcaaagccacctctcagcagcc ctttcctgagcaccttctgtgtgcggggacatcagcagtgg caacacagccatgctggggactcagggctagagacagggga ccagcctatggagagtgggtagtgtcctgcagggcaggctt gtgccctggagaaaacaaaccagggtgaggccagggacgct ggccgggttcacagggtgatggctgagcacagagtgccagg ggctggactgtcctgactctgggttggtggctgagggcctg tgtccctctatgcctctgggttggtgataatggaaacttgc tccctggagagacaggacgaatggttgatgggaaatgaatg tttgcttgtcacttggttgactgttgttgccgttagcattg ggcttcttgggccaggcagcctcaggccagcactgctgggc tccccacaggcccgacaccctcagccctgtgcagctggcct ggcgaaaccaagaggccctgatgcccaaaatagccgggaaa ccccaaccagcccagccctggcagcaggtgcctcccatttg cctgggctgggggaggggtggctctggttctggaagtttct gccagtccagctggagaagggacctgtatcccagcacccag gccgcccaagcccctgcaccagggcctgggccaggcagagt tgacatcaatcaattgggagctgctggaatgcatggaggcg gcgctctcgaggctggaggaggccagctgatttaaatcggt ccgcgtacgatgcatattaccctgttatccctaccgcggtt actggccgtcgttttacaacgtcgtgactgggaaaaccctg gcgatgctcttctcccggtgaaaacctctgacacatggctc ttctaaatccggagtttaaacgcttccttcatgtgagcaaa aggccagcaaaaggccaggaaccgtaaaaaggccgcgttgc tggcgtttttccataggctccgcccccctgacgagcatcac aaaaatcgacgctcaagtcagaggtggcgaaacccgacagg actataaagataccaggcgtttccccctggaagctccctcg -continued

```
tgcgctctcctgttccgaccctgccgcttaccggatacctg
tccgcctttctcccttcgggaagcgtggcgctttctcatag
ctcacgctgtaggtatctcagttcggtgtaggtcgttcgct
ccaagctgggctgtgtgcacgaaccccccgttcagcccgac
cgctgcgccttatccggtaactatcgtcttgagtccaaccc
ggtaagacacgacttatcgccactggcagcagccactggta
acaggattagcagagcgaggtatgtaggcggtgctacagag
ttcttgaagtggtggcctaactacggctacactagaaggac
agtatttggtatctgcgctctgctgaagccagttaccttcg
gaaaaagagttggtagctcttgatccggcaaacaaaccacc
gctggtagcggtggtttttttgtttgcaagcagcagattac
gcgcagaaaaaaaggatctcaagaagatcctttgatctttt
ctacggggtctgacgctcagtggaacgaaaactcacgttaa
gggattttggtcatgcctaggtggcaaacagctattatggg
tattatgggtctaccggtgcatgagattatcaaaaaggatc
ttcacctagatccttttaaattaaaaatgaagttttaaatc
aatctaaagtatatatgagtaaacttggtctgacagttacc
aatgcttaatcagtgaggcacctatctcagcgatctgtcta
tttcgttcatccatagttgcctgactccccgtcgtgtagat
aactacgatacgggagggcttaccatctggccccagtgctg
caatgataccgcgagacccacgctcaccggctccagattta
tcagcaataaaccagccagccggaagggccgagcgcagaag
tggtcctgcaactttatccgcctccatccagtctattaatt
gttgccgggaagctagagtaagtagttcgccagttaatagt
ttgcgcaacgttgttgccattgctacaggcatcgtggtgtc
acgctcgtcgtttggtatggcttcattcagctccggttccc
aacgatcaaggcgagttacatgatcccccatgttgtgcaaa
aaagcggttagctccttcggtcctccgatcgttgtcagaag
taagttggccgcagtgttatcactcatggttatggcagcac
tgcataattctcttactgtcatgccatccgtaagatgcttt
tctgtgactggtgagtactcaaccaagtcattctgagaata
gtgtatgcggcgaccgagttgctcttgcccggcgtcaatac
gggataataccgcgccacatagcagaactttaaaagtgctc
atcattggaaaacgttcttcggggcgaaaactctcaaggat
cttaccgctgttgagatccagttcgatgtaacccactcgtg
cacccaactgatcttcagcatcttttactttcaccagcgtt
tctgggtgagcaaaaacaggaaggcaaaatgccgcaaaaaa
gggaataagggcgacacggaaatgttgaatactcatactct
tcctttttcaatattattgaagcatttatcagggttattgt
ctcgggagcggatacatatttgaatgtatttagaaaaa
```

The two-step strategy outline above, utilizing a vector pair, can be used to delete the entire J/C cluster region (i.e., all J/C units), multiple J/C units or an individual J/C unit.

Selectable Marker Genes

The DNA constructs can be designed to modify the endogenous, target immunoglobulin gene. The homologous sequence for targeting the construct can have one or more deletions, insertions, substitutions or combinations thereof. The alteration can be the insertion of a selectable marker gene fused in reading frame with the upstream sequence of the target gene.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See, for example, Song, K-Y., et al. Proc. Nat'l Acad. Sci. U.S.A. 84:6820-6824 (1987); Sambrook, J., et al., Molecular Cloning—A Laboratory Manual, Cold Spring Harbor Laboratory, Cold Spring Harbor, N.Y. (1989), Chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, J. Mol. Appl. Genet. 1:327-341 (1982)); and the hygromycin resistance gene (hyg) (Nucleic Acids Research 11:6895-6911 (1983), and Te Riele, H., et al., Nature 348:649-651 (1990)). Other selectable marker genes include: acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline.

Methods for the incorporation of antibiotic resistance genes and negative selection factors will be familiar to those of ordinary skill in the art (see, e.g., WO 99/15650; U.S. Pat. No. 6,080,576; U.S. Pat. No. 6,136,566; Niwa et al., J. Biochem. 113:343-349 (1993); and Yoshida et al., Transgenic Research 4:277-287 (1995)).

Combinations of selectable markers can also be used. For example, to target an immunoglobulin gene, a neo gene (with or without its own promoter, as discussed above) can be cloned into a DNA sequence which is homologous to the immunoglobulin gene. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. In this particular example, those cells which are resistant to G418 and gancyclovir are most likely to have arisen by homologous recombination in which the neo gene has been recombined into the immunoglobulin gene but the tk gene has been lost because it was located outside the region of the double crossover.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5'-non-coding region (transcriptional regulatory region). Thus, the homologous region can extend beyond the coding region into the 5'-non-coding region or alternatively into the 3'-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. The mutation can be a subtle change, not exceeding about 5% of the homologous flanking sequences. Where mutation of a gene is desired, the marker gene can be inserted into an intron or an exon.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by *E. coli*, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

The present invention further includes recombinant constructs containing sequences of immunoglobulin genes. The constructs comprise a vector, such as a plasmid or viral vector, into which a sequence of the invention has been inserted, in a forward or reverse orientation. The construct can also include regulatory sequences, including, for example, a promoter, operably linked to the sequence. Large numbers of suitable vectors and promoters are known to those of skill in the art, and are commercially available. The following vectors are provided by way of example. Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmiacia), viral origin vectors (M13 vectors, bacterial phage 1 vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8). Other vectors include prokaryotic expression vectors such as pcDNA II, pSL301, pSE280, pSE380, pSE420, pTrcHisA, B, and C, pRSET A, B, and C (Invitrogen, Corp.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Invitrogen, Corp.) and variants and derivatives thereof. Other vectors include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof. Additional vectors that can be used include: pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH116A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Invitrogen), pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZ□, pGAPZ, pGAPZ□, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; □ ExCell, □ gt11, pTrc99A, pKK223-3, pGEX-1□T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2 cp LIC, pBACgus-2 cp LIC, pT7Blue-2 LIC, pT7Blue-2, □SCREEN-1, □BlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3 cp, pBACgus-2 cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, p□gal-Basic, p□gal-Control, p□gal-Promoter, p□gal-Enhancer, pCMV□, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTrip1Ex, □gt10, □gt11, pWE15, and □Trip1Ex from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRT□GAL, pNEO□GAL, pRS403, pRS404, pRS405, pRS406, pRS413, pRS414, pRS415, and pRS416 from Stratagene and variants or derivatives thereof. Two-hybrid and reverse two-hybrid vectors can also be used, for example, pPC86, pDBLeu, pDB-Trp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof. Any other plasmids and vectors may be used as long as they are replicable and viable in the host.

Techniques which can be used to allow the DNA construct entry into the host cell include, for example, calcium phosphate/DNA co precipitation, microinjection of DNA into the nucleus, electroporation, bacterial protoplast fusion with intact cells, transfection, or any other technique known by one skilled in the art. The DNA can be single or double stranded, linear or circular, relaxed or supercoiled DNA. For various techniques for transfecting mammalian cells, see, for example, Keown et al., Methods in Enzymology Vol. 185, pp. 527-537 (1990).

In one specific embodiment, heterozygous or homozygous knockout cells can be produced by transfection of primary fetal fibroblasts with a knockout vector containing immunoglobulin gene sequence isolated from isogenic DNA. In another embodiment, the vector can incorporate a promoter trap strategy, using, for example, IRES (internal ribosome entry site) to initiate translation of the Neor gene.

Site Specific Recombinases

In additional embodiments, the targeting constructs can contain site specific recombinase sites, such as, for example, lox. In one embodiment, the targeting arms can insert the site specific recombinase target sites into the targeted region such that one site specific recombinase target site is located 5' to the second site specific recombinase target site. Then, the site specific recombinase can be activated and/or applied to the cell such that the intervening nucleotide sequence between the two site specific recombinase sites is excised.

Site-specific recombinases include enzymes or recombinases that recognize and bind to a short nucleic acid site or sequence-specific recombinase target site, i.e., a recombinase recognition site, and catalyze the recombination of nucleic acid in relation to these sites. These enzymes include recombinases, transposases and integrases. Examples of sequence-specific recombinase target sites include, but are not limited to, lox sites, att sites, dif sites and frt sites. Non-limiting examples of site-specific recombinases include, but are not limited to, bacteriophage P1 Cre recombinase, yeast FLP recombinase, Inti integrase, bacteriophage λ, phi 80, P22, P2, 186, and P4 recombinase, Tn3 resolvase, the Hin recombinase, and the Cin recombinase, *E. coli* xerC and xerD recombinases, *Bacillus thuringiensis* recombinase, TpnI and the β-lactamase transposons, and the immunoglobulin recombinases.

In one embodiment, the recombination site can be a lox site that is recognized by the Cre recombinase of bacteriophage P1. Lox sites refer to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as loxP511, loxP514, lox.DELTA.86, lox.DELTA.117, loxC2, loxP2, loxP3 and lox P23. Additional example of lox sites include, but are not limited to, loxB, loxL, loxR, loxP, loxP3, loxP23, loxΔ86, loxΔ117, loxP511, and loxC2.

In another embodiment, the recombination site is a recombination site that is recognized by a recombinases other than Cre. In one embodiment, the recombinase site can be the FRT sites recognized by FLP recombinase of the 2 pi plasmid of *Saccharomyces cerevisiae*. FRT sites refer to a nucleotide sequence at which the product of the FLP gene of the yeast 2 micron plasmid, FLP recombinase, can catalyze site-specific recombination. Additional examples of the non-Cre recombinases include, but are not limited to, site-specific recombinases include: att sites recognized by the Int recombinase of bacteriophage λ (e.g. att1, att2, att3, attP, attB, attL, and attR), the recombination sites recognized by the resolvase family, and the recombination site recognized by transposase of *Bacillus thruingiensis*.

In particular embodiments of the present invention, the targeting constructs can contain: sequence homologous to a porcine immunoglobulin gene as described herein, a selectable marker gene and/or a site specific recombinase target site.

Selection of Homologously Recombined Cells

The cells can then be grown in appropriately-selected medium to identify cells providing the appropriate integration. The presence of the selectable marker gene inserted into the immunoglobulin gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the immunoglobulin gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, 1983.

The cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics. In some situations, it can be desirable to have two different modified alleles. This can be achieved by successive rounds of gene targeting or by breeding heterozygotes, each of which carries one of the desired modified alleles.

Identification of Cells that have Undergone Homologous Recombination

In one embodiment, the selection method can detect the depletion of the immunoglobulin gene directly, whether due to targeted knockout of the immunoglobulin gene by homologous recombination, or a mutation in the gene that results in a nonfunctioning or nonexpressed immunoglobulin. Selection via antibiotic resistance has been used most commonly for screening (see above). This method can detect the presence of the resistance gene on the targeting vector, but does not directly indicate whether integration was a targeted recombination event or a random integration. Certain technology, such as Poly A and promoter trap technology, increase the probability of targeted events, but again, do not give direct evidence that the desired phenotype, a cell deficient in immunoglobulin gene expression, has been achieved. In addition, negative forms of selection can be used to select for targeted integration; in these cases, the gene for a factor lethal to the cells is inserted in such a way that only targeted events allow the cell to avoid death. Cells selected by these methods can then be assayed for gene disruption, vector integration and, finally, immunoglobulin gene depletion. In these cases, since the selection is based on detection of targeting vector integration and not at the altered phenotype, only targeted knockouts, not point mutations, gene rearrangements or truncations or other such modifications can be detected.

Animal cells believed to lacking expression of functional immunoglobulin genes can be further characterized. Such characterization can be accomplished by the following techniques, including, but not limited to: PCR analysis, Southern blot analysis, Northern blot analysis, specific lectin binding assays, and/or sequencing analysis.

PCR analysis as described in the art can be used to determine the integration of targeting vectors. In one embodiment, amplimers can originate in the antibiotic resistance gene and extend into a region outside the vector sequence. Southern analysis can also be used to characterize gross modifications in the locus, such as the integration of a targeting vector into the immunoglobulin locus. Whereas, Northern analysis can be used to characterize the transcript produced from each of the alleles.

Further, sequencing analysis of the cDNA produced from the RNA transcript can also be used to determine the precise location of any mutations in the immunoglobulin allele.

In another aspect of the present invention, ungulate cells lacking at least one allele of a functional region of an ungulate heavy chain, kappa light chain and/or lambda light chain locus produced according to the process, sequences and/or constructs described herein are provided. These cells can be obtained as a result of homologous recombination. Particularly, by inactivating at least one allele of an ungulate heavy chain, kappa light chain or lambda light chain gene, cells can be produced which have reduced capability for expression of porcine antibodies. In other embodiments, mammalian cells lacking both alleles of an ungulate heavy chain, kappa light chain and/or lambda light chain gene can be produced according to the process, sequences and/or constructs described herein. In a further embodiment, porcine animals are provided in which at least one allele of an ungulate heavy chain, kappa light chain and/or lambda light chain gene is inactivated via a genetic targeting event produced according to the process, sequences and/or constructs described herein. In another aspect of the present invention, porcine animals are provided in which both alleles of an ungulate heavy chain, kappa light chain and/or lambda light chain gene are inactivated via a genetic targeting event. The gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques. Additional genes for a desired protein or regulatory sequence that modulate transcription of an existing sequence can be inserted.

In embodiments of the present invention, alleles of ungulate heavy chain, kappa light chain or lambda light chain gene are rendered inactive according to the process, sequences and/or constructs described herein, such that functional ungulate immunoglobulins can no longer be produced. In one embodiment, the targeted immunoglobulin gene can be transcribed into RNA, but not translated into protein. In another embodiment, the targeted immunoglobulin gene can be transcribed in an inactive truncated form. Such a truncated RNA may either not be translated or can be translated into a nonfunctional protein. In an alternative embodiment, the targeted immunoglobulin gene can be inactivated in such a way that no transcription of the gene occurs. In a further embodiment, the targeted immunoglobulin gene can be transcribed and then translated into a nonfunctional protein.

III. Insertion of Artificial Chromosomes Containing Human Immunoglobulin Genes

Artificial Chromosomes

One aspect of the present invention provides ungulates and ungulate cells that lack at least one allele of a functional region of an ungulate heavy chain, kappa light chain and/or lambda light chain locus produced according to the processes, sequences and/or constructs described herein, which are further modified to express at least part of a human antibody (i.e. immunoglobulin (Ig)) locus. This human locus can undergo rearrangement and express a diverse population of human antibody molecules in the ungulate. These cloned, transgenic ungulates provide a replenishable, theoretically infinite supply of human antibodies (such as polyclonal antibodies), which can be used for therapeutic, diagnostic, purification, and other clinically relevant purposes.

In one particular embodiment, artificial chromosome (ACs) can be used to accomplish the transfer of human immunoglobulin genes into ungulate cells and animals. ACs permit targeted integration of megabase size DNA fragments that contain single or multiple genes. The ACs, therefore, can introduce heterologous DNA into selected cells for production of the gene product encoded by the heterologous DNA. In a one embodiment, one or more ACs with integrated human immunoglobulin DNA can be used as a vector for introduction of human Ig genes into ungulates (such as pigs).

First constructed in yeast in 1983, ACs are man-made linear DNA molecules constructed from essential cis-acting DNA sequence elements that are responsible for the proper replication and partitioning of natural chromosomes (Murray et al. (1983), Nature 301:189-193). A chromosome requires at least three elements to function. Specifically, the elements of an artificial chromosome include at least: (1) autonomous replication sequences (ARS) (having properties of replication origins—which are the sites for initiation of DNA replication), (2) centromeres (site of kinetochore assembly that is responsible for proper distribution of replicated chromosomes at mitosis and meiosis), and (3) telomeres (specialized structures at the ends of linear chromosomes that function to both stabilize the ends and facilitate the complete replication of the extreme termini of the DNA molecule).

In one embodiment, the human Ig can be maintained as an independent unit (an episome) apart from the ungulate chromosomal DNA. For example, episomal vectors contain the necessary DNA sequence elements required for DNA replication and maintenance of the vector within the cell. Episomal vectors are available commercially (see, for example, Maniatis, T. et al., Molecular Cloning, A Laboratory Manual (1982) pp. 368-369). The AC can stably replicate and segregate along side endogenous chromosomes. In an alternative embodiment, the human IgG DNA sequences can be integrated into the ungulate cell's chromosomes thereby permitting the new information to be replicated and partitioned to the cell's progeny as a part of the natural chromosomes (see, for example, Wigler et al. (1977), Cell 11:223). The AC can be translocated to, or inserted into, the endogenous chromosome of the ungulate cell. Two or more ACs can be introduced to the host cell simultaneously or sequentially.

ACs, furthermore, can provide an extra-genomic locus for targeted integration of megabase size DNA fragments that contain single or multiple genes, including multiple copies of a single gene operatively linked to one promoter or each copy or several copies linked to separate promoters. ACs can permit the targeted integration of megabase size DNA fragments that contain single or multiple human immunoglobulin genes. The ACs can be generated by culturing the cells with dicentric chromosomes (i.e., chromosomes with two centromeres) under such conditions known to one skilled in the art whereby the chromosome breaks to form a minichromosome and formerly dicentric chromosome.

ACs can be constructed from humans (human artificial chromosomes: "HACs"), yeast (yeast artificial chromosomes: "YACs"), bacteria (bacterial artificial chromosomes: "BACs"), bacteriophage P1-derived artificial chromosomes: "PACs") and other mammals (mammalian artificial chromosomes: "MACs"). The ACs derive their name (e.g., YAC, BAC, PAC, MAC, HAC) based on the origin of the centromere. A YAC, for example, can derive its centromere from *S. cerevisiae*. MACs, on the other hand, include an active mammalian centromere while HACs refer to chromosomes that include human centromeres. Furthermore, plant artificial chromosomes ("PLACs") and insect artificial chromosomes can also be constructed. The ACs can include elements derived from chromosomes that are responsible for both replication and maintenance. ACs, therefore, are capable of stably maintaining large genomic DNA fragments such as human Ig DNA.

In one embodiment, ungulates containing YACs are provided. YACs are genetically engineered circular chromosomes that contain elements from yeast chromosomes, such as *S. cerevisiae*, and segments of foreign DNAs that can be much larger than those accepted by conventional cloning vectors (e.g., plasmids, cosmids). YACs allow the propagation of very large segments of exogenous DNA (Schlessinger, D. (1990), Trends in Genetics 6:248-253) into mammalian cells and animals (Choi et al. (1993), Nature Gen 4:117-123). YAC transgenic approaches are very powerful and are greatly enhanced by the ability to efficiently manipulate the cloned DNA. A major technical advantage of yeast is the ease with which specific genome modifications can be made via DNA-mediated transformation and homologous recombination (Ramsay, M. (1994), Mol Biotech 1:181-201). In one embodiment, one or more YACs with integrated human Ig DNA can be used as a vector for introduction of human Ig genes into ungulates (such as pigs).

The YAC vectors contain specific structural components for replication in yeast, including: a centromere, telomeres, autonomous replication sequence (ARS), yeast selectable markers (e.g., TRP1, URA3, and SUP4), and a cloning site for insertion of large segments of greater than 50 kb of exogenous DNA. The marker genes can allow selection of the cells carrying the YAC and serve as sites for the synthesis of specific restriction endonucleases. For example, the TRP1 and URA3 genes can be used as dual selectable markers to ensure that only complete artificial chromosomes are maintained. Yeast selectable markers can be carried on both sides of the centromere, and two sequences that seed telomere formation in vivo are separated. Only a fraction of one percent of a yeast cell's total DNA is necessary for replication, however, including the center of the chromosome (the centromere, which serves as the site of attachment between sister chromatids and the sites of spindle fiber attachment during mitosis), the ends of the chromosome (telomeres, which serve as necessary sequences to maintain the ends of eukaryotic chromosomes), and another short stretch of DNA called the ARS which serves as DNA segments where the double helix can unwind and begin to copy itself.

In one embodiment, YACs can be used to clone up to about 1, 2, or 3 Mb of immunoglobulin DNA. In another embodiment, at least 25, 30, 40, 50, 60, 70, 75, 80, 85, 90, or 95 kilobases.

Yeast integrating plasmids, replicating vectors (which are fragments of YACs), can also be used to express human Ig. The yeast integrating plasmid can contain bacterial plasmid sequences that provide a replication origin and a drug-resistance gene for growth in bacteria (e.g., *E. coli*), a yeast marker gene for selection of transformants in yeast, and restriction sites for inserting Ig sequences. Host cells can stably acquire this plasmid by integrating it directly into a chromosome. Yeast replicating vectors can also be used to express human Ig as free plasmid circles in yeast. Yeast or ARS-containing vectors can be stabilized by the addition of a centromere sequence. YACs have both centromeric and telomeric regions, and can be used for cloning very large pieces of DNA because the recombinant is maintained essentially as a yeast chromosome.

YACs are provided, for example, as disclosed in U.S. Pat. Nos. 6,692,954, 6,495,318, 6,391,642, 6,287,853, 6,221,588, 6,166,288, 6,096,878, 6,015,708, 5,981,175, 5,939,255, 5,843,671, 5,783,385, 5,776,745, 5,578,461, and 4,889,806; European Patent Nos. 1 356 062 and 0 648 265; PCT Publication Nos. WO 03/025222, WO 02/057437, WO 02/101044, WO 02/057437, WO 98/36082, WO 98/12335, WO 98/01573, WO 96/01276, WO 95/14769, WO 95/05847, WO 94/23049, and WO 94/00569.

In another embodiment, ungulates containing BACs are provided. BACs are F-based plasmids found in bacteria, such as *E. Coli*, that can transfer approximately 300 kb of foreign DNA into a host cell. Once the Ig DNA has been cloned into the host cell, the newly inserted segment can be replicated along with the rest of the plasmid. As a result, billions of copies of the foreign DNA can be made in a very short time. In a particular embodiment, one or more BACs with integrated human Ig DNA are used as a vector for introduction of human Ig genes into ungulates (such as pigs).

The BAC cloning system is based on the *E. coli* F-factor, whose replication is strictly controlled and thus ensures stable maintenance of large constructs (Willets, N., and R. Skurray (1987), Structure and function of the F-factor and mechanism of conjugation. In *Escherichia coli* and *Salmonella Typhimurium*: Cellular and Molecular Biology (F. C. Neidhardt, Ed) Vol. 2 pp 1110-1133, Am. Soc. Microbiol., Washington, D.C.). BACs have been widely used for cloning of DNA from various eukaryotic species (Cai et al. (1995), Genomics 29:413-425; Kim et al. (1996), Genomics 34:213-218; Misumi et al. (1997), Genomics 40:147-150; Woo et al. (1994), Nucleic Acids Res 22:4922-4931; Zimmer, R. and Gibbins, A.M.V. (1997), Genomics 42:217-226). The low occurrence of the F-plasmid can reduce the potential for recombination between DNA fragments and can avoid the lethal overexpression of cloned bacterial genes. BACs can stably maintain the human immunoglobulin genes in a single copy vector in the host cells, even after 100 or more generations of serial growth.

BAC (or pBAC) vectors can accommodate inserts in the range of approximately 30 to 300 kb pairs. One specific type of BAC vector, pBeloBac11, uses a complementation of the lacZ gene to distinguish insert-containing recombinant molecules from colonies carrying the BAC vector, by color. When a DNA fragment is cloned into the lacZ gene of pBeloBac11, insertional activation results in a white colony on X-Gal/IPTG plates after transformation (Kim et al. (1996), Genomics 34:213-218) to easily identify positive clones.

For example, BACs can be provided such as disclosed in U.S. Pat. Nos. 6,713,281, 6,703,198, 6,649,347, 6,638,722, 6,586,184, 6,573,090, 6,548,256, 6,534,262, 6,492,577, 6,492,506, 6,485,912, 6,472,177, 6,455,254, 6,383,756, 6,277,621, 6,183,957, 6,156,574, 6,127,171, 5,874,259, 5,707,811, and 5,597,694; European Patent Nos. 0 805 851; PCT Publication Nos. WO 03/087330, WO 02/00916, WO 01/39797, WO 01/04302, WO 00/79001, WO 99/54487, WO 99/27118, and WO 96/21725.

In another embodiment, ungulates containing bacteriophage PACs are provided. In a particular embodiment, one or more bacteriophage PACs with integrated human Ig DNA are used as a vector for introduction of human Ig genes into ungulates (such as pigs). For example, PACs can be provided such as disclosed in U.S. Pat. Nos. 6,743,906, 6,730,500, 6,689,606, 6,673,909, 6,642,207, 6,632,934, 6,573,090, 6,544,768, 6,489,458, 6,485,912, 6,469,144, 6,462,176, 6,413,776, 6,399,312, 6,340,595, 6,287,854, 6,284,882, 6,277,621, 6,271,008, 6,187,533, 6,156,574, 6,153,740, 6,143,949, 6,017,755, and 5,973,133; European Patent Nos. 0 814 156; PCT Publication Nos. WO 03/091426, WO 03/076573, WO 03/020898, WO 02/101022, WO 02/070696, WO 02/061073, WO 02/31202, WO 01/44486, WO 01/07478, WO 01/05962, and WO 99/63103.

In a further embodiment, ungulates containing MACs are provided. MACs possess high mitotic stability, consistent and regulated gene expression, high cloning capacity, and non-immunogenicity. Mammalian chromosomes can be comprised of a continuous linear strand of DNA ranging in size from approximately 50 to 250 Mb. The DNA construct can further contain one or more sequences necessary for the DNA construct to multiply in yeast cells. The DNA construct can also contain a sequence encoding a selectable marker gene. The DNA construct can be capable of being maintained as a chromosome in a transformed cell with the DNA construct. MACs provide extra-genomic specific integration sites for introduction of genes encoding proteins of interest and permit megabase size DNA integration so that, for example, genes encoding an entire metabolic pathway, a very large gene [e.g., such as the cystic fibrosis (CF) gene (~600 kb)], or several genes [e.g., a series of antigens for preparation of a multivalent vaccine] can be stably introduced into a cell.

Mammalian artificial chromosomes [MACs] are provided. Also provided are artificial chromosomes for other higher eukaryotic species, such as insects and fish, produced using the MACS are provided herein. Methods for generating and isolating such chromosomes. Methods using the MACs to construct artificial chromosomes from other species, such as insect and fish species are also provided. The artificial chromosomes are fully functional stable chromosomes. Two types of artificial chromosomes are provided. One type, herein referred to as SATACs [satellite artificial chromosomes] are stable heterochromatic chromosomes, and the another type are minichromosomes based on amplification of euchromatin. As used herein, a formerly dicentric chromosome is a chromosome that is produced when a dicentric chromosome fragments and acquires new telomeres so that two chromosomes, each having one of the centromeres, are produced. Each of the fragments can be replicable chromosomes.

Also provided are artificial chromosomes for other higher eukaryotic species, such as insects and fish, produced using the MACS are provided herein. In one embodiment, SATACs [satellite artificial chromosomes] are provided. SATACs are stable heterochromatic chromosomes. In another embodiment, minichromosomes are provided wherein the minichromosomes are based on amplification of euchromatin.

In one embodiment, artificial chromosomes can be generated by culturing the cells with the dicentric chromosomes under conditions whereby the chromosome breaks to form a minichromosome and formerly dicentric chromosome. In one embodiment, the SATACs can be generated from the minichromosome fragment, see, for example, in U.S. Pat. No. 5,288,625. In another embodiment, the SATACs can be generated from the fragment of the formerly dicentric chromosome. The SATACs can be made up of repeating units of short satellite DNA and can be fully heterochromatic. In one embodiment, absent insertion of heterologous or foreign DNA, the SATACs do not contain genetic information. In other embodiments, SATACs of various sizes are provided that are formed by repeated culturing under selective conditions and subcloning of cells that contain chromosomes produced from the formerly dicentric chromosomes. These chromosomes can be based on repeating units 7.5 to 10 Mb in size, or megareplicons. These megareplicaonscan be tandem blocks of satellite DNA flanked by heterologous non-satellite DNA. Amplification can produce a tandem array of identical chromosome segments [each called an amplicon] that contain two inverted megareplicons bordered by heterologous ["foreign"] DNA. Repeated cell fusion, growth on selective medium and/or BrdU [5-bromodeoxyuridine] treatment or other genome destabilizing reagent or agent, such as ionizing radiation, including X-rays, and subcloning can result in cell lines that carry stable heterochromatic or partially heterochromatic chromosomes, including a 150-200 Mb "sausage" chromosome, a 500-1000 Mb gigachromosome, a stable 250-400 Mb megachromosome and various smaller stable chromosomes derived therefrom. These chromosomes are based on these repeating units and can include human immunoglobulin DNA that is expressed. (See also U.S. Pat. No. 6,743,967

In other embodiments, MACs can be provided, for example, as disclosed in U.S. Pat. Nos. 6,743,967, 6,682, 729, 6,569,643, 6,558,902, 6,548,287, 6,410,722, 6,348,353, 6,297,029, 6,265,211, 6,207,648, 6,150,170, 6,150,160, 6,133,503, 6,077,697, 6,025,155, 5,997,881, 5,985,846, 5,981,225, 5,877,159, 5,851,760, and 5,721,118; PCT Publication Nos. WO 04/066945, WO 04/044129, WO 04/035729, WO 04/033668, WO 04/027075, WO 04/016791, WO 04/009788, WO 04/007750, WO 03/083054, WO 03/068910, WO 03/068909, WO 03/064613, WO 03/052050, WO 03/027315, WO 03/023029, WO 03/012126, WO 03/006610, WO 03/000921, WO 02/103032, WO 02/097059, WO 02/096923, WO 02/095003, WO 02/092615, WO 02/081710, WO 02/059330, WO 02/059296, WO 00/18941, WO 97/16533, and WO 96/40965.

In another aspect of the present invention, ungulates and ungulate cells containing HACs are provided. In a particular embodiment, one or more HACs with integrated human Ig DNA are used as a vector for introduction of human Ig genes into ungulates (such as pigs). In a particular embodiment, one or more HACs with integrated human Ig DNA are used to generate ungulates (for example, pigs) by nuclear transfer which express human Igs in response to immunization and which undergo affinity maturation.

Various approaches may be used to produce ungulates that express human antibodies ("human Ig"). These approaches include, for example, the insertion of a HAC containing both heavy and light chain Ig genes into an ungulate or the insertion of human B-cells or B-cell precursors into an ungulate during its fetal stage or after it is born (e.g., an immune deficient or immune suppressed ungulate) (see, for example, WO 01/35735, filed Nov. 17, 2000, U.S. Ser. No. 02/08645, filed Mar. 20, 2002). In either case, both human antibody producing cells and ungulate antibody-producing B-cells may be present in the ungulate. In an ungulate containing a HAC, a single B-cell may produce an antibody that contains a combination of ungulate and human heavy and light chain proteins. In still other embodiments, the total size of the HAC is at least to approximately 1, 2, 3, 4, 5, 6, 7, 8, 9 or 10 Mb.

For example, HACs can be provided such as disclosed in U.S. Pat. Nos. 6,642,207, 6,590,089, 6,566,066, 6,524,799, 6,500,642, 6,485,910, 6,475,752, 6,458,561, 6,455,026, 6,448,041, 6,410,722, 6,358,523, 6,277,621, 6,265,211, 6,146,827, 6,143,566, 6,077,697, 6,025,155, 6,020,142, and 5,972,649; U.S. Pat. Application No. 2003/0037347; PCT Publication Nos. WO 04/050704, WO 04/044156, WO 04/031385, WO 04/016791, WO 03/101396, WO 03/097812, WO 03/093469, WO 03/091426, WO 03/057923, WO 03/057849, WO 03/027638, WO 03/020898, WO 02/092812, and WO 98/27200.

Additional examples of ACs into which human immunoglobulin sequences can be inserted for use in the invention include, for example, BACs (e.g., pBeloBAC11 or pBAC108L; see, e.g., Shizuya et al. (1992), Proc Natl Acad Sci USA 89(18):8794-8797; Wang et al. (1997), Biotechniques 23(6):992-994), bacteriophage PACs, YACs (see, e.g., Burke (1990), Genet Anal Tech Appl 7(5):94-99), and MACs (see, e.g., Vos (1997), Nat. Biotechnol. 15(12):1257-1259; Ascenzioni et al. (1997), Cancer Lett 118(2):135-142), such as HACs, see also, U.S. Pat. Nos. 6,743,967, 6,716, 608, 6,692,954, 6,670,154, 6,642,207, 6,638,722, 6,573,090, 6,492,506, 6,348,353, 6,287,853, 6,277,621, 6,183,957, 6,156,953, 6,133,503, 6,090,584, 6,077,697, 6,025,155, 6,015,708, 5,981,175, 5,874,259, 5,721,118, and 5,270,201; European Patent Nos. 1 437 400, 1 234 024, 1 356 062, 0 959 134, 1 056 878, 0 986 648, 0 648 265, and 0 338 266; PCT Publication Nos. WO 04/013299, WO 01/07478, WO 00/06715, WO 99/43842, WO 99/27118, WO 98/55637, WO 94/00569, and WO 89/09219. Additional examples includes those AC provided in, for example, PCT Publication No. WO 02/076508, WO 03/093469, WO 02/097059; WO 02/096923; US Publication Nos US 2003/0113917 and US 2003/003435; and U.S. Pat. No. 6,025,155.

In other embodiments of the present invention, ACs transmitted through male gametogenesis in each generation. The AC can be integrating or non-integrating. In one embodiment, the AC can be transmitted through mitosis in substantially all dividing cells. In another embodiment, the AC can provide for position independent expression of a human immunogloulin nucleic acid sequence. In a particular embodiment, the AC can have a transmittal efficiency of at least 10% through each male and female gametogenesis. In one particular embodiment, the AC can be circular. In another particular embodiment, the non-integrating AC can be that deposited with the Belgian Coordinated Collections of Microorganisms—BCCM on Mar. 27, 2000 under accession number LMBP 5473 CB. In additional embodiments, methods for producing an AC are provided wherein a mitotically stable unit containing an exogenous nucleic acid transmitted through male gametogenesis is identified; and an entry site in the mitotically stable unit allows for the integration of human immunoglobulin genes into the unit.

In other embodiments, ACs are provided that include: a functional centromere, a selectable marker and/or a unique cloning site. Tin other embodiments, the AC can exhibit one or more of the following properties: it can segregate stably as an independent chromosome, immunoglobulin sequences can be inserted in a controlled way and can expressed from the AC, it can be efficiently transmitted through the male and female germline and/or the transgenic animals can bear the chromosome in greater than about 30, 40, 50, 60, 70, 80 or 90% of its cells.

In particular embodiments, the AC can be isolated from fibroblasts (such as any mammalian or human fibroblast) in which it was mitotically stable. After transfer of the AC into hamster cells, a lox (such as loxP) site and a selectable marker site can be inserted. In other embodiments, the AC can maintain mitotic stability, for example, showing a loss of less than about 5, 2, 1, 0.5 or 0.25 percent per mitosis in the absence of selection. See also, US 2003/0064509 and WO 01/77357.

Xenogenous Immunoglobulin Genes

In another aspect of the present invention, transgenic ungulates are provided that expresses a xenogenous immunoglobulin loci or fragment thereof, wherein the immunoglobulin can be expressed from an immunoglobulin locus that is integrated within an endogenous ungulate chromosome. In one embodiment, ungulate cells derived from the transgenic animals are provided. In one embodiment, the xenogenous immunoglobulin locus can be inherited by offspring. In another embodiment, the xenogenous immunoglobulin locus can be inherited through the male germ line by offspring. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In other embodiments, the transgenic ungulate that lacks any expression of functional endogenous immunoglobulins can be further genetically modified to express an xenogenous immunoglobulin loci. In an alternative embodiment, porcine animals are provided that contain an xenogeous immunoglobulin locus. In one embodiment, the xenogeous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In other embodiments, the transgenic ungulate that lacks any expression of functional endogenous immunoglobulins can be further genetically modified to express an xenogenous immunoglobulin loci. In an alternative embodiment, porcine animals are provided that contain an xenogeous immunoglobulin locus. In one embodiment, the xenogeous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

In another embodiment, porcine animals are provided that contain an xenogeous immunoglobulin locus. In one embodiment, the xenogeous immunoglobulin loci can be a heavy and/or light chain immunoglobulin or fragment thereof. In another embodiment, the xenogenous immunoglobulin loci can be a kappa chain locus or fragment thereof and/or a lambda chain locus or fragment thereof. In still further embodiments, an artificial chromosome (AC) can contain the xenogenous immunoglobulin. In one embodiment, the AC can be a yeast AC or a mammalian AC. In a further embodiment, the xenogenous locus can be a human immunoglobulin locus or fragment thereof. In one embodiment, the human immunoglobulin locus can be human chromosome 14, human chromosome 2, and human chromosome 22 or fragments thereof. In another embodiment, the human immunoglobulin locus can include any fragment of a human immunoglobulin that can undergo rearrangement. In a further embodiment, the human immunoglobulin loci can include any fragment of a human immunoglobulin heavy chain and a human immunoglobulin light chain that can undergo rearrangement. In still further embodiment, the human immunoglobulin loci can include any human immunoglobulin locus or fragment thereof that can produce an antibody upon exposure to an antigen. In a particular embodiment, the exogenous human immunoglobulin can be expressed in B cells to produce xenogenous immunoglobulin in response to exposure to one or more antigens.

Human immunoglobulin genes, such as the Ig heavy chain gene (human chromosome 414), Ig kappa chain gene (human chromosome #2) and/or the Ig lambda chain gene (chromosome #22) can be inserted into Acs, as described above. In a particular embodiment, any portion of the human heavy, kappa and/or lambda Ig genes can be inserted into ACs. In one embodiment, the nucleic acid can be at least 70, 80, 90, 95, or 99% identical to the corresponding region of a naturally-occurring nucleic acid from a human. In other embodiments, more than one class of human antibody is produced by the ungulate. In various embodiments, more than one different human Ig or antibody is produced by the ungulate. In one embodiment, an AC containing both a human Ig heavy chain gene and Ig light chain gene, such as an automatic human artificial chromosome ("AHAC," a circular recombinant nucleic acid molecule that is converted to a linear human chromosome in vivo by an endogenously expressed restriction endonuclease) can be introduced. In one embodiment, the human heavy chain loci and the light chain loci are on different chromosome arms (i.e., on different side of the centromere). In one embodiments, the heavy chain can include the mu heavy chain, and the light chain can be a lambda or kappa light chain. The Ig genes can be introduced simultaneously or sequentially in one or more than one ACs.

In particular embodiments, the ungulate or ungulate cell expresses one or more nucleic acids encoding all or part of a human Ig gene which undergoes rearrangement and expresses more than one human Ig molecule, such as a human antibody protein. Thus, the nucleic acid encoding the human Ig chain or antibody is in its unrearranged form (that is, the nucleic acid has not undergone V(D)J recombination). In particular embodiments, all of the nucleic acid segments encoding a V gene segment of an antibody light chain can be separated from all of the nucleic acid segments encoding a J gene segment by one or more nucleotides. In a particular embodiment, all of the nucleic acid segments encoding a V gene segment of an antibody heavy chain can be separated from all of the nucleic acid segments encoding a D gene segment by one or more nucleotides, and/or all of the nucleic acid segments encoding a D gene segment of an antibody heavy chain are separated from all of the nucleic acid segments encoding a J gene segment by one or more nucleotides. Administration of an antigen to a transgenic ungulate containing an unrearranged human Ig gene is followed by the rearrangement of the nucleic acid segments in the human Ig gene locus and the production of human antibodies reactive with the antigen.

In one embodiment, the AC can express a portion or fragment of a human chromosome that contains an immunoglobulin gene. In one embodiment, the AC can express at least 300 or 1300 kb of the human light chain locus, such as described in Davies et al. 1993 Biotechnology 11:911-914.

In another embodiment, the AC can express a portion of human chromosome 22 that contains at least the λ light-chain locus, including $V_\lambda$ gene segments, $J_\lambda$ gene segments, and the single $C_\lambda$ gene. In another embodiment, the AC can express at least one $V_\lambda$ gene segment, at least one $J_\lambda$ gene segment, and the $C_\lambda$ gene. In other embodiment, ACs can contain portions of the lambda locus, such as described in Popov et al. J Exp Med. 1999 May 17; 189(10):1611-20.

In another embodiment, the AC can express a portion of human chromosome 2 that contains at least the κ light-chain locus, including $V_\kappa$ gene segments, $J_\kappa$ gene segments and the single $C_\kappa$ gene. In another embodiment, the AC can express at least one $V_\kappa$ gene segment, at least one $J_\kappa$ gene segment and the $C_\kappa$ gene. In other embodiments, AC containing portions of the kappa light chain locus can be those describe, for example, in Li et al. 2000 J Immunol 164: 812-824 and Li S Proc Natl Acad Sci USA. 1987 June; 84(12):4229-33. In another embodiment, AC containing approximately 1.3 Mb of human kappa locus are provided, such as described in Zou et al FASEB J. 1996 August; 10(10):1227-32.

In further embodiments, the AC can express a portion of human chromosome 14 that contains at least the human heavy-chain locus, including $V_H$, $D_H$, $J_H$ and $C_H$ gene segments. In another embodiment, the AC can express at least one $V_H$ gene segment, at least one $D_H$ gene segment, at least one $J_H$ gene segment and at least one at least one $C_H$ gene segment. In other embodiments, the AC can express at least 85 kb of the human heavy chain locus, such as described in Choi et al. 1993 Nat Gen 4:117-123 and/or Zou et al. 1996 PNAS 96: 14100-14105.

In other embodiments, the AC can express portions of both heavy and light chain loci, such as, at least 220, 170, 800 or 1020 kb, for example, as disclosed in Green et al. 1994 Nat Gen 7:13-22; Mendez et al 1995 Genomics 26: 294-307; Mendez et al. 1997 Nat Gen 15: 146-156; Green et al. 1998 J Exp Med 188: 483-495 and/or Fishwild et al. 1996 Nat Biotech 14: 845-851. In another embodiment, the AC can express megabase amounts of human immunoglobulin, such as described in Nicholson J Immunol. 1999 Dec. 15; 163(12):6898-906 and Popov Gene. 1996 Oct. 24; 177(1-2):195-201. In addition, in one particular embodiment, MACs derived from human chromosome #14 (comprising the Ig heavy chain gene), human chromosome #2 comprising the Ig kappa chain gene) and human chromosome #22 (comprising the Ig lambda chain gene) can be introduced simultaneously or successively, such as described in US Patent Publication No. 2004/0068760 to Robl et al. In another embodiments, the total size of the MAC is less than or equal to approximately 10, 9, 8, or 7 megabases.

In a particular embodiment, human Vh, human Dh, human Jh segments and human mu segments of human immunoglobulins in germline configuration can be inserted into an AC, such as a YAC, such that the Vh, Dh, Jh and mu DNA segments form a repertoire of immunoglobulins containing portions which correspond to the human DNA segments, for example, as described in U.S. Pat. No. 5,545,807 to the Babraham Inistitute. Such ACs, after insertion into ungulate cells and generation of ungulates can produce heavy chain immunoglobulins. In one embodiment, these immunoglobulins can form functional heavy chain-light chain immunoglobulins. In another embodiment, these immunoglobulins can be expressed in an amount allowing for recovery from suitable cells or body fluids of the ungulate. Such immunoglobulins can be inserted into yeast artificial chromosome vectors, such as described by Burke, D T, Carle, G F and Olson, M V (1987) "Cloning of large segments of exogenous DNA into yeast by means of artificial chromosome vectors" Science, 236, 806-812, or by introduction of chromosome fragments (such as described by Richer, J and Lo, C W (1989) "Introduction of human DNA into mouse eggs by injection of dissected human chromosome fragments" Science 245, 175-177).

Additional information on specific ACs containing human immunoglobulin genes can be found in, for example, recent reviews by Giraldo & Montoliu (2001) Transgenic Research 10: 83-103 and Peterson (2003) Expert Reviews in Molecular Medicine 5: 1-25.

AC Transfer Methods

The human immunoglobulin genes can be first inserted into ACs and then the human-immunoglobulin-containing ACs can be inserted into the ungulate cells. Alternatively, the ACs can be transferred to an intermediary mammalian cell, such as a CHO cell, prior to insertion into the ungulate call. In one embodiment, the intermediary mammalian cell can also contain and AC and the first AC can be inserted into the AC of the mammalian cell. In particular, a YAC containing human immunoglobulin genes or fragments thereof in a yeast cell can be transferred to a mammalian cell that harbors an MAC. The YAC can be inserted into the MAC. The MAC can then be transferred to an ungulate cell. The human Ig genes can be inserted into ACs by homologous recombination. The resulting AC containing human Ig genes, can then be introduced into ungulate cells. One or more ungulate cells can be selected by techniques described herein or those known in the art, which contain an AC containing a human Ig.

Suitable hosts for introduction of the ACs are provided herein, which include but are not limited to any animal or plant, cell or tissue thereof, including, but not limited to: mammals, birds, reptiles, amphibians, insects, fish, arachnids, tobacco, tomato, wheat, monocots, dicots and algae. In one embodiment, the ACs can be condensed (Marschall et al Gene Ther. 1999 Sep.; 6(9):1634-7) by any reagent known in the art, including, but not limited to, spermine, spermidine, polyethylenimine, and/or polylysine prior to introduction into cells. The ACs can be introduced by cell fusion or microcell fusion or subsequent to isolation by any method known to those of skill in this art, including but not limited to: direct DNA transfer, electroporation, nuclear transfer, microcell fusion, cell fusion, spheroplast fusion, lipid-mediated transfer, lipofection, liposomes, microprojectile bombardment, microinjection, calcium phosphate precipitation and/or any other suitable method. Other methods for introducing DNA into cells, include nuclear microinjection, electroporation, bacterial protoplast fusion with intact cells. Polycations, such as polybrene and polyornithine, may also be used. For various techniques for transforming mammalian cells, see e.g., Keown et al. Methods in Enzymology (1990) Vol. 185, pp. 527-537; and Mansour et al. (1988) Nature 336:348-352.

The ACs can be introduced by direct DNA transformation; microinjection in cells or embryos, protoplast regeneration for plants, electroporation, microprojectile gun and other such methods known to one skilled in the art (see, e.g., Weissbach et al. (1988) Methods for Plant Molecular Biology, Academic Press, N.Y., Section VIII, pp. 421-463; Grierson et al. (1988) Plant Molecular Biology, 2d Ed., Blackie, London, Ch. 7-9; see, also U.S. Pat. Nos. 5,491,075; 5,482,928; and 5,424,409; see, also, e.g., U.S. Pat. No. 5,470,708,).

In particular embodiments, one or more isolated YACs can be used that harbor human Ig genes. The isolated YACs can be condensed (Marschall et al Gene Ther. 1999 September; 6(9):1634-7) by any reagent known in the art, including, but not limited to spermine, spermidine, polyethylenimine, and/or polylysine. The condensed YACs can then be transferred to porcine cells by any method known in the art (for example, microinjection, electroporation, lipid mediated transfection, etc). Alternatively, the condensed YAC can be transferred to oocytes via sperm-mediated gene transfer or intracytoplasmic sperm injection (ICSI) mediated gene transfer. In one embodiment, spheroplast fusion can be used to transfer YACs that harbor human Ig genes to porcine cells.

In other embodiments of the invention, the AC containing the human Ig can be inserted into an adult, fetal, or embryonic ungulate cell. Additional examples of ungulate cells include undifferentiated cells, such as embryonic cells (e.g., embryonic stem cells), differentiated or somatic cells, such as epithelial cells, neural cells epidermal cells, keratinocytes, hematopoietic cells, melanocytes, chondrocytes, B-lymphocytes, T-lymphocytes, erythrocytes, macrophages, monocytes, fibroblasts, muscle cells, cells from the female reproductive system, such as a mammary gland, ovarian cumulus, granulosa, or oviductal cell, germ cells, placental cell, or cells derived from any organ, such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, and uterus or any other cell type described herein.

Site Specific Recombinase Mediated Transfer

In particular embodiments of the present invention, the transfer of ACs containing human immunoglobulin genes to porcine cells, such as those described herein or known in the art, can be accomplished via site specific recombinase mediated transfer. In one particular embodiment, the ACs can be transferred into porcine fibroblast cells. In another particular embodiment, the ACs can be YACs.

In other embodiments of the present invention, the circularized DNA, such as an AC, that contain the site specific recombinase target site can be transferred into a cell line that has a site specific recombinase target site within its genome. In one embodiment, the cell's site specific recombinase target site can be located within an exogenous chromosome. The exogenous chromosome can be an artificial chromosome that does not integrate into the host's endogenous genome. In one embodiment, the AC can be transferred via germ line transmission to offspring. In one particular embodiment, a YAC containing a human immunoglobulin gene or fragment thereof can be circularized via a site specific recombinase and then transferred into a host cell that contains a MAC, wherein the MAC contains a site specific recombinase site. This MAC that now contains human immunoglobulin loci or fragments thereof can then be fused with a porcine cell, such as, but not limited to, a fibroblast. The porcine cell can then be used for nuclear transfer.

In certain embodiments of the present invention, the ACs that contain human immunoglobulin genes or fragments thereof can be transferred to a mammalian cell, such as a CHO cell, prior to insertion into the ungulate call. In one embodiment, the intermediary mammalian cell can also contain and AC and the first AC can be inserted into the AC of the mammalian cell. In particular, a YAC containing human immunoglobulin genes or fragments thereof in a yeast cell can be transferred to a mammalian cell that harbors a MAC. The YAC can be inserted in the MAC. The MAC can then be transferred to an ungulate cell. In particular embodiments, the YAC harboring the human Ig genes or fragments thereof can contain site specific recombinase target sites. The YAC can first be circularized via application of the appropriate site specific recombinase and then inserted into a mammalian cell that contains its own site specific recombinase target site. Then, the site specific recombinase can be applied to integrate the YAC into the MAC in the intermediary mammalian cell. The site specific recombinase can be applied in cis or trans. In particular, the site specific recombinase can be applied in trans. In one embodiment, the site specific recombinase can be expressed via transfection of a site specific recombinase expression plasmid, such as a Cre expression plasmid. In addition, one telomere region of the YAC can also be retrofitted with a selectable marker, such as a selectable marker described herein or known in the art. The human Ig genes or fragments thereof within the MAC of the intermediary mammalian cell can then be transferred to an ungulate cell, such as a fibroblast.

Figure 7:
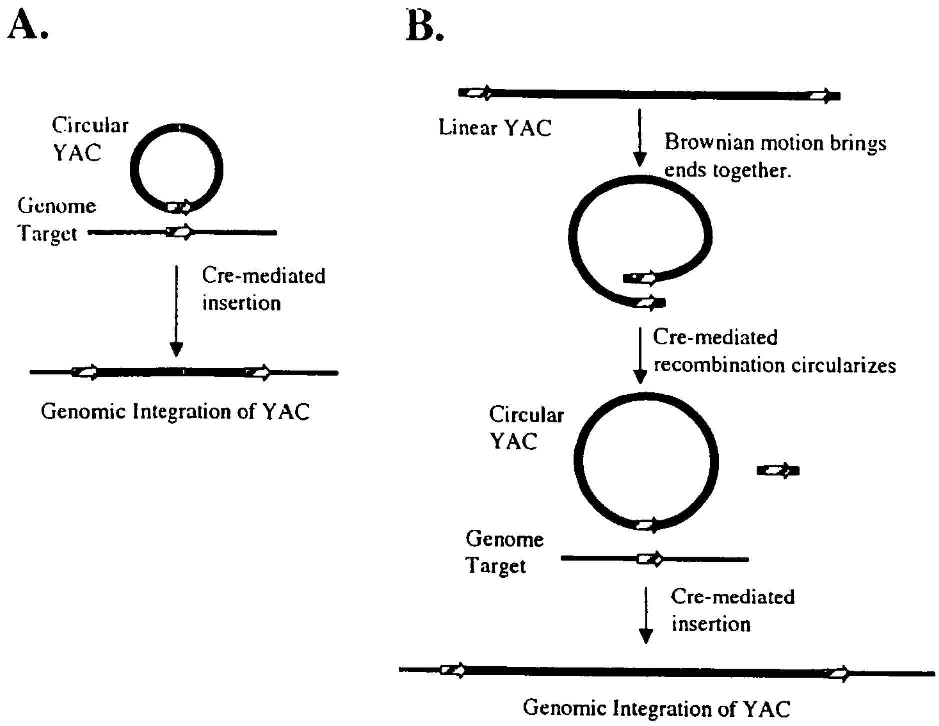
FIG. 7 illustrates the site specific recombinase mediated transfer of a YAC into a host genome. "SSRRS" stands for a specific recombinase target or recognition site.

Alternatively, the AC, such as a YAC, harboring the human Ig genes or fragments thereof can contain site specific recombinase target sites optionally located near each telomere. The YAC can first be circularized via application of the appropriate site specific recombinase and then inserted into an ungulate cell directly that contains its own site specific recombinase target site within it genome. Alternatively, the ungulate cell can harbor its own MAC, which contains a site specific recombinase target site. In this embodiment, the YAC can be inserted directly into the endogenous genome of the ungulate cell. In particular embodiments, the ungulate cell can be a fibroblast cell or any other suitable cell that can be used for nuclear transfer. See, for example, FIG. 7; Call et al., Hum Mol Genet. 2000 Jul. 22; 9(12):1745-51.

In other embodiments, methods to circularize at least 100 kb of DNA are provided wherein the DNA can then be integrated into a host genome via a site specific recombinase. In one embodiment, at least 100, 200, 300, 400, 500, 1000, 2000, 5000, 10,000 kb of DNA can be circularized. In another embodiment, at least 1000, 2000, 5000, 10,000, or 20,000 megabases of DNA can be circularized. In one embodiment, the circularization of the DNA can be accomplished by attaching site specific recombinase target sites at each end of the DNA sequence and then applying the site specific recombinase to result in circularization of the DNA. In one embodiment, the site specific recombinase target site can be lox. In another embodiment, the site specific recombinase target site can be Flt. In certain embodiments, the DNA can be an artificial chromosome, such as a YAC or any AC described herein or known in the art. In another embodiment, the AC can contain human immunoglobulin loci or fragments thereof.

In another preferred embodiment, the YAC can be converted to, or integrated within, an artificial mammalian chromosome. The mammalian artificial chromosome is either transferred to or harbored within a porcine cell. The artificial chromosome can be introduced within the porcine genome through any method known in the art including but not limited to direct injection of metaphase chromosomes, lipid mediated gene transfer, or microcell fusion.

Site-specific recombinases include enzymes or recombinases that recognize and bind to a short nucleic acid site or sequence-specific recombinase target site, i.e., a recombinase recognition site, and catalyze the recombination of nucleic acid in relation to these sites. These enzymes include recombinases, transposases and integrases. Examples of sequence-specific recombinase target sites include, but are not limited to, lox sites, att sites, dif sites and frt sites. Non-limiting examples of site-specific recombinases include, but are not limited to, bacteriophage P1 Cre recombinase, yeast FLP recombinase, Inti integrase, bacteriophage λ, phi 80, P22, P2, 186, and P4 recombinase, Tn3 resolvase, the Hin recombinase, and the Cin recombinase, *E. coli* xerC and xerD recombinases, *Bacillus thuringiensis* recombinase, TpnI and the β-lactamase transposons, and the immunoglobulin recombinases.

In one embodiment, the recombination site can be a lox site that is recognized by the Cre recombinase of bacteriophage P1. Lox sites refer to a nucleotide sequence at which the product of the cre gene of bacteriophage P1, the Cre recombinase, can catalyze a site-specific recombination event. A variety of lox sites are known in the art, including the naturally occurring loxP, loxB, loxL and loxR, as well as a number of mutant, or variant, lox sites, such as loxP511, loxP514, lox.DELTA.86, lox.DELTA.117, loxC2, loxP2, loxP3 and lox P23. Additional example of lox sites include, but are not limited to, loxB, loxL, loxR, loxP, loxP3, loxP23, loxΔ86, loxΔ117, loxP511, and loxC2.

In another embodiment, the recombination site is a recombination site that is recognized by a recombinases other than Cre. In one embodiment, the recombinase site can be the FRT sites recognized by FLP recombinase of the 2 pi plasmid of *Saccharomyces cerevisiae*. FRT sites refer to a nucleotide sequence at which the product of the FLP gene of the yeast 2 micron plasmid, FLP recombinase, can catalyze site-specific recombination. Additional examples of the non-Cre recombinases include, but are not limited to, site-specific recombinases include: att sites recognized by the Int recombinase of bacteriophage λ (e.g. att1, att2, att3, attP, attB, attL, and attR), the recombination sites recognized by the resolvase family, and the recombination site recognized by transposase of *Bacillus thruingiensis*.

IV. Production of Genetically Modified Animals

In additional aspects of the present invention, ungulates that contain the genetic modifications described herein can be produced by any method known to one skilled in the art. Such methods include, but are not limited to: nuclear transfer, intracytoplasmic sperm injection, modification of zygotes directly and sperm mediated gene transfer.

In another embodiment, a method to clone such animals, for example, pigs, includes: enucleating an oocyte, fusing the oocyte with a donor nucleus from a cell in which at least one allele of at least one immunoglobulin gene has been inactivated, and implanting the nuclear transfer-derived embryo into a surrogate mother.

Alternatively, a method is provided for producing viable animals that lack any expression of functional immunoglobulin by inactivating both alleles of the immunoglobulin gene in embryonic stem cells, which can then be used to produce offspring.

In another aspect, the present invention provides a method for producing viable animals, such as pigs, in which both alleles of the immunoglobulin gene have been rendered inactive. In one embodiment, the animals are produced by cloning using a donor nucleus from a cell in which both alleles of the immunoglobulin gene have been inactivated. In one embodiment, both alleles of the immunoglobulin gene are inactivated via a genetic targeting event.

Genetically altered animals that can be created by modifying zygotes directly. For mammals, the modified zygotes can be then introduced into the uterus of a pseudopregnant female capable of carrying the animal to term. For example, if whole animals lacking an immunoglobulin gene are desired, then embryonic stem cells derived from that animal can be targeted and later introduced into blastocysts for growing the modified cells into chimeric animals. For embryonic stem cells, either an embryonic stem cell line or freshly obtained stem cells can be used.

In a suitable embodiment of the invention, the totipotent cells are embryonic stem (ES) cells. The isolation of ES cells from blastocysts, the establishing of ES cell lines and their subsequent cultivation are carried out by conventional methods as described, for example, by Doetchmann et al., J. Embryol. Exp. Morph. 87:27-45 (1985); Li et al., Cell 69:915-926 (1992); Robertson, E. J. "Tetracarcinomas and Embryonic Stem Cells: A Practical Approach," ed. E. J. Robertson, IRL Press, Oxford, England (1987); Wurst and Joyner, "Gene Targeting: A Practical Approach," ed. A. L. Joyner, IRL Press, Oxford, England (1993); Hogen et al., "Manipulating the Mouse Embryo: A Laboratory Manual," eds. Hogan, Beddington, Costantini and Lacy, Cold Spring Harbor Laboratory Press, New York (1994); and Wang et al., Nature 336:741-744 (1992). In another suitable embodiment of the invention, the totipotent cells are embryonic germ (EG) cells. Embryonic Germ cells are undifferentiated cells functionally equivalent to ES cells, that is they can be cultured and transfected in vitro, then contribute to somatic and germ cell lineages of a chimera (Stewart et al., Dev. Biol. 161:626-628 (1994)). EG cells are derived by culture of primordial germ cells, the progenitors of the gametes, with a combination of growth factors: leukemia inhibitory factor, steel factor and basic fibroblast growth factor (Matsui et al., Cell 70:841-847 (1992); Resnick et al., Nature 359: 550-551 (1992)). The cultivation of EG cells can be carried out using methods described in the article by Donovan et al., "Transgenic Animals, Generation and Use," Ed. L. M. Houdebine, Harwood Academic Publishers (1997), and in the original literature cited therein.

Tetraploid blastocysts for use in the invention may be obtained by natural zygote production and development, or by known methods by electrofusion of two-cell embryos and subsequently cultured as described, for example, by James et al., Genet. Res. Camb. 60:185-194 (1992); Nagy and Rossant, "Gene Targeting: A Practical Approach," ed. A. L. Joyner, IRL Press, Oxford, England (1993); or by Kubiak and Tarkowski, Exp. Cell Res. 157:561-566 (1985).

The introduction of the ES cells or EG cells into the blastocysts can be carried out by any method known in the art. A suitable method for the purposes of the present invention is the microinjection method as described by Wang et al., EMBO J. 10:2437-2450 (1991).

Alternatively, by modified embryonic stem cells transgenic animals can be produced. The genetically modified embryonic stem cells can be injected into a blastocyst and then brought to term in a female host mammal in accordance with conventional techniques. Heterozygous progeny can then be screened for the presence of the alteration at the site of the target locus, using techniques such as PCR or Southern blotting. After mating with a wild-type host of the same species, the resulting chimeric progeny can then be cross-mated to achieve homozygous hosts.

After transforming embryonic stem cells with the targeting vector to alter the immunoglobulin gene, the cells can be plated onto a feeder layer in an appropriate medium, e.g., fetal bovine serum enhanced DMEM. Cells containing the construct can be detected by employing a selective medium, and after sufficient time for colonies to grow, colonies can be picked and analyzed for the occurrence of homologous recombination. Polymerase chain reaction can be used, with primers within and without the construct sequence but at the target locus. Those colonies which show homologous recombination can then be used for embryo manipulating and blastocyst injection. Blastocysts can be obtained from superovulated females. The embryonic stem cells can then be trypsinized and the modified cells added to a droplet containing the blastocysts. At least one of the modified embryonic stem cells can be injected into the blastocoel of the blastocyst. After injection, at least one of the blastocysts can be returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected, and then genotyping can be conducted to probe for the presence of the modified immunoglobulin gene.

In other embodiments, sperm mediated gene transfer can be used to produce the genetically modified ungulates described herein. The methods and compositions described herein to either eliminate expression of endogenous immunoglobulin genes or insert xenogenous immunoglobulin genes can be used to genetically modify the sperm cells via any technique described herein or known in the art. The genetically modified sperm can then be used to impregnate a female recipient via artificial insemination, intracytoplasmic sperm injection or any other known technique. In one embodiment, the sperm and/or sperm head can be incubated with the exogenous nucleic acid for a sufficient time period. Sufficient time periods include, for example, about 30 seconds to about 5 minutes, typically about 45 seconds to about 3 minutes, more typically about 1 minute to about 2 minutes. In particular embodiments, the expression of xenogenous, such as human, immunoglobulin genes in ungulates as described herein, can be accomplished via intracytoplasmic sperm injection.

The potential use of sperm cells as vectors for gene transfer was first suggested by Brackett et al., Proc., Natl. Acad. Sci. USA 68:353-357 (1971). This was followed by reports of the production of transgenic mice and pigs after in vitro fertilization of oocytes with sperm that had been incubated by naked DNA (see, for example, Lavitrano et al., Cell 57:717-723 (1989) and Gandolfi et al. Journal of Reproduction and Fertility Abstract Series 4, 10 (1989)), although other laboratories were not able to repeat these experiments (see, for example, Brinster et al. Cell 59:239-241 (1989) and Gavora et al., Canadian Journal of Animal Science 71:287-291 (1991)). Since then, there have been several reports of successful sperm mediated gene transfer in chicken (see, for example, Nakanishi and Iritani, Mol. Reprod. Dev. 36:258-261 (1993)); mice (see, for example, Maione, Mol. Reprod. Dev. 59:406 (1998)); and pigs (see, for example, Lavitrano et al. Transplant. Proc. 29:3508-3509 (1997); Lavitrano et al., Proc. Natl. Acad. Sci. USA 99:14230-5 (2002); Lavitrano et al., Mol. Reprod. Dev. 64-284-91 (2003)). Similar techniques are also described in U.S. Pat. No. 6,376,743; issued Apr. 23, 2002; U.S. Patent Publication Nos. 20010044937, published Nov. 22, 2001, and 20020108132, published Aug. 8, 2002.

In other embodiments, intracytoplasmic sperm injection can be used to produce the genetically modified ungulates described herein. This can be accomplished by co-inserting an exogenous nucleic acid and a sperm into the cytoplasm of an unfertilized oocyte to form a transgenic fertilized oocyte, and allowing the transgenic fertilized oocyte to develop into a transgenic embryo and, if desired, into a live offspring. The sperm can be a membrane-disrupted sperm head or a demembranated sperm head. The co-insertion step can include the substep of preincubating the sperm with the exogenous nucleic acid for a sufficient time period, for example, about 30 seconds to about 5 minutes, typically about 45 seconds to about 3 minutes, more typically about 1 minute to about 2 minutes. The co-insertion of the sperm and exogenous nucleic acid into the oocyte can be via microinjection. The exogenous nucleic acid mixed with the sperm can contain more than one transgene, to produce an embryo that is transgenic for more than one transgene as described herein. The intracytoplasmic sperm injection can be accomplished by any technique known in the art, see, for example, U.S. Pat. No. 6,376,743. In particular embodiments, the expression of xenogenous, such as human, immunoglobulin genes in ungulates as described herein, can be accomplished via intracytoplasmic sperm injection.

Any additional technique known in the art may be used to introduce the transgene into animals. Such techniques include, but are not limited to pronuclear microinjection (see, for example, Hoppe, P. C. and Wagner, T. E., 1989, U.S. Pat. No. 4,873,191); retrovirus mediated gene transfer into germ lines (see, for example, Van der Putten et al., 1985, Proc. Natl. Acad. Sci., USA 82:6148-6152); gene targeting in embryonic stem cells (see, for example, Thompson et al., 1989, Cell 56:313-321; Wheeler, M. B., 1994, WO 94/26884); electroporation of embryos (see, for example, Lo, 1983, Mol Cell. Biol. 3:1803-1814); cell gun; transfection; transduction; retroviral infection; adenoviral infection; adenoviral-associated infection; liposome-mediated gene transfer; naked DNA transfer; and sperm-mediated gene transfer (see, for example, Lavitrano et al., 1989, Cell 57:717-723); etc. For a review of such techniques, see, for example, Gordon, 1989, Transgenic Animals, Intl. Rev. Cytol. 115:171-229. In particular embodiments, the expression of xenogenous, such as human, immunoglobulin genes in ungulates as described herein, can be accomplished via these techniques.

Somatic Cell Nuclear Transfer to Produce Cloned, Transgenic Offspring

In a further aspect of the present invention, ungulate, such as porcine or bovine, cells lacking one allele, optionally both alleles of an ungulate heavy chain, kappa light chain and/or lambda light chain gene can be used as donor cells for nuclear transfer into recipient cells to produce cloned, transgenic animals. Alternatively, ungulate heavy chain, kappa light chain and/or lambda light chain gene knockouts can be created in embryonic stem cells, which are then used to produce offspring. Offspring lacking a single allele of a functional ungulate heavy chain, kappa light chain and/or lambda light chain gene produced according to the process, sequences and/or constructs described herein can be breed to further produce offspring lacking functionality in both alleles through mendelian type inheritance.

In another embodiment, the present invention provides a method for producing viable pigs that lack any expression of functional alpha-1,3-GT by breeding a male pig heterozygous for the alpha-1,3-GT gene with a female pig heterozygous for the alpha-1,3-GT gene. In one embodiment, the pigs are heterozygous due to the genetic modification of one allele of the alpha-1,3-GT gene to prevent expression of that allele. In another embodiment, the pigs are heterozygous due to the presence of a point mutation in one allele of the alpha-1,3-GT gene. In another embodiment, the point mutation can be a T-to-G point mutation at the second base of exon 9 of the alpha-1,3-GT gene. In one specific embodiment, a method to produce a porcine animal that lacks any expression of functional alpha-1,3-GT is provided wherein a male pig that contains a T-to-G point mutation at the second base of exon 9 of the alpha-1,3-GT gene is bred with a female pig that contains a T-to-G point mutation at the second base of exon 9 of the alpha-1,3-GT gene, or vise versa.

The present invention provides a method for cloning an animal, such as a pig, lacking a functional immunoglobulin gene via somatic cell nuclear transfer. In general, the animal can be produced by a nuclear transfer process comprising the following steps: obtaining desired differentiated cells to be used as a source of donor nuclei; obtaining oocytes from the animal; enucleating said oocytes; transferring the desired differentiated cell or cell nucleus into the enucleated oocyte, e.g., by fusion or injection, to form NT units; activating the resultant NT unit; and transferring said cultured NT unit to a host animal such that the NT unit develops into a fetus.

Nuclear transfer techniques or nuclear transplantation techniques are known in the art (Dai et al. Nature Biotechnology 20:251-255; Polejaeva et al Nature 407:86-90 (2000); Campbell et al, Theriogenology, 43:181 (1995); Collas et al, Mol. Report Dev., 38:264-267 (1994); Keefer et al, Biol. Reprod., 50:935-939 (1994); Sims et al, Proc. Natl. Acad. Sci., USA, 90:6143-6147 (1993); WO 94/26884; WO 94/24274, and WO 90/03432, U.S. Pat. Nos. 4,944,384 and 5,057,420).

A donor cell nucleus, which has been modified to alter the immunoglobulin gene, is transferred to a recipient oocyte. The use of this method is not restricted to a particular donor cell type. The donor cell can be as described herein, see also, for example, Wilmut et al Nature 385 810 (1997); Campbell et al Nature 380 64-66 (1996); Dai et al., Nature Biotechnology 20:251-255, 2002 or Cibelli et al Science 280 1256-1258 (1998). All cells of normal karyotype, including embryonic, fetal and adult somatic cells which can be used successfully in nuclear transfer can be employed. Fetal fibroblasts are a particularly useful class of donor cells. Generally suitable methods of nuclear transfer are described in Campbell et al Theriogenology 43 181 (1995), Dai et al. Nature Biotechnology 20:251-255, Polejaeva et al Nature 407:86-90 (2000), Collas et al Mol. Reprod. Dev. 38 264-267 (1994), Keefer et al Biol. Reprod. 50 935-939 (1994), Sims et al Proc. Nat'l. Acad. Sci. USA 90 6143-6147 (1993), WO-A-9426884, WO-A-9424274, WO-A-9807841, WO-A-9003432, U.S. Pat. No. 4,994,384 and U.S. Pat. No. 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (Campbell et al (Nature, 380:64-68, 1996) and Stice et al (Biol. Reprod., 20 54:100-110, 1996).

Somatic nuclear donor cells may be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In a suitable embodiment of the invention, nuclear donor cells are selected from the group consisting of epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, extended cells, cumulus cells, epidermal cells or endothelial cells. In another embodiment, the nuclear donor cell is an embryonic stem cell. In a particular embodiment, fibroblast cells can be used as donor cells.

In another embodiment of the invention, the nuclear donor cells of the invention are germ cells of an animal. Any germ cell of an animal species in the embryonic, fetal, or adult stage may be used as a nuclear donor cell. In a suitable embodiment, the nuclear donor cell is an embryonic germ cell.

Nuclear donor cells may be arrested in any phase of the cell cycle (G0, G1, G2, S, M) so as to ensure coordination with the acceptor cell. Any method known in the art may be used to manipulate the cell cycle phase. Methods to control the cell cycle phase include, but are not limited to, G0 quiescence induced by contact inhibition of cultured cells, G0 quiescence induced by removal of serum or other essential nutrient, G0 quiescence induced by senescence, G0 quiescence induced by addition of a specific growth factor; G0 or G1 quiescence induced by physical or chemical means such as heat shock, hyperbaric pressure or other treatment with a chemical, hormone, growth factor or other substance; S-phase control via treatment with a chemical agent which interferes with any point of the replication procedure; M-phase control via selection using fluorescence activated cell sorting, mitotic shake off, treatment with microtubule disrupting agents or any chemical which disrupts progression in mitosis (see also Freshney, R. I., "Culture of Animal Cells: A Manual of Basic Technique," Alan R. Liss, Inc, New York (1983).

Methods for isolation of oocytes are well known in the art. Essentially, this can comprise isolating oocytes from the ovaries or reproductive tract of an animal. A readily available source of oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. This period of time is known as the "maturation period". In certain embodiments, the oocyte is obtained from a gilt. A "gilt" is a female pig that has never had offspring. In other embodiments, the oocyte is obtained from a sow. A "sow" is a female pig that has previously produced offspring.

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated animal 35 to 48, or 39-41, hours past the onset of estrus or past the injection of human chorionic gonadotropin (hCG) or similar hormone. The oocyte can be placed in an appropriate medium, such as a hyaluronidase solution.

After a fixed time maturation period, which ranges from about 10 to 40 hours, about 16-18 hours, about 40-42 hours or about 39-41 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, such as not more than 24 hours later, or not more than 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, Mol. Reprod. Dev., 38:264-267 (1994). After fusion, the resultant fused NT units are then placed in a suitable medium until activation, for example, CR1aa medium. Typically activation can be effected shortly thereafter, for example less than 24 hours later, or about 4-9 hours later, or optimally 1-2 hours after fusion. In a particular embodiment, activation occurs at least one hour post fusion and at 40-41 hours post maturation.

The NT unit can be activated by known methods. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720, to Susko-Parrish et al. Fusion and activation can be induced by application of an AC pulse of 5 V for 5 s followed by two DC pulses of 1.5 kV/cm for 60 μs each using an ECM2001 Electrocell Manipulator (BTX Inc., San Diego, Calif.). Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units, or "fused embryos", can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media, and, in one specific example, the activated NT units can be cultured in NCSU-23 medium for about 1-4 h at approximately 38.6° C. in a humidified atmosphere of 5% CO2.

Afterward, the cultured NT unit or units can be washed and then placed in a suitable media contained in well plates which can contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. These NT units can be cultured until at least about 2 to 400 cells, about 4 to 128 cells, or at least about 50 cells.

Activated NT units can then be transferred (embryo transfers), zero(0)-144 hours post activation, to the oviduct of an female pigs. In one embodiment, the female pigs can be an estrus-synchronized recipient gilt. Crossbred gilts (large white/Duroc/Landrace) (280-400 lbs) can be used. The gilts can be synchronized as recipient animals by oral administration of 18-20 mg Regu-Mate (Altrenogest, Hoechst, Warren, N.J.) mixed into the feed. Regu-Mate can be fed for 14 consecutive days. One thousand units of Human Chorionic Gonadotropin (hCG, Intervet America, Millsboro, Del.) can then be administered i.m. about 105 h after the last Regu-Mate treatment. Embryo transfers can then be performed about 22-26 h after the hCG injection. In one embodiment, the pregnancy can be brought to term and result in the birth of live offspring. In another embodiment, the pregnancy can be terminated early and embryonic cells can be harvested.

Breeding for Desired Homozygous Knockout Animals

In another aspect, the present invention provides a method for producing viable animals that lack any expression of a functional immunoglobulin gene is provided by breeding a male heterozygous for the immunoglobulin gene with a female heterozygous for the immunoglobulin gene. In one embodiment, the animals are heterozygous due to the genetic modification of one allele of the immunoglobulin gene to prevent expression of that allele. In another embodiment, the animals are heterozygous due to the presence of a point mutation in one allele of the alpha-immunoglobulin gene. In further embodiments, such heterozygous knockouts can be bred with an ungulate that expresses xenogenous immunoglobulin, such as human. In one embodiment, a animal can be obtained by breeding a transgenic ungulate that lacks expression of at least one allele of an endogenous immunoglobulin wherein the immunoglobulin is selected from the group consisting of heavy chain, kappa light chain and lambda light chain or any combination thereof with an ungulate that expresses an xenogenous immunoglobulin. In another embodiment, a animal can be obtained by breeding a transgenic ungulate that lacks expression of one allele of heavy chain, kappa light chain and lambda light chain with an ungulate that expresses an xenogenous, such as human, immunoglobulin. In a further embodiment, an animal can be obtained by breeding a transgenic ungulate that lacks expression of one allele of heavy chain, kappa light chain and lambda light chain and expresses an xenogenous, such as human, immunoglobulin with another transgenic ungulate that lacks expression of one allele of heavy chain, kappa light chain and lambda light chain with an ungulate and expresses an xenogenous, such as human, immunoglobulin to produce a homozygous transgenic ungulate that lacks expression of both alleles of heavy chain, kappa light chain and lambda light chain and expresses an xenogenous, such as human, immunoglobulin. Methods to produce such animals are also provided.

In one embodiment, sexually mature animals produced from nuclear transfer from donor cells that carrying a homozygous knockout in the immunoglobulin gene, can be bred and their offspring tested for the homozygous knockout. These homozygous knockout animals can then be bred to produce more animals.

In another embodiment, oocytes from a sexually mature homozygous knockout animal can be in vitro fertilized using wild type sperm from two genetically diverse pig lines and the embryos implanted into suitable surrogates. Offspring from these matings can be tested for the presence of the knockout, for example, they can be tested by cDNA sequencing, and/or PCR. Then, at sexual maturity, animals from each of these litters can be mated. In certain methods according to this aspect of the invention, pregnancies can be terminated early so that fetal fibroblasts can be isolated and further characterized phenotypically and/or genotypically. Fibroblasts that lack expression of the immunoglobulin gene can then be used for nuclear transfer according to the methods described herein to produce multiple pregnancies and offspring carrying the desired homozygous knockout.

Additional Genetic Modifications

In other embodiments, animals or cells lacking expression of functional immunoglobulin, produced according to the process, sequences and/or constructs described herein, can contain additional genetic modifications to eliminate the expression of xenoantigens. The additional genetic modifications can be made by further genetically modifying cells obtained from the transgenic cells and animals described herein or by breeding the animals described herein with animals that have been further genetically modified. Such animals can be modified to eliminate the expression of at least one allele of the alpha-1,3-galactosyltransferase gene, the CMP-Neu5Ac hydroxylase gene (see, for example, U.S. Ser. No. 10/863,116), the iGb3 synthase gene (see, for example, U.S. Patent Application 60/517,524), and/or the Forssman synthase gene (see, for example, U.S. Patent Application 60/568,922). In additional embodiments, the animals discloses herein can also contain genetic modifications to express fucosyltransferase, sialyltransferase and/or any member of the family of glucosyltransferases. To achieve these additional genetic modifications, in one embodiment, cells can be modified to contain multiple genetic modifications. In other embodiments, animals can be bred together to achieve multiple genetic modifications. In one specific embodiment, animals, such as pigs, lacking expression of functional immunoglobulin, produced according to the process, sequences and/or constructs described herein, can be bred with animals, such as pigs, lacking expression of alpha-1,3-galactosyl transferase (for example, as described in WO 04/028243).

In another embodiment, the expression of additional genes responsible for xenograft rejection can be eliminated or reduced. Such genes include, but are not limited to the CMP-NEUAc Hydroxylase Gene, the isoGloboside 3 Synthase gene, and the Forssman synthase gene. In addition, genes or cDNA encoding complement related proteins, which are responsible for the suppression of complement mediated lysis can also be expressed in the animals and tissues of the present invention. Such genes include, but are not limited to CD59, DAF, MCP and CD46 (see, for example, WO 99/53042; Chen et al. Xenotransplantation, Volume 6 Issue 3 Page 194-August 1999, which describes pigs that express CD59/DAF transgenes; Costa C et al, Xenotransplantation. 2002 January; 9(1):45-57, which describes transgenic pigs that express human CD59 and H-transferase; Zhao L et al.; Diamond L E et al. Transplantation. 2001 Jan. 15; 71(1):132-42, which describes a human CD46 transgenic pigs.

Additional modifications can include expression of tissue factor pathway inhibitor (TFPI), heparin, antithrombin, hirudin, TFPI, tick anticoagulant peptide, or a snake venom factor, such as described in WO 98/42850 and U.S. Pat. No. 6,423,316, entitled "Anticoagulant fusion protein anchored to cell membrane"; or compounds, such as antibodies, which down-regulate the expression of a cell adhesion molecule by the cells, such as described in WO 00/31126, entitled "Suppression of xenograft rejection by down regulation of a cell adhesion molecules" and compounds in which co-stimulation by signal 2 is prevented, such as by administration to the organ recipient of a soluble form of CTLA-4 from the xenogeneic donor organism, for example as described in WO 99/57266, entitled "Immunosuppression by blocking T cell co-stimulation signal 2 (B7/CD28 interaction)".

In one embodiment, the animals or cells lacking expression of functional immunoglobulin, produced according to the present invention, can be further modified to transgenically express a cytoxic T-lymphocyte associated protein 4-immunoglobin (CTLA4). The animals or cells can be modified to express CTLA4 peptide or a biologically active fragment (e.g., extracellular domain, truncated form of the peptide in which at least the transmembrane domain has been removed) or derivative thereof. The peptide may be, e.g., human or porcine. The CTLA4 peptide can be mutated. Mutated peptides may have higher affinity than wildtype for porcine and/or human B7 molecules. In one specific embodiment, the mutated CTLA4 can be CTLA4 (Glu104, Tyr29). The CTLA4 peptide can be modified such that it is expressed intracellularly. Other modifications of the CTLA4 peptide include addition of a golgi retention signal to the N or C terminus. The golgi retention signal may be, e.g., the sequence KDEL. The CTLA4 peptide can be fused to a peptide dimerization domain or an immunoglobulin (Ig) molecule. The CTLA4 fusion peptides can include a linker sequence that can join the two peptides.

Certain aspects of the invention are described in greater detail in the non-limiting Examples that follow.

EXAMPLES

Example 1

Porcine Heavy Chain Targeting and Generation of Porcine Animals that Lack Expression of Heavy Chain A portion of the porcine Ig heavy-chain locus was isolated from a 3× redundant porcine BAC library. In general, BAC libraries can be generated by fragmenting pig total genomic DNA, which can then be used to derive a BAC library representing at least three times the genome of the whole animal. BACs that contain porcine heavy chain immunoglobulin can then be selected through hybridization of probes selective for porcine heavy chain immunoglobulin as described herein.

Sequence from a clone (Seq ID 1) was used to generate a primer complementary to a portion of the J-region (the primer is represented by Seq ID No. 2). Separately, a primer was designed that was complementary to a portion of Ig heavy-chain mu constant region (the primer is represented by Seq ID No. 3). These primers were used to amplify a fragment of porcine Ig heavy-chain (represented by Seq ID No. 4) that led the functional joining region (J-region) and sufficient flanking region to design and build a targeting vector. To maintain this fragment and subclones of this fragment in a native state, the *E. coli* (Stable 2, Invitrogen cat #1026-019) that harbored these fragments was maintained at 30° C. Regions of Seq. ID No. 4 were subcloned and used to assemble a targeting vector as shown in Seq. ID No. 5. This vector was transfected into porcine fetal fibroblasts that were subsequently subjected to selection with G418. Resulting colonies were screened by PCR to detect potential targeting events (Seq ID No. 6 and Seq ID No. 7, 5' screen primers; and Seq ID No. 8 and Seq ID No. 9, 3' screen primers). See FIG. 1 for a schematic illustrating the targeting. Targeting was confirmed by southern blotting. Piglets were generated by nuclear transfer using the targeted fetal fibroblasts as nuclear donors.

Nuclear Transfer.

The targeted fetal fibroblasts were used as nuclear donor cells. Nuclear transfer was performed by methods that are well known in the art (see, e.g., Dai et al., Nature Biotechnology 20: 251-255, 2002; and Polejaeva et al., Nature 407:86-90, 2000).

Enucleation of in vitro-matured oocytes (BoMed, Madison, Wis.; TransOva Genetics, Sioux City, Iowa) was begun between 40 and 42 hours post-maturation as described in Polejaeva, I. A., et al. (*Nature* 407, 86-90 (2000)). For enucleation, we incubated the oocytes in calcium-free phosphate-buffered NCSU-23 medium containing 5 μg $ml^{-1}$ cytochalasin B (Sigma) and 7.5 μg $ml^{-1}$ Hoechst 33342 (Sigma) at 38° C. for 20 min. A small amount of cytoplasm from directly beneath the first polar body was then aspirated using an 18 μM glass pipette (Humagen, Charlottesville, Va.). We exposed the aspirated karyoplast to ultraviolet light to confirm the presence of a metaphase plate.

For nuclear transfer, a single fibroblast cell was placed under the zona pellucida in contact with each enucleated oocyte. Fusion and activation were induced by application of an AC pulse of 5 V for 5 s followed by two DC pulses of 1.5 kV/cm for 60 μs each using an ECM2001 Electrocell Manipulator (BTX Inc., San Diego, Calif.). Fused embryos were cultured in NCSU-23 medium for 1-4 h at 38.6° C. in a humidified atmosphere of 5% $CO_2$, and then transferred to the oviduct of an estrus-synchronized recipient gilt. Crossbred gilts (large white/Duroc/landrace) (280-400 lbs) were synchronized as recipients by oral administration of 18-20 mg Regu-Mate (Altrenogest, Hoechst, Warren, N.J.) mixed into their feed. Regu-Mate was fed for 14 consecutive days. Human chorionic gonadotropin (hCG, 1,000 units; Intervet America, Millsboro, Del.) was administered intra-muscularly 105 h after the last Regu-Mate treatment. Embryo transfers were done 22-26 h after the hCG injection.

Nuclear transfer produced 18 healthy piglets from four litters. These animals have one functional wild-type Ig heavy-chain locus and one disrupted Ig heavy chain locus.

| | |
|---|---|
| Seq ID 2: primer from Butler subclone to amplify J to C heavy-chain (637Xba5') | ggccagacttcctcggaacagctca |
| Seq ID 3: primer for C to amplify J to C heavychain (JM1L) | ttccaggagaaggtgacggagct |
| Seq ID 6: heavychain 5' primer for 5' screen (HCKOXba5'2) | tctagaagacgctggagagaggccag |
| Seq ID 7: heavychain 3' primer for 5' screen (5'arm5') | taaagcgcatgctccagactgcctt |
| Seq ID 8: heavychain 5' primer for 3' screen (NEO4425) | catcgccttctatcgccttctt |
| Seq ID 9: heavychain 3' primer for 3' screen (650 + CA) | Aagtacttgccgcctctcagga |

Southern Blot Analysis of Cell and Pig Tissue Samples.

Cells or tissue samples were lysed overnight at 60° C. in lysis buffer (10 mM Tris, pH 7.5, 10 mM EDTA, 10 mM NaCl, 0.5% (w/v) Sarcosyl, 1 mg/ml proteinase K) and the DNA precipitated with ethanol. The DNA was then digested with NcoI or XbaI, depending on the probe to be used, and separated on a 1% agarose gel. After electrophoresis, the DNA was transferred to a nylon membrane and probed with digoxigenin-labeled probe (SEQ ID No 41 for NcoI digest, SEQ ID No 40 for XbaI digest). Bands were detected using a chemiluminescent substrate system (Roche Molecular Biochemicals).

Probes for Heavy Chain Southern:

```
HC J Probe (used with Xba I digest)
                                            (Seq ID No 40)
CTCTGCACTCACTACCGCCGGACGCGCACTGCCGTGCTGCCCATGGACCA

CGCTGGGGAGGGGTGAGCGGACAGCACGTTAGGAAGTGTGTGTGTGCGCG

TGGGTGCAAGTCGAGCCAAGGCCAAGATCCAGGGGCTGGGCCCTGTGCCC

AGAGGAGAATGGCAGGTGGAGTGTAGCTGGATTGAAAGGTGGCCTGAAGG

GTGGGGCATCCTGTTTGGAGGCTCACTCTCAGCCCCAGGGTCTCTGGTTC

CTGCCGGGGTGGGGGGCGCAAGGTGCCTACCACACCCTGCTAGCCCCTCG

TCCAGTCCCGGGCCTGCCTCTTCACCACGGAAGAGGATAAGCCAGGCTGC

AGGCTTCATGTGCGCCGTGGAGAACCCAGTTCGGCCCTTGGAGG

HC Mu Probe (used with NcoI digest)
                                            (Seq ID No 41)
GGCTGAAGTCTGAGGCCTGGCAGATGAGCTTGGACGTGCGCTGGGGAGTA

CTGGAGAAGGACTCCCGGGTGGGGACGAAGATGTTCAAGACGGGGGGCTG

CTCCTCTACGACTGCAGGCAGGAACGGGGCGTCACTGTGCCGGCGGCACC

CGGCCCCGCCCCCGCCACAGCCACAGGGGGAGCCCAGCTCACCTGGCCCA

GAGATGGACACGGACTTGGTGCCACTGGGGTGCTGGACCTCGCACACCAG

GAAGGCCTCTGGGTCCTGGGGGATGCTCACAGAGGGTAGGAGCACCCGGG

AGGAGGCCAAGTACTTGCCGCCTCTCAGGACGG
```

Example 2

Porcine Kappa Light Chain Targeting and Generation of Porcine Lacking Expression of Kappa Light Chain A portion of the porcine Ig kappa-chain locus was isolated from a 3× redundant porcine BAC library. In general, BAC libraries can be generated by fragmenting pig total genomic DNA, which can then be used to derive a BAC library representing at least three times the genome of the whole animal. BACs that contain porcine kappa chain immunoglobulin can then be selected through hybridization of probes selective for porcine kappa chain immunoglobulin as described herein.

A fragment of porcine Ig light-chain kappa was amplified using a primer complementary to a portion of the J-region (the primer is represented by Seq ID No. 10) and a primer complementary to a region of kappa C-region (represented by Seq ID No. 11). The resulting amplimer was cloned into a plasmid vector and maintained in Stable2 cells at 30° C. (Seq ID No. 12). See FIG. 2 for a schematic illustration.

Separately, a fragment of porcine Ig light-chain kappa was amplified using a primer complementary to a portion of the C-region (Seq ID No. 13) and a primer complementary to a region of the kappa enhancer region (Seq ID No. 14). The resulting amplimer was fragmented by restriction enzymes and DNA fragments that were produced were cloned, maintained in Stable2 cells at 30 degrees C. and sequenced. As a result of this sequencing, two non-overlapping contigs were assembled (Seq ID No. 15, 5' portion of amplimer; and Seq ID No. 16, 3' portion of amplimer). Sequence from the downstream contig (Seq ID No. 16) was used to design a set of primers (Seq ID No. 17 and Seq ID No. 18) that were used to amplify a contiguous fragment near the enhancer (Seq ID No. 19). A subclone of each Seq ID No. 12 and Seq ID No. 19 were used to build a targeting vector (Seq ID No. 20). This vector was transfected into porcine fetal fibroblasts that were subsequently subjected to selection with G418. Resulting colonies were screened by PCR to detect potential targeting events (Seq ID No. 21 and Seq ID No. 22, 5' screen primers; and Seq ID No. 23 and Seq Id No 43, 3' screen primers, and Seq ID No. 24 and Seq Id No 24, endogenous screen primers). Targeting was confirmed by southern blotting. Southern blot strategy design was facilitated by cloning additional kappa sequence, it corresponds to the template for germline kappa transcript (Seq ID No. 25). Fetal pigs were generated by nuclear transfer.

Nuclear Transfer.

The targeted fetal fibroblasts were used as nuclear donor cells. Nuclear transfer was performed by methods that are well known in the art (see, e.g., Dai et al., Nature Biotechnology 20: 251-255, 2002; and Polejaeva et al., Nature 407:86-90, 2000).

Oocytes were collected 46-54 h after the hCG injection by reverse flush of the oviducts using pre-warmed Dulbecco's phosphate buffered saline (PBS) containing bovine serum albumin (BSA; 4 $g^{-1}$) (as described in Polejaeva, I. A., et al. (*Nature* 407, 86-90 (2000)). Enucleation of in vitro-matured oocytes (BoMed, Madison, Wis.) was begun between 40 and 42 hours post-maturation as described in Polejaeva, I. A., et al. (Nature 407, 86-90 (2000)). Recovered oocytes were washed in PBS containing 4 $gl^{-1}$ BSA at 38° C., and transferred to calcium-free phosphate-buffered NCSU-23 medium at 38° C. for transport to the laboratory. For enucleation, we incubated the oocytes in calcium-free phosphate-buffered NCSU-23 medium containing 5 μg $ml^{-1}$ cytochalasin B (Sigma) and 7.5 μg $ml^{-1}$ Hoechst 33342 (Sigma) at 38° C. for 20 min. A small amount of cytoplasm from directly beneath the first polar body was then aspirated using an 18 μM glass pipette (Humagen, Charlottesville, Va.). We exposed the aspirated karyoplast to ultraviolet light to confirm the presence of a metaphase plate.

For nuclear transfer, a single fibroblast cell was placed under the zona pellucida in contact with each enucleated oocyte. Fusion and activation were induced by application of an AC pulse of 5 V for 5 s followed by two DC pulses of 1.5 kV/cm for 60 μs each using an ECM2001 Electrocell Manipulator (BTX Inc., San Diego, Calif.). Fused embryos were cultured in NCSU-23 medium for 1-4 h at 38.6° C. in a humidified atmosphere of 5% $CO_2$, and then transferred to the oviduct of an estrus-synchronized recipient gilt. Crossbred gilts (large white/Duroc/landrace) (280-400 lbs) were synchronized as recipients by oral administration of 18-20 mg Regu-Mate (Altrenogest, Hoechst, Warren, N.J.) mixed into their feed. Regu-Mate was fed for 14 consecutive days. Human chorionic gonadotropin (hCG, 1,000 units; Intervet America, Millsboro, Del.) was administered intra-muscularly 105 h after the last Regu-Mate treatment. Embryo transfers were done 22-26 h after the hCG injection.

Nuclear transfer using kappa targeted cells produced 33 healthy pigs from 5 litters. These pigs have one functional wild-type allele of porcine Ig light-chain kappa and one disrupted Ig light-chain kappa allele.

```
Seq ID 10: kappa J to C  caaggaqaccaagctggaactc
5' primer (kjc5'1)

Seq ID 11: kappa J to C  tgatcaagcacaccacagagacag
3' primer (kjc3'2)
```

-continued

| | |
|---|---|
| Seq ID 13: 5' primer for Kappa C to E (porKCS1) | gatgccaagccatccgtcttcatc |
| Seq ID 14: 3' primer for Kappa C to E (porKCA1) | tgaccaaagcagtgtgacggttgc |
| Seq ID 17: kappa 5' primer for amplification of enhancer region (K3'arm1S) | ggatcaaacacgcatcctcatggac |
| Seq ID 18: kappa 3' primer for amplification of enhancer region (K3'arm1A) | ggtgattggggcatggttgagg |
| Seq ID 21: kappa screen, 5' primer, 5' (kappa5armS) | cgaacccctgtgtatatagtt |
| Seq ID 22: kappa screen, 3' primer, 5, (kappaNeoA) | gagatgaggaagaggagaaca |
| Seq ID 23: kappa screen, 5' primer, 3' (kappaNeoS) | gcattgtctgagtaggtgtcatt |
| Seq ID 24: kappa screen, 3' primer, 5' (kappa5armProbe3') | cgcttcttgcagggaacacgat |
| Seq ID No 43, Kappa screen, 3' primer (kappa3armA2) | GTCTTTGGTTTTTGCTGAGGGTT |

Southern Blot Analysis of Cell and Pig Tissue Samples.

Cells or tissue samples were lysed overnight at 60° C. in lysis buffer (10 mM Tris, pH 7.5, 10 mM EDTA, 10 mM NaCl, 0.5% (w/v) Sarcosyl, 1 mg/ml proteinase K) and the DNA precipitated with ethanol. The DNA was then digested with SacI and separated on a 1% agarose gel. After electrophoresis, the DNA was transferred to a nylon membrane and probed with digoxigenin-labeled probe (SEQ ID No 42). Bands were detected using a chemiluminescent substrate system (Roche Molecular Biochemicals).

Probe for Kappa Southern:

Kappa5ArmProbe 5'/3'

(SEQ ID No 42)

gaagtgaagccagccagttcctcctgggcaggtggccaaaattacagttg acccctcctggtctggctgaaccttgccccatatggtgacagccatctgg ccagggcccaggtctccctctgaagcctttgggaggagagggagagtggc tggcccgatcacagatgcggaaggggctgactcctcaaccggggtgcaga ctctgcagggtgggtctgggcccaacacacccaaagcacgcccaggaagg aaaggcagcttggtatcactgcccagagctaggagaggcaccgggaaaat gatctgtccaagacccgttcttgcttctaaactccgaggggggtcagatga agtggttttgtttcttggcctgaagcatcgtgttccctgcaagaagcgg

Example 3

Characterization of the Porcine Lambda Gene Locus

To disrupt or disable porcine lambda, a targeting strategy has been devised that allows for the removal or disruption of the region of the lambda locus that includes a concatamer of J to C expression cassettes. BAC clones that contain portions of the porcine genome can be generated. A portion of the porcine Ig lambda-chain locus was isolated from a 3× redundant porcine BAC library. In general, BAC libraries can be generated by fragmenting pig total genomic DNA, which can then be used to derive a BAC library representing at least three times the genome of the whole animal. BACs that contain porcine lambda chain immunoglobulin can then be selected through hybridization of probes selective for porcine lambda chain immunoglobulin as described herein.

BAC clones containing a lambda J-C flanking region (see FIG. 3), can be independently fragmented and subcloned into a plasmid vector. Individual subdlones have been screened by PCR for the presence of a portion of the J to C intron. We have cloned several of these cassettes by amplifying from one C region to the next C region. This amplification was accomplished by using primers that are oriented to allow divergent extension within any one C region (Seq ID 26 and Seq ID 27). To obtain successful amplification, the extended products converge with extended products originated from adjacent C regions (as opposed to the same C region). This strategy produces primarily amplimers that extend from one C to the adjacent C. However, some amplimers are the result of amplification across the adjacent C and into the next C which lies beyond the adjacent C. These multi-gene amplimers contain a portion of a C, both the J and C region of the next J-C unit, the J region of the third J-C unit, and a portion of the C region of the third J-C unit. Seq ID 28 is one such amplimer and represents sequence that must be removed or disrupted.

Other porcine lambda sequences that have been cloned include: Seq ID No. 32, which includes 5' flanking sequence to the first lambda J/C unit of the porcine lambda light chain genomic sequence; Seq ID No. 33, which includes 3' flanking sequence to the J/C cluster region of the porcine lambda light chain genomic sequence, from approximately 200 base pairs downstream of lambda J/C; Seq ID No. 34, which includes 3' flanking sequence to the J/C cluster region of the porcine lambda light chain genomic sequence, approximately 11.8 Kb downstream of the J/C cluster region, near the enhancer; Seq ID No. 35, which includes approximately 12 Kb downstream of lambda, including the enhancer region; Seq ID No. 36, which includes approximately 17.6 Kb downstream of lambda; Seq ID No. 37, which includes approximately 19.1 Kb downstream of lambda; Seq ID No. 38, which includes approximately 21.3 Kb downstream of lambda; and Seq ID No. 39, which includes approximately 27 Kb downstream of lambda.

| | |
|---|---|
| Seq ID 26: 5'primer for lambda C to C amplimer (lamC5') | ccttcctcctgcacctgtcaac |
| Seq ID 27: 3' primer for lambda C to C amplimer (lamC3') | tagacacaccagggtggccttg |

Example 4

Production of Targeting Vectors for the Lambda Gene

Figure 4:
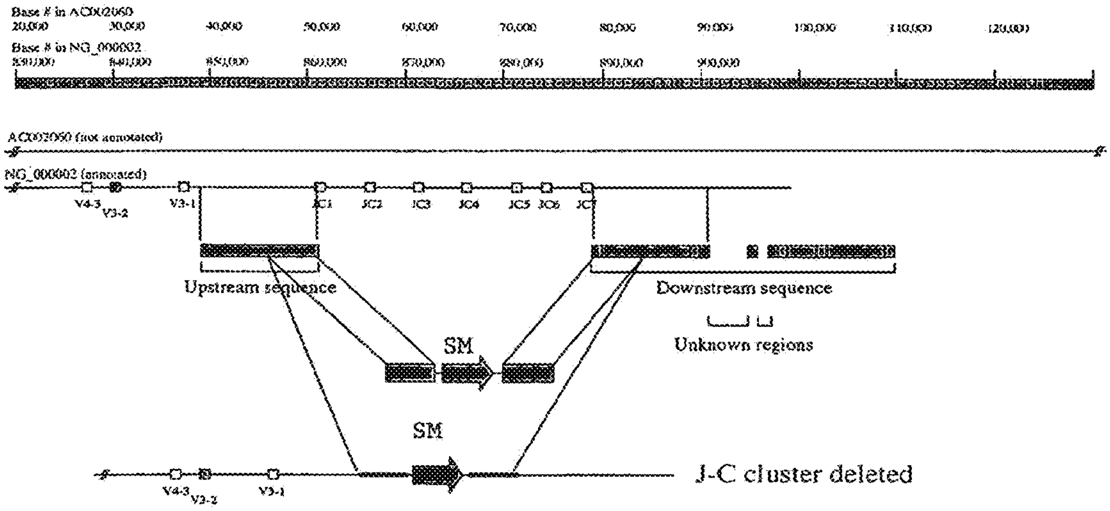
FIG. 4 represents the design of a targeting vector that disrupts the expression of the JC cluster region of the porcine lambda light chain immunoglobulin gene. "SM" stands for a selectable marker gene, which can be used in the targeting vector.
Figure 5:
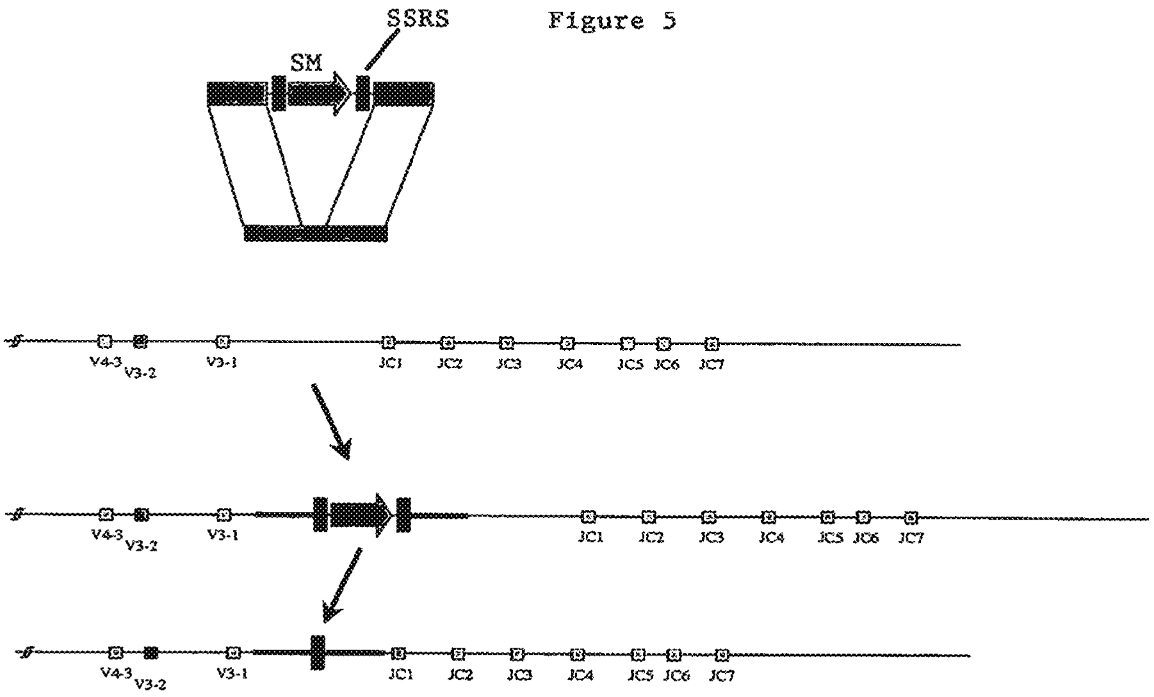
FIG. 5 illustrates a targeting strategy to insert a site specific recombinase target or recognition site into the region 5' of the JC cluster region of the porcine lambda immunoglobulin locus. "SM" stands for a selectable marker gene, which can be used in the targeting vector. "SSRRS" stands for a specific recombinase target or recognition site.

Following a first targeting strategy, shown in FIG. 4, a vector is designed and built with one targeting arm that is homologous to a region upstream of J1 (i.e., the first J/C unit or sequence) and the other arm homologous to a region that is downstream of the last C (i.e., the last J/C unit or sequence) This targeting vector utilizes a selectable marker (SM).

Seq ID No. 48 represents one example of a vector used in the first targeting strategy. Seq ID No. 48 is a lambda light chain knockout vector which includes both 5' and 3' homology arms and Neo resistance factor.

Seq ID No. 48
GCAAAAGGCCAGGAACCGTAAAAAGGCCGCGTTGCTGGCGTTTT
TCCATAGGCTCCGCCCCCCTGACGAGCATCACAAAAATCGACGC
TCAAGTCAGAGGTGGCGAAACCCGACAGGACTATAAAGATACCA
GGCGTTTCCCCCTGGAAGCTCCCTCGTGCGCTCTCCTGTTCCGA
CCCTGCCGCTTACCGGATACCTGTCCGCCTTTCTCCCTTCGGGA
AGCGTGGCGCTTTCTCAATGCTCACGCTGTAGGTATCTCAGTTC
GGTGTAGGTCGTTCGCTCCAAGCTGGGCTGTGTGCACGAACCCC
CCGTTCAGCCCGACCGCTGCGCCTTATCCGGTAACTATCGTCTT
GAGTCCAACCCGGTAAGACACGACTTATCGCCACTGGCAGCAGC
CACTGGTAACAGGATTAGCAGAGCGAGGTATGTAGGCGGTGCTA
CAGAGTTCTTGAAGTGGTGGCCTAACTACGGCTACACTAGAAGG
ACAGTATTTGGTATCTGCGCTCTGCTGAAGCCAGTTACCTTCGG
AAAAAGAGTTGGTAGCTCTTGATCCGGCAAACAAACCACCGCTG
GTAGCGGTGGTTTTTTTGTTTGCAAGCAGCAGATTACGCGCAGA
AAAAAAGGATCTCAAGAAGATCCTTTGATCTTTTCTACGGGGTC
TGACGCTCAGTGGAACGAAAACTCACGTTAAGGGATTTTGGTCA
TGAGATTATCAAAAAGGATCTTCACCTAGATCCTTTTAAATTAA
AAATGAAGTTTTAAATCAATCTAAAGTATATATGAGTAAACTTG
GTCTGACAGTTACCAATGCTTAATCAGTGAGGCACCTATCTCAG
CGATCTGTCTATTTCGTTCATCCATAGTTGCCTGACTCCCCGTC
GTGTAGATAACTACGATACGGGAGGGCTTACCATCTGGCCCCAG
TGCTGCAATGATACCGCGAGACCCACGCTCACCGGCTCCAGATT
TATCAGCAATAAACCAGCCAGCCGGAAGGGCCGAGCGCAGAAGT
GGTCCTGCAACTTTATCCGCCTCCATCCAGTCTATTAATTGTTG
CCGGGAAGCTAGAGTAAGTAGTTCGCCAGTTAATAGTTTGCGCA
ACGTTGTTGCCATTGCTACAGGCATCGTGGTGTCACGCTCGTCG
TTTGGTATGGCTTCATTCAGCTCCGGTTCCCAACGATCAAGGCG
AGTTACATGATCCCCCATGTTGTGCAAAAAAGCGGTTAGCTCCT
TCGGTCCTCCGATCGTTGTCAGAAGTAAGTTGGCCGCAGTGTTA
TCACTCATGGTTATGGCAGCACTGCATAATTCTCTTACTGTCAT
GCCATCCGTAAGATGCTTTTCTGTGACTGGTGAGTACTCAACCA
AGTCATTCTGAGAATAGTGTATGCGGCGACCGAGTTGCTCTTGC
CCGGCGTCAATACGGGATAATACCGCGCCACATAGCAGAACTTT
AAAAGTGCTCATCATTGGAAAACGTTCTTCGGGGCGALAACTCT
CAAGGATCTTACCGCTGTTGAGATCCAGTTCGATGTAACCCACT
CGTGCACCCAACTGATCTTCAGCATCTTTTACTTTCACCAGCGT

-continued

TTCTGGGTGAGCAAAAACAGGAAGGCAAAATGCCGCAAAAAAGG
GAATAAGGGCGACACGGAAATGTTGAATACTCATACTCTTCCTT
TTTCAATATTATTGAAGCATTTATCAGGGTTATTGTCTCATGAG
CGGATACATATTTGAATGTATTTAGAAAAATAAACAAATAGGGG
TTCCGCGCACATTTCCCCGAAAAGTGCCACCTGACGTCAAACAG
CTATGACCATGGCGGCCGCgtcgacAGGGTGTGGCCAAATACAG
CATGGAGTAGCCATCATAAGGAATCTTACACAAGCCTCCAAAAT
TGTGTTTCTGAAATTGGGTTTAAAGTACGTTTGCATTTTAAAAA
GCCTGCCAGAAAATACAGAAAAATGTCTGTGATATGTCTCTGGC
TGATAGGATTTTGCTTAGTTTTAATTTTGGCTTTATAATTTTCT
ATAGTTATGAAAATGTTCACAAGAAGATATATTTCATTTTAGCT
TCTAAAATAATTATAACACAGAAGTAATTTGTGCTTTAAAAAAA
TATTCAACACAGAAGTATATAAAGTALAAATTGAGGAGTTCCCA
TCGTGGCTCAGTGATTAACAAACCCAACTAGTATCCATGAGGAT
ATGGATTTGATCCCTGGCCTTGCTCAGTGGGTTGAGGATCCAGT
GTTGCTGTGAGCTGTGGTGTAGGTTGCAGACACAGCACTCTGGC
GTTGCTGTGACTCTGGCGTAGGCCGGCAGCTACAGCTCCATTTG
GACCCTTAGCCTGGGAACCTCCATATGCCTGAGATACGGCCCTA
AAAAGTCAAAAGCCAAAAAAATAGTAAAAATTGAGTGTTTCTAC
TTACCACCCCTGCCCACATCTTATGCTAAAACCCGTTCTCCAGA
GACAAACATCGTCAGGTGGGTCTATATATTTCCAGCCCTCCTCC
TGTGTGTGTATGTCCGTAAAACACACACACACACACACACACGC
ACACACACACACACGTATCTAATTAGCATTGGTATTAGTTTTTC
AAAAGGGAGGTCATGCTCTACCTTTTAGGCGGCAAATAGATTAT
TTAAACAAATCTGTTGACATTTTCTATATCAACCCATAAGATCT
CCCATGTTCTTGGAAAGGCTTTGTAAGACATCAACATCTGGGTA
AACCAGCATGGTTTTTAGGGGGTTGTGTGGATTTTTTTCATATT
TTTTAGGGCACACCTGCAGCATATGGAGGTTCCCAGGCTAGGGG
TTGAATCAGAGCTGTAGCTGCCGGCCTACACCACAGCCACAGCA
ACGCCAGATCCTTAACCCACTGAGAAAGGCCAGGGATTGAACCT
GCATCCTCATGGATGCTGGTCAGATTTATTTCTGCTGAGCCACA
ACAGGAACTCCCTGAACCAGAATGCTTTTAACCATTCCACTTTG
CATGGACATTTAGATTGTTTCCATTTAAAAATACAAATTACAAG
GAGTTCCCGTCGTGGCTCAGTGGTAACGAATTGGACTAGGAACC
ATGAGGTTTCGGGTTCGATCCCTGGCCTTGCTCGGTGGGTTAAG
GATCCAGCATTGATGTGAGATATGGTGTAGGTCGCAGACGTGGC
TCGGATCCCACGTTGCTGTGGCTCTGGCGTAGGCCGGCAACAAC
AGCTCCGATTCGACCCCTAGCCTGGGAACCTCCATGTGCCACAG
GAGCAGCCCTAGAAAAGGCAAAAAGACAAAAAAATAAAAAATTA
AAATGAAAAAATAAAATAAAAATACAAATTACAAGAGACGGCTA -continued CAAGGAAATCCCCAAGTGTGTGCAAATGCCATATATGTATAAAA
TGTACTAGTGTCTCCTCGCGGGAAAGTTGCCTAAAAGTGGGTTG
GCTGGACAGAGAGGACAGGCTTTGACATTCTCATAGGTAGTAGC
AATGGGCTTCTCAAAATGCTGTTCCAGTTTACACTCACCATAGC
AAATGACAGTGCCTCTTCCTCTCCACCCTTGCCAATAATGTGAC
AGGTGGATCTTTTTCTATTTTGTGTATCTGACAAGCAAAAAATG
AGAACAGGAGTTCCTGTCGTGGTGCAGTGGAGACAAATCTGACT
AGGAACCATGAAATTTCGGGTTCAATCCCTGGCCTCACTCAGTA
GGTAAAGGATCCAGGGTTGCAGTGAGCTGTGGGGTAGGTCGCAG
ACACAGTGCAAATTTGGCCCTGTTGTGGCTGTGGTGTAGGCCGG
CAGCTATAGCTCCAATTGGACCCCTAGCCTGGGAACCTCCTTAT
GCCGTGGGTGAGGCCCTAAAAAAAAGAGTGCAAAAAAAAAAAAT
AAGAACAAAAATGATCATCGTTTAATTCTTTATTTGATCATTGG
TGAAACTTATTTTCCTTTTATATTTTTATTGACTGATTTTATTT
CTCCTATGAATTTACCGGTCATAGTTTTGCCTGGGTGTTTTTAC
TCCGGTTTTAGTTTTGGTTGGTTGTATTTTCTTAGAGAGCTATA
GAAACTCTTCATCTATTTGGAATAGTAATTCCTCATTAAGTATT
TGTGCTGCAAAAAATTTTCCCTGATCTGTTTTATGCTTTTGTTT
GTGGGGTCTTTCACGAGAAAGCCTTTTTAGTTTTTACACCTCAG
CTTGGTTGTTTTTCTTGATTGTGTCTGTAATCTGCGGCCAACAT
AGGAAACACATTTTTACTTTAGTGTTTTTTTCCTATTTTCTTCA
AGTACGTCCATTGTTTTGGTGTCTGATTTTACTTTGCCTGGGGT
TTGTTTTTGTGTGGCAGGAATATAAACTTATGTATTTTCCAAAT
GGAGAGCCAATGGTTGTATATTTGTTGAATTCAAATGCAACTTT
ATCAAACACCAAATCATCGATTTATCACAACTCTTCTCTGGTTT
ATTGATCTAATGATCAATTCCTGTTCCACGCTGTTTTAATTATT
TTAGCTTTGTGGATTTTGGTGCCTGGTAGAGAACAAAGCCTCCA
TTATTTTCATTCAAAATAGTCCCGTCTATTATCTGCCATTGTTG
TAGTATTAGACTTTAAAATCAATTTACTGATTTTCAAAAGTTAT
TCCTTTGGTGATGTGGAATACTTTATACTTCATAAGGTACATGG
ATTCATTTGTGGGGAATTGATGTCTTTGCTATTGTGGCCATTTG
TCAAGTTGTGTAATATTTTACCCATGCCAACTTTGCATATTGTA
TGTGAGTTTATTCCCAGGGTTTTTAATAGGATGTTTATTGAAGT
TGTCAGTGTTTCCACAATTTCATCGCCTCAGTGCTTACTGTTTG
CATAAAAGGAAACCTACTCACTTTTGCCTATTGCTCTTGTATTC
AATCATTTTAGTTAACTCTTGTGTTAATTTTGAGAGTTTTTCAG
CTGACTGTCTGGGGTTTTCTTTAATAGACTAGCCCTTTGTCTGT
AAAGAATAATTTTATCGAATTTTTCTTAACACTCACACTCTCCC
CACCCCCACCCCCGCTCATCTCCTTTCATTGGGTCAAATCTGTA
GAATACAATAAAAGTAAGAGTGGGAACCTTAGCCTTTAAGTCGA
TTTTGCCTTTAAATGTGAATGTTGCTATGTTTCGGGACATTCTC -continued TTTATCAAGTTGCGGATGTTTCCTTAGATAATTAACTTAATAAA
AGACTGGATGTTTGCTTTCTTCAAATCAGAATTGTGTTGAATTT
ATATTGCTATTCTGTTTAATTTTGTTTCAAAAAATTTACATGCA
CACCTTAAAGATAACCATGACCAAATAGTCCTCCTGCTGAGAGA
AAATGTTGGCCCCAATGCCACAGGTTACCTCCCGACTCAGATAA
ACTACAATGGGAGATAAAATCAGATTTGGCAAAGCCTGTGGATT
CTTGCCATAACTCTCAGAGCATGACTTGGGTGTTTTTTCCTTTT
CTAAGTATTTTAATGGTATTTTTGTGTTACAATAGGAAATCTAG
GACACAGAGAGTGATTCAATGAGGGGAACGCATTCTGGGATGAC
TCTAGGCCTCTGGTTTGGGGAGAGCTCTATTGAAGTAAAGACAA
TGAGAGGAAGCAAGTTTGCAGGGAACTGTGAGGAATTTAGATGG
GGAATGTTGGGTTTGAGGTTTCTATAGGGCACGCAAGCAGAGAT
GCACTCAGGAGGAAGAAGGAGCATAAATCTAGAGGCAAAAAGAG
AGGTCAGGACTGGAAATAGAGATGCGAGACACCAGGGTGGCAGT
CAGAGAGCACAGTGTGGGTCAGAAGACAGTGGAAGAACACAAGG
GACAGAGAGGGATCTCCAACTTCACTGGGATGAGGGCCTTGTTG
GCCTTGACCTGAGAGATTTCCAGGAGTTGAGGGTGGGAAGGAGc
cgcggTCTAGGAAGCTTTCTAGGGTACCTCTAGGGATCCGAACA
ATGGAAGTCCGAGCTCATCGCTAATAACTTCGTATAGCATACAT
TATACGAAGTTATATTCGATGCGGCCGCAAGGGGTTCGCGTCAG
CGGGTGTTGGCGGGTGTCGGGGCTGGCTTAACTATGCGGCATCA
GAGCAGagatccCGGCGCGCCCTACCGGGTAGGGGAGGCGCTTT
TCCCAAGGCAGTCTGGAGCATGCGCTTTAGCAGCCCCGCTGGGC
ACTTGGCGCTACACAAGTGGCCTCTGGCCTCGCACACATTCCAC
ATCCACCGGTAGGCGCCAACCGGCTCCGTTCTTTGGTGGCCCCT
TCGCGCCACCTTCTACTCCTCCCCTAGTCAGGAAGTTCCCCCCC
GCCCCGCAGCTCGCGTCGTGCAGGACGTGACAAATGGAAGTAGC
ACGTCTCACTAGTCTCGTGCAGATGGACAGCACCGCTGAGCAAT
GGAAGCGGGTAGGCCTTTGGGGCAGCGGCCAATAGCAGCTTTGG
CTCCTTCGCTTTCTGGGCTCAGAGGCTGGGAAGGGGTGGGTCCG
GGGGCGGGCTCAGGGGCGGGCTCAGGGGCGGGGCGGGCGCCCGA
AGGTCCTCCGGAAGCCCGGCATTCTGCACGCTTCAAAAGCGCAC
GTCTGCCGCGCTGTTCTCCTCTTCCTCATCTCCGGGCCTTTCGA
CCTGCAGCCAATATGGGATCGGCCATTGAACAAGATGGATTGCA
CGCAGGTTCTCCGGCCGCTTGGGTGGAGAGGCTATTCGGCTATG
ACTGGGCACAACAGACAATCGGCTGCTCTGATGCCGCCGTGTTC
CGGCTGTCAGCGCAGGGGCGCCCGGTTCTTTTTGTCAAGACCGA
CCTGTCCGGTGCCCTGAATGAACTGCAGGACGAGGCAGCGCGGC
TATCGTGGCTGGCCACGACGGGCGTTCCTTGCGCAGCTGTGCTC
GACGTTGTCACTGAAGCGGGAAGGGACTGGCTGCTATTGGGCGA -continued AGTGCCGGGGCAGGATCTCCTGTCATCTCACCTTGCTCCTGCCG
AGAAAGTATCCATCATGGCTGATGCAATGCGGCGGCTGCATACG
CTTGATCCGGCTACCTGCCCATTCGACCACCAAGCGAAACATCG
CATCGAGCGAGCACGTACTCGGATGGAAGCCGGTCTTGTCAATC
AGGATGATCTGGACGAAGAGCATCAGGGGCTCGCGCCAGCCGAA
CTGTTCGCCAGGCTCAAGGCGCGCATGCCCGACGGCGAGGATCT
CGTCGTGACCCATGGCGATGCCTGCTTGCCGAATATCATGGTGG
AAAATGGCCGCTTTTCTGGATTCATCGACTGTGGCCGGCTGGGT
GTGGCGGATCGCTATCAGGACATAGCGTTGGCTACCCGTGATAT
TGCTGAAGAGCTTGGCGGCGAATGGGCTGACCGCTTCCTCGTGC
TTTACGGTATCGCCGCTCCCGATTCGCAGCGCATCGCCTTCTAT
CGCCTTCTTGACGAGTTCTTCTGAGGGGATCAATTCtctagtGA
ACAATGGAAGTCCGAGCTCATCGCTAATAACTTCGTATAGCATA
CATTATACGAAGTTATATTCGATGCGGCCGCAAGGGGTTCGCGT
CAGCGGGTGTTGGCGGGTGTCGGGGCTGGCTTAACTATGCGGCA
TCAGAGCAGtctagaGCTCGCTGATCAGCCTCGACTGTGCCTTC
TAGTTGCCAGCCATCTGTTGTTTGCCCCTCCCCCGTGCCTTCCT
TGACCCTGGAAGGTGCCACTCCCACTGTCCTTTCCTAATAAAAT
GAGGAAATTGCATCGCATTGTCTGAGTAGGTGTCATTCTATTCT
GGGGGGTGGGGTGGGGCAGGACAGCAAGGGGGAGGATTGGGAAG
ACAATAGCAGGCATGCTGGGGATGCGGTGGGCTCTATGGCTTCT
GAGGCGGAAAGAACCAGCTGGGGGCGCGCCCctcgagGGGAAGG
TATCTCCCAGGAAACTGGCCAGGACACATTGGTCCTCCGCCCTC
CCCTTCCTCCCACTCCTCCTCCAGACAGGACTGTGCCCACCCCC
TGCCACCTTTCTGGCCAGAACTGTCCATGGCAGGTGACCTTCAC
ATGAGCCCTTCCTCCCTGCCTGCCCTAGTGGGACCCTCCATACC
TCCCCCTGGACCCCGTTGTCCTTTCTTTCCAGTGTGGCCCTGAG
CATAACTGATGCCATCATGGGCTGCTGACCCACCCGGGACTGTG
TTGTGCAGTGAGTCACTTCTCTGTCATCAGGGCTTTGTAATTGA
TAGATAGTGTTTCATCATCATTAGGACCGGGTGGCCTCTATGCT
CTGTTAGTCTCCAAACACTGATGAAAACCTTCGTTGGCATAGTC
CCAGCTTCCTGTTGCCCATCCATAAATCTTGACTTAGGGATGCA
CATCCTGTCTCCAAGCAACCACCCCTCCCCTAGGCTAACTATAA
AACTGTCCCAATGGCCCTTGTGTGGTGCAGAGTTCATGCTTCCA
GATCATTTCTCTGCTAGATCCATATCTCACCTTGTAAGTCATCC
TATAATAAACTGATCCATTGATTATTTGCTTCTGTTTTTTCCAT
CTCAAAACAGCTTCTCAGTTCAGTTCGAATTTTTTATTCCCTCC
ATCCACCCATACTTTCCTCAGCCTGGGGAACCCTTGCCCCCAGT
CCCATGCCCTTCCTCCCTCTCTGCCCAGCTCAGCACCTGCCCAC
CCTCACCCTTCCTGTCACTCCCTAGGACTGGACCATCCACTGGG
GCCAGGACACTCCAGCAGCCTTGGCTTCATGGGCTCTGAAATCC -continued ATGGCCCATCTCTATTCCTCACTGGATGGCAGGTTCAGAGATGT
GAAAGGTCTAGGAGGAAGCCAGGAAGGAAACTGTTGCATGAAAG
GCCGGCCTGATGGTTCAGTACTTAAATAATATGAGCTCTGAGCT
CCCCAGGAACCAAAGCATGGAGGGAGTATGTGCCTCAGAATCTC
TCTGAGATTCAGCAAAGCCTTTGCTAGAGGGAAAATAGTGGCTC
AACCTTGAGGGCCAGCATCTTGCACCACAGTTAAAAGTGGGTAT
TTGTTTTACCTGAGGCCTCAGCATTATGGGAACCGGGCTCTGAC
ACAAACACAGGTGCAGCCCGGCAGCCTCAGAACACAGCAACGAC
CACAAGCTGGGACAGCTGCCCCTGAACGGGGAGTCCACCATGCT
TCTGTCTCGGGTACCACCAGGTCACCATCCCTGGGGGAGGTAGT
TCCATAGCAGTAGTCCCCTGATTTCGCCCCTCGGGCGTGTAGCC
AGGCAAGCTCCTGCCTCTGGACCCAGGGTGGACCCTTGCTCCCC
ACTACCCTGCACATGCCAGACAGTCAAGACCACTCCCACCTCTG
TCTGAGGCCCCCTTGGGTGTCCCAGGGCCCCCGAGCTGTCCTCT
ACTCATGGTTCTTCCACCTGGGTACAAAAGAGGCGAGGGACACT
TTTCTCAGGTTTGCGGCTCAGAAAGGTACCTTCCTAGGGTTTGT
CCACTGGGAGTCACCTCCCTTGCATCTCAATGTCAGTGGGGAAA
ACTGGGTCCCATGGGGGGATTAGTGCCACTGTGAGGCCCCTGAA
GTCTGGGGCCTCTAGACACTATGATGATGAGGGATGTGGTGAAA
AACCCCACCCCAGCCCTTCTTGCCGGGACCCTGGGCTGTGGCTC
CCCCATTGCACTTGGGGTCAGAGGGGTGGATGGTGGCTATGGTC
AGGCATGTTTCCCATGAGCTGGGGGCACCCTGGGTGACTTTCTC
CTGTGAATCCTGAATTAGCAGCTATAACAAATTGCCCAAACTCT
TAGGCTTAAAACAACACACATTTATTCCTCTGGGTCCCAGGGTC
AGAAGTCCAAAATGAGTCCTATAGGCTAAATTTGAGGTGTCTCT
GGGTTGAGCTCCTCCTGGAAGCCTTTTCCAGCCTCTAGAGTCCC
AAGTCCTTGGCTCTGGGCCCCTCCCTCAAGCTTCAAAGCCACAG
AAGCTTCTAATCTCTCTCCCTTCCCCTCTGACCTCTGCTCCCAT
CCTCATACCCTGTCCCCTCACTCTGACCCTCCTGCCTCCCTCTT
TCCCTTATAAAGACCCTGCATGGGGCCACGGAGATAATCCAGGG
TAATCGCCCCTCTTCCAGCCCTTAACTCCATCCCATCTGCAAAA
TCCCTGTCACCCCATAATGGACCTACagatctCCTAGAGTTAAC
ACTGGCCGTCGTTTTACCGGTCCGTAGTCAGGTTTAGTTCGTCC
GGCGGCGCCAGAAATCCGCGCGGTGGTTTTTGGGGGTCGGGGGT
GTTTGGCAGCCACAGACGCCCGGTGTTCGTGTCGCGCCAGTACA
TGCGGTCCATGCCCAGGCCATCCAAAAACCATGGGTCTGTCTGC
TCAGTCCAGTCGTGGACTGACCCCACGCAACGCCCAAAATAATA
ACCCCCACGAACCATAAACCATTCCCCATGGGGGACCCCGTCCC
TAACCCACGGGGCCCGTGGCTATGGCAGGCCTGCCGCCCGACGT
TGGCTGCGAGCCCTGGGCCTTCACCCGAACTTGGGGGGTGGGGT -continued GGGGAAAAGGAAGAAACGCGGGCGTATTGGCCCCAATGGGGTCT
CGGTGGGGTATCGACAGAGTGCCAGCCCTGGGACCGAACCCCGC
GTTTATGAACAAACGACCCAACACCCGTGCGTTTTATTCTGTCT
TTTTATTGCCGACATAGCGCGGGTTCCTTCCGGTATTGTCTCCT
TCCGTGTTTCAGTTAGCCTCCCCCATCTCCCGTGCAAACGTGCG
CGCCAGGTCGCAGATCGTCGGTATGGAGCCTGGGGTGGTGACGT
GGGTCTGGATCATCCCGGAGGTAAGTTGCAGCAGGGCGTCCCGG
CAGCCGGCGGGCGATTGGTCGTAATCCAGGATAAAGACGTGCAT
GGGACGGAGGCGTTTGGCCAAGACGTCCAAGGCCCAGGCAAACA
CGTTGTACAGGTCGCCGTTGGGGGCCAGCAACTCGGGGGCCCGA
AACAGGGTAAATAACGTGTCCCCGATATGGGGTCGTGGGCCCGC
GTTGCTCTGGGGCTCGGCACCCTGGGGCGGCACGGCCGTCCCCG
AAAGCTGTCCCCAATCCTCCCGCCACGACCCGCCGCCCTGCAGA
TACCGCACCGTATTGGCAAGCAGCCCGTAAACGCGGCGAATCGC
GGTCAGCATAGCCAGGTCAAGCCGCTCGCCGGGGCGCTGGCGTT
TGGCCAGGCGGTCGATGTGTCTGTCCTCCGGAAGGGCCCCCAAC
ACGATGTTTGTGCCGGGCAAGGTCGGCGGGATGAGGGCCACGAA
CGCCAGCACGGCCTGGGGGGTCATGCTGCCCATAAGGTATCGCG
CGGCCGGGTAGCACAGGAGGGCGGCGATGGGATGGCGGTCGAAG
ATGAGGGTGAGGGCCGGGGGCGGGGCATGTGAGCTCCCAGCCTC
CCCCCCGATATGAGGAGCCAGAACGGCGTCGGTCACGGTATAAG
GCATGCCCATTGTTATCTGGGCGCTTGTCATTACCACCGCCGCG
TCCCCGGCCGATATCTCACCCTGGTCAAGGCGGTGTTGTGTGGT
GTAGATGTTCGCGATTGTCTCGGAAGCCCCCAGCACCCGCCAGT
AAGTCATCGGCTCGGGTACGTAGACGATATCGTCGCGCGAACCC
AGGGCCACCAGCAGTTGCGTGGTGGTGGTTTTCCCCATCCCGTG
GGGACCGTCTATATAAACCCGCAGTAGCGTGGGcATTTTCTGCT
CCGGGCGGACTTCCGTGGCTTCTTGCTGCCGGCGAGGGCGCAAC
GCCGTACGTCGGTTGCTATGGCCGCGAGAACGCGCAGCCTGGTC
GAACGCAGACGCGTGCTGATGGCCGGGGTACGAAGCCATACGCG
CTTCTACAAGGCGCTGGCCGAAGAGGTGCGGGAGTTTCACGCCA
CCAAGATGTGCGGCACGCTGTTGACGCTGTTAAGCGGGTCGCTG
CAGGGTCGCTCGGTGTTCGAGGCCACACGCGTCACCTTAATATG
CGAAGTGGACCTGGGACCGCGCCGCCCCGACTGCATCTGCGTGT
TCCAATTCGCCAATGACAAGACGCTGGGCGGGGTTTGCTCGACA
TTGGGTGGAAACATTCCAGGCCTGGGTGGAGAGGCTTTTTGCTT
CCTCTTGCAAAACCACACTGCTCGACATTGGGTGGAAACATTCC
AGGCCTGGGTGGAGAGGCTTTTTGCTTCCTCTTGAAAACCACAC
TGCTCGACTCTACGGTCCG Seq ID No. 49 is a Lambda Light Chain 5' Arm Sequence Seq ID No. 49
AGGGTGTGGCCAAATACAGCATGGAGTAGCCATCATAAGGAATC
TTACACAAGCCTCCAAAATTGTGTTTCTGAAATTGGGTTTAAAG
TACGTTTGCATTTTAAAAAGCCTGCCAGAAAATACAGAAAAATG
TCTGTGATATGTCTCTGGCTGATAGGATTTTGCTTAGTTTTAAT
TTTGGCTTTATAATTTTCTATAGTTATGAAAATGTTCACAAGAA
GATATATTTCATTTTAGCTTCTAAAATAATTATAACACAGAAGT
AATTTGTGCTTTAAAAAAATATTCAACACAGAAGTATATAAAGT
AAAAATTGAGGAGTTCCCATCGTGGCTCAGTGATTAACAAACCC
AACTAGTATCCATGAGGATATGGATTTGATCCCTGGCCTTGCTC
AGTGGGTTGAGGATCCAGTGTTGCTGTGAGCTGTGGTGTAGGTT
GCAGACACAGCACTCTGGCGTTGCTGTGACTCTGGCGTAGGCCG
GCAGCTACAGCTCCATTTGGACCCTTAGCCTGGGAACCTCCATA
TGCCTGAGATACGGCCCTAAAAAGTCAAAAGCCAAAAAAATAGT
AAAAATTGAGTGTTTCTACTTACCACCCCTGCCCACATCTTATG
CTAAAACCCGTTCTCCAGAGACAAACATCGTCAGGTGGGTCTAT
ATATTTCCAGCCCTCCTCCTGTGTGTGTATGTCCGTAAAACACA
CACACACACACACACACGCACACACACACACACGTATCTAATTA
GCATTGGTATTAGTTTTTCAAAAGGGAGGTCATGCTCTACCTTT
TAGGCGGCAAATAGATTATTTAAACAAATCTGTTGACATTTTCT
ATATCAACCCATAAGATCTCCCATGTTCTTGGAAAGGCTTTGTA
AGACATCAACATCTGGGTAAACCAGCATGGTTTTTAGGGGGTTG
TGTGGATTTTTTTCATATTTTTTAGGGCACACCTGCAGCATATG
GAGGTTCCCAGGCTAGGGGTTGAATCAGAGCTGTAGCTGCCGGC
CTACACCACAGCCACAGCAACGCCAGATCCTTAACCCACTGAGA
AAGGCCAGGGATTGAACCTGCATCCTCATGGATGCTGGTCAGAT
TTATTTCTGCTGAGCCACAACAGGAACTCCCTGAACCAGAATGC
TTTTAACCATTCCACTTTGCATGGACATTTAGATTGTTTCCATT
TAAAAATACAAATTACAAGGAGTTCCCGTCGTGGCTCAGTGGTA
ACGAATTGGACTAGGAACCATGAGGTTTCGGGTTCGATCCCTGG
CCTTGCTCGGTGGGTTAAGGATCCAGCATTGATGTGAGATATGG
TGTAGGTCGCAGACGTGGCTCGGATCCCACGTTGCTGTGGCTCT
GGCGTAGGCCGGCAACAACAGCTCCGATTCGACCCCTAGCCTGG
GAACCTCCATGTGCCACAGGAGCAGCCCTAGAAAAGGCAAAAAG
ACAAAAAAATAAAAAATTAAAATGAAAAAATAAAATAAAAATAC
AAATTACAAGAGACGGCTACAAGGAAATCCCCAAGTGTGTGCAA
ATGCCATATATGTATAAAATGTACTAGTGTCTCCTCGCGGGAAA
GTTGCCTAAAAGTGGGTTGGCTGGACAGAGAGGACAGGCTTTGA
CATTCTCATAGGTAGTAGCAATGGGCTTCTCAAAATGCTGTTCC
AGTTTACACTCACCATAGCAAATGACAGTGCCTCTTCCTCTCCA -continued CCCTTGCCAATAATGTGACAGGTGGATCTTTTTCTATTTTGTGT
ATCTGACAAGCAAAAAATGAGAACAGGAGTTCCTGTCGTGGTGC
AGTGGAGACAAATCTGACTAGGAACCATGAAATTTCGGGTTCAA
TCCCTGGCCTCACTCAGTAGGTAAAGGATCCAGGGTTGCAGTGA
GCTGTGGGGTAGGTCGCAGACACAGTGCAAATTTGGCCCTGTTG
TGGCTGTGGTGTAGGCCGGCAGCTATAGCTCCAATTGGACCCCT
AGCCTGGGAACCTCCTTATGCCGTGGGTGAGGCCCTAAAAAAAA
GAGTGCAAAAAAAAAAAATAAGAACAAAAATGATCATCGTTTAA
TTCTTTATTTGATCATTGGTGAAACTTATTTTCCTTTTATATTT
TTATTGACTGATTTTATTTCTCCTATGAATTTACCGGTCATAGT
TTTGCCTGGGTGTTTTTACTCCGGTTTTAGTTTTGGTTGGTTGT
ATTTTCTTAGAGAGCTATAGAAACTCTTCATCTATTTGGAATAG
TAATTCCTCATTAAGTATTTGTGCTGCAAAAAATTTTCCCTGAT
CTGTTTTATGCTTTTGTTTGTGGGGTCTTTCACGAGAAAGCCTT
TTTAGTTTTTACACCTCAGCTTGGTTGTTTTTCTTGATTGTGTC
TGTAATCTGCGGCCAACATAGGAAACACATTTTTACTTTAGTGT
TTTTTTCCTATTTTCTTCAAGTACGTCCATTGTTTTGGTGTCTG
ATTTTACTTTGCCTGGGGTTTGTTTTTGTGTGGCAGGAATATAA
ACTTATGTATTTTCCAAATGGAGAGCCAATGGTTGTATATTTGT
TGAATTCAAATGCAACTTTATCAAACACCAAATCATCGATTTAT
CACAACTCTTCTCTGGTTTATTGATCTAATGATCAATTCCTGTT
CCACGCTGTTTTAATTATTTTAGCTTTGTGGATTTTGGTGCCTG
GTAGAGAACAAAGCCTCCATTATTTTCATTCAAAATAGTCCCGT
CTATTATCTGCCATTGTTGTAGTATTAGACTTTAAAATCAATTT
ACTGATTTTCAAAAGTTATTCCTTTGGTGATGTGGAATACTTTA
TACTTCATAAGGTACATGGATTCATTTGTGGGGAATTGATGTCT
TTGCTATTGTGGCCATTTGTCAAGTTGTGTAATATTTTACCCAT
GCCAACTTTGCATATTGTATGTGAGTTTATTCCCAGGGTTTTTA
ATAGGATGTTTATTGAAGTTGTCAGTGTTTCCACAATTTCATCG
CCTCAGTGCTTACTGTTTGCATAAAAGGAAACCTACTCACTTTT
GCCTATTGCTCTTGTATTCAATCATTTTAGTTAACTCTTGTGTT
AATTTTGAGAGTTTTTCAGCTGACTGTCTGGGGTTTTCTTTAAT
AGACTAGCCCTTTGTCTGTAAAGAATAATTTTATCGAATTTTTC
TTAACACTCACACTCTCCCCACCCCCACCCCCGCTGATCTCCTT
TCATTGGGTCAAATCTGTAGAATACAATAAAAGTAAGAGTGGGA
ACCTTAGCCTTTAAGTCGATTTTGCCTTTAAATGTGAATGTTGC
TATGTTTCGGGACATTCTCTTTATCAAGTTGCGGATGTTTCCTT
AGATAATTAACTTAATAAAAGACTGGATGTTTGCTTTCTTCAAA
TCAGAATTGTGTTGAATTTATATTGCTATTCTGTTTAATTTTGT
TTCAAAAAATTTACATGCACACCTTAAAGATAACCATGACCAAA
TAGTCCTCCTGCTGAGAGAAAATGTTGGCCCCAATGCCACAGGT -continued TACCTCCCGACTCAGATAAACTACAATGGGAGATAAAATCAGAT
TTGGCAAAGCCTGTGGATTCTTGCCATAACTCTCAGAGCATGAC
TTGGGTGTTTTTTCCTTTTCTAAGTATTTTAATGGTATTTTTGT
GTTACAATAGGAAATCTAGGACACAGAGAGTGATTCAATGAGGG
GAACGCATTCTGGGATGACTCTAGGCCTCTGGTTTGGGGAGAGC
TCTATTGAAGTAAAGACAATGAGAGGAAGCAAGTTTGCAGGGAA
CTGTGAGGAATTTAGATGGGGAATGTTGGGTTTGAGGTTTCTAT
AGGGCACGCAAGCAGAGATGCACTCAGGAGGAAGAAGGAGCATA
AATCTAGAGGCAAAAAGAGAGGTCAGGACTGGAAATAGAGATGC
GAGACACCAGGGTGGCAGTCAGAGAGCACAGTGTGGGTCAGAAG
ACAGTGGAAGAACACAAGGGACAGAGAGGGATCTCCAACTTCAC
TGGGATGAGGGCCTTGTTGGCCTTGACCTGAGAGATTTCCAGGA
GTTGAGGGTGGGAAGGAG Seq. ID No. 50 is a Lambda 3' Arm Sequence Seq. ID No. 50
GGGAAGGTATCTCCCAGGAAACTGGCCAGGACACATTGGTCC
TCCGCCCTCCCCTTCCTCCCACTCCTCCTCCAGACAGGACTG
TGCCCACCCCCTGCCACCTTTCTGGCCAGAACTGTCCATGGC
AGGTGACCTTCACATGAGCCCTTCCTCCCTGCCTGCCCTAGT
GGGACCCTCCATACCTCCCCCTGGACCCCGTTGTCCTTTCTT
TCCAGTGTGGCCCTGAGCATAACTGATGCCATCATGGGCTGC
TGACCCACCCGGGACTGTGTTGTGCAGTGAGTCACTTCTCTG
TCATCAGGGCTTTGTAATTGATAGATAGTGTTTCATCATCAT
TAGGACCGGGTGGCCTCTATGCTCTGTTAGTCTCCAAACACT
GATGAAAACCTTCGTTGGCATAGTCCCAGCTTCCTGTTGCCC
ATCCATAAATCTTGACTTAGGGATGCACATCCTGTCTCCAAG
CAACCACCCCTCCCCTAGGCTAACTATAAAACTGTCCCAATG
GCCCTTGTGTGGTGCAGAGTTCATGCTTCCAGATCATTTCTC
TGCTAGATCCATATCTCACCTTGTAAGTCATCCTATAATAAA
CTGATCCATTGATTATTTGCTTCTGTTTTTTCCATCTCAAAA
CAGCTTCTCAGTTCAGTTCGAATTTTTTATTCCCTCCATCCA
CCCATACTTTCCTCAGCCTGGGGAACCCTTGCCCCCAGTCCC
ATGCCCTTCCTCCCTCTCTGCCCAGCTCAGCACCTGCCCACC
CTCACCCTTCCTGTCACTCCCTAGGACTGGACCATCCACTGG
GGCCAGGACACTCCAGCAGCCTTGGCTTCATGGGCTCTGAAA
TCCATGGCCCATCTCTATTCCTCACTGGATGGCAGGTTCAGA
GATGTGAAAGGTCTAGGAGGAAGCCAGGAAGGAAACTGTTGC
ATGAAAGGCCGGCCTGATGGTTCAGTACTTAAATAATATGAG
CTCTGAGCTCCCCAGGAACCAAAGCATGGAGGGAGTATGTGC
CTCAGAATCTCTCTGAGATTCAGCAAAGCCTTTGCTAGAGGG -continued

```
AAAATAGTGGCTCAACCTTGAGGGCCAGCATCTTGCACCACA
GTTAAAAGTGGGTATTTGTTTTACCTGAGGCCTCAGCATTAT
GGGAACCGGGCTCTGACACAAACACAGGTGCAGCCCGGCAGC
CTCAGAACACAGCAACGACCACAAGCTGGGACAGCTGCCCCT
GAACGGGGAGTCCACCATGCTTCTGTCTCGGGTACCACCAGG
TCACCATCCCTGGGGGAGGTAGTTCCATAGCAGTAGTCCCCT
GATTTCGCCCCTCGGGCGTGTAGCCAGGCAAGCTCCTGCCTC
TGGACCCAGGGTGGACCCTTGCTCCCCACTACCCTGCACATG
CCAGACAGTCAAGACCACTCCCACCTCTGTCTGAGGCCCCCT
TGGGTGTCCCAGGGCCCCCGAGCTGTCCTCTACTCATGGTTC
TTCCACCTGGGTACAAAAGAGGCGAGGGACACTTTTCTCAGG
TTTGCGGCTCAGAAAGGTACCTTCCTAGGGTTTGTCCACTGG
GAGTCACCTCCCTTGCATCTCAATGTCAGTGGGGAAAACTGG
GTCCCATGGGGGGATTAGTGCCACTGTGAGGCCCCTGAAGTC
TGGGGCCTCTAGACACTATGATGATGAGGGATGTGGTGAAAA
ACCCCACCCCAGCCCTTCTTGCCGGGACCCTGGGCTGTGGCT
CCCCCATTGCACTTGGGGTCAGAGGGGTGGATGGTGGCTATG
GTCAGGCATGTTTCCCATGAGCTGGGGGCACCCTGGGTGACT
TTCTCCTGTGAATCCTGAATTAGCAGCTATAACAAATTGCCC
AAACTCTTAGGCTTAAAACAACACACATTTATTCCTCTGGGT
CCCAGGGTCAGAAGTCCAAAATGAGTCCTATAGGCTAAATTT
GAGGTGTCTCTGGGTTGAGCTCCTCCTGGAAGCCTTTTCCAG
CCTCTAGAGTCCCAAGTCCTTGGCTCTGGGCCCCTCCCTCAA
GCTTCAAAGCCACAGAAGCTTCTAATCTCTCTCCCTTCCCCT
CTGACCTCTGCTCCCATCCTCATACCCTGTCCCCTCACTCTG
ACCCTCCTGCCTCCCTCTTTCCCTTATAAAGACCCTGCATGG
GGCCACGGAGATAATCCAGGGTAATCGCCCCTCTTCCAGCCC
TTAACTCCATCCCATCTGCAAAATCCCTGTCACCCCATAATG
GACCTAC
```

In a second strategy, the targeting strategy utilizes a vector pair. One targeting vector is designed to target upstream of J1. See FIG. 5. This targeting vector utilizes a selectable marker that can be selected for or against. Any combination of positive and negative selectable markers described herein or known in the art can be used. A fusion gene composed of the coding region of Herpes simplex thymidine kinase (TK) and the Tn5 aminoglycoside phosphotransferase (Neo resistance) genes is used. This fusion gene is flanked by recognition sites for any site specific recombinase (SSRRS) described herein or known in the art, such as lox sites. Upon isolation of targeted cells through the use of G418 selection, Cre is supplied in trans to delete the marker gene (See FIG. 5). Cells that have deleted the marker gene are selected by addition of any drug known in the art that can be metabolized by TK into a toxic product, such as ganciclovir. The resulting genotype is then targeted with a second vector. The second targeting vector (FIG. 6) is designed to target downstream of last C and uses a positive/negative selection system that is flanked on only one side by a specific recombination site (lox). The recombination site is placed distally in relation to the first targeting event. Upon isolation of the targeted genotype, Cre is again supplied in trans to mediate deletion from recombination site provided in the first targeting event to the recombination site delivered in the second targeting event. The entire J to C cluster region will be removed. The appropriate genotype is again selected by administration of ganciclovir.

Two vector pairs, i.e., lambda targeting constructs, were designed and built to target the first and last J/C regions and to include site-specific recombination sites. The first vector pair was composed of Seq ID No. 44 (step 1 vector) and Seq ID No. 45 (step 2 vector). The second vector pair was composed of Seq ID No. 46 (step 2 vector) and Seq ID No. 47 (step 1 vector).

Overview of Seq ID No. 44 (Upstream Vector, Step 1, Double Lox):

Feature Map
- CDS (3 total)
  - NEO (+STOP) CDS
    - Start: 3311 End: 4114 (Complementary)
  - TK CDS (from VEC1198)
    - Start: 4118 End: 5251 (Complementary)
  - AP(R)
    - Start: 11732 End: 12589 (Complementary)
    - bla gene-Ap(r) determinant
- Enhancer (1 total)
  - CMV Enhancer
    - Start: 5779 End: 6199 (Complementary)
- Misc. Binding Site (2 total)
  - Left Homology Arm
    - Start: 238 End: 2978
  - Right Homology Arm
    - Start: 6269 End: 10600
- Misc. Feature (5 total)
  - loxP-1
    - Start: 3006 End: 3039
  - HSVTK-polyA
    - Start: 3046 End: 3304 (Complementary)
  - loxP-2
    - Start: 6212 End: 6245
- Promoter Eukaryotic (1 total)
  - Mus-PGK Promoter (correct)
    - Start: 5264 End: 5772 (Complementary)
- Replication Origin (2 total)
  - Replication Origin
    - Start: 10921 End: 11509 (Complementary)

Overview of Seq ID No. 45 (Downstream Vector, Step 2, Single Lox

Feature Map
- CDS (3 total)
  - NEO (+STOP) CDS
    - Start: 3115 End: 3918 (Complementary)
  - TK CDS (from VEC1198)
    - Start: 3922 End: 5055 (Complementary)
  - AP(R)
    - Start: 11322 End: 12179 (Complementary)
    - bla gene-Ap(r) determinant
- Enhancer (1 total)
  - CMV Enhancer
    - Start: 5583 End: 6003 (Complementary)
- Misc. Binding Site (2 total)
  - Left Homology Arm
    - Start: 222 End: 2774

Right Homology Arm
Start: 6112 End: 10226
Misc. Feature (4 total)
HSVTK-polyA
Start: 2850 End: 3108 (Complementary)
loxP-2
Start: 6016 End: 6049
Promoter Eukaryotic (1 total)
Mus-PGK Promoter (correct)
Start: 5068 End: 5576 (Complementary)
Replication Origin (2 total)
ORI
Start: 10511 End: 10511
RNaseH cleavage point
Replication Origin
Start: 10511 End: 11099 (Complementary)

Overview of Seq ID No. 46 (Upstream Vector Alternative, Step 2, Single Lox)
Feature Map
CDS (3 total)
NEO (+STOP) CDS
Start: 3311 End: 4114 (Complementary)
TK CDS (from VEC1198)
Start: 4118 End: 5251 (Complementary)
AP(R)
Start: 11698 End: 12555 (Complementary)
bla gene-Ap(r) determinant
Enhancer (1 total)
CMV Enhancer
Start: 5779 End: 6199 (Complementary)
Misc. Binding Site (2 total)
Left Homology Arm
Start: 238 End: 2978
Right Homology Arm
Start: 6235 End: 10566
Misc. Feature (4 total)
loxP-1
Start: 3006 End: 3039
HSVTK-polyA
Start: 3046 End: 3304 (Complementary)
Promoter Eukaryotic (1 total)
Mus-PGK Promoter (correct)
Start: 5264 End: 5772 (Complementary)
Replication Origin (2 total)
ORI
Start: 10887 End: 10887
RNaseH cleavage point
Replication Origin
Start: 10887 End: 11475 (Complementary)

Overview of Seq ID No. 47 (Downstream Vector Alternative, Step 1, Double Lox)
Feature Map
CDS (3 total)
NEO (+STOP) CDS
Start: 3149 End: 3952 (Complementary)
TK CDS (from VEC1198)
Start: 3956 End: 5089 (Complementary)
AP(R)
Start: 11356 End: 12213 (Complementary)
bla gene-Ap(r) determinant
Enhancer (1 total)
CMV Enhancer
Start: 5617 End: 6037 (Complementary)
Misc. Binding Site (2 total)
Left Homology Arm
Start: 222 End: 2774
Right Homology Arm
Start: 6146 End: 10260
Misc. Feature (5 total)
loxP-1
Start: 2844 End: 2877
HSVTK-polyA
Start: 2884 End: 3142 (Complementary)
loxP-2
Start: 6050 End: 6083
Promoter Eukaryotic (1 total)
Mus-PGK Promoter (correct)
Start: 5102 End: 5610 (Complementary)
Replication Origin (2 total)
Replication Origin
Start: 10545 End: 11133 (Complementary)

The first vector pair is used to produce cells in which the entire J/cluster region is deleted.

The second vector pair is used to produce cells in which the entire J/C cluster region is deleted.

Example 5

Crossbreeding of Heavy Chain Single Knockout with Kappa Single Knockout Pigs To produce pigs that have both one disrupted Ig heavy chain locus and one disrupted Ig light-chain kappa allele, single knockout animals were crossbred. The first pregnancy yielded four fetuses, two of which screened positive by both PCR and Southern for both heavy-chain and kappa targeting events (see examples 1 and 2 for primers). Fetal fibroblasts were isolated, expanded and frozen. A second pregnancy resulting from the mating of a kappa single knockout with a heavy chain single knockout produced four healthy piglets.

Fetal fibroblast cells that contain a heavy chain single knockout and a kappa chain single knockout will be used for further targeting. Such cells will be used to target the lambda locus via the methods and compositions described herein. The resulting offspring will be heterozygous knockouts for heavy chain, kappa chain and lambda chain. These animals will be further crossed with animals containing the human Ig genes as described herein and then crossbred with other single Ig knockout animals to produce porcine Ig double knockout animals with human Ig replacement genes.

This invention has been described with reference to its preferred embodiments. Variations and modifications of the invention, will be obvious to those skilled in the art from the foregoing detailed description of the invention.

We claim:

1. A transgenic porcine animal whose genome comprises a homozygous disruption of nucleotides 3296-3352 of SEQ ID NO: 29 of the joining region (J region) of the endogenous porcine heavy chain gene, wherein the porcine lacks expression of the endogenous porcine heavy chain immunoglobulin gene.

2. The transgenic porcine of claim 1, wherein the porcine animal comprises a homozygous disruption of the constant region of the endogenous porcine kappa immunoglobulin gene, wherein the disruption results in a lack of expression of the endogenous kappa immunoglobulin gene.

3. The porcine of claim 1, wherein the porcine heavy chain gene is disrupted through substitution, deletion or insertion techniques.

4. The porcine of claim 3, wherein the porcine heavy chain gene is disrupted through site specific recombinase techniques.

5. The porcine of claim 1, wherein the homozygous disruption is produced by homologous recombination.

6. The porcine of claim 1, wherein the porcine expresses a xenogenous immunoglobulin locus or fragment thereof and wherein the immunoglobulin is expressed from an immunoglobulin locus that is integrated within an endogenous porcine chromosome.

7. The porcine of claim 6, wherein the xenogenous immunoglobulin comprises a human immunoglobulin or fragment thereof.

8. The porcine of claim 6, wherein the xenogenous immunoglobulin locus is inherited by offspring.

9. The porcine of claim 6, wherein the xenogenous immunoglobulin locus is inherited through the male germ line by offspring.

10. The porcine of claim 6, wherein the porcine is produced through nuclear transfer.

11. The porcine of claim 6, wherein the immunoglobulin locus is expressed in B cells to produce xenogenous immunoglobulin in response to exposure to one or more antigens.

12. The porcine of claim 1, further comprising an additional genetic modification to eliminate the expression of a xenoantigen.

13. The porcine of claim 12, wherein the xenoantigen is alpha-1,3-galactosyltransferase.

14. The transgenic porcine of claim 2, wherein the porcine animal comprises a homozygous disruption of the constant region of the endogenous porcine lambda immunoglobulin gene, wherein the disruption results in the lack of expression of the endogenous porcine lambda immunoglobulin gene.

15. The porcine of claim 14, wherein the porcine heavy chain, kappa light chain and lambda light chain genes can be transcribed into RNA but not translated into protein.

16. The porcine of claim 14, wherein the porcine heavy chain, kappa light chain and lambda light chain genes are inactivated such that no transcription of the genes occurs.

17. The porcine of claim 14, wherein the porcine heavy chain, kappa light chain and lambda light chain genes are inactivated such that they are transcribed and then translated into non-functional proteins.

18. The porcine of any one of claims 1-14, wherein the porcine is produced by nuclear transfer.

19. Isolated cells derived from the porcine of claim 1.

20. Isolated A tissue derived from the porcine of claim 1.

* * * * *